(12) United States Patent
Sabzevari et al.

(10) Patent No.: US 12,194,094 B2
(45) Date of Patent: Jan. 14, 2025

(54) FUSION CONSTRUCTS AND METHODS OF USING THEREOF

(71) Applicant: Precigen, Inc., Germantown, MD (US)

(72) Inventors: Helen Sabzevari, Germantown, MD (US); Simon Metenou, Germantown, MD (US); Chang Hung Chen, Germantown, MD (US); Rutul Shah, Germantown, MD (US)

(73) Assignee: Precigen, Inc., Germantown, MD (US)

( * ) Notice: Subject to any disclaimer, the term of this patent is extended or adjusted under 35 U.S.C. 154(b) by 269 days.

(21) Appl. No.: 17/305,577

(22) Filed: Jul. 9, 2021

(65) Prior Publication Data

US 2022/0023420 A1    Jan. 27, 2022

Related U.S. Application Data

(60) Provisional application No. 63/173,902, filed on Apr. 12, 2021, provisional application No. 63/050,393, filed on Jul. 10, 2020.

(51) Int. Cl.
| | |
|---|---|
| *A61K 39/395* | (2006.01) |
| *A61K 38/17* | (2006.01) |
| *A61K 38/20* | (2006.01) |
| *A61K 39/00* | (2006.01) |
| *C07K 14/71* | (2006.01) |
| *C07K 16/28* | (2006.01) |
| *C07K 16/30* | (2006.01) |

(52) U.S. Cl.
CPC ...... *A61K 39/39558* (2013.01); *A61K 38/179* (2013.01); *A61K 38/1793* (2013.01); *A61K 38/2086* (2013.01); *A61K 39/001102* (2018.08); *A61K 39/001112* (2018.08); *A61K 39/001129* (2018.08); *A61K 39/00117* (2018.08); *A61K 39/001195* (2018.08); *A61K 39/4611* (2023.05); *A61K 39/4631* (2023.05); *A61K 39/464402* (2023.05); *A61K 39/464411* (2023.05); *A61K 39/464412* (2023.05); *A61K 39/464417* (2023.05); *A61K 39/464429* (2023.05); *A61K 39/464434* (2023.05); *A61K 39/46447* (2023.05); *A61K 39/464495* (2023.05); *C07K 14/71* (2013.01); *C07K 16/2818* (2013.01); *C07K 16/2857* (2013.01); *C07K 16/2863* (2013.01); *C07K 16/2866* (2013.01); *C07K 16/2875* (2013.01); *C07K 16/2878* (2013.01); *C07K 16/2884* (2013.01); *C07K 16/2887* (2013.01); *C07K 16/2896* (2013.01); *C07K 16/30* (2013.01); *C07K 16/3069* (2013.01); *C07K 16/3092* (2013.01); *A61K 2239/50* (2023.05); *A61K 2239/54* (2023.05); *A61K 2239/55* (2023.05); *A61K 2239/59* (2023.05)

(58) Field of Classification Search
None
See application file for complete search history.

(56) References Cited

U.S. PATENT DOCUMENTS

| | | | |
|---|---|---|---|
| 5,968,780 | A | 10/1999 | Fan et al. |
| 7,595,048 | B2 | 9/2009 | Honjo et al. |
| 8,354,509 | B2 | 1/2013 | Carven et al. |
| 9,629,877 | B2 | 4/2017 | Cooper et al. |
| 9,676,863 | B2 | 6/2017 | Lo |
| 9,758,582 | B2 | 9/2017 | Govindappa et al. |
| 9,809,637 | B2 | 11/2017 | Kumar et al. |
| 9,850,306 | B2 | 12/2017 | Bedi et al. |
| 9,987,500 | B2 | 6/2018 | Parapdopoulos et al. |
| 2005/0203022 | A1 | 9/2005 | Gotwals et al. |
| 2015/0086584 | A1 | 3/2015 | Gilboa et al. |
| 2016/0272960 | A1 | 9/2016 | Thanos et al. |
| 2016/0340430 | A1 | 11/2016 | Bedi et al. |
| 2017/0233747 | A1 | 8/2017 | Govindappa et al. |
| 2018/0118832 | A1 | 5/2018 | Lo et al. |
| 2018/0134766 | A1 | 5/2018 | Larson et al. |
| 2018/0179261 | A1 | 6/2018 | Kumar et al. |
| 2018/0327477 | A1 | 11/2018 | Kumar et al. |
| 2019/0048085 | A1 | 2/2019 | Dotti et al. |
| 2020/0048351 | A1 | 2/2020 | Sabzevari et al. |

FOREIGN PATENT DOCUMENTS

| | | |
|---|---|---|
| CN | 109913425 A | 6/2019 |
| EP | 2542590 B1 | 5/2017 |
| WO | 2011109789 A2 | 9/2011 |
| WO | 2013/169693 A1 | 11/2013 |
| WO | 2015/118175 A2 | 8/2015 |
| WO | 2015164594 A1 | 10/2015 |
| WO | 2016061286 A2 | 4/2016 |
| WO | 2018129331 A1 | 7/2018 |
| WO | 2018/208720 A1 | 11/2018 |
| WO | 2018205985 A1 | 11/2018 |
| WO | 2019/211489 A1 | 11/2019 |
| WO | 2020/118094 A9 | 6/2020 |
| WO | 2020/263796 A1 | 12/2020 |

OTHER PUBLICATIONS

Lloyd et al (Protein Engineering, Design & Selection, 22:159-168, 2009).*

(Continued)

*Primary Examiner* — Brad Duffy
(74) *Attorney, Agent, or Firm* — Barnes & Thornburg LLP; Gene J. Yao

(57) ABSTRACT

A fusion protein comprising: a first component comprising an antibody, or a fragment or variant thereof; and a second component comprising a cytokine trap or an adenosine deaminase or a fragment or variant thereof. In certain embodiments, the antibody is an anti-PD-1 antibody. In certain embodiments, the antibody binds to a tumor antigen, for example a MUC16 or MUC1 antigen. In certain embodiments, the cytokine trap is a TGF-β trap. A polynucleotide encoding such a fusion protein and a vector comprising such a polynucleotide. A composition comprising the fusion protein. A method of using the composition, including in the treatment of cancer.

15 Claims, 64 Drawing Sheets

Specification includes a Sequence Listing.

(56) References Cited

OTHER PUBLICATIONS

Edwards et al (J Mol Biol, 14;334(1):103-118, 2003).*
Gussow et al (Methods in Enzymology. 1991; 203: 99-121).*
Winkler et al (J. Imm., 265:4505-4514, 2000).*
Skolnick et al. (Trends in Biotechnology, 18: 34-39, 2000).*
Jones (Pharmacogenomics Journal, 1:126-134, 2001).*
Tosatto et al (Current Pharmaceutical Design, 12:2067-2086, 2006).*
Brown et al (JI, 156:3285-3291, 1996).*
Burgess et al. (J. Cell Biol. 1990; 111: 2129-2138).*
Lazar et al. (Mol. Cell. Biol. 1988; 8: 1247-1252).*
David, Justin M., et al., A novel bifunctional anti-PD-L 1/TGF-13 Trap fusion protein (M7824) efficiently reverts mesenchymalization of human lung cancer cells, Oncoimmunology, 2017, vol. 6, No. 10, e1349589, pp. 1-15.
Lan, Yan et al., Enhanced preclinical antitumor activity of M7824, a bifunctional fusion protein simultaneously targeting PD-L 1 and TGF-13., Sci. Transl. Med. 10, eaan5488 (2018), pp. 1-15.
Qian et al., Binding Affinity of Transforming Growth Factor-b for it's Type II Receptor is Determined by the C-Terminal Region of the Molecule, J Biol Chem, Nov. 29, 1996, vol. 271, No. 48, pp. 30656-30662.
Ravi, Rajani et al., Bifunctional immune checkpoint-targeted antibody-ligand traps that simultaneously disable TGFI3 enhance the efficacy of cancer immunotherapy, Nature Communications I (2018), 9:741, pp. 1-14.
Greenspan et al. 1999 Defining epitopes: It's not as easy as it seems; Nature Biotechnology, 17:936-937 (Year: 1999).
Bowie et al. Deciphering the Message in Protein Sequences: Tolerance to Amino Acid Substitutions. Science, 1990. 247: 1306-1310 (Year: 1990).
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111 :2129-2138,1990 (Year: 1990).
Bork. Powers and Pitfalls in Sequence Analysis: The 70% Hurdle. Genome Research, 2000, 10:398-400 (Year: 2000).
Strauss et al., Clinical Cancer Research, 24:1287-1295 (2018).

* cited by examiner

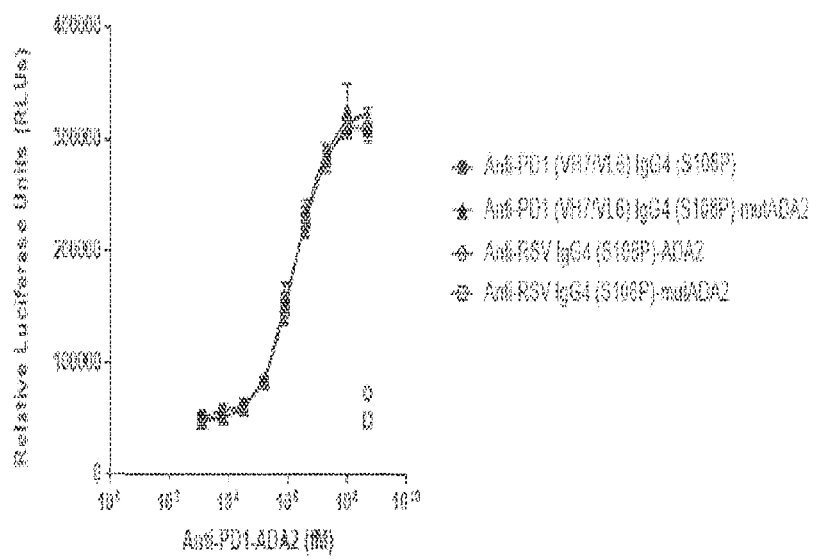
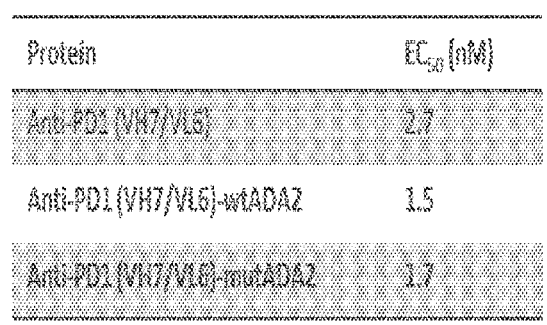
FIG. 23A

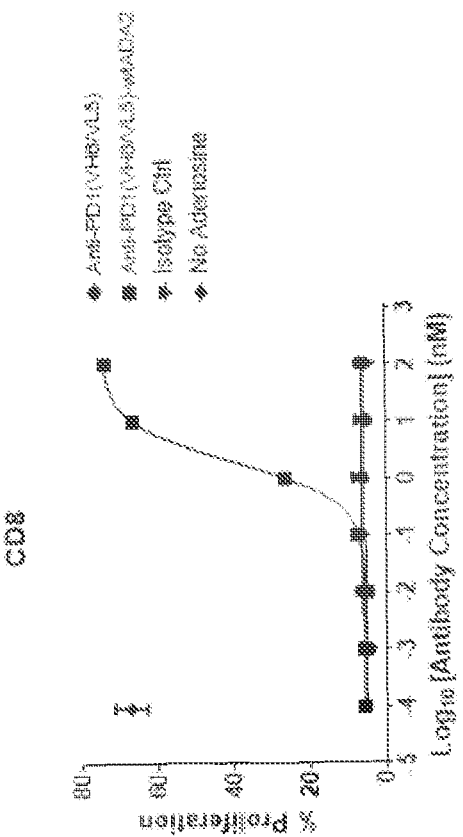
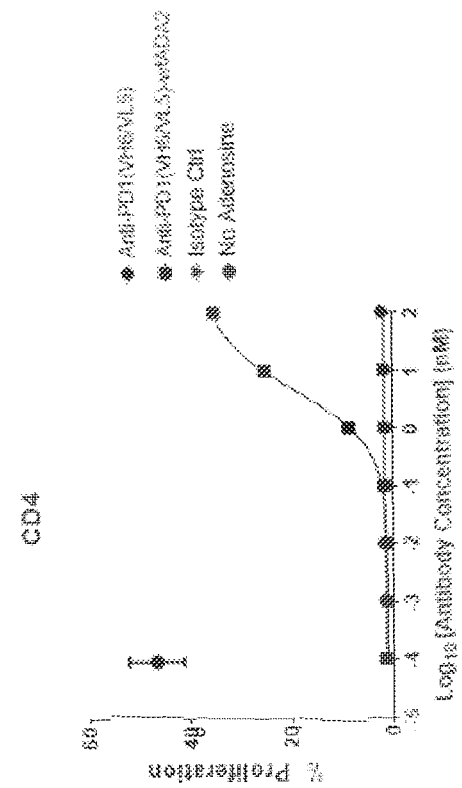
FIG. 26A
FIG. 26B

SEQUENCE LISTING

```
<160> NUMBER OF SEQ ID NOS: 564

<210> SEQ ID NO 1
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Ile Ile Phe Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Asp Asp Tyr Trp Gly Gln Gly Ala Leu Val Thr Val Ser
            100                 105                 110

Ser

<210> SEQ ID NO 2
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Glu Gly Phe Asp Tyr Trp Gly Gln Gly Thr Leu Val Thr Val
            100                 105                 110

Ser Ser

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Ala Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Arg Pro Asp Arg Ala Asn Trp His Phe Asp Tyr Trp Gly Gln
            100                 105                 110

Gly Thr Leu Val Thr Val Ser Ser
            115                 120
```

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Ala Ile Asn Pro Asn Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Gly Leu Lys Gly Asp Gly Tyr Phe Asp Tyr Trp Gly Gln
            100                 105                 110

Gly Thr Leu Val Thr Val Ser Ser
        115                 120

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 6

Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Asn Asn Trp Pro Arg
                 85                  90                  95

Thr Phe Gly Gln Gly Thr Lys Val Glu Ile Lys
                100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Lys
                 85                  90                  95

Thr Phe Gly Gln Gly Thr Lys Val Glu Ile Lys
                100                 105

<210> SEQ ID NO 10
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Asn Val Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Ser Ser Ser
                 20                  25                  30

Gly Tyr Thr Tyr Leu Asp Trp Tyr Leu Gln Lys Pro Gly Gln Ser Pro
             35                  40                  45

Gln Leu Leu Ile Tyr Leu Ala Ser Trp Arg Asp Ser Gly Val Pro Asp
         50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Met Gln Ala Glu
                 85                  90                  95

Gln Thr Pro Gly Pro Gly Asn Thr Phe Gly Gln Gly Thr Lys Leu Glu
                100                 105                 110

Ile Lys

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu His Trp Tyr Leu Gln Lys Pro Gly Gln Ser
        35                  40                  45

Pro Gln Leu Leu Ile Tyr Leu Gly Ser Trp Gln Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Glu Gln Thr Pro Arg Thr Phe Gly Gln Gly Thr Arg Leu Glu Val Lys
            100                 105                 110

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 13
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser

```
                 20                  25                  30
Gly Tyr Ser Tyr Leu His Trp Tyr Gln Gln Lys Pro Gly Gln Ala Pro
             35                  40                  45

Arg Leu Leu Ile Tyr Leu Ala Ser Tyr Leu Glu Ser Gly Val Pro Ala
         50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys
             100                 105                 110

<210> SEQ ID NO 14
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ile Pro Pro His Val Gln Lys Ser Val Asn Asn Asp Met Ile Val Thr
 1               5                  10                  15

Asp Asn Asn Gly Ala Val Lys Phe Pro Gln Leu Cys Lys Phe Cys Asp
             20                  25                  30

Val Arg Phe Ser Thr Cys Asp Asn Gln Lys Ser Cys Met Ser Asn Cys
         35                  40                  45

Ser Ile Thr Ser Ile Cys Glu Lys Pro Gln Glu Val Cys Val Ala Val
     50                  55                  60

Trp Arg Lys Asn Asp Glu Asn Ile Thr Leu Glu Thr Val Cys His Asp
 65                  70                  75                  80

Pro Lys Leu Pro Tyr His Asp Phe Ile Leu Glu Asp Ala Ala Ser Pro
                 85                  90                  95

Lys Cys Ile Met Lys Glu Lys Lys Lys Pro Gly Glu Thr Phe Phe Met
             100                 105                 110

Cys Ser Cys Ser Ser Asp Glu Cys Asn Asp Asn Ile Ile Phe Ser Glu
         115                 120                 125

Glu Tyr Asn Thr Ser Asn Pro Asp
     130                 135

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
```

```
                65                  70                  75                  80
        Glu Asp Phe Ala Val Tyr Tyr Cys Gln Gln Ser Ser Asn Trp Pro Arg
                            85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
        145                 150                 155                 160

Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 16
<211> LENGTH: 586
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
        1               5                   10                  15

Ser Leu Arg Leu Asp Cys Lys Ala Ser Gly Ile Thr Phe Ser Asn Ser
                        20                  25                  30

Gly Met His Trp Val Arg Gln Ala Pro Gly Lys Gly Leu Glu Trp Val
                    35                  40                  45

Ala Val Ile Trp Tyr Asp Gly Ser Lys Arg Tyr Tyr Ala Asp Ser Val
                50                  55                  60

Lys Gly Arg Phe Thr Ile Ser Arg Asp Asn Ser Lys Asn Thr Leu Phe
        65                  70                  75                  80

Leu Gln Met Asn Ser Leu Arg Ala Glu Asp Thr Ala Val Tyr Tyr Cys
                        85                  90                  95

Ala Thr Asn Asp Asp Tyr Trp Gly Gln Gly Thr Leu Val Thr Val Ser
                        100                 105                 110

Ser Ala Ser Thr Lys Gly Pro Ser Val Phe Pro Leu Ala Pro Cys Ser
                        115                 120                 125

Arg Ser Thr Ser Glu Ser Thr Ala Ala Leu Gly Cys Leu Val Lys Asp
                    130                 135                 140

Tyr Phe Pro Glu Pro Val Thr Val Ser Trp Asn Ser Gly Ala Leu Thr
        145                 150                 155                 160

Ser Gly Val His Thr Phe Pro Ala Val Leu Gln Ser Ser Gly Leu Tyr
                        165                 170                 175

Ser Leu Ser Ser Val Val Thr Val Pro Ser Ser Ser Leu Gly Thr Lys
                        180                 185                 190

Thr Tyr Thr Cys Asn Val Asp His Lys Pro Ser Asn Thr Lys Val Asp
                    195                 200                 205
```

```
Lys Arg Val Glu Ser Lys Tyr Gly Pro Pro Cys Pro Ser Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser Gln Glu Asp Pro Glu Val Gln Phe Asn Trp Tyr Val
        260                 265                 270

Asp Gly Val Glu Val His Asn Ala Lys Thr Lys Pro Arg Glu Glu Gln
    275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys Gly Gly Gly Ser Gly Gly Gly
        435                 440                 445

Gly Ser Ile Pro Pro His Val Gln Lys Ser Val Asn Asn Asp Met Ile
    450                 455                 460

Val Thr Asp Asn Asn Gly Ala Val Lys Phe Pro Gln Leu Cys Lys Phe
465                 470                 475                 480

Cys Asp Val Arg Phe Ser Thr Cys Asp Asn Gln Lys Ser Cys Met Ser
                485                 490                 495

Asn Cys Ser Ile Thr Ser Ile Cys Glu Lys Pro Gln Glu Val Cys Val
            500                 505                 510

Ala Val Trp Arg Lys Asn Asp Glu Asn Ile Thr Leu Glu Thr Val Cys
        515                 520                 525

His Asp Pro Lys Leu Pro Tyr His Asp Phe Ile Leu Glu Asp Ala Ala
530                 535                 540

Ser Pro Lys Cys Ile Met Lys Glu Lys Lys Lys Pro Gly Glu Thr Phe
545                 550                 555                 560

Phe Met Cys Ser Cys Ser Ser Asp Glu Cys Asn Asp Asn Ile Ile Phe
                565                 570                 575

Ser Glu Glu Tyr Asn Thr Ser Asn Pro Asp
            580                 585

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
                                    peptide

<400> SEQUENCE: 17

Asp Pro Gly Gly Gly Gly Ser Gly Gly Gly Ser Asn Pro Gly Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Ser Gly Ser Asp Pro Gly Ser
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Pro Gly Ser Gly Gly Gly Gly Ser Gly Gly Gly Ser Gly Ser
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Ser Gly Gly Gly Ser Asp
1               5                   10                  15

Pro Gly Ser

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Pro Gly Ser Gly Gly Gly Ser Gly Gly Gly Ser Gly Gly
1               5                   10                  15

Gly Gly Ser

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Pro Gly Ser Gly Ser Val Pro Leu Gly Ser Gly Ser Asn Pro Gly
```

```
1               5                   10                  15
Ser

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Pro Gly Ser Gly Gly Ser Val Pro Leu Gly Ser Gly Gly Ser Asn
1               5                   10                  15

Pro Gly Ser

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Pro Gly Val Leu Glu Arg Glu Asp Lys Pro Thr Thr Ser Lys Pro
1               5                   10                  15

Asn Pro Gly Ser
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Pro Gly Val Leu Glu Arg Glu Asp Val Pro Thr Thr Ser Tyr Pro
1               5                   10                  15

Asn Pro Gly Ser
            20

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Pro Gly Val Leu Glu Arg Glu Asp Lys Val Thr Thr Ser Lys Tyr
1               5                   10                  15

Asn Pro Gly Ser
            20

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 27

Asp Pro Val Leu Glu Arg Glu Asp Lys Val Thr Thr Ser Lys Asn Pro
1               5                   10                  15

Gly Ser

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Ile Glu Gly Arg Met Asp
1               5

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Glu Gly Lys Ser Ser Gly Ser Gly Ser Glu Ser Lys Ala Ser
1               5                   10                  15

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ser Thr Ser Gly Ser Gly Lys Pro Gly Ser Gly Glu Gly Ser Thr
1               5                   10                  15

Lys Gly

<210> SEQ ID NO 31
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
                20                  25                  30

Ala Ala Lys Glu Ala Ala Ala Lys Glu Ala Ala Ala Lys Ala
            35                  40                  45

<210> SEQ ID NO 32
<211> LENGTH: 50
<212> TYPE: PRT
<213> ORGANISM: Artificial Sequence
<220> FEATURE:
<223> OTHER INFORMATION: Description of Artificial Sequence: Synthetic
```

```
           polypeptide
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units

<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(8)
<223> OTHER INFORMATION: This sequence may encompass 6-8 residues

<400> SEQUENCE: 33

Gly Gly Gly Gly Gly Gly Gly Gly
1               5

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 1-6 "Glu Ala Ala
      Ala Lys" repeating units

<400> SEQUENCE: 34

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys
            20                  25                  30

<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
```

```
                 35                  40                  45

Lys Leu Leu Ile Tyr Ala Ala Ser Asn Gln Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Asp Asp Phe Ala Thr Tyr Tyr Cys Gln Gln Ser Lys
                 85                  90                  95

Glu Val Pro Trp Thr Phe Gly Gln Gly Thr Lys Val Glu Ile Lys
                100                 105                 110

<210> SEQ ID NO 36
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Ile
             35                  40                  45

Gly Tyr Ile Tyr Pro Tyr Asn Gly Gly Thr Gly Tyr Asn Gln Lys Phe
 50                  55                  60

Lys Ser Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
                100                 105                 110

Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Ser Gly Pro Glu Leu Val Arg Pro Gly Thr
 1               5                  10                  15

Phe Val Lys Ile Ser Cys Lys Ala Ser Gly Tyr Thr Phe Thr Asn Tyr
                20                  25                  30

Asp Ile Asn Trp Val Asn Gln Arg Pro Gly Gln Gly Leu Glu Trp Ile
             35                  40                  45

Gly Trp Ile Tyr Pro Gly Asp Gly Ser Thr Lys Tyr Asn Glu Lys Phe
 50                  55                  60

Lys Ala Lys Ala Thr Leu Thr Ala Asp Lys Ser Ser Thr Ala Tyr
 65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
```

Val Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Lys Met Thr Gln Ser Pro Ser Ser Met Tyr Ala Ser Leu Gly
1               5                   10                  15

Glu Arg Val Ile Ile Asn Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys Arg
            100                 105

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser
        115                 120

<210> SEQ ID NO 40
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Asp Ile Val Leu Thr Gln Ser Pro Thr Ile Met Ser Ala Ser Pro Gly
1               5                   10                  15

Glu Arg Val Thr Met Thr Cys Thr Ala Ser Ser Val Asn Tyr Ile
            20                  25                  30

His Trp Tyr Gln Gln Lys Ser Gly Asp Ser Pro Leu Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
            100                 105                 110

Thr Val Ser
        115

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser
        115

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
             85                  90                  95

Tyr Leu Ser Ser Arg Thr Phe Gly Gly Gly Thr Lys Leu Glu Ile Lys
             100                 105                 110

Arg

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
             20                  25                  30

Arg Thr Arg Lys Asn Gln Leu Ala Trp Tyr Gln Gln Lys Pro Gly Gln
         35                  40                  45

Ser Pro Glu Leu Leu Ile Tyr Trp Ala Ser Thr Arg Gln Ser Gly Val
 50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
             85                  90                  95

Ser Tyr Asn Leu Leu Thr Phe Gly Pro Gly Thr Lys Leu Glu Val Lys
             100                 105                 110

Arg

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Lys Leu Gln Glu Ser Gly Gly Gly Phe Val Lys Pro Gly Gly Ser
1               5                   10                  15

Leu Lys Val Ser Cys Ala Ala Ser Gly Phe Thr Phe Ser Ser Tyr Ala
             20                  25                  30

Met Ser Trp Val Arg Leu Ser Pro Glu Met Arg Leu Glu Trp Val Ala
         35                  40                  45

Thr Ile Ser Ser Ala Gly Gly Tyr Ile Tyr Ser Asp Ser Val Gln
 50                  55                  60

Gly Arg Phe Thr Ile Ser Arg Asp Asn Ala Lys Asn Thr Leu His Leu
65                  70                  75                  80

Gln Met Gly Ser Leu Arg Ser Gly Asp Thr Ala Met Tyr Tyr Cys Ala

```
                85                  90                  95
Arg Gln Gly Phe Gly Asn Tyr Gly Asp Tyr Tyr Ala Met Asp Tyr Trp
            100                 105                 110
Gly Gln Gly Thr Thr Val Thr Val Ser Ser
        115                 120
```

<210> SEQ ID NO 45
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Glu Leu Thr Gln Ser Pro Ser Ser Leu Ala Val Ser Ala Gly
1               5                   10                  15
Glu Lys Val Thr Met Ser Cys Lys Ser Gln Ser Leu Leu Asn Ser
            20                  25                  30
Arg Thr Arg Lys Asn Gln Leu Ala Trp Tyr Gln Gln Lys Thr Gly Gln
        35                  40                  45
Ser Pro Glu Leu Leu Ile Tyr Trp Ala Ser Thr Arg Gln Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Gln
                85                  90                  95
Ser Tyr Asn Leu Leu Thr Phe Gly Pro Gly Thr Lys Leu Glu Ile Lys
            100                 105                 110
Arg
```

<210> SEQ ID NO 46
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Val Lys Leu Glu Glu Ser Gly Gly Gly Phe Val Lys Pro Gly Gly Ser
1               5                   10                  15
Leu Lys Ile Ser Cys Ala Ala Ser Gly Phe Thr Phe Arg Asn Tyr Ala
            20                  25                  30
Met Ser Trp Val Arg Leu Ser Pro Glu Met Arg Leu Glu Trp Val Ala
        35                  40                  45
Thr Ile Ser Ser Ala Gly Gly Tyr Ile Phe Tyr Ser Asp Ser Val Gln
    50                  55                  60
Gly Arg Phe Thr Ile Ser Arg Asp Asn Ala Lys Asn Thr His Leu Gln
65                  70                  75                  80
Met Gly Ser Leu Arg Ser Gly Asp Thr Ala Met Tyr Tyr Cys Ala Arg
                85                  90                  95
Gln Gly Phe Gly Asn Tyr Gly Asp Tyr Tyr Ala Met Asp Tyr Trp Gly
            100                 105                 110
Gln Gly Thr Thr Val Thr Val Ser Ser
        115                 120
```

<210> SEQ ID NO 47

<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Lys Met Ala Gln Ser Pro Ser Ser Val Asn Ala Ser Leu Gly
1               5                   10                  15

Glu Arg Val Thr Ile Thr Cys Lys Ala Ser Arg Asp Ile Asn Asn Phe
            20                  25                  30

Leu Ser Trp Phe His Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Phe Thr Ile Ser Ser Leu Glu Tyr
65                  70                  75                  80

Glu Asp Val Gly Ile Tyr Tyr Cys Leu Gln Tyr Gly Asp Leu Tyr Thr
                85                  90                  95

Phe Gly Gly Gly Thr Lys Leu Glu Ile Lys
            100                 105

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Val Gln Leu Leu Glu Ser Gly Pro Gly Leu Val Arg Pro Ser Gln
1               5                   10                  15

Ser Leu Ser Leu Thr Cys Ser Val Thr Gly Tyr Ser Ile Val Ser His
            20                  25                  30

Tyr Tyr Trp Asn Trp Ile Arg Gln Phe Pro Gly Asn Lys Leu Glu Trp
        35                  40                  45

Met Gly Tyr Ile Ser Ser Asp Gly Ser Asn Glu Tyr Asn Pro Ser Leu
    50                  55                  60

Lys Asn Arg Ile Ser Ile Ser Leu Asp Thr Ser Lys Asn Gln Phe Phe
65                  70                  75                  80

Leu Lys Phe Asp Phe Val Thr Thr Ala Asp Thr Ala Thr Tyr Phe Cys
                85                  90                  95

Val Arg Gly Val Asp Tyr Trp Gly Gln Gly Thr Thr Leu Thr Val Ser
            100                 105                 110

Ser

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Gln Met Thr Gln Ser Ser Ser Phe Leu Ser Val Ser Leu Gly
1               5                   10                  15

Gly Arg Val Thr Ile Thr Cys Lys Ala Ser Asp Leu Ile His Asn Trp

```
                     20                  25                  30
Leu Ala Trp Tyr Gln Gln Lys Pro Gly Asn Ala Pro Arg Leu Leu Ile
             35                  40                  45

Ser Gly Ala Thr Ser Leu Glu Thr Gly Val Pro Ser Arg Phe Ser Gly
         50                  55                  60

Ser Gly Ser Gly Asn Asp Tyr Thr Leu Ser Ile Ala Ser Leu Gln Thr
65                  70                  75                  80

Glu Asp Ala Ala Thr Tyr Tyr Cys Gln Gln Tyr Trp Thr Thr Pro Phe
                 85                  90                  95

Thr Phe Gly Ser Gly Thr Lys Leu Glu Ile Lys
             100                 105

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Gln Leu Gln Glu Ser Gly Pro Gly Leu Val Asn Pro Ser Gln
1               5                  10                  15

Ser Leu Ser Leu Thr Cys Thr Val Thr Gly Tyr Ser Ile Thr Asn Asp
             20                  25                  30

Tyr Ala Trp Asn Trp Ile Arg Gln Phe Pro Gly Asn Lys Leu Glu Trp
         35                  40                  45

Met Gly Tyr Ile Asn Tyr Ser Gly Tyr Thr Thr Tyr Asn Pro Ser Leu
     50                  55                  60

Lys Ser Arg Ile Ser Ile Thr Arg Asp Thr Ser Lys Asn Gln Phe Phe
65                  70                  75                  80

Leu His Leu Asn Ser Val Thr Thr Glu Asp Thr Ala Thr Tyr Tyr Cys
                 85                  90                  95

Ala Arg Trp Asp Gly Gly Leu Thr Tyr Trp Gly Gln Gly Thr Leu Val
             100                 105                 110

Thr Val Ser Ala
         115

<210> SEQ ID NO 51
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ser Ser Leu Ser Ala Ser Val Gly
1               5                  10                  15

Asp Arg Val Thr Ile Thr Cys Lys Ala Ser Asp Leu Ile His Asn Trp
             20                  25                  30

Leu Ala Trp Tyr Gln Gln Lys Pro Gly Lys Ala Pro Lys Leu Leu Ile
         35                  40                  45

Ser Gly Ala Thr Ser Leu Glu Thr Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
```

```
                85                  90                  95
Thr Phe Gly Gln Gly Thr Lys Val Glu Ile Lys Arg
            100                 105

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Gly Leu Thr Tyr Trp Gly Gln Gly Thr Leu Val
            100                 105                 110

Thr Val Ser Ser
        115

<210> SEQ ID NO 53
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Asn Tyr Ser Gly Tyr Thr Thr Tyr Asn Pro Ser Leu
    50                  55                  60

Lys Ser Arg Phe Thr Ile Ser Arg Asp Asn Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Trp Asp Gly Gly Leu Thr Tyr Trp Gly Gln Gly Thr Leu Val
            100                 105                 110

Thr Val Ser Ser
        115

<210> SEQ ID NO 54
<211> LENGTH: 109
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Val Glu Ile Lys Arg
                100                 105

<210> SEQ ID NO 55
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Tyr Thr Phe Gly Gln Gly Thr Lys Val Glu Ile Lys Arg
                100                 105

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

```
Gly Arg Val Asp Pro Ala Asn Gly Asn Thr Lys Tyr Asp Pro Lys Phe
        50                  55                  60

Gln Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Val Arg Asp Tyr Tyr Gly His Thr Tyr Gly Phe Ala Phe Trp Gly Gln
            100                 105                 110

Gly Thr Leu Val Thr Val Ser Ser
            115                 120

<210> SEQ ID NO 57
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Lys Pro Thr Thr Thr Pro Ala Pro Arg Pro Pro Thr Pro Ala Pro Thr
 1               5                   10                  15

Ile Ala Ser Gln Pro Leu Ser Leu Arg Pro Glu Ala Cys Arg Pro Ala
             20                  25                  30

Ala Gly Gly Ala Val His Thr Arg Gly Leu Asp Phe Ala Cys Asp
         35                  40                  45

<210> SEQ ID NO 58
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Lys Pro Thr Thr Thr Pro Ala Pro Arg Pro Pro Thr Pro Ala Pro Thr
 1               5                   10                  15

Ile Ala Ser Gln Pro Leu Ser Leu Arg Pro Glu Ala Ser Arg Pro Ala
             20                  25                  30

Ala Gly Gly Ala Val His Thr Arg Gly Leu Asp Phe Ala Ser Asp Lys
         35                  40                  45

Pro Thr Thr Thr Pro Ala Pro Arg Pro Pro Thr Pro Ala Pro Thr Ile
 50                  55                  60

Ala Ser Gln Pro Leu Ser Leu Arg Pro Glu Ala Cys Arg Pro Ala Ala
 65                  70                  75                  80

Gly Gly Ala Val His Thr Arg Gly Leu Asp Phe Ala Cys Asp
             85                  90

<210> SEQ ID NO 59
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Lys Pro Thr Thr Thr Pro Ala Pro Arg Pro Pro Thr Pro Ala Pro Thr
 1               5                   10                  15
```

```
Ile Ala Ser Gln Pro Leu Ser Leu Arg Pro Glu Ala Ser Arg Pro Ala
             20                  25                  30

Ala Gly Gly Ala Val His Thr Arg Gly Leu Asp Phe Ala Ser Asp Lys
         35                  40                  45

Pro Thr Thr Thr Pro Ala Pro Arg Pro Pro Thr Pro Ala Pro Thr Ile
 50                  55                  60

Ala Ser Gln Pro Leu Ser Leu Arg Pro Glu Ala Ser Arg Pro Ala Ala
 65                  70                  75                  80

Gly Gly Ala Val His Thr Arg Gly Leu Asp Phe Ala Ser Asp Lys Pro
                 85                  90                  95

Thr Thr Thr Pro Ala Pro Arg Pro Pro Thr Pro Ala Pro Thr Ile Ala
                100                 105                 110

Ser Gln Pro Leu Ser Leu Arg Pro Glu Ala Cys Arg Pro Ala Ala Gly
            115                 120                 125

Gly Ala Val His Thr Arg Gly Leu Asp Phe Ala Cys Asp
        130                 135                 140
```

<210> SEQ ID NO 60
<211> LENGTH: 185
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Thr Thr Pro Ala Pro Arg Pro Pro Thr Pro Ala Pro Thr Ile Ala Ser
 1               5                  10                  15

Gln Pro Leu Ser Leu Arg Pro Glu Ala Ser Arg Pro Ala Ala Gly Gly
             20                  25                  30

Ala Val His Thr Arg Gly Leu Asp Phe Ala Ser Asp Lys Pro Thr Thr
         35                  40                  45

Thr Pro Ala Pro Arg Pro Pro Thr Pro Ala Pro Thr Ile Ala Ser Gln
 50                  55                  60

Pro Leu Ser Leu Arg Pro Glu Ala Ser Arg Pro Ala Ala Gly Gly Ala
 65                  70                  75                  80

Val His Thr Arg Gly Leu Asp Phe Ala Ser Asp Lys Pro Thr Thr Thr
                 85                  90                  95

Pro Ala Pro Arg Pro Pro Thr Pro Ala Pro Thr Ile Ala Ser Gln Pro
                100                 105                 110

Leu Ser Leu Arg Pro Glu Ala Ser Arg Pro Ala Ala Gly Gly Ala Val
            115                 120                 125

His Thr Arg Gly Leu Asp Phe Ala Ser Asp Lys Pro Thr Thr Thr Pro
        130                 135                 140

Ala Pro Arg Pro Pro Thr Pro Ala Pro Thr Ile Ala Ser Gln Pro Leu
145                 150                 155                 160

Ser Leu Arg Pro Glu Ala Cys Arg Pro Ala Ala Gly Gly Ala Val His
                165                 170                 175

Thr Arg Gly Leu Asp Phe Ala Cys Asp
            180                 185
```

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Tyr Ile Trp Ala Pro Leu Ala Gly Thr Cys Gly Val Leu Leu
1               5                   10                  15

Ser Leu Val Ile Thr Leu Tyr Cys Asn His Arg Asn
            20                  25

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 63
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 64
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 65
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 66
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 67
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 68
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

-continued

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 69
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Arg Lys Val Cys Asn Gly Ile Gly Ile Gly Glu Phe Lys Asp Ser Leu
 1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
 50                  55                  60

Val Lys Glu Ile Thr Gly Phe Leu Leu Ile Gln Ala Trp Pro Glu Asn
 65                  70                  75                  80

```
Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Gly Gly Gly Gly Ser Gly Gly Gly Ser Gly Gly Gly Ser Gly Gly
        195                 200                 205

Gly Gly Ser Phe Trp Val Leu Val Val Val Gly Gly Val Leu Ala Cys
        210                 215                 220

Tyr Ser Leu Leu Val Thr Val Ala Phe Ile Ile Phe Trp Val Arg Ser
225                 230                 235                 240

Lys Arg Ser

<210> SEQ ID NO 70
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190
```

```
Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
            210                 215                 220

Ser Asn Ile Val Leu Leu Ser Ala Glu Lys Lys Glu Gln Thr Ile
225                 230                 235                 240

Glu Ile Lys Glu Glu Val Val Gly Leu Thr Glu Thr Ser Ser Gln Pro
            245                 250                 255

Lys Asn Glu Glu Asp Ile Glu Ile Pro Ile Gln Glu Glu Glu Glu
            260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro
            290                 295
```

<210> SEQ ID NO 71
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
            210                 215                 220

Ser Asn Ile Val Leu Leu Ser Ala Glu Lys Lys Glu Gln Thr Ile
225                 230                 235                 240

Glu Ile Lys Glu Glu Val Val Gly Leu Thr Glu Thr Ser Ser Gln Pro
```

245 250 255

Lys Asn Glu Glu Asp Ile Glu
            260

<210> SEQ ID NO 72
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gacattcaga tgacccagtc tccgagctct ctgtccgcat cagtaggaga cagggtcacc    60
atcacatgca gagccagcga aagtgtcgac aattatggca ttagctttat gaactggttc   120
caacagaaac ccgggaaggc tcctaagctt ctgatttacg ctgcatccaa ccaaggctcc   180
ggggtaccct ctcgcttctc aggcagtgga tctgggacag acttcactct caccatttca   240
tctctgcagc ctgatgactt cgcaacctat tactgtcagc aaagtaagga ggttccgtgg   300
acgttcggtc aagggaccaa ggtggagatc aaa                                333

<210> SEQ ID NO 73
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caggttcagc tggtgcagtc tggagctgag gtgaagaagc ctgggagctc agtgaaggtt    60
tcctgcaaag cttctggcta caccttcact gactacaaca tgcactgggt gaggcaggct   120
cctggccaag gctggaatg gattggatat atttatcctt acaatggtgg taccggctac   180
aaccagaagt tcaagagcaa ggccacaatt acagcagacg agagtactaa cacagcctac   240
atggaactct ccagcctgag gtctgaggac actgcagtct attactgcgc aagagggcgc   300
cccgctatgg actactgggg ccaagggact ctggtcactg tctcttca                348

<210> SEQ ID NO 74
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
gacatcgagc tgacacagag cccatctagc ctggctgtgt ctgccggcga gaaagtgacc    60
atgagctgca agagcagcca gagcctgctg aacagccgga ccagaaagaa tcagctggcc   120
tggtatcagc agaagcccgg ccaatctcct gagctgctga tctactgggc agcacaaga   180 cagagcggcg tgcccgatag attcacagga tctggcagcg gcaccgactt caccctgaca   240
atcagttctg tgcaggccga ggacctggcc gtgtactact gtcagcagag ctacaacctg   300
ctgaccttcg gacccggcac caagctggaa gtgaagaga                          339

<210> SEQ ID NO 75
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
gtgaagctgc aagagtccgg cggaggcttt gtgaagcctg gcggctctct gaaagtgtcc      60
tgtgccgcca gcggcttcac ctttagcagc tacgccatga gctgggtccg actgagccct     120
gagatgagac tggaatgggt cgccaccatc agtagcgcag gcggctacat cttctacagc     180
gactctgtgc agggcagatt caccatcagc cgggacaacg ccaagaacac cctgcacctc     240
cagatgggca gtctgagaag cggcgatacc gccatgtact actgcgccag acaaggcttc     300
ggcaactacg gcgactacta tgccatggat tactggggcc agggcaccac cgtgacagtc     360
tcttct                                                                 366
```

<210> SEQ ID NO 76
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gacatcgagc tgacacagag cccatctagc ctggctgtgt ctgccggcga gaaagtgacc      60
atgagctgca agagcagcca gagcctgctg aacagccgga ccagaaagaa tcagctggcc     120
tggtatcagc agaaaaccgg acagagcccc gagctgctga tctactgggc cagcacaaga     180
cagagcggcg tgcccgatag attcacagga tctggcagcg gcaccgactt caccctgaca     240
atcagttctg tgcaggccga ggacctggcc gtgtactact gtcagcagag ctacaacctg     300
ctgaccttcg gacccggcac caagctggaa atcaagaga                             339
```

<210> SEQ ID NO 77
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
gtgaagctgg aagagtccgg cggaggcttt gtgaagcctg gcggaagcct gaagatcagc      60
tgtgccgcca gcggcttcac cttcagaaac tacgccatga gctgggtccg actgagcccc     120
gagatgagac tggaatgggt cgccacaatc agcagcgcag gcggctacat cttctacagc     180
gatagcgtgc agggcagatt caccatcagc cgggacaacg ccaagaacac cctgcacctc     240
cagatgggca gtctgagatc tggcgacacc gccatgtact actgcgccag acaaggcttc     300
ggcaactacg gcgactacta tgccatggat tactggggcc agggcaccac cgtgacagtc     360
tcttct                                                                 366
```

<210> SEQ ID NO 78
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
gacatcaaga tggctcagtc cccttctagc gtgaatgctt cgctagggga gcgtgtgacc    60
atcacatgta aagcatcacg cgacataaat aatttccttt cctggtttca tcagaaaccg   120
ggcaagtcgc ctaagacgct gatttacaga gcaaatcggt tggtagatgg agtgccaagc   180
agattcagcg ggagcggaag tggacaggat tatagcttca ctatttcatc cctggaatac   240
gaggacgtag gtatctatta ttgcctccag tatggcgatc tttacacatt tggtgggggg   300
actaagctgg agattaag                                                 318

<210> SEQ ID NO 79
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
gacgtgcaac ttctggagag cgggccaggg ctagtcaggc cctcccagtc gctttcactg    60
acttgcagtg tgaccggtta ctctattgtg agtcactact attggaactg gattcggcag   120
ttcccaggca acaaactgga atggatgggg tacatatctt ccgatggctc gaatgaatat   180
aacccatcat tgaaaaatcg tatttccatc agtctggata cgagtaaaaa ccagttttc    240 ctcaaattcg atttcgtgac tacagcagat actgccacat acttctgtgt acgaggtgtc   300
gattattggg gacagggcac aacgctgacc gtaagttct                          339

<210> SEQ ID NO 80
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
gacatccaga tgacccagag cagcagcttc ctgagcgtgt cccttggcgg cagagtgacc    60
atcacctgta aagccagcga cctgatccac aactggctgg cctggtatca gcagaagcct   120
ggcaacgctc ccagactgct gattagcggc gccacctctc tggaaacagg cgtgccaagc   180
agattttccg gcagcggctc cggcaacgac tacacactgt ctattgccag cctgcagacc   240
gaggatgccg ccacctatta ctgccagcag tactggacca ccttttcac ctttggcagc    300 ggcaccaagc tggaaatcaa g                                             321

<210> SEQ ID NO 81
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gacgttcagc tgcaagagtc tggccctggc ctggtcaatc ctagccagag cctgagcctg    60
acatgtaccg tgaccggcta cagcatcacc aacgactacg cctggaactg gatcagacag   120
ttccccggca acaagctgga atggatgggc tacatcaact acagcggcta caccacctac   180
aatcccagcc tgaagtcccg gatctccatc accagagaca ccagcaagaa ccagttcttc   240
ctgcacctga acagcgtgac caccgaggat accgccacct actactgcgc tagatgggat   300
```

```
ggcggcctga catattgggg ccagggaaca ctggtcaccg tgtctgct              348
```

<210> SEQ ID NO 82
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82

```
gacatccaga tgacccagag ccccagcagc ctgagcgcca gcgtgggcga cagggtgacc      60
atcacctgca aggccagcga cctgatccac aactggctgg cctggtacca gcagaagccc     120
ggcaaggccc ccaagctgct gatcagcggc gccaccagcc tggagaccgg cgtgcccagc     180
aggttcagcg gcagcggcag cggcaccgac ttcaccctga ccatcagcag cctgcagccc     240
gaggacttcg ccacctacta ctgccagcag tactggacca ccccctttcac cttcggccag     300 ggcaccaagg tggagatcaa gagg                                            324
```

<210> SEQ ID NO 83
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83

```
gaggtgcagc tggtggagag cggcggcggc ctggtgcagc ccggcggcag cctgaggctg      60
agctgcgccg ccagcggcta cagcatcacc aacgactacg cctggaactg ggtgaggcag     120 gccccccggca agggcctgga gtgggtgggc tacatcaact acagcggcta caccacctac     180
aaccccagcc tgaagagcag gttcaccatc agcagggaca cagcaagaa caccctgtac     240 ctgcagatga acagcctgag ggccgaggac accgccgtgt actactgcgc caggtgggac     300
ggcggcctga cctactgggg ccagggcacc ctggtgaccg tgagcagc                 348
```

<210> SEQ ID NO 84
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
gaggtgcagc tggtggagag cggcggcggc ctggtgcagc ccggcggcag cctgaggctg      60
agctgcgccg ccagcggcta cagcatcacc aacgactacg cctggaactg ggtgaggcag     120 gccccggca agggcctgga gtgggtgggc tacatcaact acagcggcta caccacctac     180
aaccccagcc tgaagagcag gttcaccatc agcagggaca cagcaagaa caccttctac     240 ctgcagatga acagcctgag ggccgaggac accgccgtgt actactgcgc caggtgggac     300
ggcggcctga cctactgggg ccagggcacc ctggtgaccg tgagcagc                 348
```

<210> SEQ ID NO 85
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
gacatcgtgc tgacacagag ccctgccatc atgtctgcca gcctcggcga gcgagtgacc    60
atgacatgta cagccagcag cagcgtgtcc agcagctacc tgcattggta tcagcagaag   120
cccggcagca gccccaagct gtggatctac agcacaagca atctggccag cggcgtgcca   180
ggcagatttt ctggttctgg cagcggcacc agctacagcc tgacaatcag cagcatggaa   240
gccgaggatg ccgccaccta ctactgccac cagtaccaca gaagccccta cacctttggc   300
ggaggcacca aggtggaaat caagcgg                                       327
```

<210> SEQ ID NO 86
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
gacatccaga tgacacagag ccctagcagc ctgtctgcca gcgtgggaga cagagtgacc    60
atcacctgta cagccagcag cagcgtgtcc agcagctacc tgcattggta tcagcagaag   120
cccggcaagg cccctaagct gctgatctac agcaccagca atctggccag cggcgtgcca   180
agcagatttt ctggctctgg cagcggcacc gacttcaccc tgaccatatc tagcctgcag   240
cctgaggact cgccaccta ctactgccac cagtaccaca gaagccccta cacctttggc    300
cagggcacca aggtggaaat caagcgg                                       327
```

<210> SEQ ID NO 87
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
gaggtgcagc tggttgaatc tggcggagga ctggttcagc ctggcggatc tctgagactg    60
tcttgtgccg ccagcggctt caacatcaag gacacctaca tgcactgggt ccgacaggcc   120
cctggcaaag gacttgagtg ggttggaaga gtggaccccg ccaacggcaa caccaaatac   180
gaccccaagt tccagggcag attcaccatc agcgccgaca ccagcaagaa caccgcctac   240
ctgcagatga acagcctgag agccgaggac accgccgtgt actattgcgt gcgggattac   300
tacggccata cctacggctt cgccttttgg ggccagggca cactggttac cgttagctct   360
```

<210> SEQ ID NO 88
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
aagcccacca ccaccctgc ccctagacct ccaaccccag cccctacaat cgccagccag     60
cccctgagcc tgaggcccga agcctgtaga cctgccgctg gcggagccgt gcacaccaga   120
ggcctggatt cgcctgcga c                                              141
```

```
<210> SEQ ID NO 89
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
aaacctacta caactcctgc ccccggcct cctacaccag ctcctactat cgcctcccag      60
ccactcagtc tcagacccga ggcttctagg ccagcggccg gaggcgcggt ccacacccgc    120
gggctggact ttgcatccga taagcccacc accaccctg ccctagacc tccaaccca      180 gccctacaa tcgccagcca gccctgagc ctgaggcccg aagcctgtag acctgccgct     240
ggcggagccg tgcacaccag aggcctggat ttcgcctgcg ac                      282

<210> SEQ ID NO 90
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
aagcctacca ccaccccgc acctcgtcct ccaaccctg cacctacgat tgccagtcag      60
cctctttcac tgcggcctga ggccagcaga ccagctgccg gcggtgccgt ccatacaaga   120
ggactggact tcgcgtccga taaacctact accactccag ccccaaggcc cccaacccca   180
gcaccgacta tcgcatcaca gcctttgtca ctgcgtcctg aagccagccg gccagctgca   240 ggggggccg tccacacaag gggactcgac tttgcgagtg ataagcccac caccacccct   300 gccctagac ctccaacccc agcccctaca atcgccagcc agccctgag cctgaggccc    360 gaagcctgta gacctgccgc tggcggagcc gtgcacacca gaggcctgga tttcgcctgc   420
gac                                                                423

<210> SEQ ID NO 91
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
aagcctacca ccaccccgc acctcgtcct ccaaccctg cacctacgat tgccagtcag      60
cctctttcac tgcggcctga ggccagcaga ccagctgccg gcggtgccgt ccatacaaga   120
ggactggact tcgcgtccga taaacctact accactccag ccccaaggcc cccaacccca   180
gcaccgacta tcgcatcaca gcctttgtca ctgcgtcctg aagccagccg gccagctgca   240 ggggggccg tccacacaag gggactcgac tttgcgagtg ataaacctac tacaactcct   300
gccccccggc ctcctacacc agctcctact atcgcctccc agccactcag tctcagaccc   360
gaggcttcta ggccagcggc cggaggcgcg gtccacaccc gcgggctgga ctttgcatcc   420
gataagccca ccaccaccc tgcccctaga cctccaaccc cagcccctac aatcgccagc   480
cagcccctga gcctgaggcc cgaagcctgt agacctgccg ctggcggagc cgtgcacacc   540
agaggcctgg atttcgcctg cgac                                         564
```

```
<210> SEQ ID NO 92
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
atctacatct gggcccctct ggccggcacc tgtggcgtgc tgctgctgag cctggtcatc      60
accctgtact gcaaccaccg gaat                                            84

<210> SEQ ID NO 93
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ttttgggtgc tggtggtggt tggtggagtc ctggcttgct atagcttgct agtaacagtg      60
gcctttatta ttttctgggt g                                               81

<210> SEQ ID NO 94
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
aagagaggcc ggaagaaact gctgtacatc ttcaagcagc ccttcatgcg gcccgtgcag      60
accacccagg aagaggacgg ctgcagctgc cggttccccg aggaagagga aggcggctgc     120
gaactg                                                               126

<210> SEQ ID NO 95
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
aggagcaagc ggagcagagg cggccacagc gactacatga acatgacccc ccggaggcct      60
ggccccaccc ggaagcacta ccagccctac gcccctccca gggacttcgc cgcctaccgg     120
agc                                                                  123

<210> SEQ ID NO 96
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctgtgcgcac gcccacgccg cagccccgcc caagaagatg gcaaagtcta catcaacatg      60
ccaggcaggg gc                                                         72
```

<210> SEQ ID NO 97
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
tacttcctgg gccggctggt ccctcggggg cgagggggctg cggaggcagc gacccggaaa    60
cagcgtatca ctgagaccga gtcgccttat caggagctcc agggtcagag gtcggatgtc   120
tacagcgacc tcaacacaca gaggccgtat tacaaa                              156
```

<210> SEQ ID NO 98
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
cgggtgaagt tcagccggag cgccgacgcc cctgcctacc agcagggcca gaaccagctg    60
tacaacgagc tgaacctggg ccggagggag gagtacgacg tgctggacaa gcggagaggc   120
cgggaccctg agatgggcgg caagccccgg agaaagaacc ctcaggaggg cctgtataac   180
gaactgcaga agacaagat ggccgaggcc tacagcgaga tcggcatgaa gggcgagcgg   240
cggaggggca agggccacga cggcctgtac cagggcctga gcaccgccac caaggatacc   300
tacgacgccc tgcacatgca ggccctgccc cccaga                              336
```

<210> SEQ ID NO 99
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
cgcaaagtgt gtaacggaat aggtattggt gaatttaaag actcactctc cataaatgct    60
acgaatatta aacacttcaa aaactgcacc tccatcagtg gcgatctcca catcctgccg   120
gtggcattta ggggtgactc cttcacacat actcctcctc tggatccaca ggaactggat   180
attctgaaaa ccgtaaagga atcacaggg ttttttgctga ttcaggcttg gcctgaaaac   240
aggacggacc tccatgcctt tgagaaccta gaaatcatac gcggcaggac caagcaacat   300
ggtcagtttt ctcttgcagt cgtcagcctg aacataacat ccttgggatt acgctccctc   360
aaggagataa gtgatggaga tgtgataatt tcaggaaaca aaaatttgtg ctatgcaaat   420
acaataaact ggaaaaaact gtttgggacc tccggtcaga aaaccaaaat tataagcaac   480
agaggtgaaa acagctgcaa ggccacaggc caggtctgcc atgccttgtg ctcccccgag   540
ggctgctggg gccggagcc cagggactgc gtctcttgcc ggaatgtcag ccgaggcagg   600
gaatgcgtgg acaagtgcaa ccttctggag ggtgagccaa gggagtttgt ggagaactct   660
gagtgcatac agtgccaccc agagtgcctg cctcaggcca tgaacatcac ctgcacagga   720
cggggaccag acaactgtat ccagtgtgcc cactacattg acggccccca ctgcgtcaag   780
acctgcccgg caggagtcat gggagaaaac aacccctgg tctggaagta cgcagacgcc   840
ggccatgtgt gccacctgtg ccatccaaac tgcacctacg gatgcactgg gccaggtctt   900
```

```
gaaggctgtc caacgaatgg gcctaagatc ccgtccatcg ccactgggat ggtgggggcc    960
ctcctcttgc tgctggtggt ggccctgggg atcggcctct tcatg                   1005
```

<210> SEQ ID NO 100
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
cgcaaagtgt gtaacggaat aggtattggt gaatttaaag actcactctc cataaatgct    60
acgaatatta aacacttcaa aaactgcacc tccatcagtg gcgatctcca catcctgccg   120
gtggcattta ggggtgactc cttcacacat actcctcctc tggatccaca ggaactggat   180
attctgaaaa ccgtaaagga aatcacaggg ttttgctga ttcaggcttg gcctgaaaac    240
aggacggacc tccatgcctt tgagaaccta gaaatcatac gcggcaggac caagcaacat   300
ggtcagtttt ctcttgcagt cgtcagcctg aacataacat ccttgggatt acgctccctc   360
aaggagataa tgatggaga tgtgataatt tcaggaaaca aaaatttgtg ctatgcaaat    420
acaataaact ggaaaaaact gtttgggacc tccggtcaga aaccaaaat tataagcaac    480 agaggtgaaa acagctgcaa ggccacaggc caggtctgcc atgccttgtg ctcccccgag   540
ggctgctggg gcccggagcc cagggactgc gtctctggtg gcggtggctc gggcggtggt   600
gggtcgggtg gcggcggatc tggtggcggt ggctcgtttt gggtgctggt ggtggttggt   660
ggagtcctgg cttgctatag cttgctagta acagtggcct ttattatttt ctgggtgagg   720
agtaagagga gc                                                       732
```

<210> SEQ ID NO 101
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
atgacaacac ccagaaattc agtaaatggg actttcccgg cagagccaat gaaaggccct    60
attgctatgc aatctggtcc aaaaccactc ttcaggagga tgtcttcact ggtgggcccc   120
acgcaaagct tcttcatgag ggaatctaag actttggggg ctgtccagat tatgaatggg   180
ctcttccaca ttgccctggg gggtcttctg atgatcccag cagggatcta tgcacccatc   240
tgtgtgactg tgtggtaccc tctctgggga ggcattatgt atattatttc cggatcactc   300
ctggcagcaa cggagaaaaa ctccaggaag tgtttggtca aggaaaaaat gataatgaat   360
tcattgagcc tctttgctgc catttctgga atgattcttt caatcatgga catacttaat   420
attaaaattt cccatttttt aaaaatggag agtctgaatt ttattagagc tcacacacca   480
tatattaaca tatacaactg tgaaccagct aatccctctg agaaaaactc cccatctacc   540
caatactgtt acagcataca atctctgttc ttgggcattt tgtcagtgat gctgatcttt   600
gccttcttcc aggaacttgt aatagctggc atcgttgaga tgaatggaa agaacgtgc    660 tccagaccca atctaacat agttctcctg tcagcagaag aaaaaaaaga acagactatt   720
gaaataaaag aagaagtggt tgggctaact gaaacatctt cccaaccaaa gaatgaagaa   780
```
gacattgaaa ttattccaat ccaagaagag gaagaagaag aaacagagac gaactttcca        840
gaacctcccc aagatcagga atcctcacca atagaaaatg cagctctcc t                  891

<210> SEQ ID NO 102
<211> LENGTH: 789
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
atgaccacac cacggaactc tgtgaatggc accttcccag cagagccaat gaagggacca         60
atcgcaatgc agagcggacc caagcctctg tttcggagaa tgagctccct ggtgggccca        120
acccagtcct tctttatgag agagtctaag acactgggcg ccgtgcagat catgaacgga        180
ctgttccaca tcgccctggg aggactgctg atgatcccag ccggcatcta cgcccctatc        240
tgcgtgaccg tgtggtaccc tctgtggggc ggcatcatgt atatcatctc cggctctctg        300
ctggccgcca cagagaagaa cagcaggaag tgtctggtga agggcaagat gatcatgaat        360
agcctgtccc tgtttgccgc catctctggc atgatcctga gcatcatgga catcctgaac        420
atcaagatca gccacttcct gaagatggag agcctgaact tcatcagagc ccacacccct        480
tacatcaaca tctataattg cgagcctgcc aacccatccg agaagaattc tccaagcaca        540
cagtactgtt attccatcca gtctctgttc ctgggcatcc tgtctgtgat gctgatcttt        600
gccttctttc aggagctggt catcgccggc atcgtggaga acgagtggaa gaggacctgc        660
agccgcccca agtccaatat cgtgctgctg tccgccgagg agaagaagga gcagacaatc        720
gagatcaagg aggaggtggt gggcctgacc gagacatcta gccagcctaa gaatgaggag        780
gatatcgag                                                                789

<210> SEQ ID NO 103
<211> LENGTH: 395
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Asp Trp Thr Trp Ile Leu Phe Leu Val Ala Ala Thr Arg Val
1               5                   10                  15

His Ser Asn Trp Val Asn Val Ile Ser Asp Leu Lys Lys Ile Glu Asp
            20                  25                  30

Leu Ile Gln Ser Met His Ile Asp Ala Thr Leu Tyr Thr Glu Ser Asp
        35                  40                  45

Val His Pro Ser Cys Lys Val Thr Ala Met Lys Cys Phe Leu Leu Glu
    50                  55                  60

Leu Gln Val Ile Ser Leu Glu Ser Gly Asp Ala Ser Ile His Asp Thr
65                  70                  75                  80

Val Glu Asn Leu Ile Ile Leu Ala Asn Asn Ser Leu Ser Ser Asn Gly
                85                  90                  95

Asn Val Thr Glu Ser Gly Cys Lys Glu Cys Glu Glu Leu Glu Glu Lys
            100                 105                 110

Asn Ile Lys Glu Phe Leu Gln Ser Phe Val His Ile Val Gln Met Phe
        115                 120                 125

Ile Asn Thr Ser Ser Gly Gly Gly Ser Gly Gly Gly Gly Ser Gly Gly

```
                130             135             140
Gly Gly Ser Gly Gly Gly Ser Gly Gly Ser Leu Gln Ile Thr
145             150             155             160

Cys Pro Pro Pro Met Ser Val Glu His Ala Asp Ile Trp Val Lys Ser
                165             170             175

Tyr Ser Leu Tyr Ser Arg Glu Arg Tyr Ile Cys Asn Ser Gly Phe Lys
            180             185             190

Arg Lys Ala Gly Thr Ser Ser Leu Thr Glu Cys Val Leu Asn Lys Ala
            195             200             205

Thr Asn Val Ala His Trp Thr Thr Pro Ser Leu Lys Cys Ile Arg Asp
            210             215             220

Pro Ala Leu Val His Gln Arg Pro Ala Pro Ser Thr Val Thr Thr
225             230             235             240

Ala Gly Val Thr Pro Gln Pro Glu Ser Leu Ser Pro Ser Gly Lys Glu
                245             250             255

Pro Ala Ala Ser Ser Pro Ser Ser Asn Asn Thr Ala Ala Thr Thr Ala
                260             265             270

Ala Ile Val Pro Gly Ser Gln Leu Met Pro Ser Lys Ser Pro Ser Thr
            275             280             285

Gly Thr Thr Glu Ile Ser Ser His Glu Ser Ser His Gly Thr Pro Ser
290             295             300

Gln Thr Thr Ala Lys Asn Trp Glu Leu Thr Ala Ser Ala Ser His Gln
305             310             315             320

Pro Pro Gly Val Tyr Pro Gln Gly His Ser Asp Thr Thr Val Ala Ile
                325             330             335

Ser Thr Ser Thr Val Leu Leu Cys Gly Leu Ser Ala Val Ser Leu Leu
            340             345             350

Ala Cys Tyr Leu Lys Ser Arg Gln Thr Pro Pro Leu Ala Ser Val Glu
            355             360             365

Met Glu Ala Met Glu Ala Leu Pro Val Thr Trp Gly Thr Ser Ser Arg
370             375             380

Asp Glu Asp Leu Glu Asn Cys Ser His His Leu
385             390             395

<210> SEQ ID NO 104
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asn Trp Val Asn Val Ile Ser Asp Leu Lys Lys Ile Glu Asp Leu Ile
1               5               10              15

Gln Ser Met His Ile Asp Ala Thr Leu Tyr Thr Glu Ser Asp Val His
            20              25              30

Pro Ser Cys Lys Val Thr Ala Met Lys Cys Phe Leu Leu Glu Leu Gln
            35              40              45

Val Ile Ser Leu Glu Ser Gly Asp Ala Ser Ile His Asp Thr Val Glu
50              55              60

Asn Leu Ile Ile Leu Ala Asn Asn Ser Leu Ser Ser Asn Gly Asn Val
65              70              75              80

Thr Glu Ser Gly Cys Lys Glu Cys Glu Glu Leu Glu Glu Lys Asn Ile
            85              90              95
```

Lys Glu Phe Leu Gln Ser Phe Val His Ile Val Gln Met Phe Ile Asn
            100                 105                 110
Thr Ser

<210> SEQ ID NO 105
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Val
                165                 170                 175

Ala Ile Ser Thr Ser Thr Val Leu Leu Cys Gly Leu Ser Ala Val Ser
            180                 185                 190

Leu Leu Ala Cys Tyr Leu Lys Ser Arg Gln Thr Pro Pro Leu Ala Ser
        195                 200                 205

Val Glu Met Glu Ala Met Glu Ala Leu Pro Val Thr Trp Gly Thr Ser
    210                 215                 220

Ser Arg Asp Glu Asp Leu Glu Asn Cys Ser His His Leu
225                 230                 235

<210> SEQ ID NO 106
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
atggattgga cctggattct gtttctggtg gccgctgcca caagagtgca cagcaactgg      60
gtgaatgtga tcagcgacct gaagaagatc gaggatctga tccagagcat gcacattgat     120
gccaccctgt acacagaatc tgatgtgcac cctagctgta aagtgaccgc catgaagtgt     180
tttctgctgg agctgcaggt gatttctctg gaaagcggag atgcctctat ccacgacaca     240

```
gtggagaatc tgatcatcct ggccaacaat agcctgagca gcaatggcaa tgtgacagag      300
tctggctgta aggagtgtga ggagctggag gagaagaaca tcaaggagtt tctgcagagc      360
tttgtgcaca tcgtgcagat gttcatcaat acaagctctg gcggaggatc tggaggaggc      420
ggatctggag gaggaggcag tggaggcgga ggatctggcg gaggatctct gcagattaca      480
tgccctcctc caatgtctgt ggagcacgcc gatatttggg tgaagtccta cagcctgtac      540
agcagagaga gatacatctg caacagcggc tttaagagaa aggccggcac ctcttctctg      600
acagagtgcg tgctgaataa ggccacaaat gtggcccact ggacaacacc tagcctgaag      660
tgcattagag atcctgccct ggtccaccag aggcctgccc ctccatctac agtgacaaca      720
gccggagtga cacctcagcc tgaatctctg agcccttctg gaaagaacc tgccgccagc       780 tctcctagct ctaataatac cgccgccaca acagccgcca ttgtgcctgg atctcagctg      840
atgcctagca agtctcctag cacaggcaca acagagatca gcagccacga atcttctcac      900
ggaacacctt ctcagaccac cgccaagaat tgggagctga cagcctctgc ctctcaccag      960
cctccaggag tgtatcctca gggccactct gatacaacag tggccatcag cacatctaca     1020
gtgctgctgt gtggactgtc tgccgtgtct ctgctggcct gttacctgaa gtctagacag     1080
acacctcctc tggcctctgt ggagatggag gccatggaag ccctgcctgt gacatgggga     1140
acaagcagca gagatgagga cctggagaat tgttctcacc acctg                     1185
```

```
<210> SEQ ID NO 107
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
aactgggtga atgtgatcag cgacctgaag aagatcgagg atctgatcca gagcatgcac       60
attgatgcca ccctgtacac agaatctgat gtgcacccta gctgtaaagt gaccgccatg      120
aagtgttttc tgctggagct gcaggtgatt tctctggaaa gcggagatgc ctctatccac      180
gacacagtgg agaatctgat catcctggcc aacaatagcc tgagcagcaa tggcaatgtg      240
acagagtctg gctgtaagga gtgtgaggag ctggaggaga gaacatcaa ggagtttctg       300 cagagctttg tgcacatcgt gcagatgttc atcaatacaa gc                         342
```

```
<210> SEQ ID NO 108
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
attacatgcc ctcctccaat gtctgtggag cacgccgata tttgggtgaa gtcctacagc        60
ctgtacagca gagagagata catctgcaac agcggcttta agagaaaggc cggcaccctct      120 tctctgacag agtgcgtgct gaataaggcc acaaatgtgg cccactggac aacacctagc      180
ctgaagtgca ttagagatcc tgccctggtc caccagaggc tgcccctcc atctacagtg       240 acaacagccg agtgacacc tcagcctgaa tctctgagcc cttctggaaa gaacctgcc        300 gccagctctc ctagctctaa taataccgcc gccacaacag ccgccattgt gcctggatct      360
```

```
cagctgatgc ctagcaagtc tcctagcaca ggcacaacag agatcagcag ccacgaatct    420
tctcacggaa caccttctca gaccaccgcc aagaattggg agctgacagc ctctgcctct    480
caccagcctc caggagtgta tcctcagggc cactctgata acagtggc catcagcaca     540 tctacagtgc tgctgtgtgg actgtctgcc gtgtctctgc tggcctgtta cctgaagtct    600
agacagacac ctcctctggc ctctgtggag atggaggcca tggaagccct gcctgtgaca    660
tggggaacaa gcagcagaga tgaggacctg gagaattgtt ctcaccacct g             711
```

<210> SEQ ID NO 109
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

```
caggtgcagc tggtcgaaag cggaggagga gtggtccagc caggacgatc cctgagactg    60
gattgtaagg cctctggaat cacattctct aacagtggaa tgcactgggt gcgccaggca    120
ccaggaaaag gactggagtg ggtggccgtc atctggtacg acgggtcaaa gcgatactat    180
gcagatagcg tgaaggaag gttcacaatt tcacgcgaca acagcaagaa tactctgttt    240
ctgcagatga actctctgag agcagaggat actgccgtgt actattgtgc taccaatgac    300
gattattggg ggcagggaac tctggtgacc gtcagttca                           339
```

<210> SEQ ID NO 110
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
caggtgcagc tggtccagag cggcgtggaa gtcaagaaac ccggggcctc agtgaaggtc    60
agctgtaaag cttccggcta caccttcaca aactactata tgtattgggt gagacaggca    120
ccaggacagg gactggagtg gatgggcggg attaaccta gtaatggagg cactaacttc     180
aacgaaaagt ttaaaaacag ggtgaccctg accacagatt caagcactac cacagcttac    240
atggagctga gtccctgca gtttgacgat acagccgtgt actattgtgc tcggagagac    300
tacaggttcg atatgggctt tgactattgg ggccagggga ctaccgtgac cgtctcctct    360
```

<210> SEQ ID NO 111
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
gagatcgtcc tgacacagag tccagcaact ctgagcctgt cccccggcga acagagctact   60 ctgtcctgcc gggcatctca gagtgtgtct agttacctgg cctggtatca gcagaagccc    120
ggccaggctc ctaggctgct gatctacgac gccagcaaca gagctaccgg gattcctgcc    180
aggttctcag gcagcgggtc cggaacagac tttaccctga caatctcaag cctggagccc    240
gaagatttcg ctgtgtacta ttgccagcag tcctctaatt ggcctcgcac ctttggccag    300
```

```
gggacaaagg tcgagatcaa g                                            321
```

<210> SEQ ID NO 112
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
gagatcgtcc tgactcagtc cccagcaacc ctgagtctgt caccaggaga aagggcaacc    60
ctgagctgcc gagcatccaa gggggtgagc acatccggat actcttatct gcactggtac   120
cagcagaaac ccggacaggc tcctcgactg ctgatctacc tggcatctta tctggagagt   180
ggcgtgcctg ctcggttctc tgggagtgga tcaggcaccg attttacact gactatttct   240
agtctggagc cagaagattt cgcagtgtac tattgccagc attctcgaga cctgcccctg   300
acatttggcg ggggaactaa ggtcgagatc aaa                                333
```

<210> SEQ ID NO 113
<211> LENGTH: 1758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
caggtgcagc tggtcgaaag cggaggagga gtggtccagc caggacgatc cctgagactg    60
gattgtaagg cctctggaat cacattctct aacagtggaa tgcactgggt gcgccaggca   120
ccaggaaaag gactggagtg ggtggccgtc atctggtacg acgggtcaaa gcgatactat   180
gcagatagcg tgaaggaag gttcacaatt tcacgcgaca cagcaagaa tactctgttt   240 ctgcagatga actctctgag agcagaggat actgccgtgt actattgtgc taccaatgac   300
gattattggg ggcagggaac tctggtgacc gtcagttcag ctagcaccaa gggcccatcg   360
gtcttccccc tggcgccctg ctccaggagc acctccgaga gcacagccgc cctgggctgc   420
ctggtcaagg actacttccc cgaaccggtg acggtgtcgt ggaactcagg cgccctgacc   480
agcggcgtgc acaccttccc ggctgtccta cagtcctcag gactctactc cctcagcagc   540
gtggtgaccg tgccctccag cagcttgggc acgaagacct acacctgcaa cgtagatcac   600
aagcccagca acaccaaggt ggacaagaga gttgagtcca atatggtcc cccatgccca   660 tcatgcccag cacctgagtt cctgggggga ccatcagtct tcctgttccc cccaaaaccc   720
aaggacactc tcatgatctc ccggaccct gaggtcacgt gcgtggtggt ggacgtgagc   780
caggaagacc ccgaggtcca gttcaactgg tacgtggatg gcgtggaggt gcataatgcc   840
aagacaaagc cgcgggagga gcagttcaac agcacgtacc gtgtggtcag cgtcctcacc   900
gtcctgcacc aggactggct gaacggcaag gagtacaagt gcaaggtctc caacaaaggc   960
ctcccgtcct ccatcgagaa aaccatctcc aaagccaaag gcagccccg agagccacag  1020 gtgtacaccc tgcccccatc ccaggaggag atgaccaaga accaggtcag cctgacctgc  1080
ctggtcaaag gcttctaccc cagcgacatc gccgtggagt gggagagcaa tgggcagccg  1140
gagaacaact acaagaccac gcctcccgtg ctggactccg acggctcctt cttcctctac  1200
agcaggctca ccgtggacaa gagcaggtgg caggagggga atgtcttctc atgctccgtg  1260
atgcatgagg ctctgcacaa ccactacaca cagaagagcc tctccctgtc tccgggtaaa  1320
```

```
ggtggaggtg gttctggagg tggaggtagt atccctcctc acgtacagaa gtccgtgaac    1380
aatgacatga ttgtcactga caataacgga gccgtcaagt ttcctcagct atgtaagttc    1440
tgcgatgttc ggttctccac atgcgataat cagaaaagct gtatgtctaa ttgcagtatc    1500
actagtatat gcgaaaaacc tcaagaagtt tgcgtcgccg tgtggcggaa aaatgatgaa    1560
aatatcacgc ttgagactgt ctgccatgat ccaaagttac cctaccacga cttcatctta    1620
gaagacgccg catcacccaa gtgcattatg aagagaaaa agaagccagg agaaacattc     1680
tttatgtgct catgctcctc tgacgaatgc aacgacaaca ttatcttctc tgaggagtat    1740
aacacctcaa atccagac                                                  1758

<210> SEQ ID NO 114
<211> LENGTH: 1758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
caggtgcagc tggtcgaaag cggaggagga gtggtccagc caggacgatc cctgagactg    60
gattgtaagg cctctggaat cacattctct aacagtggaa tgcactgggt gcgccaggca    120
ccaggaaaag gactggagtg gtggccgtc atctggtacg acgggtcaaa gcgatactat     180
gcagatagcg tgaaggaag gttcacaatt tcacgcgaca acagcaagaa tactctgttt    240
ctgcagatga actctctgag agcagaggat actgccgtgt actattgtgc taccaatgac    300
gattattggg gcagggaac tctggtgacc gtcagttcag ctagcaccaa gggcccatcg    360
gtcttccccc tggcgccctg ctccaggagc acctccgaga gcacagccgc cctgggctgc    420
ctggtcaagg actacttccc cgaaccggtg acggtgtcgt ggaactcagg cgccctgacc    480
agcggcgtgc acaccttccc ggctgtccta cagtcctcag gactctactc cctcagcagc    540
gtggtgaccg tgccctccag cagcttgggc acgaagacct acacctgcaa cgtagatcac    600
aagcccagca acaccaaggt ggacaagaga gttgagtcca aatatggtcc cccatgccca    660
ccatgcccag cacctgagtt cctggggga ccatcagtct tcctgttccc cccaaaaccc    720
aaggacactc tcatgatctc ccggacccct gaggtcacgt gcgtggtggt ggacgtgagc    780
caggaagacc ccgaggtcca gttcaactgg tacgtggatg gcgtggaggt gcataatgcc    840
aagacaaagc cgcgggagga gcagttcaac agcacgtacc gtgtggtcag cgtcctcacc    900
gtcctgcacc aggactggct gaacggcaag gagtacaagt gcaaggtctc caacaaaggc    960
ctcccgtcct ccatcgagaa aaccatctcc aaagccaaag gcagccccg agagccacag    1020 gtgtacaccc tgcccccatc ccaggaggag atgaccaaga accaggtcag cctgacctgc    1080
ctggtcaaag gcttctaccc cagcgacatc gccgtggagt gggagagcaa tgggcagccg    1140
gagaacaact acaagaccac gcctcccgtg ctggactccg acggctcctt cttcctctac    1200
agcaggctca ccgtggacaa gagcaggtgg caggagggga atgtcttctc atgctccgtg    1260
atgcatgagg ctctgcacaa ccactacaca cagaagagcc tctccctgtc tccgggtaaa    1320
ggtggaggtg gttctggagg tggaggtagt atccctcctc acgtacagaa gtccgtgaac    1380
aatgacatga ttgtcactga caataacgga gccgtcaagt ttcctcagct atgtaagttc    1440
tgcgatgttc ggttctccac atgcgataat cagaaaagct gtatgtctaa ttgcagtatc    1500
actagtatat gcgaaaaacc tcaagaagtt tgcgtcgccg tgtggcggaa aaatgatgaa    1560
```

```
aatatcacgc ttgagactgt ctgccatgat ccaaagttac cctaccacga cttcatctta    1620
gaagacgccg catcacccaa gtgcattatg aaagagaaaa agaagccagg agaaacattc    1680
tttatgtgct catgctcctc tgacgaatgc aacgacaaca ttatcttctc tgaggagtat    1740
aacacctcaa atccagac                                                 1758
```

<210> SEQ ID NO 115
<211> LENGTH: 1779
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
caggtgcagc tggtccagag cggcgtggaa gtcaagaaac ccggggcctc agtgaaggtc      60
agctgtaaag cttccggcta caccttcaca aactactata tgtattgggt gagacaggca     120
ccaggacagg gactggagtg gatgggcggg attaacccta gtaatggagg cactaacttc     180
aacgaaaagt ttaaaaacag ggtgaccctg accacagatt caagcactac cacagcttac     240
atggagctga gtccctgca gtttgacgat acagccgtgt actattgtgc tcggagagac     300
tacaggttcg atatgggctt tgactattgg ggccagggga ctaccgtgac cgtctcctct     360
gctagcacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggctc accgtggaca agagcaggtg gcaggagggg    1260
aatgtcttct catgctccgt gatgcatgag gctctgcaca accactacac acagaagagc    1320
ctctccctgt ctccgggtaa aggtggaggt ggttctggag gtggaggtag tatccctcct    1380
cacgtacaga agtccgtgaa caatgacatg attgtcactg acaataacgg agccgtcaag    1440
tttcctcagc tatgtaagtt ctgcgatgtt cggttctcca catgcgataa tcagaaaagc    1500
tgtatgtcta attgcagtat cactagtata tgcgaaaaac tcaagaagt ttgcgtcgcc    1560 gtgtggcgga aaaatgatga aaatatcacg cttgagactg tctgccatga tccaaagtta    1620
ccctaccacg acttcatctt agaagacgcc gcatcaccca gtgcattat gaaagagaaa    1680 aagaagccag gagaaacatt ctttatgtgc tcatgctcct ctgacgaatg caacgacaac    1740
attatcttct ctgaggagta taacacctca aatccagac                          1779
```

<210> SEQ ID NO 116
<211> LENGTH: 1779
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
caggtgcagc tggtccagag cggcgtggaa gtcaagaaac ccggggcctc agtgaaggtc      60
agctgtaaag cttccggcta caccttcaca aactactata tgtattgggt gagacaggca     120
ccaggacagg gactggagtg gatgggcggg attaaccctc gtaatggagg cactaacttc     180
aacgaaaagt ttaaaaacag ggtgaccctg accacagatt caagcactac cacagcttac     240
atggagctga gtccctgca gtttgacgat acagccgtgt actattgtgc tcggagagac     300
tacaggttcg atatgggctt tgactattgg ggccagggga ctaccgtgac cgtctcctct     360
gctagcacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc atcatgccca gcacctgagt tcctgggggg accatcagtc     720
ttcctgttcc cccaaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggctc accgtggaca agagcaggtg gcaggagggg    1260
aatgtcttct catgctccgt gatgcatgag gctctgcaca accactacac acagaagagc    1320
ctctccctgt ctccgggtaa aggtggaggt ggttctggag gtggaggtag tatccctcct    1380
cacgtacaga agtccgtgaa caatgacatg attgtcactg acaataacgg agccgtcaag    1440
tttcctcagc tatgtaagtt ctgcgatgtt cggttctcca catgcgataa tcagaaaagc    1500
tgtatgtcta attgcagtat cactagtata tgcgaaaaac tcaagaagt ttgcgtcgcc    1560
gtgtggcgga aaaatgatga aaatatcacg cttgagactg tctgccatga tccaaagtta    1620
ccctaccacg acttcatctt agaagacgcc gcatcaccca gtgcattat gaaagagaaa    1680
aagaagccag gagaaacatt ctttatgtgc tcatgctcct ctgacgaatg caacgacaac    1740
attatcttct ctgaggagta taacacctca aatccagac                           1779
```

<210> SEQ ID NO 117
<211> LENGTH: 981
<212> TYPE: DNA
<213> ORGANISM: Artificial Sequence
<220> FEATURE:
<223> OTHER INFORMATION: Description of Artificial Sequence: Synthetic -continued

```
        polynucleotide

<400> SEQUENCE: 117
gctagcacca agggcccatc ggtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcacctgagt tcctggggggg accatcagtc     360 ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga tgaccaag     720 aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggctc accgtggaca gagcaggtg gcaggagggg     900 aatgtcttct catgctccgt gatgcatgag gctctgcaca accactacac acagaagagc     960 ctctcccctgt ctccgggtaa a                                              981

<210> SEQ ID NO 118
<211> LENGTH: 321
<212> TYPE: DNA
<213> ORGANISM: Artificial Sequence
<220> FEATURE:
<223> OTHER INFORMATION: Description of Artificial Sequence: Synthetic
        polynucleotide

<400> SEQUENCE: 118
gagatagtta tgactcaaag ccccgctaca ttatccctgt ctccgggtga acgggccacc      60
ctgtcatgcc gggcttcaca gtcagtgtca agctatctgg catggtatca gcagaagcct     120
ggacaggccc caaggctact gatttatgac gccagcaacc gcgctacagg tattcctgct     180
aggttctcag ggtcaggctc tggaaccgac tttactctga ctatctcctc tcttgaaccc     240
gaggatttcg cggtgtacta ctgtcagcag tataataact ggccacgcac attcggccag     300
ggcactaaag tcgaaattaa g                                               321

<210> SEQ ID NO 119
<211> LENGTH: 321
<212> TYPE: DNA
<213> ORGANISM: Artificial Sequence
<220> FEATURE:
<223> OTHER INFORMATION: Description of Artificial Sequence: Synthetic
        polynucleotide

<400> SEQUENCE: 119
gagatcgtac tgactcagtc tccagccaca ttgtccctgt ccccagggga gcgcgccacc      60
ctgagctgta gagcttcaca gtccgtcagt tcttacctcg cgtggtatca gcaaaaacct     120
ggacaagctc cgaggttgct tatctatgac gcctccaacc gcgccactgg cataccagca     180
aggttcagcg gatctgggtc cggcacagat tttaccctca ctatttctag ccttgagccg     240
```

```
gaagatttcg ctgtttacta ctgccagcag cgatccaact ggcccaagac attcggccag    300
ggaactaaag tggaaatcaa a                                              321

<210> SEQ ID NO 120
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
gaaattgtgt tgacacagtc tccagccacc ctgtctttgt ctccagggga aagagccacc     60
ctctcctgca gggccagtca gagtgttagt agttacttag cctggtacca acagaaacct    120
ggccaggctc ccaggctcct catctatgat gcatccaaca gggccaacgg catcccagcc    180
aggttcagtg gcagtgggtc tgggacagac ttcactctca ccatcagcag cctagagcct    240
gaagatttcg cagtttatta ctgtcagcag agtagcaact ggcctcggac gttcggccaa    300
gggaccaagg tggaaatcaa aaga                                           324

<210> SEQ ID NO 121
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
cggaacgtgc tgacccagtc ccccttagc ctccccgtca cgcccggaga gcccgcaagt      60
atcagctgcc gcagttcaca aagtctgagt tcttctggat acacctattt ggactggtat    120
ttgcagaagc cagggcaatc cccacagctc ctgatatacc tcgcaagctg agagatagc     180 ggagtacctg atcgcttttc tggtagcgga tctggtacgg atttcactct gaagatttct    240
agggtggagg cggaggacgt ggagtgtac tactgtatgc aagccgagca gactcccggc     300
ccaggtaaca cgttcggaca ggggaccaaa ctggagatta ag                       342

<210> SEQ ID NO 122
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
gatgtggtaa tgacccagtc acctctttca ctgcctgtca ctcccggaga gccagcttca     60
atctcctgcc gtagctctca atcattgttg cacaccaatg gatacaacta cctccactgg    120
tatctccaga agcccggaca aagcccgcag ctgctgatct acctgggcag ctggcaggac    180
tccggggtgc ccgaccgatt tagcggcagt gggagcggca cggactttac actgaagatc    240
agccgagtag aggcggagga cgtgggcgtt tactactgta tgcaggcaga gcagaccccc    300
agaaccttcg gccagggcac ccggctggag gtgaaa                              336

<210> SEQ ID NO 123
<211> LENGTH: 339
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 123
caggtgcagt tggttgaaag cggaggaggc gtggttcaac ccggtagaag cctacggctg      60
tcatgtgcgg cctccggctt cacatttcga tcttacggaa tgcactgggt caggcaggca     120
cccggcaagg gtctggagtg ggtcgccata attttctatg acggcagcaa caagtattac     180
gccgacagtg ttaaggggcg gtttaccatc agcagagaca actctaaaaa cactctttat     240
ctgcaaatga actctctgcg ggcagaggat accgctgttt actattgcgc cagagatgac     300
gactactggg ggcagggtgc cttggtgact gtgagcagc                            339

<210> SEQ ID NO 124
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gaggtccagt tagtccaaag cggcggaggc gtagtgcaac ctggcagaag cctgcggtta      60
tcgtgcgccg caagcggctt cacctttagc tcttatggta tgcactgggt cagacaggcc     120
cctgggaagg gcctggagtg ggtggccgtg atctggtatg acgggagcaa caagtattac     180
gcggattccg tcaagggacg gttcaccata tcccgcgata acagcaagaa tactctttac     240
ttacagatga acagcctgag ggccgaggac accgcagtat attattgcgc tggcgaaggc     300
tttgactatt ggggtcaggg cactctggtg actgtgagca gc                        342

<210> SEQ ID NO 125
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
caggtgcagc tggtggagtc tgggggaggc gtggtccagc ctggggaggtc cctgagactc      60 gactgtaaag cgtctggaat caccttcagt aactctggca tgcactgggt ccgccaggct     120
ccaggcaagg ggctggagtg ggtggcagtt atttggtatg atggaagtaa aagatactat     180
gcagactccg tgaagggccg attcaccatc tccagagaca attccaagaa cacgctgttt     240
ctgcaaatga acagcctgag agccgaggac acggctgtgt attactgtgc gacaaacaac     300
gactactggg gccagggaac cctggtcacc gtctcctca                            339

<210> SEQ ID NO 126
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
caggtgcagc tggtggagtc tgggggaggc gtggtccagc ctggggaggtc cctgagactc      60 gactgtaaag cgtctggaat caccttcagt aactctggca tgcactgggt ccgccaggct     120
```

```
ccaggcaagg ggctggagtg ggtggcagtt atttggtatg atggaagtaa aagatactat    180
gcagactccg tgaagggccg attcaccatc tccagagaca attccaagaa cacgctgttt    240
ctgcaaatga acagcctgag agccgaggac acggctgtgt attactgtgc gagaaacgac    300
gactactggg gccagggaac cctggtcacc gtctcctca                           339

<210> SEQ ID NO 127
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caggtacagc tggtgcagag cggcgcagag gtgaagaagc caggcgcttc tgtaaaggta     60
tcctgcaagg catccgggta actttcacc ggctattaca tgcactgggt tcgtcaggca    120
cccggccagg gactagaatg gatggggcc atcaacccta atagtggcgg tactaactac    180
gcacaaaagt ttcaggggcg agtgaccatg actcgggata cctccatctc cacggcatac    240
atggagctga gtcgcttgcg gtcagatgac actgcggtgt actactgcgc tgcaggcccc    300
gaccgagcta attggcactt tgactactgg ggacaggta cactggtgac cgtgtcatca    360

<210> SEQ ID NO 128
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
caggtgcagc tggtccagag cggcgcggaa gtgaaaaagc ccggcgcttc cgtgaaggtt     60
tcttgcaaag cctctggata cacattcact ggctattata tgcactgggt cagacaggcc    120
cccggccagg gattggagtg gatgggtgca atcaacccca attctggtgg gaccaattac    180
gcacagaaac tccagggccg agtgacaatg accaccgaca cttctaccag cactgcctac    240
atggagctgc ggtctctgcg atcagacgac accgctgtgt actattgtgc aagacacggg    300
ctgaagggcg acggctattt tgactactgg ggcagggca cgctggttac cgtgagttcc    360

<210> SEQ ID NO 129
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
caggtccagc tcgtgcaaag cggagtggaa gtgaaaaagc ctggcgcttc cgtcaaggtc     60
agctgtaagg ccagcggata cacattcaca aactattaca tgtactgggt gaggcaggct    120
cccggacagg gactgaatg gatgggcgga atcaatccct ccaacggagg cacaaacttt    180
aacgaaaagt ttaagaatag agtcaccctc accacagact ccagcacaac cacagcctat    240
atggaactga aaagcctcca gtttgacgat accgctgtgt attactgtgc caggagagat    300
tacaggttct acatgggatt cgattactgg ggccaaggca caaccgtcac cgtcagctcc    360

<210> SEQ ID NO 130
```

```
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
caggtccagc tcgtgcaaag cggagtggaa gtgaaaaagc ctggcgcttc cgtcaaggtc      60
agctgtaagg ccagcggata cacattcaca aactattaca tgtactgggt gaggcaggct     120
cccggacagg gactggaatg gatgggcgga atcaatccct ccaacggagg cacaaacttt     180
aacgaaaagt ttaagaatag agtcacccct caccacagact ccagcacaac cacagcctat    240
atggaactga aaagcctcca gtttgacgat accgctgtgt attactgtgc caggagagat     300
tacaggttca acatgggatt cgattactgg ggccaaggca caaccgtcac cgtcagctcc     360

<210> SEQ ID NO 131
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
caggtccagc tcgtgcaaag cggagtggaa gtgaaaaagc ctggcgcttc cgtcaaggtc      60
agctgtaagg ccagcggata cacattcaca aactattaca tgtactgggt gaggcaggct     120
cccggacagg gactggaatg gatgggcgga atccagccct ccaacggagg cacaaacttt     180
aacgaaaagt ttaagaatag agtcacccct caccacagact ccagcacaac cacagcctat    240
atggaactga aaagcctcca gtttgacgat accgctgtgt attactgtgc caggagagat     300
tacaggttct acatgggatt cgattactgg ggccaaggca caaccgtcac cgtcagctcc     360

<210> SEQ ID NO 132
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
caggtccagc tcgtgcaaag cggagtggaa gtgaaaaagc ctggcgcttc cgtcaaggtc      60
agctgtaagg ccagcggata cacattcaca aactattaca tgtactgggt gaggcaggct     120
cccggacagg gactggaatg gatgggcgga atcgacccct ccaacggagg cacaaacttt     180
aacgaaaagt ttaagaatag agtcacccct caccacagact ccagcacaac cacagcctat    240
atggaactga aaagcctcca gtttgacgat accgctgtgt attactgtgc caggtacgat     300
tacaggttcg atatgggatt cgattactgg ggccaaggca caaccgtcac cgtcagctcc     360

<210> SEQ ID NO 133
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
caggtgcagc tggtggagtc tgggggaggc gtggtccagc ctgggaggtc cctgagactc      60
```

```
gactgtaaag cgtctggatt caccttcagt aactctggca tgcactgggt ccgccaggct    120
ccaggcaagg ggctggagtg ggtggcagtt atttggtatg atggaagtaa aagatactat    180
gcagactccg tgaagggccg attcaccatc tccagagaca attccaagaa cacgctgttt    240
ctgcaaatga acagcctgag agccgaggac acggctgtgt attactgtgc gacaaacaac    300
gactactggg gccagggaac cctggtcacc gtctcctca                           339
```

<210> SEQ ID NO 134
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134

```
gaggtccagt tagtccaaag cggcggaggc gtagtgcaac ctggcagaag cctgcggtta     60
tcgtgcgccg caagcggctt cacctttagc tcttatggta tgcactgggt cagacaggcc    120
cctgggaagg gcctggagtg ggtggccgtg atctggtatg acgggagcaa caagtattac    180
gcggattccg tcaagggacg gttcaccata tcccgcgata acagcaagaa tactctttac    240
ttacagatga acagcctgag ggccgaggac accgcagtat attattgcgc taccaataat    300
gactattggg gtcagggcac tctggtgact gtgagcagc                           339
```

<210> SEQ ID NO 135
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
gaggtgcaac tggttcagtc cggcggggc gtcgtccagc cggggcgcag tctgcgcttg      60
agctgtgctg cctctgggat tacctttagc aactccatgc attgggtgcg gcaggcaccc    120
gggaagggac tggaatgggt cgcagtgatc tggtacgatg gatcaaagcg gtattacgcc    180
gactccgtca aggccggtt cacaatcagc cgcgacaaca gcaaaaatac tttatatctt     240
cagatgaatt cccttagggc agaggatact gctgtgtatt actgcgctac taacaacgat    300 tattggggc aggggacact agtcactgtt tctagt                               336
```

<210> SEQ ID NO 136
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136

```
gaggtccagt tagtccaaag cggcggaggc gtagtgcaac ctggcagaag cctgcggtta     60
tcgtgcgccg caagcggctt cacctttagc aattctggta tgcactgggt cagacaggcc    120
cctgggaagg gcctggagtg ggtggccgtg atctggtatg acgggagcaa caagtattac    180
gcggattccg tcaagggacg gttcaccata tcccgcgata acagcaagaa tactctttac    240
ttacagatga acagcctgag ggccgaggac accgcagtat attattgcgc taccaataat    300
gactattggg gtcagggcac tctggtgact gtgagcagc                           339
```

<210> SEQ ID NO 137
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gaggtccagt tagtccaaag cggcggaggc gtagtgcaac ctggcagaag cctgcggtta      60
tcgtgcgccg caagcggctt cacctttagc tcttatggta tgcactgggt cagacaggcc     120
cctgggaagg gcctggagtg ggtggccgtg atctggtatg acgggagcaa gtattacgcg     180
gattccgtca agggacggtt caccatatcc cgcgataaca gcaagaatac tctttactta     240
cagatgaaca gcctgagggc cgaggacacc gcagtatatt attgcgctac caataatgac     300 tattgggtc agggcactct ggtgactgtg agcagc                                336

<210> SEQ ID NO 138
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
caggtgcagc tggtggagtc tgggggaggc gtggtccagc ctgggaggtc cctgagactc      60
gactgtaaag cgtctggaat caccttcagt aactctggca tgcactgggt ccgccaggct     120
ccaggcaagg gctggagtg gtggcagtt atttggtatg atggaagtaa caaaagatac      180
tatgcagact ccgtgaaggg ccgattcacc atctccagag acaattccaa gaacacgctg     240
tttctgcaaa tgaacagcct gagagccgag gacacggctg tgtattactg tgcgacaaac     300
aacgactact ggggccaggg aaccctggtc accgtctcct ca                       342

<210> SEQ ID NO 139
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
caggtgcagc tggtggagtc tgggggaggc gtggtccagc ctgggaggtc cctgagactc      60
gactgtaaag cgtctggatt caccttcagt aactctggca tgcactgggt ccgccaggct     120
ccaggcaagg gctggagtg gtggcagtt atttggtatg atggaagtaa caaaagatac      180
tatgcagact ccgtgaaggg ccgattcacc atctccagag acaattccaa gaacacgctg     240
tttctgcaaa tgaacagcct gagagccgag gacacggctg tgtattactg tgcgacaaac     300
aacgactact ggggccaggg aaccctggtc accgtctcct ca                       342

<210> SEQ ID NO 140
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 140
gaggtgcaac ttgtgcaaag cggcggcgga gtcgtgcagc ccggtcgatc tcttcgcctg    60
agttgtgctg ccagcggcat tacctttagc aattctggta tgcactgggt acgtcaggcc   120
cccggtaagg ggctagaatg ggtggctgtg atttggtacg atggttctaa gtactacgcc   180
gacagcgtta aaggccgatt caccatcagt agagacaaca gtaagaacac cctctacctc   240
cagatgaaca gtctgcgagc tgaagacact gctgtgtact actgtgccac caacaacgac   300
tactggggac agggaaccct ggtcaccgtg agtagt                              336

<210> SEQ ID NO 141
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Glu Tyr Asn Thr Ser Asn Pro
145                 150                 155                 160

Asp

<210> SEQ ID NO 142
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Pro Gln Leu Cys Lys Phe Cys Asp Val Arg Phe Ser Thr Cys Asp Asn
1               5                   10                  15

Gln Lys Ser Cys Met Ser Asn Cys Ser Ile Thr Ser Ile Cys Glu Lys
            20                  25                  30

Pro Gln Glu Val Cys Val Ala Val Trp Arg Lys Asn Asp Glu Asn Ile
        35                  40                  45

Thr Leu Glu Thr Val Cys His Asp Pro Lys Leu Pro Tyr His Asp Phe
    50                  55                  60
```

```
Ile Leu Glu Asp Ala Ala Ser Pro Lys Cys Ile Met Lys Glu Lys Lys
 65                  70                  75                  80

Lys Pro Gly Glu Thr Phe Phe Met Cys Ser Cys Ser Ser Asp Glu Cys
                 85                  90                  95

Asn Asp Asn Ile Ile Phe Ser Glu Glu Tyr Asn Thr Ser Asn Pro Asp
                100                 105                 110
```

<210> SEQ ID NO 143
<211> LENGTH: 586
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Gln Val Gln Leu Val Glu Ser Gly Gly Gly Val Val Gln Pro Gly Arg
 1               5                  10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
             35                  40                  45

Ala Val Ile Trp Tyr Asp Gly Ser Lys Arg Tyr Tyr Ala Asp Ser Val
         50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
                100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
```

```
                305                 310                 315                 320
Leu Pro Ser Ser Ile Glu Lys Thr Ile Ser Lys Ala Lys Gly Gln Pro
                    325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys Gly Gly Gly Gly Ser Gly Gly Gly
        435                 440                 445

Gly Ser Ile Pro Pro His Val Gln Lys Ser Val Asn Asn Asp Met Ile
    450                 455                 460

Val Thr Asp Asn Asn Gly Ala Val Lys Phe Pro Gln Leu Cys Lys Phe
465                 470                 475                 480

Cys Asp Val Arg Phe Ser Thr Cys Asp Asn Gln Lys Ser Cys Met Ser
                485                 490                 495

Asn Cys Ser Ile Thr Ser Ile Cys Glu Lys Pro Gln Glu Val Cys Val
            500                 505                 510

Ala Val Trp Arg Lys Asn Asp Glu Asn Ile Thr Leu Glu Thr Val Cys
        515                 520                 525

His Asp Pro Lys Leu Pro Tyr His Asp Phe Ile Leu Glu Asp Ala Ala
    530                 535                 540

Ser Pro Lys Cys Ile Met Lys Glu Lys Lys Lys Pro Gly Glu Thr Phe
545                 550                 555                 560

Phe Met Cys Ser Cys Ser Ser Asp Glu Cys Asn Asp Asn Ile Ile Phe
                565                 570                 575

Ser Glu Glu Tyr Asn Thr Ser Asn Pro Asp
            580                 585

<210> SEQ ID NO 144
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80
```

-continued

```
Met Glu Leu Lys Ser Leu Gln Phe Asp Asp Thr Ala Val Tyr Tyr Cys
                 85                  90                  95
Ala Arg Arg Asp Tyr Arg Phe Asp Met Gly Phe Asp Tyr Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Pro Gly Lys Gly
        435                 440                 445
Gly Gly Gly Ser Gly Gly Gly Ser Ile Pro Pro His Val Gln Lys
450                 455                 460
Ser Val Asn Asn Asp Met Ile Val Thr Asp Asn Asn Gly Ala Val Lys
465                 470                 475                 480
Phe Pro Gln Leu Cys Lys Phe Cys Asp Val Arg Phe Ser Thr Cys Asp
                485                 490                 495
Asn Gln Lys Ser Cys Met Ser Asn Cys Ser Ile Thr Ser Ile Cys Glu
```

```
                500                 505                 510
Lys Pro Gln Glu Val Cys Val Ala Val Trp Arg Lys Asn Asp Glu Asn
            515                 520                 525

Ile Thr Leu Glu Thr Val Cys His Asp Pro Lys Leu Pro Tyr His Asp
        530                 535                 540

Phe Ile Leu Glu Asp Ala Ala Ser Pro Lys Cys Ile Met Lys Glu Lys
545                 550                 555                 560

Lys Lys Pro Gly Glu Thr Phe Phe Met Cys Ser Cys Ser Ser Asp Glu
                565                 570                 575

Cys Asn Asp Asn Ile Ile Phe Ser Glu Glu Tyr Asn Thr Ser Asn Pro
                580                 585                 590

Asp

<210> SEQ ID NO 145
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
                  260                 265                 270
Val Gln Phe Asn Trp Tyr Val Asp Gly Val Glu Val His Asn Ala Lys
            275                 280                 285

Thr Lys Pro Arg Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
        435                 440                 445

Gly Gly Gly Ser Gly Gly Gly Ser Ile Pro Pro His Val Gln Lys
450                 455                 460

Ser Val Asn Asn Asp Met Ile Val Thr Asp Asn Asn Gly Ala Val Lys
465                 470                 475                 480

Phe Pro Gln Leu Cys Lys Phe Cys Asp Val Arg Phe Ser Thr Cys Asp
                485                 490                 495

Asn Gln Lys Ser Cys Met Ser Asn Cys Ser Ile Thr Ser Ile Cys Glu
            500                 505                 510

Lys Pro Gln Glu Val Cys Val Ala Val Trp Arg Lys Asn Asp Glu Asn
        515                 520                 525

Ile Thr Leu Glu Thr Val Cys His Asp Pro Lys Leu Pro Tyr His Asp
530                 535                 540

Phe Ile Leu Glu Asp Ala Ala Ser Pro Lys Cys Ile Met Lys Glu Lys
545                 550                 555                 560

Lys Lys Pro Gly Glu Thr Phe Phe Met Cys Ser Cys Ser Ser Asp Glu
                565                 570                 575

Cys Asn Asp Asn Ile Ile Phe Ser Glu Glu Tyr Asn Thr Ser Asn Pro
            580                 585                 590

Asp

<210> SEQ ID NO 146
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 147
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 148
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Asn Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg
            100                 105
```

<210> SEQ ID NO 149
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser
```

<210> SEQ ID NO 150
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asn Asp Asp Tyr Trp Gly Gln Gly Thr Leu Val Thr Val Ser
            100                 105                 110

Ser
```

<210> SEQ ID NO 151
<211> LENGTH: 120
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Ala Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Pro Asp Arg Ala Asn Trp His Phe Asp Tyr Trp Gly Gln
                100                 105                 110

Gly Thr Leu Val Thr Val Ser Ser
            115                 120

<210> SEQ ID NO 152
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Ala Ile Asn Pro Asn Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Gly Leu Lys Gly Asp Gly Tyr Phe Asp Tyr Trp Gly Gln
                100                 105                 110

Gly Thr Leu Val Thr Val Ser Ser
            115                 120

<210> SEQ ID NO 153
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Tyr Met Gly Phe Asp Tyr Trp Gly Gln
            100                 105                 110

Gly Thr Thr Val Thr Val Ser Ser
            115                 120

<210> SEQ ID NO 154
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asn Met Gly Phe Asp Tyr Trp Gly Gln
            100                 105                 110

Gly Thr Thr Val Thr Val Ser Ser
            115                 120

<210> SEQ ID NO 155
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Gln Pro Ser Asn Gly Gly Thr Asn Phe Asn Glu Lys Phe
    50                  55                  60

```
Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Tyr Met Gly Phe Asp Tyr Trp Gly Gln
            100                 105                 110

Gly Thr Thr Val Thr Val Ser Ser
        115                 120

<210> SEQ ID NO 156
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asp Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Tyr Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Glu Ser Gly Gly Val Val Gln Pro Gly Arg
 1               5                  10                  15

Ser Leu Arg Leu Asp Cys Lys Ala Ser Gly Phe Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asn Asp Tyr Trp Gly Gln Gly Thr Leu Val Thr Val Ser
            100                 105                 110
```

Ser

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser
```

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Glu Val Gln Leu Val Gln Ser Gly Gly Gly Val Val Gln Pro Gly Arg
1               5                   10                  15

Ser Leu Arg Leu Ser Cys Ala Ala Ser Gly Ile Thr Phe Ser Asn Ser
            20                  25                  30

Met His Trp Val Arg Gln Ala Pro Gly Lys Gly Leu Glu Trp Val Ala
        35                  40                  45

Val Ile Trp Tyr Asp Gly Ser Lys Arg Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Asn Asn Asp Tyr Trp Gly Gln Gly Thr Leu Val Thr Val Ser Ser
            100                 105                 110
```

<210> SEQ ID NO 160
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser

<210> SEQ ID NO 161
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Tyr Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Asn Asp Tyr Trp Gly Gln Gly Thr Leu Val Thr Val Ser Ser
            100                 105                 110

<210> SEQ ID NO 162
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Arg Tyr Tyr Ala Asp Ser
50                  55                  60

Val Lys Gly Arg Phe Thr Ile Ser Arg Asp Asn Ser Lys Asn Thr Leu
 65                  70                  75                  80

Phe Leu Gln Met Asn Ser Leu Arg Ala Glu Asp Thr Ala Val Tyr Tyr
                 85                  90                  95

Cys Ala Thr Asn Asn Asp Tyr Trp Gly Gln Gly Thr Leu Val Thr Val
                100                 105                 110

Ser Ser

<210> SEQ ID NO 163
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Val Glu Ser Gly Gly Gly Val Val Gln Pro Gly Arg
1               5                   10                  15

Ser Leu Arg Leu Asp Cys Lys Ala Ser Gly Phe Thr Phe Ser Asn Ser
            20                  25                  30

Gly Met His Trp Val Arg Gln Ala Pro Gly Lys Gly Leu
        35                  40                  45

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Val Gln Ser Gly Gly Gly Val Val Gln Pro Gly Arg
1               5                   10                  15

Ser Leu Arg Leu Ser Cys Ala Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Thr Asn Asn Asp Tyr Trp Gly Gln Gly Thr Leu Val Thr Val Ser Ser
                100                 105                 110

<210> SEQ ID NO 165
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Asp Thr Phe Gly Gly Gly Thr Lys Leu Glu Ile Lys
            100                 105                 110

Arg Thr Val Ala
        115

<210> SEQ ID NO 166
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 166

Gln Val Xaa Leu Xaa Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Asn Asn Pro Gly Ser Gly Gly Ser Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ser Gly Gly Phe Tyr Phe Asp Tyr Trp Gly Gln Gly Thr Thr
            100                 105                 110

Gln Ser Pro Ser Pro Gln Pro Lys Arg Arg Ala His
        115                 120

<210> SEQ ID NO 167
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Leu Tyr Ser
            20                  25                  30

```
Ser Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys His Gln
                85                  90                  95

Tyr Leu Ser Ser Asp Thr Phe Gly Gln Gly Thr Lys Val Glu Ile Lys
            100                 105                 110

Arg Thr Val Ala
        115

<210> SEQ ID NO 168
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Gly Val Asn Asn Pro Gly Ser Gly Gly Ser Asn Tyr Asn Glu Lys Phe
 50                  55                  60

Lys Gly Arg Ala Thr Ile Ser Ala Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Gly Gly Phe Tyr Phe Asp Tyr Trp Gly Gln Gly Thr Leu
            100                 105                 110

Val Thr Val Ser Ser Ala Ser Thr Lys Gly Pro Ser
        115                 120

<210> SEQ ID NO 169
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Leu Ala Arg Pro Gly Ala Ser Val Lys Met Ser Cys Lys Thr Ser Gly
 1               5                  10                  15

Tyr Thr Phe Thr Asn Tyr Trp Met His Trp Val Arg Gln Arg Pro Gly
            20                  25                  30

Gln Gly Leu Glu Trp Ile Gly Thr Ile Tyr Pro Gly Asn Ser Asp Thr
        35                  40                  45

Asn Tyr Asn Gln Lys Phe Lys Asp Lys Ala Lys Leu Thr Ala Val Thr
 50                  55                  60

Ser Ala Thr Thr Ala Tyr Met Glu Leu Ser Ser Leu Thr Asn Glu Asp
 65                  70                  75                  80
```

```
Ser Ala Val Tyr Phe Cys Thr Arg Glu Asp Ser Arg Ser Leu Tyr Tyr
                85                  90                  95

Asn Gly Trp Asp Tyr Phe Asp Tyr Trp Gly Gln Gly Thr Thr Leu Thr
            100                 105                 110

Val Ser Ser
        115

<210> SEQ ID NO 170
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Leu Thr Gln Ser Pro Ala Ser Leu Ala Val Ser Leu Gly Gln Arg Ala
1               5                   10                  15

Thr Ile Ser Cys Arg Ala Ser Glu Ser Val Asp Asn Tyr Gly Ile Ser
            20                  25                  30

Phe Leu Asn Trp Phe Gln Gln Lys Pro Gly Gln Pro Pro Lys Leu Leu
            35                  40                  45

Ile Tyr Ala Ala Ser Asn Gln Gly Ser Gly Val Pro Ala Arg Phe Ser
50                  55                  60

Gly Ser Gly Ser Gly Thr Asp Phe Ser Leu Asn Ile His Pro Met Glu
65                  70                  75                  80

Glu Asp Asp Thr Gly Met Tyr Phe Cys Gln Gln Ser Lys Glu Val Pro
                85                  90                  95

Arg Thr Phe Gly Gly Gly Thr Lys Leu Glu Ile Ile
            100                 105

<210> SEQ ID NO 171
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Trp Glu Val Arg Ala Leu Pro Ser Tyr Trp Gly
            100                 105                 110

Gln Gly Thr Leu Val Thr Val Ser Ser
            115                 120

<210> SEQ ID NO 172
<211> LENGTH: 109
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ser Tyr Glu Leu Thr Gln Pro Pro Ser Val Ser Val Ala Pro Gly Gln
1               5                   10                  15

Thr Ala Arg Ile Thr Cys Gly Ala Asn Asp Ile Gly Ser Lys Ser Val
            20                  25                  30

His Trp Tyr Gln Gln Lys Ala Gly Gln Ala Pro Val Leu Val Val Ser
        35                  40                  45

Glu Asp Ile Ile Arg Pro Ser Gly Ile Pro Glu Arg Ile Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Arg Asp Ser Asp Gln
                85                  90                  95

Tyr Val Phe Gly Thr Gly Thr Lys Val Thr Val Leu Gly
            100                 105

<210> SEQ ID NO 173
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 174
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
```

```
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105

<210> SEQ ID NO 175
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Leu Pro Arg Ala Phe Val Leu Asp Ala Met Asp Tyr Trp Gly Gln
            100                 105                 110

Gly Thr Leu Val Thr Val Ser Ser
        115                 120

<210> SEQ ID NO 176
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
```

```
                85                  90                  95
Ile Thr Phe Gly Gln Gly Thr Arg Leu Glu Ile Lys
            100                 105

<210> SEQ ID NO 177
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Ser
            20                  25                  30

Phe Ile Asn Trp Val Arg Gln Ala Pro Gly Gln Gly Leu Glu Trp Met
        35                  40                  45

Gly Gly Ile Ile Pro Ile Phe Asp Ile Thr Asn Tyr Ala Gln Lys Phe
    50                  55                  60

Gln Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Gly Asn Tyr Ala Leu Asp Ala Met Asp Tyr Trp Gly
            100                 105                 110

Gln Gly Thr Leu Val Thr Val Ser Ser
        115                 120

<210> SEQ ID NO 178
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Asp Ser Pro
                85                  90                  95

Ile Thr Phe Gly Gln Gly Thr Arg Leu Glu Ile Lys
            100                 105

<210> SEQ ID NO 179
<211> LENGTH: 342
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 179

| gatataatga cacagagccc cagctctcta gctgtgagtg ctggcgagaa ggtgaccatg | 60 |
| agctgtaaga gcagtcaaag cgtgctgtac agttccaatc agaaaaatta cctcgcatgg | 120 |
| tatcagaagc caggtcaaag ccctaagctc cttatctact gggcctcaac ccgtgaaagt | 180 |
| ggagtgcctg acagatttac tggttcaggg agcggcaccg atttcactct gactattagc | 240 |
| tctgtgcagg cagaagacct tgccgtgtat tactgtcacc agtatctgtc ttcagacacg | 300 |
| tttggaggtg ggaccaaact agaaatcaaa cgtactgtcg ca | 342 |

<210> SEQ ID NO 180
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (7)..(9)
<223> OTHER INFORMATION: a, c, t, g, unknown or other
<220> FEATURE:
<221> NAME/KEY: modified_base
<222> LOCATION: (13)..(15)
<223> OTHER INFORMATION: a, c, t, g, unknown or other

<400> SEQUENCE: 180

| caggtgnnnc tgnnncagag cggcgccgag ctggtgaggc ccggcaccag cgtgaaggtg | 60 |
| agctgcaagg ccagcggcta cgccttcacc aactacctga tcgagtgggt gaagcagagg | 120 |
| cccggccagg gcctggagtg gatcggcgtg aacaacccg gcagcggcgg cagcaactac | 180 |
| aacgagaagt tcaagggcaa ggccaccctg accgccgaca gagcagcag caccgcctac | 240 |
| atgcagctga gcagcctgac cagcgacgac agcgccgtgt acttctgcgc caggagcggc | 300 |
| ggcttctact tcgactactg ggccagggc accacccaga gccccagccc ccagcccaag | 360 |
| aggagggccc ac | 372 |

<210> SEQ ID NO 181
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

| gacatccaga tgacccagag cccccagcagc ctgagcgcca gcgtgggcga cagggtgacc | 60 |
| atcacctgca gggccagcca gagcgtgctg tacagcagca accagaagaa ctacctggcc | 120 |
| tggtaccagc agaagcccgg caaggccccc aagctgctga tctactgggc cagcaccagg | 180 |
| gagagcggcg tgcccagcag gttcagcggc agcggcagcg gcaccgactt caccctgacc | 240 |
| atcagcagcc tgcagcccga ggacttcgcc acctactact gccaccagta cctgagcagc | 300 |
| gacacccttcg gccagggcac caaggtggag atcaagagga ccgtggcc | 348 |

<210> SEQ ID NO 182
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182

```
gaggtgcagc tggtggagag cggcggcggc ctggtgcagc ccggcggcag cctgaggctg      60
agctgcgccg ccagcggcta cgccttcacc aactacctga tcgagtgggt gaggcaggcc     120
cccggcaagg gcctggagtg ggtgggcgtg aacaaccccg gcagcggcgg cagcaactac     180
aacgagaagt tcaagggcag ggccaccatc agcgccgaca cagcaagaa cacccctgtac    240
ctgcagatga acagcctgag ggccgaggac accgccgtgt actactgcgc caggagcggc     300
ggcttctact cgactactg gggccagggc accctggtga ccgtgagcag cgccagcacc     360
aagggcccca gc                                                        372
```

<210> SEQ ID NO 183
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

```
ctggccaggc ccggcgccag cgtgaagatg agctgcaaga ccagcggcta caccttcacc      60
aactactgga tgcactgggt gaggcagagg cccggccagg gcctgagtg gatcggcacc     120
atctacccg gcaacagcga caccaactac aaccagaagt tcaaggacaa ggccaagctg     180
accgccgtga ccagcgccac caccgcctac atggagctga gcagcctgac caacgaggac     240
agcgccgtgt acttctgcac cagggaggac agcaggagcc tgtactacaa cggctgggac     300
tacttcgact actggggcca gggcaccacc ctgaccgtga gcagc                    345
```

<210> SEQ ID NO 184
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 184

```
ctgacccaga gccccgccag cctggccgtg agcctgggcc agagggccac catcagctgc      60
agggccagcg agagcgtgga caactacggc atcagcttcc tgaactggtt ccagcagaag     120
cccggccagc cccccaagct gctgatctac gccgccagca accagggcag cggcgtgccc     180
gccaggttca gcggcagcgg cagcggcacc gacttcagcc tgaacatcca ccccatggag     240
gaggacgaca ccggcatgta cttctgccag cagagcaagg aggtgcccag gaccttcggc     300
ggcggcacca agctggagat catc                                           324
```

<210> SEQ ID NO 185
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185

```
caggtgcagc tggtgcagag cggcgccgag gtgaagaagc ccggcagcag cgtgaaggtg      60
agctgcaagg ccagcggcgg caccttcagc agctacgcca tcagctgggt gaggcaggcc     120
```

```
cccggccagg gcctggagtg gatgggcggc atcatcccca tcttcggcac cgccaactac    180
gcccagaagt tccagggcag ggtgaccatc accgccgacg agagcaccag caccgcctac    240
atggagctga gcagcctgag gagcgaggac accgccgtgt actactgcgc caggggcctg    300
tgggaggtga gggccctgcc cagcgtgtac tggggccagg gcaccctggt gaccgtgagc    360
agc                                                                  363

<210> SEQ ID NO 186
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186
agctacgagc tgacccagcc ccccagcgtg agcgtggccc ccggccagac cgccaggatc     60
acctgcggcg ccaacgacat cggcagcaag agcgtgcact ggtaccagca gaaggccggc    120
caggcccccg tgctggtggt gagcgaggac atcatcaggc ccagcggcat ccccgagagg    180
atcagcggca gcaacagcgg caacaccgcc accctgacca tcagcagggt ggaggccggc    240
gacgaggccg actactactg ccaggtgtgg gacagggaca gcgaccagta cgtgttcggc    300
accggcacca aggtgaccgt gctgggc                                        327

<210> SEQ ID NO 187
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
caggtgcagc tggtgcagag cggcgccgag gtgaagaagc ccggcagcag cgtgaaggtg     60
agctgcaagg ccagcggcta caccttcagc agcaacgtga tcagctgggt gaggcaggcc    120
cccggccagg gcctggagtg gatgggcggc gtgatcccca tcgtggacat cgccaactac    180
gcccagaggt tcaagggcag ggtgaccatc accgccgacg agagcaccag caccacctac    240
atggagctga gcagcctgag gagcgaggac accgccgtgt actactgcgc cagcaccctg    300
ggcctggtgc tggacgccat ggactactgg ggccagggca ccctggtgac cgtgagcagc    360

<210> SEQ ID NO 188
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
gagaccgtgc tgacccagag ccccggcacc ctgagcctga gccccggcga gagggccacc     60
ctgagctgca gggccagcca gagcctgggc agcagctacc tggcctggta ccagcagaag    120
cccggccagg cccccaggct gctgatctac ggcgccagca gcagggcccc cggcatcccc    180
gacaggttca gcggcagcgg cagcggcacc gacttcaccc tgaccatcag caggctggag    240
cccgaggact tcgccgtgta ctactgccag cagtacgccg acagccccat caccttcggc    300
cagggcacca ggctggagat caag                                           324
```

<210> SEQ ID NO 189
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
caggtgcagc tggtgcagag cggcgccgag gtgaagaagc ccggcagcag cgtgaaggtg      60
agctgcaagg ccagcggcta caccttcagc agcaacgtga tcagctgggt gaggcaggcc     120
cccggccagg gcctggagtg gatgggcggc gtgatcccca tcgtggacat cgccaactac     180
gcccagaggt tcaagggcag ggtgaccatc accgccgacg agagcaccag caccacctac     240
atggagctga gcagcctgag gagcgaggac accgccgtgt actactgcgc cctgcccagg     300
gccttcgtgc tggacgccat ggactactgg ggccagggca ccctggtgac cgtgagcagc     360

<210> SEQ ID NO 190
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
gagaccgtgc tgacccagag ccccggcacc ctgagcctga gccccggcga gagggccacc      60
ctgagctgca gggccagcca gagcctgggc agcagctacc tggcctggta ccagcagaag     120
cccggccagg cccccaggct gctgatctac ggcgccagca gcagggcccc cggcatcccc     180
gacaggttca gcggcagcgg cagcggcacc gacttcaccc tgaccatcag caggctggag     240
cccgaggact tcgccgtgta ctactgccag cagtacgccg acagccccat caccttcggc     300
cagggcacca ggctggagat caag                                            324

<210> SEQ ID NO 191
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
caggtgcagc tggtgcagag cggcgccgag gtgaagaagc ccggcagcag cgtgaaggtg      60
agctgcaagg ccagcggcgg caccttcagc accagcttca tcaactgggt gaggcaggcc     120
cccggccagg gcctggagtg gatgggcggc atcatcccca tcttcgacat caccaactac     180
gcccagaagt tccagagcag ggtgaccatc accgccgaca gagagcaccag caccgcctac     240 atggagctga gcagcctgag gagcgaggac accgccgtgt actactgcgc caggggcaac     300
ggcaactacg ccctggacgc catggactac tggggccagg gcaccctggt gaccgtgagc     360
agc                                                                   363

<210> SEQ ID NO 192
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192

```
gagatcgtgc tgacccagag ccccggcacc ctgagcctga gccccggcga gagggccacc    60
ctgagctgca gggccagcca gagcgtgagc agcagctact tcgcctggta ccagcagaag   120
cccggccagg cccccaggct gctgatctac ggcgccagca gcagggccac cggcatcccc   180
gacaggttca gcggcagcgg cagcggcacc gacttcaccc tgaccatcag caggctggag   240
cccgaggact tcgccgtgta ctactgccag cagtactacg acagcccat caccttcggc    300
cagggcacca ggctggagat caag                                          324
```

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

-continued

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234
<400> SEQUENCE: 234
000

<210> SEQ ID NO 235
<400> SEQUENCE: 235
000

```
<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
```

```
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
```

000

<210> SEQ ID NO 259
<400> SEQUENCE: 259

000

<210> SEQ ID NO 260
<400> SEQUENCE: 260

000

<210> SEQ ID NO 261
<400> SEQUENCE: 261

000

<210> SEQ ID NO 262
<400> SEQUENCE: 262

000

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

His Ala Asn Phe Cys Leu Gly Pro Cys Pro Tyr Ile Trp Ser Leu Ala
1               5                   10                  15

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Phe Cys Leu Gly Pro Cys Pro Tyr Ile Trp Ser Leu Asp Thr Ala
1               5                   10                  15

<210> SEQ ID NO 265
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ser Asn Pro Tyr Ser Ala Phe Gln Val Asp Ile Ile Val Asp Ile Ala
1               5                   10                  15

<210> SEQ ID NO 266
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 266

Thr Ser Leu Asp Ala Thr Met Ile Trp Thr Met Met Ala
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Thr Ser Leu Asp Ala Ser Ile Trp Ala Met Met Gln Asn Ala
1               5                   10

<210> SEQ ID NO 268
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cacgccaact tctgcctggg cccctgcccc tacatctgga gcctggcc                48

<210> SEQ ID NO 269
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ttctgcctgg gcccctgccc ctacatctgg agcctggaca ccgcc               45

<210> SEQ ID NO 270
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
agcaacccct acagcgcctt ccaggtggac atcatcgtgg acatcgcc                48

<210> SEQ ID NO 271
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
accagcctgg acgccaccat gatctggacc atgatggcc                39

<210> SEQ ID NO 272
<211> LENGTH: 42
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 272
accagcctgg acgccagcat ctgggccatg atgcagaacg cc                              42

<210> SEQ ID NO 273
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273
```

| | | | | | | | | | | | | | | |
|---|---|---|---|---|---|---|---|---|---|---|---|---|---|---|
| Ile | Asp | Glu | Thr | Arg | Ala | His | Leu | Leu | Lys | Glu | Lys | Met | Met | Arg |
| 1 | | | | 5 | | | | | 10 | | | | | 15 |
| Leu | Gly | Gly | Arg | Leu | Val | Leu | Asn | Thr | Lys | Glu | Glu | Leu | Ala | Asn | Glu |
| | | | 20 | | | | | 25 | | | | | 30 | | |
| Arg | Leu | Met | Thr | Leu | Lys | Ile | Ala | Glu | Met | Lys | Glu | Ala | Met | Arg | Thr |
| | | | 35 | | | | | 40 | | | | | 45 | | |
| Leu | Ile | Phe | Pro | Pro | Ser | Met | His | Phe | Gln | Ala | Lys | His | Leu | Ile |
| 50 | | | | | 55 | | | | | 60 | | | | |
| Glu | Arg | Ser | Gln | Val | Phe | Asn | Ile | Leu | Arg | Met | Met | Pro | Lys | Gly | Ala |
| 65 | | | | | 70 | | | | | 75 | | | | | 80 |
| Ala | Leu | His | Leu | His | Asp | Ile | Gly | Ile | Val | Thr | Met | Asp | Trp | Leu | Val |
| | | | | 85 | | | | | 90 | | | | | 95 | |
| Arg | Asn | Val | Thr | Tyr | Arg | Pro | His | Gly | Ile | Ala | Leu | Pro | Gly | Asp | Ser |
| | | | | 100 | | | | | 105 | | | | | 110 | |
| Leu | Leu | Arg | Asn | Phe | Thr | Leu | Val | Thr | Gln | His | Pro | Glu | Val | Ile | Tyr |
| | | | | 115 | | | | | 120 | | | | | 125 | |
| Thr | Asn | Gln | Asn | Val | Val | Leu | Ser | Lys | Phe | Glu | Thr | Ile | Phe | Phe | Thr |
| | 130 | | | | | 135 | | | | | 140 | | | | |
| Ile | Ser | Gly | Leu | Ile | His | Tyr | Ala | Pro | Val | Phe | Arg | Asp | Tyr | Val | Phe |
| 145 | | | | | 150 | | | | | 155 | | | | | 160 |
| Arg | Ser | Met | Gln | Glu | Phe | Tyr | Glu | Asp | Asn | Val | Leu | Tyr | Met | Glu | Ile |
| | | | | 165 | | | | | 170 | | | | | 175 | |
| Arg | Ala | Ser | Leu | Leu | Pro | Val | Tyr | Glu | Leu | Ser | Gly | Glu | His | His | Asp |
| | | | 180 | | | | | 185 | | | | | 190 | | |
| Glu | Glu | Trp | Ser | Val | Lys | Thr | Tyr | Gln | Glu | Val | Ala | Gln | Asp | Phe | Val |
| | | | 195 | | | | | 200 | | | | | 205 | | |
| Glu | Thr | His | Pro | Glu | Phe | Ile | Gly | Ile | Lys | Ile | Ile | Tyr | Ser | Asp | His |
| | 210 | | | | | 215 | | | | | 220 | | | | |
| Arg | Ser | Lys | Asp | Val | Ala | Val | Ile | Ala | Glu | Ser | Ile | Arg | Met | Ala | Met |
| 225 | | | | | 230 | | | | | 235 | | | | | 240 |
| Gly | Leu | Arg | Ile | Lys | Phe | Pro | Thr | Val | Val | Ala | Gly | Phe | Asp | Leu | Val |
| | | | | 245 | | | | | 250 | | | | | 255 | |
| Gly | His | Glu | Asp | Thr | Gly | His | Ser | Leu | His | Asp | Tyr | Lys | Glu | Ala | Leu |
| | | | 260 | | | | | 265 | | | | | 270 | | |
| Met | Ile | Pro | Ala | Lys | Asp | Gly | Val | Lys | Leu | Pro | Tyr | Phe | Phe | His | Ala |
| | | | 275 | | | | | 280 | | | | | 285 | | |
| Gly | Glu | Thr | Asp | Trp | Gln | Gly | Thr | Ser | Ile | Asp | Arg | Asn | Ile | Leu | Asp |
| | 290 | | | | | 295 | | | | | 300 | | | | |
| Ala | Leu | Met | Leu | Asn | Thr | Thr | Arg | Ile | Gly | His | Gly | Phe | Ala | Leu | Ser |
| 305 | | | | | 310 | | | | | 315 | | | | | 320 |

```
Lys His Pro Ala Val Arg Thr Tyr Ser Trp Lys Lys Asp Ile Pro Ile
                325                 330                 335

Glu Val Cys Pro Ile Ser Asn Gln Val Leu Lys Leu Val Ser Asp Leu
            340                 345                 350

Arg Asn His Pro Val Ala Thr Leu Met Ala Thr Gly His Pro Met Val
        355                 360                 365

Ile Ser Ser Asp Asp Pro Ala Met Phe Gly Ala Lys Gly Leu Ser Tyr
    370                 375                 380

Asp Phe Tyr Glu Val Phe Met Gly Ile Gly Met Lys Ala Asp Leu
385                 390                 395                 400

Arg Thr Leu Lys Gln Leu Ala Met Asn Ser Ile Lys Tyr Ser Thr Leu
                405                 410                 415

Leu Glu Ser Glu Lys Asn Thr Phe Met Glu Ile Trp Lys Lys Arg Trp
                420                 425                 430

Asp Lys Phe Ile Ala Asp Val Ala Thr Lys
                435                 440

<210> SEQ ID NO 274
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Ile Asp Glu Thr Arg Ala His Leu Leu Leu Lys Glu Lys Met Met Arg
1               5                   10                  15

Leu Gly Gly Arg Leu Val Leu Asn Thr Lys Glu Glu Leu Ala Asn Glu
                20                  25                  30

Arg Leu Met Thr Leu Lys Ile Ala Glu Met Lys Glu Ala Met Arg Thr
            35                  40                  45

Leu Ile Phe Pro Pro Ser Met His Phe Gln Ala Lys His Leu Ile
    50                  55                  60

Glu Arg Ser Gln Val Phe Asn Ile Leu Arg Met Met Pro Lys Gly Ala
65                  70                  75                  80

Ala Leu His Leu His Asp Ile Gly Ile Val Thr Met Asp Trp Leu Val
                85                  90                  95

Arg Asn Val Thr Tyr Arg Pro His Gly Ile Ala Leu Pro Gly Asp Ser
            100                 105                 110

Leu Leu Arg Asn Phe Thr Leu Val Thr Gln His Pro Glu Val Ile Tyr
        115                 120                 125

Thr Asn Gln Asn Val Val Trp Ser Lys Phe Glu Thr Ile Val Phe Thr
    130                 135                 140

Ile Ser Gly Leu Ile His Tyr Ala Pro Val Phe Arg Asp Tyr Val Phe
145                 150                 155                 160

Arg Ser Met Gln Glu Phe Tyr Glu Asp Asn Val Leu Tyr Met Glu Ile
                165                 170                 175

Arg Ala Arg Leu Leu Pro Val Tyr Glu Leu Ser Gly Glu His His Asp
            180                 185                 190

Glu Glu Trp Ser Val Lys Thr Tyr Gln Glu Val Ala Gln Asp Phe Val
        195                 200                 205

Glu Thr His Pro Glu Phe Ile Gly Ile Lys Ile Ile Tyr Ser Asp His
    210                 215                 220

Arg Ser Lys Asp Val Ala Val Ile Ala Glu Ser Ile Arg Met Ala Met
225                 230                 235                 240
```

-continued

Gly Leu Arg Ile Lys Phe Pro Thr Val Val Ala Gly Phe Asp Leu Ala
            245                 250                 255

Gly His Glu Asp Thr Gly His Ser Leu His Asp Tyr Lys Glu Ala Leu
        260                 265                 270

Met Ile Pro Ala Lys Asp Gly Val Lys Leu Pro Tyr Phe Phe His Ala
        275                 280                 285

Gly Glu Thr Asp Trp Gln Gly Thr Ser Ile Asp Arg Asn Ile Leu Asp
        290                 295                 300

Ala Leu Met Leu Asn Thr Thr Arg Ile Gly His Gly Phe Ala Leu Ser
305                 310                 315                 320

Lys His Pro Ala Val Arg Thr Tyr Ser Trp Lys Lys Asp Ile Pro Ile
                325                 330                 335

Glu Val Cys Pro Ile Ser Asn Gln Val Leu Lys Leu Val Ser Asp Leu
                340                 345                 350

Arg Asn His Pro Val Ala Thr Leu Met Ala Thr Gly His Pro Met Val
            355                 360                 365

Ile Ser Ser Asp Asp Pro Ala Met Phe Gly Ala Lys Gly Leu Ser Tyr
        370                 375                 380

Asp Phe Tyr Glu Val Phe Met Gly Ile Gly Gly Met Lys Ala Asp Leu
385                 390                 395                 400

Arg Thr Leu Lys Gln Leu Ala Met Asn Ser Ile Lys Tyr Ser Thr Leu
                405                 410                 415

Leu Glu Ser Glu Lys Asn Thr Phe Met Glu Ile Trp Lys Lys Arg Trp
                420                 425                 430

Asp Lys Phe Ile Ala Asp Val Ala Thr Lys
            435                 440

<210> SEQ ID NO 275
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Glu Met Lys Glu Ala Met Arg Thr Leu Ile Phe Pro Pro Ser Met His
1               5                   10                  15

Phe Phe Gln Ala Lys His Leu Ile Glu Arg Ser Gln Val Phe Asn Ile
            20                  25                  30

Leu Arg Met Met Pro Lys Gly Ala Ala Leu His Leu His Asp Ile Gly
        35                  40                  45

Ile Val Thr Met Asp Trp Leu Val Arg Asn Val Thr Tyr Arg Pro His
    50                  55                  60

Gly Ile Ala Leu Pro Gly Asp Ser Leu Leu Arg Asn Phe Thr Leu Val
65                  70                  75                  80

Thr Gln His Pro Glu Val Ile Tyr Thr Asn Gln Asn Val Val Leu Ser
                85                  90                  95

Lys Phe Glu Thr Ile Val Phe Thr Ile Ser Gly Leu Ile His Tyr Ala
            100                 105                 110

Pro Val Phe Arg Asp Tyr Val Phe Arg Ser Met Gln Glu Phe Tyr Glu
        115                 120                 125

Asp Asn Val Leu Tyr Met Glu Ile Arg Ala Arg Leu Leu Pro Val Tyr
    130                 135                 140

Glu Leu Ser Gly Glu His His Asp Glu Glu Trp Ser Val Lys Thr Tyr

```
            145                 150                 155                 160
Gln Glu Val Ala Gln Asp Phe Val Thr His Pro Glu Phe Ile Gly
                165                 170                 175
Ile Lys Ile Ile Tyr Ser Asp His Arg Ser Lys Asp Val Ala Val Ile
            180                 185                 190
Ala Glu Ser Ile Arg Met Ala Met Gly Leu Arg Ile Lys Phe Pro Thr
            195                 200                 205
Val Val Ala Gly Phe Asp Leu Val Gly His Glu Asp Thr Gly His Ser
        210                 215                 220
Leu His Asp Tyr Lys Glu Ala Leu Met Ile Pro Ala Lys Asp Gly Val
225                 230                 235                 240
Lys Leu Pro Tyr Phe His Ala Gly Glu Thr Asp Trp Gln Gly Thr
                245                 250                 255
Ser Ile Asp Arg Asn Ile Leu Asp Ala Leu Met Leu Asn Thr Thr Arg
            260                 265                 270
Ile Gly His Gly Phe Ala Leu Ser Lys His Pro Ala Val Arg Thr Tyr
        275                 280                 285
Ser Trp Lys Lys Asp Ile Pro Ile Glu Val Cys Pro Ile Ser Asn Gln
    290                 295                 300
Val Leu Lys Leu Val Ser Asp Leu Arg Asn His Pro Val Ala Thr Leu
305                 310                 315                 320
Met Ala Thr Gly His Pro Met Val Ile Ser Ser Asp Asp Pro Ala Met
                325                 330                 335
Phe Gly Ala Lys Gly Leu Ser Tyr Asp Phe Tyr Glu Val Phe Met Gly
                340                 345                 350
Ile Gly Gly Met Lys Ala Asp Leu Arg Thr Leu Lys Gln Leu Ala Met
            355                 360                 365
Asn Ser Ile Lys Tyr Ser Thr Leu Leu Glu Ser Glu Lys Asn Thr Phe
        370                 375                 380
Met Glu Ile Trp Lys Lys Arg Trp Asp Lys Phe Ile Ala Asp Val Ala
385                 390                 395                 400
Thr Lys

<210> SEQ ID NO 276
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Ile Asp Glu Thr Arg Ala His Leu Leu Leu Lys Glu Lys Met Met Arg
1               5                   10                  15
Leu Gly Gly Arg Leu Val Leu Asn Thr Lys Glu Glu Leu Ala Asn Glu
            20                  25                  30
Arg Leu Met Thr Leu Lys Ile Ala Glu Met Lys Glu Ala Met Arg Thr
        35                  40                  45
Leu Ile Phe Pro Pro Ser Met His Phe Phe Gln Ala Lys His Leu Ile
    50                  55                  60
Glu Arg Ser Gln Val Phe Asn Ile Leu Arg Met Met Pro Lys Gly Ala
65                  70                  75                  80
Ala Leu His Leu His Asp Ile Gly Ile Val Thr Met Asp Trp Leu Gly
                85                  90                  95
Gly Gly Gly Ser Gly Gly Gly Gly Ser Val Thr Glu Phe Asp Asp Ser
```

```
            100                 105                 110
Leu Leu Arg Asn Phe Thr Leu Val Thr Gln His Pro Glu Val Ile Tyr
        115                 120                 125
Thr Asn Gln Asn Val Val Trp Ser Lys Phe Glu Thr Ile Phe Phe Thr
        130                 135                 140
Ile Ser Gly Leu Ile His Tyr Ala Pro Val Phe Arg Asp Tyr Val Phe
145                 150                 155                 160
Arg Ser Met Gln Glu Phe Tyr Glu Asp Asn Val Leu Tyr Met Glu Ile
            165                 170                 175
Arg Ala Arg Leu Leu Pro Val Tyr Glu Leu Ser Gly Glu His His Asp
        180                 185                 190
Glu Glu Trp Ser Val Lys Thr Tyr Gln Glu Val Ala Gln Glu Phe Val
        195                 200                 205
Glu Thr His Pro Glu Phe Ile Gly Ile Lys Ile Tyr Ser Asp His
        210                 215                 220
Arg Ser Arg Asp Val Ala Val Ile Ala Glu Ser Ile Arg Met Ala Met
225                 230                 235                 240
Gly Leu Arg Ile Lys Phe Pro Thr Val Val Ala Gly Phe Asp Leu Ser
            245                 250                 255
Gly His Glu Asp Thr Gly His Ser Leu His Asp Tyr Lys Glu Ala Leu
            260                 265                 270
Met Ile Pro Ala Lys Asp Gly Val Lys Leu Pro Tyr Phe Phe His Ala
        275                 280                 285
Gly Glu Thr Asp Trp Gln Gly Thr Ser Ile Asp Arg Asn Ile Leu Asp
        290                 295                 300
Ala Leu Met Leu Asn Thr Thr Arg Ile Gly His Gly Phe Ala Leu Ser
305                 310                 315                 320
Lys His Pro Ala Val Arg Thr Tyr Ser Trp Lys Lys Asp Ile Pro Ile
            325                 330                 335
Glu Val Cys Pro Ile Ser Asn Gln Val Leu Lys Leu Val Ser Asp Leu
            340                 345                 350
Arg Asn His Pro Val Ala Thr Leu Met Ala Thr Gly His Pro Met Val
            355                 360                 365
Ile Ser Ser Asp Asp Pro Ala Met Phe Gly Ala Lys Gly Leu Ser Tyr
        370                 375                 380
Asp Phe Tyr Glu Val Phe Met Gly Ile Gly Gly Met Lys Ala Asp Leu
385                 390                 395                 400
Arg Thr Leu Lys Gln Leu Ala Met Asn Ser Ile Lys Tyr Ser Thr Leu
            405                 410                 415
Leu Glu Ser Glu Lys Asn Thr Phe Met Glu Ile Trp Lys Lys Arg Trp
            420                 425                 430
Asp Lys Phe Ile Ala Asp Val Ala Thr Lys
        435                 440

<210> SEQ ID NO 277
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Ile Asp Glu Thr Arg Ala His Leu Leu Lys Glu Lys Met Met Arg
1               5                   10                  15
```

Leu Gly Gly Arg Leu Val Leu Asn Thr Lys Glu Glu Leu Ala Asn Glu
            20                  25                  30

Arg Leu Met Thr Leu Lys Ile Ala Glu Met Lys Glu Ala Met Arg Thr
        35                  40                  45

Leu Ile Phe Pro Pro Ser Met His Phe Phe Gln Ala Lys His Leu Ile
50                  55                  60

Glu Arg Ser Gln Val Phe Asn Ile Leu Arg Met Met Pro Lys Gly Ala
65                  70                  75                  80

Ala Leu His Leu His Asn Ile Gly Ile Val Thr Met Asp Trp Leu Gly
                85                  90                  95

Gly Gly Gly Ser Gly Gly Gly Ser Val Thr Glu Phe Asp Asp Ser
            100                 105                 110

Leu Leu Arg Asn Phe Thr Leu Val Thr Gln His Pro Glu Val Ile Tyr
        115                 120                 125

Thr Asn Gln Asn Val Val Trp Ser Lys Phe Glu Thr Ile Phe Phe Thr
130                 135                 140

Ile Ser Gly Leu Ile His Tyr Ala Pro Val Phe Arg Asp Tyr Val Phe
145                 150                 155                 160

Arg Ser Met Gln Glu Phe Tyr Glu Asp Asn Val Leu Tyr Met Glu Ile
                165                 170                 175

Arg Ala Arg Leu Leu Pro Val Tyr Glu Leu Ser Gly Glu His His Asp
        180                 185                 190

Glu Glu Trp Ser Val Lys Thr Tyr Gln Glu Val Ala Gln Asp Phe Val
            195                 200                 205

Glu Thr His Pro Glu Phe Ile Gly Ile Lys Ile Tyr Ser Asp His
210                 215                 220

Arg Ser Tyr Asp Val Ala Val Ile Ala Glu Ser Ile Arg Met Ala Met
225                 230                 235                 240

Gly Leu Arg Ile Lys Phe Pro Thr Val Val Ala Gly Phe Asp Leu Val
            245                 250                 255

Gly His Glu Asp Thr Gly His Ser Leu His Asp Tyr Lys Glu Ala Leu
        260                 265                 270

Met Ile Pro Ala Lys Asp Gly Val Lys Leu Pro Tyr Phe Phe His Ala
    275                 280                 285

Gly Glu Thr Asp Trp Gln Gly Thr Ser Ile Asp Arg Asn Ile Leu Asp
290                 295                 300

Ala Leu Met Leu Asn Thr Thr Arg Ile Gly His Gly Phe Ala Leu Ser
305                 310                 315                 320

Lys His Pro Ala Val Arg Thr Tyr Ser Trp Lys Lys Asp Ile Pro Ile
                325                 330                 335

Glu Val Cys Pro Ile Ser Asn Gln Val Leu Lys Leu Val Ser Asp Leu
        340                 345                 350

Arg Asn His Pro Val Ala Thr Leu Met Ala Thr Gly His Pro Met Val
            355                 360                 365

Ile Ser Ser Asp Asp Pro Ala Met Phe Gly Ala Lys Gly Leu Ser Tyr
        370                 375                 380

Asp Phe Tyr Glu Val Phe Met Gly Ile Gly Gly Met Lys Ala Asp Leu
385                 390                 395                 400

Arg Thr Leu Lys Gln Leu Ala Met Asn Ser Ile Lys Tyr Ser Thr Leu
                405                 410                 415

Leu Glu Ser Glu Lys Asn Thr Phe Met Glu Ile Trp Lys Lys Arg Trp
            420                 425                 430

Asp Lys Phe Ile Ala Asp Val Ala Thr Lys

```
                435                 440
```

<210> SEQ ID NO 278
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Ile Asp Glu Thr Arg Ala His Leu Leu Lys Glu Lys Met Met Arg
1               5                   10                  15

Leu Gly Gly Arg Leu Val Leu Asn Thr Lys Glu Glu Leu Ala Asn Glu
            20                  25                  30

Arg Leu Met Thr Leu Lys Ile Ala Glu Met Lys Glu Ala Met Arg Thr
        35                  40                  45

Leu Ile Phe Pro Pro Ser Met His Phe Phe Gln Ala Lys His Leu Ile
    50                  55                  60

Glu Arg Ser Gln Val Phe Asn Ile Leu Arg Met Met Pro Lys Gly Ala
65                  70                  75                  80

Ala Leu His Leu His Asp Ile Gly Ile Val Thr Met Asp Trp Leu Val
                85                  90                  95

Arg Asn Val Thr Tyr Arg Pro His Cys His Ile Cys Phe Thr Pro Arg
            100                 105                 110

Gly Ile Met Gln Phe Arg Phe Ala His Pro Thr Pro Arg Pro Ser Glu
        115                 120                 125

Lys Cys Ser Lys Trp Ile Leu Leu Glu Asp Tyr Arg Lys Arg Val Gln
    130                 135                 140

Asn Val Thr Glu Phe Asp Asp Ser Leu Leu Arg Asn Phe Thr Leu Val
145                 150                 155                 160

Thr Gln His Pro Glu Val Ile Tyr Thr Asn Gln Asn Val Val Trp Ser
                165                 170                 175

Lys Phe Glu Thr Ile Phe Phe Thr Ile Ser Gly Leu Ile His Tyr Ala
            180                 185                 190

Pro Val Phe Arg Asp Tyr Val Phe Arg Ser Met Gln Glu Phe Tyr Glu
        195                 200                 205

Asp Asn Val Leu Tyr Met Glu Ile Arg Ala Arg Leu Leu Pro Val Tyr
    210                 215                 220

Glu Leu Ser Gly Glu His His Asp Glu Glu Trp Ser Val Lys Thr Tyr
225                 230                 235                 240

Gln Glu Val Ala Gln Lys Phe Val Glu Thr His Pro Glu Phe Ile Gly
                245                 250                 255

Ile Lys Ile Ile Tyr Ser Asp His Arg Ser Lys Asp Val Ala Val Ile
            260                 265                 270

Ala Glu Ser Ile Arg Met Ala Met Gly Leu Arg Ile Lys Phe Pro Thr
        275                 280                 285

Val Val Ala Gly Phe Asp Leu Val Gly His Glu Asp Thr Gly His Ser
    290                 295                 300

Leu His Asp Tyr Lys Glu Ala Leu Met Ile Pro Ala Lys Asp Gly Val
305                 310                 315                 320

Lys Leu Pro Tyr Phe Phe His Ala Gly Glu Thr Asp Trp Gln Gly Thr
                325                 330                 335

Ser Ile Asp Arg Asn Ile Leu Asp Ala Leu Met Leu Asn Thr Thr Arg
            340                 345                 350
```

```
Ile Gly His Gly Phe Ala Leu Ser Lys His Pro Ala Val Arg Thr Tyr
            355                 360                 365

Ser Trp Lys Lys Asp Ile Pro Ile Glu Val Cys Pro Ile Ser Asn Gln
370                 375                 380

Val Leu Lys Leu Val Ser Asp Leu Arg Asn His Pro Val Ala Thr Leu
385                 390                 395                 400

Met Ala Thr Gly His Pro Met Val Ile Ser Ser Asp Pro Ala Met
                    405                 410                 415

Phe Gly Ala Lys Gly Leu Ser Tyr Asp Phe Tyr Glu Val Phe Met Gly
            420                 425                 430

Ile Gly Gly Met Lys Ala Asp Leu Arg Thr Leu Lys Gln Leu Ala Met
            435                 440                 445

Asn Ser Ile Lys Tyr Ser Thr Leu Leu Glu Ser Glu Lys Asn Thr Phe
450                 455                 460

Met Glu Ile Trp Lys Lys Arg Trp Asp Lys Phe Ile Ala Asp Val Ala
465                 470                 475                 480

Thr Lys
```

<210> SEQ ID NO 279
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Ile Asp Glu Thr Arg Ala His Leu Leu Lys Glu Lys Met Met Arg
1               5                   10                  15

Leu Gly Gly Arg Leu Val Leu Asn Thr Lys Glu Glu Leu Ala Asn Glu
                20                  25                  30

Arg Leu Met Thr Leu Lys Ile Ala Glu Met Lys Glu Ala Met Arg Thr
                35                  40                  45

Leu Ile Phe Pro Pro Ser Met His Phe Phe Gln Ala Lys His Leu Ile
    50                  55                  60

Glu Arg Ser Gln Val Phe Asn Ile Leu Arg Met Met Pro Lys Gly Ala
65                  70                  75                  80

Ala Leu His Leu His Asp Ile Gly Ile Val Thr Met Asp Trp Leu Val
                85                  90                  95

Arg Asn Val Thr Tyr Arg Pro His Cys His Ile Cys Phe Thr Pro Arg
                100                 105                 110

Gly Ile Met Gln Phe Arg Phe Ala His Pro Thr Pro Arg Pro Ser Glu
            115                 120                 125

Lys Cys Ser Lys Trp Ile Leu Leu Glu Asp Tyr Arg Lys Arg Val Gln
130                 135                 140

Asn Val Thr Glu Phe Asp Asp Ser Leu Leu Arg Asn Phe Thr Leu Val
145                 150                 155                 160

Thr Gln His Pro Glu Val Ile Tyr Thr Asn Gln Asn Val Val Trp Ser
                165                 170                 175

Lys Phe Glu Thr Ile Phe Phe Thr Ile Ser Gly Leu Ile His Tyr Ala
                180                 185                 190

Pro Val Phe Arg Asp Tyr Val Phe Arg Ser Met Gln Glu Phe Tyr Glu
            195                 200                 205

Asp Asn Val Leu Tyr Met Glu Ile Arg Ala Gln Leu Leu Pro Val Tyr
210                 215                 220
```

-continued

Glu Leu Ser Gly Glu His His Asp Glu Glu Trp Ser Val Lys Thr Tyr
225                 230                 235                 240

Gln Glu Val Ala Gln Lys Phe Val Glu Thr His Pro Glu Phe Ile Gly
            245                 250                 255

Ile Lys Ile Ile Tyr Asn Asp His Arg Ser Lys Asp Val Ala Val Ile
        260                 265                 270

Ala Glu Ser Ile Arg Met Ala Met Gly Leu Arg Ile Lys Phe Pro Thr
    275                 280                 285

Val Val Ala Gly Phe Asp Leu Val Gly His Glu Asp Thr Gly His Ser
290                 295                 300

Leu His Asp Tyr Lys Glu Ala Leu Met Ile Pro Ala Lys Asp Gly Val
305                 310                 315                 320

Lys Leu Pro Tyr Phe Phe His Ala Gly Glu Thr Asp Trp Gln Gly Thr
            325                 330                 335

Ser Ile Asp Arg Asn Ile Leu Asp Ala Leu Met Leu Asn Thr Thr Arg
        340                 345                 350

Ile Gly His Gly Phe Ala Leu Ser Lys His Pro Ala Val Arg Thr Tyr
    355                 360                 365

Ser Trp Asp Lys Asp Ile Pro Ile Glu Val Cys Pro Ile Ser Asn Gln
370                 375                 380

Val Leu Lys Leu Val Ser Asp Leu Arg Asn His Pro Val Ala Thr Leu
385                 390                 395                 400

Met Ala Thr Gly His Pro Met Val Ile Ser Asp Asp Pro Ala Met
            405                 410                 415

Phe Gly Ala Lys Gly Leu Ser Tyr Asp Phe Tyr Glu Val Phe Met Gly
            420                 425                 430

Ile Gly Gly Met Lys Ala Asp Leu Arg Thr Leu Lys Gln Leu Ala Met
        435                 440                 445

Asn Ser Ile Lys Tyr Ser Thr Leu Leu Glu Ser Glu Lys Asn Thr Phe
    450                 455                 460

Met Glu Ile Trp Lys Lys Arg Trp Asp Lys Phe Ile Ala Asp Val Ala
465                 470                 475                 480

Thr Lys

<210> SEQ ID NO 280
<211> LENGTH: 932
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

-continued

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys Gly Gly Gly Ser Gly Gly Gly
        435                 440                 445

Gly Ser Ile Asp Glu Thr Arg Ala His Leu Leu Leu Lys Glu Lys Met
450                 455                 460

Met Arg Leu Gly Gly Arg Leu Val Leu Asn Thr Lys Glu Glu Leu Ala
465                 470                 475                 480

Asn Glu Arg Leu Met Thr Leu Lys Ile Ala Glu Met Lys Glu Ala Met
                485                 490                 495

Arg Thr Leu Ile Phe Pro Pro Ser Met His Phe Phe Gln Ala Lys His
            500                 505                 510

Leu Ile Glu Arg Ser Gln Val Phe Asn Ile Leu Arg Met Met Pro Lys

```
            515                 520                 525
Gly Ala Ala Leu His Leu His Asp Ile Gly Ile Val Thr Met Asp Trp
    530                 535                 540
Leu Val Arg Asn Val Thr Tyr Arg Pro His Cys His Ile Cys Phe Thr
545                 550                 555                 560
Pro Arg Gly Ile Met Gln Phe Arg Phe Ala His Pro Thr Pro Arg Pro
                    565                 570                 575
Ser Glu Lys Cys Ser Lys Trp Ile Leu Leu Glu Asp Tyr Arg Lys Arg
                580                 585                 590
Val Gln Asn Val Thr Glu Phe Asp Asp Ser Leu Leu Arg Asn Phe Thr
            595                 600                 605
Leu Val Thr Gln His Pro Glu Val Ile Tyr Thr Asn Gln Asn Val Val
        610                 615                 620
Trp Ser Lys Phe Glu Thr Ile Phe Phe Thr Ile Ser Gly Leu Ile His
625                 630                 635                 640
Tyr Ala Pro Val Phe Arg Asp Tyr Val Phe Arg Ser Met Gln Glu Phe
                    645                 650                 655
Tyr Glu Asp Asn Val Leu Tyr Met Glu Ile Arg Ala Arg Leu Leu Pro
                660                 665                 670
Val Tyr Glu Leu Ser Gly Glu His Asp Glu Glu Trp Ser Val Lys
            675                 680                 685
Thr Tyr Gln Glu Val Ala Gln Lys Phe Val Thr His Pro Glu Phe
        690                 695                 700
Ile Gly Ile Lys Ile Ile Tyr Ser Asp His Arg Ser Lys Asp Val Ala
705                 710                 715                 720
Val Ile Ala Glu Ser Ile Arg Met Ala Met Gly Leu Arg Ile Lys Phe
                    725                 730                 735
Pro Thr Val Val Ala Gly Phe Asp Leu Val Gly His Glu Asp Thr Gly
                740                 745                 750
His Ser Leu His Asp Tyr Lys Glu Ala Leu Met Ile Pro Ala Lys Asp
            755                 760                 765
Gly Val Lys Leu Pro Tyr Phe Phe His Ala Gly Glu Thr Asp Trp Gln
        770                 775                 780
Gly Thr Ser Ile Asp Arg Asn Ile Leu Asp Ala Leu Met Leu Asn Thr
785                 790                 795                 800
Thr Arg Ile Gly His Gly Phe Ala Leu Ser Lys His Pro Ala Val Arg
                    805                 810                 815
Thr Tyr Ser Trp Lys Lys Asp Ile Pro Ile Glu Val Cys Pro Ile Ser
                820                 825                 830
Asn Gln Val Leu Lys Leu Val Ser Asp Leu Arg Asn His Pro Val Ala
            835                 840                 845
Thr Leu Met Ala Thr Gly His Pro Met Val Ile Ser Ser Asp Asp Pro
        850                 855                 860
Ala Met Phe Gly Ala Lys Gly Leu Ser Tyr Asp Phe Tyr Glu Val Phe
865                 870                 875                 880
Met Gly Ile Gly Gly Met Lys Ala Asp Leu Arg Thr Leu Lys Gln Leu
                    885                 890                 895
Ala Met Asn Ser Ile Lys Tyr Ser Thr Leu Leu Glu Ser Glu Lys Asn
                900                 905                 910
Thr Phe Met Glu Ile Trp Lys Lys Arg Trp Asp Lys Phe Ile Ala Asp
            915                 920                 925
Val Ala Thr Lys
        930
```

<210> SEQ ID NO 281
<211> LENGTH: 932
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 281

```
Gln Val Gln Leu Val Glu Ser Gly Gly Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
```

```
                355                 360                 365
Asp Ile Ala Val Glu Trp Glu Ser Asn Gly Gln Pro Glu Asn Asn Tyr
370                 375                 380
Lys Thr Thr Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
            405                 410                 415
Ser Cys Ser Val Met His Glu Ala Leu His Asn His Tyr Thr Gln Lys
            420                 425                 430
Ser Leu Ser Leu Ser Pro Gly Lys Gly Gly Gly Ser Gly Gly Gly
        435                 440                 445
Gly Ser Ile Asp Glu Thr Arg Ala His Leu Leu Lys Glu Lys Met
    450                 455                 460
Met Arg Leu Gly Gly Arg Leu Val Leu Asn Thr Lys Glu Glu Leu Ala
465                 470                 475                 480
Asn Glu Arg Leu Met Thr Leu Lys Ile Ala Glu Met Lys Glu Ala Met
                485                 490                 495
Arg Thr Leu Ile Phe Pro Pro Ser Met His Phe Phe Gln Ala Lys His
            500                 505                 510
Leu Ile Glu Arg Ser Gln Val Phe Asn Ile Leu Arg Met Met Pro Lys
        515                 520                 525
Gly Ala Ala Leu His Leu His Asp Ile Gly Ile Val Thr Met Asp Trp
    530                 535                 540
Leu Val Arg Asn Val Thr Tyr Arg Pro His Cys His Ile Cys Phe Thr
545                 550                 555                 560
Pro Arg Gly Ile Met Gln Phe Arg Phe Ala His Pro Thr Pro Arg Pro
                565                 570                 575
Ser Glu Lys Cys Ser Lys Trp Ile Leu Leu Glu Asp Tyr Arg Lys Arg
            580                 585                 590
Val Gln Asn Val Thr Glu Phe Asp Asp Ser Leu Leu Arg Asn Phe Thr
        595                 600                 605
Leu Val Thr Gln His Pro Glu Val Ile Tyr Thr Asn Gln Asn Val Val
    610                 615                 620
Trp Ser Lys Phe Glu Thr Ile Phe Phe Thr Ile Ser Gly Leu Ile His
625                 630                 635                 640
Tyr Ala Pro Val Phe Arg Asp Tyr Val Phe Arg Ser Met Gln Glu Phe
                645                 650                 655
Tyr Glu Asp Asn Val Leu Tyr Met Glu Ile Arg Ala Gln Leu Leu Pro
            660                 665                 670
Val Tyr Glu Leu Ser Gly Glu His His Asp Glu Glu Trp Ser Val Lys
        675                 680                 685
Thr Tyr Gln Glu Val Ala Gln Lys Phe Val Glu Thr His Pro Glu Phe
    690                 695                 700
Ile Gly Ile Lys Ile Ile Tyr Asn Asp His Arg Ser Lys Asp Val Ala
705                 710                 715                 720
Val Ile Ala Glu Ser Ile Arg Met Ala Met Gly Leu Arg Ile Lys Phe
                725                 730                 735
Pro Thr Val Val Ala Gly Phe Asp Leu Val Gly His Glu Asp Thr Gly
            740                 745                 750
His Ser Leu His Asp Tyr Lys Glu Ala Leu Met Ile Pro Ala Lys Asp
        755                 760                 765
Gly Val Lys Leu Pro Tyr Phe Phe His Ala Gly Glu Thr Asp Trp Gln
    770                 775                 780
```

-continued

```
Gly Thr Ser Ile Asp Arg Asn Ile Leu Asp Ala Leu Met Leu Asn Thr
785                 790                 795                 800

Thr Arg Ile Gly His Gly Phe Ala Leu Ser Lys His Pro Ala Val Arg
            805                 810                 815

Thr Tyr Ser Trp Asp Lys Asp Ile Pro Ile Glu Val Cys Pro Ile Ser
        820                 825                 830

Asn Gln Val Leu Lys Leu Val Ser Asp Leu Arg Asn His Pro Val Ala
            835                 840                 845

Thr Leu Met Ala Thr Gly His Pro Met Val Ile Ser Ser Asp Asp Pro
    850                 855                 860

Ala Met Phe Gly Ala Lys Gly Leu Ser Tyr Asp Phe Tyr Glu Val Phe
865                 870                 875                 880

Met Gly Ile Gly Gly Met Lys Ala Asp Leu Arg Thr Leu Lys Gln Leu
            885                 890                 895

Ala Met Asn Ser Ile Lys Tyr Ser Thr Leu Leu Glu Ser Glu Lys Asn
        900                 905                 910

Thr Phe Met Glu Ile Trp Lys Lys Arg Trp Asp Lys Phe Ile Ala Asp
    915                 920                 925

Val Ala Thr Lys
    930

<210> SEQ ID NO 282
<211> LENGTH: 939
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
            85                  90                  95

Ala Arg Arg Asp Tyr Arg Phe Asp Met Gly Phe Asp Tyr Trp Gly Gln
        100                 105                 110

Gly Thr Thr Val Thr Val Ser Ser Ala Ser Thr Lys Gly Pro Ser Val
    115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
```

```
                195                 200                 205
Pro Ser Asn Thr Lys Val Asp Lys Arg Val Glu Ser Lys Tyr Gly Pro
210                 215                 220

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro Gly Lys Gly
            435                 440                 445

Gly Gly Gly Ser Gly Gly Gly Ser Ile Asp Glu Thr Arg Ala His
450                 455                 460

Leu Leu Leu Lys Glu Lys Met Met Arg Leu Gly Gly Arg Leu Val Leu
465                 470                 475                 480

Asn Thr Lys Glu Glu Leu Ala Asn Glu Arg Leu Met Thr Leu Lys Ile
                485                 490                 495

Ala Glu Met Lys Glu Ala Met Arg Thr Leu Ile Phe Pro Pro Ser Met
                500                 505                 510

His Phe Phe Gln Ala Lys His Leu Ile Glu Arg Ser Gln Val Phe Asn
            515                 520                 525

Ile Leu Arg Met Met Pro Lys Gly Ala Ala Leu Leu His Asp Ile
530                 535                 540

Gly Ile Val Thr Met Asp Trp Leu Val Arg Asn Val Thr Tyr Arg Pro
545                 550                 555                 560

His Cys His Ile Cys Phe Thr Pro Arg Gly Ile Met Gln Phe Arg Phe
                565                 570                 575

Ala His Pro Thr Pro Arg Pro Ser Glu Lys Cys Ser Lys Trp Ile Leu
                580                 585                 590

Leu Glu Asp Tyr Arg Lys Arg Val Gln Asn Val Thr Glu Phe Asp Asp
            595                 600                 605

Ser Leu Leu Arg Asn Phe Thr Leu Val Thr Gln His Pro Glu Val Ile
610                 615                 620
```

Tyr Thr Asn Gln Asn Val Val Trp Ser Lys Phe Glu Thr Ile Phe Phe
625                 630                 635                 640

Thr Ile Ser Gly Leu Ile His Tyr Ala Pro Val Phe Arg Asp Tyr Val
            645                 650                 655

Phe Arg Ser Met Gln Glu Phe Tyr Glu Asp Asn Val Leu Tyr Met Glu
            660                 665                 670

Ile Arg Ala Arg Leu Leu Pro Val Tyr Glu Leu Ser Gly Glu His His
            675                 680                 685

Asp Glu Glu Trp Ser Val Lys Thr Tyr Gln Glu Val Ala Gln Lys Phe
690                 695                 700

Val Glu Thr His Pro Glu Phe Ile Gly Ile Lys Ile Ile Tyr Ser Asp
705                 710                 715                 720

His Arg Ser Lys Asp Val Ala Val Ile Ala Glu Ser Ile Arg Met Ala
                725                 730                 735

Met Gly Leu Arg Ile Lys Phe Pro Thr Val Val Ala Gly Phe Asp Leu
            740                 745                 750

Val Gly His Glu Asp Thr Gly His Ser Leu His Asp Tyr Lys Glu Ala
            755                 760                 765

Leu Met Ile Pro Ala Lys Asp Gly Val Lys Leu Pro Tyr Phe Phe His
770                 775                 780

Ala Gly Glu Thr Asp Trp Gln Gly Thr Ser Ile Asp Arg Asn Ile Leu
785                 790                 795                 800

Asp Ala Leu Met Leu Asn Thr Thr Arg Ile Gly His Gly Phe Ala Leu
                805                 810                 815

Ser Lys His Pro Ala Val Arg Thr Tyr Ser Trp Lys Lys Asp Ile Pro
            820                 825                 830

Ile Glu Val Cys Pro Ile Ser Asn Gln Val Leu Lys Leu Val Ser Asp
            835                 840                 845

Leu Arg Asn His Pro Val Ala Thr Leu Met Ala Thr Gly His Pro Met
850                 855                 860

Val Ile Ser Ser Asp Asp Pro Ala Met Phe Gly Ala Lys Gly Leu Ser
865                 870                 875                 880

Tyr Asp Phe Tyr Glu Val Phe Met Gly Ile Gly Gly Met Lys Ala Asp
                885                 890                 895

Leu Arg Thr Leu Lys Gln Leu Ala Met Asn Ser Ile Lys Tyr Ser Thr
            900                 905                 910

Leu Leu Glu Ser Glu Lys Asn Thr Phe Met Glu Ile Trp Lys Lys Arg
            915                 920                 925

Trp Asp Lys Phe Ile Ala Asp Val Ala Thr Lys
930                 935

<210> SEQ ID NO 283
<211> LENGTH: 939
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met

```
            35                  40                  45
Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Pro Gly Lys Gly
                435                 440                 445

Gly Gly Gly Ser Gly Gly Gly Gly Ser Ile Asp Glu Thr Arg Ala His
                450                 455                 460
```

```
Leu Leu Leu Lys Glu Lys Met Met Arg Leu Gly Gly Arg Leu Val Leu
465                 470                 475                 480

Asn Thr Lys Glu Glu Leu Ala Asn Glu Arg Leu Met Thr Leu Lys Ile
                    485                 490                 495

Ala Glu Met Lys Glu Ala Met Arg Thr Leu Ile Phe Pro Pro Ser Met
                500                 505                 510

His Phe Phe Gln Ala Lys His Leu Ile Glu Arg Ser Gln Val Phe Asn
            515                 520                 525

Ile Leu Arg Met Met Pro Lys Gly Ala Ala Leu His Leu His Asp Ile
        530                 535                 540

Gly Ile Val Thr Met Asp Trp Leu Val Arg Asn Val Thr Tyr Arg Pro
545                 550                 555                 560

His Cys His Ile Cys Phe Thr Pro Arg Gly Ile Met Gln Phe Arg Phe
                565                 570                 575

Ala His Pro Thr Pro Arg Pro Ser Glu Lys Cys Ser Lys Trp Ile Leu
                580                 585                 590

Leu Glu Asp Tyr Arg Lys Arg Val Gln Asn Val Thr Glu Phe Asp Asp
            595                 600                 605

Ser Leu Leu Arg Asn Phe Thr Leu Val Thr Gln His Pro Glu Val Ile
        610                 615                 620

Tyr Thr Asn Gln Asn Val Val Trp Ser Lys Phe Glu Thr Ile Phe Phe
625                 630                 635                 640

Thr Ile Ser Gly Leu Ile His Tyr Ala Pro Val Phe Arg Asp Tyr Val
                645                 650                 655

Phe Arg Ser Met Gln Glu Phe Tyr Glu Asp Asn Val Leu Tyr Met Glu
                660                 665                 670

Ile Arg Ala Gln Leu Leu Pro Val Tyr Glu Leu Ser Gly Glu His His
            675                 680                 685

Asp Glu Glu Trp Ser Val Lys Thr Tyr Gln Glu Val Ala Gln Lys Phe
        690                 695                 700

Val Glu Thr His Pro Glu Phe Ile Gly Ile Lys Ile Ile Tyr Asn Asp
705                 710                 715                 720

His Arg Ser Lys Asp Val Ala Val Ile Ala Glu Ser Ile Arg Met Ala
                725                 730                 735

Met Gly Leu Arg Ile Lys Phe Pro Thr Val Val Ala Gly Phe Asp Leu
                740                 745                 750

Val Gly His Glu Asp Thr Gly His Ser Leu His Asp Tyr Lys Glu Ala
            755                 760                 765

Leu Met Ile Pro Ala Lys Asp Gly Val Lys Leu Pro Tyr Phe Phe His
        770                 775                 780

Ala Gly Glu Thr Asp Trp Gln Gly Thr Ser Ile Asp Arg Asn Ile Leu
785                 790                 795                 800

Asp Ala Leu Met Leu Asn Thr Thr Arg Ile Gly His Gly Phe Ala Leu
                805                 810                 815

Ser Lys His Pro Ala Val Arg Thr Tyr Ser Trp Asp Lys Asp Ile Pro
                820                 825                 830

Ile Glu Val Cys Pro Ile Ser Asn Gln Val Leu Lys Leu Val Ser Asp
            835                 840                 845

Leu Arg Asn His Pro Val Ala Thr Leu Met Ala Thr Gly His Pro Met
        850                 855                 860

Val Ile Ser Ser Asp Asp Pro Ala Met Phe Gly Ala Lys Gly Leu Ser
865                 870                 875                 880
```

```
Tyr Asp Phe Tyr Glu Val Phe Met Gly Ile Gly Met Lys Ala Asp
            885                 890                 895

Leu Arg Thr Leu Lys Gln Leu Ala Met Asn Ser Ile Lys Tyr Ser Thr
            900                 905                 910

Leu Leu Glu Ser Glu Lys Asn Thr Phe Met Glu Ile Trp Lys Lys Arg
            915                 920                 925

Trp Asp Lys Phe Ile Ala Asp Val Ala Thr Lys
            930                 935

<210> SEQ ID NO 284
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Ser Ile Asp Glu Thr Arg Ala His Leu Leu Lys Glu Lys Met Met
1                5                  10                  15

Arg Leu Gly Gly Arg Leu Val Leu Asn Thr Lys Glu Glu Leu Ala Asn
            20                  25                  30

Glu Arg Leu Met Thr Leu Lys Ile Ala Glu Met Lys Glu Ala Met Arg
        35                  40                  45

Thr Leu Ile Phe Pro Pro Ser Met His Phe Phe Gln Ala Lys His Leu
    50                  55                  60

Ile Glu Arg Ser Gln Val Phe Asn Ile Leu Arg Met Met Pro Lys Gly
65                  70                  75                  80

Ala Ala Leu His Leu His Asp Ile Gly Ile Val Thr Met Asp Trp Leu
                85                  90                  95

Val Arg Asn Val Thr Tyr Arg Pro His Cys His Ile Cys Phe Thr Pro
            100                 105                 110

Arg Gly Ile Met Gln Phe Arg Phe Ala His Pro Thr Pro Arg Pro Ser
        115                 120                 125

Glu Lys Cys Ser Lys Trp Ile Leu Leu Glu Asp Tyr Arg Lys Arg Val
    130                 135                 140

Gln Asn Val Thr Glu Phe Asp Asp Ser Leu Leu Arg Asn Phe Thr Leu
145                 150                 155                 160

Val Thr Gln His Pro Glu Val Ile Tyr Thr Asn Gln Asn Val Val Trp
                165                 170                 175

Ser Lys Phe Glu Thr Ile Phe Phe Thr Ile Ser Gly Leu Ile His Tyr
            180                 185                 190

Ala Pro Val Phe Arg Asp Tyr Val Phe Arg Ser Met Gln Glu Phe Tyr
        195                 200                 205

Glu Asp Asn Val Leu Tyr Met Glu Ile Arg Ala Arg Leu Leu Pro Val
    210                 215                 220

Tyr Glu Leu Ser Gly Glu His His Asp Glu Glu Trp Ser Val Lys Thr
225                 230                 235                 240

Tyr Gln Glu Val Ala Gln Lys Phe Val Glu Thr His Pro Glu Phe Ile
                245                 250                 255

Gly Ile Lys Ile Ile Tyr Ser Asp His Arg Ser Lys Asp Val Ala Val
            260                 265                 270

Ile Ala Glu Ser Ile Arg Met Ala Met Gly Leu Arg Ile Lys Phe Pro
        275                 280                 285

Thr Val Val Ala Gly Phe Asp Leu Val Gly His Glu Asp Thr Gly His
    290                 295                 300
```

Ser Leu His Asp Tyr Lys Glu Ala Leu Met Ile Pro Ala Lys Asp Gly
305                 310                 315                 320

Val Lys Leu Pro Tyr Phe Phe His Ala Gly Glu Thr Asp Trp Gln Gly
            325                 330                 335

Thr Ser Ile Asp Arg Asn Ile Leu Asp Ala Leu Met Leu Asn Thr Thr
            340                 345                 350

Arg Ile Gly His Gly Phe Ala Leu Ser Lys His Pro Ala Val Arg Thr
            355                 360                 365

Tyr Ser Trp Lys Lys Asp Ile Pro Ile Glu Val Cys Pro Ile Ser Asn
370                 375                 380

Gln Val Leu Lys Leu Val Ser Asp Leu Arg Asn His Pro Val Ala Thr
385                 390                 395                 400

Leu Met Ala Thr Gly His Pro Met Val Ile Ser Ser Asp Asp Pro Ala
                405                 410                 415

Met Phe Gly Ala Lys Gly Leu Ser Tyr Asp Phe Tyr Glu Val Phe Met
            420                 425                 430

Gly Ile Gly Gly Met Lys Ala Asp Leu Arg Thr Leu Lys Gln Leu Ala
            435                 440                 445

Met Asn Ser Ile Lys Tyr Ser Thr Leu Leu Glu Ser Glu Lys Asn Thr
450                 455                 460

Phe Met Glu Ile Trp Lys Lys Arg Trp Asp Lys Phe Ile Ala Asp Val
465                 470                 475                 480

Ala Thr Lys

<210> SEQ ID NO 285
<211> LENGTH: 2796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 285
caggtgcagc tggtcgaaag cggaggagga gtggtccagc caggacgatc cctgagactg      60
gattgtaagg cctctggaat cacattctct aacagtggaa tgcactgggt gcgccaggca     120
ccaggaaaag gactgagtg gtggccgtc atctggtacg acgggtcaaa gcgatactat      180
gcagatagcg tgaaaggaag gttcacaatt tcacgcgaca cagcaagaa tactctgttt     240 ctgcagatga actctctgag agcagaggat actgccgtgt actattgtgc taccaatgac     300
gattattggg gcagggaac tctggtgacc gtcagttcag ctagcaccaa gggcccatcg     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660
ccatgcccag cacctgagtt cctgggggga ccatcagtct tcctgttccc cccaaaaccc     720
aaggacactc tcatgatctc ccggacccct gaggtcacgt gcgtggtggt ggacgtgagc     780
caggaagacc ccgaggtcca gttcaactgg tacgtggatg gcgtggaggt gcataatgcc     840
aagacaaagc cgcgggagga gcagttcaac agcacgtacc gtgtggtcag cgtcctcacc     900
gtcctgcacc aggactggct gaacggcaag gagtacaagt gcaaggtctc caacaaaggc     960

-continued

```
ctcccgtcct ccatcgagaa aaccatctcc aaagccaaag ggcagccccg agagccacag   1020
gtgtacaccc tgcccccatc ccaggaggag atgaccaaga accaggtcag cctgacctgc   1080
ctggtcaaag gcttctaccc cagcgacatc gccgtggagt gggagagcaa tgggcagccg   1140
gagaacaact acaagaccac gcctcccgtg ctggactccg acggctcctt cttcctctac   1200
agcaggctca ccgtggacaa gagcaggtgg caggagggga atgtcttctc atgctccgtg   1260
atgcatgagg ctctgcacaa ccactacaca cagaagagcc tctccctgtc tccgggtaaa   1320
ggtggaggtg gttctggagg tggaggtagt atcgacgaaa ccagagcaca cttactgctg   1380
aaagagaaaa tgatgcgcct gggcgggaga ttggtgttaa atactaagga agagctggca   1440
aatgaaagac tcatgacact gaagattgct gaaatgaagg aggcgatgag gacgctgatc   1500
tttccgcctt ccatgcactt cttccaagct aaacacctga tcgaaagatc ccaagtgttt   1560
aacatcctga ggatgatgcc taaggggggcc gctctgcacc ttcacgatat tgggattgta   1620
acaatggact ggctggtaag gaacgtgaca tacagacctc attgccatat ttgttttact   1680 cccgaggaa tcatgcaatt caggtttgcc cacccaactc ctcggccaag cgagaagtgt   1740
agtaagtgga ttttgctgga agattaccgt aagcgcgtgc agaatgtgac agagtttgat   1800
gactccctgc tccgcaattt taccctggtg acccagcacc ccgaagttat atacactaac   1860
caaaatgtcg tgtggtccaa gtttgagacg atcttcttca cgatttcagg cttgatccac   1920
tacgccccgg tctttcggga ttatgtgttt aggagtatgc aggagtttta tgaggataat   1980
gttctgtaca tggagatccg agcccggctg cttccagtct acgaactatc cggcgaacac   2040
catgacgagg aatggagcgt caagacctat caagaggtgg cccagaagtt cgtagaaacg   2100
catccagagt tcatcggtat taagattatc tactctgatc accgctcaaa ggatgtggct   2160
gtcatcgccg agtctatacg gatggccatg ggcctgcgga ttaagttccc taccgtcgtc   2220
gccggattcg acctcgttgg gcatgaggat actggccata gtctccatga ctataaagaa   2280
gcccttatga tcccagcaaa ggacggagtg aagctgcccct acttcttcca cgcaggggag   2340
accgactggc agggaacgag catcgaccgg aacatacttg atgcactcat gcttaatacc   2400
acacgaatcg gccacggctt cgctctctcc aagcacccag ccgtgagaac ctacagctgg   2460
aagaaggata tccccatcga ggtttgtccc atcagcaatc aggtgctgaa attggtgagt   2520
gacctgagaa accacccagt cgcaacatta atggccactg ccaccctat ggtgatttca   2580 agcgatgatc cagccatgtt cggagcaaaa ggactcagtt acgacttcta tgaggtattc   2640
atgggtattg gtggtatgaa ggcagacctg cggactctta agcagttggc aatgaactca   2700
attaagtact ctaccttatt ggagtctgaa aagaacacat ttatggagat ctggaaaaag   2760
cgctgggaca aattcatcgc agatgttgcc acaaaa                             2796
```

<210> SEQ ID NO 286
<211> LENGTH: 2796
<212> TYPE: DNA
<213> ORGANISM: Artificial Sequence
<220> FEATURE:
<223> OTHER INFORMATION: Description of Artificial Sequence: Synthetic
    polynucleotide <400> SEQUENCE: 286

```
caggtgcagc tggtcgaaag cggaggagga gtggtccagc caggacgatc cctgagactg    60
gattgtaagg cctctggaat cacattctct aacagtggaa tgcactgggt gcgccaggca   120
ccaggaaaag gactggagtg ggtggccgtc atctggtacg acgggtcaaa gcgatactat   180
```

```
gcagatagcg tgaaaggaag gttcacaatt tcacgcgaca acagcaagaa tactctgttt    240
ctgcagatga actctctgag agcagaggat actgccgtgt actattgtgc taccaatgac    300
gattattggg ggcagggaac tctggtgacc gtcagttcag ctagcaccaa gggcccatcg    360
gtcttccccc tggcgccctg ctccaggagc acctccgaga gcacagccgc cctgggctgc    420
ctggtcaagg actacttccc cgaaccggtg acggtgtcgt ggaactcagg cgccctgacc    480
agcggcgtgc acaccttccc ggctgtccta cagtcctcag gactctactc cctcagcagc    540
gtggtgaccg tgccctccag cagcttgggc acgaagacct acacctgcaa cgtagatcac    600
aagcccagca acaccaaggt ggacaagaga gttgagtcca atatggtccc ccatgccca    660 ccatgcccag cacctgagtt cctggggga ccatcagtct tcctgttccc cccaaaaccc    720
aaggacactc tcatgatctc ccggacccct gaggtcacgt gcgtggtggt ggacgtgagc    780
caggaagacc ccgaggtcca gttcaactgg tacgtggatg gcgtggaggt gcataatgcc    840
aagacaaagc cgcgggagga gcagttcaac agcacgtacc gtgtggtcag cgtcctcacc    900
gtcctgcacc aggactggct gaacggcaag gagtacaagt gcaaggtctc caacaaaggc    960
ctcccgtcct ccatcgagaa aaccatctcc aaagccaaag gcagccccg agagccacag   1020 gtgtacaccc tgcccccatc ccaggaggag atgaccaaga accaggtcag cctgacctgc   1080
ctggtcaaag gcttctaccc cagcgacatc gccgtggagt gggagagcaa tgggcagccg   1140
gagaacaact acaagaccac gcctcccgtg ctggactccg acggctcctt cttcctctac   1200
agcaggctca ccgtggacaa gagcaggtgg caggagggga atgtcttctc atgctccgtg   1260
atgcatgagg ctctgcacaa ccactacaca cagaagagcc tctccctgtc tccgggtaaa   1320
ggtggaggtg ttctggagg tggaggtagt atcgacgaaa ccagagcaca cttactgctg   1380
aaagagaaaa tgatgcgcct gggcgggaga ttggtgttaa atactaagga agagctggca   1440
aatgaaagac tcatgacact gaagattgct gaaatgaagg aggcgatgag gacgctgatc   1500
tttccgcctt ccatgcactt cttccaagct aaacacctga tcgaaagatc ccaagtgttt   1560
aacatcctga ggatgatgcc taagggggcc gctctgcacc ttcacgatat tgggattgta   1620
acaatggact ggctggtaag gaacgtgaca tacagacctc attgccatat ttgttttact   1680
ccccgaggaa tcatgcaatt caggtttgcc cacccaactc ctcggccaag cgagaagtgt   1740
agtaagtgga ttttgctgga agattaccgt aagcgcgtgc agaatgtgac agagtttgat   1800
gactccctgc tccgcaattt taccctggtg acccagcacc ccgaagttat atacactaac   1860
caaaatgtcg tgtggtccaa gtttgagacg atcttcttca cgatttcagg cttgatccac   1920
tacgccccgg tctttcggga ttatgtgttt aggagtatgc aggagtttta tgaggataat   1980
gttctgtaca tggagatccg agcccagctg cttccagtct acgaactatc cggcgaacac   2040
catgacgagg aatggagcgt caagacctat caagaggtgg cccagaagtt cgtagaaacg   2100
catccagagt tcatcggtat taagattatc tacaatgatc accgctcaaa ggatgtggct   2160
gtcatcgccg agtctatacg gatggccatg ggcctgcgga ttaagttccc taccgtcgtc   2220
gccggattcg acctcgttgg gcatgaggat actggccata gtctccatga ctataaagaa   2280
gcccttatga tcccagcaaa ggacggagtg aagctgccct acttcttcca cgcagggggag   2340 accgactggc agggaacgag catcgaccgg aacatacttg atgcactcat gcttaatacc   2400
acacgaatcg gccacggctt cgctctctcc aagcacccag ccgtgagaac ctacagctgg   2460
gataaggata tccccatcga ggtttgtccc atcagcaatc aggtgctgaa attggtgagt   2520
gacctgagaa accacccagt cgcaacatta atggccactg gccaccctat ggtgatttca   2580
```
agcgatgatc cagccatgtt cggagcaaaa ggactcagtt acgacttcta tgaggtattc    2640
atgggtattg gtggtatgaa ggcagacctg cggactctta agcagttggc aatgaactca    2700
attaagtact ctaccttatt ggagtctgaa agaacacat ttatggagat ctggaaaaag    2760
cgctgggaca aattcatcgc agatgttgcc acaaaa                              2796

<210> SEQ ID NO 287
<211> LENGTH: 2817
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 287
caggtgcagc tggtccagag cggcgtggaa gtcaagaaac ccggggcctc agtgaaggtc      60
agctgtaaag cttccggcta caccttcaca aactactata tgtattgggt gagacaggca     120
ccaggacagg gactggagtg gatgggcggg attaaccctg gtaatggagg cactaacttc     180
aacgaaaagt ttaaaaacag ggtgaccctg accacagatt caagcactac cacagcttac     240
atggagctga agtccctgca gtttgacgat acagccgtgt actattgtgc tcggagagac     300
tacaggttcg atatgggctt tgactattgg ggccagggga ctaccgtgac cgtctcctct     360
gctagcacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggctc accgtggaca agagcaggtg gcaggagggg    1260
aatgtcttct catgctccgt gatgcatgag gctctgcaca accactacac acagaagagc    1320 ctctcccctgt ctccgggtaa aggtggaggt ggttctggag gtggaggtag tatcgacgaa    1380
accagagcac acttactgct gaaagagaaa atgatgcgcc tgggcgggag attggtgtta    1440
aatactaagg aagagctggc aaatgaaaga ctcatgacac tgaagattgc tgaaatgaag    1500
gaggcgatga ggacgctgat ctttcgcgcct tccatgcact tcttccaagc taaacacctg    1560
atcgaaagat cccaagtgtt taacatcctg aggatgatgc ctaaggggggc cgctctgcac    1620 cttcacgata ttgggattgt aacaatggac tggctggtaa ggaacgtgac atacagacct    1680
cattgccata tttgttttac tccccgagga atcatgcaat tcaggtttgc ccacccaact    1740
cctcggccaa gcgagaagtg tagtaagtgg attttgctgg aagattaccg taagcgcgtg    1800

```
cagaatgtga cagagtttga tgactccctg ctccgcaatt ttaccctggt gacccagcac    1860
cccgaagtta tatacactaa ccaaaatgtc gtgtggtcca agtttgagac gatcttcttc    1920
acgatttcag gcttgatcca ctacgccccg gtctttcggg attatgtgtt taggagtatg    1980
caggagtttt atgaggataa tgttctgtac atggagatcc gagcccggct gcttccagtc    2040
tacgaactat ccggcgaaca ccatgacgag gaatggagcg tcaagaccta tcaagaggtg    2100
gcccagaagt tcgtagaaac gcatccagag ttcatcggta ttaagattat ctactctgat    2160
caccgctcaa aggatgtggc tgtcatcgcc gagtctatac ggatggccat gggcctgcgg    2220
attaagttcc ctaccgtcgt cgccggattc gaccctcgttg ggcatgagga tactggccat    2280
agtctccatg actataaaga agcccttatg atcccagcaa aggacggagt gaagctgccc    2340
tacttcttcc acgcagggga gaccgactgg caggaacga gcatcgaccg gaacatactt    2400
gatgcactca tgcttaatac cacacgaatc ggccacggct cgctctctc caagcaccca    2460 gccgtgagaa cctacagctg gaagaaggat atccccatcg aggtttgtcc catcagcaat    2520
caggtgctga aattggtgag tgacctgaga accacccag tcgcaacatt aatggccact    2580
ggccacccta tggtgatttc aagcgatgat ccagccatgt tcggagcaaa aggactcagt    2640
tacgacttct atgaggtatt catgggtatt ggtggtatga aggcagacct gcggactctt    2700
aagcagttgg caatgaactc aattaagtac tctaccttat tggagtctga aaagaacaca    2760
tttatggaga tctggaaaaa gcgctgggac aaattcatcg cagatgttgc cacaaaaa     2817

<210> SEQ ID NO 288
<211> LENGTH: 2817
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
caggtgcagc tggtccagag cggcgtggaa gtcaagaaac ccggggcctc agtgaaggtc      60
agctgtaaag cttccggcta caccttcaca aactactata tgtattgggt gagacaggca     120
ccaggacagg gactggagtg gatgggcggg attaaccctg gtaatggagg cactaacttc     180
aacgaaaagt ttaaaaacag ggtgaccctg accacagatt caagcactac acagcttac     240 atggagctga gtccctgca gtttgacgat acagccgtgt actattgtgc tcggagagac     300
tacaggttcg atatgggctt tgactattgg ggccagggga ctaccgtgac cgtctcctct     360
gctagcacca agggcccatc ggtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accatgccca gcacctgagt tcctggggg accatcagtc     720 ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtct ccaacaaagg cctcccgtcc tccatcgaga aaaccatctc caaagccaaa    1020
```

```
gggcagcccc gagagccaca ggtgtacacc ctgcccccat cccaggagga gatgaccaag      1080
aaccaggtca gcctgacctg cctggtcaaa ggcttctacc ccagcgacat cgccgtggag      1140
tgggagagca atgggcagcc ggagaacaac tacaagacca cgcctcccgt gctggactcc      1200
gacggctcct tcttcctcta cagcaggctc accgtggaca gagcaggtg gcaggagggg       1260 aatgtcttct catgctccgt gatgcatgag gctctgcaca accactacac acagaagagc      1320 ctctcccctgt ctccgggtaa aggtggaggt ggttctggag gtggaggtag tatcgacgaa     1380
accagagcac acttactgct gaaagagaaa atgatgcgcc tgggcgggag attggtgtta     1440
aatactaagg aagagctggc aaatgaaaga ctcatgacac tgaagattgc tgaaatgaag     1500
gaggcgatga ggacgctgat cttttccgcct tccatgcact tcttccaagc taaacacctg    1560
atcgaaagat cccaagtgtt taacatcctg aggatgatgc taaggggggc cgctctgcac    1620
cttcacgata ttgggattgt aacaatggac tggctggtaa ggaacgtgac atacagacct    1680
cattgccata tttgttttac tccccgagga atcatgcaat tcaggtttgc ccacccaact    1740
cctcggccaa gcgagaagtg tagtaagtgg attttgctgg aagattaccg taagcgcgtg    1800
cagaatgtga cagagtttga tgactccctg ctccgcaatt ttaccctggt gacccagcac    1860
cccgaagtta tatacactaa ccaaaatgtc gtgtggtcca agtttgagac gatcttcttc    1920
acgatttcag gcttgatcca ctacgccccg gtctttcggg attatgtgtt taggagtatg   1980
caggagtttt atgaggataa tgttctgtac atggagatcc gagcccagct gcttccagtc    2040
tacgaactat ccggcgaaca ccatgacgag gaatggagcg tcaagaccta tcaagaggtg   2100
gcccagaagt tcgtagaaac gcatccagag ttcatcggta ttaagattat ctacaatgat   2160
caccgctcaa aggatgtggc tgtcatcgcc gagtctatac ggatggccat gggcctgcgg   2220
attaagttcc ctaccgtcgt cgccggattc gacctcgttg gcatgaggga tactggccat   2280
agtctccatg actataaaga agcccttatg atcccagcaa aggacggagt gaagctgccc   2340
tacttcttcc acgcagggga gaccgactgg cagggaacga gcatcgaccg gaacatactt   2400
gatgcactca tgcttaatac cacacgaatc ggccacggct tcgctctctc caagcaccca   2460
gccgtgagaa cctacagctg ggataaggat atccccatcg aggtttgtcc catcagcaat   2520
caggtgctga aattggtgag tgacctgaga aaccacccag tcgcaacatt aatggccact   2580 ggccaccta tggtgatttc aagcgatgat ccagccatgt tcggagcaaa aggactcagt    2640
tacgacttct atgaggtatt catgggtatt ggtggtatga aggcagacct gcggactctt   2700
aagcagttgg caatgaactc aattaagtac tctaccttat tggagtctga aaagaacaca   2760
tttatggaga tctggaaaaa gcgctggac aaattcatcg cagatgttgc cacaaaa        2817
```

<210> SEQ ID NO 289
<211> LENGTH: 592
<212> TYPE: PRT
<213> ORGANISM: Homo sapiens

<400> SEQUENCE: 289

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr

```
                50                  55                  60
Asp Asn Asn Gly Ala Val Lys Phe Pro Gln Leu Cys Lys Phe Cys Asp
 65                  70                  75                  80

Val Arg Phe Ser Thr Cys Asp Asn Gln Lys Ser Cys Met Ser Asn Cys
                 85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
                115                 120                 125

Pro Lys Leu Pro Tyr His Asp Phe Ile Leu Glu Asp Ala Ala Ser Pro
                130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Val Ile Phe Gln Val
                180                 185                 190

Thr Gly Ile Ser Leu Leu Pro Pro Leu Gly Val Ala Ile Ser Val Ile
                195                 200                 205

Ile Ile Phe Tyr Cys Tyr Arg Val Asn Arg Gln Gln Lys Leu Ser Ser
                210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
                275                 280                 285

Lys Gln Asn Thr Ser Glu Gln Phe Glu Thr Val Ala Val Lys Ile Phe
                290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
                340                 345                 350

His Ala Lys Gly Asn Leu Gln Glu Tyr Leu Thr Arg His Val Ile Ser
                355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
                435                 440                 445

Tyr Met Ala Pro Glu Val Leu Glu Ser Arg Met Asn Leu Glu Asn Val
                450                 455                 460

Glu Ser Phe Lys Gln Thr Asp Val Tyr Ser Met Ala Leu Val Leu Trp
465                 470                 475                 480
```

```
Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 290
<211> LENGTH: 567
<212> TYPE: PRT
<213> ORGANISM: Homo sapiens

<400> SEQUENCE: 290

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
```

```
                    260                 265                 270
Thr Val Ala Val Lys Ile Phe Pro Tyr Glu Glu Tyr Ala Ser Trp Lys
                275                 280                 285

Thr Glu Lys Asp Ile Phe Ser Asp Ile Asn Leu Lys His Glu Asn Ile
            290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
            370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
            530                 535                 540

Asp Arg Leu Ser Gly Arg Ser Cys Ser Glu Lys Ile Pro Glu Asp
545                 550                 555                 560

Gly Ser Leu Asn Thr Thr Lys
                565

<210> SEQ ID NO 291
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 292
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 293
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Gly Gly Gly Ser Gly Gly Gly Ser
1               5

<210> SEQ ID NO 294
<211> LENGTH: 586
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

```
Gly Met His Trp Val Arg Gln Ala Pro Gly Lys Gly Leu Glu Trp Val
        35                  40                  45
Ala Val Ile Trp Tyr Asp Gly Ser Lys Arg Tyr Tyr Ala Asp Ser Val
        50                  55                  60
Lys Gly Arg Phe Thr Ile Ser Arg Asp Asn Ser Lys Asn Thr Leu Phe
65                  70                  75                  80
Leu Gln Met Asn Ser Leu Arg Ala Glu Asp Thr Ala Val Tyr Tyr Cys
                85                  90                  95
Ala Thr Asn Asp Asp Tyr Trp Gly Gln Gly Thr Leu Val Thr Val Ser
                100                 105                 110
Ser Ala Ser Thr Lys Gly Pro Ser Val Phe Pro Leu Ala Pro Cys Ser
        115                 120                 125
Arg Ser Thr Ser Glu Ser Thr Ala Ala Leu Gly Cys Leu Val Lys Asp
        130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Lys
                180                 185                 190
Thr Tyr Thr Cys Asn Val Asp His Lys Pro Ser Asn Thr Lys Val Asp
                195                 200                 205
Lys Arg Val Glu Ser Lys Tyr Gly Pro Pro Cys Pro Pro Cys Pro Ala
        210                 215                 220
Pro Glu Phe Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Glu Asp Pro Glu Val Gln Phe Asn Trp Tyr Val
                260                 265                 270
Asp Gly Val Glu Val His Asn Ala Lys Thr Lys Pro Arg Glu Glu Gln
        275                 280                 285
Phe Asn Ser Thr Tyr Arg Val Val Ser Val Leu Thr Val Leu His Gln
290                 295                 300
Asp Trp Leu Asn Gly Lys Glu Tyr Lys Cys Lys Val Ser Asn Lys Gly
305                 310                 315                 320
Leu Pro Ser Ser Ile Glu Lys Thr Ile Ser Lys Ala Lys Gly Gln Pro
                325                 330                 335
Arg Glu Pro Gln Val Tyr Thr Leu Pro Pro Ser Gln Glu Glu Met Thr
                340                 345                 350
Lys Asn Gln Val Ser Leu Thr Cys Leu Val Lys Gly Phe Tyr Pro Ser
        355                 360                 365
Asp Ile Ala Val Glu Trp Glu Ser Asn Gly Gln Pro Glu Asn Asn Tyr
        370                 375                 380
Lys Thr Thr Pro Pro Val Leu Asp Ser Asp Gly Ser Phe Phe Leu Tyr
385                 390                 395                 400
Ser Arg Leu Thr Val Asp Lys Ser Arg Trp Gln Glu Gly Asn Val Phe
                405                 410                 415
Ser Cys Ser Val Met His Glu Ala Leu His Asn His Tyr Thr Gln Lys
                420                 425                 430
Ser Leu Ser Leu Ser Leu Gly Lys Gly Gly Gly Ser Gly Gly Gly Gly
        435                 440                 445
```

```
Gly Ser Ile Pro Pro His Val Gln Lys Ser Val Asn Asn Asp Met Ile
            450                 455                 460

Val Thr Asp Asn Asn Gly Ala Val Lys Phe Pro Gln Leu Cys Lys Phe
465                 470                 475                 480

Cys Asp Val Arg Phe Ser Thr Cys Asp Asn Gln Lys Ser Cys Met Ser
                485                 490                 495

Asn Cys Ser Ile Thr Ser Ile Cys Glu Lys Pro Gln Glu Val Cys Val
            500                 505                 510

Ala Val Trp Arg Lys Asn Asp Glu Asn Ile Thr Leu Glu Thr Val Cys
            515                 520                 525

His Asp Pro Lys Leu Pro Tyr His Asp Phe Ile Leu Glu Asp Ala Ala
530                 535                 540

Ser Pro Lys Cys Ile Met Lys Glu Lys Lys Pro Gly Glu Thr Phe
545                 550                 555                 560

Phe Met Cys Ser Cys Ser Ser Asp Glu Cys Asn Asp Asn Ile Ile Phe
                565                 570                 575

Ser Glu Glu Tyr Asn Thr Ser Asn Pro Asp
            580                 585
```

<210> SEQ ID NO 295
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

```
Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
        435                 440                 445

Gly Gly Gly Ser Gly Gly Gly Ser Ile Pro Pro His Val Gln Lys
    450                 455                 460

Ser Val Asn Asn Asp Met Ile Val Thr Asp Asn Asn Gly Ala Val Lys
465                 470                 475                 480

Phe Pro Gln Leu Cys Lys Phe Cys Asp Val Arg Phe Ser Thr Cys Asp
                485                 490                 495

Asn Gln Lys Ser Cys Met Ser Asn Cys Ser Ile Thr Ser Ile Cys Glu
            500                 505                 510

Lys Pro Gln Glu Val Cys Val Ala Val Trp Arg Lys Asn Asp Glu Asn
        515                 520                 525

Ile Thr Leu Glu Thr Val Cys His Asp Pro Lys Leu Pro Tyr His Asp
530                 535                 540

Phe Ile Leu Glu Asp Ala Ala Ser Pro Lys Cys Ile Met Lys Glu Lys
545                 550                 555                 560

Lys Lys Pro Gly Glu Thr Phe Phe Met Cys Ser Cys Ser Ser Asp Glu
                565                 570                 575

Cys Asn Asp Asn Ile Ile Phe Ser Glu Glu Tyr Asn Thr Ser Asn Pro
            580                 585                 590

Asp

<210> SEQ ID NO 296
<211> LENGTH: 218
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 296

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 297
<211> LENGTH: 1758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
caggtgcagc tggtcgaaag cggaggagga gtggtccagc caggacgatc cctgagactg      60
gattgtaagg cctctggaat cacattctct aacagtggaa tgcactgggt gcgccaggca     120
ccaggaaaag gactggagtg ggtggccgtc atctggtacg acgggtcaaa gcgatactat     180
gcagatagcg tgaaaggaag gttcacaatt tcacgcgaca acagcaagaa tactctgttt     240
ctgcagatga actctctgag agcagaggat actgccgtgt actattgtgc taccaatgac     300
gattattggg gcagggaac tctggtgacc gtcagttcag ctagcaccaa gggcccatcg     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660

```
ccatgcccag cacctgagtt cctgggggga ccatcagtct tcctgttccc cccaaaaccc    720
aaggacactc tcatgatctc ccggacccct gaggtcacgt gcgtggtggt ggacgtgagc    780
caggaagacc ccgaggtcca gttcaactgg tacgtggatg gcgtggaggt gcataatgcc    840
aagacaaagc cgcgggagga gcagttcaac agcacgtacc gtgtggtcag cgtcctcacc    900
gtcctgcacc aggactggct gaacggcaag gagtacaagt gcaaggtctc caacaaaggc    960
ctcccgtcct ccatcgagaa aaccatctcc aaagccaaag gcagccccg agagccacag    1020
gtgtacaccc tgcccccatc ccaggaggag atgaccaaga accaggtcag cctgacctgc    1080
ctggtcaaag gcttctaccc cagcgacatc gccgtggagt gggagagcaa tgggcagccg    1140
gagaacaact acaagaccac gcctcccgtg ctggactccg acggctcctt cttcctctac    1200
agcaggctca ccgtggacaa gagcaggtgg caggagggga atgtcttctc atgctccgtg    1260
atgcatgagg ctctgcacaa ccactacaca cagaagagcc tctccctgtc tctgggtaaa    1320
ggtggaggtg gttctggagg tggaggtagt atccctcctc acgtacagaa gtccgtgaac    1380
aatgacatga ttgtcactga caataacgga gccgtcaagt tcctcagct atgtaagttc    1440
tgcgatgttc ggttctccac atgcgataat cagaaaagct gtatgtctaa ttgcagtatc    1500
actagtatat gcgaaaaacc tcaagaagtt tgcgtcgccg tgtggcggaa aaatgatgaa    1560
aatatcacgc ttgagactgt ctgccatgat ccaaagttac cctaccacga cttcatctta    1620
gaagacgccg catcacccaa gtgcattatg aagagaaaa agaagccagg agaaacattc    1680
tttatgtgct catgctcctc tgacgaatgc aacgacaaca ttatcttctc tgaggagtat    1740
aacacctcaa atccagac                                                  1758
```

<210> SEQ ID NO 298
<211> LENGTH: 1779
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 298

```
caggtgcagc tggtccagag cggcgtggaa gtcaagaaac ccggggcctc agtgaaggtc     60
agctgtaaag cttccggcta caccttcaca aactactata tgtattgggt gagacaggca    120
ccaggacagg gactggagtg gatgggcggg attaacccta gtaatggagg cactaacttc    180
aacgaaaagt ttaaaaacag ggtgaccctg accacagatt caagcactac cacagcttac    240
atggagctga gtccctgca gtttgacgat acagccgtgt actattgtgc tcggagagac    300
tacaggttcg atatgggctt tgactattgg ggccagggga ctaccgtgac cgtctcctct    360
gctagcacca agggcccatc ggtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc cccatgcccc accatgccca gcacctgagt tcctgggggg accatcagtc    720
ttcctgttcc cccaaaaccc aaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
```

| | |
|---|---|
| cgtgtggtca gcgtcctcac cgtcctgcac caggactggc tgaacggcaa ggagtacaag | 960 |
| tgcaaggtct ccaacaaagg cctcccgtcc tccatcgaga aaaccatctc caaagccaaa | 1020 |
| gggcagcccc gagagccaca ggtgtacacc ctgcccccat cccaggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggctc accgtggaca agagcaggtg gcaggagggg | 1260 |
| aatgtcttct catgctccgt gatgcatgag gctctgcaca accactacac acagaagagc | 1320 |
| ctctccctgt ctctgggtaa aggtggaggt ggttctggag gtggaggtag tatccctcct | 1380 |
| cacgtacaga agtccgtgaa caatgacatg attgtcactg acaataacgg agccgtcaag | 1440 |
| tttcctcagc tatgtaagtt ctgcgatgtt cggttctcca catgcgataa tcagaaaagc | 1500 |
| tgtatgtcta attgcagtat cactagtata tgcgaaaaac ctcaagaagt ttgcgtcgcc | 1560 |
| gtgtggcgga aaaatgatga aaatatcacg cttgagactg tctgccatga tccaaagtta | 1620 |
| ccctaccacg acttcatctt agaagacgcc gcatcaccca agtgcattat gaaagagaaa | 1680 |
| aagaagccag agaaacatt ctttatgtgc tcatgctcct ctgacgaatg caacgacaac | 1740 |
| attatcttct ctgaggagta taacacctca aatccagac | 1779 |

<210> SEQ ID NO 299
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299

| | |
|---|---|
| gagatcgtcc tgacacagag tccagcaact ctgagcctgt cccccggcga acgagctact | 60 |
| ctgtcctgcc gggcatctca gagtgtgtct agttacctgg cctggtatca gcagaagccc | 120 |
| ggccaggctc ctaggctgct gatctacgac gccagcaaca gagctaccgg gattcctgcc | 180 |
| aggttctcag gcagcgggtc cggaacagac tttaccctga caatctcaag cctggagccc | 240 |
| gaagatttcg ctgtgtacta ttgccagcag tcctctaatt ggcctcgcac ctttggccag | 300 |
| gggacaaagg tcgagatcaa gcgtacggtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 300
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 300

| | |
|---|---|
| gagatcgtcc tgactcagtc cccagcaacc ctgagtctgt caccaggaga aagggcaacc | 60 |
| ctgagctgcc gagcatccaa gggggtgagc acatccggat actcttatct gcactggtac | 120 |
| cagcagaaac ccggacaggc tcctcgactg ctgatctacc tggcatctta tctggagagt | 180 |

-continued

```
ggcgtgcctg ctcggttctc tgggagtgga tcaggcaccg attttacact gactatttct      240
agtctggagc cagaagattt cgcagtgtac tattgccagc attctcgaga cctgcccctg      300
acatttggcg ggggaactaa ggtcgagatc aaacgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc       600 acccatcagg gcctgagctc gcccgtcaca aagagcttca caggggaga gtgt             654
```

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

```
<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Thr Thr Tyr Tyr Trp Val
1               5

<210> SEQ ID NO 311
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ser Ile Ser Tyr Ser Gly Asn Thr Tyr Tyr Asn Pro Ser Leu Lys Ser
1               5                   10                  15

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

His Leu Gly Tyr Asn Gly Arg Tyr Leu Pro Phe Asp Tyr
1               5                   10

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser Ser Thr Tyr Tyr Trp Gly
1               5

<210> SEQ ID NO 314
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ser Ile Ser Tyr Ser Gly Ser Thr Tyr Tyr Asn Pro Ser Leu Lys Ser
1               5                   10                  15

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 315

Ser Thr Thr Tyr Tyr Trp Gly
1               5

<210> SEQ ID NO 316
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ser Ile Ser Tyr Ser Gly Thr Thr Tyr Tyr Asn Pro Ser Leu Lys Ser
1               5                  10                  15

<210> SEQ ID NO 317
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

His Leu Gly Tyr Asn Ser Asn Trp Tyr Pro Phe Asp Tyr
1               5                  10

<210> SEQ ID NO 318
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ser His Ala Met Ser
1               5

<210> SEQ ID NO 319
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Thr Ile Thr Gly Gly Gly Gly Ser Ile Tyr Tyr Ala Asp Ser Val Lys
1               5                  10                  15

<210> SEQ ID NO 320
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Asn Arg Ala Gly Glu Gly Tyr Phe Asp Tyr
1               5                  10

<210> SEQ ID NO 321
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Thr Gly Thr Ser Ser Asp Val Gly Phe Tyr Asn Tyr Val Ser
1               5                   10

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Asp Val Thr Asn Arg Pro Ser
1               5

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Ser Ser Tyr Thr Ser Ile Ser Thr Trp Val
1               5                   10

<210> SEQ ID NO 324
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asp Val Ser Asn Arg Pro Ser
1               5

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Ser Tyr Thr Asn Ile Ser Thr Trp Val
1               5                   10

<210> SEQ ID NO 326
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Thr Gly Thr Ser Ser Asp Val Gly Ser Tyr Asn Arg Val Ser
```

```
<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Glu Val Ser Asn Arg Pro Ser
1               5

<210> SEQ ID NO 328
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ser Ser Tyr Thr Ser Ser Ser Thr Trp Val
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Gly Asp Asn Ile Gly Asn Lys Asp Val His
1               5                   10

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Arg Asp Ser Asn Arg Pro Ser
1               5

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Val Trp Asp Ser Ile Trp Val
1               5

<210> SEQ ID NO 332
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 332

Ser Ser Tyr Thr Ser Ile Ser Thr Trp Val
1               5                   10

<210> SEQ ID NO 333
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Leu Gln Leu Gln Glu Ser Gly Pro Gly Leu Val Lys Pro Ser Glu
1               5                   10                  15

Thr Leu Thr Leu Thr Cys Thr Val Ser Gly Asp Ser Ile Ser Ser Thr
            20                  25                  30

Thr Tyr Tyr Trp Val Trp Ile Arg Gln Pro Pro Gly Lys Gly Leu Glu
        35                  40                  45

Trp Ile Gly Ser Ile Ser Tyr Ser Gly Asn Thr Tyr Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Ser Ser Val Ala Ala Thr Asp Ala Leu Tyr Tyr
                85                  90                  95

Cys Ala Arg His Leu Gly Tyr Asn Gly Arg Tyr Leu Pro Phe Asp Tyr
            100                 105                 110

Trp Gly Gln Gly Thr Leu Val Thr Val Ser Ser
        115                 120

<210> SEQ ID NO 334
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Asp Ala Asp Thr Ala Val Tyr Tyr
                85                  90                  95

Cys Ala Arg His Leu Gly Tyr Asn Gly Arg Tyr Leu Pro Phe Asp Tyr
            100                 105                 110

Trp Gly Gln Gly Thr Leu Val Thr Val Ser Ser
        115                 120

<210> SEQ ID NO 335

<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Leu Gln Leu Gln Glu Ser Gly Pro Gly Leu Val Lys Pro Ser Glu
1               5                   10                  15

Thr Leu Thr Leu Thr Cys Thr Val Ser Ala Asp Ser Ile Ser Ser Thr
            20                  25                  30

Thr Tyr Tyr Trp Val Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Val Ser Val Asp Thr Ser Lys Asn Gln Phe
65                  70                  75                  80

Ser Leu Lys Leu Asn Ser Val Ala Ala Thr Asp Thr Ala Leu Tyr Tyr
                85                  90                  95

Cys Ala Arg His Leu Gly Tyr Asn Gly Arg Tyr Leu Pro Phe Asp Tyr
            100                 105                 110

Trp Gly Gln Gly Thr Leu Val Thr Val Ser Ser
        115                 120

<210> SEQ ID NO 336
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Thr Tyr Tyr Trp Gly Trp Ile Arg Gln Pro Pro Gly Lys Gly Leu Glu
        35                  40                  45

Trp Ile Gly Ser Ile Ser Tyr Ser Gly Thr Thr Tyr Tyr Asn Pro Ser
    50                  55                  60

Leu Lys Ser Arg Val Thr Ile Pro Val Asp Thr Ser Lys Asn Gln Ile
65                  70                  75                  80

Ser Leu Lys Leu Ser Ser Val Thr Ala Ala Asp Thr Ser Leu Tyr Tyr
                85                  90                  95

Cys Ala Arg His Leu Gly Tyr Asn Ser Asn Trp Tyr Pro Phe Asp Tyr
            100                 105                 110

Trp Gly Gln Gly Thr Leu Val Thr Val Ser Ser
        115                 120

<210> SEQ ID NO 337
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Thr Ile Thr Gly Gly Gly Ser Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Ala Gly Glu Gly Tyr Phe Asp Tyr Trp Gly Gln Gly
            100                 105                 110

Thr Leu Val Thr Val Ser Ser
            115

<210> SEQ ID NO 338
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Glu Leu
        35                  40                  45

Met Ile Tyr Asp Val Thr Asn Arg Pro Ser Gly Val Ser Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ile
                85                  90                  95

Ser Thr Trp Val Phe Gly Gly Gly Thr Lys Leu Thr Val Leu
            100                 105                 110

<210> SEQ ID NO 339
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Glu Val
        35                  40                  45

Met Ile Tyr Asp Val Ser Asn Arg Pro Ser Gly Val Ser Asp Arg Phe
50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ile
                 85                  90                  95

Ser Thr Trp Val Phe Gly Gly Gly Thr Lys Leu Thr Val Leu
            100                 105                 110
```

<210> SEQ ID NO 340
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
                20                  25                  30

Asn Tyr Val Ser Trp Tyr Gln Gln His Pro Gly Lys Ala Pro Glu Leu
            35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Asn Ile
                 85                  90                  95

Ser Thr Trp Val Phe Gly Gly Gly Thr Lys Leu Thr Val Leu
            100                 105                 110
```

<210> SEQ ID NO 341
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

```
Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
                20                  25                  30

Asn Arg Val Ser Trp Tyr Gln Gln Pro Pro Gly Thr Ala Pro Glu Val
            35                  40                  45

Ile Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Trp Val Phe Gly Gly Gly Thr Lys Leu Thr Val Leu
            100                 105                 110
```

<210> SEQ ID NO 342
<211> LENGTH: 105
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 342

Ser Tyr Glu Leu Thr Gln Pro Leu Ser Val Ser Val Ala Leu Gly Gln
1               5                   10                  15

Thr Ala Arg Ile Thr Cys Gly Gly Asp Asn Ile Gly Asn Lys Asp Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Gly Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ile Trp Val Phe
                85                  90                  95

Gly Gly Gly Thr Lys Leu Thr Val Leu
            100                 105

<210> SEQ ID NO 343
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 343

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Glu Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ile
                85                  90                  95

Ser Thr Trp Val Phe Gly Gly Gly Thr Lys Leu Thr Val Leu
            100                 105                 110

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 344
agtactactt actactgggt c                                           21

<210> SEQ ID NO 345
<211> LENGTH: 48
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 345
agtatctctt atagtgggaa cacctactac aatccgtccc tcaagagt                48

<210> SEQ ID NO 346
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
catctagggt ataatgggag gtacctcccc tttgactac                          39

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
agtagtactt actactgggg c                                             21

<210> SEQ ID NO 348
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
agtatctctt atagtgggag cacctactac aatccgtccc tcaagagt                48

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
agtactactt actactgggg c                                             21

<210> SEQ ID NO 350
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
agtatctctt atagtgggac cacctactac aacccgtccc tcaagagt                48

<210> SEQ ID NO 351
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
catctcgggt ataacagcaa ctggtaccct tttgactac                             39

<210> SEQ ID NO 352
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
agccatgcca tgagc                                                       15

<210> SEQ ID NO 353
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
actattactg gtggtggtgg tagcatatac tacgcagact ccgtgaaggg c                51

<210> SEQ ID NO 354
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aaccgcgctg gggagggtta ctttgactac                                       30

<210> SEQ ID NO 355
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
actggaacca gcagtgacgt tggtttttat aactatgtct cc                         42

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gatgtcacta atcggccctc a                                                21

<210> SEQ ID NO 357
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
agctcatata caagcatcag cacttgggtg                                30

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gatgtcagta atcggccctc a                                         21

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
agctcatata caaacatcag cacttgggtg                                30

<210> SEQ ID NO 360
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
actggaacca gcagtgacgt tggtagttat aaccgtgtct cc                  42

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gaggtcagta atcggccctc a                                         21

<210> SEQ ID NO 362
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
agctcatata caagcagcag cacttgggtg                                30

<210> SEQ ID NO 363
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363

```
gggggagaca acattggaaa taaagatgtg cac                           33

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
agggatagca accggccctc t                                       21

<210> SEQ ID NO 365
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
caggtgtggg acagcatttg ggtg                                    24

<210> SEQ ID NO 366
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
agctcatata caagcatcag cacttgggtg                              30

<210> SEQ ID NO 367
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 367
cagctgcagc tgcaggagtc gggcccagga ctggtgaagc cttcggagac cctgaccctc    60
acctgcactg tctctggtga ctccatcagc agtactactt actactgggt ctggatccgc   120 cagccccag ggaagggact ggagtggatt gggagtatct cttatagtgg aacacctac    180 tacaatccgt ccctcaagag tcgagtcacc atatccgtag acacgtccaa gaaccacttc   240
tccctgaagc tgagttctgt ggccgccaca gacacggctc tatattactg tgcgagacat   300
ctagggtata atgggaggta cctcccctttt gactactggg gccagggaac cctggtcacc   360
gtctcctcc                                                          369

<210> SEQ ID NO 368
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 368
cagctgcagc tgcaggagtc gggcccagga ctggtgaagc cttcggagac cctgtccctc    60
```

```
acctgcactg tctctggtgg ctccatcagc agtagtactt actactgggg ctggatccgc    120 cagccccag  ggaagggact  ggagtggatt gggagtatct cttatagtgg gagcacctac    180
tacaatccgt cccctcaagag tcgagtcacc atatccgtag acacgtccaa gaaccagttc    240
tccctgaagc tgagctctgt gaccgacgca gacacggctg tgtattactg tgcgagacat    300
ctagggtata atgggaggta cctccccttt gactactggg gccagggaac cctggtcacc    360
gtctcctcc                                                             369
```

<210> SEQ ID NO 369
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 369

```
cagctgcagc tgcaggagtc gggcccagga ctggtgaagc cttcggagac cctgaccctc     60
acctgcactg tctctgctga ctccatcagc agtactactt actactgggt ctggatccgc    120 cagccccag  ggaagggact  ggagtggatt gggagtatct cttatagtgg gagcacctac    180
tacaatccgt cccctcaagag tcgagtcacc gtatccgtag acacgtccaa gaaccagttc    240
tccctgaagc tgaactctgt ggccgccaca gacacggctc tatattactg tgcgagacat    300
ctagggtata atgggaggta cctccccttt gactactggg gccagggaac cctggtcacc    360
gtctcctcc                                                             369
```

<210> SEQ ID NO 370
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 370

```
cagctgcagc tgcaggagtc gggcccagga ctggtgaagc cctcggagac cctgtccctc     60
acctgcactg tctctggtgg ctccatcagc agtactactt actactgggg ctggatccgc    120 cagccccag  ggaaggggct  ggagtggatt gggagtatct cttatagtgg gaccacctac    180 tacaaccgt  cccctcaagag tcgagtcacc atccccgtag acacgtccaa gaaccagatc    240
tccctgaaac tgagctctgt gaccgccgca gacacgtctt tgtattattg tgcgagacat    300
ctcgggtata acagcaactg gtacccttt gactactggg gccagggaac cctggtcacc    360
gtctcctca                                                             369
```

<210> SEQ ID NO 371
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 371

```
gaggtgcagc tgttggagtc tgggggaggc ttggtacagc ctgggggtc cctgagactg      60 tcctgcgcag cctctggatt cacctttagc agccatgcca tgagctgggt ccgccaggct    120
ccagggaagg ggctggagtg ggtctcaact attactggtg tggtggtag catatactac    180
```

-continued

```
gcagactccg tgaagggccg gttcaccatc tccagagaca attccaagaa cacgctgtat      240
ctgcaaatga acagcctgag agccgaggac acggccgtat attattgtgc gaaaaaccgc      300
gctggggagg gttactttga ctactggggc cagggaaccc tggtcaccgt ctcctca         357
```

<210> SEQ ID NO 372
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 372

```
cagtctgccc tgactcagcc tgcctccgtg tctgggtctc ctggacagtc gatcaccatc      60
tcctgcactg gaaccagcag tgacgttggt ttttataact atgtctcctg gtaccaacag      120
cacccaggca agcccccga actcatgatt tatgatgtca ctaatcggcc ctcaggggtt       180
tctgatcgct tctctggctc caagtctggc aacacggcct ccctgaccat ctctgggctc      240
caggctgagg acgaggctga ttattactgc agctcatata caagcatcag cacttgggtg     300
ttcggcggag ggaccaagct gaccgtccta                                        330
```

<210> SEQ ID NO 373
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 373

```
cagtctgccc tgactcagcc tgcctccgtg tctgggtctc ctggacagtc gatcaccatc      60
tcctgcactg gaaccagcag tgacgttggt ttttataact atgtctcctg gtaccaacag      120
cacccaggca agcccccga agtcatgatt tatgatgtca gtaatcggcc ctcaggggtt       180
tctgatcgct tctctggctc caagtctggc aacacggcct ccctgactat ctctgggctc      240
caggctgagg acgaggctga ttattactgc agctcatata caagcatcag cacttgggtg     300
ttcggcggag ggaccaagct gactgtccta                                        330
```

<210> SEQ ID NO 374
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 374

```
cagtctgccc tgactcagcc tgcctccgtg tctgggtctc ctggacagtc gatcaccatc      60
tcctgcactg gaaccagcag tgacgttggt ttttataact atgtctcctg gtaccaacag      120
cacccaggca agcccccga actcatgatt tatgatgtca gtaatcggcc ctcaggggtt       180
tctgatcgct tctctggctc caagtctggc aacacggcct ccctgaccat ctctgggctc      240
caggctgagg acgaggctga ttattactgc agctcatata caaacatcag cacttgggtg     300
ttcggcggag ggaccaagct gaccgtccta                                        330
```

<210> SEQ ID NO 375
<211> LENGTH: 330
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 375
cagtcggccc tgactcagcc tccctccgtg tccgggtctc ctggacagtc agtcaccatc      60
tcctgcactg gaaccagcag tgacgttggt agttataacc gtgtctcctg gtaccagcag     120
cccccaggca cagcccccga agtcattatt tatgaggtca gtaatcggcc ctcaggggtc     180
cctgatcgct tctctgggtc caagtctggc aacacggcct ccctgaccat ctctgggctc     240
caggctgagg acgaggctga ttattactgc agctcatata caagcagcag cacttgggtg     300
ttcggcggag ggaccaagct gaccgtccta                                      330

<210> SEQ ID NO 376
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376
tcctatgagc tgactcagcc actctcagtg tcagtggccc tgggacagac ggccaggatt      60
acctgtgggg gagacaacat tggaaataaa gatgtgcact ggtaccagca gaagccaggc     120
caggcccctg tgctggtcat ctatagggat agcaaccggc cctctgggat ccctgaggga     180
ttctctggct ccaactcggg gaacacggcc accctgacca tcagcagagc caagccgggg     240
gatgaggctg actattactg tcaggtgtgg gacagcattt gggtgttcgg cggagggacc     300
aagctgaccg tccta                                                      315

<210> SEQ ID NO 377
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 377
cagtctgccc tgactcagcc tgcctccgtg tctgggtctc ctggacagtc gatcaccatc      60
tcctgcactg gaaccagcag tgacgttggt ttttataact atgtctcctg gtaccaacag     120
cacccaggca aagcccccga actcatgatt tatgatgtca gtaatcggcc ctcaggggtt     180
tctgatcgct tctctggctc caagtctggc aacacggcct ccctgaccat ctctgggctc     240
caggctgagg acgaggctga ttattactgc agctcatata caagcatcag cacttgggtg     300
ttcggcggag ggaccaagct gaccgtccta                                      330

<210> SEQ ID NO 378
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ser Tyr Ala Ile Ser
1               5
```

<210> SEQ ID NO 379
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gly Ile Ile Pro Ile Phe Asp Thr Ala Asn Tyr Ala Gln Lys Phe Gln
1               5                   10                  15

<210> SEQ ID NO 380
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Pro Gly Leu Ala Ala Ala Tyr Asp Thr Gly Ser Leu Asp Tyr
1               5                   10

<210> SEQ ID NO 381
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Arg Ala Ser Gln Ser Val Arg Ser Tyr Leu Ala
1               5                   10

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Asp Ala Ser Asn Arg Ala Thr
1               5

<210> SEQ ID NO 383
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Gln Gln Arg Asn Tyr Trp Pro Leu Thr
1               5

<210> SEQ ID NO 384
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 385
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys
            100                 105

<210> SEQ ID NO 386
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe

```
             50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Gly Leu Ala Ala Tyr Asp Thr Gly Ser Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
450

<210> SEQ ID NO 387
```

<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 387

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 388
<211> LENGTH: 265
<212> TYPE: PRT
<213> ORGANISM: Homo sapiens

<400> SEQUENCE: 388

Phe Leu Asp Ser Pro Asp Arg Pro Trp Asn Pro Pro Thr Phe Ser Pro
1               5                   10                  15

Ala Leu Leu Val Val Thr Glu Gly Asp Asn Ala Thr Phe Thr Cys Ser
            20                  25                  30

Phe Ser Asn Thr Ser Glu Ser Phe Val Leu Asn Trp Tyr Arg Met Ser
        35                  40                  45

Pro Ser Asn Gln Thr Asp Lys Leu Ala Ala Phe Pro Glu Asp Arg Ser
    50                  55                  60

Gln Pro Gly Gln Asp Cys Arg Phe Arg Val Thr Gln Leu Pro Asn Gly
65                  70                  75                  80

Arg Asp Phe His Met Ser Val Val Arg Ala Arg Arg Asn Asp Ser Gly
                85                  90                  95

Thr Tyr Leu Cys Gly Ala Ile Ser Leu Ala Pro Lys Ala Gln Ile Lys
            100                 105                 110

```
Glu Ser Leu Arg Ala Glu Leu Arg Val Thr Glu Arg Arg Ala Glu Val
            115                 120                 125

Pro Thr Ala His Pro Ser Pro Ser Pro Arg Pro Ala Gly Gln Phe Gln
130                 135                 140

Thr Leu Val Val Gly Val Gly Gly Leu Leu Gly Ser Leu Val Leu
145                 150                 155                 160

Leu Val Trp Val Leu Ala Val Ile Cys Ser Arg Ala Ala Arg Gly Thr
                165                 170                 175

Ile Gly Ala Arg Arg Thr Gly Gln Pro Leu Lys Glu Asp Pro Ser Ala
            180                 185                 190

Val Pro Val Phe Ser Val Asp Tyr Gly Glu Leu Asp Phe Gln Trp Arg
        195                 200                 205

Glu Lys Thr Pro Glu Pro Pro Val Pro Cys Val Pro Glu Gln Thr Glu
    210                 215                 220

Tyr Ala Thr Ile Val Phe Pro Ser Gly Met Gly Thr Ser Ser Pro Ala
225                 230                 235                 240

Arg Arg Gly Ser Ala Asp Gly Pro Arg Ser Ala Gln Pro Leu Arg Pro
                245                 250                 255

Glu Asp Gly His Cys Ser Trp Pro Leu
            260                 265
```

<210> SEQ ID NO 389

<400> SEQUENCE: 389

000

<210> SEQ ID NO 390
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Val Ser His
            20                  25                  30

Tyr Tyr Trp Ser Trp Ile Arg Gln His Pro Gly Lys Gly Leu Glu Trp
        35                  40                  45

Ile Gly Tyr Ile Ser Ser Asp Gly Ser Asn Tyr Asn Pro Ser Leu
    50                  55                  60

Lys Ser Leu Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Met Val Thr Val Ser
            100                 105                 110

Ser
```

<210> SEQ ID NO 391
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 391

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Val Ser His
            20                  25                  30

Tyr Tyr Trp Gly Trp Ile Arg Gln Pro Pro Gly Lys Gly Leu Glu Trp
        35                  40                  45

Ile Gly Tyr Ile Ser Ser Asp Gly Ser Asn Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Val Arg Gly Val Asp Tyr Trp Gly Gln Gly Thr Met Val Thr Val Ser
            100                 105                 110

Ser

<210> SEQ ID NO 392
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Val Ser His
            20                  25                  30

Tyr Tyr Met Ser Trp Val Arg Gln Ala Pro Gly Lys Gly Leu Glu Trp
        35                  40                  45

Val Ser Val Ile Ser Ser Asp Gly Ser Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 393
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ser Ile Val Ser His
            20                  25                  30

Tyr Tyr Met His Trp Val Arg Gln Ala Pro Gly Lys Gly Leu Glu Trp

```
            35                  40                  45
Val Ser Ala Ile Ser Ser Asp Gly Ser Asn Glu Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Gly Val Asp Tyr Trp Gly Gln Gly Thr Leu Val Thr Val Ser
            100                 105                 110

Ser
```

<210> SEQ ID NO 394
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Val Ser His
             20                  25                  30

Tyr Tyr Trp Ser Trp Ile Arg Gln His Pro Gly Lys Gly Leu Glu Trp
         35                  40                  45

Ile Gly Tyr Ile Ser Ser Asp Gly Ser Asn Glu Tyr Asn Pro Ser Leu
 50                  55                  60

Lys Ser Leu Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Phe Cys
                 85                  90                  95

Val Arg Gly Val Asp Tyr Trp Gly Gln Gly Thr Met Val Thr Val Ser
            100                 105                 110

Ser
```

<210> SEQ ID NO 395
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ser Ile Val Ser His
             20                  25                  30

Tyr Tyr Ile Ser Trp Val Arg Gln Ala Pro Gly Gln Gly Leu Glu Trp
         35                  40                  45

Met Gly Gly Ile Ser Ser Asp Gly Ser Asn Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Val Arg Gly Val Asp Tyr Trp Gly Gln Gly Thr Leu Val Thr Val Ser
            100                 105                 110
Ser
```

<210> SEQ ID NO 396
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Val Ser His
            20                  25                  30

Tyr Tyr Trp Ser Trp Ile Arg Gln Pro Pro Gly Lys Gly Leu Glu Trp
        35                  40                  45

Ile Gly Tyr Ile Ser Ser Asp Gly Ser Asn Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Thr Val Thr Val Ser
            100                 105                 110
Ser
```

<210> SEQ ID NO 397
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Val Ser His
            20                  25                  30

Tyr Tyr Trp His Trp Ile Arg Gln Pro Pro Gly Lys Gly Leu Glu Trp
        35                  40                  45

Met Gly Tyr Ile Ser Ser Asp Gly Ser Asn Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Val Arg Gly Val Asp Tyr Trp Gly Gln Gly Thr Leu Val Thr Val Ser
            100                 105                 110
Ser
```

<210> SEQ ID NO 398
<211> LENGTH: 113
<212> TYPE: PRT
<213> ORGANISM: Artificial Sequence
<220> FEATURE:

<223> OTHER INFORMATION: Description of Artificial Sequence: Synthetic
       polypeptide

<400> SEQUENCE: 398

Gln Val Gln Leu Gln Glu Ser Gly Pro Gly Leu Val Lys Pro Ser Gln
1               5                   10                  15

Thr Leu Ser Leu Thr Cys Ala Val Tyr Gly Tyr Ser Ile Val Ser His
            20                  25                  30

Tyr Tyr Trp Ser Trp Ile Arg Gln Pro Pro Gly Lys Gly Leu Glu Trp
        35                  40                  45

Ile Gly Glu Ile Ser Ser Asp Gly Ser Asn Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 399
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Val Ser His
            20                  25                  30

Tyr Tyr Trp Gly Trp Ile Arg Gln Pro Pro Gly Lys Gly Leu Glu Trp
        35                  40                  45

Ile Gly Ser Ile Ser Ser Asp Gly Ser Asn Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Gly Val Asp Tyr Trp Gly Gln Gly Thr Leu Val Thr Val Ser
            100                 105                 110

Ser

<210> SEQ ID NO 400
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Ser Ile Val Ser His
            20                  25                  30

```
Tyr Tyr Trp Asn Trp Val Arg Gln Ala Pro Gly Lys Gly Leu Glu Trp
             35                  40                  45

Val Ala Tyr Ile Ser Ser Asp Gly Ser Asn Glu Tyr Asn Pro Ser Leu
 50                      55                  60

Lys Asn Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Gly Val Asp Tyr Trp Gly Gln Gly Thr Thr Val Thr Val Ser
            100                 105                 110

Ser

<210> SEQ ID NO 401
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Val Ser His
             20                  25                  30

Tyr Tyr Trp Asn Trp Ile Arg Gln His Pro Gly Lys Gly Leu Glu Trp
             35                  40                  45

Ile Gly Tyr Ile Ser Ser Asp Gly Ser Asn Glu Tyr Asn Pro Ser Leu
 50                      55                  60

Lys Asn Leu Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Val Arg Gly Val Asp Tyr Trp Gly Gln Gly Thr Met Val Thr Val Ser
            100                 105                 110

Ser

<210> SEQ ID NO 402
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Val Ser His
             20                  25                  30

Tyr Tyr Trp Asn Trp Ile Arg Gln Pro Pro Gly Lys Gly Leu Glu Trp
             35                  40                  45

Ile Gly Tyr Ile Ser Ser Asp Gly Ser Asn Glu Tyr Asn Pro Ser Leu
 50                      55                  60

Lys Asn Arg Val Thr Met Ser Val Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95
```

Val Arg Gly Val Asp Tyr Trp Gly Gln Gly Thr Met Val Thr Val Ser
                100                 105                 110
Ser

<210> SEQ ID NO 403
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ser Ile Val Ser His
            20                  25                  30

Tyr Tyr Trp Asn Trp Val Arg Gln Ala Pro Gly Lys Gly Leu Glu Trp
            35                  40                  45

Val Ser Tyr Ile Ser Ser Asp Gly Ser Asn Glu Tyr Asn Pro Ser Leu
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Val Asp Tyr Trp Gly Gln Gly Thr Leu Val Thr Val Ser
                100                 105                 110

Ser

<210> SEQ ID NO 404
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 404
caggtgcaac tgcaggaatc aggtccaggc ttggtcaagc catcgcagac tcttagtctg      60
acatgcaccg tgagtggcta tagcatcgtg tcgcactatt attggtcttg gatcaggcag     120
catccaggaa agggactgga gtggatcggg tacattagca gcgatgggag caactattac     180
aacccatctc tgaagtccct ggtaactatt agcgtggata caagcaaaaa tcagttttca     240
ttaaagctct cttcagtgac cgcagctgat accgccgtct attattgcgt gcgggggtg      300 gactactggg gtcagggcac catggttact gtgtcatca                            339

<210> SEQ ID NO 405
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 405
caggtacagc tgcaggagag tggccctggt ttagtaaagc catcagatac actttcactt      60
acctgcgccg tgtctggtta ttctatcgtg agccactatt actggggatg gatccgccag     120
ccccctggca aagtcttga gtggattggc tatataagtt cggatggcag taactattac     180

```
aatccttctc tgaagagccg tgtcactatg agcgtggaca ctagcaaaaa ccagttcagc      240
ctgaagctgt cctccgtcac cgccgtagac accgctgtct actattgtgt taggggggtg      300
gactactggg gccaaggcac catggtcacg gtgagcagc                             339
```

<210> SEQ ID NO 406
<211> LENGTH: 338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

```
gaggtgcagc tcgtcgagtc cggaggcggt ctggtgcaac ccggccgttc tttgcggctg      60
agttgcgctg ccagtgggta tagcatcgtg agtcactatt acatgcattg ggttcgtcaa      120 gccccctggca agggactaga gtgggtgtcc gccatctcct cagacggtag taatgagtac     180
gcggacagcg tagagggtag attcaccatt tctcgggaca atgccaaaaa tagttatacc     240
tccaaatgaa ttcccttagg gccgaagaca ctgccgtgta ctactgtgtt cggggcgtgg      300
actactgggg cagggggaca ttggtgactg tgagctca                              338
```

<210> SEQ ID NO 407
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 407

```
caggtccaac tgcaggaatc tggccccgga ctggttaaac catctcagac actctccctg      60
acctgcaccg tgtctggata cagcatcgtt tctcattatt actggtcatg gattaggcag      120
catcccggaa aagggcttga atggattggc tacatctcct ccgacggctc caatgagtac      180
aacccatcac ttaaatctct ggtcacgata agcgtagaca catctaaaaa tcagttctca     240
ttaaagctca gctctgttac agctgccgac accgctgtgt acttctgtgt gcgagggggtt     300 gactactggg ggcagggcac aatggtgaca gtgtcttcc                             339
```

<210> SEQ ID NO 408
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 408

```
caggttcaac tggttcagtc cggagccgag gtcaaaaagc ctggatcctc tgtgaaggtg      60
tcatgtaagg cttctggcta cagcatcgtc tcacattatt acatatcttg ggtgcgacag      120
gcccccggcc aggggctcga gtggatggga ggtatttcct ccgacgggag taacaattac      180
gctcagaaat ttcagggccg ggtgaccatt accgccgacg aaagtacaag caccgcttat      240
atggaattaa gctcttttaag atcagaggac acggctgtgt actactgtgt aaggggcgtg      300
gattactggg gtcaggggac gctcgtcacc gtctcgagc                             339
```

<210> SEQ ID NO 409
<211> LENGTH: 339

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 409
caggtccagc tccaggaatc cggcccaggg ttggtgaagc cttcggagac cctgtctctg      60
acatgcacag tcagcggcta tagtatcgtc tcccactatt attggtcttg gattcggcaa     120
cctccaggca aggggttaga atggattgga tacatctcaa gcgatgggtc caataactac     180
aacccaagtc tcaaaagtag agtgactatc tctgtggata ccagtaaaaa ccagttttca     240
ctcaagttga gttccgtcac cgccgccgac acagccgttt actactgtgt tcggggagtg     300
gactactggg gccaaggtac cacggttacc gtgagcagc                            339

<210> SEQ ID NO 410
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 410
caggtgcagc tgcaggagag cggccccggc ctggtgaagc ccagcgacac cctgagcctg      60
acctgcgccg tgagcggcta cagcatcgtg agccactact actggcactg gatcagacag     120
ccccccggca agggcctgga gtggatgggc tacatcagca gcgacggcag caacgacttc     180
aaccccagcc tgaagaccag aatcaccatc agcagagaca ccagcaagaa ccagttcagc     240
ctgaagctga gcagcgtgac cgccgtggac accgccgtgt actactgcgt gagaggcgtg     300
gactactggg gccagggcac cctggtgacc gtgagcagc                            339

<210> SEQ ID NO 411
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 411
caggtgcagc tgcaggagag cggccccggc ctggtgaagc ccagccagac cctgagcctg      60
acctgcgccg tgtacggcta cagcatcgtg agccactact actggagctg gatcagacag     120
ccccccggca agggcctgga gtggatcggc gagatcagca gcgacggcag caacaactac     180
aaccccagcc tgaagagcag agtgaccatc agcgtggaca ccagcaagaa ccagttcagc     240
ctgaagctga gcagcgtgac cgccgccgac accgccgtgt actactgcgt gagaggcgtg     300
gactactggg gccagggcac cctggtgacc gtgagcagc                            339

<210> SEQ ID NO 412
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 412
caggtgcagc tgcaggagag cggccccggc ctggtgaagc ccagcgagac cctgagcctg      60
```

```
acctgcgccg tgagcggcta cagcatcgtg agccactact actggggctg gatcagacag    120 cccccggca agggcctgga gtggatcggc agcatcagca gcgacggcag caactactac    180
aaccccagcc tgaagagcag agtgaccatc agcgtggaca ccagcaagaa ccagttcagc    240
ctgaagctga gcagcgtgac cgccgccgac accgccgtgt actactgcgt gagaggcgtg    300
gactactggg gccagggcac cctggtgacc gtgagcagc                           339

<210> SEQ ID NO 413
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 413
caggtgcagc tggtggagag cggcggcggc gtggtgcagc ccggcagaag cctgagactg    60
agctgcgccg ccagcggcta cagcatcgtg agccactact actggaactg ggtgagacag    120 gccccggca agggcctgga gtgggtggcc tacatcagca gcgacggcag caacgagtac    180
aaccccagcc tgaagaacag attcaccatc agcagagaca acagcaagaa caccctgtac    240
ctgcagatga acagcctgag agccgaggac accgccgtgt actactgcgt gagaggcgtg    300
gactactggg gccagggcac caccgtgacc gtgagcagc                           339

<210> SEQ ID NO 414
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 414
caggtgcagc tgcaggagag cggccccggc ctggtgaagc ccagccagac cctgagcctg    60
acctgcaccg tgagcggcta cagcatcgtg agccactact actggaactg gatcagacag    120
caccccggca agggcctgga gtggatcggc tacatcagca gcgacggcag caacgagtac    180
aaccccagcc tgaagaacct ggtgaccatc agcgtggaca ccagcaagaa ccagttcagc    240
ctgaagctga gcagcgtgac cgccgccgac accgccgtgt actactgcgt gagaggcgtg    300
gactactggg gccagggcac catggtgacc gtgagcagc                           339

<210> SEQ ID NO 415
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 415
caggtgcagc tgcaggagag cggccccggc ctggtgaagc ccagcgacac cctgagcctg    60
acctgcgccg tgagcggcta cagcatcgtg agccactact actggaactg gatcagacag    120 cccccggca agggcctgga gtggatcggc tacatcagca gcgacggcag caacgagtac    180
aaccccagcc tgaagaacag agtgaccatg agcgtggaca ccagcaagaa ccagttcagc    240
ctgaagctga gcagcgtgac cgccgtggac accgccgtgt actactgcgt gagaggcgtg    300
gactactggg gccagggcac catggtgacc gtgagcagc                           339
```

<210> SEQ ID NO 416
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 416
gaggtgcagc tgctggagag cggcggcggc ctggtgcagc ccggcggcag cctgagactg      60
agctgcgccg ccagcggcta cagcatcgtg agccactact actggaactg ggtgagacag     120
gcccccggca agggcctgga gtgggtgagc tacatcagca gcgacggcag caacgagtac     180
aaccccagcc tgaagaacag attcaccatc agcagagaca cagcaagaa cacccctgtac     240 ctgcagatga acagcctgag agccgaggac accgccgtgt actactgcgt gagaggcgtg     300
gactactggg gccagggcac cctggtgacc gtgagcagc                            339

<210> SEQ ID NO 417
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Asp Ile Asn Asn Phe
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Leu Gln Tyr Gly Asp Leu Tyr Thr
                85                  90                  95

Phe Gly Gly Gly Thr Lys Val Glu Ile Lys
            100                 105

<210> SEQ ID NO 418
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Asp Ile Gln Met Thr Gln Ser Pro Ser Ser Leu Ser Ala Ser Val Gly
1               5                   10                  15

Asp Arg Val Thr Ile Thr Cys Gln Ala Ser Arg Asp Ile Asn Asn Phe
            20                  25                  30

Leu Asn Trp Tyr Gln Gln Lys Pro Gly Lys Ala Pro Lys Leu Leu Ile
        35                  40                  45

Tyr Arg Ala Asn Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro

```
65                  70                  75                  80

Glu Asp Ile Ala Thr Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 419
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Asn Asn Phe
            20                  25                  30

Leu Gly Trp Tyr Gln Gln Lys Pro Gly Lys Ala Pro Lys Arg Leu Ile
        35                  40                  45

Tyr Arg Ala Asn Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gln Gly Thr Lys Val Glu Ile Lys
            100                 105

<210> SEQ ID NO 420
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Arg Asp Ile Asn Asn Phe
            20                  25                  30

Leu Ala Trp Tyr Gln Gln Lys Pro Gly Gln Ala Pro Arg Leu Leu Ile
        35                  40                  45

Tyr Arg Ala Asn Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln Tyr Gly Asp Leu Tyr Thr
                85                  90                  95

Phe Gly Gln Gly Thr Lys Val Glu Ile Lys
            100                 105

<210> SEQ ID NO 421
<211> LENGTH: 106
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 421

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Asp Ile Asn Asn Phe
            20                  25                  30

Leu Ala Trp Tyr Gln Gln Lys Pro Gly Gln Ala Pro Arg Leu Leu Ile
        35                  40                  45

Tyr Arg Ala Asn Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 422
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Glu Ile Val Leu Thr Gln Ser Pro Asp Phe Gln Ser Val Thr Pro Lys
1               5                   10                  15

Glu Lys Val Thr Ile Thr Cys Arg Ala Ser Arg Asp Ile Asn Asn Phe
            20                  25                  30

Leu His Trp Tyr Gln Gln Lys Pro Asp Gln Ser Pro Lys Leu Leu Ile
        35                  40                  45

Lys Arg Ala Asn Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Leu Gln Tyr Gly Asp Leu Tyr Thr
                85                  90                  95

Phe Gly Gln Gly Thr Lys Val Glu Ile Lys
            100                 105

<210> SEQ ID NO 423
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Asn Asn Phe
            20                  25                  30

Leu Ala Trp Phe Gln Gln Lys Pro Gly Lys Ala Pro Lys Ser Leu Ile
        35                  40                  45

Tyr Arg Ala Asn Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 424
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Asn Asn Phe
            20                  25                  30

Leu Ala Trp Tyr Gln Gln Lys Pro Gly Lys Ala Pro Lys Leu Leu Leu
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 425
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Asn Asn Phe
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Gly Asp Leu Tyr Thr
                85                  90                  95

Phe Gly Gly Gly Thr Lys Val Glu Ile Lys
            100                 105

<210> SEQ ID NO 426
<211> LENGTH: 106
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 426

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Asn Asn Phe
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gln Gly Thr Lys Val Glu Ile Lys
            100                 105

<210> SEQ ID NO 427
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Arg Asp Ile Asn Asn Phe
            20                  25                  30

Leu Ser Trp Tyr Gln Gln Lys Pro Gly Gln Ala Pro Arg Leu Leu Ile
        35                  40                  45

Tyr Arg Ala Asn Arg Leu Val Asp Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln Tyr Gly Asp Leu Tyr Thr
                85                  90                  95

Phe Gly Gln Gly Thr Lys Val Glu Ile Lys
            100                 105

<210> SEQ ID NO 428
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Arg Asp Ile Asn Asn Phe
            20                  25                  30

Leu Ser Trp Tyr Gln Gln Lys Pro Gly Gln Ala Pro Arg Leu Leu Ile
        35                  40                  45
```

Tyr Arg Ala Asn Arg Leu Val Asp Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Leu Gln Tyr Gly Asp Leu Tyr Thr
                 85                  90                  95

Phe Gly Gln Gly Thr Lys Val Glu Ile Lys
            100                 105

<210> SEQ ID NO 429
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 429
gacatacaga tgactcagag cccctcctca ctctcggcat cagtcggcga cagggtcaca      60
attacctgtc aggcttctcg cgacattaat aacttcctga attggtatca gcaaaagccc    120
gggaaggccc ctaagctgtt gatttataga gcaaataatc tcgaaaccgg cgtgcccagt    180
aggtttagcg ggtccgggag cggaacagac ttcacattca ccatttctag tttgcagccc    240
gaagacattg ctacatattt ttgcctgcag tacggggatc tctacacttt cggggggcgga   300 acaaaggttg agataaaa                                                 318

<210> SEQ ID NO 430
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 430
gatattcaaa tgacgcagtc accctcatcg ctctctgcgt cagtagggga tcgtgtcacg      60
ataacctgtc aagcatcaag ggacatcaac aacttcctca actggtacca acagaagcct    120
ggcaaggcac ctaaactcct gatctaccgg gctaacaacc tagaaaccgg ggttccgagc    180
cgattcagtg ggtctggaag cgggacagac tttacgttca ctattagttc gctacagccc    240
gaagacattg cgacatatta ctgtcttcag tatggggatt tgtataccct tgggggaggc    300
accaaggtag agataaag                                                 318

<210> SEQ ID NO 431
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 431
gacatccaga tgactcagag cccgtcttct ctatccgcaa gtgtaggcga tcgtgtcacc      60
atcacatgcc gggcttcccg ggatatcaac aacttccttg ggtggtatca gcagaagccc    120
ggaaaagccc ccaaacggct catctacaga gcgaattccc tgcagtcagg tgtccccagt    180
aggttcagcg gatcaggctc ggggaccgaa ttcactctga ccattagctc actgcagcct    240
gaggatttcg ctacttacta ttgcctgcaa tacggcgatc tgtacacttt cgggcagggc    300
accaaggtgg aaataaaa                                                 318

<210> SEQ ID NO 432
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 432
gaaatcgtac tgacccagtc tcccggaacc ctgagtctct cacccggcga gcgcgcaaca     60
ctgtcgtgta gggccagtag ggacataaat aacttcctag cctggtacca acaaaaaccg    120
ggtcaggctc caagactgtt gatctataga gctaactcca gggccaccgg catcccagac    180
cgattctcag gctccggatc tggaaccgac ttcacgctca ccattagccg actagaacct    240
gaggactttg ctgtatacta ttgcctgcag tacggcgacc tgtataccct tggacagggt    300
accaaggtcg agatcaag                                                 318

<210> SEQ ID NO 433
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 433
gagatcgtac ttacgcagag cccagcaact ctgtctctgt cccccggaga acgggccacc     60
ctgtcgtgcc gggccagccg tgatattaat aatttcctgg cctggtatca acaaaaaccg    120
gggcaggctc ctcgactgtt gatctaccgg gccaacaata gagcaactgg tatccctgct    180
cgcttctccg gcagtgggcc aggtacagac ttcaccctga ctatttcgtc actcgaacca    240
gaagactttg ccgtgtatta ttgcttacaa tacggggatc tgtacacttt cggaggagga    300
actaaggtcg aaattaag                                                 318

<210> SEQ ID NO 434
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434
gagatcgtgc tgacccagag ccccgacttc cagagcgtga cccccaagga aaggtgacc     60 atcacctgca gagccagcag agacatcaac aacttcctgc actggtacca gcagaagccc    120
gaccagagcc ccaagctgct gatcaagaga gccaaccaga gcttcagcgg cgtgcccagc    180
agattcagcg gcagcggcag cggcaccgac ttcaccctga ccatcaacag cctggaggcc    240
gaggacgccg ccacctacta ctgcctgcag tacggcgacc tgtacacctt cggccagggc    300
accaaggtgg agatcaag                                                 318

<210> SEQ ID NO 435
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 435

```
gacatccaga tgacccagag ccccagcagc ctgagcgcca gcgtgggcga cagagtgacc    60
atcacctgca gagccagcag agacatcaac aacttcctgg cctggttcca gcagaagccc   120
ggcaaggccc ccaagagcct gatctacaga gccaacagcc tgcagagcgg cgtgcccagc   180
agattcagcg gcagcggcag cggcaccgac ttcaccctga ccatcagcag cctgcagccc   240
gaggacttcg ccacctacta ctgcctgcag tacggcgacc tgtacacctt cggcggcggc   300
accaaggtgg agatcaag                                                 318
```

<210> SEQ ID NO 436
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436

```
gacatccaga tgacccagag ccccagcagc ctgagcgcca gcgtgggcga cagagtgacc    60
atcacctgca gagccagcag agacatcaac aacttcctgg cctggtacca gcagaagccc   120
ggcaaggccc ccaagctgct gctgtacaga gccaacagac tggagagcgg cgtgcccagc   180
agattcagcg gcagcggcag cggcaccgac tacaccctga ccatcagcag cctgcagccc   240
gaggacttcg ccacctacta ctgcctgcag tacggcgacc tgtacacctt cggcggcggc   300
accaaggtgg agatcaag                                                 318
```

<210> SEQ ID NO 437
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437

```
gacatccaga tgacccagag ccccagcagc ctgagcgcca gcgtgggcga cagagtgacc    60
atcacctgca aggccagcag agacatcaac aacttcctga gctggtacca gcagaagccc   120
ggcaaggccc ccaagctgct gatctacaga gccaacagac tggtggacgg cgtgcccagc   180
agattcagcg gcagcggcag cggcaccgac ttcaccttca ccatcagcag cctgcagccc   240
gaggacatcg ccacctacta ctgcctgcag tacggcgacc tgtacacctt cggcggcggc   300
accaaggtgg agatcaag                                                 318
```

<210> SEQ ID NO 438
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 438

```
gacatccaga tgacccagag ccccagcagc ctgagcgcca gcgtgggcga cagagtgacc    60
atcacctgca aggccagcag agacatcaac aacttcctga gctggtacca gcagaagccc   120
ggcaaggccc ccaagctgct gatctacaga gccaacagac tggtggacgg cgtgcccagc   180
agattcagcg gcagcggcag cggcaccgac ttcaccctga ccatcagcag cctgcagccc   240
```

```
gaggacttcg ccacctacta ctgcctgcag tacggcgacc tgtacacctt cggccagggc    300
accaaggtgg agatcaag                                                  318
```

<210> SEQ ID NO 439
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 439

```
gagatcgtgc tgacccagag ccccggcacc ctgagcctga gccccggcga gagagccacc     60
ctgagctgca aggccagcag agacatcaac aacttcctga ctggtacca gcagaagccc    120 ggccaggccc ccagactgct gatctacaga gccaacagac tggtggacgg catccccgac    180
agattcagcg gcagcggcag cggcaccgac ttcaccctga ccatcagcag actggagccc    240
gaggacttcg ccgtgtacta ctgcctgcag tacggcgacc tgtacacctt cggccagggc    300
accaaggtgg agatcaag                                                  318
```

<210> SEQ ID NO 440
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 440

```
gagatcgtgc tgacccagag ccccgccacc ctgagcctga gccccggcga gagagccacc     60
ctgagctgca aggccagcag agacatcaac aacttcctga gctggtacca gcagaagccc    120
ggccaggccc ccagactgct gatctacaga gccaacagac tggtggacgg catccccgcc    180
agattcagcg gcagcggcag cggcaccgac ttcaccctga ccatcagcag cctggagccc    240
gaggacttcg ccgtgtacta ctgcctgcag tacggcgacc tgtacacctt cggccagggc    300
accaaggtgg agatcaag                                                  318
```

<210> SEQ ID NO 441
<211> LENGTH: 589
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Val Ser His
            20                  25                  30

Tyr Tyr Trp Gly Trp Ile Arg Gln Pro Pro Gly Lys Gly Leu Glu Trp
        35                  40                  45

Ile Gly Ser Ile Ser Ser Asp Gly Ser Asn Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

-continued

Val Arg Gly Val Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
            195                 200                 205

Lys Lys Val Glu Pro Lys Ser Cys Asp Lys Thr His Thr Cys Pro Pro
            210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
            290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys Gln Gly Gly Gly Ser
            435                 440                 445

Gly Gly Gly Gly Ser Ile Pro Pro His Val Gln Lys Ser Val Asn Asn
            450                 455                 460

Asp Met Ile Val Thr Asp Asn Asn Gly Ala Val Lys Phe Pro Gln Leu
465                 470                 475                 480

Cys Lys Phe Cys Asp Val Arg Phe Ser Thr Cys Asp Asn Gln Lys Ser
                485                 490                 495

Cys Met Ser Asn Cys Ser Ile Thr Ser Ile Cys Glu Lys Pro Gln Glu
            500                 505                 510

```
Val Cys Val Ala Val Trp Arg Lys Asn Asp Glu Asn Ile Thr Leu Glu
            515                 520                 525

Thr Val Cys His Asp Pro Lys Leu Pro Tyr His Asp Phe Ile Leu Glu
        530                 535                 540

Asp Ala Ala Ser Pro Lys Cys Ile Met Lys Glu Lys Lys Pro Gly
545                 550                 555                 560

Glu Thr Phe Phe Met Cys Ser Cys Ser Ser Asp Cys Asn Asp Asn
                565                 570                 575

Ile Ile Phe Ser Glu Glu Tyr Asn Thr Ser Asn Pro Asp
            580                 585
```

<210> SEQ ID NO 442
<211> LENGTH: 1769
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 442

| | | |
|---|---|---|
| caggtgcagc tgcaggagag cggccccggc ctggtgaagc ccagcgagac cctgagcctg | 60 |
| acctgcgccg tgagcggcta cagcatcgtg agccactact actggggctg gatcagacag | 120 |
| ccccccggca agggcctgga gtggatcggc agcatcagca gcgacggcag caactactac | 180 |
| aaccccagcc tgaagagcag agtgaccatc agcgtggaca ccagcaagaa ccagttcagc | 240 |
| ctgaagctga gcagcgtgac cgccgccgac accgccgtgt actactgcgt gagaggcgtg | 300 |
| gactactggg gccagggcac cctggtgacc gtgagcagcg ctagcaccaa gggcccatcg | 360 |
| gtcttccccc tggcaccctc ctccaagagc acctctgggg gcacagcggc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag gactctactc cctcagcagc | 540 |
| gtggtgaccg tgccctccag cagcttgggc acccagacct acatctgcaa cgtgaatcac | 600 |
| aagcccagca acaccaaggt ggacaagaaa gtgagcccaa atcttgtgac aaaactcaca | 660 |
| catgcccacc gtgcccagca cctgaactcc tggggggacc gtcagtcttc ctcttccccc | 720 |
| caaaacccaa ggacaccctc atgatctccc ggaccctga ggtcacatgc gtggtggtgg | 780 |
| acgtgagcca cgaagaccct gaggtcaagt tcaactggta cgtggacggc gtggaggtgc | 840 |
| ataatgccaa gacaaagccg cgggaggagc agtacaacag cacgtaccgt gtggtcagcg | 900 |
| tcctcaccgt cctgcaccag gactggctga atggcaagga gtacaagtgc aaggtctcca | 960 |
| acaaagccct cccagccccc atcgagaaaa ccatctccaa agccaagggg cagccccgag | 1020 |
| aaccacaggt gtacaccctg cccccatccc gggaggagat gaccaagaac caggtcagcc | 1080 |
| tgacctgcct ggtcaaaggc ttctatccca gcgacatcgc cgtggagtgg gagagcaatg | 1140 |
| ggcagccgga gaacaactac aagaccacgc ctcccgtgct ggactccgac ggctccttct | 1200 |
| tcctctacag caagctcacc gtggacaaga gcaggtggca gcaggggaac gtcttctcat | 1260 |
| gctccgtgat gcatgaggct ctgcacaacc actacacgca gaagagcctc tccctgtctc | 1320 |
| cgggtaaagg tggaggtggt tctggaggtg gaggtagtat ccctcctcac gtacagaagt | 1380 |
| ccgtgaacaa tgacatgatt gtcactgaca ataacggagc cgtcaagttt cctcagctat | 1440 |
| gtaagttctg cgatgttcgg ttctccacat gcgataatca gaaaagctgt atgtctaatt | 1500 |
| gcagtatcac tagtatatgc gaaaaaccct aagaagtttg cgtcgccgtg tggcggaaaa | 1560 |
| atgatgaaaa tatcacgctt gagactgtct gccatgatcc aaagttaccc taccacgact | 1620 |

```
tcatcttaga agacgccgca tcacccaagt gcattatgaa agagaaaaag aagccaggag   1680
aaacattctt tatgtgctca tgctcctctg acgaatgcaa cgacaacatt atcttctctg   1740
aggagtataa cacctcaaat ccagactga                                     1769
```

```
<210> SEQ ID NO 443
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Ile Asn Asn Phe
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Gly Asp Leu Tyr Thr
                85                  90                  95

Phe Gly Gln Gly Thr Lys Val Glu Ile Lys Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

```
<210> SEQ ID NO 444
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444
```

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
            50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 445
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser
        115

<210> SEQ ID NO 446
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

```
Ala Arg Ser Tyr Tyr Arg Ser Ala Trp Phe Ala Tyr Trp Gly Gln Gly
                100                 105                 110

Thr Leu Val Thr Val Ser Ser
        115

<210> SEQ ID NO 447
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Ala Phe Ser Asn Phe
            20                  25                  30

Trp Met Asn Trp Val Gln Ala Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
                100                 105                 110

Thr Leu Val Thr Val Ser Arg
        115

<210> SEQ ID NO 448
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Phe
            20                  25                  30

Trp Met Asn Trp Val Arg Gln Met Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Tyr Arg Ser Ala Trp Phe Ala Tyr Trp Gly Gln Gly
                100                 105                 110

Thr Leu Val Thr Val Ser Leu
        115

<210> SEQ ID NO 449
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys
            100                 105

<210> SEQ ID NO 450
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Asn Trp Pro Leu
                85                  90                  95

Thr Phe Gly Gly Gly Thr Lys Val Glu Ile Lys
            100                 105

<210> SEQ ID NO 451
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Thr Ser
            20                  25                  30
```

Ile His Trp Tyr Gln Gln Lys Pro Gly Gln Ala Pro Arg Leu Leu Ile
            35                  40                  45

Tyr Tyr Ala Ser Glu Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Asn Asn Trp Pro Leu
                 85                  90                  95

Thr Phe Gly Gly Gly Thr Lys Val Glu Ile Lys
            100                 105

<210> SEQ ID NO 452
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Gly Thr Ser
             20                  25                  30

Ile His Trp Tyr Gln Gln Lys Pro Gly Lys Ala Pro Lys Leu Leu Ile
            35                  40                  45

Tyr Tyr Ala Ser Glu Ser Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Asn Trp Pro Leu
                 85                  90                  95

Thr Phe Gly Gly Gly Thr Lys Val Glu Ile Lys
            100                 105

<210> SEQ ID NO 453
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Asp Ile Val Met Thr Gln Ser Pro Ser Leu Leu Ser Ala Ser Thr Gly
 1               5                  10                  15

Asp Arg Val Thr Ile Ser Cys Arg Ala Ser Gln Ser Ile Gly Thr Ser
             20                  25                  30

Ile His Trp Tyr Gln Gln Lys Pro Gly Lys Ala Pro Glu Leu Leu Ile
            35                  40                  45

Tyr Tyr Ala Ser Glu Ser Ile Ser Gly Val Pro Ser Arg Phe Ser Gly
 50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Ser Asn Asn Trp Pro Leu
                 85                  90                  95

Thr Phe Gly Gln Gly Thr Lys Val Glu Ile Lys
            100                 105

<210> SEQ ID NO 454
<211> LENGTH: 200
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 454

Gln Val Gln Leu Gln Gln Ser Gly Ala Glu Leu Val Arg Pro Gly Ser
1               5                   10                  15

Ser Val Lys Ile Ser Cys Lys Thr Ser Gly Tyr Ala Phe Ser Asn Phe
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Ala Ser Ala Val Tyr Phe Cys
                85                  90                  95

Ala Arg Ser Tyr Tyr Arg Ser Ala Trp Phe Ala Tyr Trp Gly Gln Gly
            100                 105                 110

Thr Leu Val Ser Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr
        195                 200

<210> SEQ ID NO 455
<211> LENGTH: 155
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 455

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Asn Trp Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln
145                 150                 155

<210> SEQ ID NO 456
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser Ala Ser Thr Lys Gly Pro Ser Val
            115                 120                 125

<210> SEQ ID NO 457
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

```
Thr Leu Val Thr Val Ser Ser Ala Ser Thr Lys Gly Pro Ser Val
        115                 120                 125

<210> SEQ ID NO 458
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Phe
            20                  25                  30

Trp Met Asn Trp Val Arg Gln Ala Pro Gly Gln Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Ser Ala Ser Thr Lys Gly Pro Ser Val
        115                 120                 125

<210> SEQ ID NO 459
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Gln Val Gln Leu Val Gln Ser Gly Ala Glu Val Lys Lys Pro Gly Ala
1               5                   10                  15

Thr Val Lys Ile Ser Cys Lys Val Ser Gly Tyr Ala Phe Ser Asn Phe
            20                  25                  30

Trp Met Asn Trp Val Gln Gln Ala Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Arg Ala Ser Thr Lys Gly Pro Ser Val
        115                 120                 125

<210> SEQ ID NO 460
<211> LENGTH: 127
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 460

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ala Phe Ser Asn Phe
            20                  25                  30

Trp Met Asn Trp Val Arg Gln Met Pro Gly Lys Gly Leu Glu Trp Met
        35                  40                  45

Gly Gln Ile Tyr Pro Gly Asp Gly Asp Thr Asn Tyr Asn Gly Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Tyr Tyr Arg Ser Ala Trp Phe Ala Tyr Trp Gly Gln Gly
            100                 105                 110

Thr Leu Val Thr Val Ser Leu Ala Ser Thr Lys Gly Pro Ser Val
        115                 120                 125

<210> SEQ ID NO 461
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Trp Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser
        115                 120                 125

<210> SEQ ID NO 462
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser

```
            20                  25                  30

Ile His Trp Tyr Gln Gln Lys Pro Gly Gln Ala Pro Arg Leu Leu Ile
         35                  40                  45

Tyr Tyr Ala Ser Glu Ser Ile Ser Gly Ile Pro Ala Arg Phe Ser Gly
     50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser
        115                 120                 125

<210> SEQ ID NO 463
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Ile Gly Thr Ser
            20                  25                  30

Ile His Trp Tyr Gln Gln Lys Pro Gly Gln Ala Pro Arg Leu Leu Ile
         35                  40                  45

Tyr Tyr Ala Ser Glu Ser Ile Ser Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Asn Trp Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser
        115                 120                 125

<210> SEQ ID NO 464
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Ala Ile Gln Leu Thr Gln Ser Pro Ser Ser Leu Ser Ala Ser Val Gly
1               5                  10                  15

Asp Arg Val Thr Ile Thr Cys Arg Ala Ser Gln Ser Ile Gly Thr Ser
            20                  25                  30

Ile His Trp Tyr Gln Gln Lys Pro Gly Lys Ala Pro Lys Leu Leu Ile
         35                  40                  45

Tyr Tyr Ala Ser Glu Ser Ile Ser Gly Val Pro Ser Arg Phe Ser Gly
     50                  55                  60

Ser Gly Ser Gly Thr Asp Phe Thr Leu Thr Ile Ser Ser Leu Gln Pro
```

-continued

```
                65                  70                  75                  80
Glu Asp Phe Ala Thr Tyr Tyr Cys Gln Gln Ser Asn Asn Trp Pro Leu
                    85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser
                115                 120                 125

<210> SEQ ID NO 465
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Asp Ile Val Met Thr Gln Ser Pro Ser Leu Leu Ser Ala Ser Thr Gly
1               5                   10                  15

Asp Arg Val Thr Ile Ser Cys Arg Ala Ser Gln Ser Ile Gly Thr Ser
                20                  25                  30

Ile His Trp Tyr Gln Gln Lys Pro Gly Lys Ala Pro Glu Leu Leu Ile
                35                  40                  45

Tyr Tyr Ala Ser Glu Ser Ile Ser Gly Val Pro Ser Arg Phe Ser Gly
            50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Ser Asn Asn Trp Pro Leu
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser
                115                 120                 125

<210> SEQ ID NO 466
<211> LENGTH: 595
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Phe
                20                  25                  30

Trp Met Asn Trp Val Arg Gln Ala Pro Gly Gln Gly Leu Glu Trp Met
                35                  40                  45

Gly Gln Ile Tyr Pro Gly Asp Gly Asp Thr Asn Tyr Asn Gly Lys Phe
            50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Ser Tyr Tyr Arg Ser Ala Trp Phe Ala Tyr Trp Gly Gln Gly
                100                 105                 110

Thr Leu Val Thr Val Ser Ser Ala Ser Thr Lys Gly Pro Ser Val Phe
```

-continued

```
            115                 120                 125
Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Gly Gly Gly Ser Ile Pro Pro His Val
    450                 455                 460

Gln Lys Ser Val Asn Asn Asp Met Ile Val Thr Asp Asn Asn Gly Ala
465                 470                 475                 480

Val Lys Phe Pro Gln Leu Cys Lys Phe Cys Asp Val Arg Phe Ser Thr
                485                 490                 495

Cys Asp Asn Gln Lys Ser Cys Met Ser Asn Cys Ser Ile Thr Ser Ile
            500                 505                 510

Cys Glu Lys Pro Gln Glu Val Cys Val Ala Val Trp Arg Lys Asn Asp
        515                 520                 525

Glu Asn Ile Thr Leu Glu Thr Val Cys His Asp Pro Lys Leu Pro Tyr
    530                 535                 540
```

His Asp Phe Ile Leu Glu Asp Ala Ala Ser Pro Lys Cys Ile Met Lys
545                 550                 555                 560

Glu Lys Lys Lys Pro Gly Glu Thr Phe Phe Met Cys Ser Cys Ser Ser
                565                 570                 575

Asp Glu Cys Asn Asp Asn Ile Ile Phe Ser Glu Glu Tyr Asn Thr Ser
            580                 585                 590

Asn Pro Asp
        595

<210> SEQ ID NO 467
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Ser
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Asn Trp Pro Leu
                85                  90                  95

Thr Phe Gly Gln Gly Thr Lys Val Glu Ile Lys Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 468
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Arg Ile Trp Phe Ile Pro Arg Ser Ser Trp Tyr Glu Arg Ala
1               5                   10

<210> SEQ ID NO 469
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ile Trp Phe Ile Pro Arg Ser Ser Trp Tyr Glu Arg Ala
1               5                   10

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Phe Ile Pro Arg Ser Ser Trp Tyr Glu Arg Ala
1               5                   10

<210> SEQ ID NO 471
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Phe Ile Pro Arg Ser Ser Trp Tyr Glu Arg Ala
1               5                   10

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Ile Pro Arg Ser Ser Trp Tyr Glu Arg Ala
1               5                   10

<210> SEQ ID NO 473
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Pro Arg Ser Ser Trp Tyr Glu Arg Ala
1               5

<210> SEQ ID NO 474
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 474

Lys Arg Ile Trp Phe Ile Pro Arg Ser Ser Trp Tyr Glu Arg
1               5                   10

<210> SEQ ID NO 475
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Lys Arg Ile Trp Phe Ile Pro Arg Ser Ser Trp Tyr Glu
1               5                   10

<210> SEQ ID NO 476
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Lys Arg Ile Trp Phe Ile Pro Arg Ser Ser Trp Tyr
1               5                   10

<210> SEQ ID NO 477
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Lys Arg Ile Trp Phe Ile Pro Arg Ser Ser Trp
1               5                   10

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Lys Arg Ile Trp Phe Ile Pro Arg Ser Ser
1               5                   10

<210> SEQ ID NO 479
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Lys Arg Ile Trp Phe Ile Pro Arg Ser
1               5

<210> SEQ ID NO 480
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Arg Ile Trp Phe Ile Pro Arg Ser Ser Trp Tyr Glu Arg
1               5                   10

<210> SEQ ID NO 481
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ile Trp Phe Ile Pro Arg Ser Ser Trp Tyr Glu
1               5                   10

<210> SEQ ID NO 482
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Trp Phe Ile Pro Arg Ser Ser Trp Tyr
1               5

<210> SEQ ID NO 483
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Asp Arg Arg Ile Phe Trp Trp Ser Leu Arg Ser Ala Pro Gly Ala
1               5                   10                  15

<210> SEQ ID NO 484
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

His Val Arg Leu His His Tyr Leu Arg His Arg Ser Leu Pro Asn
1               5                   10                  15

<210> SEQ ID NO 485
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Arg Phe Phe Thr Arg Phe Pro Trp His Tyr His Ala Ser Arg Leu
```

```
                    1               5                  10                  15

<210> SEQ ID NO 486
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Arg Leu Ala His Ser His Arg His Arg Ser His Val Ala Leu Thr
1               5                  10                  15

<210> SEQ ID NO 487
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Arg Arg Trp Val Arg Tyr Pro Val His Leu His Ser Pro Ile Val
1               5                  10                  15

<210> SEQ ID NO 488
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Pro Pro Tyr His Arg Phe Trp Arg Gly His Arg His Ala Val Gln
1               5                  10                  15

<210> SEQ ID NO 489
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

His Arg Ile Ser His Phe Ala His Arg Tyr Leu Ala Arg Leu His
1               5                  10                  15

<210> SEQ ID NO 490
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Trp His Trp Arg His Arg Ile Pro Leu Gln Leu Ala Ala Gly Arg
1               5                  10                  15

<210> SEQ ID NO 491
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 491

Gly Trp His Ser Leu Leu His Ser Arg Tyr His Arg Ile Ala Ala
1               5                   10                  15

<210> SEQ ID NO 492
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Phe Val Trp Val Arg Phe His Arg Leu Pro Arg Gln Ile Tyr Thr
1               5                   10                  15

<210> SEQ ID NO 493
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Trp His Lys Tyr Phe Leu Arg Arg Pro Leu Ser Val Arg Thr Arg
1               5                   10                  15

<210> SEQ ID NO 494
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Val Pro Met Ala Leu Asn His Gly Val Tyr Val Met Val Ser Ser
1               5                   10                  15

<210> SEQ ID NO 495
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Arg Lys Trp Phe Leu Gln His Arg Arg Met Pro Val Ser Val Leu
1               5                   10                  15

<210> SEQ ID NO 496
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Ser Gly Arg Arg His Leu His Arg His His Ile Phe Ser Leu Pro
1               5                   10                  15

<210> SEQ ID NO 497

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Gly Trp Ile Thr Phe His Arg Arg His His Asp Arg Val Leu Ser
1               5                   10                  15

<210> SEQ ID NO 498
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Arg Leu His Gly His Arg Ser His Arg Phe Thr His Val Ala Gln
1               5                   10                  15

<210> SEQ ID NO 499
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Lys Arg Ile Trp Phe Ile Pro Arg Ser Ser Trp Tyr Glu Arg Ala
1               5                   10                  15

<210> SEQ ID NO 500
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Met Pro Leu Ser Arg Tyr Trp Trp Leu Phe Ser His Arg Pro Arg
1               5                   10                  15

<210> SEQ ID NO 501
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Arg His Leu Ser His Phe Lys Trp Leu Arg Ser His Gly Leu Asp
1               5                   10                  15

<210> SEQ ID NO 502
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502
```

```
Arg Arg Phe His Phe His Ser Arg Met Val Ala Val Asp Asn Ser
1               5                   10                  15
```

<210> SEQ ID NO 503
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

```
His Ala Asn Phe Cys Leu Gly Pro Cys Pro Tyr Ile Trp Ser Leu Ala
1               5                   10                  15
```

<210> SEQ ID NO 504
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

```
Phe Cys Leu Gly Pro Cys Pro Tyr Ile Trp Ser Leu Asp Thr Ala
1               5                   10                  15
```

<210> SEQ ID NO 505
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

```
Ser Asn Pro Tyr Ser Ala Phe Gln Val Asp Ile Ile Val Asp Ile Ala
1               5                   10                  15
```

<210> SEQ ID NO 506
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

```
Thr Ser Leu Asp Ala Thr Met Ile Trp Thr Met Met Ala
1               5                   10
```

<210> SEQ ID NO 507
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

```
Thr Ser Leu Asp Ala Ser Ile Trp Ala Met Met Gln Asn Ala
1               5                   10
```

<210> SEQ ID NO 508
<211> LENGTH: 42
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 508
aggatctggt tcatccccag gagcagctgg tacgagaggg cc                        42

<210> SEQ ID NO 509
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
atctggttca tccccaggag cagctggtac gagagggcc                            39

<210> SEQ ID NO 510
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
ttcatcccca ggagcagctg gtacgagagg gcc                                  33

<210> SEQ ID NO 511
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
ttcatcccca ggagcagctg gtacgagagg gcc                                  33

<210> SEQ ID NO 512
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
atccccagga gcagctggta cgagagggcc                                      30

<210> SEQ ID NO 513
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
cccaggagca gctggtacga gagggcc                                         27

<210> SEQ ID NO 514
<211> LENGTH: 42
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 514
aagaggatct ggttcatccc caggagcagc tggtacgaga gg                         42

<210> SEQ ID NO 515
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
aagaggatct ggttcatccc caggagcagc tggtacgag                             39

<210> SEQ ID NO 516
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
aagaggatct ggttcatccc caggagcagc tggtac                                36

<210> SEQ ID NO 517
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
aagaggatct ggttcatccc caggagcagc tgg                                   33

<210> SEQ ID NO 518
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
aagaggatct ggttcatccc caggagcagc                                       30

<210> SEQ ID NO 519
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
aagaggatct ggttcatccc caggagc                                          27

<210> SEQ ID NO 520
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
aggatctggt tcatccccag gagcagctgg tacgagagg              39

<210> SEQ ID NO 521
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
atctggttca tccccaggag cagctggtac gag                    33

<210> SEQ ID NO 522
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
tggttcatcc ccaggagcag ctggtac                           27

<210> SEQ ID NO 523
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gacaggagga tcttctggtg gagcctgagg agcgcccccg gcgcc        45

<210> SEQ ID NO 524
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
cacgtgaggc tgcaccacta cctgaggcac aggagcctgc ccaac        45

<210> SEQ ID NO 525
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
aggttcttca ccaggttccc ctggcactac cacgccagca ggctg        45

<210> SEQ ID NO 526
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
aggctggccc acagccacag gcacaggagc cacgtggccc tgacc     45

<210> SEQ ID NO 527
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
aggaggtggg tgaggtaccc cgtgcacctg cacagcccca tcgtg     45

<210> SEQ ID NO 528
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
cccccctacc acaggttctg gaggggccac aggcacgccg tgcag     45

<210> SEQ ID NO 529
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
cacaggatca gccacttcgc ccacaggtac ctggccaggc tgcac     45

<210> SEQ ID NO 530
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
tggcactgga ggcacaggat cccctgcag ctggccgccg gcagg     45

<210> SEQ ID NO 531
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ggctggcaca gcctgctgca cagcaggtac cacaggatcg ccgcc     45

<210> SEQ ID NO 532
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
ttcgtgtggg tgaggttcca caggctgccc aggcagatct acacc    45

<210> SEQ ID NO 533
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
tggcacaagt acttcctgag gaggcccctg agcgtgagga ccagg    45

<210> SEQ ID NO 534
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
gtgcccatgg ccctgaacca cggcgtgtac gtgatggtga gcagc    45

<210> SEQ ID NO 535
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
aggaagtggt tcctgcagca caggaggatg cccgtgagcg tgctg    45

<210> SEQ ID NO 536
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
agcggcagga ggcacctgca caggcaccac atcttcagcc tgccc    45

<210> SEQ ID NO 537
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ggctggatca ccttccacag gaggcaccac gacagggtgc tgagc    45

<210> SEQ ID NO 538
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
aggctgcacg gccacaggag ccacaggttc acccacgtgg cccag     45

<210> SEQ ID NO 539
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
aagaggatct ggttcatccc caggagcagc tggtacgaga gggcc     45

<210> SEQ ID NO 540
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
atgcccctga gcaggtactg gtggctgttc agccacaggc ccagg     45

<210> SEQ ID NO 541
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
aggcacctga gccacttcaa gtggctgagg agccacggcc tggac     45

<210> SEQ ID NO 542
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
aggaggttcc acttccacag caggatggtg gccgtggaca acagc     45

<210> SEQ ID NO 543
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
cacgccaact tctgcctggg cccctgcccc tacatctgga gcctggcc     48

<210> SEQ ID NO 544
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ttctgcctgg gcccctgccc ctacatctgg agcctggaca ccgcc     45

<210> SEQ ID NO 545
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
agcaacccct acagcgcctt ccaggtggac atcatcgtgg acatcgcc                48

<210> SEQ ID NO 546
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
accagcctgg acgccaccat gatctggacc atgatggcc                          39

<210> SEQ ID NO 547
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
accagcctgg acgccagcat ctgggccatg atgcagaacg cc                      42

<210> SEQ ID NO 548
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 549
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Glu Pro Lys Ser Cys Asp Lys Thr His Thr Cys Pro
1               5                   10

<210> SEQ ID NO 550
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys

<210> SEQ ID NO 551
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 551

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 552
<211> LENGTH: 98
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 552

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 553
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 553

Gly Gln Pro Arg Glu Pro Gln Val Tyr Thr Leu Pro Pro Ser Arg Glu
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 554
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 554

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 555
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 2-6 "Gly Gly Gly
      Gly Ser" repeating units

<400> SEQUENCE: 555

Gly Gly Gly Gly Ser Gly Gly Gly Ser Gly Gly Gly Gly Ser Gly
 1               5                   10                  15

Gly Gly Gly Ser Gly Gly Gly Ser Gly Gly Gly Gly Ser
            20                  25                  30

<210> SEQ ID NO 556
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(75)
<223> OTHER INFORMATION: This sequence may encompass 0-15 "Gly Gly Gly
      Gly Ser" repeating units

<400> SEQUENCE: 556

Gly Gly Gly Gly Ser Gly Gly Gly Ser Gly Gly Gly Gly Ser Gly
 1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Ser Gly Gly Gly
            35                  40                  45

Gly Ser Gly Gly Gly Ser Gly Gly Gly Ser Gly Gly Gly Gly
       50                  55                  60

Ser Gly Gly Gly Gly Ser Gly Gly Gly Ser
 65                  70                  75

<210> SEQ ID NO 557
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 0-15 "Gly Ser"
      repeating units

<400> SEQUENCE: 557

Gly Ser Gly Ser Gly Ser Gly Ser Gly Ser Gly Ser Gly Ser Gly Ser
```

```
                1               5                   10                  15
Gly Ser Gly Ser Gly Ser Gly Ser Gly Ser Gly Ser
            20                  25                  30
```

<210> SEQ ID NO 558
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This sequence may encompass 0-15 "Ser Gly"
      repeating units

<400> SEQUENCE: 558

```
Ser Gly Ser Gly Ser Gly Ser Gly Ser Gly Ser Gly Ser Gly Ser Gly
1               5                   10                  15
Ser Gly Ser Gly Ser Gly Ser Gly Ser Gly Ser Gly Ser Gly
            20                  25                  30
```

<210> SEQ ID NO 559
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(45)
<223> OTHER INFORMATION: This sequence may encompass 0-15 "Gly Ser Gly"
      repeating units

<400> SEQUENCE: 559

```
Gly Ser Gly Gly Ser Gly Gly Ser Gly Gly Ser Gly Gly Ser Gly Gly
1               5                   10                  15
Ser Gly Gly Ser Gly Gly Ser Gly Gly Ser Gly Gly Ser Gly Gly Ser
            20                  25                  30
Gly Gly Ser Gly Gly Ser Gly Gly Ser Gly Gly Ser Gly
        35                  40                  45
```

<210> SEQ ID NO 560
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(60)
<223> OTHER INFORMATION: This sequence may encompass 0-15 "Ser Gly Ser
      Gly" repeating units

<400> SEQUENCE: 560

```
Ser Gly Ser Gly Ser Gly Ser Gly Ser Gly Ser Gly Ser Gly Ser Gly
1               5                   10                  15
Ser Gly Ser Gly Ser Gly Ser Gly Ser Gly Ser Gly Ser Gly Ser Gly
            20                  25                  30
Ser Gly Ser Gly Ser Gly Ser Gly Ser Gly Ser Gly Ser Gly Ser Gly
        35                  40                  45
Ser Gly Ser Gly Ser Gly Ser Gly Ser Gly Ser Gly
    50                  55                  60
```

```
<210> SEQ ID NO 561
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Glu Ser Lys Tyr Gly Pro Pro Cys Pro Pro Cys Pro
1               5                   10

<210> SEQ ID NO 562
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 562

His His His His His His
1               5

<210> SEQ ID NO 563
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gly Gly Gly Gly Ser Gly Gly Gly Gly Ser
1               5                   10

<210> SEQ ID NO 564
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Val Val Gly Val Val Gly Gly Leu Leu Gly Ser Leu Val Leu Leu Val
1               5                   10                  15

Trp Val Leu Ala Val Ile
            20
```

FUSION CONSTRUCTS AND METHODS OF USING THEREOF

CROSS-REFERENCE TO RELATED APPLICATIONS

The present application claims the benefit of U.S. Provisional Patent Application Nos. 63/050,393, filed Jul. 10, 2020, and 63/173,902, filed Apr. 12, 2021, which are each hereby incorporated by reference in their entireties.

SEQUENCE LISTING

The instant application contains a Sequence Listing which has been submitted electronically in ASCII format and is hereby incorporated by reference in its entirety. The ASCII copy, created on Aug. 31, 2021, is named 75594-343221_SL.txt and is 483,038 bytes in size.

BACKGROUND OF THE DISCLOSURE

Recently, monoclonal antibody-based cancer immunotherapy based on the interruption of suppressive signals that are delivered to the adaptive immune system has shown promise in the clinic. With the FDA approval of CTLA-4 antibody inhibitor (e.g., ipilimumab) and PD-1 inhibitors (e.g., pembrolizumab, nivolumab), more treatment options are now available to treat solid tumors including lung cancer, renal cell cancer, and ovarian cancer. However, in the majority of indications where PD-1/PD-L1 and TGF-β are co-expressed (e.g., ovarian, gastric and colorectal) little to no response to immune checkpoint inhibitors has been observed. Accordingly, there is a continuing need in the art to obtain safer and more effective treatments for cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a fusion protein comprising: (a) a first component that is an antibody, or a fragment or variant thereof; and (b) a second component that is: (i) a cytokine trap, or fragment or variant thereof; or (ii) an adenosine deaminase (ADA), or fragment or variant.

In certain embodiments, first component is an immunoglobulin G (IgG) antibody, for example an IgG1, IgG2, IgG3, or IgG4 antibody. In certain embodiments, the antibody is an IgG1 or IgG4 antibody.

In certain embodiments, the antibody fragment of the first component is a Fab, (Fab)$_2$, (Fab')$_2$, Fv, (Fv)$_2$, or scFv.

In certain embodiments, the antibody, or fragment or variant thereof, of the first component comprises a variable region of a heavy chain ($V_H$) and a variable region of a light chain ($V_L$).

In certain embodiments, the antibody, or fragment or variant thereof, of the first component comprises a fragment crystallizable region ($F_C$), for example an $F_C1$, $F_C2$, $F_C3$, or $F_C4$ region, or a fragment or variant thereof. In certain embodiments, the antibody, or fragment or variant thereof, comprises an $F_C1$ region. In certain embodiments, the $F_C$ comprises at least one mutation.

In certain embodiments, the antibody, or fragment or variant thereof, of the first component comprises a scFv and an $F_C$.

In certain embodiments, the antibody, or fragment or variant thereof, of the first component binds to a tumor antigen expressed on the surface of a tumor cell. Examples of such a tumor antigen include CD19, BCMA, CD23, BAFF-R, GPRC5D, CD44, CAIX, CD5, CD30, CD70, CD44v6, CD44v7, CD44v8, CD174, CD28, CD128, CD138, CS1, CLL-1, L1-CAM, FAP, ROR1, CEA, EGP-2, EGP-40, HER2, HER3, Folate-binding Protein, GD2, GD3, IL-13R-a2, IL-11Rα, EphA2, CSPG4, KDR, EDB-F, mesothelin, CD22, EGFR, Folate receptor α, MUC-1, MUC-4, MUC-16, MAGE-A1, h5T4, PSMA, PSCA, GPC3, c-met, TAG-72, EGFR, CD20, EGFRvIII, CD123, and VEGF-R2. In certain embodiments, the tumor antigen is a mucin, for example a MUC1, MUC2, MUC3A, MUC3B, MUC4, MUC5AC, MUC5B, MUC6, MUC7, MUC8, MUC12, MUC13, MUC15, MUC16, MUC17, MUC19, or MUC20 antigen.

In certain embodiments, the antibody, or fragment or variant thereof, of the first component binds to MUC16. For example, the antibody, or fragment or variant thereof, may comprise a $V_L$ region comprising a sequence that is at least 80% identical to any one of SEQ ID NOs: 417-428 and/or a $V_H$ region comprising a sequence that is at least 80% identical to any one of SEQ ID NOs: 390-403. In certain embodiments, the antibody, or fragment or variant thereof, comprises a $V_H$ region comprising a sequence that is at least 80% identical to SEQ ID NO: 399 and/or a $V_L$ region comprising a sequence that is at least 80% identical to SEQ ID NO: 426. In certain embodiments, the antibody, or fragment or variant thereof, comprises a heavy chain sequence that is at least 80% identical to SEQ ID NO: 441 and/or a light chain sequence that is at least 80% identical to SEQ ID NO: 443.

In certain embodiments, the antibody, or fragment or variant thereof, of the first component binds to MUC1. For example, the antibody, or fragment or variant thereof, may comprise a $V_L$ region comprising a sequence that is at least 80% identical to any one of SEQ ID NOs: 449-453, and/or a $V_H$ region comprising a sequence that is at least 80% identical to any one of SEQ ID NOs: 444-448. In certain embodiments, the antibody, or fragment or variant thereof, comprises a $V_H$ region comprising a sequence that is at least 80% identical to SEQ ID NO: 444. In certain embodiments, the antibody, or fragment or variant thereof, comprises a $V_H$ region comprising a sequence that is at least 80% identical to SEQ ID NO: 444 and a $V_L$ region comprising a sequence that is at least 0% identical to any one of SEQ ID NOs: 449-453. In certain embodiments, the antibody, or fragment or variant thereof, comprises a heavy chain sequence that is at least 80% identical to SEQ ID NO: 466 and/or a light chain sequence that is at least 80% identical to SEQ ID NO: 467.

In certain embodiments, the antibody, or fragment or variant thereof, of the first component binds to programmed cell death protein-1 (PD-1). Such an antibody will be referred to herein as an "anti-PD-1 antibody."

In certain embodiments, the antibody of the first component is an IgG4 antibody comprising a sequence having at least 80% sequence identity to SEQ ID NO: 146 or 292 and having a mutation at position 108 thereof. For example, the antibody may be an IgG4 antibody comprising a sequence having at least 80% sequence identity to SEQ ID NO: 146 or 292 and having a S108P mutation (i.e., amino acid proline in place of serine at position 108).

In certain embodiments, the antibody, or fragment or variant thereof, of the first component comprises a $V_H$ or a $V_L$ that is connected to the second component by a linker.

In certain embodiments, the antibody, or fragment or variant thereof, of the first component comprises a $V_H$ and a $V_L$ and the $V_H$ and $V_L$ are connected to each other by a second linker, for example one comprising a sequence of any one of SEQ ID NOs: 17-34.

In certain embodiments, the anti-PD-1 antibody, or fragment or variant thereof, comprises a $V_H$ Comprising a sequence that is at least 80% identical to any one of SEQ ID NOs: 1-7, 149-164, 333-337, and 384 and/or a $V_L$ Comprising a sequence that is at least 80% identical to any one of SEQ ID NOs: 8-13, 148, 338-343, and 385. For example, the antibody, or fragment or variant thereof, may comprise: a $V_H$ Comprising a sequence that is at least 90% identical to SEQ ID NO: 6 and a $V_L$ Comprising a sequence that is at least 90% identical to SEQ ID NO: 12; a $V_H$ Comprising a sequence that is at least 90% identical to SEQ ID NO: 7 and a $V_L$ Comprising a sequence that is at least 90% identical to SEQ ID NO: 13; a $V_H$ Comprising a sequence that is at least 90% identical to SEQ ID NO: 333 and a $V_L$ Comprising a sequence that is at least 90% identical to SEQ ID NO: 338; a $V_H$ Comprising a sequence that is at least 90% identical to SEQ ID NO: 334 and a $V_L$ Comprising a sequence that is at least 90% identical to SEQ ID NO: 339; a $V_H$ Comprising a sequence that is at least 90% identical to SEQ ID NO: 335 and a $V_L$ Comprising a sequence that is at least 90% identical to SEQ ID NO: 340; a $V_H$ Comprising a sequence that is at least 90% identical to SEQ ID NO: 336 and a $V_L$ Comprising a sequence that is at least 90% identical to SEQ ID NO: 341; a $V_H$ Comprising a sequence that is at least 90% identical to SEQ ID NO: 337 and a $V_L$ Comprising a sequence that is at least 90% identical to SEQ ID NO: 342; a $V_H$ Comprising a sequence that is at least 90% identical to SEQ ID NO: 335 and a $V_L$ Comprising a sequence that is at least 90% identical to SEQ ID NO: 343; a $V_H$ Comprising a sequence that is at least 90% identical to SEQ ID NO: 384 and a $V_L$ Comprising a sequence that is at least 90% identical to SEQ ID NO: 385; or a $V_H$ Comprising a sequence that is at least 90% identical to SEQ ID NO: 386 and a $V_L$ Comprising a sequence that is at least 90% identical to SEQ ID NO: 387.

In certain embodiments, the anti-PD-1 antibody, or fragment or variant thereof, is: AM-0001; AMP-224; balstilimab; budigalimab; BI 754091; camrelizumab; cemiplimab; cetrelimab; dostarlinab; JTX-4014; MEDI-0680; MGA012; nivolumab; pembrolizumab; pidilizunab; prolgolimab; sasanlimab; sintilimab; spartalizumab; STI-1110; tislelizumab; toripalimab; or zimberelimab; or a fragment or variant thereof. For example, the anti-PD-1 antibody, or fragment or variant thereof, is: pembrolizumab; nivolumab; zimberelimab; or cetrelimab; or a fragment or variant thereof. In certain embodiments, the anti-PD-1 antibody, or fragment or variant thereof, of the first component is cetrelimab, or a fragment or variant thereof.

In certain embodiments, the anti-PD-1 antibody, or fragment or variant thereof, comprises a sequence that is at least 90% identical to SEQ ID NO: 15 and a sequence that is at least 90% identical to SEQ ID NO: 16 or 143. In certain embodiments, the anti-PD-1 antibody, or fragment or variant thereof, comprises a sequence that is at least 80% identical to SEQ ID NO: 296 and a sequence that is at least 80% identical to any one of SEQ ID NOs: 144, 145, and 295. In certain embodiments, the anti-PD-1 antibody, or fragment or variant thereof, comprises a sequence that is at least 80% identical to SEQ ID NO: 13 or 15 and a sequence that is at least 80% identical to SEQ ID NO: 294 or 295.

In certain embodiments, the second component of the fusion protein is a cytokine trap, for example a TGF-β cytokine trap. The TGF-β cytokine trap may, for example, comprise: a transforming growth factor receptor (TGFβR) or a fragment or variant thereof; an anti-TGF-β antibody or an antigen binding fragment or variant thereof; a TGF-β inhibitory peptide or a fragment or variant thereof; and/or a TGF-β antagonistic peptide or a fragment or variant thereof.

In certain embodiments, the TGF-β cytokine trap comprises a transforming growth factor beta receptor II (TGFβRII) or a fragment or variant thereof.

In certain embodiments, the TGF-β cytokine trap comprises a TGFβR extracellular domain or a fragment or variant thereof. In certain embodiments, the TGF-β cytokine trap comprises a TGFβRII extracellular domain, or a fragment or variant thereof, for example comprising a sequence that is at least 80% identical to any one of SEQ ID NOs: 14, 141, and 142. In certain embodiments, the TGFβRII extracellular domain, or a fragment or variant thereof, binds TGF-β1 and/or TGF-β3. In certain embodiments, the TGFβRII extracellular domain, or a fragment or variant thereof, binds TGF-β1 and TGF-β3 but does not bind TGF-β2 or binds TGF-β2 at a lower affinity than it does TGF-β1 and TGF-β3.

In certain embodiments, the TGF-β cytokine trap comprises a sequence that is at least 80% identical to any one of SEQ ID NOs: 14, 141, and 142.

In certain embodiments, the TGF-β cytokine trap comprises an anti-TGF-β antibody or an antigen binding fragment or variant thereof. The antibody, or antigen binding fragment or variant thereof, may for example comprise a variable region of a heavy chain ($V_H$) and a variable region of a light chain ($V_L$). In certain embodiments, the antibody, or antigen binding fragment or variant thereof, may comprise a $V_H$ comprising a sequence that is at least 80% identical to any one of SEQ ID NOs: 166, 168, 169, 171, 173, and 175 and/or a $V_L$ comprising a sequence that is at least 80% identical to any one of SEQ ID NOs: 165, 167, 170, 172, 174, 176, and 178.

In certain embodiments, the TGF-β cytokine trap comprises a TGF-β inhibitory peptide or a fragment or variant thereof, for example comprising a sequence that is at least 80% identical to any one of SEQ ID NOs: 468-507 and 263-267. In certain embodiments, the TGF-β cytokine trap comprises two or more TGF-β inhibitory peptides, or fragments or variants thereof. The two or more TGF-β inhibitory peptides, or fragments or variants thereof, may be connected by linker(s).

In certain embodiments, the TGF-β cytokine trap comprises a TGF-β antagonistic peptide or a fragment or variant thereof. In certain embodiments, the TGF-β cytokine trap comprising two or more TGF-β antagonistic peptides, or a fragments or variants thereof. The two or more TGF-β antagonistic peptides, or fragments or variants thereof, may be connected by linker(s).

In certain embodiments, the second component of the fusion protein is an ADA or a fragment or variant thereof.

In certain embodiments, the ADA, of fragment or variant thereof, is adenosine deaminase 2 (ADA2) or a fragment or variant thereof, for example one comprising a sequence that is at least 80% identical to any one of SEQ ID NOs: 273-279 and 284. In certain embodiments, the ADA2, or fragment or variant thereof, comprises at least one amino acid substitution or deletion.

In certain embodiments, the first and second components are connected by a linker. The linker may, for example, comprise: $(G4S)_n$, wherein n is 2, 3, 4, 5, or 6 (SEQ ID NO:

555); (Gly)$_n$, wherein n is 6, 7, or 8 (SEQ ID NO: 33); (EAAAK)$_n$, wherein n is 1, 2, 3, 4, 5, or 6 (SEQ ID NO: 34); A(EAAAK)$_4$ALEA(EAAAK)$_4$ A (SEQ ID NO: 31); and/or a sequence of any one of SEQ ID NOs: 17-34.

Also provided herein a polynucleotide encoding the fusion protein as described above. Further provided is an expression vector comprising such a polynucleotide operably linked to a promoter, for example, a constitutive promoter, a tissue specific promoter, or an inducible promoter. The promoter may be a small molecule ligand-inducible two polypeptide ecdysone receptor-based gene switch promoter. The vector may be an adenoviral vector.

Further provided herein is a pharmaceutical composition comprising: the fusion protein as described above or a polynucleotide encoding the same; and a pharmaceutically-acceptable excipient. In certain embodiments, the polynucleotide may be contained in an expression vector.

Also provided is a method of treating cancer, the method comprising contacting a cell with the fusion protein as described above or a polynucleotide encoding the same. In embodiments wherein the cell is contacted with a polynucleotide, the polynucleotide may be contained in an expression vector and the cell contacted with the vector. In certain embodiments the cell is a cancer cell. In certain embodiments, the cell is a mammalian cell. In certain embodiments, the mammalian cell is an immune cell. In certain embodiments, the immune cell is a T cell.

Further provided is a method of treating cancer in a subject in need of such treatment, the method comprising administering the aforementioned composition comprising the fusion protein to a subject. In certain embodiments, the cancer is a refractory cancer. In certain embodiments, the subject is non-responsive to a treatment with an anti-PD-1 antibody or a CTLA-4 antibody. In certain embodiments, the method further comprises administering one or more additional anti-cancer agent, for example a PD-1 inhibitor (e.g., an anti-PD-1 antibody, or a fragment or variant thereof), PD-L1 inhibitor, and/or a CTLA-4 inhibitor (e.g., an anti-CTLA-4 antibody or a fragment or variant thereof). In certain embodiments, the method further comprises administering a cytokine, for example a fusion protein comprising IL-15 and IL-15Rα. In certain embodiments, the subject is a mammalian subject, for example a human. In certain embodiments, the cancer is mesothelioma, glioblastoma, endometrial cancer, colorectal cancer, gastric cancer, cervical cancer, ovarian cancer, pancreatic cancer, prostate cancer, breast cancer, stomach cancer, bladder cancer, liver cancer, Hodgkin's lymphoma, lung cancer, skin cancer, renal cancer, head and neck cancer, melanoma, bronchus cancer, urinary tract cancer, anal cancer, brain cancer, esophageal cancer, cervical cancer, uterine cancer, cancer of the oral cavity or pharynx, kidney cancer, testicular cancer, biliary tract cancer, small bowel cancer, appendix cancer, salivary gland cancer, thyroid gland cancer, adrenal gland cancer, osteosarcoma, chondrosarcoma, or a cancer of a hematological tissue. In certain embodiments, the cancer is cutaneous squamous-cell carcinoma, melanoma or basal cell cancer. In certain embodiments, the cancer is non-small cell lung cancer (NSLC) or small cell lung cancer (SCLC). In certain embodiments, the cancer is triple negative breast cancer (TNBC).

In certain embodiments, the method further comprises administering an effective amount of T cells engineered to express an exogenous receptor. In certain embodiments, the exogenous receptor is a chimeric antigen receptor, for example one that comprises an antigen binding domain that binds to an epitope on CD19, BCMA, CD23, BAFF-R, GPRC5D, CD44, CAIX, CD5, CD30, CD70, CD44v6, CD44v7, CD44v8, CD174, CD28, CD128, CD138, CS1, CLL-1, L1-CAM, FAP, ROR1, CEA, EGP-2, EGP-40, HER2, HER3, Folate-binding Protein, GD2, GD3, IL-13R-a2, IL-11Rα, EphA2, CSPG4, KDR, EDB-F, mesothelin, CD22, EGFR, Folate receptor α, MUC-1, MUC-4, MUC-16, MAGE-A1, h5T4, PSMA, PSCA, GPC3, c-met, TAG-72, EGFR, CD20, EGFRvIII, CD123, or VEGF-R2. In certain embodiments, the chimeric antigen receptor is an engineered T-cell receptor. In certain embodiments, the chimeric antigen receptor comprises an antigen binding domain comprising a sequence that is at least 90% identical to any one of SEQ ID NOs: 37-56. In certain embodiments, the chimeric antigen receptor comprises an antigen binding domain comprising a sequence that is at least 90% identical to SEQ ID NO: 35 or 36. In certain embodiments, the effective amount of engineered T-cells is at least $10^2$ cells/kg, at least $10^4$ cells/kg, or at least $10^5$ cells/kg. In certain embodiments, the engineered T-cells further express a cytokine, for example a fusion protein comprising IL-15 and IL-15Rα.

Also provided is a use of a fusion protein of the present invention, or a polynucleotide encoding the same, in the manufacture of a medicament for use in the treatment of cancer.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 23A-23C are graphs showing the effect of various variants of anti-PD-1 and anti-PD-1-ADA2 fusion proteins on PD-L1/PD-1 interaction.

FIG. 26A-26D are graphs depicting the effect of variants of anti-PD-1-wtADA2 on T cell proliferation.

DETAILED DESCRIPTION OF THE DISCLOSURE

Figure 1:
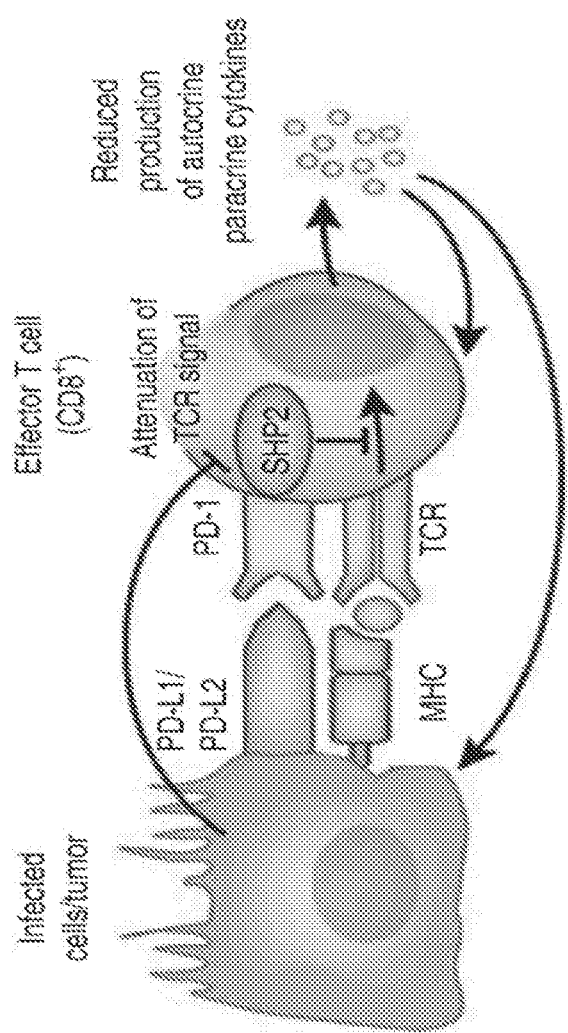
FIG. 1 is a schematic of PD-1/PD-L1 in immunosuppression.

The following description and examples illustrate certain embodiments of the present invention.

It is to be understood that the present disclosure is not limited to the particular embodiments described herein and as such can vary. Those of skill in the art will recognize that there are variations and modifications of the present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an," and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment," "certain embodiments," "other embodiments," or "another embodiment" means that a particular feature, structure, or characteristic described in connection with the embodiment is included in at least one embodiment of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Polynucleotide" or "oligonucleotide" as used herein refers to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs.

"Transfection," "transformation," or "transduction" as used herein refer to the introduction of one or more exogenous polynucleotides into a host cell by using physical or chemical methods. The polynucleotide sequences and vectors disclosed or contemplated herein can be introduced into a cell by, for example, transfection, transformation, or transduction. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

"Polypeptide," "peptide," and their grammatical equivalents as used herein refer to a polymer of amino acid residues. The polypeptide can optionally include glycosylation or other modifications typical for a given protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides or proteins described herein in an engineered cell can be associated with post-translational modifications of one or more amino acids of the polypeptide or protein. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

The term "fragment" when used in reference to a polypeptide or a nucleic acid refers to a truncated polypeptide or nucleic acid that retains the primary function of the referenced polypeptide or nucleic acid.

The term "variant" when used in reference to a polypeptide or a nucleic acid refers to a polypeptide or nucleic acid that differs from the parent polypeptide or nucleic acid but has at least 50% sequence identity with the referenced polypeptide or nucleic acid and retains the primary function of the parent polypeptide or nucleic acid.

The terms "identical" and its grammatical equivalents as used herein or "sequence identity" in the context of two nucleic acid sequences or amino acid sequences of polypeptides refer to the residues in the two sequences which are the same when aligned for maximum correspondence over a specified comparison window. A "comparison window," as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.*, 2:482 (1981); by the alignment algorithm of Needleman and Wunsch, *J. Mol. Biol.*, 48:443 (1970); by the search for similarity method of Pearson and Lipman, *Proc. Nat. Acad. Sci. U.S.A.*, 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene,* 73:237-244 (1988) and Higgins and Sharp, *CABIOS,* 5:151-153 (1989); Corpet et al., *Nucleic Adds Res.*, 16:10881-10890 (1988); Huang et al., *Computer Applications in the Biosciences,* 8:155-165 (1992); and Pearson et al., *Methods in Molecular Biology,* 24:307-331 (1994). Alignment is also often performed by inspection and manual alignment. In one class of embodiments, the polypeptides herein are at least 80%, 85%, 90%, 95%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, the percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In some embodiments, the substantial identity exists over a region of the sequences that is at least about 50 residues in length, over a region of at least about 100 residues, and in some embodiments, the sequences are substantially identical over at least about 150 residues. In some embodiments, the sequences are substantially identical over the entire length of the coding regions.

"Homology" is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available. Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed "homologs." For example, any naturally occurring proteins can be modified by any available mutagenesis method. When expressed, this mutagenized nucleic acid encodes a polypeptide that is homologous to the protein encoded by the original nucleic acid.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., Gene Therapy, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad Sci. USA*, 77: 3567 (1980); O'Hare et al., Proc. Natl. Acad. Sci. USA, 78: 1527 (1981); Mulligan & Berg, *Proc. Natl. Acad. Sci. USA*, 78: 2072 (1981); Colberre-Garapin et al., *J. Mol. Biol.*, 150:1 (1981); Santerre et al., *Gene*, 30: 147 (1984); Kent et al., *Science*, 237: 901-903 (1987); Wigler et al., *Cell* 11: 223 (1977); Szybalska & Szybalski, *Proc. Natl. Acad Sci. USA*, 48: 2026 (1962); Lowy et al., *Cell*, 22: 817 (1980); and U.S. Pat. Nos. 5,122,464 and 5,770,359.

The term "coding sequence" as used herein refers to a segment of a polynucleotide that encodes for protein or polypeptide. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence. Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The terms "induce" and "induction," and their grammatical equivalents as used herein, refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

The term "antibody," also known as immunoglobulin (Ig), as used herein can refer to a monoclonal or polyclonal antibody. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. The antibodies can be from any animal origin. An antibody can be IgG (including IgG1, IgG2, IgG3, and IgG4), IgA (including IgA1 and IgA2), IgD, IgE, or IgM, and IgY. In some embodiments, the antibody can be whole antibodies, including single-chain whole antibodies. In some embodiments, the antibody can be a fragment of an antibody, which can include, but are not limited to, a Fab, a Fab', a F(ab')$_2$, a Fd (consisting of $V_H$ and CH1), a Fv fragment (consisting of $V_H$ and $V_L$), a single-chain variable fragment (scFv), a single-chain antibody, a disulfide-linked variable fragment (dsFv), and fragments comprising either a $V_L$ or $V_H$ domain. A whole antibody typically consists of four polypeptides: two identical copies of a heavy (H) chain polypeptide and two identical copies of a light (L) chain polypeptide. Each of the heavy chains contains one N-terminal variable ($V_H$) region and three C-terminal constant (CH1, CH2 and CH3) regions, and each light chain contains one N-terminal variable ($V_L$) region and one C-terminal constant ($C_L$) region. The variable regions of each pair of light and heavy chains form the antigen binding site of an antibody. The $V_H$ and $V_L$ regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. Preferably, the term "CDR" is a CDR as defined by Kabat, based on sequence comparisons. CDRH1, CDRH2 and CDRH3 denote the heavy chain CDRs, and CDRL1, CDRL2 and CDRL3 denote the light chain CDRs.

The terms "fragment of an antibody," "antibody fragment," "fragment of an antibody," "antigen-binding portion" or its grammatical equivalents are used interchangeably herein to mean one or more fragments or portions of an antibody that retain the ability to specifically bind to an antigen (see, generally, Holliger et al., Nat. Biotech., 23(9): 1126-1129 (2005)). The antibody fragment desirably comprises, for example, one or more CDRs, the variable region (or portions thereof), the constant region (or portions thereof), or combinations thereof. Non-limiting examples of antibody fragments include (1) a Fab fragment, which is a monovalent fragment consisting of the $V_L$, $V_H$, $C_L$, and CH1 domains; (2) a F(ab')2 fragment, which is a bivalent fragment comprising two Fab fragments linked by a disulfide bridge at the stalk region; (3) a Fv fragment consisting of the $V_L$ and $V_H$ domains of a single arm of an antibody; (4) a single chain Fv (scFv), which is a monovalent molecule consisting of the two domains of the Fv fragment (i.e., $V_L$ and $V_H$) joined by a linker which enables the two domains to be synthesized as a single polypeptide chain (see, e.g., Bird et al., Science, 242: 423-426 (1988); Huston et al., *Proc. Natl. Acad Sci. USA*, 85: 5879-5883 (1988); and Osbourn et al., *Nat. Biotechnol.*, 16: 778 (1998)) and (5) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Pat. No. 8,603,950.

"Antigen recognition moiety," "antigen recognition domain," "antigen binding domain," or "antigen binding region" refers to a molecule or portion of a molecule that specifically binds to an antigen. In some embodiments, the antigen recognition moiety is an antibody, antibody like molecule or fragment thereof.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —NH$_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein.

The term "proliferative disease" as referred to herein refers to a unifying concept in which excessive proliferation of cells and/or turnover of cellular matrix contributes significantly to the pathogenesis of the disease, including cancer. In some embodiments, the proliferative disease is cancer.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to cancer.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment," "treating," or its grammatical equivalents refers to obtaining a desired pharmacologic and/or physiologic effect. In embodiments, the effect is therapeutic, i.e., the effect partially or completely cures a disease and/or adverse symptom attributable to the disease. In some embodiments, the term "treating" can include "preventing" a disease or a condition.

As used herein, a "treatment interval" refers to a treatment cycle, for example, a course of administration of a therapeutic agent that can be repeated, e.g., on a regular schedule. In embodiments, a dosage regimen can have one or more periods of no administration of the therapeutic agent in between treatment intervals. For example, a treatment interval can include one dose of a fusion protein administered in combination with (prior, concurrently or after) administration of a second therapeutic agent, e.g. CAR-T cells.

The terms "administered in combination" or "co-administration" or "co-administering" or "co-providing" as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the first treatment and second treatment can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional, e.g., secondary, treatment. The order of administration of the first and secondary treatment can also be reversed.

The terms "therapeutically effective amount," therapeutic amount," "immunologically effective amount," "anti-tumor effective amount," "tumor-inhibiting effective amount," and their grammatical equivalents, refer to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

As used herein, reference to a particular polypeptide (e.g., antibody, ligand, or receptor) shall include any and all forms of that polypeptide, including fragments and variants that retain at least part of the activity of the polypeptide. Unless indicated differently, reference to a particular polypeptide includes all mammalian species thereof (e.g., human, canine, feline, equine, and bovine). For example, the term "PD-1" necessarily includes any active form of PD-1, including fragments and variants that retain at least partial PD-1 activity.

Fusion Proteins

In some embodiments, the fusion protein (or fragment or variant thereof) provided herein comprise: (a) a first component that is an antibody, or a fragment or variant thereof; and (b) a second component this is a cytokine trap or an adenosine deaminase (ADA) or a fragment or variant thereof. In certain embodiments, the antibody, or fragment or variant thereof, of the first component binds to programmed cell death protein-1 (PD-1). Such an antibody will be referred to herein as an "anti-PD-1 antibody." In certain other embodiments, the antibody, or fragment or variant thereof, of the first component binds to a tumor antigen expressed on the surface of a tumor cell.

In some embodiments of the fusion protein comprising an anti-PD-1 antibody, the fusion protein comprises prembrolizumab (Ketruda®) fused to a cytokine trap (e.g., TGF-β trap). In some embodiments, the fusion protein comprises nivolumab (Opdivo®) fused to a cytokine trap (e.g., TGF-β trap). In some embodiments, the fusion protein comprises zimberelimab (WBP3055) fused to a cytokine trap (e.g., TGF-β trap). In some embodiments, the fusion protein comprises cetrelimab (JNJ-63723283) can be fused to a cytokine trap (e.g., TGF-β trap).

In certain embodiments wherein the antibody, or fragment or variant thereof, binds to a tumor antigen expressed on the surface of a tumor cell, the tumor antigen may be a MUC1 antigen. In certain other such embodiments, the tumor antigen is a MUC16 antigen.

In some embodiments, the fusion protein (or fragment or variant thereof) described herein comprises a cytokine trap as described above and an antibody, a fragment or a variant of the antibody that targets immune checkpoint genes. In some embodiments, an antibody or a fragment of the antibody or a variant of the antibody that target immune checkpoints, such as cytotoxic T lymphocyte associated protein-4 (CTLA-4) and programmed cell death-ligand-1 (PDL1), can be fused to a TGF-β trap molecule via a linker. In some embodiments, the PD-L1 inhibitor is atezolizumab.

U.S. patent application publication number U.S. 2015/0225483A1, incorporated herein by reference, describes a bi-functional fusion protein that combines a PD-L1 antibody with the soluble extracellular domain of transforming growth factor beta receptor type II (TGFβRII) as a neutralizing "Trap," into a single molecule. Specifically, the protein is a heterotetramer, consisting of the two immunoglobulin light chains of anti-PD-L1, and two heavy chains comprising the heavy chain of anti-PD-L genetically fused via a flexible glycine-serine linker to the extracellular domain of the human TGFβRII (see FIG. 1). This anti-PD-L1/TGFʹP Trap molecule is designed to target two major mechanisms of immunosuppression in the tumor microenvironment. US patent application publication number US2015/0225483A1 describes administration of the Trap molecule at doses based on the patient's weight.

In some embodiments, the fusion protein (or fragment or variant thereof) provided herein comprises an anti-PD-1 from Table 1 fused to an adenosine deaminase (e.g., ADA2) described herein or a functional variant or derivative thereof. In some embodiments, the fusion protein comprises prembrolizumab (Keytruda®) fused to an adenosine deaminase (e.g., ADA2). In some embodiments, the fusion protein comprises nivolumab (Opdivo®) fused to an adenosine deaminase (e.g., ADA2). In some embodiments, the fusion protein comprises zimberelimab (WBP3055) fused to an adenosine deaminase (e.g., ADA2). In some embodiments, the fusion protein comprises cetrelimab (JNJ-63723283) fused to an adenosine deaminase (e.g., ADA2).

Programmed Cell Death Protein and Other Check-Point Inhibitors

Programmed cell death protein 1, also known as PD-1, is a family of inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells. For purposes of the present invention, it will be explicitly understood that the term "PD-1" encompass all known and previously identified terms and titles of PD-1, including, for example, PD-1, PD-1, programmed cell death protein 1, programmed cell death 1, programmed cell death 1 receptor, programmed cell death 1 protein, CD279, cluster of differentiation 279, hPD-1, PDCD1, CD279 antigen, systemic lupus erythematosus susceptibility 2, HPD-L, HSLE1, and/or SLEB2.

PD-1 was previously identified using a subtraction cloning based approach to select for genes upregulated during TCR-induced activated T cell death. Like CTLA-4, PD-1 is rapidly induced on the surface of T-cells in response to anti-CD3 (Agata et al., 25 *Int. Immunol.* 8:765 (1996)). In contrast to CTLA-4, however, PD-1 is also induced on the surface of B-cells (in response to anti-IgM). PD-1 is also expressed on a subset of thymocytes and myeloid cells (Agata et al., supra Nishimura et al., *Int. Immunol.* 8:773 (1996)).

The nucleic acid and amino acid sequences of a representative human PD-1 biomarker is available to the public at the GenBank database under NM_005018.2 and NP_005009.2 and is shown in Table 26 (see also Ishida et al. 20 *EMBO J* 11:3887 (1992); Shinohara et al. *Genomics* 23:704 (1994); U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al., *EMBO J.* 11:3887 (1992); Shinohara et al., *Genomics* 23:704 (1994); and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron, *Immunol. Today* 18:286 (1997)). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al., *Immunol. Today* 20(6):285-8 (1999)). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

As used herein, the term "anti-PD-1" is used synonymously with "PD-1 antibody", "anti-PD-1 antibody" and "PD-1 inhibitor," and each of these terms refers to a polypeptide capable of inhibiting PD-1 biological activity and/or downstream event(s) mediated by PD-1. For clarity, the term "anti-PD-1" encompasses anti-PD-1 proteins and fragments and variants thereof that are capable of inhibiting PD-1 biological activity and/or downstream event(s) mediated by PD-1. Anti-PD-1 proteins encompass polypeptides that block, antagonize, suppress or reduce (to any degree including significantly) PD-1 biological activity, including downstream events mediated by PD-1, such as PD-1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the terms "anti-PD-1, "PD-1 antibody," "anti-PD-1 antibody," and "PD-1 inhibitor" encompass all the previously identified terms, titles, and functional states and characteristics whereby PD-1 itself or a PD-1 biological activity, is substantially nullified, decreased, or neutralized in any meaningful degree. In some embodiments, an anti-PD-1 antibody binds PD-1 and upregulates anti-tumor immune response.

As used herein, the terms "PD-1 ligand" and "PD-L" refer to binding partners of the PD-1 receptor and includes all known PD-1 ligands polypeptides, including PD-L1 (Freeman et al., *J. Exp. Med.* 192:1027 (2000)) and PD-L2 (Latchman et al., *Nat. Immunol.* 2:flinker (2001)). PD-1 ligand proteins comprise a signal sequence, and an IgV domain, an IgC domain, a transmembrane domain, and a short cytoplasmic tail. Both PD-L1 (see, e.g., Freeman et al., *J. Exp. Med* 192:1027 (2000) for sequence data) and PD-L2 (see, e.g., Latchman et al., *Nat. Immunol.* 2:261 (2000) for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, e.g., Butte et al., *Immunity* 27:111 (2007)).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al., *Immunity* 11:423 (1999)), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

Many B7 polypeptides are capable of providing costimulatory or inhibitory signals to immune cells to promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In some embodiments, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

The PD-1/PD-L1 signaling axis can promote tumor mediated immune evasion. In some cases, PD-L1 can be overexpressed by tumor cells, accessory cells, such as myeloid-derived suppressor cell (MDSCs), tumor associated macrophages (AMs), antigen presenting cells (APCs), in the tumor microenvironment. In some cases, PD-1 can be upregulated by "exhausted" T cells and can signal to suppress effector T cells function upon binding to its ligand (PD-L1, PD-L2, and CD380). Blockade of the PD-1/PD-L1 pathway by anti-PD-1 or anti-PD-L1 can restore the function of exhausted T cells and promote tumor cell killing (FIG. 1).

In some embodiment, of the present invention, the PD-1 inhibitor is selected or derived from a full-length, fragment, or variant of an antibody from Table 1.

TABLE 1

PD-1 Antibodies

| Name | Also Known as | Company | Reference(s) |
|---|---|---|---|
| cemiplimab | Libtayo, cemiplimab, REGN2810 | Regeneron, Sanofi | WO 2015/112800 |
| pembrolizumab | Keytruda, MK-3475, SCH 900475, lambrolizumab | Merck (MSD), Schering-Plough | WO 2008/156712, U.S. Pat. No. 8,354,509, U.S. Pat. No. 8,952,136, U.S. Pat. No. 8,900,587 |
| nivolumab | Opdivo, ONO-4538, MDX-1106, BMS-936558, 5C4 | BMS, Medarex, Ono | U.S. Pat. No. 8,728,474, U.S. Pat. No. 8,779,105, U.S. Pat. No. 8,008,449, U.S. Pat. No. 9,067,999, U.S. Pat. No. 9,073,994 |
| toripalimab | JS001, JS-001, TAB001, triprizumab | Junmeng Biosciences, Shanghai Junshi, TopAlliance Bio | Si-Yang Liu et al., *J. Hematol. Oncol.* 10: 136 (2017) |
| sintilimab | Tyvyt, IBI308 | Adimab, Innovent, Lilly | WO 2017/024465, WO 2017/025016, WO 2017/132825, WO 2017/133540 |
| LY3434172 | — | Lilly, Zymeworks | ClinicalTrials.gov Identifier: NCT03936959 |
| JTX-4014 | — | Jounce Therapeutics Inc. | U.S. 2018/0118829; ClinicalTrials.gov Identifier: NCT03790488; Papdopolous et al., *Cancer Immunol Immunother* 70(3): 763-772 (2021)) |
| 609 A | 609A | 3S Bio; Sunshine Guojian Pharma | ClinicalTrials.gov Identifier: NCT03998345 |
| Sym021 | — | Symphogen A/S | Gjetting et al., *mAbs* 11(4): 666-680 (2019 |
| LZM009 | — | Livzon Pharmaceutical Group | ClinicalTrials.gov Identifier: NCT03286296 |
| budigalimab | ABBV-181, PR-1648817 | Abbvie | Powderly et al., *Annals of Oncology* 29(8) (2018); |

TABLE 1-continued

| PD-1 Antibodies | | | |
|---|---|---|---|
| Name | Also Known as | Company | Reference(s) |
| IB | IBI-318 | Innovent, Lilly | ClinicalTrials.gov Identifier: NCT03000257 ClinicalTrials.gov Identifier: NCT03875157 |
| SCT-I10A | — | Sinocelltech Ltd. | ClinicalTrials.gov Identifier: NCT03821363 |
| SG001 | — | CSPC ZhongQi Pharmaceutical Technology Co., Ltd. | ClinicalTrials.gov Identifier: NCT03852823 |
| AMP-224 | GSK-2661380 | Astra Zeneca, Glaxo Smith Kline | Floudas et al., *Clin. Colorectal Cancer* 18(4) (2019) |
| AMG 404 | AMG404 | Amgen | ClinicalTrials.gov Identifier: NCT03853109 |
| AK112 | — | Akesobio Australia Pty Ltd | ClinicalTrials.gov Identifier: NCT04047290 |
| CS1003 | — | CStone Pharma | Li et al., *Acta Pharmacologica Sinica* 42: 142-148 (2021) |
| MEDI0680 | AMP-514 | Astra Zeneca, Amplimmune, Medimmune | WO 2012/145493, WO 2014/194293 |
| RO7121661 | — | Roche | ClinicalTrials.gov Identifier: NCT03708328 |
| F520 | — | Shandong New Time Pharmaceutical Co. | ClinicalTrials.gov Identifier: NCT03657381 |
| sasanlimab | PF-06801591, RN-888 | Pfizer | Cho et al., *Annals of Oncology* 30(5) (2019) |
| BI 754091 | BI754091 | Boehringer Ingelheim | Kang et al., *J. Clin. Oncology* 38(15) (2020) |
| cetrelimab | JNJ-63723283 | Janssen Biotech | Rutkowski et al., *J. Clin. Oncology* 37: 8 (2019) |
| HerinCAR-PD-1 | — | Ningbo Cancer Hospital | ClinicalTrials.gov Identifier: NCT02873390 |
| HX008 | — | Taizhou Hanzhong Bio | Zhang et al, *mAbs* 12(1) (2020); ClinicalTrials.gov Identifier: NCT03704246 |
| zimberelimab | WBP3055, GLS-010, AB122 | Arcus, Guangzhou Gloria Bio, Harbin Gloria Pharma, WuXi Biologies | US 2019/0270815, Si-Yang Liu et al., *J. Hematol. Oncol.* 10: 136 (2017) |
| retifanlimab | MGA012, INCMGA00012 | Incyte, MacroGenics | WO 2017/19846 |
| balstilimab | AGEN2034, AGEN-2034 | Agenus, Ludwig Inst., Sloan-Kettering | WO 2017/040790 |
| pidilizumab | CT-011, hBat-1, MDV9300 | CureTech, Medivation, Teva | Rosenblatt et al., *J Immunother.* 34(5): 409-118 (2011) |
| teripalimab | — | Henan Cancer Hospital | ClinicalTrials.gov Identifier: NCT03985670 |
| CBT-501 | GB226, GB 226, Genolimzumab, Genormab | CBT Pharmaceuticals, Genor | ClinicalTrials.gov Identifier: NCT03053466. |
| BAT1306 | — | Bio-Thera Solutions | Wu et al., *J. Clin. Oncol.* 37(4) (2019) |

TABLE 1-continued

| PD-1 Antibodies | | | |
|---|---|---|---|
| Name | Also Known as | Company | Reference(s) |
| tislelizumab | BGB-A317 | BeiGene, Celgene | WO 2015/35606, US 2015/0079109 |
| AK105 | — | Akeso, HanX Bio | ClinicalTrials.gov Identifier: NCT03866967 |
| spartalizumab | PDR001, BAP049 | Dana-Farber, Novartis | WO 2015/112900; Lin et al., *Ann. of Oncology*, 29: 8 (2018) |
| prolgolimab | BCD-100 | Biocad | Kaplon et al., *mAbs* 10(2): 183-203 (2018) |
| serplulimab | HLX10 | Henlix Biotech | ClinicalTrials.gov Identifier: NCT04297995 |
| dostarlimab | ANB011, TSR-042, ABT1, WBP-285 | AnaptysBio, Tesaro | WO 2014/179664 |
| camrelizumab | SHR-1210 | Incyte, Jiangsu Hengrui, Shanghai Hengrui | WO 2015/085847; Si-Yang Liu et al., *J. Hematol. Oncol.* 10: 136 (2017) |
| IBI319 | IBI-319 | Innovent Biologies (Suzhou) Co. Ltd., Lilly | ClinicalTrials.gov Identifier: NCT04708210 |
| KY1043 | — | Kymab | Van Krinks, Kymab poster no. P625, "KY1043, a novel PD-L1 IL-2 immunocytokine directed towards CD25, delivers potent anti-tumour activity in vitro and in vivo" |
| STI-1110 | — | Sorrento Therapeutics | WO 2014/194302 |
| CA05100948 | Antibody 948 | UCB Biopharma | U.S. Pat. No. 8,993,731 |
| Nb97 | MY2935, MY2626 | Fudan University, Novamab | Xian et al., *Biochem. & Biophys. Res. Comm's* 519(3), 267-273 (2019) |
| ENUM 388D4 | — | Enumeral | Scheuplein et al., *Immunology*, Abstract 4871 (2016) |
| hAb-10D3 | hAb-10D3 | BPS Bioscience | U.S. Pat. No. 10,759,859 |
| Unknown | — | Isis Innovation | WO 2010/029434 |
| ANB030 | — | AnaptysBio Inc. | Grebinoski et al., *Current Opinion in Immunol.* 67: 1-9 (2020) |
| MCLA-134 | — | Merus N.V. | WO 2019/009727 |
| hAb21 | — | Suzhou Stainwei Biotech Inc. | U.S. 2020/0277376 |
| — | — | Ampsource | U.S. 2019/0367617 |
| — | — | Reyoung (Suzhou) Biology Science & Technology Co. | U.S. 2019/0071501 |
| — | — | Xencor, Inc. | WO 2018/071918 |
| — | — | Crown Bioscience Inc. | WO 2016/014688 |
| — | — | Beijing Hanmi | U.S. 2020/0299412 |
| — | — | Beijing Hanmi | U.S. 2021/0032343 |

TABLE 1-continued

| PD-1 Antibodies | | | |
| --- | --- | --- | --- |
| Name | Also Known as | Company | Reference(s) |
| — | — | Beijing Hanmi | U.S. 2019/0367615 |
| — | — | MabQuest | WO 2016/020856 |
| — | — | Fuso Pharma, Hokkaido U. | WO 2018/034226 |
| — | — | Eureka Therapeutics, Inc., Sloan-Kettering | WO 2016/210129 |
| — | — | Sutro Biopharma, Inc. | WO 2016/077397 |
| — | — | Y-Biologics | U.S. 2019/0248900 |
| — | — | Harbour Biomed Ltd. | WO 2017/016497 |
| — | — | Shanghai PharmaExplorer Co. | Liu et al., *Sci. Rep.* 9(1) (2019) |
| — | — | Bio X Cell | Grasselly et al., *Front Immunol* 9: 2100 (2018) |
| — | — | Tongji University | Cai et al., *Invest. New Drugs* 37(5): 799-809 (2019) |
| — | — | Janssen Biotech | U.S. 2018/0355061 |
| — | — | Shanghai Henlius Biotech, Inc. | U.S. 2019/0218295 |
| — | — | Ultrahuman Nine Ltd. | WO 2019/170898 |
| — | — | CytomX | WO 2017/011580 |
| — | — | Nanjing Legend Biotech | WO 2017/133633 |
| — | — | Aduro Biotech | U.S. Pat. No. 10,494,436 |
| — | — | Sutro Biopharm | U.S. Pat. No. 10,822,414 |
| — | — | Versitech Ltd. | U.S. Pat. No. 10,047,137 |
| — | — | STCube & Co., University of Texas | WO 2016/160792 |
| — | — | Tayu Huaxia Biotech Medivcal Group Co. | U.S. 2019/0144543 |
| — | — | Hangzhou Sumgen Biotechnology | U.S. 2019/0016799 |
| — | — | Jiangsu Hengrui Medicine Co, Shanghai Hengrui Pharmaceutical Co | WO 2015/085847 |
| — | — | Salubris (Chengdu) Biotech Co. | WO 2019/201169 |
| — | — | Kadmon Corp. | U.S. Pat. No. 10,407,502 |
| — | — | Augusta University Research Institute | WO 2019/051164 |
| — | — | Abbvie Biotherapeutics Inc. | WO 2018/053106 |
| — | — | Lyvgen Biopharma Holdings Ltd. | WO 2017/087599 |
| — | — | Crescendo Biologies Ltd. | WO 2018/127711 |
| — | — | Zhejiang Teruisi Pharmaceutics Inc. | U.S. 2019/0322747 |
| — | — | Biosion Inc. | WO 2019/204132 |
| — | — | Celgene Corp. | U.S. 2017/0088618 |
| — | — | Asia Biotech Pte. Ltd. | WO 2017/058115 |
| — | — | The Brigham and Women's Hospital | U.S. Pat. No. 10,934,352 |
| — | — | Singapore Immunology Network (SIgN), Institute of Medical Biology, Agency for Science, Technology and Research (A*STAR) | Seidel et al., *Front. Oncol.* 28 (2018) |
| — | — | Chinese People Liberation Army General Hospital | Sun et al., *J. Gastrointest Oncol.* 11(6): 1421-1430 (2020) |

TABLE 1-continued

PD-1 Antibodies

| Name | Also Known as | Company | Reference(s) |
|---|---|---|---|
| — | — | Immunomedics Inc. | U.S. Pat. No. 10,669,338 |
| — | — | Xiangtan Tenghua Bio | WO 2018/162944 |
| — | — | Beijing Dongfang Biotech | U.S. 2019/0144541 |
| — | — | REMD Biotherapeutics | WO 2018/119474 |
| — | — | Rinat Neuroscience Corp. | U.S. Pat. No. 10,155,037 |
| — | — | Medimmune, Wyeth | WO 2004/056875 |
| — | — | Fudan University | Yuan et al., *Invest. New Drugs* 39(1): 34-51 (2021) |

Each of the references identified in Table 1 is incorporated herein by reference.

In certain embodiments, the PD-1 inhibitor comprises an amino acid sequence having at least about 80%, at least about 85%, at least about 90%, at least about 95%, at least about 98%, at least about 99%, or 100% sequence identity to any of the antibodies identified in Table 1. For example, in some embodiments, the PD-1 inhibitor comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity to any of the antibodies identified in Table 1.

In some embodiments, the anti-PD-1 inhibitor is pembrolizumab (Keytruda®). In some embodiments, the PD-1 inhibitor is nivolumab (Opdivo®). In some embodiments, the PD-1 inhibitor is zimberelimab (WBP3055). In some embodiments, the PD-1 inhibitor is cetrelimab (JNJ-63723283). In certain embodiments, the PD-1 inhibitor comprises an amino acid sequence having at least about 80%, at least about 85%, at least about 90%, at least about 95%, at least about 98%, at least about 99%, or 100% sequence identity to: a) pembrolizumab (Keytruda®); b) nivolumab (Opdivo®); c) zimberelimab (WBP3055); or d) cetrelimab (JNJ-63723283).

In some embodiments, the anti-PD-1 is selected or derived from those described in U.S. patent application publication numbers U.S. 2019/0270815A1 and U.S. 2019/0225689A1, each of which is incorporated herein by reference.

In some embodiments, the anti-PD-1 is capable of specifically binding to human PD-1 at a Kd value of $\leq 10^{-13}$ M (e.g., $\leq 5 \times 10^{-7}$ M, $\leq 2 \times 10^{-7}$ M, $\leq 10^{-7}$ M, $\leq 5 \times 10^{-8}$ M, $\leq 2 \times 10^{-8}$ M, $\leq 10^{-8}$ M, $\leq 5 \times 10^{-9}$ M, $\leq 2 \times 10^{-9}$ M, $\leq 10^{-9}$ M, $\leq 5 \times 10^{-10}$ M, $\leq 2 \times 10^{-10}$ M, $\leq 10^{-10}$ M, $\leq 5 \times 10^{-11}$ M, $\leq 2 \times 10^{-11}$ M, $\leq 10^{-11}$ M, $\leq 5 \times 10^{-12}$ M, $\leq 2 \times 10^{-12}$ M, $\leq 10^{-12}$ M, $\leq 5 \times 10^{-13}$ M, $\leq 2 \times 10^{-13}$ M, and $\leq 10^{-13}$ M). In some embodiments, the anti-PD-1 is capable of specifically binding to human PD-1 at a Kd value of no more than $10^{-8}$ M (e.g. no more than $\leq 9 \times 10^{-9}$ M, $\leq 8 \times 10^{-9}$ M, $\leq 7 \times 10^{-9}$ M, $\leq 6 \times 10^{-9}$ M, $\leq 5 \times 10^{-9}$ M, $\leq 4 \times 10^{-9}$ M, $\leq 3 \times 10^{-9}$ M, $\leq 2 \times 10^{-9}$ M, or $\leq 10^{-9}$ M). The Kd value may be measured by plasmon resonance binding assay.

In some embodiments, the anti-PD-1 binds to human PD-1 with an $EC_{50}$ (i.e. 50% binding concentration) of 0.1 nM-100 nM (e.g. 0.1 nM-50 nM, 0.1 nM-30 nM, 0.1 nM-20 nM, 0.1 nM-10 nM, or 0.1 nM-1 nM). In some embodiments, the anti-PD-1 inhibits the binding of human PD-1 to its ligand at an $IC_{50}$ of 0.2 nM-100 nM (e.g. 0.2 nM-50 nM, 0.2 nM-30 nM, 0.2 nM-20 nM, 0.2 nM-10 nM, or 1 nM-10 nM), as measured in a competition assay.

In some embodiments, the anti-PD-1 has substantially reduced or depleted effector function. In certain embodiments, the anti-PD-1 has a constant region of IgG4 isotype that has reduced or depleted effector function. In some embodiments, the anti-PD-1 has a fully human IgG sequence, for example an IgG4 sequence. In certain embodiments, the anti-PD-1 does not mediate ADCC and/or CDC.

In certain embodiments, the anti-PD-1 comprises a heavy chain CDR comprising an amino acid sequence selected from the group consisting of: SEQ ID NOs: 310-320, 378-380, and sequences having at least 80%, at least 85%, at least 90%, at least 95%, at least 98%, at least 99%, or 100% sequence identity therewith. In certain embodiments, the anti-PD-1 comprises a light chain CDR comprising an amino acid sequence selected from the group consisting of: SEQ ID NOs: 321-332, 381-383, and sequences having at least 80%, at least 85%, at least 90%, at least 95%, at least 98%, at least 99%, or 100% sequence identity therewith.

In certain embodiments, the anti-PD-1 comprises at least one, two, three, four, five, or six CDRs, each comprising an amino acid sequence individually selected from: SEQ ID NOs: 310-312 and 321-323; SEQ ID NOs: 312-314, 321, 323, and 324; SEQ ID NOs: 310, 312, 314, 321, 324, and 325; SEQ ID NOs: 310, 312, 314, 321, 324, and 332; SEQ ID NOs: 315-317 and 326-328; SEQ ID NOs: 318-320 and 329-331; or SEQ ID NOs: 378-383. In certain embodiments, the anti-PD-1 comprises a heavy chain variable region comprising the amino acid sequences of: SEQ ID NOs: 310, 311, and/or 312; SEQ ID NOs: 312, 313, and/or 314; SEQ ID NOS: 310, 312, and/or 314; SEQ ID NOs: 315, 316, and/or 317; SEQ ID NOs: 318, 319, and/or 320; or SEQ ID NOs: 378, 379, and/or 380. In certain embodiments, the anti-PD-1 comprises a light chain variable region comprising the amino acid sequences of: SEQ ID NOs: 321, 322, and/or 323; SEQ ID NOs: 321, 323, and/or 324; SEQ ID NOs: 321, 324, and/or 325; SEQ II) NOs: 326, 327, and/or 328; SEQ ID NOs: 329, 330, and/or 331; SEQ ID NOs: 321, 324, and/or 332; or SEQ ID NOs: 381, 382, and/or 383. In certain embodiments, the anti-PD-1 comprises: a heavy chain variable region comprising the amino acid sequences of SEQ ID NOs: 310, 311, and/or 312 and a light chain variable region comprising the amino acid sequences of SEQ ID NOs: 321, 322, and/or 323; a heavy chain variable region comprising the amino acid sequences of SEQ ID NOs: 312, 313, and/or 314 and a light chain variable region comprising the amino acid sequences of SEQ ID NOs: 321, 323, and/or 324; a heavy chain variable region comprising the amino acid sequences of SEQ ID NOs: 310, 312, and/or 314 and a light chain variable region comprising the amino acid sequences of SEQ ID NOs: 321, 324, and/or 325; a heavy chain variable region comprising the amino acid sequences of SEQ ID NOs: 315, 316, and/or 317 and a light chain variable region comprising the amino acid sequences of SEQ ID NOs: 326, 327, and/or 328; a heavy chain variable region comprising the amino acid sequences of SEQ ID NOs: 318, 319, and/or 320 and a light chain variable region comprising the amino acid sequences of SEQ ID NOs: 329, 330, and/or 331; a heavy chain variable region comprising the amino acid sequences of SEQ ID NOs: 310, 312, and/or 315 and a light chain variable region comprising the amino acid sequences of SEQ ID NOs: 321, 324, and/or 332; or a heavy chain variable region comprising the amino acid sequences of SEQ ID NOs: 378, 379, and/or 380 and a light chain variable region comprising the amino acid sequences of SEQ ID NOs: 381, 382, and/or 383. In each of the aforementioned embodiments, the CDRs may instead comprise amino acid sequences having at least 80%, at least 85%, at least 90%, at least 95%, at least 98%, or at least 99% sequence identity with the recited sequences.

In certain embodiments, the fusion protein comprises: three heavy chain CDRs, the CDRs comprising, respectively, amino acid sequences of SEQ ID NOs: 378, 379, and 380, or sequences having at least 80%, at least 85%, at least 90%, at least 95%, at least 98%, at least 99%, or 100% sequence identity therewith; and three light chain CDRs, the CDRs comprising, respectively, amino acid sequences of SEQ ID NOs: 381, 382, and 383, or sequences having at least 80%, at least 85%, at least 90%, at least 95%, at least 98%, at least 99%, or 100% sequence identity therewith.

In certain embodiments, the fusion protein comprises: three heavy chain CDRs, the CDRs comprising, respectively, amino acid sequences of SEQ ID NOs: 378, 379, and 380; and three light chain CDRs, the CDRs comprising, respectively, amino acid sequences of SEQ ID NOs: 381, 382, and 383.

In certain embodiments, the anti-PD-1 comprises a heavy chain variable region comprising an amino acid sequence of one of SEQ ID NOs: 333-337, 384, or a sequence having at least 80%, at least 85%, at least 90%, at least 95%, at least 98%, at least 99%, or 100% sequence identity with such a sequence. In certain embodiments, the anti-PD-1 comprises a light chain variable region comprising an amino acid sequence of one of SEQ ID NOs: 338-343, 385, or a sequence having at least 80%, at least 85%, at least 90%, at least 95%, at least 98%, at least 99%, or 100% sequence identity with such a sequence.

In certain embodiments, the anti-PD-1 comprises: a heavy chain variable region comprising an amino acid sequence of SEQ ID NO: 333 and a light chain variable region comprising an amino acid sequence of SEQ ID NO: 338; a heavy chain variable region comprising an amino acid sequence of SEQ ID NO: 334 and a light chain variable region comprising an amino acid sequence of SEQ ID NO: 339; a heavy chain variable region comprising an amino acid sequence of SEQ ID NO: 335 and a light chain variable region comprising an amino acid sequence of SEQ ID NO: 340; a heavy chain variable region comprising an amino acid sequence of SEQ ID NO: 336 and a light chain variable region comprising an amino acid sequence of SEQ ID NO: 341; a heavy chain variable region comprising an amino acid sequence of SEQ ID NO: 337 and a light chain variable region comprising an amino acid sequence of SEQ ID NO: 342; a heavy chain variable region comprising an amino acid sequence of SEQ ID NO: 335 and a light chain variable region comprising an amino acid sequence of SEQ ID NO: 343; or a heavy chain variable region comprising an amino acid sequence of SEQ ID NO: 384 or a light chain variable region comprising an amino acid sequence of SEQ ID NO: 385. In each of the aforementioned embodiments, the heavy and light chain variable regions may instead comprise amino acid sequences having at least 80%, at least 85%, at least 90%, at least 95%, at least 98%, or at least 99% sequence identity with the recited sequences.

In certain embodiments, the anti-PD-1 comprises a heavy chain comprising an amino acid sequence of SEQ ID NO: 386, or a sequence having at least 80%, at least 85%, at least 90%, at least 95%, at least 98%, at least 99%, or 100% sequence identity therewith, and a light chain comprising an amino acid sequence of SEQ ID NO: 387, or a sequence having at least 80%, at least 85%, at least 90%, at least 95%, at least 98%, at least 99%, or 100% sequence identity therewith. In certain embodiments, the anti-PD-1 comprises a heavy chain comprising and amino acid sequence of SEQ ID NO: 386 and a light chain comprising an amino acid sequence of SEQ ID NO: 387.

In certain embodiments, the anti-PD-1 is a fully human monoclonal antibody that comprises a human constant region of the IgG4 isotype and; a heavy chain variable region comprising the amino acid sequence of SEQ ID NO: 333 and a light chain variable region comprising the amino acid sequence of SEQ ID NO: 338; a heavy chain variable region comprising the amino acid sequence of SEQ ID NO: 334 and a light chain variable region comprising the amino acid sequence of SEQ ID NO: 339; a heavy chain variable region comprising the amino acid sequence of SEQ ID NO: 335 and a light chain variable region comprising the amino acid sequence of SEQ ID NO: 340; a heavy chain variable region comprising the amino acid sequence of SEQ ID NO: 335 and a light chain variable region comprising the amino acid sequence of SEQ ID NO: 343; a heavy chain variable region comprising the amino acid sequence of SEQ ID NO: 336 and a light chain variable region comprising the amino acid sequence of SEQ ID NO: 341; a heavy chain variable region comprising the amino acid sequence of SEQ ID NO: 337 and a light chain variable region comprising the amino acid sequence of SEQ ID NO: 342; or a heavy chain variable region comprising an amino acid sequence of SEQ ID NO: 384 and a light chain variable region comprising an amino acid sequence of SEQ ID NO: 385. In each of the aforementioned embodiments, the heavy and light chain variable regions may instead comprise amino acid sequences having at least 80%, at least 85%, at least 90%, at least 95%, at least 98%, or at least 99% sequence identity with the recited sequences.

In some embodiments, the anti-PD-1 competes for the same epitope as any of the aforementioned antibodies. For example, the anti-PD-1 may block the binding of the antibody to human PD-1 at an $IC_{50}$ value (i.e. 50% inhibition concentration) of below $10^{-6}$ M, below $10^{-7}$ M, below $10^{-7.3}$ M, below $10^{-8}$ M, below $10^{-8.5}$ M, below $10^{-9}$, or below $10^{-10}$ M. The $IC_{50}$ values are determined based on a competition assay such as ELISA assays, radioligand competition binding assays, and FACS analysis.

In some embodiments, the anti-PD-1 binds to a human PD-1 comprising the amino acid sequence in Table 26, and reproduced below:

(SEQ ID NO: 388)
FLDSPDRPWNPPTFSPALLVVTEGDNATFTCSFSNTSESFVLNWYRMS

PSNQTDKLAAFPEDRSQPGQDCRFRVTQLPNGRDFHMSVVRARRNDSG

TYLCGAISLAPKAQIKESLRAELRVTERRAEVPTAHPSPSPRPAGQFQ

TLVVGVVGGLLGSLVLLVWVLAVICSRAARGTIGARRTGQPLKEDPSA

VPVFSVDYGELDFQWREKTPEPPVPCVPEQTEYATIVFPSGMGTSSPA

RRGSADGPRSAQPLRPEDGHCSWPL

In some embodiments, the anti-PD-1 binds to an epitope of human PD-1 comprising at least one of the following residues of SEQ ID NO: 388; V41, P60, D62, L105, A106, P107, K108, A109 and Q110, shown in emphasis below.

(SEQ ID NO: 388)
FLDSPDRPWNPPTFSPALLVVTEGDNATFTCSFSNTSESFVLNWYRMS

PSNQTDKLAAFPEDRSQPGQDCRFRVTQLPNGRDFHMSVVRARRNDSG

TYLCGAISLAPKAQIKESLRAELRVTERRAEVPTAHPSPSPRPAGQFQ

TLVVGVVGGLLGSLVLLVWVLAVICSRAARGTIGARRTGQPLKEDPSA

VPVFSVDYGELDFQWREKTPEPPVPCVPEQTEYATIVFPSGMGTSSPA

RRGSADGPRSAQPLRPEDGHCSWPL

In some embodiments, the anti-PD-1 is capable of blocking the binding of human PD-1 to its ligand and thereby: inducing production of IL-2 in CD4+ T cells; inducing production of IFNγ in CD4+ T cells; inducing proliferation of CD4+ T cells; and/or reversing the T cells' suppressive function.

In some embodiments, the anti-PD-1 is a monoclonal antibody, a polyclonal antibody, a fully human antibody, a humanized antibody, a chimeric antibody, a recombinant antibody, a bispecific antibody, a labeled antibody, a bivalent antibody, or an anti-idiotypic antibody. In some embodiments, the anti-PD-1 is a fully human monoclonal antibody, optionally produced by a transgenic mouse or rat, for example, a transgenic rat having inactivated endogenous expression of rat immunoglobulin genes and carrying recombinant human immunoglobulin loci having J-locus deletion and a C-kappa mutation.

In some embodiments, the anti-PD-1 is a camelized single domain antibody, a diabody, a scFv, an scFv dimer, a BsFv, a dsFv, a (dsFv)2, a dsFv-dsFv', an Fv fragment, a Fab, a Fab, a F(ab')2, a ds diabody, a nanobody, a domain antibody, or a bivalent domain antibody.

In some embodiments, the anti-PD-1 further comprises an immunoglobulin constant region.

In some embodiments, the anti-PD-1 further comprises a conjugate. The conjugate may, for example, be a detectable label, a pharmacokinetic modifying moiety, or a purification moiety.

Tumor Antigen-Binding Antibody

In certain embodiments, the antibody, or fragment or variant thereof, of the first component binds to a tumor antigen expressed on the surface of a tumor cell.

The antibody, or fragment or variant thereof, can be an antibody, antibody fragment, scFv, $F_C$-containing polypeptide, fusion antibody, polypeptide, peptide, aptamer, ligand, nucleic acid, or any combination thereof. In one embodiment, the antibody, or fragment or variant thereof, can bind to a molecule present in a cell or tissue. In one aspect, the targeting moiety can bind a molecule in a diseased cell or tissue, such as a cancer cell or tumor. In another aspect, the antibody, or fragment or variant thereof, can bind a normal cell or tissue, such as an immune cell. In another aspect, the antibody, or fragment or variant thereof, can bind a cellular or extracellular molecule that modulates the immune response. In another aspect, the antibody, or fragment or variant thereof, binds a growth factor receptor, growth factor, cytokine receptor, cytokine, or cell surface molecule. In one embodiment, the antibody, or fragment or variant thereof, binds to an epitope on CD19, BCMA, CD44, a-Folate receptor, CAIX, CD30, ROR1, CEA, EGP-2, EGP-40, HER2, HER3, Folate-binding Protein, GD2, GD3, IL-13R-a2, KDR, EDB-F, mesothelin, CD22, EGFR, Folate receptor α, MUC1, MUC4, MUC16, MAGE-A1, h5T4, PSMA, TAG-72, EGFR, CD20, EGFRvIII, CD123 or VEGF-R2. In one embodiment the antibody, or fragment or variant thereof, binds to an epitope on MUC1, MUC2, MUC3A, MUC3B, MUC4, MUC5AC, MUC5B, MUC6, MUC7, MUC8, MUC12, MUC13, MUC15, MUC16, MUC 17, MUC19, or MUC20. In one embodiment the antibody, or fragment or variant thereof, binds to an epitope on MUC1. In one embodiment, the antibody, or fragment or variant thereof, binds to an epitope on MUC16. In one embodiment, the antibody, or fragment or variant thereof, includes an antibody, antibody fragment, scFv, or Fc-containing polypeptide. In some cases, the antibody is immunoglobulin G (IgG) antibody. In some embodiments, the IgG is IgG 1, IgG2, IgG3, or IgG4. In one embodiment, the IgG is IgG1. In other cases, the fragment of the antibody is a Fab, (Fab)$_2$, (Fab')$_2$, Fv, (Fv)$_2$, or scFv of the antibody. In another case, the antibody comprises a variable region of heavy chain ($V_H$) and a variable region of light chain ($V_L$). In some embodiments, the antibody further comprises fragment crystallizable region ($F_C$). In yet another case, the $F_C$ is human $F_C1$, $F_C2$, $F_C3$, $F_C4$, or a fragment thereof. In some embodiments, the $F_C$ further comprises one or more mutations. In some embodiments, the antibody comprises the scFv and the $F_C$ fragment.

MUCIN I, Cell Surface Associated Protein (MUC1)

MUC1 (mucin 1, cell surface associated protein) is a mucin-type glycoprotein that is expressed on the apical borders of normal secretory epithelial cells. MUC1 forms a heterodimer following synthesis as a single polypeptide and cleavage of the precursor into two subunits in the endoplasmic reticulum. MUC1 N-terminal (MUC1 N-ter, MUC1-N) subunit contains variable numbers of 20 amino acid tandem repeats that are imperfect with highly conserved variations and are modified by O-linked glycans. MUC 1-N is tethered to the cell surface by dimerization with the about 23 kDa C-terminal subunit (MUC1 C-ter, MUC1-C), which includes a 58 amino acid extracellular region, a 28 amino acid transmembrane domain and a 72-amino acid cytoplasmic domain (CD). The tumor targeting moiety as described herein includes antibodies that bind to the 58 amino acid portion of the MUC1-C/ECD. Examples of MUC1 antibodies are described in U.S. Pat. No. 10,059,775, U.S. Patent Application Publication No. 20180036441, U.S. Pat. No. 9,932,407, U.S. Patent Application Publication Nos. 20180112007, 20180222998, WO2018071583, U.S. Pat. No. 7,202,346, all of which are herein incorporated by reference in their entireties.

In one embodiment, the targeting moiety is a tumor targeting moiety that binds to an epitope on MUC1. In some embodiments, the anti-MUC1 antibody fragment is a Fab, Fab2, (Fab')2, Fv, (Fv)2, scFv, scFv-Fc, Fc, diabody, triabody, or mini body of the anti-MUC1. In some embodiments, the anti-MUC1 antibody fragment is a single-domain antibody of the anti-MUC1 antibody. In some embodiments, the single-domain antibody is a $V_{NAR}$ or $V_HH$ fragment of the anti-MUC1 antibody.

In some embodiments, the variable region of heavy chain ($V_H$) of an anti-MUC1 antibody or a fragment/variant thereof comprises one or more polypeptide sequences as shown in any one of SEQ ID NOs: 444-448. In some embodiments, the variable region of heavy chain ($V_H$) of an anti-MUC1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 444-448.

In some embodiments, the variable region of light chain ($V_L$) of an anti-MUC1 antibody or a fragment/variant thereof comprises one or more polypeptide sequences as shown in any one of SEQ ID NOs: 449-453. In some embodiments, the variable region of light chain ($V_L$) of an anti-MUC1 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 449-453.

In some embodiments, the anti-MUC1 antibody, or a fragment/variant thereof, comprises a variable region of light chain ($V_L$) comprising a sequence that is at least 80% identical to of any one of SEQ ID NOs: 449-453 and a heavy chain ($V_H$) comprising a sequence that is at least 80% identical to SEQ ID NO: 444.

MUCIN 16, *Cell Surface Associated Protein* (MUC16)

MUC16 (also known as CA-125 (cancer antigen 125, carcinoma antigen 125, or carbohydrate antigen 125) or mucin 16), is a member of the mucin family of glycoproteins. MUC 16 has been shown to play a role in advancing tumorigenesis and tumor proliferation by several different mechanisms.

MUC16 is a large carbohydrate antigen, also known as CA-125. MUC16 is encoded by the MUC16 gene located on human chromosome 19. MUC16 is a highly glycosylated multidomain type I transmembrane protein comprising 3 domains. The C-terminal domain contains multiple extracellular SEA (sea urchin sperm protein, enterokinase, and agrin) modules that have an autoproteolytic activity. SEA harbors two proteolytic sites proximal to the transmembrane (TM) domain. A large cleaved domain termed CA-125 is released into circulation at acidic pH. CA-125 is commonly used as disease biomarker for ovarian cancer. The highly conserved truncated extracellular membrane tethered protein domain called MUC16ecto domain. A MUC16 antibody was identified that specifically bound the ectodomain of MUC16 that is retained on the tumor cell surface. "Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

In one embodiment the targeting moiety is a tumor targeting moiety that binds to an epitope on MUC16. In some embodiments, the anti-MUC16 antibody fragment is a Fab, Fab$_2$, (Fab')$_2$, Fv, (Fv)$_2$, scFv, scFv-F$_C$, F$_C$, diabody, triabody, or mini body of the anti-MUC16. In some embodiments, the anti-MUC16 antibody fragment is a single-domain antibody of the anti-MUC16 antibody. In some embodiments, the single-domain antibody is a $V_{NAR}$ or $V_HH$ fragment of the anti-MUC16 antibody.

In some embodiments, the variable region of heavy chain ($V_H$) of an anti-MUC16 antibody or a fragment/variant thereof comprises one or more polypeptide sequences as shown in any one of SEQ ID NOs: 390-403. In some embodiments, the variable region of heavy chain ($V_H$) of an anti-MUC 16 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 390-403.

In some embodiments, the variable region of light chain ($V_L$) of an anti-MUC16 antibody or a fragment/variant thereof comprises one or more polypeptide sequences as shown in any one of SEQ ID NOs: 417-428. In some embodiments, the variable region of light chain ($V_L$) of an anti-MUC16 antibody or a fragment/variant thereof comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 417-428.

Cytokine Trap

Cytokines have an impact on many biological processes. Inhibiting cytokines can have clinical benefits for example, in cancer. Several cytokines have been shown to be causative agents in a variety of diseases. Such cytokines, include but are not limited to IL-1, IL-4, IL-6, TNF-α, TGF-beta and its various isoforms. The term "cytokine trap" as used herein refers to blockers or neutralizers of cytokine action. Examples of such cytokine traps can include but are not limited to extracellular domains of the cytokine receptors, antibodies that bind to cytokines, and peptides that bind to the cytokines (e.g. inhibitory peptides). In some embodiments, the cytokine is TGF-β. In some embodiments, the cytokine is TGF-β1. In some embodiments, the cytokine is TGF-β3. In some embodiments, the cytokine is TGF-β1 and TGF-β3. In further embodiments, cytokine traps that target TGF-β (e.g. TGF-β trap) can include the extracellular domain of TGF-βRII or its variants thereof (for example, SEQ ID NOs: 141 and 142), anti-TGF-β antibodies and inhibitory peptides of TGF-β1, TGF-β2 and/or TGF-β3.

Transforming Growth Factor-β

Transforming growth factor-β (TGF-β) is a multifunctional set of peptides that can control proliferation, differentiation, and other functions in many cell types. TGF-β can act synergistically with TGF-α in inducing transformation. It also can act as a negative autocrine growth factor. Dysregulation of TGF-β activation and signaling can result in apoptosis. Many cells can synthesize TGF-β and almost all of them have specific receptors for this peptide. TGF-β1, TGF-β2, and TGF-β3 all can function through the same receptor signaling systems. TGF-β1 can play an important role in controlling the immune system, and can show different activities on different types of cell, or cells at different developmental stages. Most immune cells (or leukocytes) can secrete TGF-β1. TGF-β1 is a peptide of 112 amino acid residues derived by proteolytic cleavage from the C-terminal of a precursor protein. TGF-β, a small secreted polypeptide, can signal through TGFβRII, which can recruit and phosphorylate the type I dimeric receptor (TGFβRI). TGFβRI can phosphorylate and activate SMADs which can be transcription factors regulating genes involved in cell proliferation, differentiation, apoptosis and growth. Many advanced stage cancers are known to over-express both the TGF-β and TGFβR promoting aggressive tumor formation. Inhibiting the TGFB signaling pathway can be a key therapeutic strategy in treating cancer.

Figure 2:
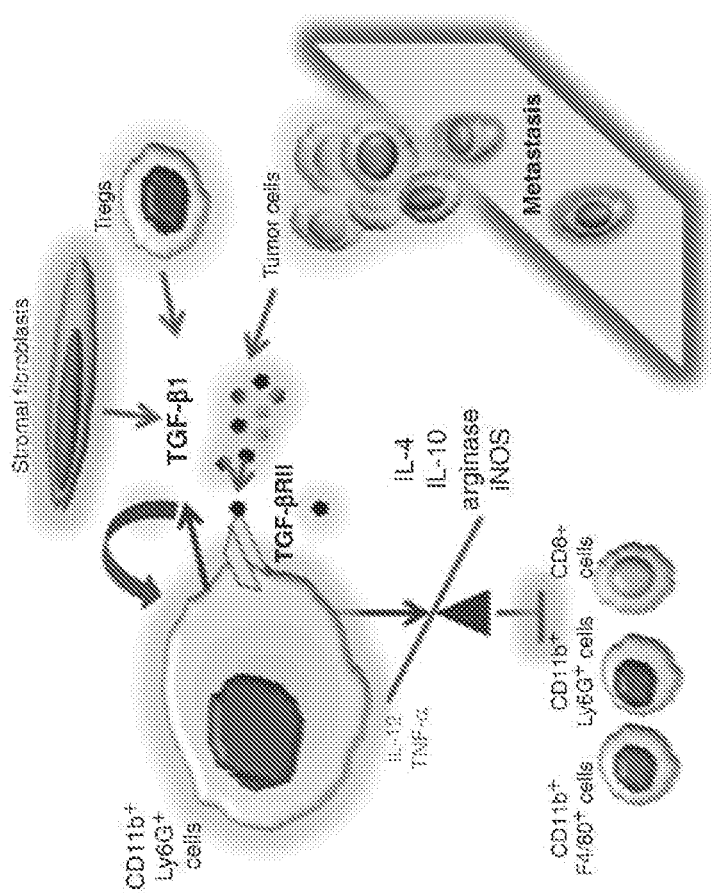
FIG. 2 is a schematic of TGF-3 in immunosuppression.
Figure 3:
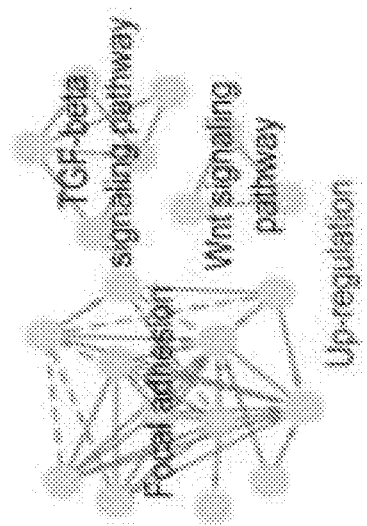
FIG. 3 shows TGF-β associated gene cluster correlated with metastatic disease and poor prognosis in subset of ovarian cancer patients (enriched in Stage III/IV).

Some T cells (e.g., regulatory T cells) can release TGF-β1 to inhibit the actions of other T cells. IL-1 and IL-2 dependent proliferation of activated T cells, and the activation of quiescent helper T cells and cytotoxic T cells can be prevented by the activity of TGF-β1. Similarly, TGF-β1 can inhibit the secretion and activity of many other cytokines including, but not limited to, interferon-γ, tumor necrosis factor alpha (TNF-αt) and various interleukins. It can also decrease the expression levels of cytokine receptors, such as the IL-2 receptor, to down-regulate the activity of immune cells. However, TGF-β1 can also increase the expression of certain cytokines in T cells and can promote their proliferation, particularly if the cells are immature (FIG. 2).

TGF-β1 can have similar effects on B cells that vary according to the differentiation state of the cell. It can inhibit proliferation and can stimulate apoptosis of B cells, and can play a role in controlling the expression of antibody, transferrin, and MHC class II proteins on immature and mature B cells.

The effects of TGF-β1 on macrophages and monocytes can be predominantly suppressive; this cytokine can inhibit the proliferation of these cells and can prevent their production of reactive oxygen (e.g., superoxide ($O_2^-$)) and nitrogen (e.g., nitric oxide (NO)) intermediates. However, as with other cell types, TGF-β1 can also have the opposite effect on cells of myeloid origin. For example, TGF-β1 can act as a chemoattractant, directing an immune response to some pathogens; macrophages and monocytes can respond to low levels of TGF-β1 in a chemotactic manner. Furthermore, the expression of monocytic cytokines (including IL-1α, IL-1β, and TNF-α), and phagocytic killing by macrophages can be increased by the action of TGF-β1 (FIG. 2).

Transforming Growth Factor-Beta III (TGF-β3), a subset of a cytokine family, is responsible for a plethora of functions including cellular proliferation, embryogenesis, immune system regulation, and differentiation.

Transforming Growth Factor-β Receptor Type II (TGFβRII)

TGF-β receptors (TGFβR) are single pass serine/threonine kinase receptors. They can exist in several different isoforms that can be homodimeric or heterodimeric. The number of characterized ligands in the TGF-β superfamily can far exceed the number of known receptors, suggesting the promiscuity between the ligand and receptor interactions. Three TGF-β superfamily receptors (TGFβR) specific for TGF-β can be distinguished by their structural and functional properties. TGFβRI (ALK5) and TGFβRII can have similar ligand-binding affinities and can be distinguished from each other only by peptide mapping. Both TGFβRI and TGFβRII can have a high affinity for TGF-β1 and low affinity for TGF-β2. TGFβRIII (β-glycan) can have a high affinity for both homodimeric TGF-β1 and TGF-β2 and in addition the heterodimer TGF-β1,2. The TGFβ receptors can also bind to TGF-β3. By "TGFβRII" or "TGFβ Receptor II" is meant a polypeptide having the wild-type human TGFβ Receptor Type 2 Isoform A sequence (e.g., the amino acid sequence of NCBI Reference Sequence (RefSeq) Accession No. NP_001020018 (SEQ ID NO: 289), or a polypeptide having the wild-type human TGFβ Receptor Type 2 Isoform B sequence (e.g., the amino acid sequence of NCBI RefSeq Accession No. NP_003233 (SEQ ID NO: 290) or having a sequence substantially identical the amino acid sequence of SEQ ID NO: 289 or of SEQ ID NO: 290. The TGFβRII may retain at least 0.1%, 0.5%, 1%, 5%, 10%, 25%, 35%, 50%, 75%, 90%, 95%, or 99% of the TGFβ-binding activity of the wild-type sequence. The polypeptide of expressed TGFβRII lacks the signal sequence.

TGF-β1 can reduce the efficacy of the MHC II in astrocytes and dendritic cells, which in turn can decrease the activation of appropriate helper T cell populations. TGF-β1 can promote tumor growth as cancer progresses and in some embodiments, does not suppress inflammatory cells responses but can promote regulatory T cell function. TGF-β1 can be produced by tumor cells, tumor-associated fibroblast cells, regulatory T cells and immature myeloid cells. TGF-β1 can inhibit T cell priming and promote an exhausted phenotype. TGF-β1 can suppress the anti-tumor activity of innate immune cell populations including natural killer cells, macrophages and dendritic cells. TGF-β receptor II can be upregulated by tumor-associated myeloid cells and can promote metastasis.

TGF-β Trap Fusion Proteins, or Fragments or Variants Thereof

Provided herein is a fusion protein, or a fragment or a variant thereof, comprising a cytokine trap that can neutralize the cytokine (for instance, TGF-β). In certain cases, a cytokine trap can be a TGF-β trap (also referred to as TGF-βRII or fragment or variant thereof) that comprises SEQ ID NO. 142. Examples of TGF-β trap can include, but are not limited to, extracellular domain (ECD) of the receptor (e.g., TGFβRII), or a functional variant or derivative thereof, TGF-β inhibitory peptides (for instance, SEQ ID NOs: 468-507 and 263-267), or an anti-TGF-β antibodies. In some embodiments, the anti-TGF-β antibody comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 166, 168, 169, 171, 173, 175, or 177. In some embodiments, the anti-TGF-β antibody comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 165, 167, 170, 172, 174, 176, or 178. In certain embodiments, a TGF-β trap can specifically bind or have high affinity for TGF-β1 or TGF-β2 or TGF-β3. In other embodiments, a TGF-β trap can specifically bind or have high affinity for TGF-β1, TGF-β2 and TGF-β3. In other embodiments, a TGF-β trap can specifically bind or have high affinity for TGF-β1 and TGF-β3. In further embodiments, a TGF-β trap can have low affinity for or not bind TGF-β2.

The fusion protein (or fragment or variant thereof) provided herein can elicit a synergistic anti-tumor effect due to the simultaneous blockade of the interaction between e.g., PD-L1, MUC1, and MUC16 on tumor cells and PD-1, MUC1, and MUC16 on immune cells, and the neutralization of e.g., TGF-β in the tumor microenvironment. Without being bound by theory, this effect is obtained from simultaneous blocking the two major immune escape mechanisms and the targeted depletion of the TGF-β in the tumor microenvironment by a single molecular entity. This depletion can be achieved by one or more of the following: (1) anti-PD-1, anti-MUC1, or anti-MUC16 targeting of tumor cells; (2) binding of the TGF-β in the tumor microenvironment by the TGF-β trap (e.g., TGFbRII); and/or (3) destruction of the bound TGF-β through the PD-L1 receptor mediated endocytosis. The fusion protein (or fragment or variant thereof) provided herein (e.g., PD-1 inhibitor or antibody, anti-MUC16 antibody, or anti-MUC1 antibody fused to a cytokine trap such as a TGF-β trap) can also promote natural killer cell-mediated killing of tumor cells.

TGFβ-RII Fusion

In some embodiments, the cytokine trap (e.g., TGF-β trap) is a cytokine receptor (e.g., TGFβRII). In some embodiments, the cytokine receptor sequence in a fusion protein described herein comprises an extracellular domain (ECD) of the receptor (e.g., TGFβRII), or a functional variant or derivative thereof. In some embodiments, the extracellular domain (ECD) of TGFβRII comprises a polypeptide sequence as shown in SEQ ID NO: 14. In some embodiments, the cytokine receptor sequence in a fusion protein, or a fragment or a variant thereof, described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 14. In some embodiments, the cytokine receptor sequence in a fusion protein described herein comprises an extracellular domain (ECD) of the receptor (e.g., TGFβRII), or a functional variant or derivative thereof. In some embodiments, the extracellular domain (ECD) of TGFβRII comprises a polypeptide sequence as shown in SEQ ID NO: 141. In some embodiments, the cytokine receptor sequence in a fusion protein, or a fragment or a variant thereof, described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 141. In some embodiments, the cytokine receptor sequence in a fusion protein described herein comprises an extracellular domain (ECD) of the receptor (e.g., TGFβRII), or a fragment or variant thereof. In some embodiments, the extracellular domain (ECD) of TGFβRII comprises a polypeptide sequence as shown in SEQ ID NO: 142. In some embodiments, the cytokine receptor sequence in a fusion protein, or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 142. In some embodiments, the cytokine receptor sequence in a fusion protein, or a fragment or a variant thereof described herein binds TGF-β1 and/or TGF-β3 but does not bind TGF-β2. In certain embodiments, the cytokine receptor sequence in a fusion protein or, a fragment or a variant thereof described herein only binds TGF-β1. In certain embodiments, the cytokine receptor sequence in a fusion protein, or a fragment or a variant thereof described herein only binds TGF-β3. In certain embodiments, the cytokine receptor sequence in a fusion protein, or a fragment or variant thereof, described herein only binds TGF-β1 and/or TGF-β3 but has low to no affinity for TGF-β2.

In some embodiments, the antibody of the first component is fused to TGFβRII or a fragment thereof (e.g., ECD of TGFβRII). In some embodiments, the antibody moiety is fused to TGFβRII or a fragment thereof (e.g., ECD of TGFβRII) via a linker. In some embodiments, the antibody moiety is fused to at least one extracellular domain of TGFβRII. In some embodiments, the antibody moiety is fused to at least one extracellular domain of TGFβRII via a linker.

In some embodiments, the antibody fragment or variant of the first component is a Fab, Fab$_2$, (Fab')$_2$, Fv, (Fv)$_2$, scFv, scFv-F$_C$, F$_C$, diabody, triabody, or minibody of the antibody of the first component. In some embodiments, the antibody fragment is a single-domain antibody of the antibody. In some embodiments, the single-domain antibody is a V$_{NAR}$ or V$_H$H fragment of the antibody.

Figure 4:
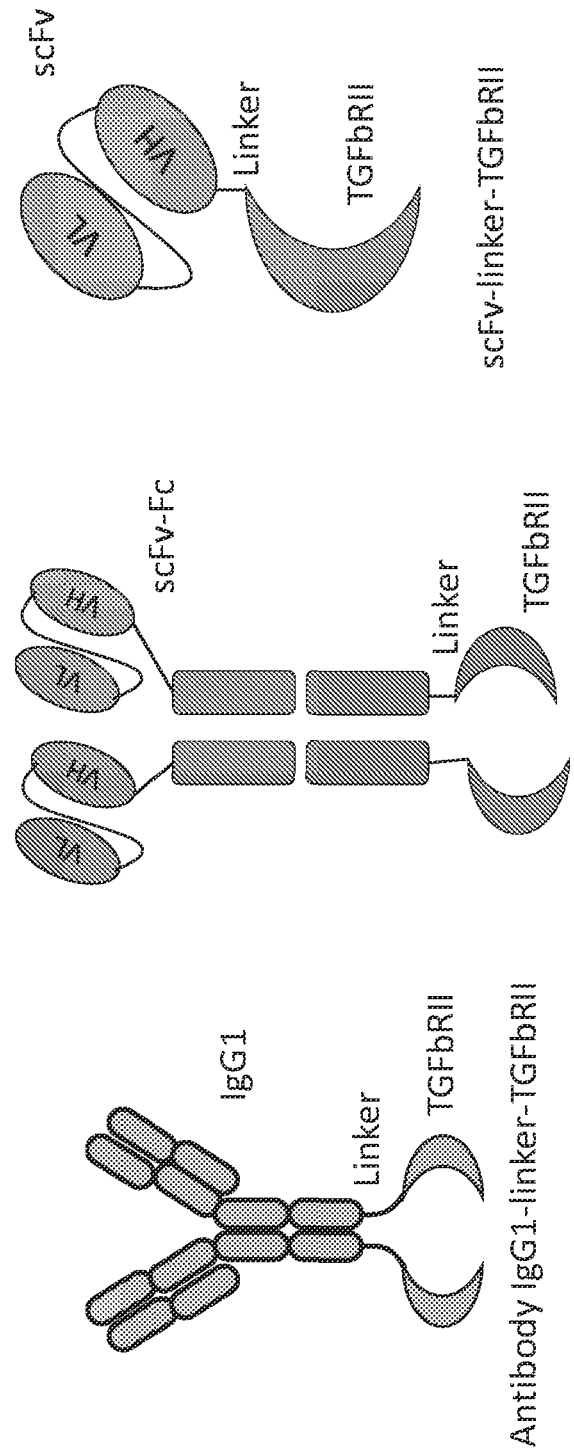
FIG. 4A, FIG. 4B, and FIG. 4C show a schematic design of antibody-TGFRII fusion protein design. In other exemplary embodiments, ADA2 can be fused to the antibody.

Non-limiting exemplary fusion proteins are illustrated in FIGS. 4A-4C.

In some embodiments, the TGF-β trap (e.g., TGFβRII) is fused to a variable region of heavy chain (V$_H$) of the antibody of the first component or a fragment or variant thereof. In other embodiments, the TGF-β trap is fused to IgG of the antibody of the first component (for example, FIG. 4A). In certain aspects, the IgG is IgG1, IgG2, IgG3, or IgG4. In an embodiment, the IgG is IgG4. In another embodiment, the IgG4 comprises a sequence having at least 80% sequence identity to SEQ ID NO 146 (wild type), SEQ ID NO: 291, SEQ ID NO: 292 or SEQ ID NO: 147 (S108P). In some embodiments, the TGF-β trap (e.g., TGFβRII) is fused to a variable region of heavy chain (V$_H$) of the antibody of the first component, or a fragment or variant thereof, via a linker. In some embodiments, the TGF-β trap (e.g., TGFβRII) is fused to a constant region of the V$_H$ of the antibody, or a fragment or variant thereof, via a linker. Examples of V$_H$ sequence of an anti-PD-1 antibody or fragment or variant thereof include but are not limited to SEQ ID NOs: 1-7 and 149-164. Examples of V$_L$ sequence of an anti-PD-1 antibody or fragment or variant thereof include but are not limited to SEQ ID NOs: 8-13 and 148. Examples of V$_H$ sequence of a MUC1 targeting antibody or fragment or variant thereof include but are not limited to SEQ ID NOs: 444-448. Examples of V$_L$ sequence of a MUC1 targeting antibody or fragment or variant thereof include but are not limited to SEQ ID NOs: 449-453. Examples of V$_H$ sequence of a MUC16 targeting antibody or fragment or variant thereof include but are not limited to SEQ ID NOs: 390-403. Examples of V$_L$ sequence of a MUC16 targeting antibody or fragment or variant thereof include but are not limited to SEQ ID NOs: 417-428. In some embodiments, the TGF-3 trap (e.g., TGFβRII) is fused a variable region of light chain (V$_L$) of the antibody, or a fragment or variant thereof. In some embodiments, the TGF-β trap (e.g., TGFβRII) is fused to a constant region of the V$_L$ of the antibody, or a fragment or variant thereof, via a linker. In some embodiments, the TGF-β trap (e.g., TGFβRII) is fused a variable region of light chain (V$_L$) of the antibody, or a fragment or variant thereof, via a linker. In one aspect, the TGF-β trap (e.g., TGFβRII) is fused to either the N- or C-terminus of the V$_L$ or V$_H$ chain, or a fragment or variant thereof, via a linker.

The term "anti-PD-1 (VL/VH)-TGFβRII" or "anti-PD-1 (VH/VL)-TGFβRII" is used interchangeably and denotes the specific VL or VH used in the fusion protein. In some embodiments, the terms "anti-PD-1 (VL/VH)-TGFβRII" or "anti-PD-1 (VH/VL)-TGFβRII" refers to TGF-β trap (e.g., TGFβRII) fused to constant region of the heavy chain of anti-PD-1 or alternatively, refers to TGF-β trap (e.g., TGFβRII) fused to constant region of the light chain of anti-PD-1.

In some embodiments, the TGF-β trap (e.g., TGFβRII) is fused to a Fab of the antibody of the first component, or a fragment or variant thereof. In some embodiments, the TGF-β trap (e.g., TGFβRII) is fused to a Fab of the antibody, or a fragment or variant thereof, via a linker. In some embodiments, the TGF-β trap (e.g., TGFβRII) is fused to a Fab$_2$, of the antibody, or a fragment or variant thereof. In some embodiments, the TGF-β trap (e.g., TGFβRII) is fused to a Fab$_2$, of the antibody, or a fragment or variant thereof, via a linker. In some embodiments, the TGF-β trap (e.g., TGFβRII) is fused to a (Fab')$_2$ of the antibody, or a fragment or variant thereof. In some embodiments, the TGF-β trap (e.g., TGFβRII) is fused to a (Fab')$_2$, of the antibody, or a fragment or variant thereof, via a linker. In one aspect, the TGF-β trap (e.g., TGFβRII) is fused to either the N- or C-terminus of the Fab or (Fab')$_2$ of the antibody, or a fragment or variant thereof, via a linker.

In some embodiments, the TGF-β trap (e.g., TGFβRII) is fused to an Fv of the antibody of the first component, or a fragment or variant thereof. In some embodiments, the TGF-β trap (e.g., TGFβRII) is fused to a Fv of the antibody, or a fragment or variant thereof, via a linker. In some embodiments, the TGF-β trap (e.g., TGFβRII) is fused to a (Fv)$_2$, of the antibody, or a fragment or variant thereof. In some embodiments, the TGF-β trap (e.g., TGFβRII) is fused to a (Fv)$_2$, of the antibody, or a fragment or variant thereof, via a linker. In one aspect, the TGF-β trap (e.g., TGFβRII) is fused to either the N- or C-terminus of the Fv or (Fv)$_2$, of the antibody, or a fragment or variant thereof, via a linker.

In some embodiments, the TGF-β trap (e.g., TGFβRII) is fused to a scFv of the antibody of the first component, or a fragment or variant thereof. In some embodiments, the TGF-β trap (e.g., TGFβRII) is fused to a scFv of the antibody, or a fragment or variant thereof, via a linker. In some embodiments, the TGF-β trap (e.g., TGFβRII) is fused to a scFv-F$_C$ of the antibody, or a fragment or variant thereof. In some embodiments, the TGF-β trap (e.g., TGFβRII) is fused to a scFv-F$_C$ of the antibody, or a fragment or variant thereof, via a linker. In one aspect, the TGF-β trap (e.g., TGFβRII) is fused to either the N- or C-terminus of the scFv or scFv-FC of the antibody, or a fragment or variant thereof, via a linker.

In some embodiments, the TGF-β trap (e.g., TGFβRII) is fused to a F$_C$ of the antibody of the first component, or a fragment or variant thereof. In some embodiments, the TGF-β trap (e.g., TGFβRII) is fused to a F$_C$ of the antibody, or a fragment or variant thereof, via a linker. In some embodiments, the TGF-β trap (e.g., TGFβRII) is linked to a C-terminus F$_C$ of the antibody, or a fragment or variant thereof. In some embodiments, the TGF-β trap (e.g., TGFβRII) is linked to a C-terminus F$_C$ of the antibody, or a fragment or variant thereof, via a linker. In some embodiments, the TGF-β trap (e.g., TGFβRII) is linked to an N-terminus F$_C$ of the antibody, or a fragment or variant thereof. In some embodiments, the TGF-β trap (e.g., TGFβRII) is linked to an N-terminus F$_C$ of the antibody, or a fragment or variant thereof, via a linker.

In some embodiments, the TGF-β trap (e.g., TGFβRII) is fused to a diabody of the antibody of the first component, or a fragment or variant thereof. In some embodiments, the TGF-β trap (e.g., TGFβRII) is fused to a diabody of the antibody, or a fragment or variant thereof, via a linker. In some embodiments, the TGF-β trap (e.g., TGFβRII) is fused to a triabody of the antibody, or a fragment or variant thereof. In some embodiments, the TGF-β trap (e.g., TGFβRII) is fused to a triabody of the antibody, or a fragment or variant thereof, via a linker. In some embodiments, the TGF-β trap (e.g., TGFβRII) is fused to a minibody of the antibody, or a fragment or variant thereof. In some embodiments, the TGF-β trap (e.g., TGFβRII) is fused to a minibody of the antibody, or a fragment or variant thereof, via a linker. In one aspect, the TGF-β trap (e.g., TGFβRII) is fused to either the N- or C-terminus of the minibody of the antibody, or a fragment or variant thereof, via a linker.

In some embodiments, the TGF-β trap (e.g., TGFβRII) is fused to a V$_{NAR}$ of the antibody of the first component, or a fragment or variant thereof. In some embodiments, the TGF-β trap (e.g., TGFβRII) is fused to a V$_{NAR}$ of the antibody, or a fragment or variant thereof, via a linker. In all embodiments, as described, the TGF-β trap (e.g., TGFβRII) is fused to either the N- or C-terminus of the V$_{NAR}$ of the antibody, or a fragment or variant thereof, via a linker.

In some embodiments, the TGF-β trap (e.g., TGFβRII) is fused to a V$_H$H of the antibody of the first component, or a fragment or variant thereof. In some embodiments, the TGF-β trap (e.g., TGFβRII) is fused to a V$_H$H of the antibody, or a fragment or variant thereof, via a linker. In all embodiments, as described, the TGF-β trap (e.g., TGFβRII) is fused to either the N- or C-terminus of the V$_H$H of the antibody, or a fragment or variant thereof, via a linker.

In some embodiments, the antibody, or fragment or variant thereof, of the first component is fused to TGFβRII or a fragment or a variant thereof (e.g., ECD of TGFβRII). In some embodiments, the antibody moiety is fused to TGFβRII or a fragment or a variant thereof (e.g., ECD of TGFβRII) via a linker. In some embodiments, the antibody moiety is fused to at least one extracellular domain of TGFβRII. In some embodiments, the antibody moiety is fused to at least one extracellular domain of TGFβRII via a linker. Non-limiting exemplary fusion proteins are illustrated in FIGS. 4A-4C.

In some embodiments, the antibody fragment is a Fab, Fab$_2$, (Fab')$_2$, Fv, (Fv)$_2$, scFv, scFv-F$_C$, F$_C$, diabody, triabody, or minibody of the antibody of the first component. In some embodiments, the antibody fragment is a single-domain antibody of the antibody. In some embodiments, the single-domain antibody is a V$_{NAR}$ or V$_H$H fragment of the antibody.

In some embodiments, the variable region of heavy chain (V$_H$) of anti-PD-1 antibody, or a fragment or variant thereof, comprises one or more polypeptide sequences as shown in any one of SEQ ID NOs: 1-7, 149-164, 333-337, and 384. In some embodiments, the variable region of heavy chain (V$_H$) of anti-PD-1 antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 1-7, 149-164, 333-337, and 384.

In some embodiments, the variable region of light chain (V$_L$) of anti-PD-1 antibody, or a fragment or variant thereof, comprises one or more polypeptide sequences as shown in any one of SEQ ID NOs: 8-13, 148, 338-343, and 385. In some embodiments, the variable region of light chain (V$_L$) of anti-PD-1 antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 8-13, 148, 338-343, and 385.

In some embodiments, the fusion protein comprises a variable region of heavy chain (V$_H$) comprising a polypeptide sequence as shown in SEQ ID NO: 6 and a variable region of light chain (V$_L$) comprising a polypeptide sequence as shown in SEQ ID NO: 12. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a sequence as shown in SEQ ID NO: 15 and a sequence as shown in SEQ ID NO: 16.

In some embodiments, the fusion protein comprises a variable region of heavy chain (V$_H$) comprising a polypeptide sequence as shown in SEQ ID NO: 333 and a variable region of light chain (V$_L$) comprising a polypeptide sequence as shown in SEQ ID NO: 338. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 333 and a variable region of light chain (V$_L$) that is at least 80%, at least 85%, at least 90%, at least 95%, at least 98%, at least 99%, or 100% identical to a sequence as shown in SEQ ID NO: 338.

In some embodiments, the fusion protein comprises a variable region of heavy chain (V$_H$) comprising a polypeptide sequence as shown in SEQ ID NO: 334 and a variable region of light chain (V$_L$) comprising a polypeptide sequence as shown in SEQ ID NO: 339. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 334 and a variable region of light chain (V$_L$) that is at least 80%, at least 85%, at least 90%, at least 95%, at least 98%, at least 99%, or 100% identical to a sequence as shown in SEQ ID NO: 339.

In some embodiments, the fusion protein comprises a variable region of heavy chain (V$_H$) comprising a polypeptide sequence as shown in SEQ ID NO: 335 and a variable region of light chain (V$_L$) comprising a polypeptide sequence as shown in SEQ ID NO: 340. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 335 and a variable region of light chain (V$_L$) that is at least 80%, at least 85%, at least 90%, at least 95%, at least 98%, at least 99%, or 100% identical to a sequence as shown in SEQ ID NO: 340.

In some embodiments, the fusion protein comprises a variable region of heavy chain (V$_H$) comprising a polypeptide sequence as shown in SEQ ID NO: 336 and a variable region of light chain (V$_L$) comprising a polypeptide sequence as shown in SEQ ID NO: 341. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 336 and a variable region of light chain (V$_L$) that is at least 80%, at least 85%, at least 90%, at least 95%, at least 98%, at least 99%, or 100% identical to a sequence as shown in SEQ ID NO: 341.

In some embodiments, the fusion protein comprises a variable region of heavy chain (V$_H$) comprising a polypeptide sequence as shown in SEQ ID NO: 337 and a variable region of light chain (V$_L$) comprising a polypeptide sequence as shown in SEQ ID NO: 342. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 337 and a variable region of light chain (V$_L$) that is at least 80%, at least 85%, at least 90%, at least 95%, at least 98%, at least 99%, or 100% identical to a sequence as shown in SEQ ID NO: 342.

In some embodiments, the fusion protein comprises a variable region of heavy chain (V$_H$) comprising a polypeptide sequence as shown in SEQ ID NO: 335 and a variable region of light chain (V$_L$) comprising a polypeptide sequence as shown in SEQ ID NO: 343. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 335 and a variable region of light chain (V$_L$) that is at least 80%, at least 85%, at least 90%, at least 95%, at least 98%, at least 99%, or 100% identical to a sequence as shown in SEQ ID NO: 343.

In some embodiments, the fusion protein comprises a variable region of heavy chain (V$_H$) comprising a polypeptide sequence as shown in SEQ ID NO: 384 and a variable region of light chain (V$_L$) comprising a polypeptide sequence as shown in SEQ ID NO: 385. In some embodiments, the fusion protein comprises a variable region of heavy chain (V$_H$) that is at least 80%, at least 85%, at least 90%, at least 95%, at least 98%, at least 99%, or 100% identical to a sequence as shown in SEQ ID NO: 384 and a variable region of light chain (V$_L$) that is at least 80%, at least 85%, at least 90%, at least 95%, at least 98%, at least 99%, or 100% identical to a sequence as shown in SEQ ID NO: 385.

In some embodiments, the variable region of heavy chain (V$_H$) of a MUC1 targeting antibody, or a fragment or variant thereof, comprises one or more polypeptide sequences as shown in any one of SEQ ID NOs: 444-448. In some embodiments, the variable region of heavy chain (V$_H$) of a MUC1 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 444-448.

In some embodiments, the variable region of light chain (V$_L$) of a MUC1 targeting antibody, or a fragment or variant thereof, comprises one or more polypeptide sequences as shown in any one of SEQ ID NOs: 449-453. In some embodiments, the variable region of light chain (V$_L$) of a MUC1 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 449-453.

In some embodiments, the fusion protein comprises a variable region of heavy chain (V$_H$) comprising a polypeptide sequence as shown in SEQ ID NO: 444. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 444.

In some embodiments, the fusion protein comprises a heavy chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 466.

In some embodiments, the fusion protein comprises a light chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 467.

In some embodiments, the variable region of heavy chain (V$_H$) of a MUC16 targeting antibody, or a fragment or variant thereof, comprises one or more polypeptide sequences as shown in any one of SEQ ID NOs: 390-403. In some embodiments, the variable region of heavy chain (V$_H$) of a MUC16 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 390-403.

In some embodiments, the variable region of light chain (V$_L$) of a MUC16 targeting antibody, or a fragment or variant thereof, comprises one or more polypeptide sequences as shown in any one of SEQ ID NOs: 417-428. In some embodiments, the variable region of light chain (V$_L$) of a MUC16 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 417-428.

In some embodiments, the fusion protein comprises a variable region of heavy chain (V$_H$) comprising a polypeptide sequence as shown in SEQ ID NO: 399. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 399.

In some embodiments, the fusion protein comprises a variable region of light chain (V$_L$) comprising a polypeptide sequence as shown in SEQ ID NO: 426. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 426.

In some embodiments, the fusion protein comprises a heavy chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 441.

In some embodiments, the fusion protein comprises a light chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 443.

In certain embodiments, the fusion protein comprises a fully human monoclonal antibody that comprises a human constant region of the IgG4 isotype and a heavy chain variable region and a light chain variable region as described above.

In certain embodiments, the fusion protein comprises a heavy chain CDR comprising an amino acid sequence selected from the group consisting of: SEQ ID NOs: 310-320, 378-380, and sequences having at least 80%, at least 85%, at least 90%, at least 95%, at least 98%, at least 99%, or 100% sequence identity therewith. In certain embodiments, the fusion protein comprises a light chain CDR comprising an amino acid sequence selected from the group consisting of: SEQ ID NOs: 321-332, 381-383, and sequences having at least 80%, at least 85%, at least 90%, at least 95%, at least 98%, at least 99%, or 100% sequence identity therewith.

In certain embodiments, the fusion protein comprises at least one, two, three, four, five, or six CDRs, each comprising an amino acid sequence individually selected from: SEQ ID NOs: 310-312 and 321-323; SEQ ID NOs: 312-314, 321, 323, and 324; SEQ ID NOs: 310, 312, 314, 321, 324, and 325; SEQ ID NOs: 310, 312, 314, 321, 324, and 332; SEQ ID NOs: 315-317 and 326-328; SEQ ID NOs: 318-320 and 329-331; or SEQ ID NOs: 378-383. In certain embodiments, the fusion protein comprises a heavy chain variable region comprising the amino acid sequences of: SEQ ID NOs: 310, 311, and/or 312; SEQ ID NOs: 312, 313, and/or 314; SEQ ID NOS: 310, 312, and/or 314; SEQ ID NOs: 315, 316, and/or 317; SEQ ID NOs: 318, 319, and/or 320; or SEQ ID NOs: 378, 379, and/or 380. In certain embodiments, the fusion protein comprises a light chain variable region comprising the amino acid sequences of: SEQ ID NOs: 321, 322, and/or 323; SEQ ID NOs: 321, 323, and/or 324; SEQ ID NOs: 321, 324, and/or 325; SEQ TD NOs: 326, 327, and/or 328; SEQ ID NOs: 329, 330, and/or 331; SEQ ID NOs: 321, 324, and/or 332; or SEQ ID NOs: 381, 382, and/or 383. In certain embodiments, the fusion protein comprises: a heavy chain variable region comprising the amino acid sequences of SEQ ID NOs: 310, 311, and/or 312 and a light chain variable region comprising the amino acid sequences of SEQ ID NOs: 321, 322, and/or 323; a heavy chain variable region comprising the amino acid sequences of SEQ ID NOs: 312, 313, and/or 314 and a light chain variable region comprising the amino acid sequences of SEQ TD NOs: 321, 323, and/or 324; a heavy chain variable region comprising the amino acid sequences of SEQ ID NOs: 310, 312, and/or 314 and a light chain variable region comprising the amino acid sequences of SEQ ID NOs: 321, 324, and/or 325; a heavy chain variable region comprising the amino acid sequences of SEQ ID NOs: 315, 316, and/or 317 and a light chain variable region comprising the amino acid sequences of SEQ ID NOs: 326, 327, and/or 328; a heavy chain variable region comprising the amino acid sequences of SEQ ID NOs: 318, 319, and/or 320 and a light chain variable region comprising the amino acid sequences of SEQ ID NOs: 329, 330, and/or 331; a heavy chain variable region comprising the amino acid sequences of SEQ ID NOs: 310, 312, and/or 315 and a light chain variable region comprising the amino acid sequences of SEQ ID NOs: 321, 324, and/or 332; or a heavy chain variable region comprising the amino acid sequences of SEQ ID NOs: 378, 379, and/or 380 and a light chain variable region comprising the amino acid sequences of SEQ ID NOs: 381, 382, and/or 383. In each of the aforementioned embodiments, the CDRs may instead comprise amino acid sequences having at least 80%, at least 85%, at least 90%, at least 95%, at least 98%, or at least 99% sequence identity with the recited sequences.

In certain embodiments, the fusion protein comprises: three heavy chain CDRs, the CDRs comprising, respectively, amino acid sequences of SEQ ID NOs: 378, 379, and 380, or sequences having at least 80%, at least 85%, at least 90%, at least 95%, at least 98%, at least 99%, or 100% sequence identity therewith; and three light chain CDRs, the CDRs comprising, respectively, amino acid sequences of SEQ ID NOs: 381, 382, and 383, or sequences having at least 80%, at least 85%, at least 90%, at least 95%, at least 98%, at least 99%, or 100% sequence identity therewith.

In certain embodiments, the fusion protein comprises: three heavy chain CDRs, the CDRs comprising, respectively, amino acid sequences of SEQ ID NOs: 378, 379, and 380; and three light chain CDRs, the CDRs comprising, respectively, amino acid sequences of SEQ ID NOs: 381, 382, and 383.

In certain embodiments, the fusion protein comprises a heavy chain comprising an amino acid sequence of SEQ ID NO: 386, or a sequence having at least 80%, at least 85%, at least 90%, at least 95%, at least 98%, at least 99%, or 100% sequence identity therewith, and a light chain comprising an amino acid sequence of SEQ ID NO: 387, or a sequence having at least 80%, at least 85%, at least 90%, at least 95%, at least 98%, at least 99%, or 100% sequence identity therewith. In certain embodiments, the fusion protein comprises a heavy chain comprising and amino acid sequence of SEQ ID NO: 386 and a light chain comprising an amino acid sequence of SEQ ID NO: 387.

In some embodiments of the present invention, the fusion protein comprises an anti-PD-1 moiety selected or derived from a full-length, fragment, or variant of one or more antibody from Table 1.

In some embodiments, the fusion protein comprises an anti-PD-1 moiety that is selected or derived from a full-length, fragment, or variant of pembrolizumab (Keytruda®), nivolumab (Opdivo®), zimberelimab (WBP3055), or cetrelimab (JNJ-63723283).

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a sequence as shown in SEQ ID NO: 15 and a sequence as shown in SEQ ID NO: 143.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 294.

In embodiments, the fusion protein comprises a sequence as shown in SEQ ID NO: 15 and a sequence as shown in SEQ ID NO: 294.

In some embodiments, the fusion protein comprises a variable region of heavy chain ($V_H$) comprising a polypeptide sequence as shown in SEQ ID NO: 7 and a variable region of light chain ($V_L$) comprising a polypeptide sequence as shown in SEQ ID NO: 13. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145.

In some embodiments, the fusion protein comprises a sequence as shown in SEQ ID NO: 296 and a sequence as shown in SEQ ID NO: 145.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 144.

In some embodiments, the fusion protein comprises a sequence as shown in SEQ ID NO: 296 and a sequence as shown in SEQ ID NO: 144.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 296 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 295.

In some embodiments, the fusion protein comprises a sequence as shown in SEQ ID NO: 296 and a sequence as shown in SEQ ID NO: 295.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145. In some embodiments, the fusion protein comprises a sequence as shown in SEQ ID NO: 145.

In some embodiments, the fusion protein comprises a linker and a variable region of heavy chain ($V_H$) comprising a polypeptide sequence as shown in SEQ ID NO: 16 and a variable region of light chain ($V_L$) comprising a polypeptide sequence as shown in SEQ ID NO: 15. In some embodiments, the fusion protein comprises a linker and a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a variable region of heavy chain ($V_H$) comprising a polypeptide sequence as shown in SEQ ID NO: 1. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 1.

In some embodiments, the fusion protein comprises a variable region of heavy chain ($V_H$) comprising a polypeptide sequence as shown in SEQ ID NO: 2. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 2.

In some embodiments, the fusion protein comprises a variable region of heavy chain ($V_H$) comprising a polypeptide sequence as shown in SEQ ID NO: 3. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 3.

In some embodiments, the fusion protein comprises a variable region of heavy chain ($V_H$) comprising a polypeptide sequence as shown in SEQ ID NO: 4. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 4.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 6. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6.

In some embodiments, the fusion protein comprises a variable region of heavy chain ($V_H$) comprising a polypeptide sequence as shown in SEQ ID NO: 7. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7.

In some embodiments, the fusion protein comprises a variable region of heavy chain ($V_H$) comprising a polypeptide sequence as shown in SEQ ID NO: 5 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 149 and a variable region of light chain (V$_L$) comprising a polypeptide sequence as shown in SEQ ID NO: 8. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 157 and a variable region of light chain (V$_L$) comprising a polypeptide sequence as shown in SEQ ID NO: 8. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 158 and a variable region of light chain (V$_L$) comprising a polypeptide sequence as shown in SEQ ID NO: 8. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 5. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain (V$_H$) comprising a polypeptide sequence as shown in SEQ ID NO: 149. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain (V$_H$) comprising a polypeptide sequence as shown in SEQ ID NO: 157. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of light chain (V$_L$) comprising a polypeptide sequence as shown in SEQ ID NO: 8. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 149. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain (V$_H$) comprising a polypeptide sequence as shown in SEQ ID NO: 150. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 150.

In some embodiments, the fusion protein comprises a variable region of heavy chain (V$_H$) comprising a polypeptide sequence as shown in SEQ ID NO: 151. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 151.

In some embodiments, the fusion protein comprises a variable region of heavy chain (V$_H$) comprising a polypeptide sequence as shown in SEQ ID NO: 152. In some embodiments, the fusion protein comprises a variable region of heavy chain (V$_H$) that is at least 50%, at least 55%, at least 60%, at least 65%, at least 70%, at least 75%, at least 80%, In some embodiments, the fusion protein comprises a variable region of heavy chain (V$_H$) comprising a polypeptide sequence as shown in SEQ ID NO: 153. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 153.

In some embodiments, the fusion protein comprises a variable region of heavy chain (V$_H$) comprising a polypeptide sequence as shown in SEQ ID NO: 154. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 154.

In some embodiments, the fusion protein comprises a variable region of heavy chain (V$_H$) comprising a polypeptide sequence as shown in SEQ ID NO: 155. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 155.

In some embodiments, the fusion protein comprises a variable region of heavy chain (V$_H$) comprising a polypeptide sequence as shown in SEQ ID NO: 156. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 156.

In some embodiments, the fusion protein comprises a variable region of heavy chain (V$_H$) comprising a polypeptide sequence as shown in SEQ ID NO: 157. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain (V$_H$) comprising a polypeptide sequence as shown in SEQ ID NO: 159. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 159.

In some embodiments, the fusion protein comprises a variable region of heavy chain (V$_H$) comprising a polypeptide sequence as shown in SEQ ID NO: 160. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 160.

In some embodiments, the fusion protein comprises a variable region of heavy chain (V$_H$) comprising a polypeptide sequence as shown in SEQ ID NO: 161. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 161.

In some embodiments, the fusion protein comprises a variable region of heavy chain (V$_H$) comprising a polypeptide sequence as shown in SEQ ID NO: 162. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 162.

In some embodiments, the fusion protein comprises a variable region of heavy chain (V$_H$) comprising a polypeptide sequence as shown in SEQ ID NO: 163. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 163.

In some embodiments, the fusion protein comprises a variable region of heavy chain (V$_H$) comprising a polypeptide sequence as shown in SEQ ID NO: 164. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 164.

In some embodiments, the fusion protein comprises a variable region of light chain (V$_L$) comprising a polypeptide sequence as shown in SEQ ID NO: 8. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of light chain (V$_L$) comprising a polypeptide sequence as shown in SEQ ID NO: 9. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 9.

In some embodiments, the fusion protein comprises a variable region of light chain (V$_L$) comprising a polypeptide sequence as shown in SEQ ID NO: 10. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 10.

In some embodiments, the fusion protein comprises a variable region of light chain ($V_L$) comprising a polypeptide sequence as shown in SEQ ID NO: 11. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 11.

In some embodiments, the fusion protein comprises a variable region of light chain ($V_L$) comprising a polypeptide sequence as shown in SEQ ID NO: 12. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a variable region of light chain ($V_L$) comprising a polypeptide sequence as shown in SEQ ID NO: 13. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a variable region of light chain ($V_L$) comprising a polypeptide sequence as shown in SEQ ID NO: 148. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 148.

In some embodiments, the fusion protein comprises a polypeptide sequence as shown in SEQ ID NO: 15. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a polypeptide sequence as shown in SEQ ID NO: 16. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 16.

In some embodiments, the fusion protein comprises a polypeptide sequence as shown in SEQ ID NO: 143. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 143.

In some embodiments, the fusion protein comprises a polypeptide sequence as shown in SEQ ID NO: 144. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 144.

In some embodiments, the fusion protein comprises a polypeptide sequence as shown in SEQ ID NO: 145. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 145.

Anti-TGF β Antibodies—Fusion Proteins, or Fragments or Variants Thereof

In other embodiments, the cytokine trap is an antibody, antibody fragment or an antibody variant against TGF-β. In such embodiments, such antibodies can include pan-neutralizing anti-TGFβ antibody, or an anti-receptor antibody that blocks the receptor from binding to TGFβ1, 2 and/or 3. In certain embodiments, the antibody fragment or variant is a Fab, Fab$_2$, (Fab')$_2$, Fv, (Fv)$_2$, scFv, scFv-F$_C$, F$_C$, diabody, triabody, or minibody of the TGFβ antibody. In some embodiments, the anti-TGF-β antibody or fragment or variant thereof binds to TGF-β1, TGF-β2, and TGF-_β3. In certain embodiments, the anti-TGF-β antibody or fragment or variant thereof binds to TGF-β1. In certain embodiments, the anti-TGF-β antibody or fragment or variant thereof binds to TGF-β3. In certain embodiments, the anti-TGF-β antibody or fragment or variant thereof binds to TGF-β1 and TGF-β2. In certain embodiments, the anti-TGF-β antibody or fragment or variant thereof binds to TGF-β1 and TGF-β3. Examples of VH sequence of a TGF-β antibody or fragment or variant thereof include but are not limited to SEQ ID Nos. 166, 168, 169, 171, 173, 175, and 177. Examples of $V_L$ sequence of a TGF-β antibody or fragment or variant thereof include but are not limited to SEQ ID NOs: 165, 167, 170, 172, 174, 176, and 178. In some embodiments, the anti-TGF-β antibody comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 166, 168, 169, 171, 173, 175, or 177. In some embodiments, the anti-TGF-β antibody comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence selected from any one of SEQ ID NOs: 165, 167, 170, 172, 174, 176, or 178.

TGF-β Antagonistic Peptides—Fusion Proteins, or Fragments or Variants Thereof

In certain embodiments, the cytokine trap can include TGF-β antagonistic peptides or TGF-β inhibitory peptides. Such peptides can be generated de novo using phage display. In some embodiments, such peptides can be derived from segments of TGF-β isoform(s) or TGF-β receptor(s), Examples of TGF-β antagonistic peptides can include but are not limited to SEQ ID NOs: 468-507 and 263-267. Examples of TGF-β inhibitory peptides can include but are not limited to SEQ ID NOs: 468-507 and 263-267. In some embodiments, the peptides can be fused to $V_H$ and/or $V_L$ of the antibody of the first component, or a fragment or variant thereof, via a linker. In another embodiment, one peptide can be fused to the antibody of the first component, or a fragment or variant thereof. In a further embodiment, more than one peptide can be fused to the antibody of the first component, or a fragment or variant thereof. When more than one peptide is utilized, the peptide can be fused with or without a linker to form concatemers. When more than one peptide is utilized, the same peptide can be used to form concatemers. Alternatively, a combination of two or more different peptides can be used to form concatemers.

Adenosine

Adenosine is a key immune modulator in the tumor microenvironment. Extracellular adenosine suppresses inflammatory response upon binding to the A2A adenosine receptor (A2AR) which is predominantly expressed subtype in most immune cells. Several tumors express high levels of CD39 and CD73, the ectonucleotidases responsible for converting ATP and ADP to AMP, and AMP to adenosine, respectively. Accordingly, adenosine promotes suppressive activity of regulatory T cells by inducing the expression of Foxp3, CD39 and CD73. Additionally, hypoxia induces the accumulation of extracellular adenosine in the tumor microenvironment through the induction of CD39 and CD73. In addition, high levels of extracellular adenosine in the tumor microenvironment is maintained by the hypoxia-inducible factor(HIF)-dependent inhibition of the nucleotide transporter ENT-1, and the inhibition of adenosine kinase preventing the relocation of adenosine in the intracellular space and preventing the formation of AMP, respectively. Accordingly, targeting the reduction of extracellular adenosine in the tumor microenvironment is understood to enhance immune cell function and promote tumor cell killing.

In embodiments provided herein are fusion proteins that comprise an adenosine deaminase (e.g., ADA2) to target reduction of extracellular adenosine in the tumor microenvironment.

Adenosine Deaminase

Adenosine deaminase (also known as adenosine aminohydrolase, or ADA) ADA irreversibly deaminates adenosine, converting it to the related nucleoside inosine by the substitution of the amino group for a keto group. Inosine can then be deribosylated (removed from ribose) by another enzyme called purine nucleoside phosphorylase (PNP), converting it to hypoxanthine. ADA is needed for the breakdown of adenosine from food and for the turnover of nucleic acids in tissues. Its primary function in humans is the development and maintenance of the immune system. However, ADA association has also been observed with epithelial cell differentiation, neurotransmission, and gestation maintenance. There are 2 isoforms of ADA: ADA1 and ADA2.

ADA1 is found in most body cells, particularly lymphocytes and macrophages, where it is present not only in the cytosol and nucleus but also as the ecto-form on the cell membrane attached to dipeptidyl peptidase-4 (aka, CD26). ADA1 is involved mostly in intracellular activity, and exists both in small form (monomer) and large form (dimer). The interconversion of small to large forms is regulated by a 'conversion factor' in the lung.

ADA2 was first identified in human spleen. It was subsequently found in other tissues including the macrophage where it co-exists with ADA1. The two isoforms regulate the ratio of adenosine to deoxyadenosine. ADA2 is found predominantly in the human plasma and serum, and exists mainly as a homodimer. ADA2 is the predominant form present in human blood plasma and is increased in many diseases, particularly those associated with the immune system: for example rheumatoid arthritis, psoriasis, and sarcoidosis. The plasma ADA2 isoform is also increased in most cancers. ADA2 is not ubiquitous but co-exists with ADA1 in monocytes-macrophages.

ADA2 Fusion Proteins, or Fragments or Variants Thereof

Provided herein is a fusion protein or a fragment or a variant thereof comprising: (1) an immune checkpoint inhibitor, such as a PD-1 inhibitor or antibody, or an antibody that binds a tumor antigen expressed on the surface of a tumor cell; and (2) an adenosine deaminase (e.g., ADA2) that can neutralize adenosine. The fusion protein or a fragment or a variant thereof provided herein (e.g., PD-1 inhibitor or antibody fused to an adenosine deaminase (e.g., ADA2) can elicit a synergistic anti-tumor effect due to the simultaneous blockade of the interaction between e.g., PD-L1, MUC1, and MUC16 on tumor cells on tumor cells and PD-1, MUC1, and MUC16 on tumor cells on immune cells, and the neutralization of e.g., adenosine in the tumor microenvironment. Without being bound by theory, this effect is obtained from simultaneous blocking the two major immune escape mechanisms and the targeted depletion of adenosine in the tumor microenvironment by a single molecular entity. This depletion can be achieved by one or more of the following: (1) anti-PD-1, anti-MUC1, or anti-MUC16 targeting of tumor cells; (2) binding of the adenosine in the tumor microenvironment by an adenosine deaminase (e.g., ADA2); and (3) destruction of the bound adenosine through the PD-L1 receptor mediated endocytosis.

In some embodiments, the adenosine deaminase (e.g., ADA2) is a part of the fusion protein or a fragment or a variant thereof. In some embodiments the fusion protein or a fragment or a variant thereof comprises the adenosine deaminase (e.g., ADA2) fused to the antibody of the first component optionally via a cleavable or non-cleavable linker. In some embodiments, an adenosine deaminase is an adenosine deaminase 2 (ADA2). In some embodiments, the fusion protein described herein comprises an adenosine deaminase (e.g., ADA2) described herein or a functional variant or derivative thereof. Examples of ADA2 and variants are described in WO 2016061286, herein incorporated by reference in its entirety. In some embodiments, the TGF-β cytokine trap comprises any one of ADA2 mutant 1, ADA2 mutant 2, ADA2 mutant 3, ADA2 mutant 4, ADA2 mutant 5, ADA2 mutant 6, or ADA2 mutant 7. In some embodiments, the fusion protein or a fragment or a variant thereof provided herein comprises the antibody fused to the ADA protein, or fragment thereof, via a linker.

In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 284. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 273. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 274. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 275. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 276. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 277. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 278. In some embodiments, the fusion protein or a fragment or a variant thereof described herein comprises a polypeptide sequence having at least 50%, at least 55%, at least 60%, at least 65%, at least 70%, at least 75%, at least 80%, at least 85%, at least 90%, at least 95%, at least 99%, at least 99.5% or 100% identity with the polypeptide sequence of SEQ ID NO: 279.

In some embodiments, the fusion protein or a fragment or a variant thereof described herein comprises an adenosine deaminase (e.g., ADA2) as described above and an antibody, a fragment or a variant of the antibody that targets immune checkpoint genes. In some embodiments, an antibody or a fragment or a variant of the antibody that target immune checkpoints, such as cytotoxic T lymphocyte associated protein-4 (CTLA-4) and programmed cell death-1 (PD-1), or an antibody that binds to a tumor antigen expressed on the surface of a tumor cell can be fused to an adenosine deaminase (e.g., ADA2) molecule via a linker.

In some embodiments, an antibody, or fragment or variant thereof, of the first component is fused to an adenosine deaminase (e.g., ADA2) or a fragment thereof. In some embodiments, the antibody moiety is fused to an adenosine deaminase (e.g., ADA2) via a linker. In some embodiments, the antibody moiety is fused to at least one domain of ADA2. In some embodiments, the antibody moiety is fused to at least one domain of ADA2 via a linker.

In some embodiments, the antibody of the first component, or fragment or variant thereof, is a Fab, Fab$_2$, (Fab')$_2$, Fv, (Fv)$_2$, scFv, scFv-F$_C$, F$_C$, diabody, triabody, or minibody of the antibody. In some embodiments, the antibody fragment is a single-domain antibody of the antibody. In some embodiments, the single-domain antibody is a V$_{NAR}$ or V$_H$H fragment of the antibody.

Figures 33A, 33B, 33C:
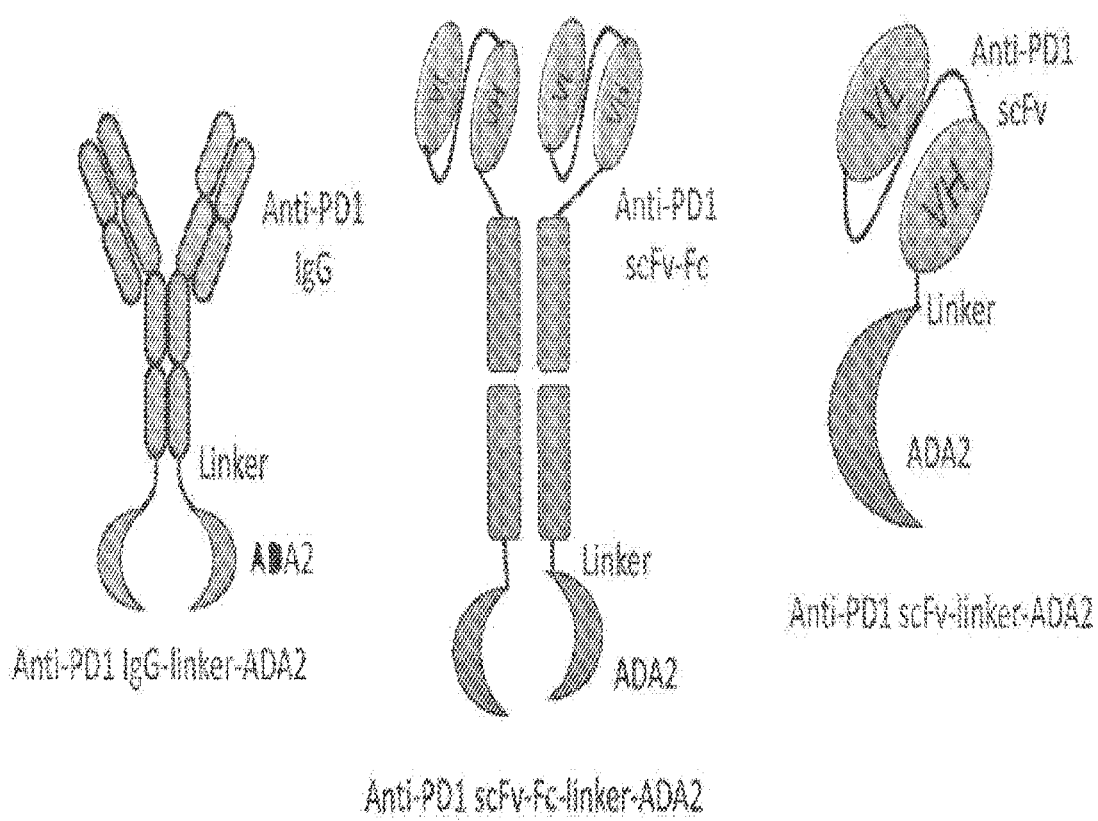
FIGS. 33A-33C show a schematic design of anti-PD-1-adenosine deaminase 2 (ADA2) design: anti-PD-1-ADA2.

Non-limiting exemplary fusion proteins comprising anti-PD-1 are illustrated in FIGS. 33A-33C. In some embodiments, the fusion protein comprising an antibody or a fragment or a variant thereof fused to an adenosine deaminase (e.g., ADA2) can elicit a synergistic anti-tumor effect due to the simultaneous blockade of the interaction between PD-L1 on tumor cells or PD-1 on immune cells or anti-MUC1 or anti-MUC16 targeting of tumor cells, and targeting of the reduction of extracellular adenosine in the tumor microenvironment.

In some embodiments, the adenosine deaminase (e.g., ADA2) is fused to a variable region of heavy chain (V$_H$) of the antibody of the first component, or a fragment or variant thereof. In other embodiments, the adenosine deaminase is fused to IgG of the antibody (for example, FIG. 4a). In certain aspects, the IgG is IgG1, IgG2, IgG3, or IgG4. In an embodiment, the IgG is IgG4. In another embodiment, the IgG4 is SEQ ID NO 146 (wild type), SEQ ID NO: 291, SEQ ID NO: 292 or SEQ ID NO: 147 (S108P). In some embodiments, the adenosine deaminase (e.g., ADA2) is fused to a variable region of heavy chain (V$_H$) of the antibody, or a fragment or variant thereof, via a linker. In some embodiments, the adenosine deaminase (e.g., ADA2) is fused to a constant region of the V$_H$ of the antibody, or a fragment or variant thereof, via a linker. In some embodiments, the adenosine deaminase (e.g., ADA2) is fused a variable region of light chain (V$_L$) of the antibody, or a fragment or variant thereof. In some embodiments, the adenosine deaminase (e.g., ADA2) is fused a variable region of light chain (V$_L$) of the antibody, or a fragment or variant thereof, via a linker. In some embodiments, the adenosine deaminase (e.g., ADA2) is fused to a constant region of the V$_L$ of the antibody, or a fragment or variant thereof, via a linker. In one aspect, the adenosine deaminase is fused to either the N- or C-terminus of the V$_H$ or V$_L$ of the antibody, or a fragment or variant thereof, via a linker.

In some embodiments, the adenosine deaminase (e.g., ADA2) is fused to a Fab of the antibody of the first component, or a fragment or variant thereof. In some embodiments, the adenosine deaminase (e.g., ADA2) is fused to a Fab of the antibody, or a fragment or variant thereof, via a linker. In some embodiments, the adenosine deaminase (e.g., ADA2) is fused to a Fab$_2$, of the antibody, or a fragment or variant thereof. In some embodiments, the adenosine deaminase (e.g., ADA2) is fused to a Fab$_2$, of the antibody, or a fragment or variant thereof, via a linker. In some embodiments, the adenosine deaminase (e.g., ADA2) is fused to a (Fab')$_2$ of the antibody, or a fragment or variant thereof. In some embodiments, the adenosine deaminase (e.g., ADA2) is fused to a (Fab')$_2$, of the antibody, or a fragment or variant thereof, via a linker. In one aspect, the adenosine deaminase is fused to either the N- or C-terminus of the Fab or Fab$_2$ of the antibody, or a fragment or variant thereof, via a linker.

In some embodiments, the adenosine deaminase (e.g., ADA2) is fused to a Fv of the antibody of the first component, or a fragment or variant thereof. In some embodiments, the adenosine deaminase (e.g., ADA2) is fused to a Fv of the antibody, or a fragment or variant thereof, via a linker. In some embodiments, the adenosine deaminase (e.g., ADA2) is fused to a (Fv)$_2$, of the antibody, or a fragment or variant thereof. In some embodiments, the adenosine deaminase (e.g., ADA2) is fused to a (Fv)$_2$ of the antibody, or a fragment or variant thereof, via a linker. In one aspect, the adenosine deaminase is fused to either the N- or C-terminus of the Fv or (Fv)$_2$, of the antibody, or a fragment or variant thereof, via a linker.

In some embodiments, the adenosine deaminase (e.g., ADA2) is fused to a scFv of the antibody of the first component, or a fragment or variant thereof. In some embodiments, the adenosine deaminase (e.g., ADA2) is fused to a scFv of the antibody, or a fragment or variant thereof, via a linker. In some embodiments, the adenosine deaminase (e.g., ADA2) is fused to a scFv-F$_C$ of the antibody, or a fragment or variant thereof. In some embodiments, the adenosine deaminase (e.g., ADA2) is fused to a scFv-F$_C$ of the antibody, or a fragment or variant thereof, via a linker. In one aspect, the adenosine deaminase is fused to either the N- or C-terminus of the scFv or scFv-F$_C$ of the antibody, or a fragment or variant thereof, via a linker.

In some embodiments, the adenosine deaminase (e.g., ADA2) is fused to a F$_C$ of the antibody of the first component, or a fragment or variant thereof. In some embodiments, the adenosine deaminase (e.g., ADA2) is fused to a $F_C$ of the antibody, or a fragment or variant thereof, via a linker. In some embodiments, the adenosine deaminase (e.g., ADA2) is linked to a C-terminus $F_C$ of the antibody, or a fragment or variant thereof. In some embodiments, the adenosine deaminase (e.g., ADA2) is linked to a C-terminus $F_C$ of the antibody, or a fragment or variant thereof, via a linker. In some embodiments, the adenosine deaminase (e.g., ADA2) is linked to a N-terminus $F_C$ of the antibody, or a fragment or variant thereof. In some embodiments, the adenosine deaminase (e.g., ADA2) is linked to an N-terminus $F_C$ of the antibody, or a fragment or variant thereof, via a linker.

In some embodiments, the adenosine deaminase (e.g., ADA2) is fused to a diabody of the antibody of the first component, or a fragment or variant thereof. In some embodiments, the adenosine deaminase (e.g., ADA2) is fused to a diabody of the antibody, or a fragment or variant thereof, via a linker. In some embodiments, the adenosine deaminase (e.g., ADA2) is fused to a triabody of the antibody, or a fragment or variant thereof. In some embodiments, the adenosine deaminase (e.g., ADA2) is fused to a triabody of the antibody, or a fragment or variant thereof, via a linker. In some embodiments, the adenosine deaminase (e.g., ADA2) is fused to a minibody of the antibody, or a fragment or variant thereof. In some embodiments, the adenosine deaminase (e.g., ADA2) is fused to a minibody of the antibody, or a fragment or variant thereof, via a linker.

In some embodiments, the adenosine deaminase (e.g., ADA2) is fused to a $V_{NAR}$ of the antibody of the first component, or a fragment or variant thereof. In some embodiments, the adenosine deaminase (e.g., ADA2) is fused to a $V_{NAR}$ of the antibody, or a fragment or variant thereof, via a linker. In one aspect, the adenosine deaminase is fused to either the N- or C-terminus of the $V_{NAR}$ of the antibody, or a fragment or variant thereof, via a linker.

In some embodiments, the adenosine deaminase (e.g., ADA2) is fused to a $V_HH$ of the antibody of the first component, or a fragment or variant thereof. In some embodiments, the adenosine deaminase (e.g., ADA2) is fused to a $V_HH$ of the antibody, or a fragment or variant thereof, via a linker. In one aspect, the adenosine deaminase is fused to either the N- or C-terminus of the $V_HH$ of the antibody, or a fragment or variant thereof, via a linker.

In some embodiments, the variable region of heavy chain ($V_H$) of anti-PD-1 antibody, or a fragment or variant thereof, comprises one or more polypeptide sequences as shown in any one of SEQ ID NOs: 1-7, 149-164, 333-337, and 384. In some embodiments, the variable region of heavy chain ($V_H$) of anti-PD-1 antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 1-7, 149-164, 333-337, and 384.

In some embodiments, the variable region of light chain ($V_L$) of anti-PD-1 antibody, or a fragment or variant thereof, comprises one or more polypeptide sequences as shown in any one of SEQ ID NOs: 8-13, 148, 338-343, and 385. In some embodiments, the variable region of light chain ($V_L$) of anti-PD-1 antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 8-13, 148, 338-343, and 385.

In some embodiments, the fusion protein comprises a variable region of heavy chain ($V_H$) comprising a polypeptide sequence as shown in SEQ ID NO: 6 and a variable region of light chain ($V_L$) comprising a polypeptide sequence as shown in SEQ ID NO: 12. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a variable region of heavy chain ($V_H$) comprising a polypeptide sequence as shown in SEQ ID NO: 333 and a variable region of light chain ($V_L$) comprising a polypeptide sequence as shown in SEQ ID NO: 338. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 333 and a variable region of light chain ($V_L$) that is at least 80%, at least 85%, at least 90%, at least 95%, at least 98%, at least 99%, or 100% identical to a sequence as shown in SEQ ID NO: 338.

In some embodiments, the fusion protein comprises a variable region of heavy chain ($V_H$) comprising a polypeptide sequence as shown in SEQ ID NO: 334 and a variable region of light chain ($V_L$) comprising a polypeptide sequence as shown in SEQ ID NO: 339. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 334 and a variable region of light chain ($V_L$) that is at least 80%, at least 85%, at least 90%, at least 95%, at least 98%, at least 99%, or 100% identical to a sequence as shown in SEQ ID NO: 339.

In some embodiments, the fusion protein comprises a variable region of heavy chain ($V_H$) comprising a polypeptide sequence as shown in SEQ ID NO: 335 and a variable region of light chain ($V_L$) comprising a polypeptide sequence as shown in SEQ ID NO: 340. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 335 and a variable region of light chain ($V_L$) that is at least 80%, at least 85%, at least 90%, at least 95%, at least 98%, at least 99%, or 100% identical to a sequence as shown in SEQ ID NO: 340.

In some embodiments, the fusion protein comprises a variable region of heavy chain ($V_H$) comprising a polypeptide sequence as shown in SEQ ID NO: 336 and a variable region of light chain ($V_L$) comprising a polypeptide sequence as shown in SEQ ID NO: 341. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 336 and a variable region of light chain ($V_L$) that is at least 80%, at least 85%, at least 90%, at least 95%, at least 98%, at least 99%, or 100% identical to a sequence as shown in SEQ ID NO: 341.

In some embodiments, the fusion protein comprises a variable region of heavy chain ($V_H$) comprising a polypeptide sequence as shown in SEQ ID NO: 337 and a variable region of light chain ($V_L$) comprising a polypeptide sequence as shown in SEQ ID NO: 342. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 337 and a variable region of light chain ($V_L$) that is at least 80%, at least 85%, at least 90%, at least 95%, at least 98%, at least 99%, or 100% identical to a sequence as shown in SEQ ID NO: 342.

In some embodiments, the fusion protein comprises a variable region of heavy chain ($V_H$) comprising a polypeptide sequence as shown in SEQ ID NO: 335 and a variable region of light chain ($V_L$) comprising a polypeptide sequence as shown in SEQ ID NO: 343. In some embodiments, the fusion protein comprises a variable region of heavy chain ($V_H$) that is at least 80%, at least 85%, at least 90%, a at least 95%, at least 98%, at least 99%, or 100% identical to a sequence as shown in SEQ ID NO: 335 and a variable region of light chain ($V_L$) that is at least 80%, at least 85%, at least 90%, at least 95%, at least 98%, at least 99%, or 100% identical to a sequence as shown in SEQ ID NO: 343.

In some embodiments, the fusion protein comprises a variable region of heavy chain ($V_H$) comprising a polypeptide sequence as shown in SEQ ID NO: 384 and a variable region of light chain ($V_L$) comprising a polypeptide sequence as shown in SEQ ID NO: 385. In some embodiments, the fusion protein comprises a variable region of heavy chain ($V_H$) that is at least 80%, at least 85%, at least 90%, at least 95%, at least 98%, at least 99%, or 100% identical to a sequence as shown in SEQ ID NO: 384 and a variable region of light chain ($V_L$) that is at least 80%, at least 85%, at least 90%, at least 95%, at least 98%, at least 99%, or 100% identical to a sequence as shown in SEQ ID NO: 385.

In some embodiments, the variable region of heavy chain ($V_H$) of a MUC1 targeting antibody, or a fragment or variant thereof, comprises one or more polypeptide sequences as shown in any one of SEQ ID NOs: 444-448. In some embodiments, the variable region of heavy chain ($V_H$) of a MUC1 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 444-448.

In some embodiments, the variable region of light chain ($V_L$) of a MUC1 targeting antibody, or a fragment or variant thereof, comprises one or more polypeptide sequences as shown in any one of SEQ ID NOs: 449-453. In some embodiments, the variable region of light chain ($V_L$) of a MUC1 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 449-453.

In some embodiments, the fusion protein comprises a variable region of heavy chain ($V_H$) comprising a polypeptide sequence as shown in SEQ ID NO: 444. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 444.

In some embodiments, the fusion protein comprises a heavy chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 466.

In some embodiments, the fusion protein comprises a light chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 467.

In some embodiments, the variable region of heavy chain ($V_H$) of a MUC16 targeting antibody, or a fragment or variant thereof, comprises one or more polypeptide sequences as shown in any one of SEQ ID NOs: 390-403. In some embodiments, the variable region of heavy chain ($V_H$) of a MUC16 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 390-403.

In some embodiments, the variable region of light chain ($V_L$) of a MUC16 targeting antibody, or a fragment or variant thereof, comprises one or more polypeptide sequences as shown in any one of SEQ ID NOs: 417-428. In some embodiments, the variable region of light chain ($V_L$) of a MUC16 targeting antibody, or a fragment or variant thereof, comprises one or more polypeptide sequences having at least 50%, at least 55%, at least 60%, at least 65%, at least 70%, at least 75%, at least 80%, at least 85%, at least 90%, at least 95%, at least 99%, at least 99.5% or 100% identity with any one of polypeptide sequences as shown in SEQ ID NOs: 417-428.

In some embodiments, the fusion protein comprises a variable region of heavy chain ($V_H$) comprising a polypeptide sequence as shown in SEQ ID NO: 399. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 399.

In some embodiments, the fusion protein comprises a variable region of light chain ($V_L$) comprising a polypeptide sequence as shown in SEQ ID NO: 426. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 426.

In some embodiments, the fusion protein comprises a heavy chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 441.

In some embodiments, the fusion protein comprises a light chain sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 443.

In certain embodiments, the fusion protein comprises a fully human monoclonal antibody that comprises a human constant region of the IgG4 isotype and a heavy chain variable region and a light chain variable region as described above.

In certain embodiments, the fusion protein comprises a heavy chain CDR comprising an amino acid sequence selected from the group consisting of: SEQ ID NOs: 310-320, 378-380, and sequences having at least 80%, at least 85%, at least 90%, at least 95%, at least 98%, at least 99%, or 100% sequence identity therewith. In certain embodiments, the fusion protein comprises a light chain CDR comprising an amino acid sequence selected from the group consisting of: SEQ ID NOS: 321-332, 381-383, and sequences having at least 80%, at least 85%, at least 90%, at least 95%, at least 98%, at least 99%, or 100% sequence identity therewith.

In certain embodiments, the fusion protein comprises at least one, two, three, four, Five, or six CDRs, each comprising an amino acid sequence individually selected from: SEQ ID NOs: 310-312 and 321-323; SEQ ID NOs: 312-314; 321, 323, and 324; SEQ ID NOs: 310, 312, 314, 321, 324, and 325; SEQ ID NOs: 310, 312, 314, 321, 324, and 332; SEQ ID NOs: 315-317 and 326-328; SEQ ID NOs: 318-320 and 329-331; or SEQ ID NOs: 378-383. In certain embodiments, the fusion protein comprises a heavy chain variable region comprising the amino acid sequences of: SEQ ID NOs: 310, 311, and/or 312; SEQ ID NOs: 312, 313, and/or 314; SEQ ID NOS: 310, 312, and/or 314; SEQ ID NOs: 315, 316, and/or 317; SEQ ID NOs: 318, 319, and/or 320; or SEQ ID NOs: 378, 379, and/or 380. In certain embodiments, the fusion protein comprises a light chain variable region comprising the amino acid sequences of: SEQ ID NOS: 321, 322, and/or 323; SEQ ID NOs: 321, 323, and/or 324; SEQ ID NOs: 321, 324, and/or 325; SEQ ID NOs: 326, 327, and/or 328; SEQ ID NOs: 329, 330, and/or 331; SEQ ID NOs: 321, 324, and/or 332; or SEQ ID NOs: 381, 382, and/or 383. In certain embodiments, the fusion protein comprises: a heavy chain variable region comprising the amino acid sequences of SEQ ID NOs: 310, 311, and/or 312 and a light chain variable region comprising the amino acid sequences of SEQ ID NOs: 321, 322, and/or 323; a heavy chain variable region comprising the amino acid sequences of SEQ ID NOs: 312, 313, and/or 314 and a light chain variable region comprising the amino acid sequences of SEQ ID NOs: 321, 323, and/or 324; a heavy chain variable region comprising the amino acid sequences of SEQ ID NOs: 310, 312, and/or 314 and a light chain variable region comprising the amino acid sequences of SEQ ID NOs: 321, 324, and/or 325; a heavy chain variable region comprising the amino acid sequences of SEQ ID NOs: 315, 316, and/or 317 and a light chain variable region comprising the amino acid sequences of SEQ ID NOs: 326, 327, and/or 328; a heavy chain variable region comprising the amino acid sequences of SEQ ID NOs: 318, 319, and/or 320 and a light chain variable region comprising the amino acid sequences of SEQ ID NOs: 329, 330, and/or 331; a heavy chain variable region comprising the amino acid sequences of SEQ ID NOs: 310, 312, and/or 315 and a light chain variable region comprising the amino acid sequences of SEQ ID NOs: 321, 324, and/or 332; or a heavy chain variable region comprising the amino acid sequences of SEQ ID NOs: 378, 379, and/or 380 and a light chain variable region comprising the amino acid sequences of SEQ ID NOs: 381, 382, and/or 383. In each of the aforementioned embodiments, the CDRs may instead comprise amino acid sequences having at least 80%, at least 85%, at least 90%, at least 98%, or at least 99% sequence identity with the recited sequences.

In certain embodiments, the fusion protein comprises: three heavy chain CDRs, the CDRs comprising, respectively, amino acid sequences of SEQ ID NOs: 378, 379, and 380, or sequences having at least 80%, at least 85%, at least 90%, at least 95%, at least 98%, at least 99%, or 100% sequence identity therewith; and three light chain CDRs, the CDRs comprising, respectively, amino acid sequences of SEQ ID NOs: 381, 382, and 383, or sequences having at least 80%, at least 85%, at least 90%, at least 95%, at least 98%, at least 99%, or 100% sequence identity therewith.

In certain embodiments, the fusion protein comprises: three heavy chain CDRs, the CDRs comprising, respectively, amino acid sequences of SEQ ID NOs: 378, 379, and 380; and three light chain CDRs, the CDRs comprising, respectively, amino acid sequences of SEQ ID NOs: 381, 382, and 383.

In certain embodiments, the fusion protein comprises a heavy chain comprising an amino acid sequence of SEQ ID NO: 386, or a sequence having at least 80%, at least 85%, at least 90%, at least 95%, at least 98%, at least 99%, or 100% sequence identity therewith, and a light chain comprising an amino acid sequence of SEQ ID NO: 387, or a sequence having at least 80%, at least 85%, at least 90%, at least 95%, at least 98%, at least 99%, or 100% sequence identity therewith. In certain embodiments, the fusion protein comprises a heavy chain comprising and amino acid sequence of SEQ ID NO: 386 and a light chain comprising an amino acid sequence of SEQ ID NO: 387.

In some embodiments of the present invention, the fusion protein comprises an anti-PD-1 moiety that is selected or derived from a full-length, fragment, or variant of an antibody from Table 1.

In some embodiments, the fusion protein comprises an anti-PD-1 moiety that is selected or derived from a full-length, fragment, or variant of pembrolizumab (Keytruda®), nivolumab (Opdivo®), zimberelimab (WBP3055), or cetrelimab (JNJ-63723283).

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO:

12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 280.

In some embodiments, the fusion protein comprises a sequence as shown in SEQ ID NO: 12 and a sequence as shown in SEQ ID NO: 280.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 281.

In some embodiments, the fusion protein comprises a sequence as shown in SEQ ID NO: 12 and a sequence as shown in SEQ ID NO: 281.

In some embodiments, the fusion protein comprises a variable region of heavy chain ($V_H$) comprising a polypeptide sequence as shown in SEQ ID NO: 7 and a variable region of light chain ($V_L$) comprising a polypeptide sequence as shown in SEQ ID NO: 13. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 282.

In some embodiments, the fusion protein comprises a sequence as shown in SEQ ID NO: 13 and a sequence as shown in SEQ ID NO: 282.

In some embodiments, the fusion protein comprises a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13 and a sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 283.

In some embodiments, the fusion protein comprises a sequence as shown in SEQ ID NO: 13 and a sequence as shown in SEQ ID NO: 283.

In some embodiments, the fusion protein comprises a variable region of heavy chain ($V_H$) comprising a polypeptide sequence as shown in SEQ ID NO: 1. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 1.

In some embodiments, the fusion protein comprises a variable region of heavy chain ($V_H$) comprising a polypeptide sequence as shown in SEQ ID NO: 2. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 2.

In some embodiments, the fusion protein comprises a variable region of heavy chain ($V_H$) comprising a polypeptide sequence as shown in SEQ ID NO: 3. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 3.

In some embodiments, the fusion protein comprises a variable region of heavy chain ($V_H$) comprising a polypeptide sequence as shown in SEQ ID NO: 4. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 4.

In some embodiments, the fusion protein comprises a variable region of heavy chain ($V_H$) comprising a polypeptide sequence as shown in SEQ ID NO: 5. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain ($V_H$) comprising a polypeptide sequence as shown in SEQ ID NO: 6. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 6.

In some embodiments, the fusion protein comprises a variable region of heavy chain ($V_H$) comprising a polypeptide sequence as shown in SEQ ID NO: 7. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 7.

In some embodiments, the fusion protein comprises a variable region of heavy chain ($V_H$) comprising a polypeptide sequence as shown in SEQ ID NO: 149. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain (V$_H$) comprising a polypeptide sequence as shown in SEQ ID NO: 150. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 150.

In some embodiments, the fusion protein comprises a variable region of heavy chain (V$_H$) comprising a polypeptide sequence as shown in SEQ ID NO: 151. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 151.

In some embodiments, the fusion protein comprises a variable region of heavy chain (V$_H$) comprising a polypeptide sequence as shown in SEQ ID NO: 152. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 152.

In some embodiments, the fusion protein comprises a variable region of heavy chain (V$_H$) comprising a polypeptide sequence as shown in SEQ ID NO: 153. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 153.

In some embodiments, the fusion protein comprises a variable region of heavy chain (V$_H$) comprising a polypeptide sequence as shown in SEQ ID NO: 154. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 154.

In some embodiments, the fusion protein comprises a variable region of heavy chain (V$_H$) comprising a polypeptide sequence as shown in SEQ ID NO: 155. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 155.

In some embodiments, the fusion protein comprises a variable region of heavy chain (V$_H$) comprising a polypeptide sequence as shown in SEQ ID NO: 156. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 156.

In some embodiments, the fusion protein comprises a variable region of heavy chain (V$_H$) comprising a polypeptide sequence as shown in SEQ ID NO: 157. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain (V$_H$) comprising a polypeptide sequence as shown in SEQ ID NO: 159. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 159.

In some embodiments, the fusion protein comprises a variable region of heavy chain (V$_H$) comprising a polypeptide sequence as shown in SEQ ID NO: 160. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 160.

In some embodiments, the fusion protein comprises a variable region of heavy chain (V$_H$) comprising a polypeptide sequence as shown in SEQ ID NO: 161. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 161.

In some embodiments, the fusion protein comprises a variable region of heavy chain (V$_H$) comprising a polypeptide sequence as shown in SEQ ID NO: 162. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 162.

In some embodiments, the fusion protein comprises a variable region of heavy chain (V$_H$) comprising a polypeptide sequence as shown in SEQ ID NO: 163. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 163.

In some embodiments, the fusion protein comprises a variable region of heavy chain (V$_H$) comprising a polypeptide sequence as shown in SEQ ID NO: 164. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 164.

In some embodiments, the fusion protein comprises a variable region of light chain ($V_L$) comprising a polypeptide sequence as shown in SEQ ID NO: 8. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of light chain ($V_L$) comprising a polypeptide sequence as shown in SEQ ID NO: 9. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 9.

In some embodiments, the fusion protein comprises a variable region of light chain ($V_L$) comprising a polypeptide sequence as shown in SEQ ID NO: 10. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 10.

In some embodiments, the fusion protein comprises a variable region of light chain ($V_L$) comprising a polypeptide sequence as shown in SEQ ID NO: 11. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 11.

In some embodiments, the fusion protein comprises a variable region of light chain ($V_L$) comprising a polypeptide sequence as shown in SEQ ID NO: 12. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 12.

In some embodiments, the fusion protein comprises a variable region of light chain ($V_L$) comprising a polypeptide sequence as shown in SEQ ID NO: 13. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 13.

In some embodiments, the fusion protein comprises a variable region of light chain ($V_L$) comprising a polypeptide sequence as shown in SEQ ID NO: 148. In some embodiments, the fusion protein comprises a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 148.

In some embodiments, the fusion protein comprises a polypeptide sequence as shown in SEQ ID NO: 15. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 15.

In some embodiments, the fusion protein comprises a polypeptide sequence as shown in SEQ ID NO: 280. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 280.

In some embodiments, the fusion protein comprises a polypeptide sequence as shown in SEQ ID NO: 281. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 281.

In some embodiments, the fusion protein comprises a polypeptide sequence as shown in SEQ ID NO: 282. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 282.

In some embodiments, the fusion protein comprises a polypeptide sequence as shown in SEQ ID NO: 283. In some embodiments, the fusion protein comprises a polypeptide sequence that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 283.

In some embodiments, the fusion protein comprises a variable region of heavy chain ($V_H$) comprising a polypeptide sequence as shown in SEQ ID NO: 5 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain ($V_H$) comprising a polypeptide sequence as shown in SEQ ID NO: 149 and a variable region of light chain ($V_L$) comprising a polypeptide sequence as shown in SEQ ID NO: 8. In some embodiments, the fusion protein comprises a variable region of heavy chain ($V_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149 and a variable region of light chain ($V_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 157 and a variable region of light chain (V$_L$) comprising a polypeptide sequence as shown in SEQ ID NO: 8. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 158 and a variable region of light chain (V$_L$) comprising a polypeptide sequence as shown in SEQ ID NO: 8. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158 and a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

In some embodiments, the fusion protein comprises a variable region of heavy chain (V$_H$) comprising a polypeptide sequence as shown in SEQ ID NO: 5. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 5.

In some embodiments, the fusion protein comprises a variable region of heavy chain (V$_H$) comprising a polypeptide sequence as shown in SEQ ID NO: 149. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 149.

In some embodiments, the fusion protein comprises a variable region of heavy chain (V$_H$) comprising a polypeptide sequence as shown in SEQ ID NO: 157. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 157.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of heavy chain (V$_H$) comprising a polypeptide sequence as shown in SEQ ID NO: 158. In some embodiments, the fusion protein comprises a variable region of heavy chain (V$_H$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 158.

In some embodiments, the fusion protein comprises a variable region of light chain (V$_L$) comprising a polypeptide sequence as shown in SEQ ID NO: 8. In some embodiments, the fusion protein comprises a variable region of light chain (V$_L$) that is at least 50%, at least 55%, at least 60%, at least 65%, at least 70%, at least 75%, at least 80%, at least 85%, at least 90%, at least 95%, at least 99%, at least 99.5%, or 100% identical to a sequence as shown in SEQ ID NO: 8.

Linkers

In some embodiments, the linker comprises one or more polypeptide sequences having at least 80% sequence identity to any one of SEQ ID NOs: 17-34. In some embodiments, the linker can be a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). A non-limiting example of a flexible linker can have the sequence of (Gly-Gly-Gly-Gly-Ser)n, wherein n can be 1, 2, 3, 4, 5, 6, 7, 8, 9, or 10 (SEQ ID NO: 32). By adjusting the copy number "n," the length of this exemplary GS linker can be optimized to achieve appropriate separation of functional domains, or to maintain necessary inter-domain interactions. Besides GS linkers, other flexible linkers can be utilized for recombinant fusion proteins. In some embodiment, a flexible linker can have the sequence of (Gly)n, wherein n can be 6, 7, or 8 (SEQ ID NO: 33). In some cases, flexible linkers can also be rich in small or polar amino acids such as Gly and Ser, but can contain additional amino acids such as Thr and Ala to maintain flexibility. In some cases, the linker described herein can be a rigid linker. A rigid linker can be utilized to maintain a fixed distance between domains of the fusion protein or a fragment or a variant thereof described herein. Non-limiting examples of rigid linkers can be: alpha helix-forming linkers, pro-rich sequence, (XP)n, X-Pro backbone, (EAAAK)n (n=1-6) (SEQ ID NO: 34). Rigid linkers can exhibit relatively stiff structures by adopting α-helical structures or by containing multiple Pro residues in some cases. In some embodiments, the immune checkpoint inhibitor, such as a PD-1 inhibitor, and the cytokine trap (e.g., TGF-β trap) that can neutralize the cytokine (e.g., TGF-β) in a fusion protein or a fragment or a variant thereof described herein can be separated by an intervening sequence encoding an intervening linker polypeptide. In some embodiments, the immune checkpoint inhibitor, such as a PD-1 inhibitor, and the ADA2 (or mutants thereof) in a fusion protein or a fragment or a variant thereof described herein can be separated by an intervening sequence encoding an intervening linker polypeptide. In certain embodiments, the linker polypeptide comprises disclosed in the table below:

TABLE 2

Linker amino acid sequences and polynucleotide sequences

| SEQ ID NO | Linkers |
|---|---|
| 17 | DPGGGGSGGGGSNPGS |
| 18 | GGGGSGGGGSGSDPGS |
| 19 | DPGSGGGGSGGGGSGS |
| 20 | GGGGSGGGGSGGGGSDPGS |
| 21 | DPGSGGGGSGGGGSGGGGS |
| 22 | DPGSGSVPLGSGSNPGS |
| 23 | DPGSGGSVPLGSGGSNPGS |
| 24 | DPGVLEREDKPTTSKPNPGS |
| 25 | DPGVLEREDVPTTSYPNPGS |
| 26 | DPGVLEREDKVTTSKYNPGS |
| 27 | DPVLEREDKVTTSKNPGS |
| 28 | DIEGRMD |
| 29 | GEGKSSGSGSESKAS |
| 30 | GSTSGSGKPGSGEGSTKG |
| 31 | A(EAAAK)₄ALEA(EAAAK)₄A |
| 32 | (G4S)n, n = 1-10 |
| 33 | (Gly)n, n = 6-8 |
| 34 | (EAAAK)n, n = 1-6 |

In some embodiments, the linker can be a flexible linker, a rigid linker, an in dv cleavable linker, or any combination thereof. In some cases, the linker can connect functional domains together (as in flexible and rigid linkers) or releasing free functional domain in vivo as in in vivo cleavable linkers. In some embodiments, linkers can improve biological activity, increase expression yield, and achieving desirable pharmacokinetic profiles. In some embodiments, the linker can also comprise hydrazone, peptide, disulfide, or thioester.

In some cases, the linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (G4S)n, wherein n is 1, 2, 3, 4, 5, 6, 7, 8, 9 or 10 (SEQ ID NO: 32). In some embodiment, a flexible linker can have the sequence of (Gly)n, wherein n can be 6, 7, or 8 (SEQ ID NO: 33). In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility. By adjusting the copy number "n," the length of these non-limiting exemplary linkers can be optimized to achieve appropriate separation of functional domains, or to maintain necessary inter-domain interactions. Besides GS linkers, other flexible linkers can be utilized for the fusion protein or a fragment or a variant thereof described herein. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein or a fragment or a variant thereof domains. In addition, although flexible linkers do not have rigid structures, they can serve as a passive linker to keep a distance between functional domains. The length of flexible linkers can be adjusted to allow for proper folding or to achieve optimal biological activity of the fusion protein or a fragment or a variant thereof.

The linker described herein can further include a rigid linker in some cases. A rigid linker can be utilized to maintain a fixed distance between domains of the fusion protein or a fragment or a variant thereof described herein. Examples of rigid linkers can be: alpha helix-forming linkers, pro-rich sequence, (XP)n, X-Pro backbone, (EAAAK)n (n=1-6) (SEQ ID NO: 34), to name a few. Rigid linkers can exhibit relatively stiff structures by adopting «-helical structures or by containing multiple Pro residues in some cases.

In some embodiments, the linker described herein can be a cleavable linker. In other cases a linker is not cleavable. Linkers that are not cleavable can covalently join functional domains of the fusion protein or a fragment or a variant thereof together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in di cleavage of a linker in a recombinant fusion protein can also be carried out by proteases that can be expressed in di under pathological conditions (e.g. cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioester. For example, a hydrazone can confer serum stability. In other cases, a hydrazone can allow for cleavage in an acidic compartment. An acidic compartment can have a pH up to 7. A linker can also include a thioether. A thioether can be nonreducible. A thioether can be designed for intracellular proteolytic degradation.

In some cases, a linker can be engineered linker. For example, a linker can be designed to comprise chemical characteristics such as hydrophobicity. In some cases, at least two different linker polypeptide sequences can encode the same polypeptide linker sequence. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker. In some cases, a polypeptide linker can also include one or more GS linker sequences, for instance, (G4S)n (SEQ ID NO: 556), (GS)n (SEQ ID NO: 557), (SG)n (SEQ ID NO: 558), (GSG)n (SEQ ID NO: 559), and (SGSG)n (SEQ ID NO: 560), wherein n can be any number from zero to fifteen.

Methods of Treating Cancer

Also provided herein is a method of treating cancer with the fusion protein of the present invention. The development of monoclonal antibodies targeting blockade of an immune checkpoint pathway, such as PD-1 and PD-L1/2 signaling pathway and CTLA-4 and CD80/86 signaling pathway, have revolutionized cancer treatment demonstrating durable clinical activity in several cancer indications including, but not limited to, melanoma (e.g., advanced or metastatic melanoma), lung cancer (e.g., non-small cell lung cancer and small cell lung cancer), breast cancer (e.g., HER-2 negative breast cancer, estrogen-receptor+/HER-2-breast cancer, and triple negative breast cancer), pancreatic cancer (e.g., pancreatic adenocarcinoma), renal cell carcinoma, bladder cancer, head and neck squamous cell carcinoma, MSI-high colorectal carcinoma, Merkel cell carcinoma, and Hodgkin lymphoma, as well as gastric, head and neck, prostate, gynecologic, and hematologic cancers. Despite the durable responses, the response rate remains very low, and several patients have developed resistance leading to disease progression. Furthermore, in several indications, such as ovarian, gastroesophageal, prostate, pancreas and many other cancers, checkpoint inhibitors have failed to show any substantive clinical responses.

The failure of checkpoint blockade can be attributed to the complexity of the immunosuppressive factors present in the tumor microenvironment. These factors can include, but not limited to, suppressive cells, such as myeloid derived suppressive cells, tumor-associated macrophages (TAM); suppressive cytokine and growth factors, such as TGF-β and interleukin 10 (IL-10); and metabolic derivative, such as adenosine and indoleamine 2,3-dioxygenase (IDO) byproducts. Anti-PD-1-TGFβRII fusion protein provided herein is an example of a therapy that can target two negative suppressive pathways in the tumor microenvironment. These pathways can include cell intrinsic interactions mediated by tumor cells to immune, in which PD-1/PD-L1 interaction can play a major role, and cell extrinsic interactions mediated by immunosuppressive cytokines, of which TGF-β can be a prominent member.

In some embodiments, the cancer is, but not limited to, glioblastoma, colorectal, gastric, cervical, ovarian, pancreatic, prostate, breast, and renal cancers. In addition, the fusion proteins as described herein can be amenable to indications, such as in non-small cell cancer (NSCL) and melanoma, in which response rate of checkpoint blockades is lower and TGF-β is highly expressed.

Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, triple negative breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, hepatocellular carcinoma (HCC), choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present disclosure is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma.

In certain embodiments, anti-PD-1-TGFβRII fusion protein provided herein is an example of a therapy that can be used to treat cancers that have about 0, 5, 10, 15, 20, 25, 30, 35, 40, 45, 50, 55, 60, 65, 70, 75, 80, 85, 90 or 95% average response rate to standard therapy (including but not limited to chemotherapy, chemotherapy and current clinical trial therapies). In certain embodiments, anti-PD-1-ADA2 fusion protein provided herein is an example of a therapy that can be used to treat cancers that have about 0, 5, 10, 15, 20, 25, 30, 35, 40, 45, 50, 55, 60, 65, 70, 75, 80, 85, 90 or 95% average response rate to standard therapy (including but not limited to chemotherapy, chemotherapy and current clinical trial therapies). Such cancers include but are not limited to, Hodgkin's lymphoma, melanoma, non-small cell lung cancer (NSCLC), microsatellite instability (MSI)-high or mismatch repair (MMR)-deficient solid tumors, CSCC, RCC, CRC, melanoma, Merkel cell cancer, bladder cancer, RCC, hepatocellular carcinoma (HCC), head & neck cancer (H&N), cervical cancer, gastric cancer, small cell lung cancer (SCLC), endometrial cancer, mesothelioma, ovarian cancer, triple negative breast cancer (TNBC), breast cancer, colorectal cancer (CRC), pancreatic cancer, prostate cancer.

Combination Therapy

In some embodiments, the fusion protein is administered as a combination therapy with an additional therapeutic agent. In some embodiments, an additional therapeutic agent comprises a biological molecule, such as an antibody. For example, treatment can involve the combined administration of the fusion protein with antibodies against tumor-associated antigens including, but not limited to, antibodies that bind EGFR, HER2/ErbB2, and/or VEGF. In certain embodiments, the additional therapeutic agent is an antibody specific for a cancer stem cell marker. In certain embodiments, the additional therapeutic agent is an antibody that is an angiogenesis inhibitor (e.g., an anti-VEGF or VEGF receptor antibody). In certain embodiments, the additional therapeutic agent is bevacizumab (AVASTIN), ramucirumab, trastuzumab (HERCEPTIN), pertuzumab (OMNITARG), panitumumab (VECTIBIX), nimotuzumab, zalutumumab, or cetuximab (ERBITUX). In some embodiments, an additional therapeutic agent comprises an agent such as a small molecule. For example, treatment can involve the combined administration of the fusion protein or a fragment or a variant thereof provided herein with a small molecule that acts as an inhibitor against tumor-associated antigens including, but not limited to, EGFR, HER2 (ErbB2), and/or VEGF. In some embodiments, the fusion protein or a fragment or a variant thereof is administered in combination with a protein kinase inhibitor selected from the group consisting of: gefitinib (IRESSA), erlotinib (TARCEVA), sunitinib (SUTENT), lapatanib, vandetanib (ZACTIMA), AEE788, CI-1033, cediranib (RECENTIN), sorafenib (NEXAVAR), and pazopanib (GW786034B). In some embodiments, an additional therapeutic agent comprises an mTOR inhibitor. In another embodiment, the additional therapeutic agent is chemotherapy or other inhibitors that reduce the number of Tc, cells. In certain embodiments, the therapeutic agent is cyclophosphamide or an anti-CTLA4 antibody. In another embodiment, the additional therapeutic reduces the presence of myeloid-derived suppressor cells. In a further embodiment, the additional therapeutic is carbotaxol. In a further embodiment, the additional therapeutic agent is ibrutinib.

In some embodiments, the method can further comprise one or more checkpoint inhibitors in combination with the fusion protein or a fragment or a variant thereof as described herein. In some embodiments, the additional checkpoint inhibitor can be an anti-CTLA-4 antibody. The anti-CTLA-4 antibody (e.g., ipilimumab) has shown durable anti-tumor activities and prolonged survival in participants with advanced melanoma, resulting in its Food and Drug Administration (FDA) approval in 2011. See Hodi et al., Improved survival with ipilimumab in patients with metastatic melanoma. N Engl J Med. (2010) Aug. 19; 363(8):711-23. In some embodiments, the one or more checkpoint inhibitors can be an anti-PD-L1 antibody. In some embodiments, the anti-PD-L1 antibody can be a full length atezolizumab (anti-PD-L1), avelumab (anti-PD-L1), durvalumab (anti-PD-L1), or a fragment or a variant thereof. In some embodiments, the one or more checkpoint inhibitors can be any one or more of CD27 inhibitor, CD28 inhibitor, CD40 inhibitor, CD122 inhibitor, CD137 inhibitor, OX40 (also known as CD134) inhibitor, GITR inhibitor, ICOS inhibitor, or any combination thereof. In some embodiments, the one or more checkpoint inhibitors can be any one or more of A2AR inhibitor, B7-H3 (also known as CD276) inhibitor, B7-H4 (also known as VTCN1) inhibitor, BTLA inhibitor, IDO inhibitor, KIR inhibitor, LAG3 inhibitor, TIM-3 inhibitor, VISTA inhibitor, or any combination thereof.

In certain embodiments, an additional therapeutic agent comprises a second immunotherapeutic agent. In some embodiments, the additional immunotherapeutic agent includes, but is not limited to, a colony stimulating factor, an interleukin, an antibody that blocks immunosuppressive functions (e.g., an anti-CTLA-4 antibody, anti-CD28 antibody, anti-CD3 antibody, anti-PD-L1 antibody, anti-TIGIT antibody), an antibody that enhances immune cell functions (e.g., an anti-GITR antibody, an anti-OX-40 antibody, an anti-CD40 antibody, or an anti-4-1BB antibody), a toll-like receptor (e.g., TLR4, TLR7, TLR9), a soluble ligand (e.g., GITRL, GITRL-Fc, OX-40L, OX-40L-Fc, CD40L, CD40L-Fc, 4-1BB ligand, or 4-1BB ligand-Fc), or a member of the B7 family (e.g., CD80, CD86). In some embodiments, the additional immunotherapeutic agent targets CTLA-4, CD28, CD3, PD-L1, TIGIT, GITR, OX-40, CD-40, or 4-1BB.

In some embodiments, the additional therapeutic agent is an additional immune checkpoint inhibitor. In some embodiments, the additional immune checkpoint inhibitor is an anti-PD-L1 antibody, an anti-CTLA-4 antibody, an anti-CD28 antibody, an anti-TIGIT antibody, an anti-LAG3 antibody, an anti-TIM3 antibody, an anti-GITR antibody, an anti-4-1BB antibody, or an anti-OX-40 antibody. In some embodiments, the additional therapeutic agent is an anti-TIGIT antibody. In some embodiments, the additional therapeutic agent is an anti-PD-L1 antibody selected from the group consisting of: BMS935559 (MDX-1105), atezolizumab (MPDL3280A), durvalumab (MEDI4736), and avelumab (MSB0010718C). In some embodiments, the additional therapeutic agent is an anti-CTLA-4 antibody selected from the group consisting of: ipilimumab (YERVOY) and tremelimumab. In some embodiments, the additional therapeutic agent is an anti-LAG-3 antibody selected from the group consisting of: BMS-986016 and LAG525. In some embodiments, the additional therapeutic agent is an anti-OX-40 antibody selected from the group consisting of: MEDI6469, MEDI0562, and MOXR0916. In some embodiments, the additional therapeutic agent is an anti-4-1BB antibody selected from the group consisting of: PF-05082566. In some embodiments, the fusion protein or a fragment or a variant thereof can be administered in combination with a biologic molecule selected from the group consisting of: cytokines, adrenomedullin (AM), angiopoietin (Ang), BMPs, BDNF, EGF, erythropoietin (EPO), FGF, GDNF, granulocyte colony stimulating factor (G-CSF), granulocyte-macrophage colony stimulating factor (GM-CSF), macrophage colony stimulating factor (M-CSF), stem cell factor (SCF), GDF9, HGF, HDGF, IGF, migration-stimulating factor, myostatin (GDF-8), NGF, neurotrophins, PDGF, thrombopoietin, TGF-α, TGF-β, TNF-α, VEGF, PlGF, gamma-IFN, IL-1, IL-2, IL-3, IL-4, IL-5, IL-6, IL-7, IL-12, IL-15, and IL-18.

Cytokines

In some cases, the cytokine comprises at least one chemokine, interferon, interleukin, lymphokine, tumor necrosis factor, or variant or combination thereof. In some cases, the cytokine is an interleukin. In some cases the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and functional variants and fragments thereof. In some embodiments, the cytokines can be membrane bound or secreted. In embodiments, the cytokine is soluble IL-15, soluble IL-15/

IL-15R-α complex (e.g., ALT-803). In certain cases, the interleukin can comprise membrane bound IL-15 (mbIL-15) or a fusion of IL-15 and IL-15Rα. In some embodiments, a mbIL-15 is a membrane-bound chimeric IL-15 which can be co-expressed with a modified immune effector cell described herein. In some embodiments, the mbIL-15 comprises a full-length IL-15 (e.g., a native IL-15 polypeptide) or fragment or variant thereof, fused in frame with a full length IL-15Rα, fragment or variant thereof. In some cases, the IL-15 is indirectly linked to the IL-15Rα through a linker. In some instances, the mbIL-15 is as described in Hurton et al., "Tethered IL-15 augments antitumor activity and promotes a stem-cell memory subset in tumor-specific T cells," PNAS 2016. In some cases, the cytokine is expressed in the same immune effector cell as the CAR.

In some embodiments, the mbIL-15 is expressed with a cell tag such as HER1t, HER-1t-1, CD20t-1 or CD20 as described herein. The mbIL-15 can be expressed in-frame with HER1t, HER-It-1, CD20t-1 or CD20.

In some embodiments, the mbIL-15 can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In another aspect, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties. In some embodiments, the cytokines described above can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

In some embodiments, the fusion protein as described herein can be under the control of an inducible promoter for gene transcription. In one aspect, the inducible promoter can be a gene switch ligand inducible promoter. In some cases, an inducible promoter can be a small molecule ligand-inducible two polypeptide ecdysone receptor-based gene switch, such as RHEOSWITCH® gene switch.

Gene Switches

Provided herein are gene switch polypeptides, polynucleotides encoding ligand-inducible gene switch polypeptides, and methods and systems incorporating these polypeptides and/or polynucleotides. The term "gene switch" refers to the combination of a response element associated with a promoter, and for instance, an ecdysone receptor (EcR) based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., 1992; No et al., 1996). Later, Suhr et al., 1998 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283, 173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the antibody with the TGF-β cytokine trap, thereby resulting in dimerization of the DNA binding domain and the transactivation domain. Since the DNA binding and transactivation domains reside on two different molecules, the background activity in the absence of ligand is greatly reduced.

Certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter ("IP") can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/US2002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); WO 2018/132494 (PCT/US2018/013196); and U.S. Pat. No. 9,402,919; each of which is incorporated by reference in its entirety.

As used herein, the term "ligand," as applied to ligand-activated ecdysone receptor-based gene switches are small molecules of varying solubility (such as diacylhydrazine compounds) having the capability of activating a gene switch to stimulate gene expression (i.e., therein providing ligand inducible expression of polynucleotides (e.g., mRNAs, miRNAs, etc) and/or polypeptides). Examples of such ligands include, but are not limited to those described in: WO 2004/072254 (PCT/US2004/003775); WO 2004/005478 (PCT/US2003/021149); WO 2005/017126 (PCT/US2004/005149); WO 2004/078924 (PCT/US2004/005912); WO 2008/153801 (PCT/US2008/006757); WO 2009/114201 (PCT/US2009/001639); WO 2013/036758 (PCT/US2012/054141); WO 2014/144380 (PCT/US2014/028768); and, WO 2016/044390 (PCT/US2015/050375); each of which are hereby incorporated by reference herein in the entirety.

Examples of ligands also include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,258,603; 6,013,836; 5,117,057; 5,530,028; 5,378,726; 7,304,161; 7,851,220; 8,748,125; 9,272,986; 7,456,315; 7,563,928; 8,524,948; 9,102,648; 9,169,210; 9,255,273; and, 9,359,289; oxadiazolines as described in U.S. Pat. Nos. 8,669,072; and, 8,895,306; dibenzoylalkyl cyanohydrazines such as those disclosed in European Application No. 2,461,809; N-alkyl-N,N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Pat. Nos. 7,375,093; 8,129,355; and, 9,802,936; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxy-cholesterol-3-sulfate (ECHS), 7-ketocholesterol-3-sulfate, famesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxybenzoyl)-hydrazide), RG-115932 ((R)-3,5-Dimethyl-benzoic acid N-(1-tert-butyl-butyl)N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., WO 2008/153801 (PCT/US2008/006757); and, WO 2013/036758 (PCT/US2012/054141), both of which are incorporated herein by reference in their entireties.

For example, a ligand for the ecdysone receptor-based gene switch may be selected from any suitable ligands. Both naturally occurring ecdysone or ecdysone analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for several reasons including, for example: lower manufacturing cost, metabolic stability, absence from insects, plants, or mammals, and environmental acceptability. U.S. Pat. No. 6,379,945 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057. Use of tebufenozide as a chemical ligand for the ecdysone receptor from Drosophila melanogaster is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkylN'-aroyl hydrazine. (See U.S. Pat. No. 6,723,531).

In some embodiments, the ligand for an ecdysone-based gene switch system is a diacylhydrazine ligand or chiral diacylhydrazine ligand. The ligand used in the gene switch system may be compounds of Formula I

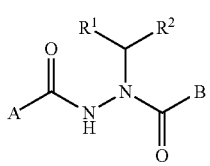

Formula I wherein A is alkoxy, arylalkyloxy or aryloxy; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; or pharmaceutically acceptable salts, hydrates, crystalline forms or amorphous forms thereof.

In another embodiment, the ligand may be enantiomerically enriched compounds of Formula II

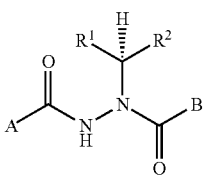

Formula II wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; with the proviso that R1 does not equal R2; wherein the absolute configuration at the asymmetric carbon atom bearing R1 and R2 is predominantly S; or pharmaceutically acceptable salts, hydrates, crystalline forms or amorphous forms thereof.

In certain embodiments, the ligand may be enantiomerically enriched compounds of Formula III

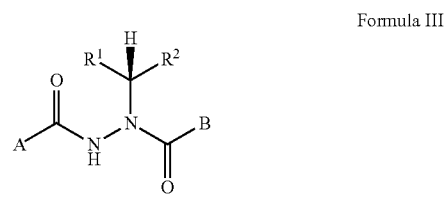

Formula III wherein A is alkoxy, arylalkyloxy, aryloxy, arylalkyl, optionally substituted aryl or optionally substituted heteroaryl; B is optionally substituted aryl or optionally substituted heteroaryl; and R1 and R2 are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl; with the proviso that R1 does not equal R2; wherein the absolute configuration at the asymmetric carbon atom bearing R1 and R2 is predominantly R; or pharmaceutically acceptable salts, hydrates, crystalline forms or amorphous forms thereof.

In some embodiments, a ligand may be (R)-3,5-dimethylbenzoic acid N-(1-tertbutyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention. See U.S. Pat. Nos. 8,076,517; 8,884,060; and, 9,598,355; each of which are fully incorporated by reference herein.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system also includes those utilizing the FK506 binding domain are FK506, Cyclosporin A, or Rapamycin. FK506, rapamycin, and their analogs are disclosed in U.S. Pat. Nos. 6,649,595; 6,187,757; 7,276,498; and, 7,273,874.

In some embodiments, a diacylhydrazine ligand for inducible gene expression is administered at unit daily dose of about 5, 10, 15, 20, 25, 30, 35, 40, 50, 60, 70, 80, 90, 100 or 120 mg. In some embodiments, the diacylhydrazine ligand is administered at a unit daily dose of about 5 mg. In some embodiments, the diacylhydrazine ligand is administered at a unit daily dose of about 10 mg. In some embodiments, the diacylhydrazine ligand is administered at a unit daily dose of about 15 mg. In some embodiments, the diacylhydrazine ligand is administered daily at a unit daily dose of about 20 mg.

In some embodiments, the combination therapy with two or more therapeutic agents can use agents that work by different mechanisms of action, although this is not required. Combination therapy using agents with different mechanisms of action can result in additive or synergetic effects. Combination therapy can allow for a lower dose of each agent than is used in monotherapy, thereby reducing toxic side effects and/or increasing the therapeutic index of the agent(s). Combination therapy can decrease the likelihood that resistant cancer cells will develop. In some embodiments, combination therapy comprises a therapeutic agent that affects the immune response (e.g., enhances or activates the response) and a therapeutic agent that affects (e.g., inhibits or kills) the tumor/cancer cells.

In certain embodiments, in addition to administering the fusion protein or a fragment or a variant thereof described herein, the method or treatment further comprises administering at least one additional therapeutic agent. An additional therapeutic agent can be administered prior to, concurrently with, and/or subsequently to, administration of the agent. In some embodiments, the at least one additional therapeutic agent comprises 1, 2, 3, or more additional therapeutic agents.

Therapeutic agents that can be administered in combination with the fusion protein or a fragment or a variant thereof described herein include chemotherapeutic agents. Thus, in some embodiments, the method or treatment involves the administration of an agent described herein in combination with a chemotherapeutic agent or in combination with a cocktail of chemotherapeutic agents. In some embodiments, the methods can further comprise one or more antineoplastic agents, such as cisplatin, capecitabine, or 5-fluorouracil, in combination with the fusion protein or a fragment or a variant thereof as described herein. Treatment with an agent can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA Useful classes of chemotherapeutic agents include, for example, anti-tubulin agents, auristatins, DNA minor groove binders, DNA replication inhibitors, alkylating agents (e.g., platinum complexes such as cisplatin, mono(platinum), bis (platinum) and tri-nuclear platinum complexes and carboplatin), anthracyclines, antibiotics, anti-folates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor.

The fusion protein or a fragment or a variant thereof provided herein can be used alone or in combination with conventional therapeutic regimens such as surgery, irradiation, chemotherapy and/or bone marrow transplantation (autologous, syngeneic, allogeneic or unrelated). A set of tumor antigens can be useful, e.g., in a large fraction of cancer patients.

Fusion Proteins in Combination with Chimeric Receptors

In some embodiments, the fusion protein is administered as a combination therapy with an additional therapeutic agent. In some embodiments, an additional therapeutic agent comprises a chimeric receptor, such as chimeric antigen receptor or an engineered T-cell receptor. For example, treatment can involve the simultaneous administration of the fusion protein with a chimeric receptor. In some embodiments, the treatment can involve the co-administration of a fusion protein and a modified effector cell comprising a chimeric receptor. In some embodiments, the treatment can involve the sequential administration of a modified effector cell which comprises a chimeric receptor followed by the administration of the fusion protein. In another embodiment, the treatment can involve the sequential administration of a fusion protein followed by the administration of a modified effector cell which comprises a chimeric receptor. In one aspect, there can be a lag of at least 0.5, 1, 2, 3, 4, 5, 6, 8, 10, 12, 15, 18, 20, or 24 hours between administrations. In another aspect, there can be at least 1, 2, 3, 4, 5, 6, 7, 8, 9, 10, 11, 12, 13, 14, 15, 16, 17, 18, 19, 20, 21, 22, 23, 24, 25, 26 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 75, 90 or more days in between administrations.

In some embodiments, modified immune effector cells are modified immune cells that comprise T cells and/or natural killer cells. T cells or T lymphocytes are a subtype of white blood cells that are involved in cell-mediated immunity.

Exemplary T cells include T helper cells, cytotoxic T cells, TH17 cells, stem memory T cells (TSCM), naïve T cells, memory T cells, effector T cells, regulatory T cells, or natural killer T cells. In certain aspects, the embodiments described herein include making and/or expanding the modified immune effector cells (e.g., T-cells, Tregs, NK-cell or NK T-cells) that comprises transfecting the cells with an expression vector containing a DNA (or RNA) construct encoding the chimeric receptor.

In some embodiments, described herein includes a modified effector cell which comprises a chimeric receptor expressed on the surface of the cell. In some instances, the chimeric receptor comprises an antigen binding region that enables recognition and binding to a tumor antigen, e.g., a tumor-associated antigen or a tumor-specific antigen. In some instances, the antigen binding region comprises an antibody or binding fragment, for example, an Fab, an Fab', an F(ab')$_2$, an F(ab')$_3$, an scFv, an sc(Fv)$_2$, a dsFv, a diabody, a minibody, and a nanobody or binding fragments thereof. In some cases, the antigen binding region comprises a scFv. In some cases, the chimeric receptor comprises a scFv (e.g., a chimeric antigen receptor (CAR)). In some instances, the chimeric antigen receptor comprises a pattern-recognition receptor. In other cases, the chimeric receptor comprises an engineered T-cell receptor (TCR).

Further provided herein is an immune effector cell comprising a cell tag for use as a kill switch, selection marker, a biomarker, or a combination thereof. In some embodiments, the cell tag comprises HER1t, HER1t-1, CD20t-1 or CD20. In some cases, the cell tag comprises HER1t, and said HER1t comprises the polypeptide sequence of SEQ ID NO: 68. In some instances, the cell tag comprises HER1t-1, and the HER1t-1 comprises the polypeptide sequence of SEQ ID NO: 69.

Chimeric Antigen Receptors (CARs)

A chimeric antigen receptor (CAR) is an engineered receptor which grafts an exogenous specificity onto an immune effector cell. In some instances, a CAR comprises an extracellular domain (ectodomain) that comprises an antigen binding domain, a stalk region, a transmembrane domain and an intracellular (endodomain) domain. In some instances, the intracellular domain further comprises one or more intracellular signaling domains. In some instances, a CAR described herein comprises an antigen binding domain, a stalk region, a transmembrane domain, one or more costimulatory domains, and a signaling domain for T-cell activation.

An antigen binding domain can comprise complementary determining regions of a monoclonal antibody, variable regions of a monoclonal antibody, and/or antigen binding fragments thereof. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor can contain three CDRs (CDR1, CDR2, and CDR3). In some instances, an antigen binding domain comprises F(ab')$_2$, Fab', Fab, Fv, or scFv. In some cases, an antigen binding domain is a scFv. In some cases, an antigen binding domain is a Fab. In some cases, an antigen binding domain is a Fab'. In some cases, an antigen binding domain is F(ab')$_2$. In some cases, an antigen binding domain is an Fv.

In some embodiments, a CAR described herein comprises an antigen binding domain that binds to an epitope on CD19, BCMA, CD23, BAFF-R, GPRC5D, CD44, CAIX, CD5, CD30, CD70, CD44v6, CD44v7, CD44v8, CD174, CD28, CD128, CD138, CS1, CLL-1, L1-CAM, FAP, ROR1, CEA, EGP-2, EGP-40, HER2, HER3, Folate-binding Protein, GD2, GD3, IL-13R-a2, IL-11Rα, EphA2, CSPG4, KDR, EDB-F, mesothelin, CD22, EGFR, Folate receptor α, MUC-1, MUC-4, MUC-16, MAGE-A1, h5T4, PSMA, PSCA, GPC3, c-met, TAG-72, EGFR, CD20, EGFRvIII, CD123 or VEGF-R2. In some embodiments, a CAR described herein comprises an antigen binding domain that binds to an epitope on MUC16. In some embodiments, a CAR described herein comprises an antigen binding domain that binds to an epitope on CD19 or CD33. In some instances, a CAR described herein comprises an antigen binding domain that binds to an epitope on CD19. In some cases, a CAR described herein comprises an antigen binding domain that binds to an epitope on CD33. In further embodiments, a CAR described herein comprises an autoantigen or an antigen binding region that binds to an epitope on HLA-A2, myelin oligodendrocyte glycoprotein (MOG), factor VIII (FVII), MAdCAM1, SDF1, or collagen type II.

In some embodiments, the CARs and methods described herein can be used for the treatment of a hyperproliferative disease, such as a cancer, an autoimmune disease or for the treatment of an infection, such as a viral, bacterial or parasitic infection. In some aspects, the CAR targets an antigen that is elevated in cancer cells, in autoimmune cells or in cells that are infected by a virus, bacteria or parasite. Pathogens that may be targeted include, without limitation, *Plasmodium*, trypanosome, *Aspergillus, Candida*, Hepatitis A, Hepatitis B, Hepatitis C, HSV, HPV, RSV, EBV, CMV, JC virus, BK virus, or Ebola pathogens. Autoimmune diseases can include graft-versus-host disease, rheumatoid arthritis, lupus, celiac disease, Crohn's disease, Sjogren Syndrome, polymyalgia rheumatic, multiple sclerosis, neuromyelitis optica, ankylosing spondylitis, Type 1 diabetes, alopecia areata, vasculitis, temporal arteritis, bullous pemphigoid, psoriasis, pemphigus vulgaris, or autoimmune uveitis.

The pathogen recognized by a CAR may be essentially any kind of pathogen, but in some embodiments the pathogen is a fungus, bacteria, or virus. Exemplary viral pathogens include those of the families of Adenoviridae, Epstein-Barr virus (EBV), Cytomegalovirus (CMV), Respiratory Syncytial Virus (RSV), JC virus, BK virus, HPV, HSV, HHV family of viruses, Hepatitis family of viruses, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis*, and *Stachybotrys*. Exemplary pathogenic bacteria include *Streptococcus, Pseudomonas, Shigella, Campylobacter, Staphylococcus, Helicobacter, E. coli, Rickettsia, Bacillus, Bordetella, Chlamydia*, Spirochetes, and *Salmonella*. In some embodiments the pathogen receptor Dectin-1 may be used to generate a CAR that recognizes the carbohydrate structure on the cell wall of fungi such as *Aspergillus*. In another embodiment, CARs can be made based on an antibody recognizing viral determinants (e.g., the glycoproteins from CMV and Ebola) to interrupt viral infections and pathology.

In some embodiments, a "stalk" region, or a "spacer" or "hinge" region, is used to link the antigen-binding domain to the transmembrane domain. In some instances, a "stalk domain" or "stalk region" comprise any oligonucleotide- or polypeptide that functions to link the transmembrane domain to, either the extracellular domain or, the cytoplasmic domain in the polypeptide chain. In some embodiments, it is flexible enough to allow the antigen-binding domain to orient in different directions to facilitate antigen recognition. In some instances, the stalk region comprises the hinge region from IgG1. In alternative instances, the stalk region comprises the CH2CH3 region of immunoglobulin and optionally portions of CD3. In some cases, the stalk region comprises a CD8α hinge region, an IgG4-Fc 12 amino acid hinge region (ESKYGPPCPPCP) (SEQ ID NO: 561) or IgG4 hinge regions as described in WO/2016/073755.

The transmembrane domain can be derived from either a natural or a synthetic source. Where the source is natural, the domain can be derived from any membrane-bound or transmembrane protein. Suitable transmembrane domains can include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. Alternatively the transmembrane domain can be synthetic, and can comprise hydrophobic residues such as leucine and valine. In some embodiments, a triplet of phenylalanine, tryptophan and valine is found at one or both termini of a synthetic transmembrane domain. Optionally, a short oligonucleotide or polypeptide linker, in some embodiments, between 2 and 10 amino acids in length may form the linkage between the transmembrane domain and the cytoplasmic signaling domain of a CAR. In some embodiments, the linker is a glycine-serine linker.

In some embodiments, the transmembrane domain comprises a CD8α transmembrane domain or a CD3ζ transmembrane domain. In some embodiments, the transmembrane domain comprises a CD8α transmembrane domain. In other embodiments, the transmembrane domain comprises a CD3ζ transmembrane domain.

The intracellular domain can comprise one or more costimulatory domains. Exemplary costimulatory domains include, but are not limited to, CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD8, CD27, CD28, 4-1BB (CD137), ICOS, DAP10, DAP12, OX40 (CD134) or fragment or combination thereof. In some instances, a CAR described herein comprises one or more, or two or more of costimulatory domains selected from CD27, CD28, 4-1BB (CD137), ICOS, OX40 (CD134) or fragment or combination thereof. In some instances, a CAR described herein comprises one or more, or two or more of costimulatory domains selected from CD8, CD28, 4-1BB (CD137), or fragment or combination thereof. In some instances, a CAR described herein comprises one or more, or two or more of costimulatory domains selected from CD28, 4-1BB (CD137), or fragment or combination thereof. In some instances, a CAR described herein comprises costimulatory domains CD28 and 4-1BB (CD137) or their respective fragments thereof. In some instances, a CAR described herein comprises costimulatory domains CD28 and OX40 (CD134) or their respective fragments thereof. In some instances, a CAR described herein comprises costimulatory domains CD8 and CD28 or their respective fragments thereof. In some instances, a CAR described herein comprises costimulatory domains CD28 or a fragment thereof. In some instances, a CAR described herein comprises costimulatory domains 4-1BB (CD137) or a fragment thereof. In some instances, a CAR described herein comprises costimulatory domains OX40 (CD134) or a fragment thereof. In some instances, a CAR described herein comprises costimulatory domains CD8 or a fragment thereof.

In some embodiments, the intracellular domain further comprises a signaling domain for T-cell activation. In some instances, the signaling domain for T-cell activation comprises a domain derived from TCR zeta, FcR gamma, FcR beta, CD3 gamma, CD3 delta, CD3 epsilon, CD5, CD22, CD79a, CD79b or CD66d. In some cases, the signaling domain for T-cell activation comprises a domain derived from CD3ζ.

In some embodiments, a CAR described herein is administered to a subject with one or more additional therapeutic agents that include but are not limited to cytokines as described herein. In further embodiments, an immune effector cell expressing a CAR described herein expresses membrane-bound IL-15 ("mIL-15 or mbIL-15"). In aspects of the invention, the mbIL-15 comprises a fusion protein between IL-15 and IL-15Rα. In further embodiments, the mbIL-15 comprises an amino acid sequence having at least 90%, 91%, 92%, 93%, 94%, 95%, 96%, 97%, 98%, 99% or 100% identity with the amino acid sequence of SEQ ID NO: 69. In certain cases, the CAR and the cytokine is expressed in separate vectors. In specific cases, the vectors can be lentiviral vectors, retroviral vectors or Sleeping Beauty transposons.

CD19-Specific CARs

CD19 is a cell surface glycoprotein of the immunoglobulin superfamily and is found predominately in malignant B-lineage cells. In some instances, CD19 has also been detected in solid tumors such as pancreatic cancer, liver cancer, and prostate cancer.

In some embodiments, described herein include a CD19-specific CAR, in which the antigen binding domain comprises a F(ab')$_2$, Fab', Fab, Fv, or scFv. In some instances, the antigen binding domain recognizes an epitope on CD19. In some embodiments, the antigen binding domain recognizes an epitope on CD19 that is also recognized by FMC63. In some embodiments the scFv and/or VH/VL domains is derived from FMC63. FMC63 generally refers to a mouse monoclonal IgG1 antibody raised against Nalm-1 and -16 cells expressing CD19 of human origin (Ling, N. R., el al. (1987). Leucocyte typing III. 302). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, the antigen binding domain recognizes an epitope on CD19 that is also recognized by JCAR014, JCAR015, JCAR017, or 19-28z CAR (Juno Therapeutics). In some embodiments, described herein include a CD19-specific CAR-T cell, in which the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by JCAR014, JCAR015, JCAR017, or 19-28z CAR (Juno Therapeutics). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, a CD19-specific CAR-T cell described herein comprises an anti-CD19 antibody described in US20160152723. In some embodiments, a CD19-specific CAR-T cell described herein comprises an anti-CD19 antibody described in WO2015/123642. In some embodiments, a CD19-specific CAR-T cell described herein comprises an anti-CD19 scFv derived from clone FMC63 (Nicholson et al. Construction and characterization of a functional CD19 specific single chain Fv fragment for immunotherapy of B lineage leukemia and lymphoma. Mol. Immunol., 34:1157-1165, 1997).

In some embodiments, the antigen binding domain recognizes an epitope on CD19 that is also recognized by KTE-C19 (Kite Pharma, Inc.). In some embodiments, described herein include a CD19-specific CAR-T cell, in which the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by KTE-C19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, a CD19-specific CAR-T cell described herein comprises an anti-CD19 antibody described in WO2015187528 or fragment or derivative thereof.

In some embodiments, the antigen binding domain recognizes an epitope on CD19 that is also recognized by CTL019 (Novartis). In some embodiments, described herein include a CD19-specific CAR-T cell, in which the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by CTL019. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by UCART19 (Cellectis). In some embodiments, described herein include a CD19-specific CAR-T cell, in which the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by UCART19. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, the antigen binding domain recognizes an epitope on CD19 that is also recognized by BPX-401 (Bellicum). In some embodiments, described herein include a CD19-specific CAR-T cell, in which the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some embodiments, described herein include a CD19-specific CAR-T cell comprises a scFv antigen binding domain, and the antigen binding domain recognizes an epitope on CD19 that is also recognized by BPX-401. In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affirmed). In some instances, the CD19-specific CAR further comprises a transmembrane domain selected from a CD8alpha transmembrane domain or a CD3ζ transmembrane domain; one or more costimulatory domains selected from CD27, CD28, 4-1BB (CD137), ICOS, DAP10, OX40 (CD134) or fragment or combination thereof; and a signaling domain from CD3ζ.

In some embodiments, described herein include a CD19-specific CAR-T cell, in which the antigen binding domain comprises a F(ab')₂, Fab', Fab, Fv, or scFv. In some instances, the antigen binding domain recognizes an epitope on CD19. In some cases, the antigen binding domain recognizes an epitope on CD19 that is also recognized by blinatumomab (Amgen), coltuximabravtansine (ImmunoGen Inc./Sanofi-aventis), MOR208 (Morphosys AG/Xencor Inc.), MEDI-551 (Medimmune), denintuzumabmafodotin (Seattle Genetics), B4 (or DI-B4) (Merck Serono), taplitumomabpaptox (National Cancer Institute), XmAb 5871 (Amgen/Xencor, Inc.), MDX-1342 (Medarex) or AFM11 (Affirmed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

In some cases, a CD19-specific CAR-T cell described herein comprise a scFv antigen binding domain, and the antigen binding domain recognizes an epitope on CD19 that is also recognized by FMC63, blinatumomab (Amgen), coltuximabravtansine (ImmunoGen Inc./Sanofi-aventis), MOR208 (Morphosys AG/Xencor Inc.), MEDI-551 (Medimmune), denintuzumabnafodotin (Seattle Genetics), B4 (or DI-B4) (Merck Serono), taphtumomabpaptox (National Cancer Institute), XmAb 5871 (Amgen/Xencor, Inc.), MDX-1342 (Medarex) or AFM11 (Affirmed). In some instances, the CD19-specific CAR-T cell further comprises a transmembrane domain selected from a CD8alpha transmembrane domain or a CD3ζ transmembrane domain; one or more costimulatory domains selected from CD27, CD28, 4-1BB (CD137), ICOS, DAP10, DAP12, OX40 (CD134) or fragment or combination thereof; and a signaling domain from CD3ζ.

CD33-Specific CARs

"CD33," is a 67 kDa single pass transmembrane glycoprotein and is a member of the sialic acid-binding immunoglobulin-like lectins (Siglecs) super-family. CD33 is characterized by a V-set Ig-like domain responsible for sialic acid binding and a C2-set Ig-like domain in its extracellular domain. Alternative splicing of CD33 mRNA leads to a shorter isoform (CD33m) lacking the V-set Ig-like domain as well as the disulfide bond linking the V- and C2-set Ig-like domains. In healthy subjects, CD33 is primarily expressed as a myeloid differentiation antigen found on normal multipotent myeloid precursors, unipotent colony-forming cells, monocytes and maturing granulocytes. CD33 is expressed on more than 80% of myeloid leukemia cells but not on normal hematopoietic stem cells or mature granulocytes. (Andrews, R. et al., The L4F3 antigen is expressed by unipotent and multipotent colony-forming cells but not by their precursors, Blood, 68(5):1030-5 (1986)). CD33 has been reported to be expressed on malignant myeloid cells, activated T cells and activated NK cells and is found on at least a subset of blasts in the vast majority of AML patients (Pollard, J. et al., Correlation of CD33 expression level with disease characteristics and response to gemtuzumab ozogamicin containing chemotherapy in childhood AML, Blood, 119(16):3705-11 (2012)). In addition to broad expression on AML blasts, CD33 may be expressed on stem cells underlying AML.

In embodiments, the antigen binding moiety of a CAR described herein is specific to CD33 (CD33 CAR). The CD33-specific CAR, when expressed on the cell surface, redirects the specificity of T cells to human CD33. In embodiments, the antigen binding domain comprises a single chain antibody fragment (scFv) comprising a variable domain light chain (VL) and variable domain heavy chain (VH) of a target antigen specific monoclonal anti-CD33 antibody joined by a flexible linker, such as a glycine-serine linker or a Whitlow linker. In embodiments, the scFv are M195, m2H12, DRB2, and/or My9-6. In embodiments, the scFv is humanized, for example, hM195. In some embodiments, the antigen binding moiety may comprise VH and VL that are directionally linked, for example, from N to C terminus, VH-linker-VL or VL-linker-VH.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:35 (hM195 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:36 (hM195 VH).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:37 (M2H12 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:38 (M2H12 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:39 (DRB2 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:40 (DRB2 VL).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:41 (My9-6 VH).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:42 (My9-6 VL).

MUC16-Specific CARs

MUC16 is a large carbohydrate antigen, also known as CA-125. MUC16 is encoded by the MUC16 gene located on human chromosome 19. MUC16 is a highly glycosylated multi-domain type I transmembrane protein comprising 3 domains. The C-terminal domain contains multiple extracellular SEA (sea urchin sperm protein, enterokinase, and agrin) modules that have an autoproteolytic activity. SEA harbors two proteolytic sites proximal to the transmembrane (TM) domain. A large cleaved domain termed CA-125 is released into circulation at acidic pH. CA-125 is commonly used as disease biomarker for ovarian cancer. The highly conserved truncated extracellular membrane tethered protein domain called MUC16ecto domain. A MUC16 antibody was identified that specifically bound the ectodomain of MUC16 that is retained on the tumor cell surface. "Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

In embodiments, the antigen binding moiety of a CAR described herein is specific to MUC16 (MUC16 CAR). The MUC16-specific CAR, when expressed on the cell surface, redirects the specificity of T cells to human MUC16. In embodiments, the antigen binding domain comprises a single chain antibody fragment (scFv) comprising a variable domain light chain (VL) and variable domain heavy chain (VH) of a target antigen specific monoclonal anti-MUC16 antibody joined by a flexible linker, such as a glycine-serine linker or a Whitlow linker. In embodiments, the scFv are MUC16-1 scFv (SEQ ID NOs: 43-44), MUC16-2 scFv (SEQ ID NOs: 45-46), MUC16-3 scFv (SEQ ID NOs: 4748), MUC16-4 scFv (SEQ ID NOs: 49-50), MUC16-5 scFv (SEQ ID NOs: 51-52), MUC16-6 scFv (SEQ ID NOs: 53-54) or MUC16-7 scFv (SEQ ID NOs: 55-56). In embodiments, the scFv is humanized.

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:43 (MUC16-1).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:44 (MUC16-1).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:45 (MUC16-2).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:46 (MUC16-2).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:47 (MUC16-3).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:48 (MUC16-3).

In embodiments, a CAR described herein comprises an antigen-binding moiety comprising a $V_L$ polypeptide having at least 90%, 91%, 92%, 93%, 94%, 95%, 96%, 97%, 98%, 99% or 100% identity with the amino acid sequence of SEQ ID NO:49 (MUC16-4).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:50 (MUC16-4).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:51 (MUC16-5).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:52 (MUC16-5).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:53 (MUC16-5).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:54 (MUC16-6).

In embodiments, a CAR described herein comprises an antigen-binding moiety comprising a VL polypeptide having at least 90%, 91%, 92%, 93%, 94%, 95%, 96%, 97%, 98%, 99% or 100% identity with the amino acid sequence of SEQ ID NO:55 (MUC16-7).

In embodiments, a CAR described herein comprises an antigen-binding moiety comprising a VH polypeptide having at least 90%, 91%, 92%, 93%, 94%, 95%, 96%, 97%, 98%, 99% or 100% identity with the amino acid sequence of SEQ ID NO:56 (MUC16-7).

In some embodiments, the antigen binding moiety can comprise VH and VL that are directionally linked, for example, from N to C terminus, VH-linker-VL or VL-linker-VH.

Engineered T-Cell Receptors ("TCRs")

In some embodiments, the chimeric receptor comprises an engineered T-cell receptor. The T cell receptor (TCR) is composed of two chains ($\alpha\beta$ or $\gamma\delta$) that pair on the surface of the T cell to form a heterodimeric receptor. In some instances, the $\alpha\beta$ TCR is expressed on most T cells in the body and is known to be involved in the recognition of specific MHC-restricted antigens. Each $\alpha$ and $\beta$ chain are composed of two domains: a constant domain (C) which anchors the protein to the cell membrane and is associated with invariant subunits of the CD3 signaling apparatus; and a variable domain (V) that confers antigen recognition through six loops, referred to as complementarity determining regions (CDRs). In some instances, each of the V domains comprises three CDRs; e.g., CDR1, CDR2 and CDR3 with CDR3 as the hypervariable region. These CDRs interact with a complex formed between an antigenic peptide bound to a protein encoded by the major histocompatibility complex (pepMHC) (e.g., HLA-A, HLA-B, HLA-C, HLA-DPA1, HIA-DPB1, HLA-DQA1, HLA-DQB1, HLA-DRA, or HLA-DRB1 complex). In some instances, the constant domain further comprises a joining region that connects the constant domain to the variable domain. In some cases, the beta chain further comprises a short diversity region which makes up part of the joining region.

In some cases, such TCR are reactive to specific tumor antigen, e.g. NY-ESO, Mage A3, Titin. In other cases, such TCR are reactive to specific neoantigens expressed within a patient's tumor (i.e. patient-specific, somatic, non-synonymous mutations expressed by tumors). In some cases, engineered TCRs can be affinity-enhanced.

In some embodiments, a TCR is described using the International Immunogenetics (IMGT) TCR nomenclature, and links to the IMGT public database of TCR sequences. For example, there can be several types of alpha chain variable (V$\alpha$) regions and several types of beta chain variable (V$\beta$) regions distinguished by their framework, CDR1, CDR2, and CDR3 sequences. As such, a V$\alpha$ type can be referred to in IMGT nomenclature by a unique TRAV number. For example, "TRAV21" defines a TCR V$\alpha$ region having unique framework and CDR1 and CDR2 sequences, and a CDR3 sequence which is partly defined by an amino acid sequence which is preserved from TCR to TCR but which also includes an amino acid sequence which varies from TCR to TCR. Similarly, "TRBV5-1" defines a TCR Vβ region having unique framework and CDR1 and CDR2 sequences, but with only a partly defined CDR3 sequence.

In some cases, the beta chain diversity region is referred to in IMGT nomenclature by the abbreviation TRBD.

In some instances, the unique sequences defined by the IMGT nomenclature are widely known and accessible to those working in the TCR field. For example, they can be found in the IMGT public database and in "T cell Receptor Factsbook," (2001) LeFranc and LeFranc, Academic Press, ISBN 0-12-441352-8.

In some embodiments, an αβ heterodimeric TCR is, for example, transfected as full length chains having both cytoplasmic and transmembrane domains. In some cases, the TCRs contain an introduced disulfide bond between residues of the respective constant domains, as described, for example, in WO 2006/000830.

In some instances, TCRs described herein are in single chain format, for example see WO 2004/033685. Single chain formats include αβ TCR polypeptides of the Vα-L-Vβ, Vβ-L-Vα, Vα-Cα-L-Vβ, Vα-L-Vβ-Cβ, Vα-Cα-L-Vβ-Cβ types, wherein Vα and Vβ are TCR α and β variable regions respectively, Cα and Cβ are TCR α and β constant regions respectively, and L is a linker sequence. In certain embodiments single chain TCRs of the invention may have an introduced disulfide bond between residues of the respective constant domains, as described in WO 2004/033685.

The TCR described herein may be associated with a detectable label, a therapeutic agent or a PK modifying moiety.

Exemplary detectable labels for diagnostic purposes include, but are not limited to, fluorescent labels, radiolabels, enzymes, nucleic acid probes and contrast reagents.

Therapeutic agents which may be associated with the TCRs described herein include immunomodulators, radioactive compounds, enzymes (perforin for example) or chemotherapeutic agents. To ensure that toxic effects are exercised in the desired location the toxin could be inside a liposome linked to a TCR so that the compound is released in a controlled manner. In some cases, the controlled release minimize damaging effects during the transport in the body and ensure that the toxin has maximum effect after binding of the TCR to the relevant antigen presenting cells.

In some embodiments, additional suitable therapeutic agents include for instance:

a. small molecule cytotoxic agents, e.g., compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate glucuronate, auristatin E vincristine and doxorubicin;

b. peptide cytotoxins, i.e. proteins or fragments thereof with the ability to kill mammalian cells. For example, ricin, diphtheria toxin, *pseudomonas* bacterial exotoxin A, DNase and RNase;

c. radio-nuclides, i.e. unstable isotopes of elements which decay with the concurrent emission of one or more of α or β particles, or γ rays. For example, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

d. immuno-stimulants, i.e. immune effector molecules which stimulate immune response. For example, cytokines such as IL-2 and IFN-γ, e. superantigens and mutants thereof;

f. TCR-HLA fusions;

g. chemokines such as IL-8, platelet factor 4, melanoma growth stimulatory protein, etc;

h. antibodies or fragments thereof, including anti-T cell or NK cell determinant antibodies (e.g. anti-CD3, anti-CD28 or anti-CD16);

i. alternative protein scaffolds with antibody like binding characteristics j. complement activators; and k. xenogeneic protein domains, allogeneic protein domains, viral/bacterial protein domains, viral/bacterial peptides.

Doses

Suitable dosages of the fusion protein and modified immune effector cells used will depend on the age and weight of the subject and the particular drug used. Dosages and therapeutic regimens of the fusion protein and modified immune effector cells can be determined by a skilled artisan.

In certain embodiments, the fusion protein is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the fusion protein is administered at a dose of about 1 mg/kg, about 3 mg/kg, about 5 mg/kg, about 10 mg/kg, about 20 mg/kg, about 30 mg/kg, or about 40 mg/kg. In some embodiments, the fusion protein is administered at a dose of about 1-3 mg/kg, or about 3-10 mg/kg. In some embodiments, the fusion protein is administered at a dose of about 0.5-2, 2-4, 2-5, 5-15, or 5-20 mg/kg. The dosing schedule can vary from e.g., once a week to once every 2, 3, or 4 weeks. In some embodiments, the fusion protein is administered at a dose from about 10 to 20 mg/kg every other week. In another embodiment, the fusion protein is administered at a dose of about 1 mg/kg once every two weeks, about 3 mg/kg once every two weeks, 10 mg/kg once every two weeks, 3 mg/kg once every four weeks, or 5 mg/kg once every four weeks.

In other embodiments, the fusion protein is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. In some embodiments, the fusion protein is administered at a dose of about 200 mg, about 250 mg, about 300 mg, about 350 mg, about 400 mg, about 450 mg, or about 500 mg. In some embodiments, the fusion protein is administered at a dose of 200 or 300 mg. In some embodiments, the fusion protein is administered at a dose of about 250-450 mg, or about 300-400 mg. In some embodiments, the fusion protein is administered at a dose of about 200-300 mg, 250-350 mg, 300-400 mg, 350450 mg, or 400-500 mg. The dosing schedule can vary from e.g., once a week to once every 2, 3, 4, 5, or 6 weeks. In one embodiment the fusion protein is administered at a dose from about 300 mg to 400 mg once every three or once every four weeks. In some embodiments, the fusion protein is administered at a dose from about 300 mg once every three weeks. In some embodiments, the fusion protein is administered at a dose from about 400 mg once every four weeks. In some embodiments, the fusion protein is administered at a dose from about 300 mg once every four weeks. In some embodiments, the fusion protein is administered at a dose from about 400 mg once every three weeks. The fusion protein can be administered one or more times, e.g., one, two, three, four, five, six, seven or more times. In some embodiments, the fusion protein is administered six times. The fusion protein can be administered at least 5 days, e.g., about 5, 6, 7, 8, 9, 10, 11, 12, 13, 14, 20, 25, 30, 35, or 40 days, after administration of CAR-expressing cells, e.g., MUC16, CD33, CD19 or BCMA-specific CAR expressing cells. In some embodiments, the fusion protein can be administered about 8 days or about 15 days after administration of CAR-expressing cells, e.g., MUC16 specific CAR expressing cells or CD33 specific CAR expressing cells.

The fusion protein can be administered by a variety of methods known in the art, although for many therapeutic applications, the preferred route/mode of administration is intravenous injection or infusion. For example, the fusion protein can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the fusion protein can be administered by intravenous infusion at a rate of less than 10 mg/min; preferably less than or equal to 5 mg/min to reach a dose of about 1 to 100 mg/m2, preferably about 5 to 50 mg/m2, about 7 to 25 mg/m2 and more preferably, about 10 mg/m2.

The fusion protein can be administered by intravenous infusion at a rate of more than 20 mg/min, e.g., 20-40 mg/min, and typically greater than or equal to 40 mg/min to reach a dose of about 35 to 440 mg/m2, typically about 70 to 310 mg/m2, and more typically, about 110 to 130 mg/m2. In embodiments, the infusion rate of about 110 to 130 mg/m2 achieves a level of about 3 mg/kg. In other embodiments, the fusion protein can be administered by intravenous infusion at a rate of less than 10 mg/min, e.g., less than or equal to 5 mg/min to reach a dose of about 1 to 100 mg/m2, e.g., about 5 to 50 mg/m2, about 7 to 25 mg/m2, or, about 10 mg/m2. In some embodiments, the antibody is infused over a period of about 30 min.

Modified Effector Cell Doses

In some embodiments, an amount of modified effector cells is administered to a subject in need thereof and the amount is determined based on the efficacy and the potential of inducing a cytokine-associated toxicity. In some cases, an amount of modified effector cells comprises about $10^5$ to about $10^9$ modified effector cells/kg. In some cases, an amount of modified effector cells comprises about $10^5$ to about $10^8$ modified effector cells/kg. In some cases, an amount of modified effector cells comprises about $10^5$ to about $10^7$ modified effector cells/kg. In some cases, an amount of modified effector cells comprises about $10^6$ to about $10^9$ modified effector cells/kg. In some cases, an amount of modified effector cells comprises about $10^6$ to about $10^8$ modified effector cells/kg. In some cases, an amount of modified effector cells comprises about $10^7$ to about $10^9$ modified effector cells/kg. In some cases, an amount of modified effector cells comprises about $10^5$ to about $10^6$ modified effector cells/kg. In some cases, an amount of modified effector cells comprises about $10^6$ to about $10^7$ modified effector cells/kg. In some cases, an amount of modified effector cells comprises about $10^7$ to about $10^8$ modified effector cells/kg. In some cases, an amount of modified effector cells comprises about $10^8$ to about $10^9$ modified effector cells/kg. In some instances, an amount of modified effector cells comprises about $10^9$ modified effector cells/kg. In some instances, an amount of modified effector cells comprises about $10^8$ modified effector cells/kg. In some instances, an amount of modified effector cells comprises about $10^7$ modified effector cells/kg. In some instances, an amount of modified effector cells comprises about $10^6$ modified effector cells/kg. In some instances, an amount of modified effector cells comprises about $10^5$ modified effector cells/kg.

In some embodiments, the modified effector cells are modified T cells. In some instances, the modified T cells are CAR-T cells. In some cases, an amount of CAR-T cells comprises about $10^5$ to about $10^9$ CAR-T cells/kg. In some cases, an amount of CAR-T cells comprises about $10^5$ to about $10^8$ CAR-T cells/kg. In some cases, an amount of CAR-T cells comprises about $10^5$ to about $10^7$ CAR-T cells/kg. In some cases, an amount of CAR-T cells comprises about $10^6$ to about $10^9$ CAR-T cells/kg. In some cases, an amount of CAR-T cells comprises about $10^6$ to about $10^8$ CAR-T cells/kg. In some cases, an amount of CAR-T cells comprises about $10^7$ to about $10^9$ CAR-T cells/kg. In some cases, an amount of CAR-T cells comprises about $10^5$ to about $10^6$ CAR-T cells/kg. In some cases, an amount of CAR-T cells comprises about $10^6$ to about $10^7$ CAR-T cells/kg. In some cases, an amount of CAR-T cells comprises about $10^7$ to about $10^8$ CAR-T cells/kg. In some cases, an amount of CAR-T cells comprises about $10^8$ to about $10^9$ CAR-T cells/kg. In some instances, an amount of CAR-T cells comprises about $10^9$ CAR-T cells/kg. In some instances, an amount of CAR-T cells comprises about $10^8$ CAR-T cells/kg. In some instances, an amount of CAR-T cells comprises about $10^7$ CAR-T cells/kg. In some instances, an amount of CAR-T cells comprises about $10^6$ CAR-T cells/kg. In some instances, an amount of CAR-T cells comprises about $10^5$ CAR-T cells/kg.

In some embodiments, the CAR-T cells are CD19-specific CAR-T cells. In some cases, an amount of CD19-specific CAR-T cells comprises about $10^5$ to about $10^9$ CAR-T cells/kg. In some cases, an amount of CD19-specific CAR-T cells comprises about $10^5$ to about $10^8$ CAR-T cells/kg. In some cases, an amount of CD19-specific CAR-T cells comprises about $10^5$ to about $10^7$ CAR-T cells/kg. In some cases, an amount of CD19-specific CAR-T cells comprises about $10^6$ to about $10^9$ CAR-T cells/kg. In some cases, an amount of CD19-specific CAR-T cells comprises about $10^6$ to about $10^8$ CAR-T cells/kg. In some cases, an amount of CD19-specific CAR-T cells comprises about $10^7$ to about $10^9$ CAR-T cells/kg. In some cases, an amount of CD19-specific CAR-T cells comprises about $10^5$ to about $10^6$ CAR-T cells/kg. In some cases, an amount of CD19-specific CAR-T cells comprises about $10^6$ to about $10^7$ CAR-T cells/kg. In some cases, an amount of CD19-specific CAR-T cells comprises about $10^7$ to about $10^8$ CAR-T cells/kg. In some cases, an amount of CD19-specific CAR-T cells comprises about $10^8$ to about $10^9$ CAR-T cells/kg. In some instances, an amount of CD19-specific CAR-T cells comprises about $10^9$ CAR-T cells/kg. In some instances, an amount of CD19-specific CAR-T cells comprises about $10^8$ CAR-T cells/kg. In some instances, an amount of CD19-specific CAR-T cells comprises about $10^7$ CAR-T cells/kg. In some instances, an amount of CD19-specific CAR-T cells comprises about $10^6$ CAR-T cells/kg. In some instances, an amount of CD19-specific CAR-T cells comprises about $10^5$ CAR-T cells/kg.

In some embodiments, the modified T cells are engineered TCR T-cells. In some cases, an amount of engineered TCR T-cells comprises about $10^5$ to about $10^9$ TCR cells/kg. In some cases, an amount of engineered TCR cells comprises about $10^5$ to about $10^8$ TCR cells/kg. In some cases, an amount of engineered TCR cells comprises about $10^5$ to about $10^7$ TCR cells/kg. In some cases, an amount of engineered TCR cells comprises about 106 to about $10^9$ TCR cells/kg. In some cases, an amount of engineered TCR cells comprises about $10^6$ to about $10^8$ TCR cells/kg. In some cases, an amount of engineered TCR cells comprises about $10^7$ to about $10^9$ TCR cells/kg. In some cases, an amount of engineered TCR cells comprises about $10^5$ to about $10^6$ TCR cells/kg. In some cases, an amount of engineered TCR cells comprises about $10^6$ to about $10^7$ TCR cells/kg. In some cases, an amount of engineered TCR cells comprises about $10^7$ to about $10^8$ TCR cells/kg. In some cases, an amount of engineered TCR cells comprises about $10^8$ to about $10^9$ TCR cells/kg. In some instances, an amount of engineered TCR cells comprises about $10^9$ TCR cells/kg. In some instances, an amount of engineered TCR cells comprises about $10^8$ TCR cells/kg. In some instances, an amount of engineered TCR cells comprises about $10^7$ TCR cells/kg. In some instances, an amount of engineered TCR cells comprises about $10^6$ TCR cells/kg. In some instances, an amount of engineered TCR cells comprises about $10^5$ TCR cells/kg.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Expression and Purification System of Fusion Proteins

The fusion protein or a fragment or a variant thereof described herein can be produced from cells by culturing a host cell transformed with the expression vector comprising one or more polynucleotides encoding the fusion protein or a fragment or a variant thereof, under conditions, and for an amount of time, sufficient to allow expression of the fusion protein, or a fragment or a variant thereof. For example, polypeptides expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells can vary depending on a number of factors, and can be easily optimized as needed. The fusion protein or a fragment or a variant thereof described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the fusion protein or a fragment or a variant thereof can be purified or isolated. The term "purified" or "isolated" as applied to any of the fusion proteins or fragments or variants thereof described herein can refer to a polypeptide or a protein that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% by weight of the total protein in a sample.

The fusion protein or a fragment or a variant thereof described herein can be isolated or purified in a variety of ways depending on what other components are present in the sample. Standard purification methods include electrophoretic, molecular, immunological, and chromatographic techniques, including ion exchange, hydrophobic, affinity, and reverse-phase HPLC chromatography. For example, the fusion protein or a fragment or a variant thereof can be purified using a standard anti-fusion protein antibody affinity column. Ultrafiltration and diafiltration techniques, in conjunction with protein concentration, are also useful. (See, e.g., Scopes (1994) "Protein Purification, 3' edition," Springer-Verlag, New York City, N.Y.) The degree of purification necessary can vary depending on the desired use. In some instances, no purification of the expressed fusion protein or a fragment or variant thereof is necessary.

Methods for determining the yield or purity of a purified fusion protein or a fragment or a variant thereof can include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain). Once expressed, purified, or after being purified following expression, a fusion protein or a fragment or a variant thereof described herein can be assayed for any one of a numbered of desired properties using in vitro or in vivo assays such as any of those described herein. For example, a fusion protein or a fragment or a variant thereof described herein can be assayed for e.g., its ability to inhibit PD-1 and trap TGF-β.

The fusion protein or a fragment or a variant thereof described herein can be produced using a variety of techniques. For example, a polynucleotide encoding a fusion protein or a fragment or a variant thereof described herein can be inserted into an expression vector that contains transcriptional and translational regulatory sequences, which can include, e.g., promoter sequences, ribosomal binding sites, transcriptional start and stop sequences, translational start and stop sequences, transcription terminator signals, polyadenylation signals, and enhancer or activator sequences. In some embodiments, the regulatory sequences can include a promoter and transcriptional start and stop sequences. In addition, the expression vector can include more than one replication system such that it can be maintained in two different organisms, for example, in mammalian or insect cells for expression and in a prokaryotic host for cloning and amplification.

Several possible vector systems are available for the expression of the fusion protein or a fragment or a variant thereof from nucleic acids in mammalian cells (e.g., host cells). For example, one class of vectors relies upon the integration of the desired gene sequences into the host cell genome. Cells which have stably integrated DNA can be selected by simultaneously introducing drug resistance genes such as *E. coli* gpt (Mulligan and Berg, *Proc Natl Acad Sci USA* 78:2072 (1981)) or Tn5 neo (Southern and Berg (1982) *Mol Appl Genet* 1:327). The selectable marker gene can be either linked to the DNA gene sequences to be expressed, or introduced into the same cell by co-transfection (Wigler et al., Cell 16:77 (1979)). Another class of vectors utilizes DNA elements which confer autonomously replicating capabilities to an extrachromosomal plasmid. These vectors can be derived from animal viruses, such as bovine papillomavirus (Sarver et al., Proc Natl Acad Sci USA, 79:7147 (1982)), polyoma virus (Deans et al., Proc Natl Acad Sci USA 81:1292 (1984)), or SV40 virus (Lusky and Botchan, Nature 293:79 (1981)). The expression vectors can be introduced into cells (e.g., host cells) in a manner suitable for subsequent expression of the nucleic acid. The method of introduction is largely dictated by the targeted cell type, discussed below. Non-limiting exemplary methods can include $CaPO_4$ precipitation, liposome fusion, lipofectin, electroporation, viral infection, dextran-mediated transfection, polybrene-mediated transfection, protoplast fusion, and direct microinjection.

Appropriate host cells for the expression of the fusion protein or a fragment or a variant thereof can include, but not limited to, yeast, bacteria, insect, plant, and, as described above, mammalian cells. Of interest are bacteria such as E. coli, fungi such as Saccharomyces cerevisiae and Pichia pastoris, insect cells such as SF9, mammalian cell lines (e.g., human cell lines), as well as primary cell lines (e.g., primary mammalian cells). In some embodiments, the fusion protein or a fragment or a variant thereof can be expressed in Chinese hamster ovary (CHO) cells or in a suitable myeloma cell line such as (NS0). Suitable cell lines also include, for example, BHK-21 (baby hamster kidney) cells; 293 (human embryonic kidney) cells; HMEpC (Human Mammary Epithelial cells; 3T3 (mouse embryonic fibroblast) cells.

The methods described herein provide for the expression and purification of the fusion protein or a fragment or a variant thereof in various cell-based expression systems, such as protein production in bacterial, mammalian, insect, yeast, and chymadomonas cells. Protein expression can be constitutive or inducible with inducers such as copper sulfate, sugars such as galactose, methanol, methylamine, thiamine, tetracycline, or IPTG. After the fusion protein or a fragment or a variant thereof is expressed in the host cells, the host cells are lysed to liberate the fusion protein or a fragment or a variant thereof for purification. Methods of lysing the various host cells are featured in "Sample Preparation-Tools for Protein Research" EMD Bioscience and in the Current Protocols in Protein Sciences (CPPS). A non-limiting exemplary purification method is affinity chromatography, such as ion-metal affinity chromatograph using nickel, cobalt, or zinc affinity resins for e.g., a histidine-tagged fusion protein or fragment or variant thereof. Methods of purifying histidine-tagged proteins are described by Clontech using their Talonx cobalt resin and by Novagen in their pET system manual, 10th edition. Another non-limiting exemplary purification strategy is by immuno-affinity chromatography, for example, anti-myc antibody conjugated resin can be used to affinity purify e.g., a myc-tagged fusion protein or fragment or variant thereof. Enzymatic digestion with serine proteases, such as thrombin and enterokinase, cleave and release the fusion protein or a fragment or a variant thereof from the histidine or myc tag, releasing the fusion protein or a fragment or a variant thereof from the affinity resin while the histidine-tags and myc-tags are left attached to the affinity resin.

Methods of introducing and expressing polynucleotides encoding the fusion protein or a fragment or a variant thereof into a cell (e.g., a host cell) are known in the art. In the context of an expression vector, the vector comprising the polynucleotide encoding the fusion protein or a fragment or a variant thereof can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. (See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing polynucleotides encoding the fusion protein or a fragment or a variant thereof into a host cell can include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some embodiments, the expression vector can have the necessary 5' upstream and 3' downstream regulatory elements such as promoter sequences, ribosome recognition and binding TATA box, and 3' UTR AAUAAA transcription termination sequence for the efficient gene transcription and translation in its respective host cell. The expression vector can have additional sequence such as 6x-histidine (SEQ ID NO: 562), V5, thioredoxin, glutathione-S-transferase, c-Myc, VSV-G, HSV, FLAG, maltose binding peptide, metal-binding peptide, HA and "secretion" signals (Honeybee melittin, .alpha.-factor, PHO, Bip), which are incorporated into the expressed fusion protein or fragment or variant thereof. In addition, there can be enzyme digestion sites incorporated after these sequences to facilitate enzymatic removal of them after they are not needed. These additional sequences are useful for the detection of the fusion protein expression, for protein purification by affinity chromatography, enhanced solubility of the recombinant protein in the host cytoplasm, and/or for secreting the fusion protein out into the culture media, into the periplasm of the prokaryote bacteria, or the spheroplast of the yeast cells. The expression of the fusion protein can be constitutive in the host cells or it can be induced, e.g., with copper sulfate, sugars, such as galactose, methanol, methylamine, thiamine, tetracycline, infection with baculovirus, and (isopropyl-beta-D-thiogalactopyranoside) IPTG, a stable synthetic analog of lactose.

Non-limiting examples of expression vectors and host cells can include the pET vectors (Novagen), pGEX vectors (Amersham Pharmacia), and pMAL vectors (New England labs. Inc.) for protein expression in E. coli host cell such as BL21, BL21(DE3) and AD494(DE3)pLysS, Rosetta (DE3), and Origami (DE3) (Novagen); the strong CMV promoter-based pcDNA3.1 (Invitrogen) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech), pAd/CMV/V5-DEST, pAd-DEST vector (Invitrogen) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4V5-DEST™, pLenti6/V5-DEST™, and pLenti6.2/V5-GW/lacZ (Invitrogen) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (Clontech) and pFastBac™-HT (Invitrogen) for the expression in *Spodopera frugiperda* 9 (S9) and Sfl1 insect cell lines; pMT/BiP/V5-His (Invitrogen) for the expression in *Drosophila* Schneider S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (Invitrogen) vectors for expression in yeast *Saccharomyces cerevisiae*. Recent advances in the large scale expression heterologous proteins in *Chlamydomonas reinhardtii* are described by Griesbeck C. et. al. *Mol. Biotechnol.* 34:213-33 (2006) and Fuhrmann M., *Methods Mol. Med.* 94:191-5 (2004).

Besides cell-based expression systems, cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix.

In some embodiments, a continuous cell-free translation system can be used to produce the fusion protein or a fragment or a variant thereof. A continuous cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. Large scale cell-free production is described by Chang G. et. al., Science 310:1950-3 (2005).

Other commercially available cell-free expression systems include the Expressway™ Cell-Free Expression Systems (Invitrogen), which utilize an *E. coli*-based in vivo system for efficient, coupled transcription and translation reactions to produce up to milligram quantities of active recombinant protein in a tube reaction format; the Rapid Translation System (RTS) (Roche Applied Science), which also uses an *E. coli*-based in vitro system; and the TNT Coupled Reticulocyte Lysate Systems (Promega), which uses rabbit reticulocyte-based in-vitro system.

In other exemplary production methods, the fusion protein or a fragment or a variant thereof described herein can be synthesized de novo in whole or in part, using chemical methods. For example, the component amino acid sequences of the fusion protein or a fragment or a variant thereof can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

Methods for detecting and/or measuring the amount of endotoxin present in a sample (both before and after purification) can be based on commercial kits that are available. For example, the concentration of endotoxin in a protein sample can be determined using the QCL-1000 Chromogenic kit (BioWhittaker), the *Limulus amebocyte* lysate (LAL)-based kits such as the Pyrotell®, Pyrotell®-T, Pyrochrome®, Chromo-LAL, and CSE kits available from the Associates of Cape Cod Incorporated. In some embodiments, endotoxins can be removed from the fusion protein preparations using a variety of commercially available reagents including, without limitation, the ProteoSpin™ Endotoxin Removal Kits (Norgen Biotek Corporation), Detoxi-Gel Endotoxin Removal Gel (Thermo Scientific; Pierce Protein Research Products), MiraCLEAN® Endotoxin Removal Kit (Mirus), or Acrodisc™-Mustang® E membrane (Pall Corporation).

In some embodiments, following expression and purification, the fusion protein or a fragment or a variant thereof described herein can be modified. The modifications can be covalent or non-covalent modifications. Such modifications can be introduced into the fusion protein or a fragment or a variant thereof by, e.g., reacting targeted amino acid residues of the fusion protein or a fragment or a variant thereof with an organic derivatizing agent that is capable of reacting with selected side chains or terminal residues. Suitable sites for modification can be chosen using any of a variety of criteria including, e.g., structural analysis or amino acid sequence analysis of the fusion protein or a fragment or a variant thereof.

In some exemplary production methods, the fusion protein or a fragment or a variant thereof as described herein can be conjugated to a heterologous moiety. In some embodiments, the heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides can include, e.g., an antigenic tag (e.g., FLAG, polyhistidine, hemagglutinin (HA), glutathione-S-transferase (GST), or maltose-binding protein (MBP)) for use in purifying antibodies or fragments or variants thereof. Heterologous polypeptides can also include polypeptides that are useful as diagnostic or detectable markers, for example, luciferase, green fluorescent protein (GFP), or chloramphenicol acetyl transferase (CAT). Where the heterologous moiety is a polypeptide, the moiety can be incorporated into the fusion protein or a fragment or a variant thereof described herein, resulting in a fusion protein comprising the heterologous moiety.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the promoter is a constitutive promoter, a tissue specific promoter, or an inducible promoter. In some embodiments, the inducible promoter is a small molecule ligand-inducible two polypeptide ecdysone receptor-based gene switch.

Additional promoter elements, e.g., enhancers, can regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it can appear that individual elements can function either cooperatively or independently to activate transcription.

Reporters

Reporter genes can be used for identifying potentially transfected cells and for evaluating the functionality of regulatory sequences. In general, a reporter gene is a gene that is not present in or expressed by the host cell and that encodes a polypeptide whose expression is manifested by some easily detectable property, e.g., enzymatic activity. Expression of the reporter gene is assayed at a suitable time after the polypeptides encoding the fusion protein or a fragment or a variant thereof has been introduced into the host cells. Suitable reporter genes can include, but not limited to, genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, a polynucleotide construct with the minimal 5' flanking region showing the highest level of expression of reporter gene is identified as the promoter. Such promoter regions can be linked to a reporter gene and used to evaluate agents for the ability to modulate promoter-driven transcription.

Fragments and Variants

The term "fragment" or "variant" refers to variants and derivatives of the fusion protein described herein, containing one or more binding moieties to e.g., PD-1, MUC1, MUC16 and/or TGF-β. In certain embodiments, amino acid sequence variants of the fusion protein are contemplated. For example, in some embodiments, amino acid sequence variants of the fusion protein described herein are contemplated to improve the binding affinity and/or other biological properties of the fusion protein. Exemplary method for preparing amino acid variants include, but are not limited to, introducing appropriate modifications into the nucleotide sequence encoding the fusion protein, or by peptide synthesis. Such modifications include, for example, deletions from, and/or insertions into and/or substitutions of residues within the amino acid sequences of the fusion protein.

Any combination of deletion, insertion, and substitution can be made to the various domains to arrive at the final fusion protein, provided that the final fusion protein possesses the desired characteristics, e.g., PD-1 inhibition, MUC1/16 binding ability, and TGF-β trap. In some embodiments, fusion protein variants having one or more amino acid substitutions are provided. In some embodiments, sites of interest for substitution mutagenesis can include the CDRs and framework regions. In some embodiments, amino acid substitutions can be introduced into the variable domains of the target-binding protein of interest and the products screened for a desired activity, e.g., retained/improved antigen binding, decreased immunogenicity, or improved antibody-dependent cell mediated cytotoxicity (ADCC) or complement dependent cytotoxicity (CDC). Both conservative and non-conservative amino acid substitutions can be contemplated for preparing the antibody variants (e.g., anti-PD-1 antibody variants).

In another example of a substitution to create a variant fusion protein can be substituting one or more hypervariable region residues in a parent antibody. In general, variants are then selected based on improvements in desired properties compared to a parent antibody, for example, increased affinity, reduced affinity, reduced immunogenicity, increased pH dependence of binding. For example, an affinity matured variant antibody can be generated, e.g., using phage display-based affinity maturation techniques, such as those described herein and known in the field. Substitutions can be made in hypervariable regions (HVR) of a parent antibody to generate variants, and variants are then selected based on binding affinity, i.e., by affinity maturation. In some embodiments of affinity maturation, diversity can be introduced into the variable genes chosen for maturation by any of a variety of methods (e.g., error-prone PCR, chain shuffling, or oligonucleotide-directed mutagenesis). A secondary library can be then created. The library can be then screened to identify any antibody variants with the desired affinity. Another method to introduce diversity can involve HVR-directed approaches, in which several HVR residues (e.g., 4-6 residues at a time) can be randomized. HVR residues involved in antigen binding can be specifically identified, e.g., using alanine scanning mutagenesis or modeling. Substitutions can be in one, two, three, four, or more sites within a parent antibody sequence.

In some embodiments, a fragment or a variant of the fusion protein, as described herein can comprise a VL and a VH domain with amino acid sequences corresponding to the amino acid sequence of a naturally occurring VL or VH domain, respectively, but that has been "humanized," i.e., by replacing one or more amino acid residues in the amino acid sequence of the naturally occurring VL or VH domains (and in particular in the framework sequences) by one or more of the amino acid residues that occur at the corresponding position(s) in a VL or VH domain from a conventional 4-chain antibody from a human. This can be performed in a manner known in the field, which can be clear to the skilled person, for example on the basis of the further description herein. It should be noted that such humanized fusion protein or a fragment or a variant thereof are obtained in any suitable manner known per se and thus are not strictly limited to polypeptides that have been obtained using a polypeptide that comprises a naturally occurring VL and/or VH domain as a starting material.

In some embodiments, a fragment or a variant of the fusion protein, as described herein, comprises a VL and a VH domain with amino acid sequences corresponding to the amino acid sequence of a naturally occurring VL or VH domain, respectively, but that has been "camelized," i.e., by replacing one or more amino acid residues in the amino acid sequence of a naturally occurring VL or VH domain from a conventional 4-chain antibody by one or more of the amino acid residues that occur at the corresponding position(s) in a VL or a VH domain of a heavy chain antibody. Such "camelizing" can be preferably inserted at amino acid positions that form and/or are present at the VH-VL interface, and/or at the so-called Camelidae hallmark residues (see for example WO 94/04678 and Davies and Riechmann (1994 and 1996)). In some embodiments, the VH sequence that is used as a starting material or starting point for generating or designing the camelized single domain can be a VH sequence from a mammal, e.g., a human, such as a VH3 sequence. It should be noted that such camelized fusion protein or a fragment or a variant thereof, in certain embodiments, can be obtained in any suitable manner known in the field and thus are not strictly limited to polypeptides that have been obtained using a polypeptide that comprises a naturally occurring VL and/or VH domain as a starting material.

For example, both "humanization" and "camelization" can be performed by providing a nucleotide sequence that encodes a naturally occurring VL and/or VH domain, respectively, and then changing, one or more codons in the nucleotide sequence in such a way that the new polynucleotide sequence encodes a "humanized" or "camelized" fusion protein or a fragment or a variant thereof, respectively. This polynucleotide can then be expressed, so as to provide the desired binding capabilities (e.g., PD-1). Alternatively, in other embodiments, the fusion protein or a fragment or a variant thereof comprises a "humanized" or "camelized" antibody synthesized de now using known peptide synthesis technique from the amino acid sequence of a naturally occurring antibody comprising a VL and/or VH domain. In some embodiments, the fusion protein or a fragment or a variant thereof comprises a "humanized" or "camelized" antibody synthesized de now using known peptide synthesis technique from the amino acid sequence or nucleotide sequence of a naturally occurring antibody comprising a VL and/or VH domain, respectively, a nucleotide sequence encoding the desired humanized or camelized antibody of the disclosure, respectively, is designed and then synthesized de now using known techniques for nucleic acid synthesis, after which the nucleic acid thus obtained is expressed in using known expression techniques, so as to provide the desired antibody.

Other suitable methods and techniques for obtaining the fusion protein or a fragment or a variant thereof, starting from naturally occurring sequences for VL or VH domains, for example, comprises combining one or more parts of one or more naturally occurring VL or VH sequences (such as one or more framework (FR) sequences and/or complementarity determining region (CDR) sequences), and/or one or more synthetic or semi-synthetic sequences, and/or a naturally occurring sequence for a CH2 domain, and a naturally occurring sequence for a CH3 domain comprising amino acid substitutions that favor formation of heterodimer over homodimer, in a suitable manner, so as to provide the fusion protein or a fragment or a variant thereof.

Antibody Engineering

In some embodiments, it can be desirable to change certain amino acids containing exposed side-chains to another amino acid residue in order to provide for greater chemical stability of a final antibody, as follows. The deamidation of asparagine can occur on N-G or D-G sequences and result in the creation of an isoaspartic acid residue that introduces a kink into the polypeptide chain and decreases its stability (isoaspartic acid effect). In some embodiments, the antibodies of the fusion protein of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem can occur at a Asp-Gly sequence. Reissner and Aswad (2003) Cell. Mol. Life Sci. 60:1281. Isoaspartate formation can debilitate or completely abrogate binding of an antibody to its target antigen. See, Presta (2005) J. Allergy Clin. Immunol. 116:731 at 734. In some embodiments, the asparagine can be changed to glutamine (Gln). It can also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) J. Chromatog. 662:261. In addition, any methionine residues (typically solvent exposed Met) in CDRs can be changed to Lys, Leu, Ala, or Phe in order to reduce the possibility that the methionine sulfur would oxidize, which can reduce antigen binding affinity and also can contribute to molecular heterogeneity in the final antibody preparation. Id. In some embodiments, the methionine can be changed to alanine (Ala). Additionally, in order to prevent or minimize potential scissile Asn-Pro peptide bonds, it can be desirable to alter any Asn-Pro combinations found in a CDR to Gln-Pro, Ala-Pro, or Asn-Ala. Antibodies with such substitutions can be subsequently screened to ensure that the substitutions do not decrease the affinity or specificity of the antibody for human PD-L1, or other desired biological activity to unacceptable levels.

An antibody of the fusion protein disclosed herein can also be conjugated to a chemical moiety such as a radionuclide or other detectable label. Radionuclides include $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$Cu, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe. Fluorescent or chemiluminescent labels can include fluorophores, such as rare earth chelates, fluorescein and its derivatives, rhodamine and its derivatives, isothiocyanate, phycoerythrin, phycocyanin, allophycocyanin, o-phthaladehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating antibody molecules to the various moieties can be employed, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating antibodies are conventional and very well known in the art.

Pharmaceutical Compositions

The present disclosure provides a composition comprising the fusion protein or a fragment or a variant thereof described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the fusion protein or a fragment or a variant thereof. Any suitable carrier can be used within the context of the present disclosure, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. In some cases, the fusion protein or a fragment or a variant thereof is part of a composition formulated to protect the fusion protein or a fragment or a variant thereof from damage prior to administration. For example, the composition can be formulated to reduce loss of the fusion protein or a fragment or a variant thereof on devices used to prepare, store, or administer the fusion protein or a fragment or a variant thereof, such as glassware, syringes, or needles. The composition can be formulated to decrease the light sensitivity and/or temperature sensitivity of the fusion protein or a fragment or a variant thereof. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the fusion protein or a fragment or a variant thereof, and facilitate its administration. Formulations for fusion protein or a fragment or a variant thereof-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the fusion protein or a fragment or a variant thereof can be present in a composition with other therapeutic or biologically-active agents. For example, factors that control inflammation, such as ibuprofen or steroids, can be part of the composition to reduce swelling and inflammation associated with in tian administration of the fusion protein or a fragment or a variant thereof. Antibiotics, i.e., microbicides and fungicides, can be present to treat existing infection and/or reduce the risk of future infection, such as infection associated with the administration procedures.

In some instances, pharmaceutical compositions comprising the presently described fusion protein or a fragment or a variant thereof are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intraarticular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include the presently described fusion protein or a fragment or a variant thereof and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating can be provided around the compositions. In some embodiments, the compositions are formulated into particles (for example for administration by capsule) and some or all of the particles can be coated. In some embodiments, the compositions are formulated into particles (for example for administration by capsule) and some or all of the particles can be microencapsulated. In some embodiments, the compositions can be formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and an anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrollidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits and Articles of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In some embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. The label also indicates directions for use of the contents, such as in the methods described herein.

Use of Fusion Protein

Also disclosed herein is a use of a fusion protein of the present invention, or a polynucleotide encoding the same, in the manufacture of a medicament for use in the treatment of cancer.

Embodiments of the Invention (E1-E130) Include

E1. A fusion protein comprising:
(a) a first component that is an antibody, or a fragment or variant thereof; and
(b) a second component that is: (i) a cytokine trap, or fragment or variant thereof; or (ii) an adenosine deaminase (ADA), or fragment or variant thereof.

E2. The fusion protein of embodiment E1, wherein the first and second components are connected by a linker.

E3. The fusion protein of embodiment E1 or E2, wherein the first component is an immunoglobulin G (IgG).

E4. The fusion protein of any one of embodiments E1-E3, wherein the first component is IgG1, IgG2, IgG3, or IgG4.

E5. The fusion protein of any one of embodiments E1-E4, wherein the first component is IgG1 or IgG4.

E6. The fusion protein of any one of embodiments E1-E3, wherein the first component is a Fab, (Fab)2, (Fab')2, Fv, (Fv)2, or scFv.

E7. The fusion protein of any one of embodiments E1-E6, wherein the first component comprises a variable region of a heavy chain (VH) and a variable region of a light chain (VL).

E8. The fusion protein of any one of embodiments E1-E7, wherein the first component comprises a fragment crystallizable region (FC).

E9. The fusion protein of any one of embodiments E1-E8, wherein the first component comprises an FC1, FC2, FC3, or FC4 region, or a fragment or variant thereof.

E10. The fusion protein of any one of embodiments E1-E9, wherein the first component comprises an FC1 region.

E11. The fusion protein of any one of embodiments E1-E10, wherein the first component comprises an $F_C$ comprising a mutation.

E12. The fusion protein of any one of embodiments E1-E11, wherein the first component comprises a scFv and an FC.

E13. The fusion protein of any one of embodiments E1-E12, wherein the first component binds to a tumor antigen expressed on the surface of a tumor cell.

E14. The fusion protein of any one of embodiments E1-E13, wherein the first component binds to a tumor antigen expressed on the surface of a tumor cell, wherein the tumor antigen is selected from CD19, BCMA, CD23, BAFF-R, GPRC5D, CD44, CAIX, CD5, CD30, CD70, CD44v6, CD44v7, CD44v8, CD174, CD28, CD128, CD138, CS1, CLL-1, L1-CAM, FAP, ROR1, CEA, EGP-2, EGP-40, HER2, HER3, Folate-binding Protein, GD2, GD3, IL-13R-a2, IL-11R□, EphA2, CSPG4, KDR, EDB-F, mesothelin, CD22, EGFR, Folate receptor α, MUC-1, MUC-4, MUC-16, MAGE-A1, h5T4, PSMA, PSCA, GPC3, c-met, TAG-72, EGFR, CD20, EGFRvIII, CD123, and VEGF-R2.

E15. The fusion protein of any one of embodiments E1-E14, wherein the first component binds to a tumor antigen expressed on the surface of a tumor cell, wherein the tumor antigen is a mucin.

E16. The fusion protein of any one of embodiments E1-E15, wherein the first component binds to a tumor antigen expressed on the surface of a tumor cell, and wherein the tumor antigen is selected from MUC1, MUC2, MUC3A, MUC3B, MUC4, MUC5AC, MUC5B, MUC6, MUC7, MUC8, MUC12, MUC13, MUC15, MUC16, MUC17, MUC19, and MUC20 antigen.

E17. The fusion protein of any one of embodiments E1-E16, wherein the first component binds to a tumor antigen expressed on the surface of a tumor cell, and wherein the tumor antigen is MUC16 or MUC1.

E18. The fusion protein of any one of embodiments E1-E17, wherein the first component binds to a tumor antigen expressed on the surface of a tumor cell, and wherein the tumor antigen is MUC16.

E19. The fusion protein of any one of embodiments E1-E18, wherein the first component comprises a VL region comprising a sequence that is at least 80% identical to any one of SEQ ID NOs: 417-428.

E20. The fusion protein of any one of embodiments E1-E19, wherein the first component comprises a VH region comprising a sequence that is at least 80% identical to any one of SEQ ID NOs: 390-403.

E21. The fusion protein of any one of embodiments E1-E20, wherein the first component comprises: (a) a VL region comprising a sequence that is at least 80% identical to any one of SEQ ID NOs: 417-428; and (b) a VH region comprising a sequence that is at least 80% identical to any one of SEQ ID NOs: 390-403.

E22. The fusion protein of any one of embodiments E1-E21, wherein the first component comprises a VH region comprising a sequence that is at least 80% identical to SEQ ID NO: 399.

E23. The fusion protein of any one of embodiments E1-E22, wherein the first component comprises: (a) a VL region comprising a sequence that is at least 80% identical to SEQ ID NO: 426; and (b) a VH region comprising a sequence that is at least 80% identical to any one of SEQ ID NO: 399.

E24. The fusion protein of any one of embodiments E1-E18, wherein the first component comprises a heavy chain sequence that is at least 80% identical to SEQ ID NO: 441.

E25. The fusion protein of any one of embodiments E1-E18, wherein the first component comprises a light chain sequence that is at least 80% identical to SEQ ID NO: 443.

E26. The fusion protein of any one of embodiments E1-E18, E24, and E25, wherein the first component comprises: (a) a heavy chain sequence that is at least 80% identical to SEQ ID NO: 441; and (b) a light chain sequence that is at least 80% identical to SEQ ID NO: 443.

E27. The fusion protein of any one of embodiments E1-E17, wherein the first component binds to a tumor antigen expressed on the surface of a tumor cell, and wherein the tumor antigen is MUC1.

E28. The fusion protein of any one of embodiments E1-E17 and E27, wherein the first component comprises a VL region comprising a sequence that is at least 80% identical to any one of SEQ ID NOs: 449-453.

E29. The fusion protein of any one of embodiments E1-E17, E27, and E28, wherein the first component comprises a VH region comprising a sequence that is at least 80% identical to any one of SEQ ID NOs: 444-448.

E30. The fusion protein of any one of embodiments E1-E17 and E27-E29, wherein the first component comprises: (a) a VL region comprising a sequence that is at least 80% identical to any one of SEQ ID NOs: 449-453; and (b) a VH region comprising a sequence that is at least 80% identical to any one of SEQ ID NOs: 444-448.

E31. The fusion protein of any one of embodiments E1-E17 and E27-E30, wherein the first component comprises a VH region comprising a sequence that is at least 80% identical to SEQ ID NO: 444.

E32. The fusion protein of any one of embodiments E1-E17 and E27-E31, wherein the first component comprises a heavy chain sequence that is at least 80% identical to SEQ ID NO: 466.

E33. The fusion protein of any one of embodiments E1-E17 and E27-E32, wherein the first component comprises a light chain sequence that is at least 80% identical to SEQ ID NO: 467.

E34. The fusion protein of any one of embodiments E1-E17 and E27-E33, wherein the first component comprises: (a) a heavy chain sequence that is at least 80% identical to SEQ ID NO: 466; and (b) a light chain sequence that is at least 80% identical to SEQ ID NO: 467.

E35. The fusion protein of any one of embodiments E1-E12, wherein the first component binds to programmed cell death protein-1 (PD-1).

E36. The fusion protein of embodiment E35, wherein the first component is an IgG4 antibody comprising a sequence having at least 80% sequence identity to SEQ ID NO: 146 or 292 and having a mutation at position 108 thereof.

E37. The fusion protein of embodiment E35 or E36, wherein the first component is an IgG4 antibody comprising a sequence having at least 80% sequence identity to SEQ ID NO: 146 or 292 and having a S108P mutation.

E38. The fusion protein of embodiment E35, wherein the first component comprises a variable region of a heavy chain (VH) and is connected to the second component by a linker.

E39. The fusion protein of embodiment E35 or E36, wherein the first component comprises a variable region of a light chain (VL) and is connected to the second component by a linker.

E40. The fusion protein of embodiment E38 or E39, wherein the first component comprises a VH connected to a VL by a second linker.

E41. The fusion protein of embodiment E40, wherein the second linker comprises a sequence of any one of SEQ ID NOs: 17-34.

E42. The fusion protein of any one of embodiments E35 and E38-E41, wherein the first component comprises a VH comprising a sequence that is at least 80% identical to any one of SEQ ID NOs: 1-7, 149-164, 333-337, and 384.

E43. The fusion protein of any one of embodiments E35 and E38-E42, wherein the first component comprises a VL comprising a sequence that is at least 80% identical to any one of SEQ ID NOs: 8-13, 148, 338-343, and 385.

E44. The fusion protein of any one of embodiments E35 and E38-E43, wherein the first component comprises: (a) a VH comprising a sequence that is at least 90% identical to SEQ ID NO: 6; and (b) a VL comprising a sequence that is at least 90% identical to SEQ ID NO: 12.

E45. The fusion protein of any one of embodiments E35 and E38-E43, wherein the first component comprises: (a) a VH comprising a sequence that is at least 90% identical to SEQ ID NO: 7; and (b) a VL comprising a sequence that is at least 90% identical to SEQ ID NO: 13.

E46. The fusion protein of any one of embodiments E35 and E38-E43, wherein the first component comprises: (a) a VH comprising a sequence that is at least 90% identical to SEQ ID NO: 333; and (b) a VL comprising a sequence that is at least 90% identical to SEQ ID NO: 338.

E47. The fusion protein of any one of embodiments E35 and E38-E43, wherein the first component comprises: (a) a VH comprising a sequence that is at least 90% identical to SEQ ID NO: 334; and (b) a VL comprising a sequence that is at least 90% identical to SEQ ID NO: 339.

E48. The fusion protein of any one of embodiments E35 and E38-E43, wherein the first component comprises: (a) a VH comprising a sequence that is at least 90% identical to SEQ ID NO: 335; and (b) a VL comprising a sequence that is at least 90% identical to SEQ ID NO: 340.

E49. The fusion protein of any one of embodiments E35 and E38-E43, wherein the first component comprises: (a) a VH comprising a sequence that is at least 90% identical to SEQ ID NO: 336; and (b) a VL comprising a sequence that is at least 90% identical to SEQ ID NO: 341.

E50. The fusion protein of any one of embodiments E35 and E38-E43, wherein the first component comprises: (a) a VH comprising a sequence that is at least 90% identical to SEQ ID NO: 337; and (b) a VL comprising a sequence that is at least 90% identical to SEQ ID NO: 342.

E51. The fusion protein of any one of embodiments E35 and E38-E43, wherein the first component comprises: (a) a VH comprising a sequence that is at least 90% identical to SEQ ID NO: 335; and (b) a VL comprising a sequence that is at least 90% identical to SEQ ID NO: 343.

E52. The fusion protein of any one of embodiments E35 and E38-E43, wherein the first component comprises: (a) a VH comprising a sequence that is at least 90% identical to SEQ ID NO: 384; and (b) a VL comprising a sequence that is at least 90% identical to SEQ ID NO: 385.

E53. The fusion protein of any one of embodiments E35 and E38-E43, wherein the first component comprises: (a) a VH comprising a sequence that is at least 90% identical to SEQ ID NO: 386; and (b) a VL comprising a sequence that is at least 90% identical to SEQ ID NO: 387.

E54. The fusion protein of embodiment E35, wherein the first component is selected from: AM-0001, AMP-224, balstilimab, budigalimab, BI 754091, camrelizumab, cemiplimab, cetrelimab, dostarlimab, JTX-4014, MEDI-0680, MGA012, nivolumab, pembrolizumab, pidilizumab, prolgolimab, sasanlimab, sintilimab, spartalizumab, STI-1110, tislelizumab, toripalimab, and zimberelimab; or a fragment or variant thereof.

E55. The fusion protein of embodiment E35 or E54, wherein the first component is selected from: pembrolizumab, nivolumab, zimberelimab and cetrelimab; or a fragment or variant thereof.

E56. The fusion protein of any one of embodiments E35, E54, or E55, wherein the first component is cetrelimab, or a fragment or variant thereof.

E57. The fusion protein of embodiment E35, wherein the first component comprises: (a) a sequence that is at least 90% identical to SEQ ID NO: 15; and (b) a sequence that is at least 90% identical to SEQ ID NO: 16 or 143.

E58. The fusion protein of embodiment E35 comprising: (a) a sequence that is at least 80% identical to SEQ ID NO: 296; and (b) a sequence that is at least 80% identical to any one of SEQ ID NOs: 144, 145, and 295.

E59. The fusion protein of embodiment E35 comprising: (a) a sequence that is at least 80% identical to SEQ ID NO: 13 or 15; and (b) a sequence that is at least 80% identical to SEQ ID NO: 294 or 295.

E60. The fusion protein of any one of embodiments E1-E59, wherein the second component is a cytokine trap.

E61. The fusion protein of any one of embodiments E1-E60, wherein the cytokine trap is a TGF-β cytokine trap.

E62. The fusion protein of any one of embodiments E1-E61, wherein the cytokine trap is a TGF-β cytokine trap comprising: a transforming growth factor receptor (TGFβR), or a fragment or variant thereof; an anti-TGF-β antibody, or an antigen binding fragment or variant thereof; a TGF-β inhibitory peptide or a fragment or variant thereof; and/or a TGF-β antagonistic peptide or a fragment or variant thereof.

E63. The fusion protein of any one of embodiments E1-E62, wherein the cytokine trap is a TGF-β cytokine trap comprising a transforming growth factor beta receptor II (TGFβRII), or a fragment or variant thereof.

E64. The fusion protein of any one of embodiments E1-E63, wherein the cytokine trap is a TGF-β cytokine trap comprising a TGFβR extracellular domain, or a fragment or variant thereof.

E65. The fusion protein of any one of embodiments E1-E64, wherein the cytokine trap is a TGF-β cytokine trap comprising a TGFβRII extracellular domain, or a fragment or variant thereof.

E66. The fusion protein of any one of embodiments E1-E65, wherein the cytokine trap is a TGF-β cytokine trap comprising a TGFβRII extracellular domain, or fragment or variant thereof, comprising a sequence that is at least 80% identical to any one of SEQ ID NOs: 14, 141, and 142.

E67. The fusion protein of any one of embodiments E1-E66, wherein the cytokine trap is a TGF-β cytokine trap comprising a TGFβRII extracellular domain, or fragment or variant thereof, that binds TGF-β 1 and/or TGF-β3.

E68. The fusion protein of any one of embodiments E1-E67, wherein the cytokine trap is a TGF-β cytokine trap comprising a TGFβRII extracellular domain, or fragment or variant thereof, that does not bind TGF-β2 or binds TGF-β2 at a lower affinity than it does TGF-β 1 and TGF-β3.

E69. The fusion protein of any one of embodiments E1-E68, wherein the cytokine trap is a TGF-β cytokine trap comprising a sequence that is at least 80% identical to any one of SEQ ID NOs: 14, 141, and 142.

E70. The fusion protein of any one of embodiments E1-E69, wherein the cytokine trap is a TGF-β cytokine trap comprising a sequence that is at least 80% identical to SEQ ID NO: 14.

E71. The fusion protein of any one of embodiments E1-E70, wherein the cytokine trap is a TGF-β cytokine trap comprising an anti-TGF-β antibody or an antigen binding fragment or variant thereof.

E72. The fusion protein of any one of embodiments E1-E71, wherein the cytokine trap is a TGF-β cytokine trap comprising an anti-TGF-β antibody, or an antigen binding fragment or variant thereof, comprising a variable region of a heavy chain (VH) and a variable region of a light chain (VL).

E73. The fusion protein of any one of embodiments E1-E72, wherein the cytokine trap is a TGF-β cytokine trap comprising an anti-TGF-β antibody, or an antigen binding fragment or variant thereof, comprising a VH comprising a sequence that is at least 80% identical to any one of SEQ ID NOs: 166, 168, 169, 171, 173, and 175.

E74. The fusion protein of any one of embodiments E1-E73, wherein the cytokine trap is a TGF-β cytokine trap comprising an anti-TGF-β antibody, or an antigen binding fragment or variant thereof, comprising a VL comprising a sequence that is at least 80% identical to any one of SEQ ID NOs: 165, 167, 170, 172, 174, 176, and 178.

E75. The fusion protein of any one of embodiments E1-E74, wherein the cytokine trap is a TGF-β cytokine trap comprising an anti-TGF-β antibody, or an antigen binding fragment or variant thereof, comprising: (a) a VH comprising a sequence that is at least 80% identical to any one of SEQ ID NOs: 166, 168, 169, 171, 173, and 175; and (b) a VL comprising a sequence that is at least 80% identical to any one of SEQ ID NOs: 165, 167, 170, 172, 174, 176, and 178.

E76. The fusion protein of any one of embodiments E1-E75, wherein the cytokine trap is a TGF-β cytokine trap comprising an anti-TGF-β antibody, or an antigen binding fragment or variant thereof, comprising a VL comprising a sequence that is at least 80% identical to any one of SEQ ID NOs: 165, 167, 170, 172, 174, 176, and 178.

E77. The fusion protein of any one of embodiments E1-E76, wherein the cytokine trap is a TGF-β cytokine trap comprising a TGF-β inhibitory peptide, or a fragment or variant thereof.

E78. The fusion protein of any one of embodiments E1-E77, wherein the cytokine trap is a TGF-β cytokine trap comprising a TGF-β inhibitory peptide, or a fragment or variant thereof, comprising a sequence that is at least 80% identical to any one of SEQ ID NOs: 468-507 and 263-267.

E79. The fusion protein of any one of embodiments E1-E78, wherein the cytokine trap is a TGF-β cytokine trap comprising two or more TGF-β inhibitory peptides, or fragments or variants thereof.

E80. The fusion protein of any one of embodiments E1-E79, wherein the cytokine trap is a TGF-β cytokine trap comprising two or more TGF-β inhibitory peptides, or fragments or variants thereof, that are connected by linker(s).

E81. The fusion protein of any one of embodiments E1-E80, wherein the cytokine trap is a TGF-β cytokine trap comprising a TGF-β antagonistic peptide, or a fragment or variant thereof.

E82. The fusion protein of any one of embodiments E1-E81, wherein the cytokine trap is a TGF-β cytokine trap comprising two or more TGF-β antagonistic peptides, or fragments or variants thereof.

E83. The fusion protein of any one of embodiments E1-E82, wherein the cytokine trap is a TGF-β cytokine trap comprising two or more TGF-β antagonistic peptides, or fragments or variants thereof, that are connected by linker(s).

E84. The fusion protein of any one of embodiments E1-E59, wherein the second component is an ADA, or a fragment or variant thereof.

E85. The fusion protein of any one of embodiments E1-E59, wherein the ADA is adenosine deaminase 2 (ADA2), or a fragment or variant thereof.

E86. The fusion protein of any one of embodiments E1-E59 and E85, wherein the ADA is a fragment or variant of ADA2 that comprises at least one amino acid substitution or deletion.

E87. The fusion protein of any one of embodiments E1-E59, E85, and E86, wherein the ADA comprises a sequence that is at least 80% identical to any one of SEQ ID NOs: 273-279 and 284.

E88. The fusion protein of any one of embodiments E1-E87, wherein the first and second components are connected by a linker comprising (G4S)n, wherein n is 2, 3, 4, 5, or 6 (SEQ ID NO: 555).

E89. The fusion protein of any one of embodiments E1-E88, wherein the first and second components are connected by a linker comprising (Gly)n, wherein n is 6, 7, or 8 (SEQ ID NO: 33).

E90. The fusion protein of any one of embodiments E1-E89, wherein the first and second components are connected by a linker comprising (EAAAK)n, wherein n is 1, 2, 3, 4, 5, or 6 (SEQ ID NO: 34).

E91. The fusion protein of any one of embodiments E1-E90, wherein the first and second components are connected by a linker comprising A (EAAAK)4ALEA (EAAAK)4A (SEQ ID NO: 31).

E92. The fusion protein of any one of embodiments E1-E91, wherein the first and second components are connected by a linker comprising a sequence of any one of SEQ ID NOs: E17-E34.

E93. A polynucleotide encoding the fusion protein of any one of embodiments E1-92.

E94. An expression vector comprising the polynucleotide of embodiment E93 operably linked to a promoter.

E95. The vector of embodiment E94, wherein the promoter is constitutive, tissue specific, and/or inducible.

E96. The vector of embodiment E94, wherein the promoter is a small molecule ligand-inducible two polypeptide ecdysone receptor-based gene switch.

E97. The vector of any one of embodiments E94-E96, wherein the vector is an adenoviral vector.

E98. A pharmaceutical composition comprising: (a) the fusion protein of any one of embodiments E1-E92, or a polynucleotide encoding the same; and (b) a pharmaceutically-acceptable excipient.

E99. The pharmaceutical composition of embodiment E98, comprising an expression vector comprising the polynucleotide.

E100. A method of treating cancer, the method comprising contacting a cell with the fusion protein of any one of embodiments E1-E92, or a polynucleotide encoding the same.

E101. The method of embodiment E100, wherein the cell is contacted with an expression vector comprising the polynucleotide.

E102. The method of embodiments E100 or E101, wherein the cell is a cancer cell.

E103. The method of any one of embodiments E100-E102, wherein the cell is a mammalian cell.

E104. A method of treating cancer in a subject in need of such treatment, the method comprising administering to the subject the pharmaceutical composition of embodiments E98 or E99.

E105. The method of embodiment E104, wherein the cancer is a refractory cancer.

E106. The method of embodiment E104 or E105, wherein the subject is non-responsive to treatment with an anti-PD-1 antibody or a CTLA-4 antibody.

E107. The method of any one of embodiments E104-E106, further comprising administering one or more additional anti-cancer agents.

E108. The method of any one of embodiments E104-E107, further comprising administering a PD-1 inhibitor, PD-L1 inhibitor, and/or a CTLA-4 inhibitor.

E109. The method of embodiment E108, wherein the PD-1 inhibitor is an anti-PD-1 antibody, or a fragment or variant thereof.

E110. The method of embodiment E108, wherein the CTLA-4 inhibitor is an anti-CTLA-4 antibody, or a fragment or variant thereof.

E111. The method of any one of embodiments E104-E110, further comprising administering a cytokine.

E112. The method of any one of embodiments E104-E111, further comprising administering a cytokine that is a fusion protein comprising IL-15 and IL-15Rα.

E113. The method of any one of embodiments E104-E112, wherein the subject is a mammal.

E114. The method of any one of embodiments E104-E113, wherein the subject is human.

E115. The method of any one of embodiments E104-E114, wherein the cancer is selected from mesothelioma, glioblastoma, endometrial cancer, colorectal cancer, gastric cancer, cervical cancer, ovarian cancer, pancreatic cancer, prostate cancer, breast cancer, stomach cancer, bladder cancer, liver cancer, Hodgkin's lymphoma, lung cancer, skin cancer, renal cancer, head and neck cancer, melanoma, bronchus cancer, urinary tract cancer, anal cancer, brain cancer, esophageal cancer, cervical cancer, uterine cancer, cancer of the oral cavity or pharynx, kidney cancer, testicular cancer, biliary tract cancer, small bowel cancer, appendix cancer, salivary gland cancer, thyroid gland cancer, adrenal gland cancer, osteosarcoma, chondrosarcoma, and a cancer of a hematological tissue.

E116. The method of any one of embodiments E104-E115, wherein the cancer is cutaneous squamous-cell carcinoma, melanoma, or basal cell cancer.

E117. The method of any one of embodiments E104-E115, wherein the cancer is non-small cell lung cancer (NSLC) or small cell lung cancer (SCLC).

E118. The method of any one of embodiments E104-E115, wherein the cancer is triple negative breast cancer (TNBC).

E119. The method of any one of embodiments E104-E118, further comprising administering an effective amount of T cells engineered to express an exogenous receptor.

E120. The method of embodiment E119, wherein the exogenous receptor is a chimeric antigen receptor.

E121. The method of embodiment E120, wherein the chimeric antigen receptor comprises an antigen binding domain that binds to an epitope on CD19, BCMA, CD23, BAFF-R, GPRC5D, CD44, CAIX, CD5, CD30, CD70, CD44v6, CD44v7, CD44v8, CD174, CD28, CD128, CD138, CS1, CLL-1, L1-CAM, FAP, ROR1, CEA, EGP-2, EGP-40, HER2, HER3, Folate-binding Protein, GD2, GD3, IL-13R-a2, IL-11R□, EphA2, CSPG4, KDR, EDB-F, mesothelin, CD22, EGFR, Folate receptor α, MUC-1, MUC-4, MUC-16, MAGE-A1, h5T4, PSMA, PSCA, GPC3, c-met, TAG-72, EGFR, CD20, EGFRvIII, CD123, or VEGF-R2.

E122. The method of embodiment E120 or E121, wherein the chimeric antigen receptor is an engineered T-cell receptor.

E123. The method of any one of embodiments E120-E122, wherein the chimeric antigen receptor comprises an antigen binding domain comprising a sequence that is at least 90% identical to any one of SEQ ID NOs: 37-56.

E124. The method of any one of embodiments E120-E122, wherein the chimeric antigen receptor comprises an antigen binding domain comprising a sequence that is at least 90% identical to SEQ ID NO: 35 or 36.

E125. The method of any one of embodiments E119-E124, wherein the effective amount of engineered T-cells is at least 102 cells/kg.

E126. The method of any one of embodiments E119-E125, wherein the effective amount of engineered T-cells is at least 104 cells/kg.

E127. The method of any one of embodiments E119-E126, wherein the effective amount of engineered T-cells is at least 105 cells/kg.

E128. The method of any one of embodiments E119-E127, wherein the engineered T-cells express a cytokine.

E129. The method of any one of embodiments E119-E128, wherein the engineered T-cells express a cytokine comprising a fusion protein comprising IL-15 and IL-15Rα.

E130. A use of the fusion protein of any one of embodiments E1-E92, or a polynucleotide encoding the same, in the manufacture of a medicament for use in the treatment of cancer.

EXAMPLES

These examples are provided for illustrative purposes only and do not in any way limit the scope of the claims provided herein.

Example 1. Fusion Protein of Anti-PD-1-TGF-β Trap

Anti-PD-1 VHs and VLs were synthesized and formatted in IgG, scFv-Fc or scFv configurations with TGFβRII fused at C-terminal by linker (G4S)2 (SEQ ID NO: 563). Anti-PD-1-trap fusion proteins were transiently expressed in Expi293 cells according to manufacturer's protocol. To purify the fusion proteins, the transfected supernatants were loaded to onto a protein L column using AKTA AVANT. The column was washed with PBS, before the protein was eluted with IgG elution buffer (Pierce). The eluted protein was then buffer-exchanged into PBS using a PD-10 column (GE Healthcare).

Surface Plasmon Resonance

Surface plasma resonance (SPR) analysis was performed using Biacore3000, CM5 chip, an amine-coupling kit, 10×HBS-P running buffer and Glycine for regeneration (GE Healthcare). For anti-PD-1 kinetic assay, purified PD-1 Fc fusion protein was immobilized on CM5 chip using a pre-defined ligand immobilization program. Purified anti-PD-1-Trap fusion proteins were diluted in HBS-P running buffer to a range of final concentrations and injected. Dissociation was allowed to proceed followed by a pulse of 10 mM Glycine (pH 1.5) for regeneration of the chip surface.

To investigate if the anti-PD-1-trap fusion protein could simultaneously bind to PD-1 and TGFβRII, 100 nM of anti-PD-1 trap fusion protein was injected to PD-1 immobilized CM5 chip for 3 minutes, followed by 3 minutes of dissociation. Subsequently, different isoforms of TGF-β were injected to examine the binding of TGF-β to PD-1 bond anti-PD-1-trap fusion protein.

Figure 6:
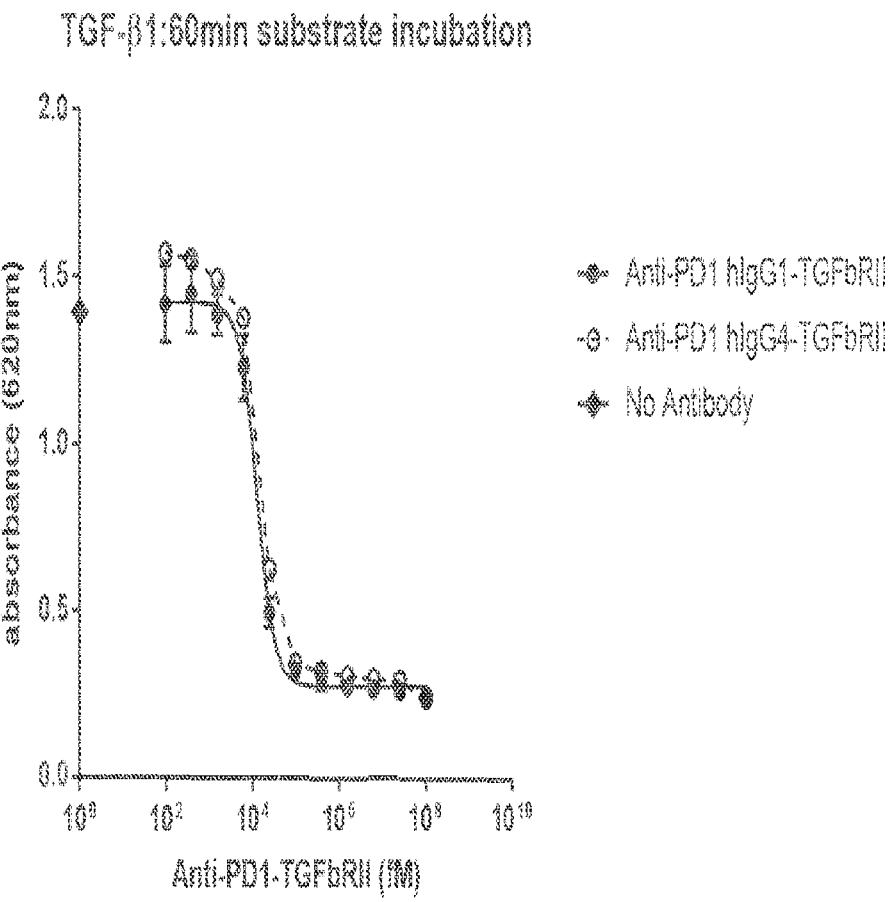
FIG. 6 is a graph showing neutralization of TGF-β isoform signaling by anti-PD-1 (VH6-VL5) IgG1-TGFβRII and anti-PD-1 (VH6-VL5) IgG4-TGFβRII.
Figure 7:
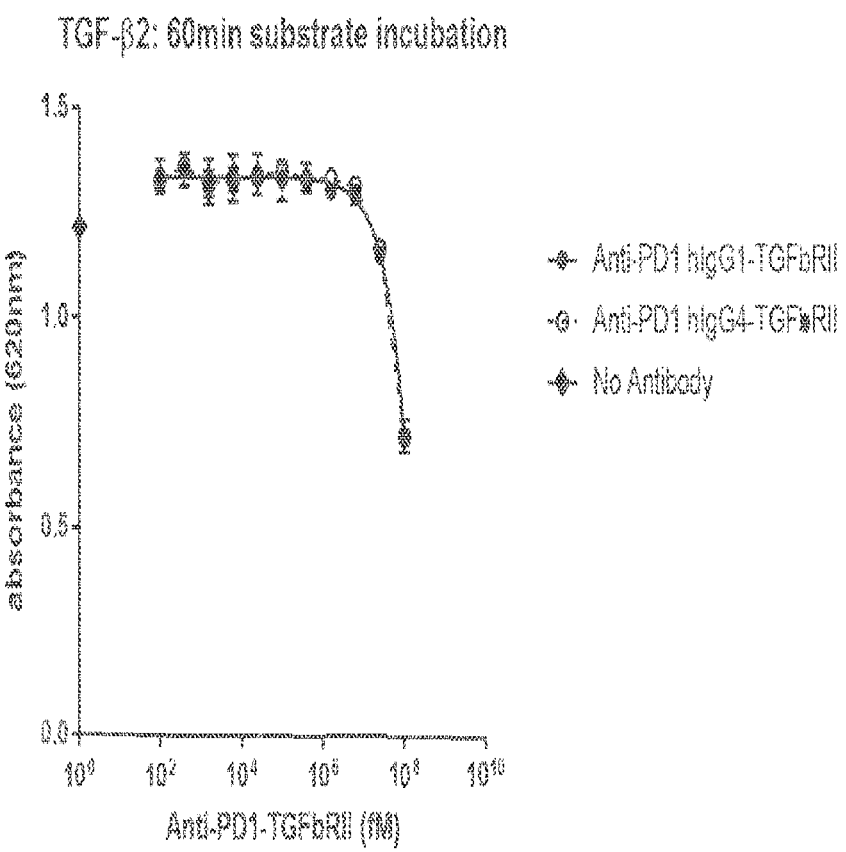
FIG. 7 is a graph showing neutralization of TGF-β2 isoform by anti-PD-1(VH6-VL5) IgG1-TGFβRII and anti-PD-1(VH6-VL5) IgG4-TGFβRII.
Figure 8:
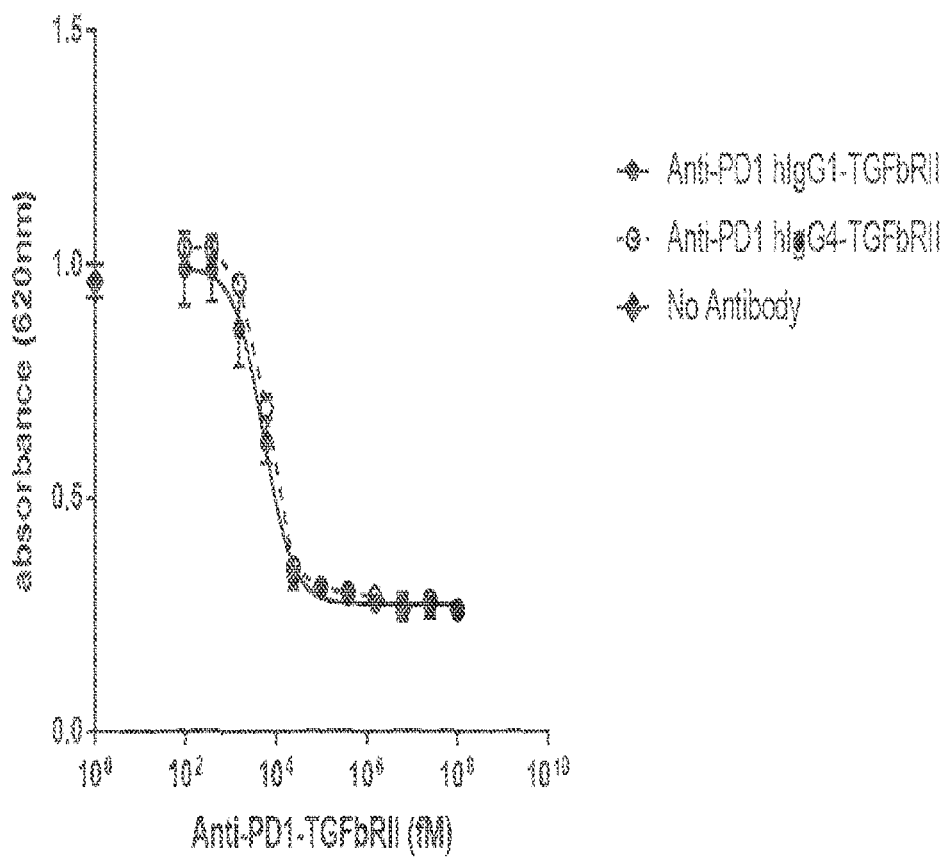
FIG. 8 is a graph showing neutralization of TGF-β3 isoform signaling by anti-PD-1(VH6-VL5) IgG1-TGFβRII and anti-PD-1(VH6-VL5) IgG4-TGFβRII.

To analyze the binding affinity of anti-PD-1-TGFβRII to TGF-β isoforms, anti-PD-1-TGFβRII were immobilized on CM5 chip and then TGF-β proteins were diluted in HBS-P running buffer to a range of final concentrations and injected to measure the binding affinity of TGF-β to immobilized anti-PD-1-TGFβRII. Affinity of anti-PD-1 (VH6-VL5 or VH7-VL6)-TGFβRII fusion protein to immobilized PD-1 is shown in Table 3 (FIGS. 6-8). Affinity of TGF-β isoforms to immobilized anti-PD-1 IgG4 antibody (VH6-VL5)-TGFβRII fusion protein is shown in Table 4. As observed, the fusion protein bound to TGF-β1 and TGF-β3 with high affinity and bound to TGF-β2 with lower affinity.

TABLE 3

Affinity of anti-PD-1-TGFβRII to immobilized PD-1

| Anti-PD-1-TGFβRII format | $K_D$ (M) |
| --- | --- |
| Anti-PD-1(VH7-VL6) IgG4-TGFβRII | 3.79e−11 |
| Anti-PD-1(VH6-VL5) IgG4-TGFβRII | 2.95e−11 |
| Anti-PD-1(VH7-VL6) IgG1-TGFβRII | 8.11e−13 |
| Anti-PD-1(VH6-VL5) IgG1-TGFβRII | 7.64e−12 |
| Anti-PD-1(VH7-VL6) scFv-Fc-TGFβRII | 3.53e−10 |
| Anti-PD-1(VH6-VL5) scFv-Fc-TGFβRII | 2.79e−10 |
| Anti-PD-1(VH7-VL6) scFv-TGFβRII | 7.77e−9 |
| Anti-PD-1(VH6-VL5) scFv-TGFβRII | 1.97e−8 |

TABLE 4

Affinity of TGF-β to immobilized anti-PD-1(VH6-VL5) IgG4-TGFβRII

| Anti-PD-1-TGFβRII | TGF-β isoform | $K_D$ (M) |
| --- | --- | --- |
| Anti-PD-1(VH6-VL5) IgG4-TGFβRII | TGF-β1 | 5.22e−12 |
| | TGF-β2 | 8.59e−10 |
| | TGF-β3 | 2.19e−12 |

Binding affinity of various anti-PD-1 variants fused to TGFβRII were assessed by surface plasmon resonance (SPR) assay using Biacore 3000. PD-1 fused to human Fc region was immobilized on sensor chip CM5. Different concentrations of various fusion proteins were injected in solution phase and data was analyzed using BIAevaluation to calculate KD of the fusion proteins. As shown in Table 5, variants such as anti-PD-1(VH6-VL5)-TGFβRII fusion protein and anti-PD-1 (VH7-VL6)-TGFβRII fusion protein were found to have similar binding affinity to PD-1 compared to respective anti-PD-1 alone.

TABLE 5

Affinity of two anti-PD-1-TGFβRII fusion proteins as compared to the respective anti-PD-1 alone

| Fusion Protein | Binding affinity to PD-1-Fc antigen ($K_D$, M) |
| --- | --- |
| Anti-PD-1(VH6-VL5)-TGFβRII | 3.42E−13 |
| Anti-PD-1(VH6-VL5) | 4.74E−13 |
| Anti-PD-1(VH7-VL6)-TGFβRII | 6.69E−13 |
| Anti-PD-1(VH7-VL6) | 2.44E−13 |

PD-1/PD-L1 Blockade Assay

Figure 5:
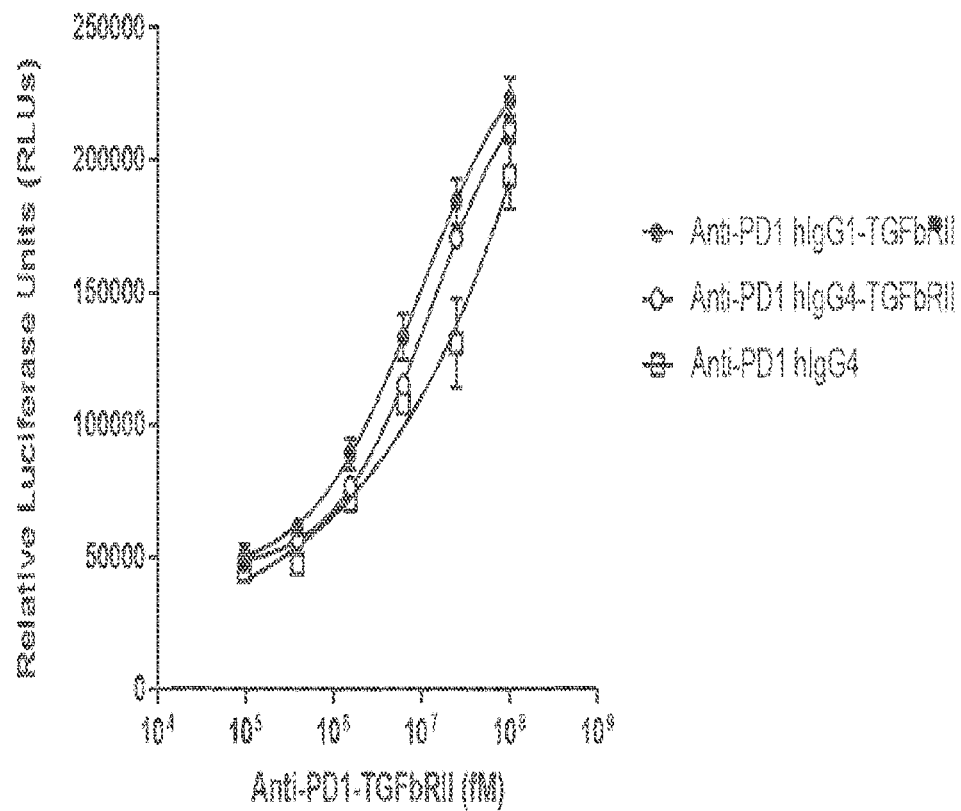
FIG. 5 is a graph showing blockade of PD-1/PD-L1 interaction by anti-PD-1 (VH6-VL5) IgG1-TGFβRII and anti-PD-1 (VH6-VL5) IgG4-TGFβRII.

To investigate if the anti-PD-1-TGFβRII fusion proteins could function as an anti-PD-1 by blocking the PD-1/PD-L1 interaction, a PD-1/PD-L1 blockade bioassay kit from Promega was employed. In brief, the PD-L1 aAPC/CHO-K1 cells were thawed one day prior to the start of the assay and allowed to recover overnight at 37° C., 5% $CO_2$ for 16 to 20 hours. To generate a dose response curve, serial dilutions of anti-PD-1 TGFβRII proteins ranging from 100 nM to 0.098 nM were prepared. The plates were then removed from the incubator and cell media was discarded. Antibodies of interest were then added directly to the plate containing PD-L1 aAPC/CHO-K1 cells. Following this step, PD-1 effector cells were then thawed and added to the 96-well plate. Plates were incubated for at 37° C., 5% $CO_2$ for 6 hours. Bio-Glo™ luciferase substrate reagent (Promega) was added to each well and Relative Luciferase Units (RLUs) were measured on a Glomax 96-microplate luminometer. The $IC_{50}$ of the anti-PD-1 TGFβRII proteins were determined by fitting the RLU-concentration data to a four parameter logistic equation. These values were used as a measure of PD-1/PD-L1 blocking potency (FIG. 5).

HEK-Blue TGF-β Assay

To examine the efficacy of anti-PD-1 TGFβRII fusion proteins to neutralize the function of TGF-β, a stable cell line with induced reporter gene (HEK-Blue™ TGB-β reporter cell line, Invitrogen) was utilized. This stable cell line allows for the detection of bioactive TGF-β via the activation of TGF-β/SMAD pathway, leading to the production of secreted embryonic alkaline phosphatase (SEAP), which can be quantified. In brief, TGF-β1, TGF-β2, and TGF-β3 were diluted to a pre-determined $EC_{50}$ concentration and added to a flat bottom 96-well plate. To generate a dose response curve, serial dilutions of anti-PD-1 TGFβRII proteins were then added to the plate containing different isoforms of TGF-β. Plates were incubated for 30 minutes at 37° C. The HEK-Blue™ TGF-β cells were then added to the plate at a final concentration of $0.7 \times 10^6$ cells/mL. Plates were then incubated at 37° C., 5% $CO_2$ for a total of 20 hours. Following the incubation, an aliquot of supernatant was removed and added to a plate containing the QUANTI-Blue™ substrate (Invitrogen) used to quantify secreted SEAP. Plates were incubated for one hour at 37° C. The plates were then read on a SpectraMax Plus plate reader at 620 to 655 nm. The $IC_{50}$ was determined by fitting absorbance-concentration data to a four-parameter logistic equation (GraphPad Prism). Results of the efficacy of various anti-PD-1 TGFβRII fusion proteins in comparison to controls are depicted in FIGS. 5-8.

Tables 6 and 7 further lists various fusion protein constructs tested and the inhibition of TGF-β1 induced reported gene activity.

TABLE 6

Summary of $IC_{50}$-inhibition of TGF-β1 induced reporter gene activity for various fusion constructs

| Fusion Protein | $IC_{50}$ (pM) |
| --- | --- |
| Anti-PD-1 (VL5-VH6).IgG4 | 9.0 |
| Anti-PD-1 (VL5-VH6).IgG4(S108P). TGFbRII | 9.7 |
| Anti-PD-1 (VL5-VH6) ScFv-Fc | 4.3 |
| Anti-PD-1 (VL6-VH7).IgG4. TGFbRII | 5.6 |
| Anti-PD-1 (VL6-VH7).IgG4(S108P). TGFbRII | 9.3 |
| Anti-PD-1 (nVL1-nVH3).IgG4-TGFbRII | 10.7 |
| Anti-PD-1 (nVL1-nVH3).scFv-Fc-TGFbRII | 6.5 |
| Anti-PD-1 (nVL1-nVH7).IgG4-TGFbRII | 15.1 |
| Anti-PD-1 (nVL1-nVH8).IgG4-TGFbRII | 54.5 |
| Anti-RSV IgG4-TGFbRII | 8.6 |
| Anti-RSV S108P IgG4-TGFbRII | 6.9 |
| Anti-RSV scFv-Fc4 | 8.9 |

TABLE 7

Summary of TGF-β1 neutralization activity of various fusion constructs

| Fusion Protein | $IC_{50}$ (pM) |
| --- | --- |
| Anti-PD-1 (VL5/VH6).IgG4-Linker2 -TGFbRII | 1.2 |
| Anti-PD-1 (VL5/VH6).IgG4-Linker12 -TGFbRII | 2.7 |
| Anti-PD-1 (VL5/VH6).IgG4-Linker7 -TGFbRII | 1.1 |
| Anti-PD-1 (VL5/VH6).IgG4-Lmker8-TGFbRII | 1.2 |
| Anti-PD-1 (VL5/VH6).IgG4-Linker10 -TGFbRII | 1.9 |

PD-1 Binding of Various Anti-PD-1IgG4-TGFbRII Fusion Constructs

PD-1-Fc antigen and reference antigen was immobilized on Biacore CM5 surface. 6-12 replicated series diluted concentrations of various anti-PD-1 IgG4-TGFbRII (Table 8) were series injected on PD-1-Fc antigen and reference surface. Kinetics data was evaluated for 1:1 model: Langmuir with mass transfer. As observed in in the table, the binding affinity ($K_D$) of Anti-PD-1 IgG4-TGFbRII with PD-1-Fc antigen was between $10^{12}$ to $10^{10}$ range.

TABLE 8

PD-1 binding affinity analysis of PD-1 IgG4-TGFbRII fusion proteins

| Fusion Protein | $K_D$ (M) |
| --- | --- |
| Anti-PD-1 (nVL1-nVH3).IgG4 | 1.48E−11 |
| Anti-PD-1 (nVL1-nVH3).IgG4-TGFbRII | 2.77E−11 |
| Anti-PD-1 (nVL1-nVH3).IgG4(S108P) | 1.41E−11 |
| Anti-PD-1 (nVL1-nVH3).IgG4-(S108P)-TGFbRII | 8.16E−12 |
| Anti-PD-1 (nVL1-nVH7).IgG4-TGFbRII | 1.47E−10 |
| Anti-PD-1 (nVL1-nVH8).IgG4-TGFbRII | 3.21E−10 |

Figure 20:
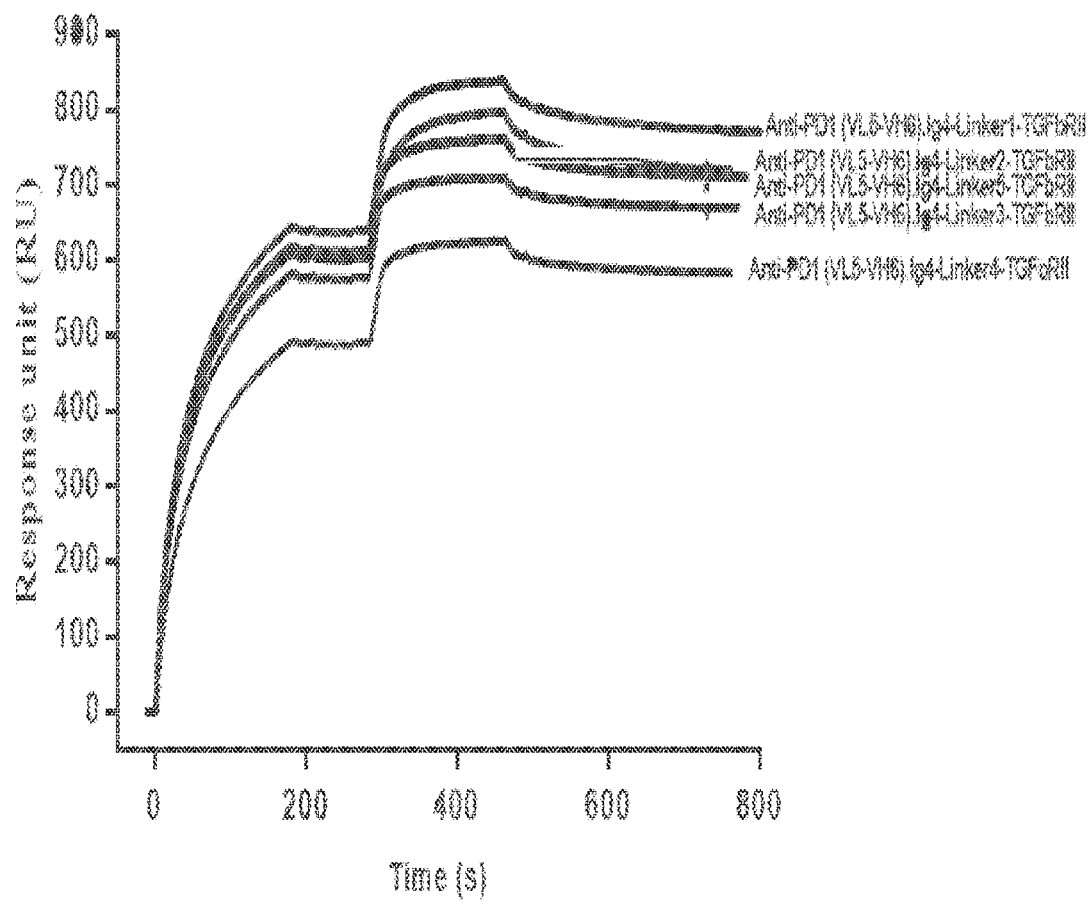
FIG. 20 is a graph depicting Biacore analysis of simultaneous binding of TGF-b1 and PD-1 by anti-PD-1 (VH6/VL5)-TGFRII fusion proteins using different linkers.

Simultaneous PD-1 and TGF-β1 Binding of Various Anti-PD-1 IgG4-TGFβRII Fusion Constructs To investigate if the anti-PD-1-TGFRII fusion proteins (Table 9) with different linkers could simultaneously bind to PD-1 and TGF-β1, the following constructs were made and tested in a Biacore experiment. PD-1-Fc antigen was immobilized on a Biacore CM5 chip surface. Anti-PD-1 (VL5-VH6). IgG4-linker-TGFbRII was injected over sensor surfaces, followed by TGFβ1 over sensor surfaces. As shown in FIG. 20, all the anti-PD-1 (VL5-VH6). IgG4-linker-TGFRII constructs bound to both of PD-1-Fc antigen and TGF β1 simultaneously.

TABLE 9

Anti-PD-1 (VL5-VH6).IgG4-linker-TGFRII constructs with various linkers

| Fusion protein | Linker |
| --- | --- |
| Anti-PD-1 (VL5-VH6).IgG4-Linker 2 -TGFbRII | GGGGSGGGS (Linker 2) (SEQ ID NO. 293) |
| Anti-PD-1 (VL5-VH6).IgG4-Linker12 -TGFbRII | DPVLEREDKVTTSKNPGS (linker 12) (SEQ ID NO: 27) |
| Anti-PD-1 (VL5-VH6).IgG4-Linker7 -TGFbRII | DPGSGSVPLGSGSNPGS (linker7) (SEQ ID NO: 22) |
| Anti-PD-1 (VL5-VH6).IgG4-Linker8 -TGFbRII | DPGSGGSVPLGSGGSNPGS (linker 8) (SEQ ID NO: 23) |
| Anti-PD-1 (VL5-VH6).IgG4-Linker10 -TGFbRII | DPGVLEREDVPTTSYPNPGS (linker10) (SEQ ID NO: 25) |

Example 2. Anti-PD-1-TGF-β Trap Promotes T Cell Activation in In Vitro Culture

To assess the ability of the anti-PD-1-TGF-β trap to promote T cells functions, peripheral blood mononuclear cells (PBMCs) purified using Ficoll-Hypaque from a leukapheresis product (obtained from a normal healthy donor under an Institutional Review Board (IRB) approved protocol) were used in vitro. PBMCs were labeled with the cell proliferation dye CellTrace violet and stimulated with anti-CD3 and anti-CD28. At the end of the incubation culture supernatants were collected and stored until used for IFN-γ release assay. The cells were labeled with fluorescent conjugated antibodies to assess T cell proliferation.

Figure 9A:
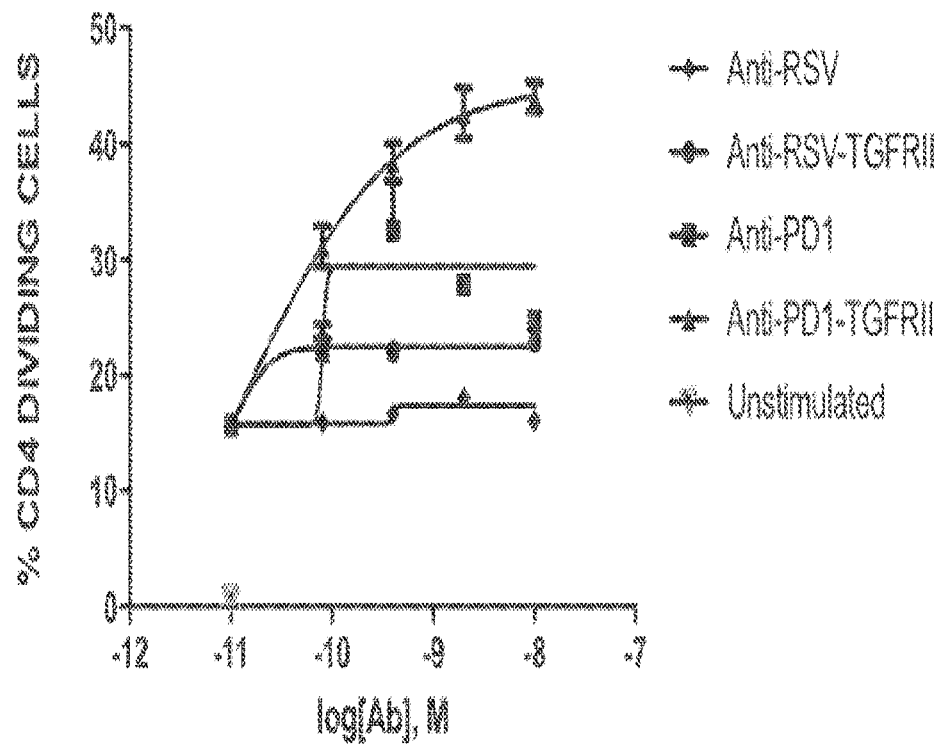
FIG. 9A, FIG. 9B, and FIG. 9C are graphs showing enhanced proliferation and IFN-γ production by stimulated PBMCs in the presence of anti-PD-1-TGFRII fusion protein in a dose dependent manner compared to anti-PD-1 or control antibodies.
Figure 9B:
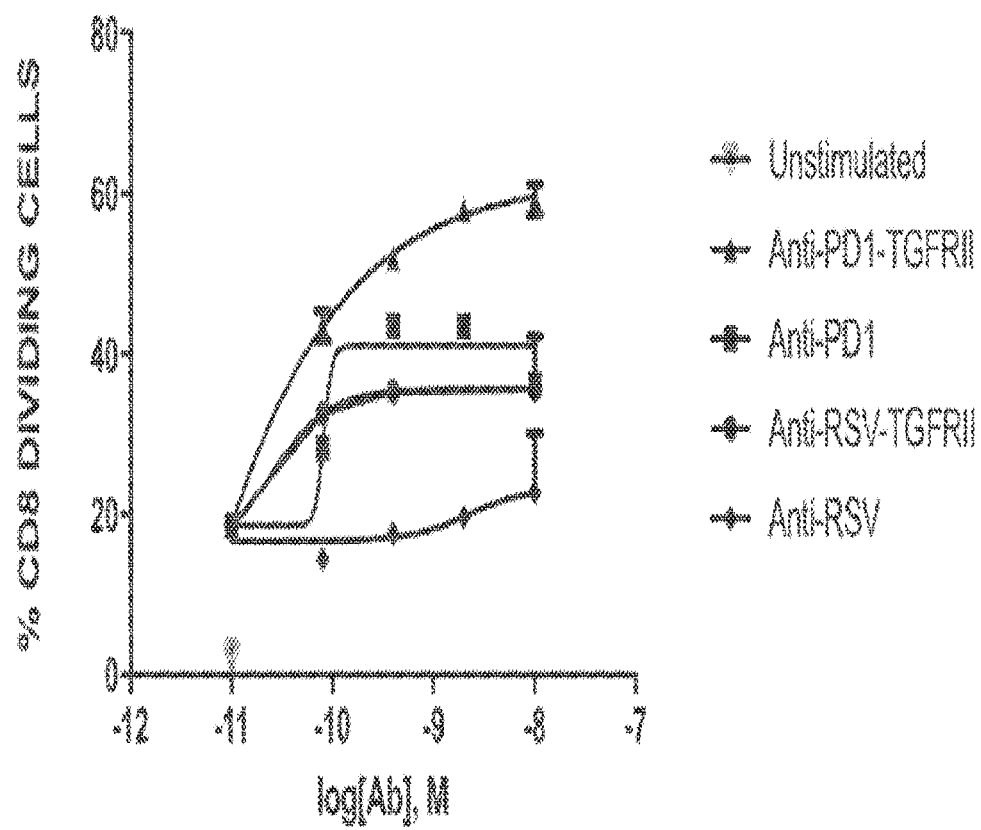
Figure 9C:
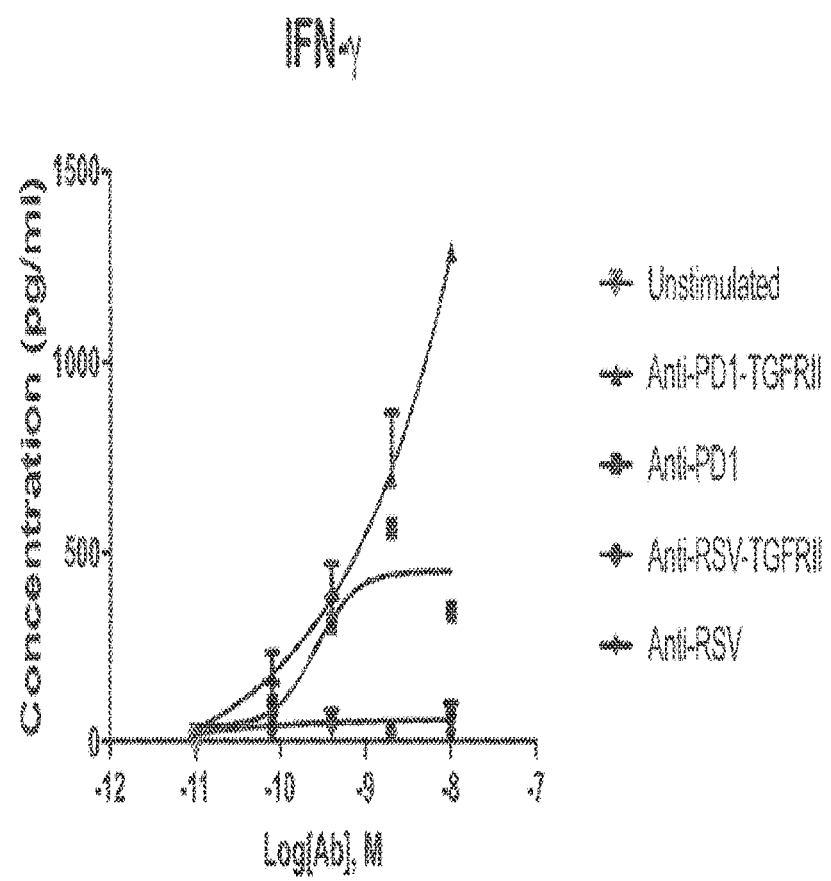

Stimulated PBMCs in the presence of anti-PD-1-TGF-β trap showed enhanced proliferation and IFN-γ production in a dose dependent manner compared to anti-PD-1 or anti-RSV control antibodies suggesting the ability of the fusion molecule to target both the PD-1/PD-L1 and TGF-β pathways (FIGS. 9A-9C). The data also demonstrates an additive enhanced effect of the fusion molecule compared to anti-PD-1 alone.

Anti PD-1-TGF-RII Exhibits Superior Anti-Tumor Response Compared to and PD-1 Alone in an In Vitro Model of Colorectal Cancer Effectiveness of anti-PD-1-TGFRII fusion protein was evaluated in an in vitro model of colorectal cancer. PBMCs purified from healthy donor were co-cultured with cancer cell line HT-29 for 5 days. The cells were stimulated with anti-CD3 in the presence of isotype control, anti-PD-1 or anti-PD-1-TGFRII fusion protein. The culture supernatants were collected and IFN-γ levels were quantified by MSD per manufacturer's protocol. The cells were collected and target occupancy on T cells were analyzed by flow cytometry. The levels of TGF-β1, TGF-β2 and TGF-β3 in cell culture supernatants were quantified by Luminex per manufacturer's protocol.

Figure 9D:
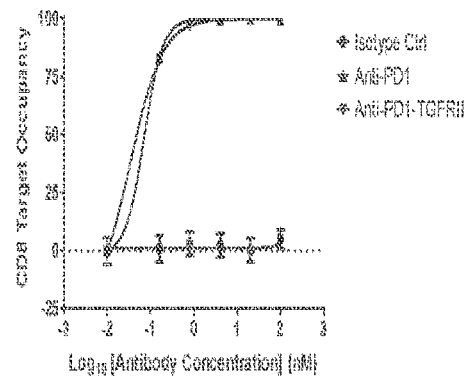
FIG. 9D and FIG. 9E are graphs showing PD-1 receptor occupancy on CD8$^+$ T cells and IFN-γ production respectively when anti-PD-1-TGFRII fusion protein is added to co-culture of PBMC and colorectal cancer (colorectal adenocarcinoma) cell line.

FIG. 9D, shows that anti-PD-1-TGFRII binds to PD-1 on CD8+ T cell surface similar to that of anti PD-1. As shown in FIG. 9E anti-PD-1-TGFRII fusion protein promoted higher level of IFN-γ production compared to anti-PD-1 or isotype control. FIG. 9H. TGF-β1 produced in HT-29 PBMC coculture system is completely neutralized upon anti-PD-1-TGFRII treatment even at the lowest dose tested. FIG. 9I. TGF-β2 produced in HT-29 PBMC coculture system is partially neutralized upon anti-PD-1-TGFRII treatment. Overall, results from this in vitro model exhibit superior anti-tumor response of anti-PD-1-TGFRII fusion protein compared to an anti-PD-1 antibody.

Anti-PD-1-TGFRII Exhibits Superior Anti-Tumor Response Compared to Anti-PD-1 Alone in an In Vitro Model of Head and Neck Cancer Effectiveness of anti-PD-1-TGFRII fusion protein was evaluated in an in vitro model of head and neck cancer. PBMCs purified from healthy donor were co-cultured with cancer cell line Detroit 562 for 5 days. The cells were stimulated with anti-CD3 in the presence of isotype control, anti-PD-1 or anti-PD-1-TGFRII fusion protein. The culture supernatants were collected and IFN-γ levels were quantified by MSD per manufacturer's protocol. The cells were collected and target occupancy on T cells were analyzed by flow cytometry. The levels of TGF-β1, TGF-β 2 and TGF-33 in cell culture supernatants were quantified by luminex per manufacturer's protocol.

Figure 9F:
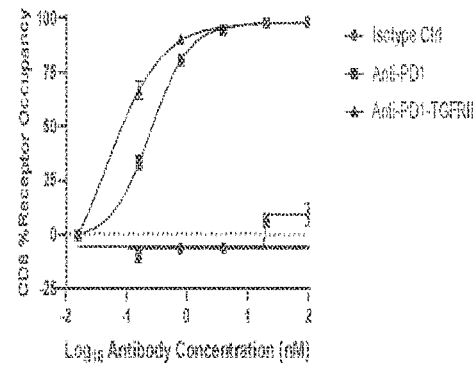
FIG. 9F and FIG. 9G are graphs showing PD-1 receptor occupancy on CD8+ T cells and IFN-γ production respectively when anti-PD-1-TGFRII fusion protein is added to co-culture of PBMC and head and neck cancer (pharyngeal carcinoma) cell line.
Figure 9E:
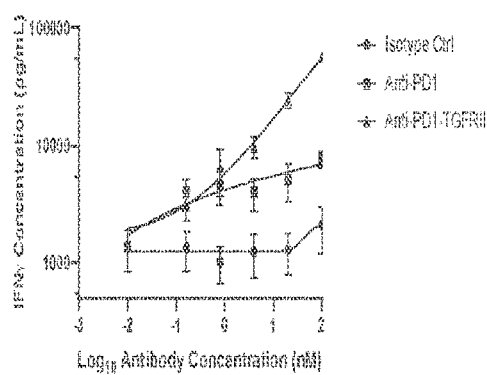
Figure 9G:
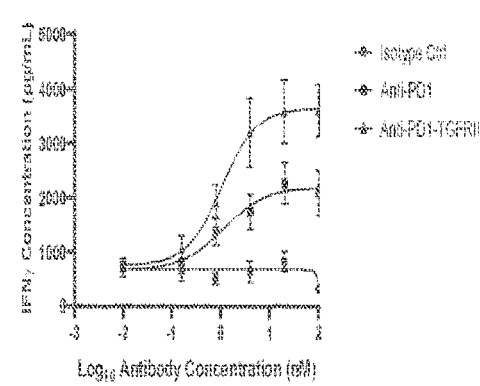
Figure 9H:
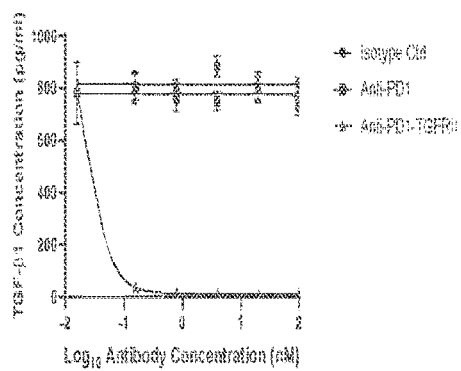
FIG. 9H and FIG. 9I are graphs depicting TGF-β1 and TGF-β2 concentration respectively in supernatant of PBMC and colorectal cancer (colorectal adenocarcinoma) cells co-culture in presence of anti-PD-1-TGFRII fusion protein.
Figure 9J:
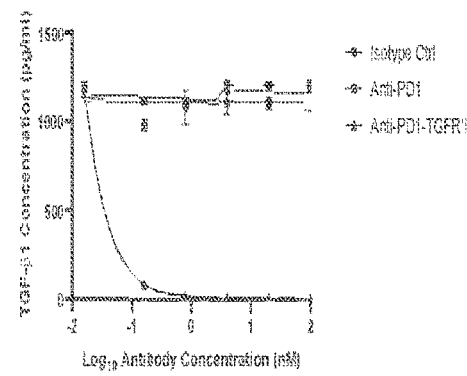
FIG. 9J and FIG. 9K are graphs depicting TGF-β1 and TGF-β2 concentration respectively in supernatant of PBCM and head and neck cancer (pharyngeal carcinoma) cells co-culture in presence of anti-PD-1-TGFRII fusion protein.
Figure 9I:
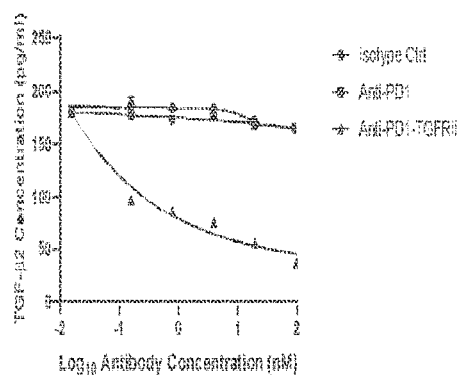
Figure 9K:
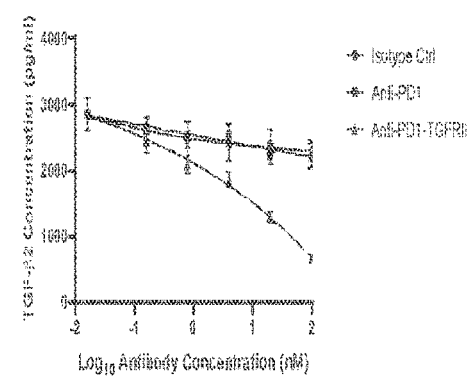

FIG. 9F, shows that anti-PD-1-TGFRII binds to PD-1 on CD8+ T cell surface similar to that of anti PD-1. As shown in FIG. 9G, anti-PD-1-TGFRII fusion protein promoted higher level of IFN-γ production compared to anti-PD-1 or isotype control. FIG. 9J. TGF-β1 produced in Detroit 562 PBMC coculture system is completely neutralized upon anti-PD-1-TGFRII treatment even at the lowest dose tested. FIG. 9K. TGF-β 2 produced in Detroit 562 PBMC coculture system is partially neutralized upon anti-PD-1-TGFRII treatment. Overall, results from this in vitro model exhibit superior anti-tumor response of anti-PD-1-TGFRII fusion protein compared to an anti-PD-1 antibody.

Anti PD-1-TGF-RI Exhibits Superior Anti-Tumor Response Compared to and PD-1 Alone in an In Vitro 3D Tumor Spheroid Model of Colorectal Cancer Effectiveness of anti-PD-1-TGFRII fusion protein was evaluated in an in vitro 3D tumor spheroid model of colorectal cancer. 3D tumor spheroids were generated by coculturing colorectal cancer cell line HT-29 and a fibroblast cell line. PBMCs purified from healthy donor were then added to spheroid culture. The cells were stimulated with anti-CD3 in the presence of isotype control, anti-PD-1 or anti-PD-1-TGFRII fusion protein for 5 days. The culture supernatants were collected and IFN-γ levels were quantified by MSD per manufacturer's protocol.

Figure 9L:
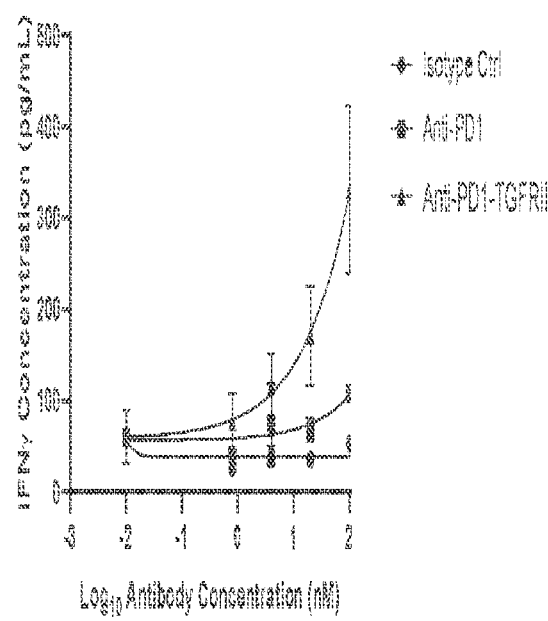
FIG. 9L and FIG. 9M are graphs depicting IFN-γ production respectively in 3D spheroid culture of colorectal cancer (colorectal adenocarcinoma) cells or head & neck cancer (pharyngeal carcinoma) cells and PBMC in presence of anti-PD-1-TGFRII fusion protein as compared to anti-PD-1 alone.

As shown in FIG. 9L, anti-PD-1-TGFRII fusion protein promoted higher level of IFN-γ production compared to anti-PD-1 or isotype control. Overall, result from this 3D tumor spheroid model exhibit superior anti-tumor response of anti-PD-1-TGFRII fusion protein compared to an anti-PD-1 antibody.

Anti-PD-1-TGF-RII Exhibits Superior Anti-Tumor Response Compared to and PD-1 Alone in an In Vitro 3D Tumor Spheroid Model of Head and Neck Cancer Effectiveness of anti-PD-1-TGFRII fusion protein was evaluated in an in vitro 3D tumor spheroid model of colorectal cancer. 3D tumor spheroids were generated by coculturing Detroit 562 cell line and a fibroblast cell line. PBMCs purified from healthy donor were then added to spheroid culture. The cells were stimulated with anti-CD3 in the presence of isotype control, anti-PD-1 or anti-PD-1-TGFRII fusion protein for 5 days. The culture supernatants were collected and IFN-γ levels were quantified by MSD per manufacturer's protocol.

Figure 9M:
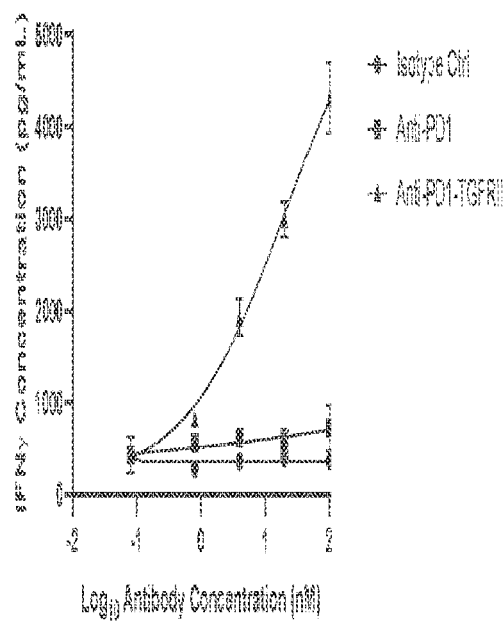
Figure 10A:
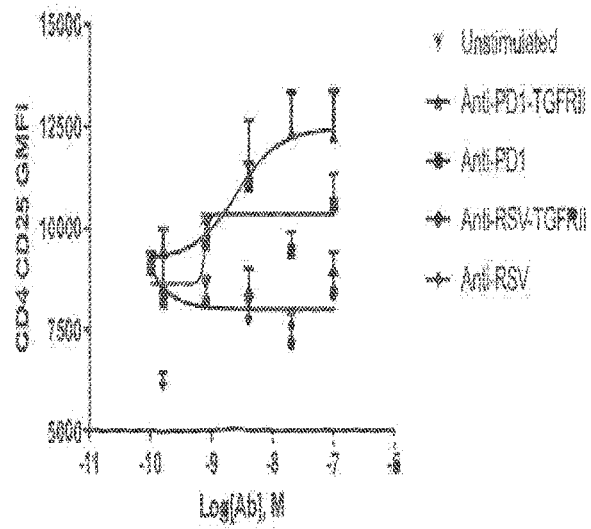
FIGS. 10A-10D show effect of anti-PD-1-TGFRII fusion protein treatment on T cell proliferation and activation in the presence of recombinant TGF-β1.
Figure 10C:
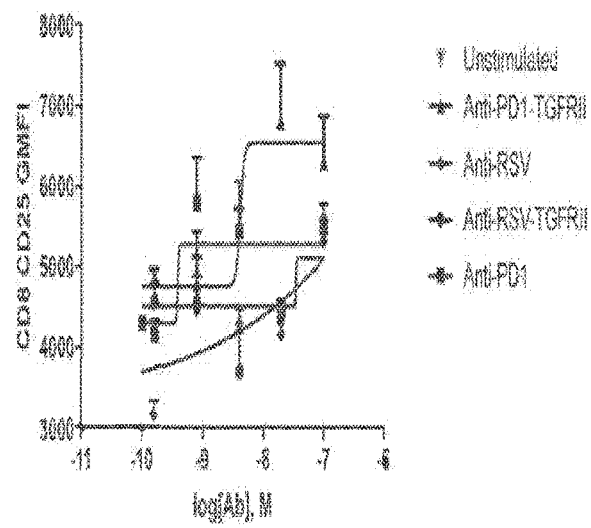
Figure 10B:
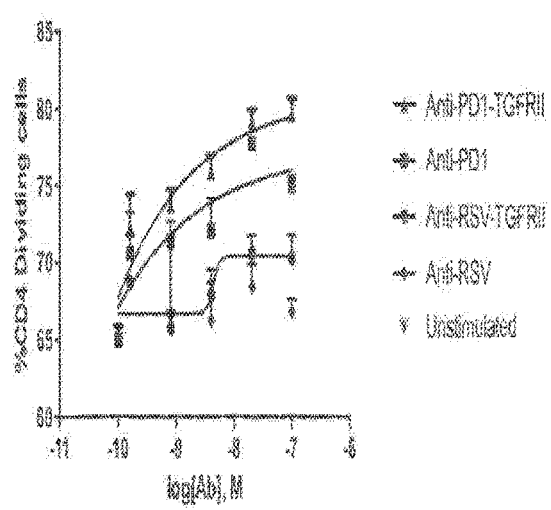
Figure 10D:
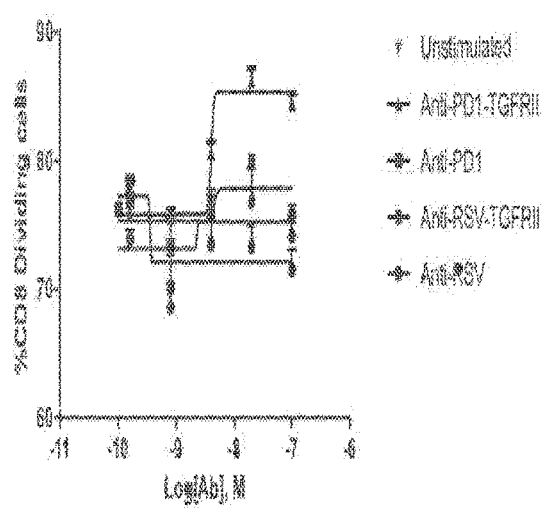
Figure 11A:
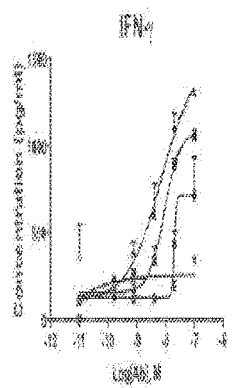
FIGS. 11A-11F show expression of various cytokines by PBMC in the presence recombinant TGF-β1 and in the presence of anti-PD-1, anti-PD-1-TGFRII fusion protein or control antibodies.
Figure 11B:
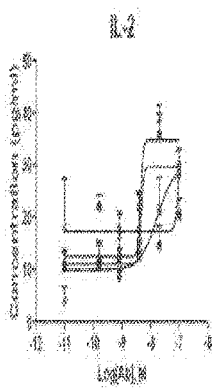
Figure 11C:
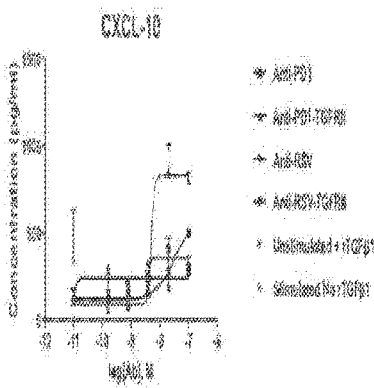
Figure 11D:
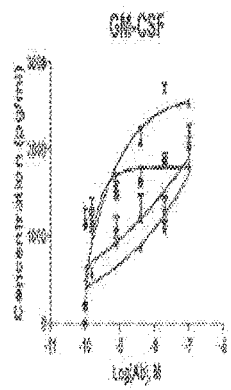
Figure 11E:
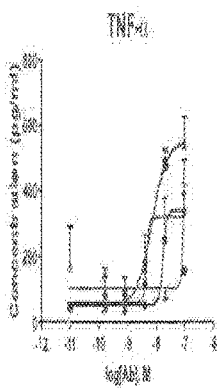
Figure 11F:
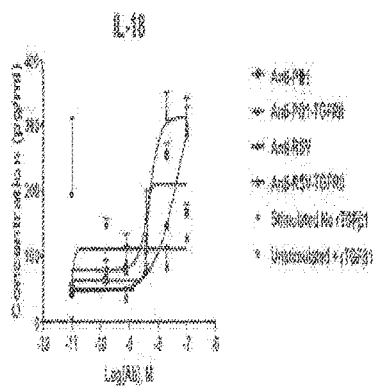

As shown in FIG. 9M, anti-PD-1-TGFRII fusion protein promoted higher level of IFN-γ production compared to anti-PD-1 or isotype control. Overall, result from this 3D tumor spheroid model exhibit superior anti-tumor response of anti-PD-1-TGFRII fusion protein compared to an anti-PD-1 antibody.

Example 3. Anti-PD-1-TGF-β Trap has Superior Activity Compared to Anti-PD-1 in the Presence of Recombinant TGF-β1 In Vitro To assess the ability of the anti-PD-1-TGF-β trap to promote T cells functions, in an environment with high levels of TGF-β, PBMCs were stimulated as above in the presence of recombinant TGF-β 1. At the end of the incubation, culture supernatants were collected and stored until used for cytokine analyses. The cells were labeled with fluorescent conjugated antibodies and assessed for T cell proliferation and the upregulation of IL-2 receptor alpha or CD25 as a readout for activation.

Recombinant TGF-β1 suppressed T cell activation, proliferation and cytokine and chemokine production (FIG. 10 and FIG. 11). This suppression was reversed significantly by the anti-PD-1-TGF-β1 trap in a dose dependent manner compared to anti-PD-1. The data suggests the ability of the fusion protein to neutralize high amount of exogenous TGF-β1 and disrupt the PD-1/PD-L1 pathway resulting in enhance T cell immune responses. Thus, the blockade of the PD-1/PD-L1 and neutralization of TGF-β by the fusion molecule can be an attractive immunotherapy for eliciting potent anti-tumor responses in cancer indications where checkpoint inhibitors treatments have failed.

Figure 12A:
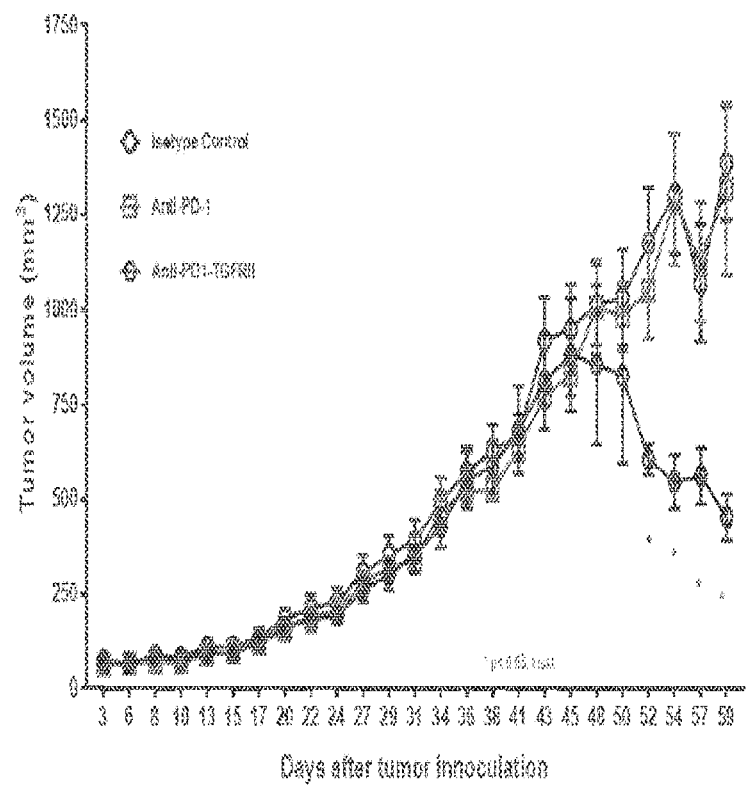
FIG. 12A shows the effect of anti-PD-1-TGFRII fusion protein on tumor growth as compared to anti-PD-1 alone in a humanized mouse model of colorectal cancer.
Figure 12B:
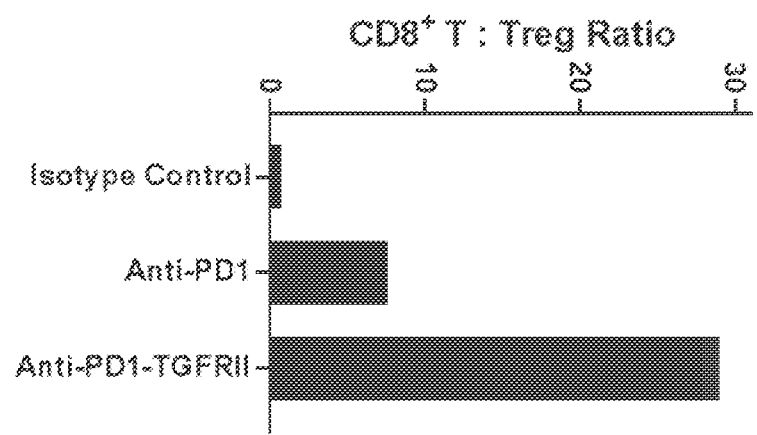
FIG. 12B shows that treatment with anti-PD-1-TGFRII fusion protein significantly increases CD8$^+$ T cell to T$_{reg}$ ratio in tumor in a humanized mouse model of colorectal cancer.
Figure 12C:
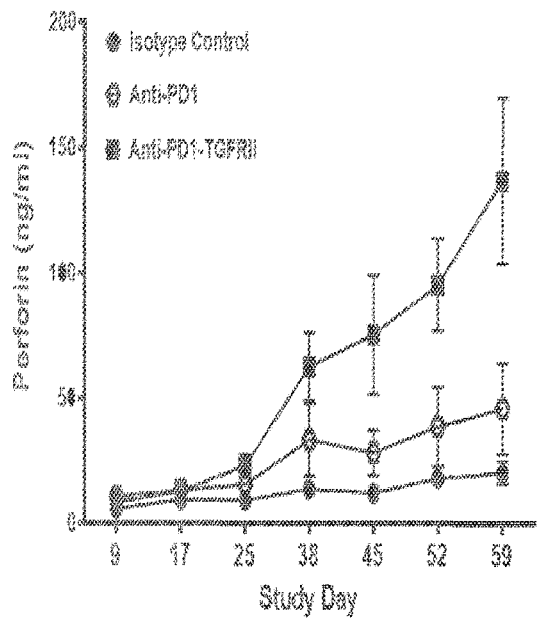
FIG. 12C shows the effect of anti-PD-1-TGFRII fusion protein treatment on perforin expression levels as compared to anti-PD-1 treatment in a humanized mouse model of colorectal cancer.
Figure 12D:
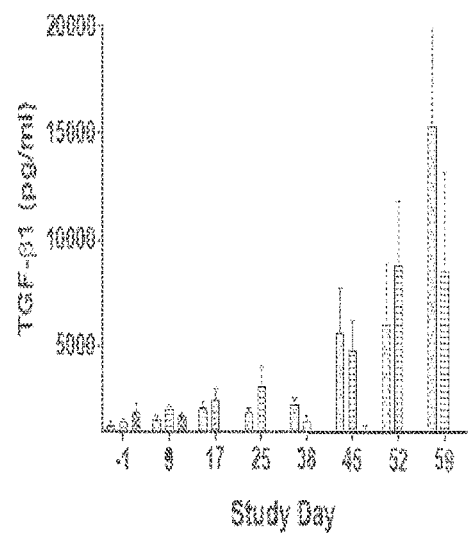
FIG. 12D and FIG. 12E shows the effect of anti-PD-1-TGFRII fusion protein treatment on TGF-β1 and TGF-β2 concentrations as compared to anti-PD-1 treatment respectively in a humanized mouse model of colorectal cancer.
Figure 12E:
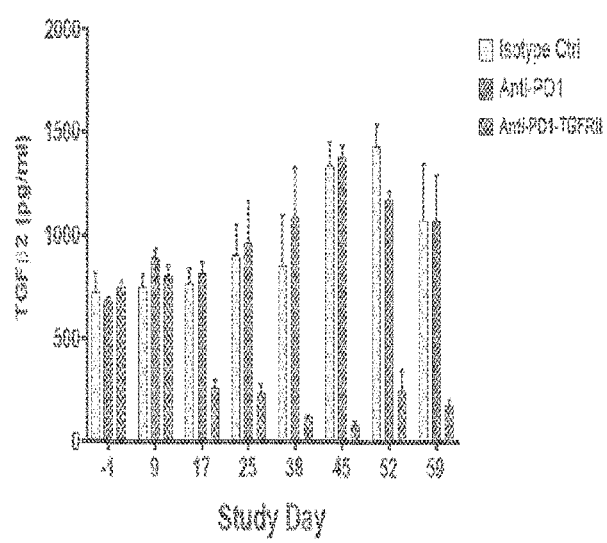

Example 4. Anti-PD-1-TGF-RII Exhibits Superior Anti-Tumor Response Compared to Anti-PD-1 Alone in a Humanized Mouse Model of Colorectal Cancer The ability of anti-PD-1-TGFRII fusion protein to inhibit colorectal cancer tumor was evaluated in a humanized mouse model. Humanized NOG mice were administered HT-29 cancer cells. Tumor-bearing mice were randomized and administered twice weekly with either anti-PD-1-TG-FRII fusion protein, an anti-PD-1 antibody alone or an isotype control. As seen in the FIG. 12A, anti-PD-1-TGFRII fusion protein significantly inhibited tumor growth compared to anti-PD-1 and the isotype control. Analyses of the tumors at the end of the study showed that anti-PD-1-TGFRII fusion protein treated mice had higher frequency of tumor infiltrating lymphocytes (TILs). Analysis of tumors from anti-PD-1-TGFRII treated mice also showed higher ratio of CD8+ T cells to regulatory T cells (Tregs).

Example 5. Anti-PD-1-TGFRII Exhibits Superior Anti-Tumor Response Compared to Anti-PD-1 Alone in an In Vitro Model of Head and Neck Cancer Effectiveness of anti-PD-1-TGFRII fusion protein was evaluated in an in vitro model of head and neck cancer. PBMCs purified from healthy donor were co-cultured with cancer cell line Detroit 562 for 48 hours. The cells were stimulated with anti-CD3 in the presence of isotype control, anti-PD-1 or anti-PD-1-TGFRII fusion protein. The culture supernatants were collected and IFN-γ levels were quantified by MSD per manufacture's protocol. The cell pellets from co-culture at the end of culture period were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Figure 13A:
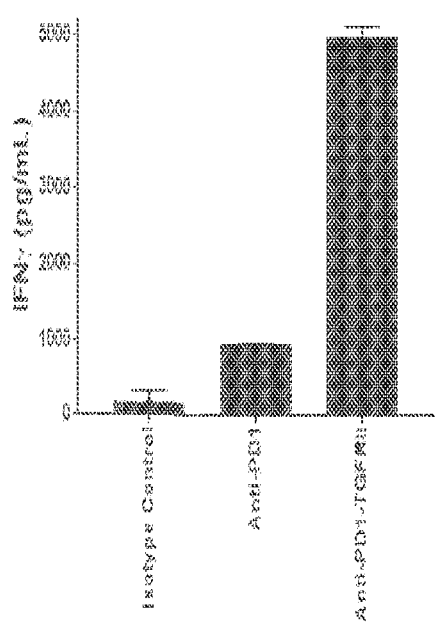
FIG. 13A shows treatment with anti-PD-1-TGFRII fusion protein significantly improved IFNγ production compared to anti-PD-1 treatment in an in vitro model of head and neck cancer.
Figure 13B:
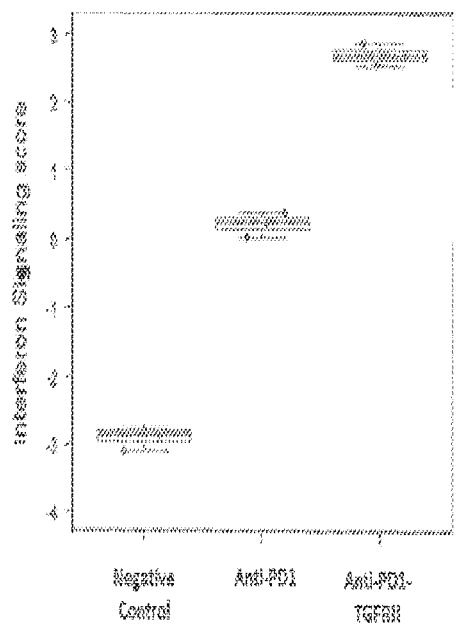
FIGS. 13B-13G show treatment with anti-PD-1-TGFRII fusion protein significantly increases T-cell function as evidenced by expression analysis of various pathway genes.
Figure 13C:
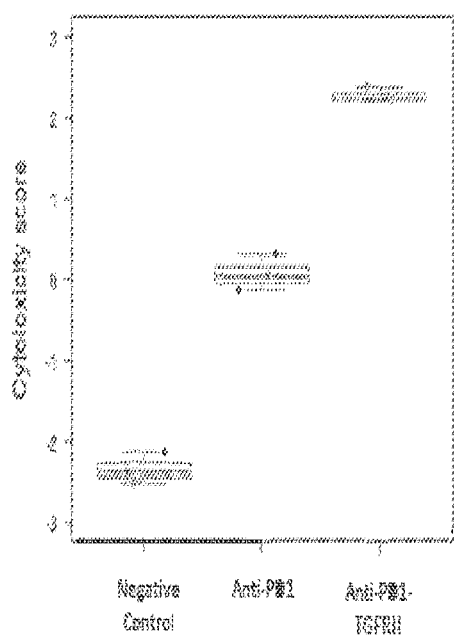
Figure 13D:
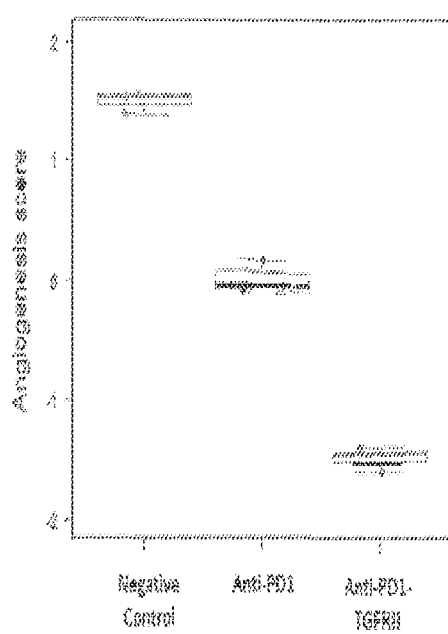
Figure 13E:
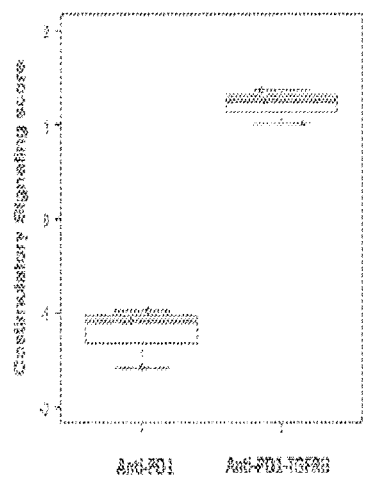
Figure 13F:
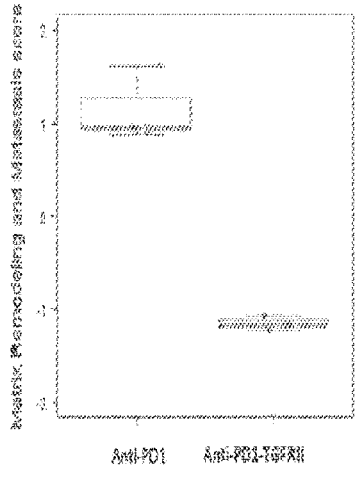
Figure 13G:
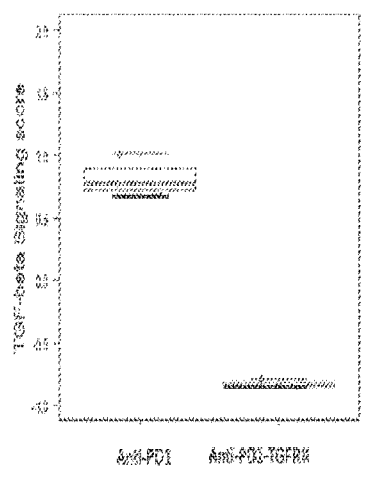

As shown in FIG. 13A, anti-PD-1-TGFRII fusion protein promoted higher level of IFN-γ production compared to anti-PD-1 or isotype control. Anti-PD-1-TGFRII fusion protein treatment resulted in significant upregulation of interferon pathway genes (FIG. 13B) as well as cytotoxic genes (FIG. 13C) compared to anti-PD-1 treatment highlighting improved cytotoxic function in presence of tumor compared to an anti-PD-1 antibody. Furthermore, anti-PD-1-TGFRII fusion protein treatment resulted in significant downregulation of genes involved in tumor metastasis and angiogenesis pathways (FIG. 13D). Overall, results from this in vitro model exhibit superior anti-tumor response of anti-PD-1-TGFRII fusion protein compared to an anti-PD-1 antibody.

Figure 14A:
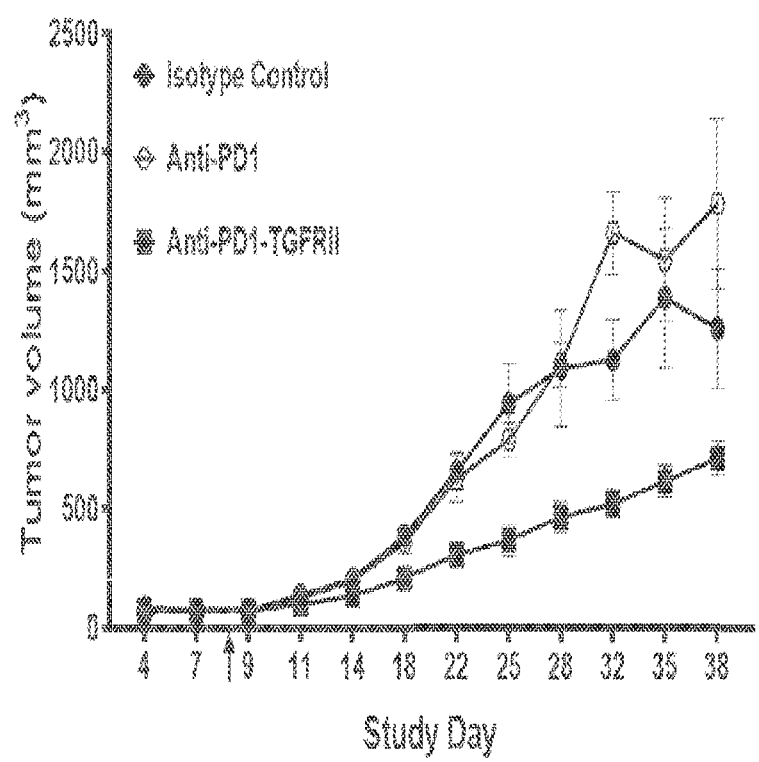
FIG. 14A shows the effect of anti-PD-1-TGFRII fusion protein on tumor growth as compared to anti-PD-1 alone in a humanized mouse model of head and neck cancer.
Figure 14B:
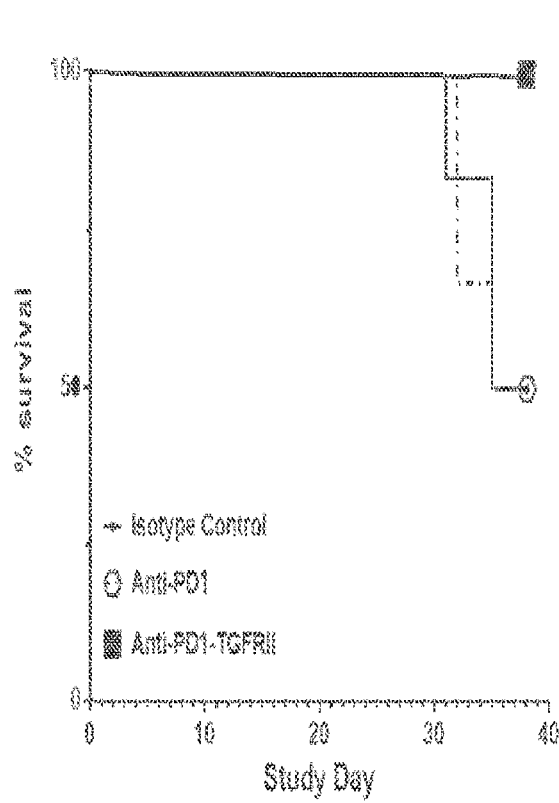
FIG. 14B shows survival of tumor bearing mice in humanized mouse model of head and neck cancer when treated with anti-PD-1-TGFRII fusion protein vs. anti-PD-1 alone or isotype control.
Figure 14C:
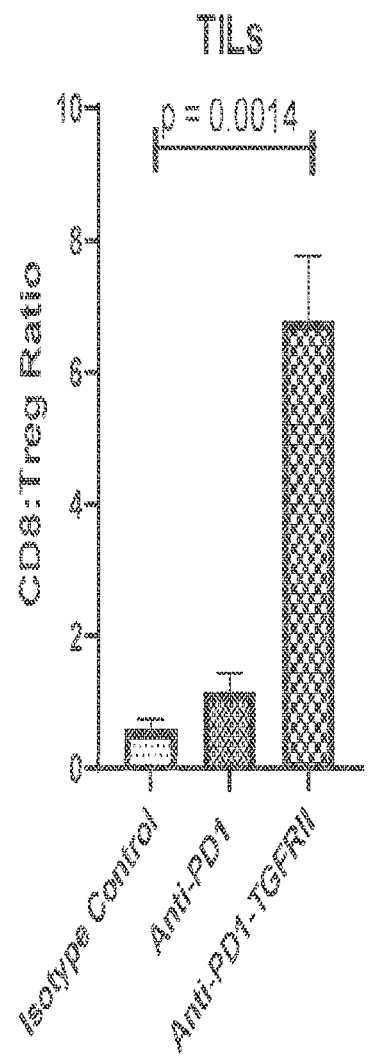
FIG. 14C shows ratio of CD8$^+$ T cells to regulatory T cells in tumors of mice treated with anti-PD-1-TGFRII fusion protein in a humanized mouse model of head and neck cancer.
Figure 14D:
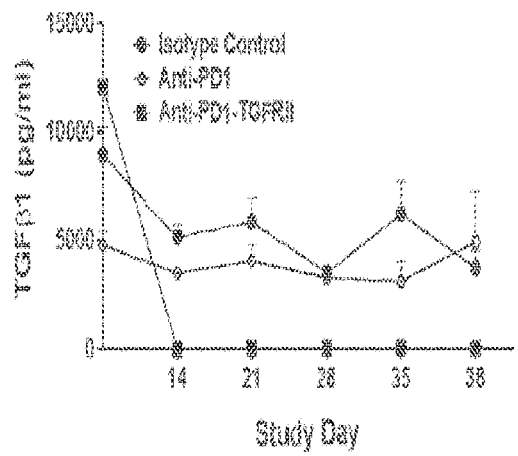
FIG. 14D and FIG. 14E shows the effect of anti-PD-1-TGFRII fusion protein on TGF-β1 and TGF-β2 concentrations as compared to anti-PD-1 alone in a humanized mouse model of head and neck cancer.
Figure 14E:
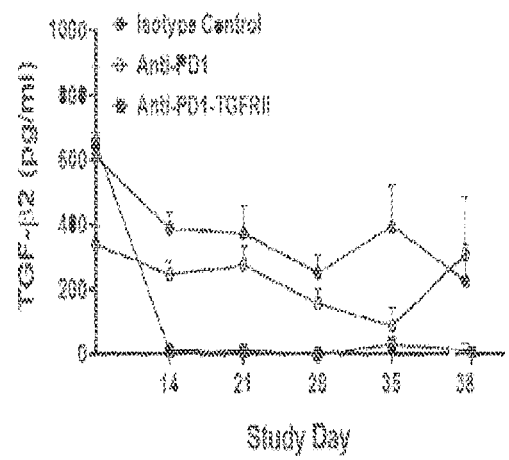
Figure 14F:
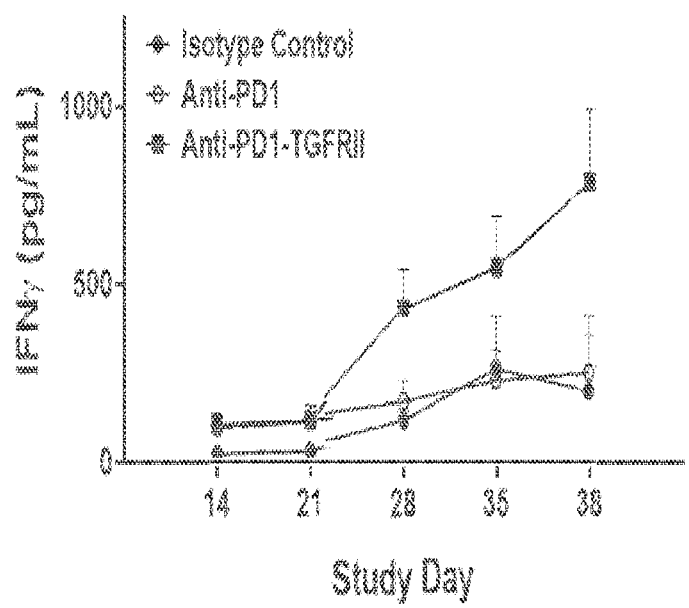
FIG. 14F shows the effect of anti-PD-1-TGFRII fusion protein on IFN-γ production in a humanized mouse model of head and neck cancer.

Example 6. Anti-PD-1-TGFRII Exhibits Superior Anti-Tumor Response Compared to Anti-PD-1 Alone in a Humanized Mouse Model of Head and Neck Cancer Ability of anti-PD-1-TGFRII fusion protein to inhibit head and neck cancer was evaluated in a humanized mouse model. Humanized NSG mice were administered D562 cell line. Tumor-bearing mice were randomized in and administered twice weekly with anti-PD-1-TGFRII fusion protein, an anti-PD-1 antibody alone or an isotype control. As seen in FIG. 14, Anti-PD-1-TGFRII fusion protein significantly inhibited tumor growth (FIG. 14A), improved survival of tumor bearing mice (FIG. 14B) and increase in IFNγ levels (FIG. 14F) compared to anti-PD-1 and the isotype control. Treatment with anti-PD-1-TGFRII fusion protein significantly improved CD8$^+$ T cells to Treg ratio in tumors (FIG. 14C).

Example 7. Anti-PD-1-TGFRII Exhibits Superior Anti-Tumor Response Compared to Anti-PD-1 Alone in Primary Colorectal Cancer (CRC) Patient Samples Effectiveness of anti-PD-1-TGFRII fusion protein was evaluated in primary colorectal cancer patient samples. PBMCs from CRC patients were co-cultured with dissociated tumor cells. The cells were stimulated in the presence of isotype control, anti-PD-1 or anti-PD-1-TGFRII fusion protein. The culture supernatants were collected and IFN-γ levels were quantified by MSD per manufacturer's protocol. TGF-β levels were assessed by Luminex per the manufacturer's protocol. The cell pellets from co-culture at the end of culture period were harvested by centrifugation and RNA was purified using the Qiagen RNAeasy micro kit according the manufacturer's protocol. Purified RNA was used for gene expression analysis using the NanoString according to the manufacturer's instructions. Gene expression was analyzed using Nanostring nCounter software.

Figure 15B:
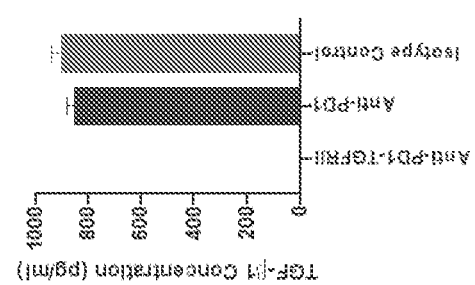
FIGS. 15A-15B shows the effect of anti-PD-1(VH7/VL6)-TGFRII fusion protein on IFN-γ production and TGF-β1 concentration in primary colorectal cancer patient samples.
Figure 15A:
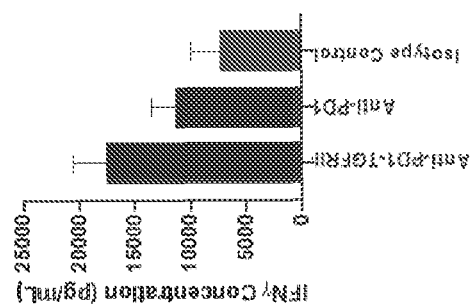
Figure 15C:
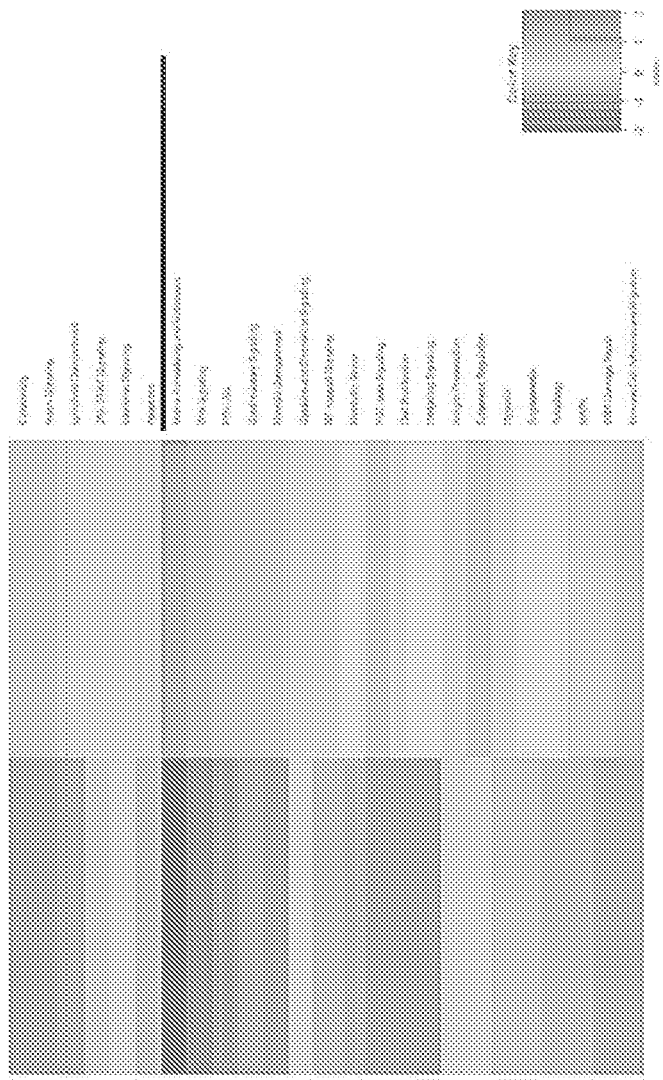
FIG. 15C shows the gene expression analysis of primary colorectal cancer patient samples co-cultured with anti-PD-1(VH7/VL6)-TGFRII fusion protein.

As shown in FIG. 15A, anti-PD-1-TGFRII fusion protein promoted higher level of IFN-γ production compared to anti-PD-1 or isotype control. Anti-PD-TGFRII fusion protein completely neutralized TGF-β1 produced by patient PBMC and dissociated tumor cells (FIG. 15B). Anti-PD-1-TGFRII fusion protein treatment resulted in significant upregulation of cytotoxic genes (FIG. 15C) compared to anti-PD-1 treatment highlighting improved cytotoxic function in presence of tumor compared to an anti-PD-1 antibody. Furthermore, anti-PD-1-TGFRII fusion protein treatment resulted in significant downregulation of genes involved in tumor metastasis and angiogenesis pathways (FIG. 15C). As expected TGF-β signaling pathway is significantly downregulated in anti-PD-1-TGFRII fusion protein treatment group. Overall, results from this patient derived samples exhibit superior anti-tumor response of anti-PD-1-TGFRII fusion protein compared to an anti-PD-1 antibody.

Example 8. Anti-PD-1-TGFRII Exhibits Increased Cytotoxicity Compared to Anti-PD-L1-TGFRII in an In Vitro Model of Ovarian Cancer Effectiveness of anti-PD-1-TGFRII was compared with anti-PD-L1-TGFRII in an in vitro model of ovarian cancer. PBMCs purified from healthy donors were co-cultured with cancer cell line SK-OV-3. The immune cells were stimulated in the presence of isotype control, anti-PD-1-TGFRII fusion protein or anti-PD-L1-TGFRII fusion protein. The killing of tumor cells was assessed across culture period using Incucyte live cell analysis system.

Figure 16:
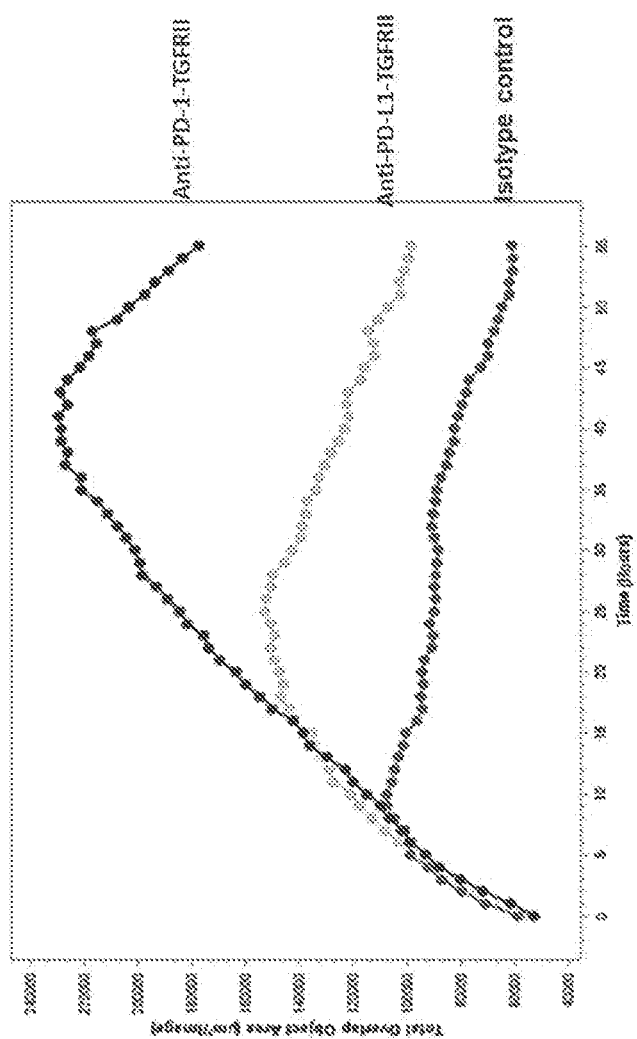
FIG. 16 shows a graph depicting the results of a cytotoxicity assay of anti-PD-1 (VH7/VL6)-TGFRII fusion protein compared to anti-PD-L1-TGFRII fusion protein.

As shown in FIG. 16, the presence of anti-PD-1-TGFRII fusion protein exhibited increased killing of tumor cells when compared to anti-PD-L1-TGFRII fusion protein. Overall, anti-PD-1-TGFRII exhibits improved cytotoxicity when compared to anti-PD-L1-TGFRII.

Example 9. Combination of Anti-PD-1-TGF-RII with CAR-T Significantly Enhanced 3D Tumor Spheroid Killing when Compared to Combination with Anti-PD-1 or CAR-T Alone Combination of anti-PD-1-TGFRII fusion protein with CAR-T cells was evaluated in an in vitro 3D tumor spheroid model of ovarian cancer. In this example, the CAR-T cells were engineered to express MUC16 CAR. 3D tumor spheroids were generated by co-culturing ovarian cancer cell line SK-OV-3 and a fibroblast cell line. CAR-T cells were then added to the 3D tumor spheroid culture in the presence of anti-PD-1-TGFRII fusion protein or anti-PD-1. The target specific killing of 3D tumor spheroid was assessed across time using Incucyte live cell analysis system.

Figure 17:
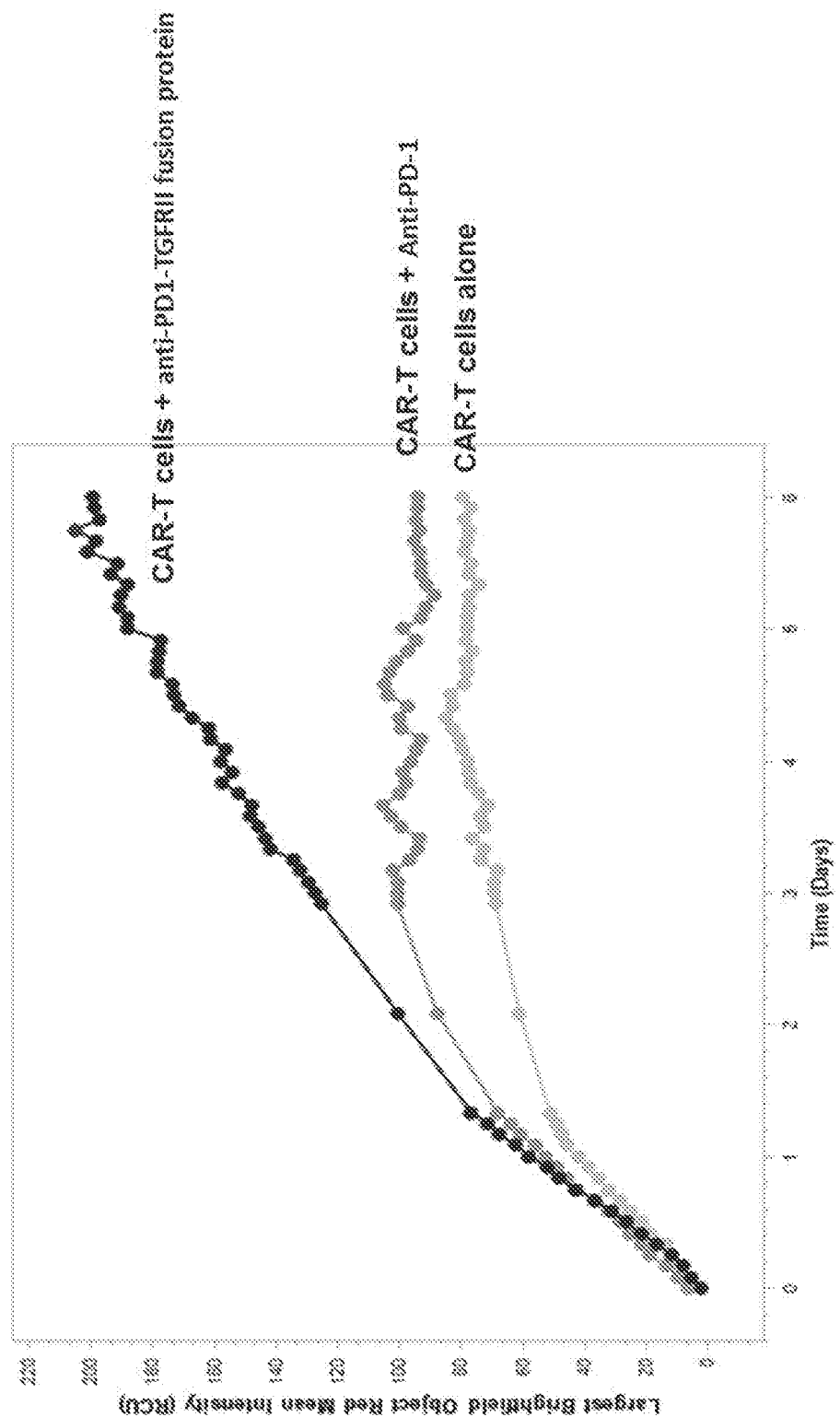
FIG. 17 is a graph depicting the results of a cytotoxicity assay of anti-PD-1(VH7/VL6)-TGFRII fusion protein in combination with a chimeric receptor antigen (CAR) T cells vs. anti-PD-1 in combination with a CAR T cells vs. CAR T cells alone.

As shown in FIG. 17, the combination of anti-PD-1-TGFRII fusion protein with CAR-T cells showed increased killing of 3-D tumor spheroids when compared to the combination of anti-PD-1 and CAR-T cells or CAR-T cells alone. Overall, result from this kill assay suggest that addition of anti-PD-1-TGF-RII to CAR-T cells enhances the anti-tumor response of CAR-T cells.

Example 10 Combination of Anti-PD-1-TGF-RII with CD33 Specific CAR-T Cells

CAR-T cells were co-cultured with MOLM-13 AML tumor cell line in a cytotoxicity assay and the cultures were incubated in the IncuCyte S3 live cell analysis instrument. In this example, the CAR-T cells were engineered to express CD33 CAR. Anti PD-1 or anti-PD-1-TGFRII was added to the indicated cultures at an equimolar concentration. Sytox Green was directly added at the start of the culture to allow for the identification and enumeration of dying cells in the culture. Analysis was performed using the IncuCyte S3 Software. The data presented in the graph shown is the mean±SD from triplicate wells, with 5 scans/well taken.

Figure 18A:
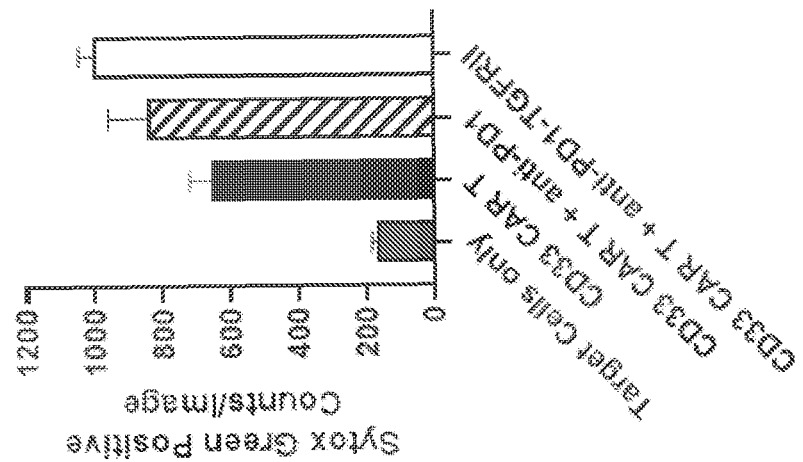
FIG. 18A and FIG. 18B are graphs depicting the results of a cytotoxicity assay of anti-PD-1 (VH6/VL5)-TGFRII fusion protein in combination with CD33 CAR-T and a cytotoxicity assay of anti-PD-1 (VH7/VL6)-TGFRII fusion protein in combination with CD33 CAR-T respectively.

As shown in FIG. 18A, the combination of anti-PD-1 (VH6/VL5)-TGFRII fusion protein with the CD33 CAR T cells showed increased killing as compared to CAR T cells and anti-PD-1(VH6/VL5) combination or CAR T cells alone.

Figure 18B:
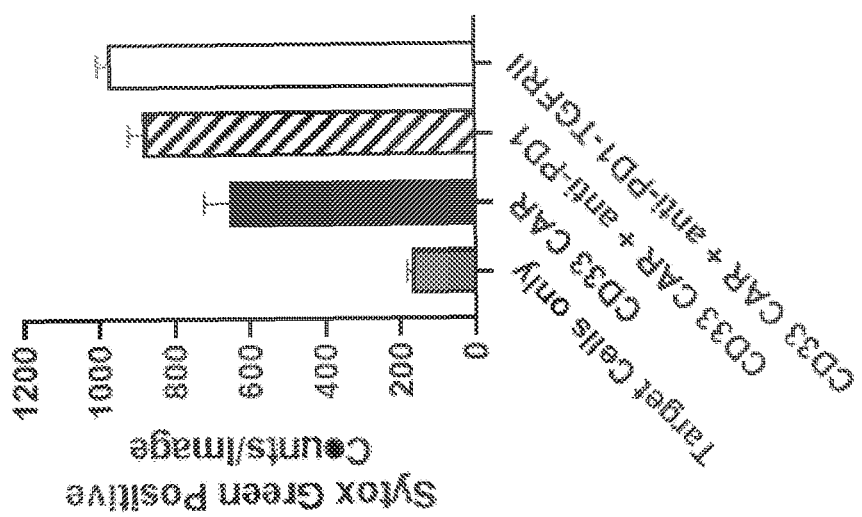

As shown in FIG. 18B, the combination of anti-PD-1 (VH7/VL6)-TGFRII fusion protein with the CD33 CAR-T cells showed increased killing compared to CAR-T cells and anti-PD-1 combination or CAR-T cells alone. Overall, the result for these cytotoxicity assays demonstrate that anti-PD-1 (VH6/VL5)-TGFRII fusion protein and anti-PD-1 (VH7/VL6)-TGFRII fusion protein enhance the anti-tumor immune responses of CAR-T cells.

Example 11. Combination of Anti-PD-1-TGF-RII with CD19 CAR-T Cells Enhances Tumor Cell Killing CD19 CAR-T cells are co-cultured with tumor cells expressing CD19 antigen on cell surface in presence of anti-PD-1-TGFRII fusion protein or anti-PD-1. The combination of anti-PD-1-TGFRII fusion protein with CD19 CAR-T cells shows increased killing of tumor cells as compared to the combination of anti-PD-1 and CAR-T cells or CAR-T cells alone.

Example 12. Combination of Anti-PD-1-TGF-RII with ROR1 Specific CAR-T Enhances Tumor Cell Killing ROR1 CAR-T cells are co-cultured with tumor cells expressing ROR1 antigen on cell surface in presence of anti-PD-1-TGFRII fusion protein or anti-PD-1. The combination of anti-PD-1-TGFRII fusion protein with ROR1 CAR-T cells shows increased killing of tumor cells as compared to the combination of anti-PD-1 and CAR-T cells or CAR-T cells alone.

Example 13. Combination of Anti-PD-1-TGF-RII with BCMA Specific CAR-T Improves Cytotoxic Potential of CAR-T Cells BCMA specific CAR-T cells are co-cultured with tumor cell line expressing BCMA antigen in presence or absence of anti-PD-1-TGFRII fusion protein or anti-PD-1. The combination of anti-PD-1-TGFRII fusion protein with CAR-T cells improves cytotoxic potential of CAR-T cells compared to the combination of anti-PD-1 and CAR-T cells or CAR-T cells alone.

Example 14. Combination of Anti-PD-1-TGF-RII with PSMA Specific CAR-T Enhances Tumor Cell Killing by CAR-T Cells PSMA specific CAR-T cells are co-cultured with tumor cell line expressing PSMA antigen in presence or absence of anti-PD-1-TGFRII fusion protein or anti-PD-1. The combination of anti-PD-1-TGFRII fusion protein with CAR-T cells improves cytotoxicity of CAR-T cells when compared to the combination of anti-PD-1 and CAR-T cells or CAR-T cells alone.

Example 15. NK Cell Target Cell Lysis was Improved by Anti-PD-1-TGFRII

The ability of anti-PD-1 (VH7/VL6)-TGFRII and anti-PD-1 (VH6/VL5)-TGFRII to promote natural killer cell-mediated killing of tumor cells was assessed in an in vitro model of ovarian cancer. Effector NK cells were purified from healthy donor and co-cultured with SK-OV-3 target cell line overnight at different E:T cell ratios in the presence of anti-RSV-TFGBRII (control), anti-PD-1 (VH6/VL5) and anti-PD-1 (VH7/VL6), anti-PD-1 (VH7/VL6)-TGFRII and anti-PD-1 (VH6/VL5)-TGFRII. Propidium iodine was added to the culture to identify dead cells and cell death was assayed using the Nexcelom Celigo.

Figure 19A:
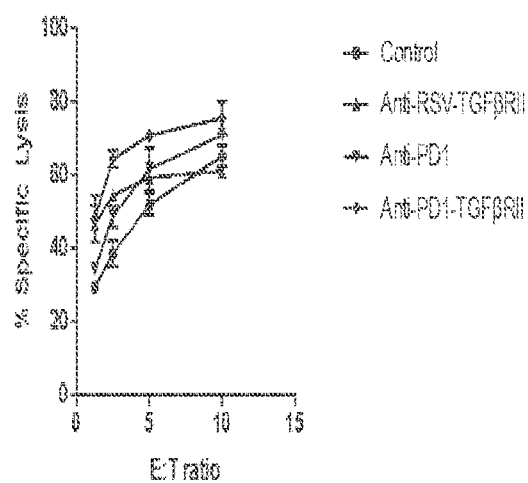
FIG. 19A and FIG. 19B are graphs depicting tumor cell lysis using anti-PD-1 (VH6/VL5)-TGFRII fusion protein and anti-PD-1 (VH7/VL6)-TGFRII fusion protein respectively when co-cultured with NK cells.
Figure 19B:
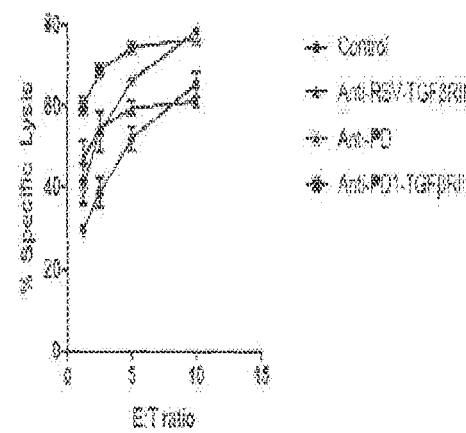

As seen in FIG. 19A and FIG. 19B, anti-PD-1-TGFBRII fusion proteins promoted higher tumor cell killing compared to anti-PD-1 or the TGFBRII alone (Anti-RSV-TGFBRII).

Example 16: Fusion Protein of Anti-PD-1-ADA2

Anti-PD-1 VHs and VLs were synthesized and formatted in IgG, scFv-Fc or scFv configurations with adenosine deaminase 2 (ADA2) fused at C-terminal by linker (G4S) 2 (SEQ ID NO: 563). Anti-PD-1-adenosine deaminase fusion proteins were transiently expressed in Expi293 cells according to the manufacturer's protocol and purified using AKTA AVANT system.

Surface Plasmon Resonance

Surface plasma resonance (SPR) analysis was performed using Biacore3000, CM5 chip, an amine-coupling kit, 10×HBS-P running buffer and Glycine for. For anti-PD-1 kinetic assay, recombinant PD-1 Fc protein was immobilized on chip using a pre-defined ligand immobilization program. Purified anti-PD-1-adenosine deaminase fusion proteins were diluted in running buffer to a range of final concentrations and injected. Dissociation was allowed to proceed followed by regeneration of the chip surface.

TABLE 10

Affinity of anti-PD-1-ADA2 to immobilized PD-1

| Fusion protein | $K_D$ (M) |
|---|---|
| Anti-PD-1 (VH7-VL6) IgG4-ADA2 | 6.63e−14 |
| Anti-PD-1 (VH6-VL5) IgG4-ADA2 | 6.16e−14 |
| Anti-PD-1 (VH7-VL6) IgG1-ADA2 | 5.09e−13 |
| Anti-PD-1 (VH6-VL5) IgG1-ADA2 | 3.09e−13 |
| Anti-PD-1 (VH7-VL6) scFv-Fc-ADA2 | 5.63e−10 |
| Anti-PD-1 (VH6-VL5) scFv-Fc-ADA2 | 1.84e−12 |
| Anti-PD-1 (VH7-VL6) scFv-ADA2 | 1.3e−10 |
| Anti-PD-1 (VH6-VL5) scFv-ADA2 | 3.46e−9 |

PD-1/PD-L1 Blockade Assay

Figure 21:
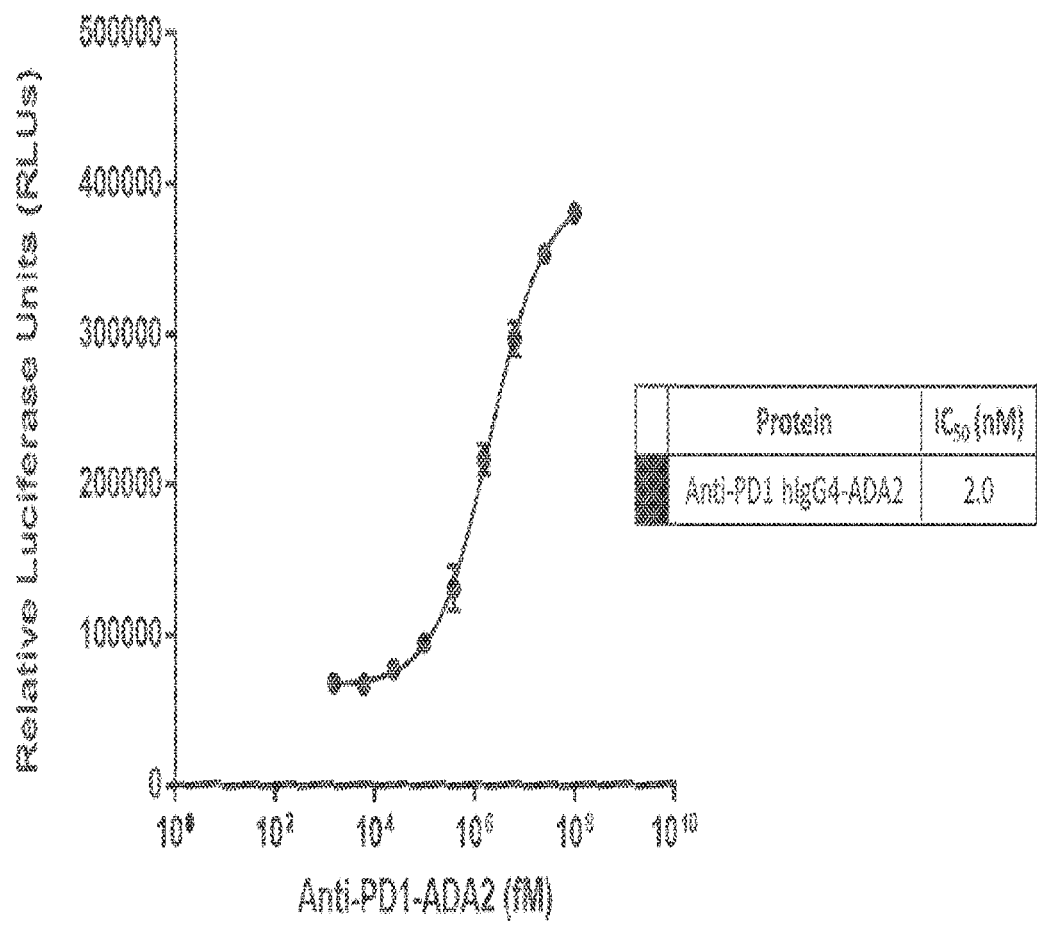
FIG. 21 is a graph showing blockade of PD-1/PD-L1 interaction by anti-PD-1 IgG4-ADA2.

To investigate whether the anti-PD-1-ADA2 fusion proteins could function as a PD-1 inhibitor by blocking the PD-1/PD-L1 interaction, a PD-1/PD-L1 blockade bioassay kit from Promega was used as described in Example 1. The values in Table 10 were used as a measure of PD-1/PD-L1 blocking potency (FIG. 21).

ADA Enzymatic Activity Assay

To determine the anti-PD-1-ADA2 fusion protein enzymatic activity, the colorimetric Adenosine Deaminase (ADA) Activity Kit (Abcam) was utilized according to the manufacturer's recommendations. Two-minute and 30-minute time points were selected to calculate the ADA enzymatic activity over time.

Figure 22:
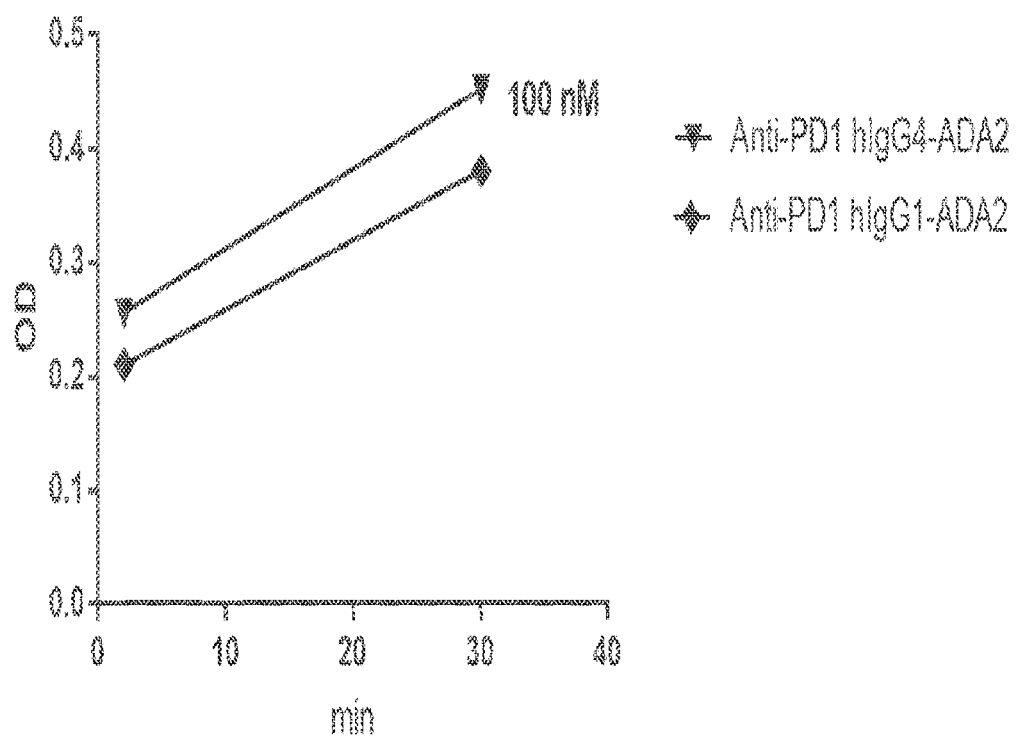
FIG. 22 is a graph showing ADA2 enzymatic activity measured for anti-PD-1 hIgG1-ADA2 and anti-PD-1 hIgG4-ADA2.

As shown in FIG. 22, anti-PD-1-ADA2 fusion proteins exhibited enzymatic activity over time.

Example 17: PD-1 Binding Affinity Analysis of Anti-PD-1 IgG4 S108P-wtADA2 and -mutADA2

PD-1-Fc antigen and reference were immobilized on a Biacore CM5 surface, then 6-12 replicated series diluted concentrations of anti-PD-1-IgG4-S108P-wtADA2 and -mutADA2 were series-injected on PD-1-Fc antigen and reference surface. Kinetics data was evaluated for 1:1 model: Langmuir with mass transfer. Results are shown in Table 11.

TABLE 11

Binding affinity of anti-PD-1 (VH6/VL5) and (VH7/VL6) IgG4 S108P and the anti-PD-1-wtADA2 and -mutADA2

| Analyte | $K_D$ (M) |
|---|---|
| Anti-PD-1 (VH6/VL5) IgG4 S108P | 3.34e−13 |
| Anti-PD-1 (VH6/VL5) IgG4 S108P-ADA2 | 7.53e−13 |
| Anti-PD-1 (VH6/VL5) IgG4 S108P-mutADA2 | 2.18e−13 |
| Anti-PD-1 (VH7/VL6) IgG4 S108P | 3.92e−13 |
| Anti-PD-1 (VH7/VL6) IgG4 S108P-ADA2 | 4.13e−13 |
| Anti-PD-1 (VH7/VL6) IgG4 S108P-mutADA2 | 3.38e−13 |

Example 18: Anti-PD-1-ADA2 Fusion Proteins Effectively Blocked PD-L1/PD-1 Signaling Ability of anti-PD-1-ADA2 fusion proteins to block PD-1/PD-L1 interaction was evaluated using a reporter bioassay as mentioned in Example 12.

Figure 23B:
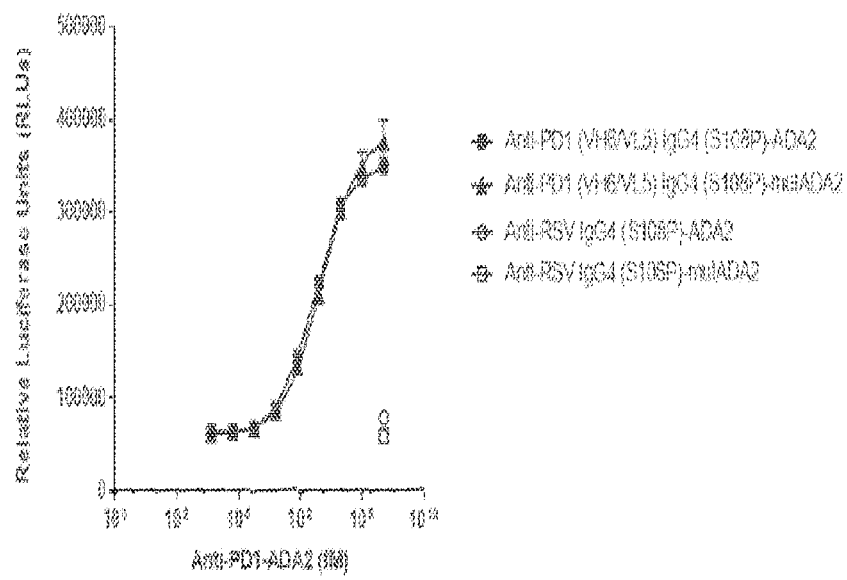
Figure 23C:
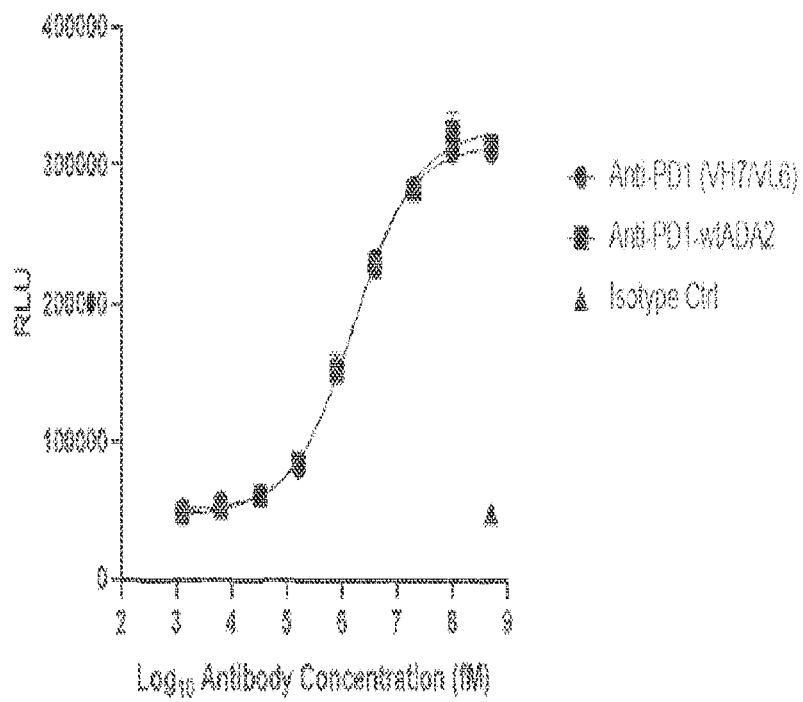
Figures 24A, 24B:
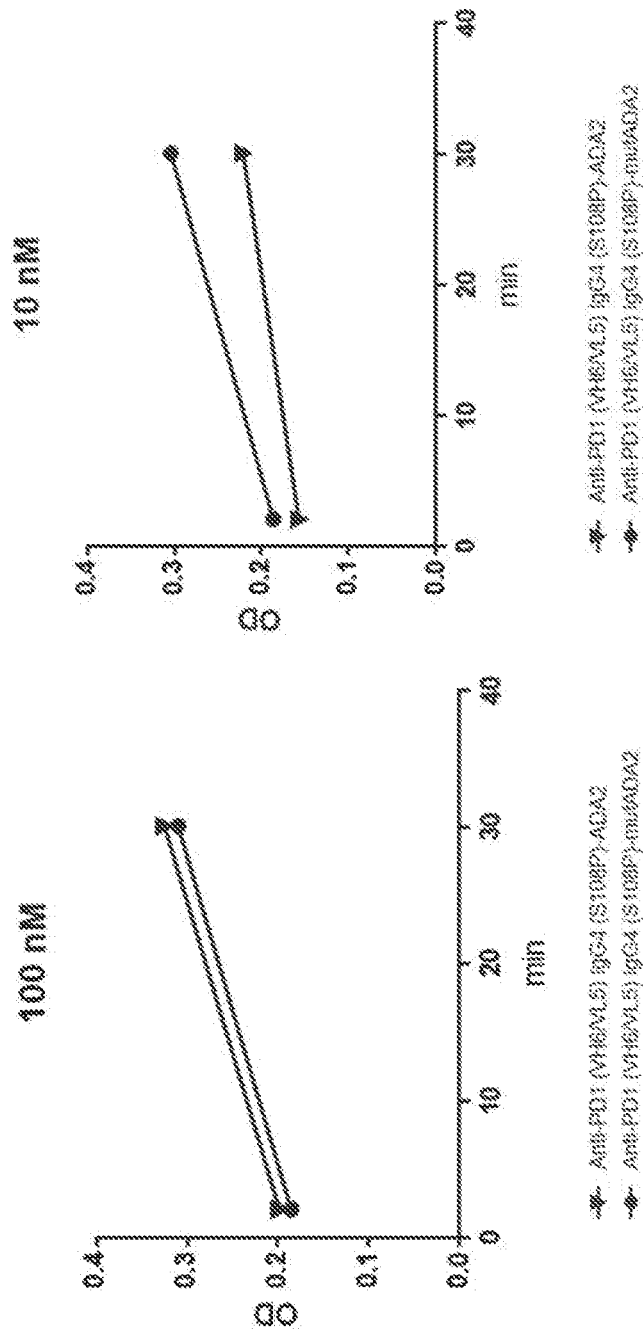
FIGS. 24A-24F are graphs showing the enzymatic activity of various variants of anti-PD-1-ADA2 fusion proteins as measured by ADA enzymatic activity.
Figure 24C:
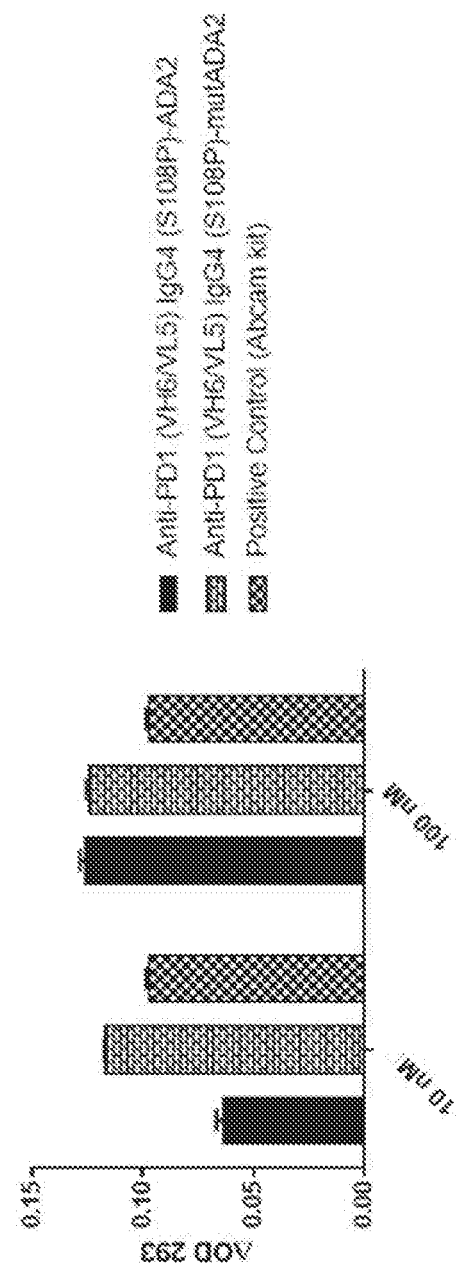
Figures 24D, 24E:
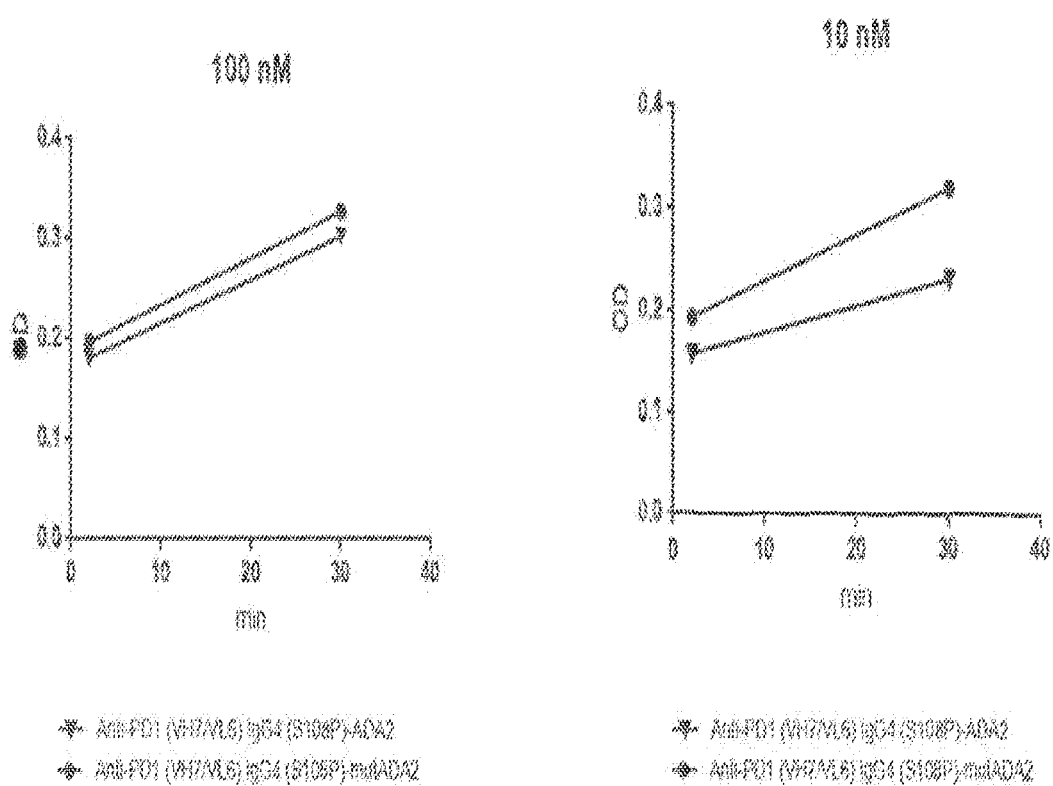
Figure 24F:
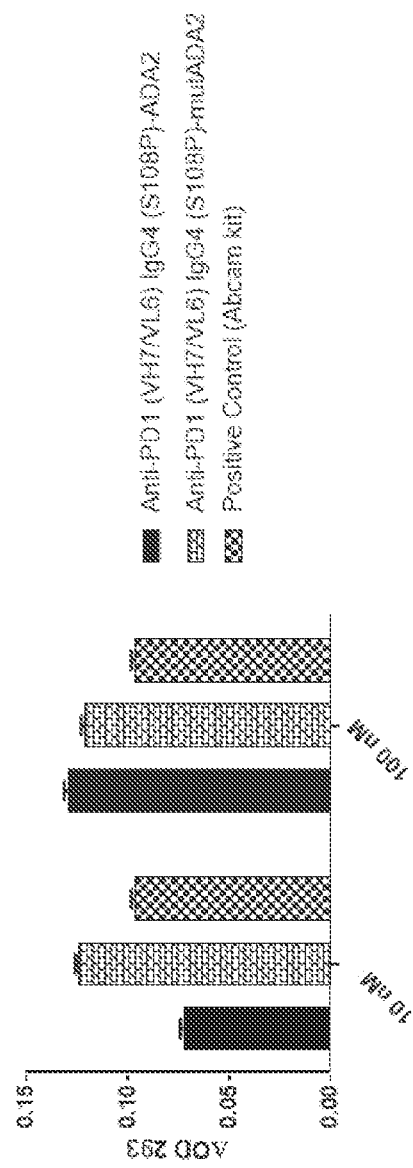

As shown in FIG. 23A-23B, anti-PD-1 (VH7/VL6)-wtADA2 and -mut7ADA2, and anti-PD-1 (VH6/VL5)-wtADA2 and -mut7ADA2 blocked PD-1/PD-L1 interaction with similar potency.

Example 19: ADA2 Enzymatic Activity

The ability of anti-PD-1-ADA2 fusion proteins to enzymatically degrade adenosine was evaluated utilizing an in vitro ADA enzymatic activity assay, as described in Example 12.

As shown in FIG. 24A-24F, at lower concentrations of adenosine, the mut7ADA2 has higher enzymatic activity as compared to the wtADA2.

Example 20: Anti-PD-1-mut7-ADA2 has Higher Enzymatic Activity than Anti-PD-1-wtADA2

The Michaelis Menten constants (Km) of anti-PD-1(VH6/VL5)-wtADA2 and anti-PD-1(VH6/VL5)-mut7ADA2 were measured using the fluorometric ADA2 enzyme assay kit.

Figure 25:
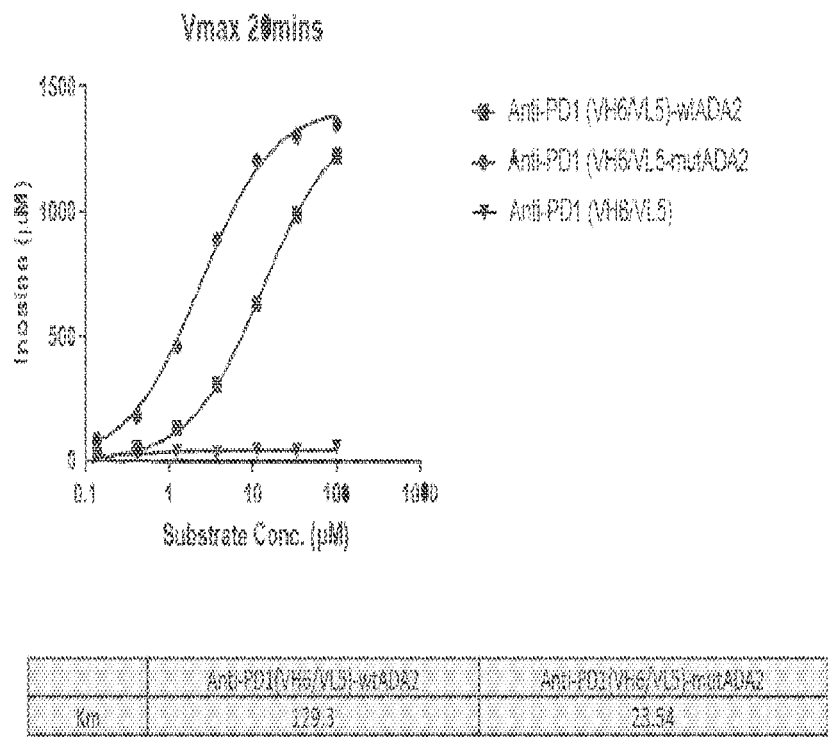
FIG. 25 is a graph showing the enzymatic activity of anti-PD-1-mutADA2 vs. anti-PD-1-wtADA2 as measured by ADA enzymatic activity.

As shown in FIG. 25, anti-PD-1-mut7ADA2 has a higher Km compared to anti-PD-1-wtADA2.

Example 21: Anti-PD-1-wtADA2 Reverses Adenosine-Mediated Suppression of T Cell Proliferation The ability of anti-PD-1-wtADA2 to promote T cell proliferation was assessed in vitro using normal donor PBMCs. CellTrace Violet-labeled PBMCs co-cultured in media containing 1 mM adenosine were stimulated in the presence of increasing concentrations of anti-PD-1(VH6/VL5)-wtADA2 and anti-PD-1(VH6/VL5). The supernatants were collected for cytokine analysis. The cells were assayed for T cell proliferation by flow cytometry.

Figures 26C, 26D:
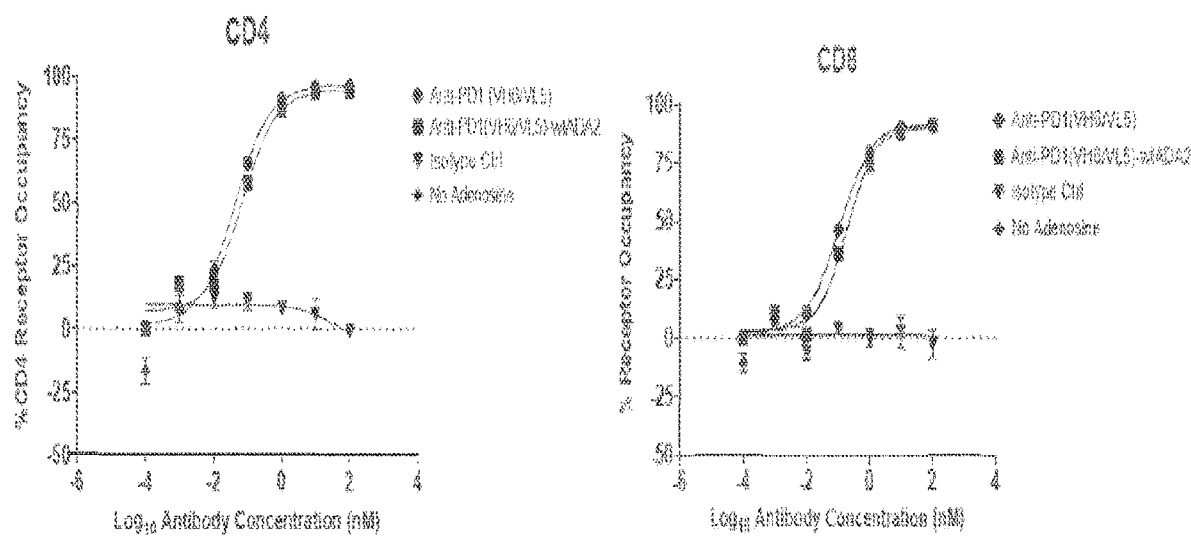

The data showed that anti-PD-1 (VH6/VL5)-wtADA2 significantly reversed the adenosine-mediated suppression of CD4$^+$ (FIG. 26A) and CD8$^+$ T cells (FIG. 26B) as compared to anti-PD-1 (VH6/VL5) or isotype control. As shown in FIGS. 26C and D, both anti-PD-1 and anti-PD-1-wtADA2 similarly occupied PD-1 receptor on CD4$^+$ (FIG. 26C) and CD8$^+$ T cells (FIG. 26D).

The ability of anti-PD-1(VH7/VL6)-wtADA2 to promote T cells function was further assessed by stimulating PBMCs in media containing adenosine in the presence of increasing concentrations of anti-PD-1 (VH7/VL6), anti-PD-1(VH7/VL6)-wtADA2, or isotype controls. The culture supernatants were collected and assayed for IFNγ production.

Figure 26E:
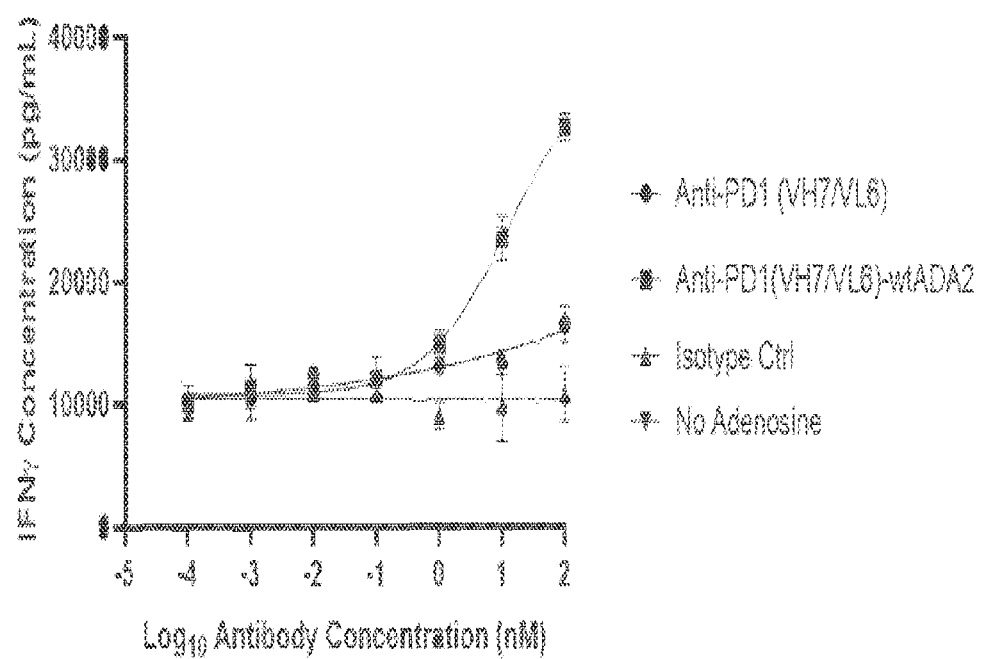
FIG. 26E is a graph depicting IFNγ production by anti-PD-1-wtADA2 as compared to anti-PD-1 or isotype control.

FIG. 26E shows that anti-PD-1(VH7/VL6)-wtADA2 treatment induced significantly more IFN-γ as compared to anti-PD-1 or isotype control.

Example 22: WtADA2 and mutADA2 Showed Comparable Reversal of Adenosine-Mediated Suppression of T Cell Proliferation The effectiveness of wtADA2 and mutADA2 to reverse adenosine-mediated suppression of T cell proliferation was assessed by stimulating labeled PBMCs in a media containing adenosine in the presence of increasing concentration of anti-PD-1-wtADA2, anti-PD-1-mutADA2, anti-RSV-wtADA2, and anti-RSV-mutADA2. The cells were stained, then analyzed for proliferation by flow cytometry.

Figure 27A:
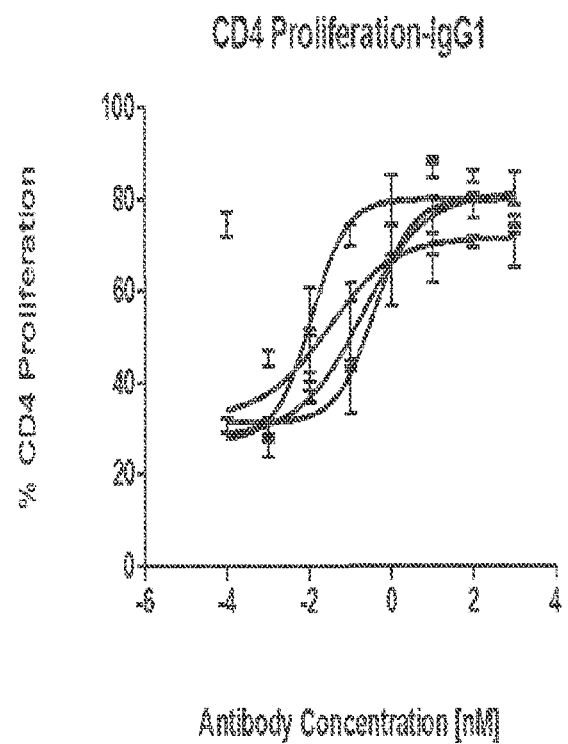
FIGS. 27A-27B are graphs depicting the effectiveness of wtADA2 and mutADA2 to reverse adenosine-mediated suppression of T cell proliferation.
Figure 27B:
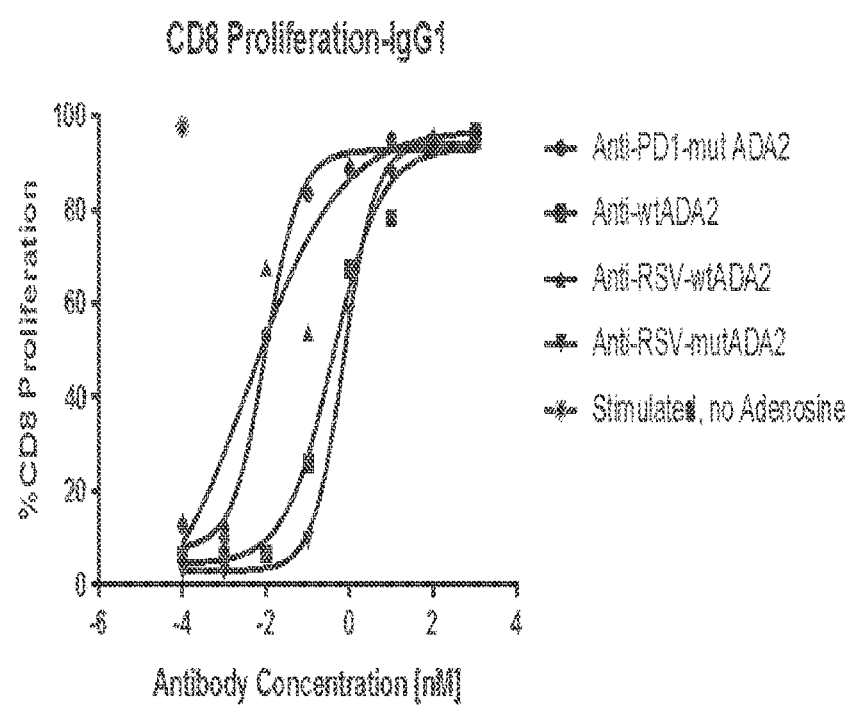

As shown in FIG. 27, both the wtADA2 and mutADA fusion proteins were equally effective at reversing the adenosine-mediated suppression of CD4 T cells (FIG. 27A) and CD8 T cells (FIG. 27B).

Example 23: Blockade of PD-1-PDL1 Interaction by Anti-PD-1(VH6/VL5)-ADA2

The ability of various forms of anti-PD-1-ADA2 fusion proteins to block PD-1/PD-L1 interaction was evaluated using a reporter bioassay as mentioned in Example 12.

Figure 28:
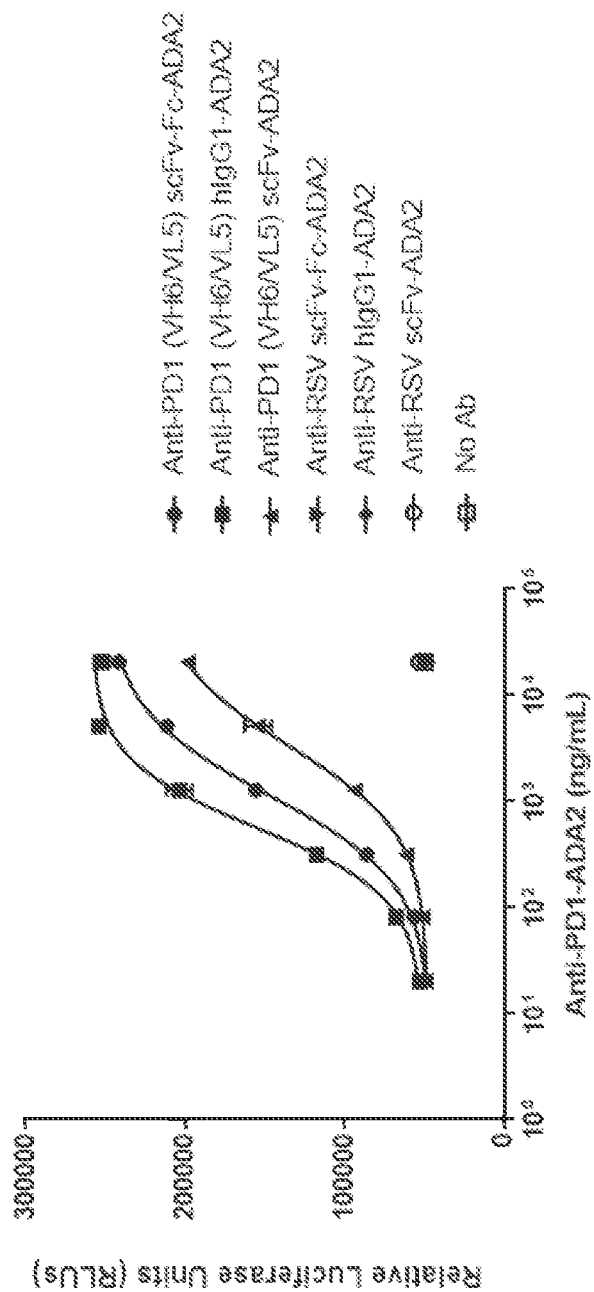
FIG. 28 is a graph depicting the effect of variants of anti-PD-1-ADA2 fusion proteins on the blockade of PD-1-PDL1 interaction.

As shown in FIG. 28, anti-PD-1 (VH6/VL5) scFv-Fc-ADA2, hIgG1-ADA2, and scFv-ADA2 all showed functional activity as measured by the PD-1/PD-L1 Blockade Bioassay.

Example 24: ADA Enzymatic Activity of Anti-PD-1-ADA2-scFv-Fc

The ability of various forms of anti-PD-1-ADA2 fusion proteins to enzymatically degrade adenosine was evaluated in an in vitro ADA enzymatic activity assay, as described in Example 12.

Figure 29:
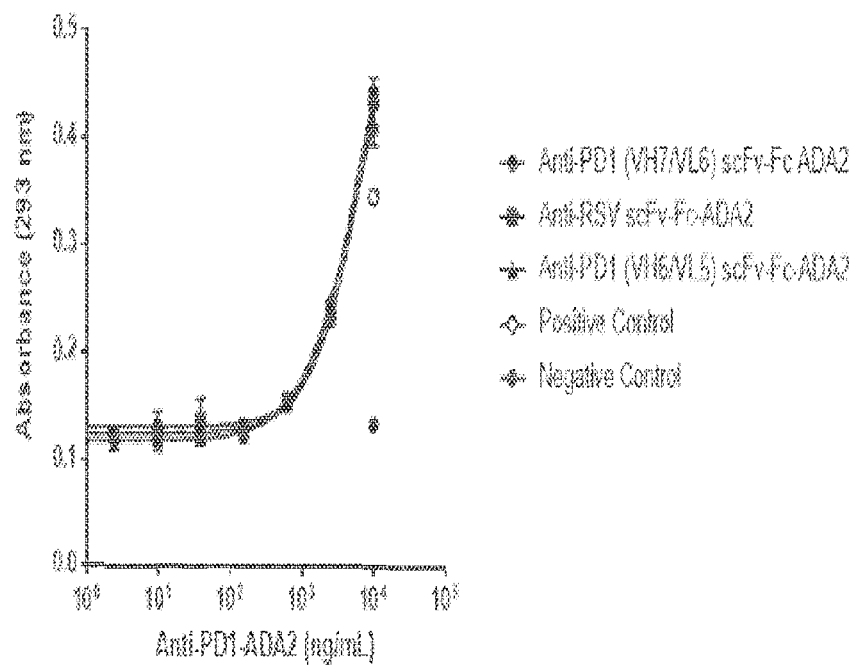
FIG. 29 a graph showing the enzymatic activity of anti-PD-1-ADA2-scFv-Fc as measured by ADA enzymatic activity.

As shown in FIG. 29, anti-PD-1 (VH7/VL6) scFv-Fc-ADA2 and (VH6/VL5) scFv-Fc-ADA2 had similar ADA2 enzymatic activity as compared to the control.

Figure 30:
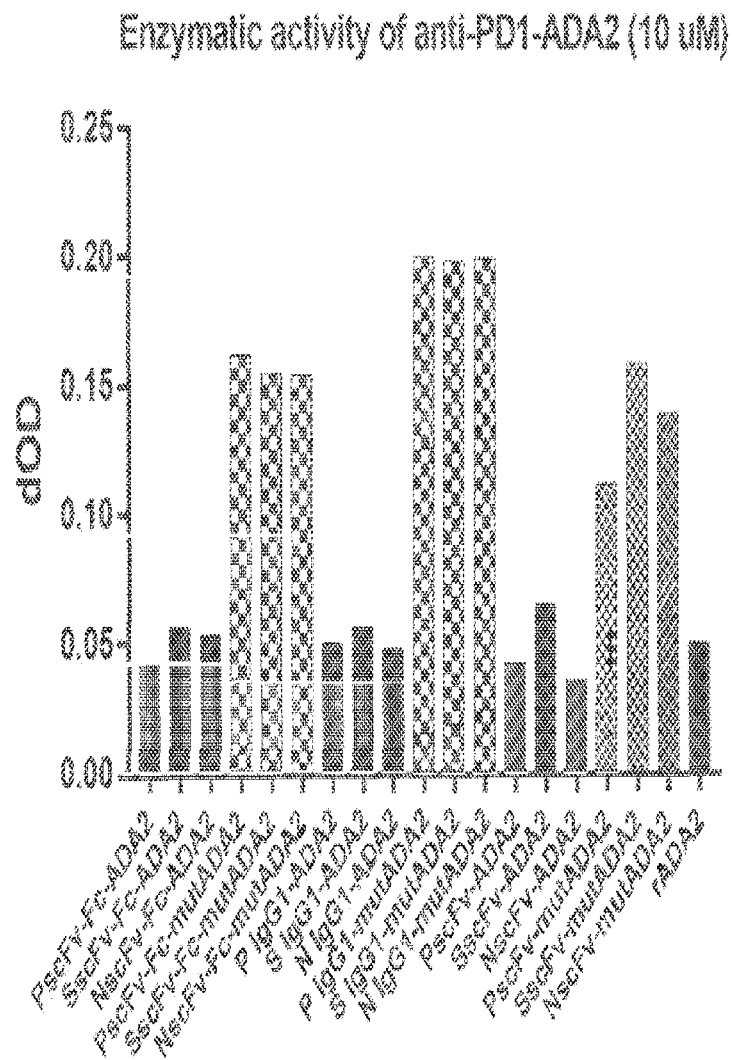
FIG. 30 is a bar graph showing the enzymatic activity of variants of anti-PD-1-ADA2 as measured by ADA enzymatic activity.

Example 25: ADA Enzymatic Activity of Various Anti-PD-1-ADA2 and Anti-PD-1-mutADA2 Constructs ADA enzymatic activity assay was conducted as described in Example 12. As shown in FIG. 30, at 10 nM of adenosine, mutADA2 was seen to exhibit higher enzymatic activity as compared to the wtADA2.

Example 26: Anti-PD-1-ADA2 Promoted IFN-γ Production and Proliferation of Tumor-Infiltrating Lymphocytes (TILs) in Primary CRC Patient Tumor PBMCs purified from CRC patients were co-cultured with matched dissociated tumor cells. CellTrace Violet-labeled cells were stimulated with anti-CD3 and anti-CD28 in the presence of isotype control, anti-PD-1 (VH6/VL5), or anti-PD-1 (VH6/VL5)-wtADA2 fusion protein. The culture supernatants were collected and IFN-γ levels were quantified by MSD per the manufacturer's protocol and cells were assessed for T cell proliferation. For gene expression analysis, the cells pellets were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Figure 31A:
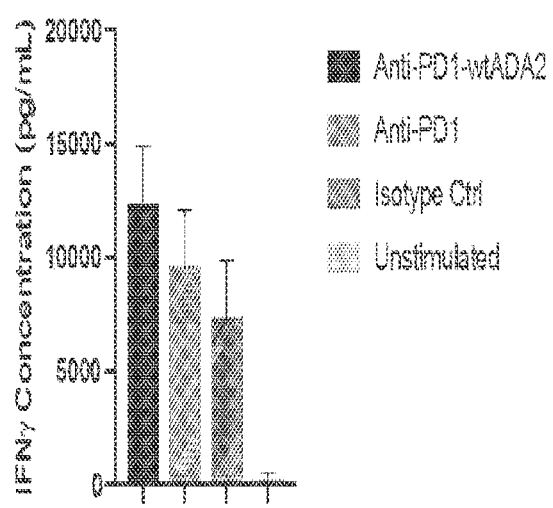
FIGS. 31A-31B are graphs depicting the effect of anti-PD-1-wtADA2 on IFN-γ production and proliferation of tumor-infiltrating lymphocytes (TILs) in primary CRC patient tumor.
Figure 31B:
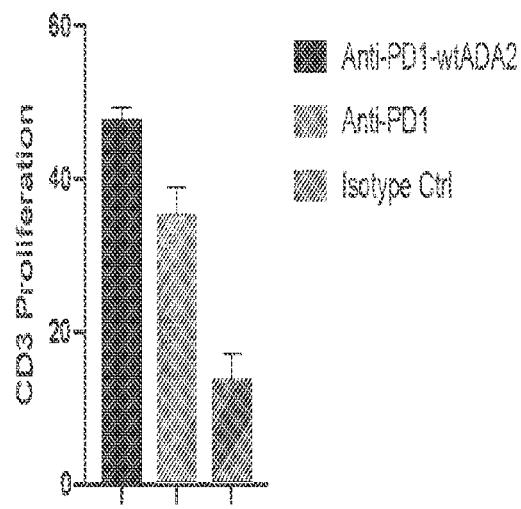

As shown in FIG. 31A, anti-PD-1-wtADA2 fusion protein promoted higher level of IFN-γ production and T cell proliferation (FIG. 31B) as compared to anti-PD-1 or isotype control. In addition, anti-PD-1-wtADA2 fusion protein treatment resulted in significant upregulation of IFN-γ signaling and chemokine signaling genes and cytotoxic genes (FIG. 31C) as compared to anti-PD-1 treatment, highlighting improved cytotoxic function of T cells in the presence of tumor as compared to an anti-PD-1 antibody.

Example 27: Effect of Anti-PD-1-wtADA2 Fusion Protein in a Humanized Mouse Model of Lung Cancer NSG mice humanized with PBMCs were inoculated intraprancreatically (ortotopic injection) with the pancreatic cancer cell line Panc.08.fLuc.eGFP. Mice body weight was measured weekly and tumor weights were measured at the end of the study on day 38. Mice were randomized into treatment groups and treated twice weekly with HBSS (vehicle control), anti-PD-1 (VH6/VL5), and anti-PD-1 (VH6/VL5)-wtADA2.

Figure 32:
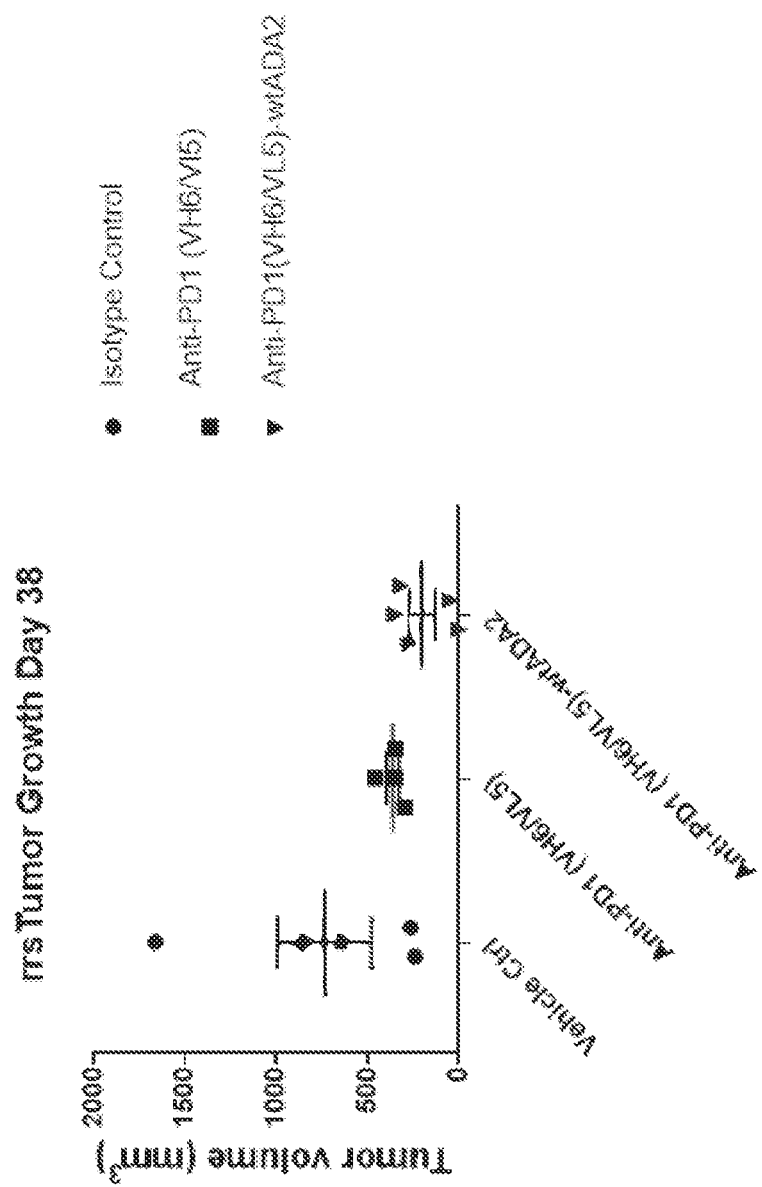
FIG. 32 is a graph depicting the effect of anti-PD-1 vs. anti-PD-1-wtADA2 on tumor volume of a humanized mouse model of lung cancer.

As can be seen in FIG. 32, mice treated with anti-PD-wtADA2 had significantly smaller tumors compared to mice treated with anti-PD-1 or isotype control.

Example 28: Treatment of Anti-PD-1(VH6/VL5)-wtADA2 Downregulated the Adenosine Pathway, Angiogenesis and Upregulated Cytotoxicity and Cytokine Genes PBMCs purified from CRC patients were co-cultured with matched dissociated tumor cells. CellTrace Violet-labeled cells were stimulated with anti-CD3 and anti-CD28 in the presence of isotype control, anti-PD-1 (VH6/VL5) or anti-PD-1 (VH6/VL5)-wtADA2 fusion protein. The culture supernatants were collected and IFN-γ levels were quantified by MSD per manufacturer's protocol and cells assess for T cell proliferation. For gene expression analysis, the cultures were duplicated and the cells pellets were harvested by centrifugation and RNA was purified using the Qiagen RNAeasy micro kit according the manufacturer's protocol. Purified RNA was used for gene expression analysis using the nanostring according to the manufacturer's instructions. Gene expression was analyzed using Nanostring nCounter software.

Anti-PD-1-wtADA2 fusion protein promoted higher level of IFN-γ production and T cell proliferation compared to anti-PD-1 or isotype control (data not shown). Anti-PD-1-wtADA2 fusion protein treatment also resulted in significant upregulation of IFN-γ signaling and chemokine signaling genes and cytotoxic genes compared to anti-PD-1 treatment highlighting improved cytotoxic function of T cells in the presence of tumor compared to an anti-PD-1 antibody (data not shown).

Example 29: Anti-PD-1(VH7-VL6)-mutADA2 Inhibits the PDL-1/PD1 Pathway

To assess the effect of an anti-PD-1(VH7-VL6)-mutADA2 on the PDL1/PD1 pathway, the Promega PD1/PDL1 blockade assay was used. Briefly, effector Jurkat T cells expressing PD-1 and a luciferase reporter under a Nuclear Factor of Activated T-Cells ("NFAT") response element, artificial antigen presenting cells (aAPC), and CHO-K1 cells engineered to express PD-L1 and a T cell receptor activator were thawed and rested overnight in complete T cell media at 37° C. in a CO2 incubator. The cells were then co-cultured in the presence of increasing concentrations of anti-PD-1 (VH7-VL6)-mutADA2. The bioluminescent signal was detected and quantified using the Bio-Glo™ Luciferase Assay System and the GloMax® Discover System luminometer.

Figure 34:
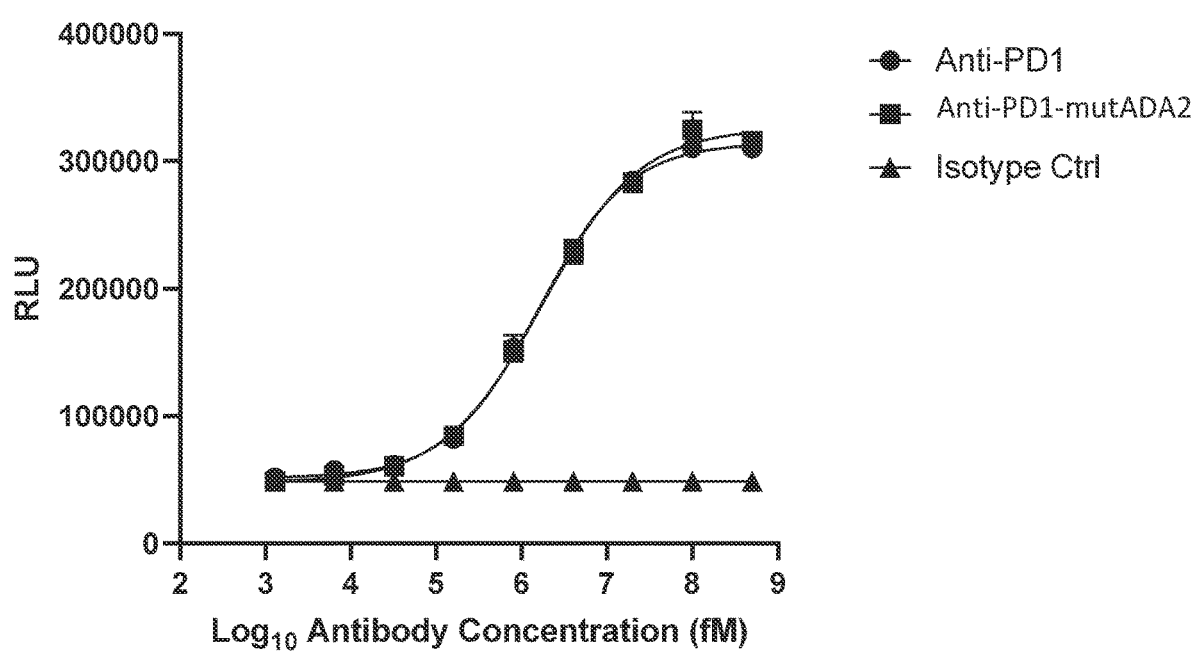
FIG. 34 is a graph depicting the effect of an anti-PD-1-mutADA2 on the blockade of PD-1-PD-L1 interaction.

The addition of anti-PD-1(VH7-VL6)-mutADA2 was found to inhibit the inhibitory signal and reverse the bioluminescence signal. As can been seen in FIG. 34, anti-PD-1 (VH7/VL6)-mutADA2 inhibits the inhibitory signal of PD1/PDL1 pathway in a dose-dependent manner.

Figure 35A:
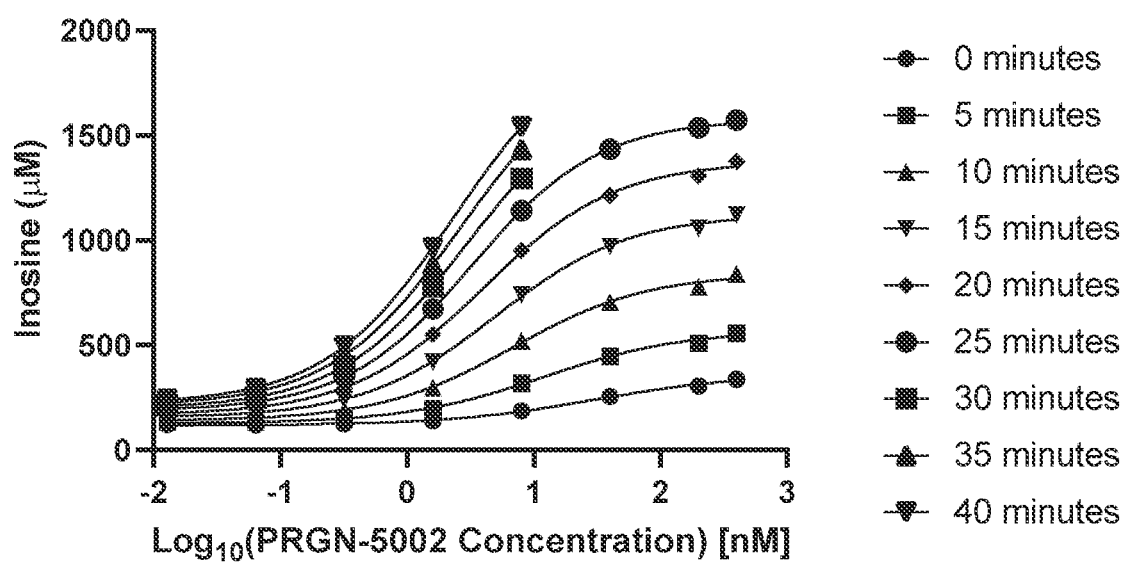
FIGS. 35A-35B are graphs depicting anti-PD-1-wtADA2 catalyzing adenosine into inosine in both a dose-dependent (FIG. 35A) and a substrate concentration-dependent (FIG. 35B) manner.
Figure 35B:
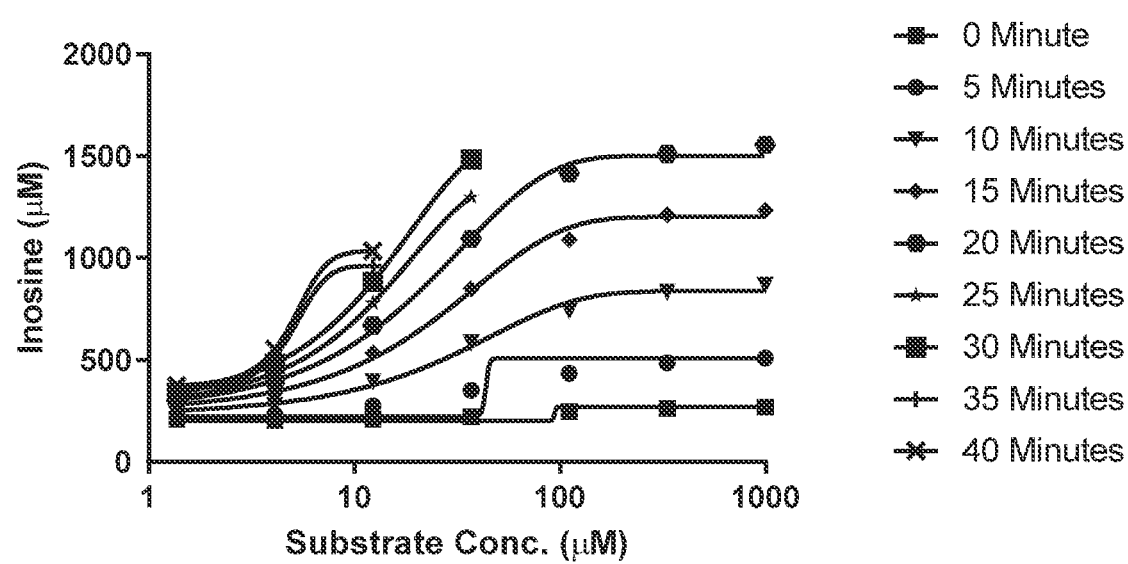

Example 30: Anti-PD-1(VH6/VL5)-wtADA2 Catalyzes Adenosine into Inosine in Dose-Dependent and Substrate Concentration-Dependent Manner To assess the ability of anti-PD-1(VH6/VL6)-wtADA2 to catalyze adenosine into inosine, the adenosine deaminase activity assay was used. Initially 100 μM of adenosine was incubated with different concentrations of anti-PD-1(VH6/VL6)-wtADA2 at different times. As can been seen FIGS. 35A-35B, anti-PD-1(VH6/VL6)-wtADA2 catalyzed adenosine in both a concentration and time dependent manner.

Example 31: Anti-PD-1(VH6/VL5)-wtADA2 and Anti-PD-1(VH6/VL5)-mutADA2 Reverses Adenosine-Mediated Suppression of T Cell Proliferation in Dose-Dependent Manner Adenosine has been shown to suppress T cell activation and effector function (e.g., proliferation, cytokine production, and cytotoxicity). To assess the ability of anti-PD-1 (VH6/VL5)-wtADA2 and anti-PD-1(VH6/VL5)-mutADA2 to reverse the adenosine-mediated suppression of T cell functions, peripheral mononuclear cells (PBMCs) were stimulated with anti-CD3 antibody in the presence of adenosine (100 mM) and increasing concentrations of either 100 mM, a control antibody-ADA2, or anti-PD1. The PBMCs were stained with CellTrace Violet to monitor T cell proliferation and the culture supernatants were collected at the end of the incubation and screened for IFN-γ production.

Figure 36A:
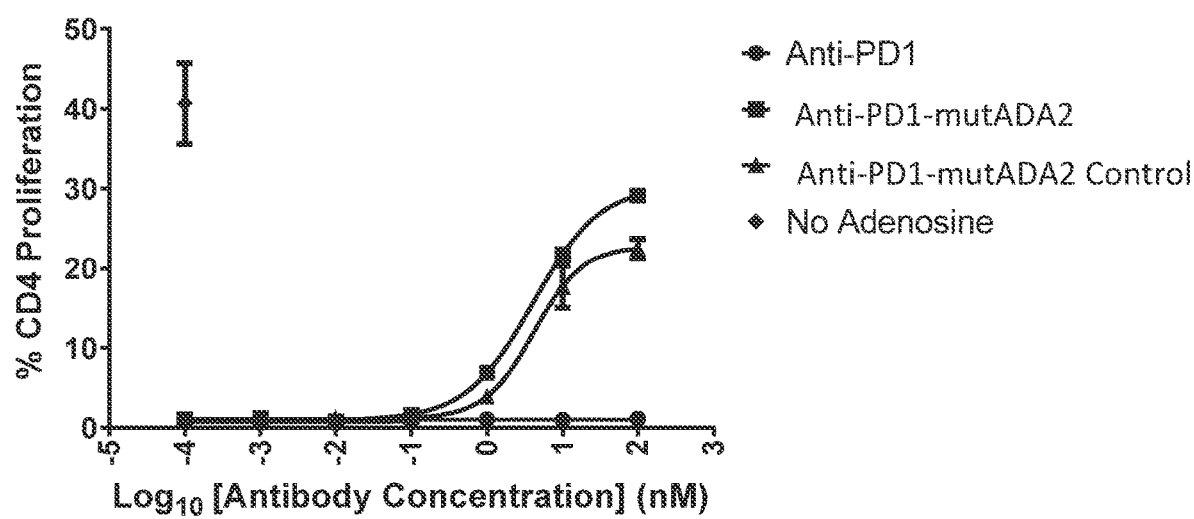
FIG. 36A-36C are graphs depicting anti-PD-1-wtADA2 and anti-PD-1-mutADA2 reversing the adenosine-mediated suppression of T cell proliferation in a dose-dependent manner.
Figure 36B:
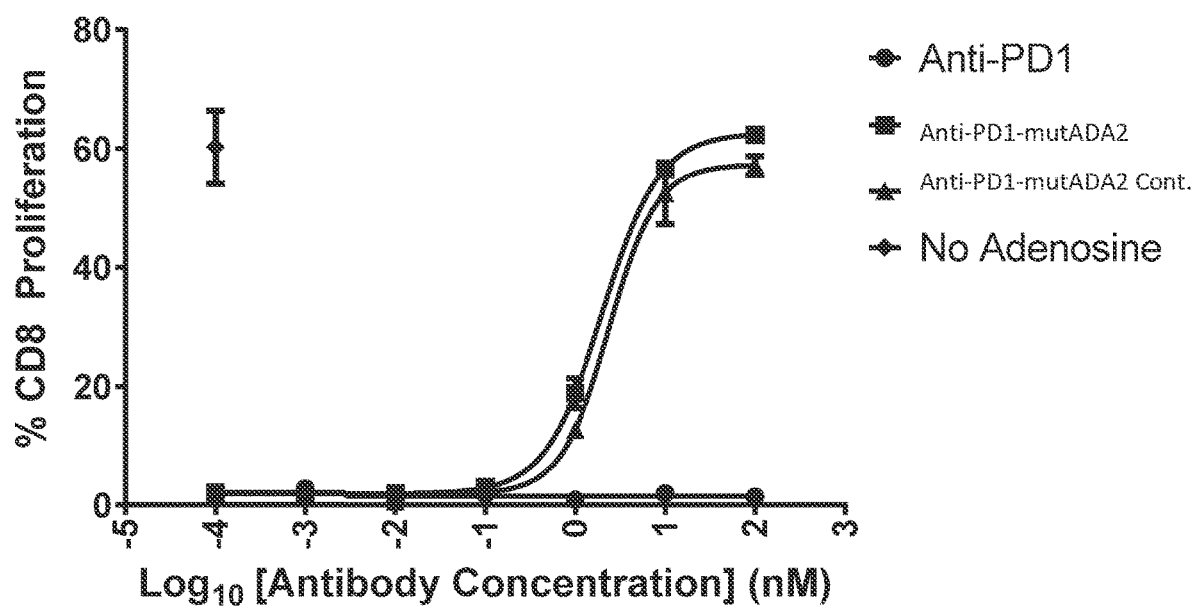
Figure 36C:
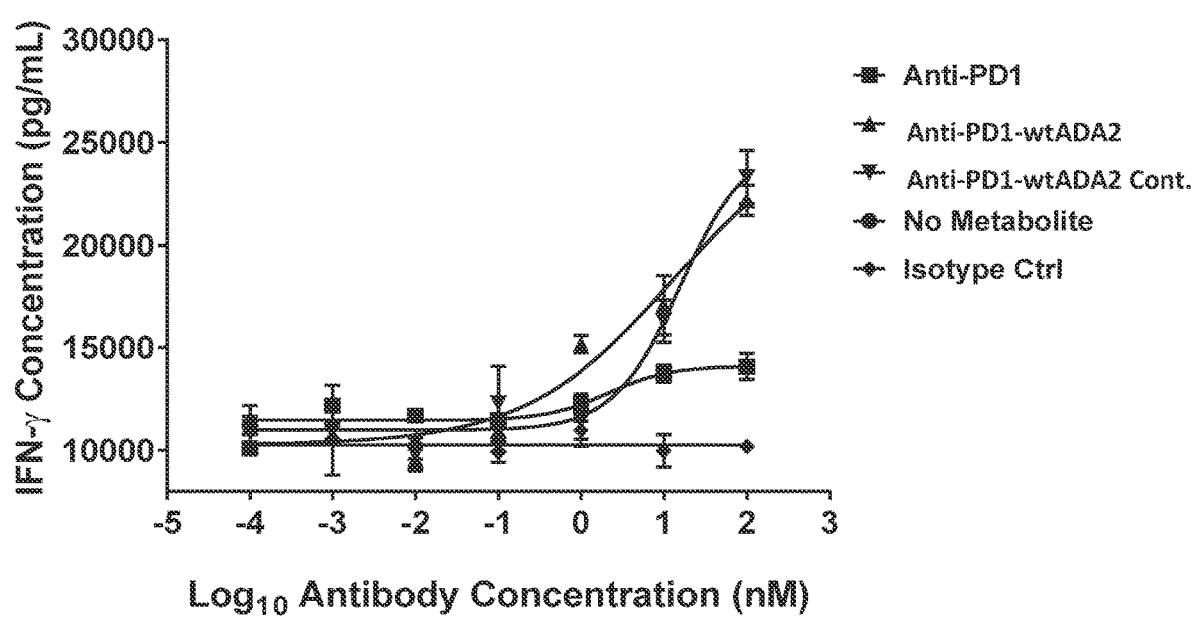

As can be in FIGS. 36A-36C, addition of adenosine was found to completely inhibit T cell proliferation, yet this inhibition was specifically reversed by anti-PD-1(VI-6/VL5)-mutADA2 (FIGS. 36A and 36AB) anti-PD-1(VH6/VL5)-wtADA2 (FIG. 36C) or its control and not by anti-PD1 in a dose-dependent manner.

Example 32: Anti-PD-1(VH7/VL6)-wtADA2 and Anti-PD-1(VH6/VL5)-wtADA2 Reverses Inhibition of T Cell Function Mediated by Adenosine Produced by Tumor Cells in the Presence of ATP To determine whether anti-PD-1(VH7/VL6)-wtADA2 and anti-PD-1(VH6/VL5)-wtADA2 is able to reverse the inhibition of T cells function mediated by tumor cells in the presence of ATP, several human tumor cell lines shown to convert ATP into adenosine were co-cultured with the T cells in the presence of ATP and increasing concentrations of either anti-PD-1(VH7/VL6)-wtADA2 or anti-PD-1(VH6/VL5)-wtADA2, anti-PD1, or isotype controls. The culture supernatants were collected at the end of the incubation and screened for IFN-γ production.

Figure 37A:
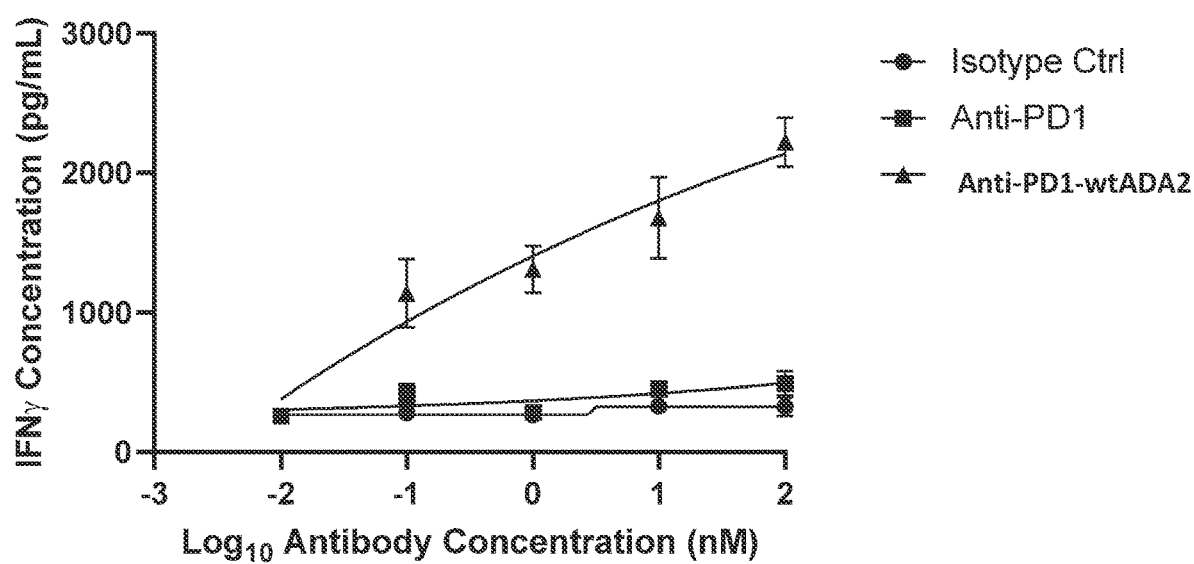
FIGS. 37A-37C are graphs depicting anti-PD-1-wtADA2 reversing, in a dose-dependent manner, the inhibition of T cell function (IFN-γ production) mediated by adenosine in three different tumor cell lines (A549, SKOV3, and Panc.08).
Figure 37B:
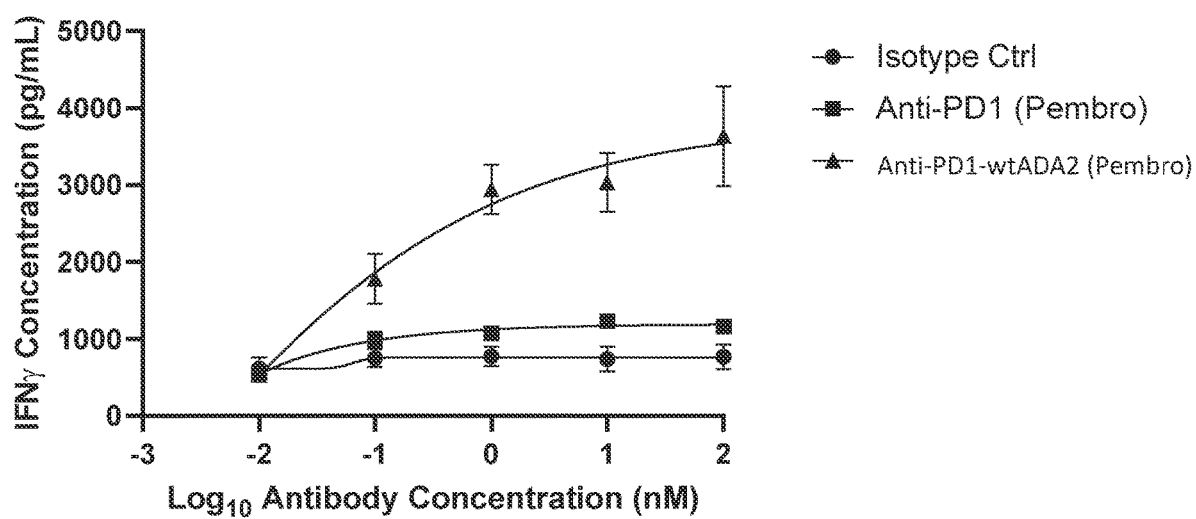
Figure 37C:
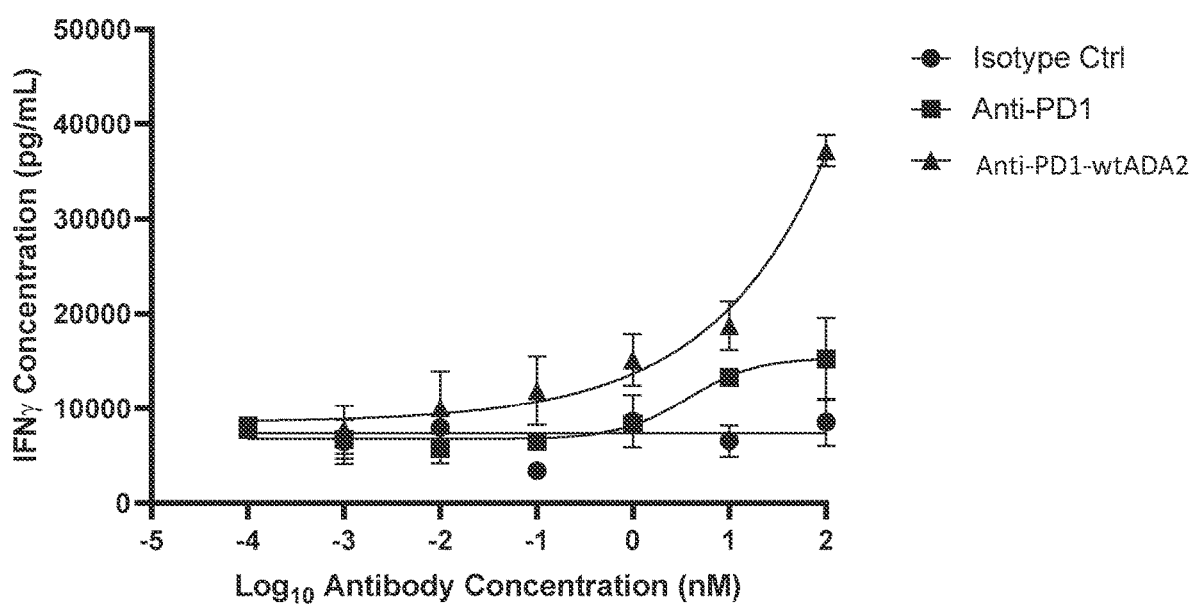

As can been seen in FIGS. 37A and 37B, anti-PD-1(VH7/VL6)-wtADA2) reversed the suppression of IFN-γ production in a dose-dependent manner in tumor cell lines A549, and SKOV3 respectively. And as can be seen in FIG. 37C, anti-PD-1(VH6/VL5)-wtADA2 and reversed the suppression of IFN-γ production in a dose-dependent manner in tumor cell line Panc.08.

Example 33: Anti-PD-1(VH6/VL5)-wtADA2 Inhibits Growth of A549 Tumor in NSG Mouse To assess the ability of anti-PD-1(VH6/VL5)-wtADA2 to inhibit or delay tumor growth, A549 tumor cells were implanted subcutaneously into humanized NSG mice. Mice were randomized by tumor volume into treatment groups and administered anti-PD-1(VH6/VL5)-wtADA2, anti-PD1, or isotype control.

Figure 38:
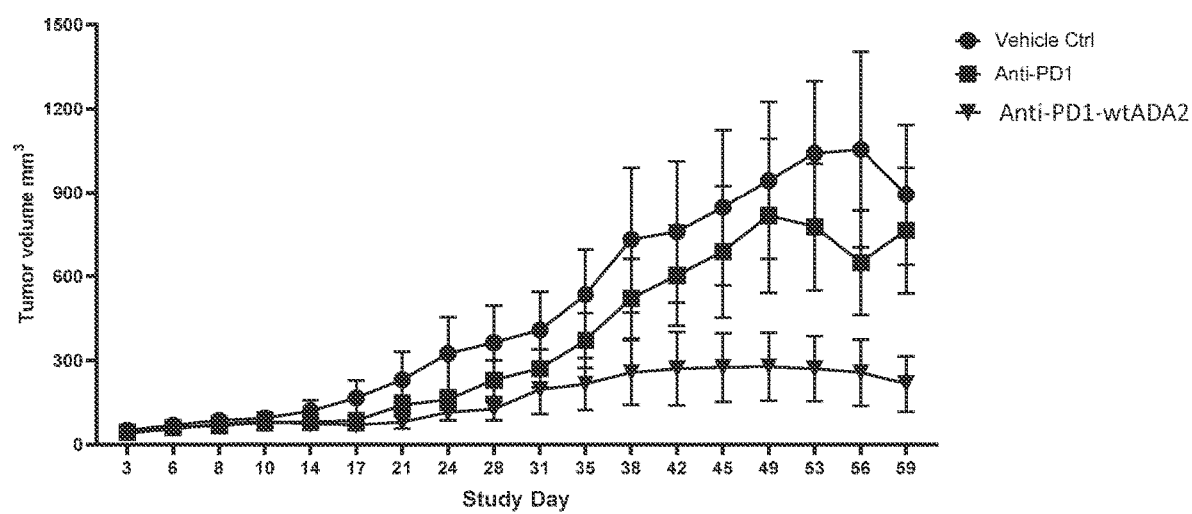
FIG. 38 is a graph depicting anti-PD-1-wtADA2 inhibiting growth of an A549 tumor in a NOD scid gamma ("NSG") mouse.

As can be seen in in FIG. 38, anti-PD-1(VH6/VL5)-wtADA2 significantly delayed A549 tumor growth as compared to anti-PD1 or isotype control.

Example 34: Method of Manufacturing Anti-PD-1 Fusion Proteins

Fusion proteins are synthesized comprising: a) an anti-PD-1 heavy chain variable region comprising the amino acid sequence of any one of SEQ ID NOs: 333-337 or SEQ ID NOs: 384, or SEQ ID NO: 386; and b) an anti-PD-1 light chain variable region comprising the amino acid sequence of any one of SEQ ID NOs: 338-343, SEQ ID NO: 385, or SEQ ID NO: 387. The fusion proteins are formatted in IgG, scFv-Fc or scFv configurations with TGFβRII fused at the C-terminal by linker (G4S) 2 (SEQ ID NO: 563). The anti-PD-1-trap fusion proteins are then transiently expressed in Expi293 cells according to the manufacturer's protocol. To purify the fusion proteins, the transfected supernatants are loaded onto a protein L column using AKTA AVANT and the column is washed with PBS before the protein is eluted with IgG elution buffer (Pierce). The eluted protein is then buffer-exchanged into PBS using a PD-10 column (GE Healthcare).

Example 35: Anti-MUC16 Antibodies

The MUC16 binding affinity of anti-MUC16 IgGs was analyzed using Biacore. MUC16-Fc antigen and reference were immobilized on Biacore CMS surface, 6-12 replicate series diluted concentrations of anti-MUC16 IgG on MUC16-Fc antigen and reference surface were injected. The kinetics were evaluated for 1:1 model: Langmuir with mass transfer.

As shown in Table 12, anti-MUC16 VL10/VH10, VL7/VH10, VL9/VH10 and VL8/VH2 IgG showed strong interaction with MUC16-Fc antigen by Biacore. The binding affinity (KD) was in the 1-4 μM range.

TABLE 12

Biacore binding affinity of humanized variants of anti-MUC16 antibodies

| Ligand | Analyte | $k_a$ (1/Ms) | $k_d$ (1/s) | $K_D(M)$ |
|---|---|---|---|---|
| MUC16-Fc | Anti-MUC16 $V_L8/V_H13$ IgG | 3.56e5 | 3.77e−5 | 1.06e−10 |
|  | Anti-MUC16 $V_L10/V_H10$ IgG | 4.78e5 | 7.42e−7 | 1.55e−12 |
|  | Anti-MUC16 $V_L8/V_H10$ IgG | 4.62e5 | 2.2e−6 | 4.77e−12 |
|  | Anti-MUC16 $V_L9/V_H10$ IgG | 6.5e5 | 8.62e−7 | 1.33e−12 |
|  | Anti-MUC16 $V_L8/V_H2$ IgG | 5.42e5 | 7.31e−7 | 1.35e−12 |

Example 36: TGFβ1 Binding to Anti-MUC16 $V_L10/V_H10$ hIgG1-TGFβRII

Figure 39:
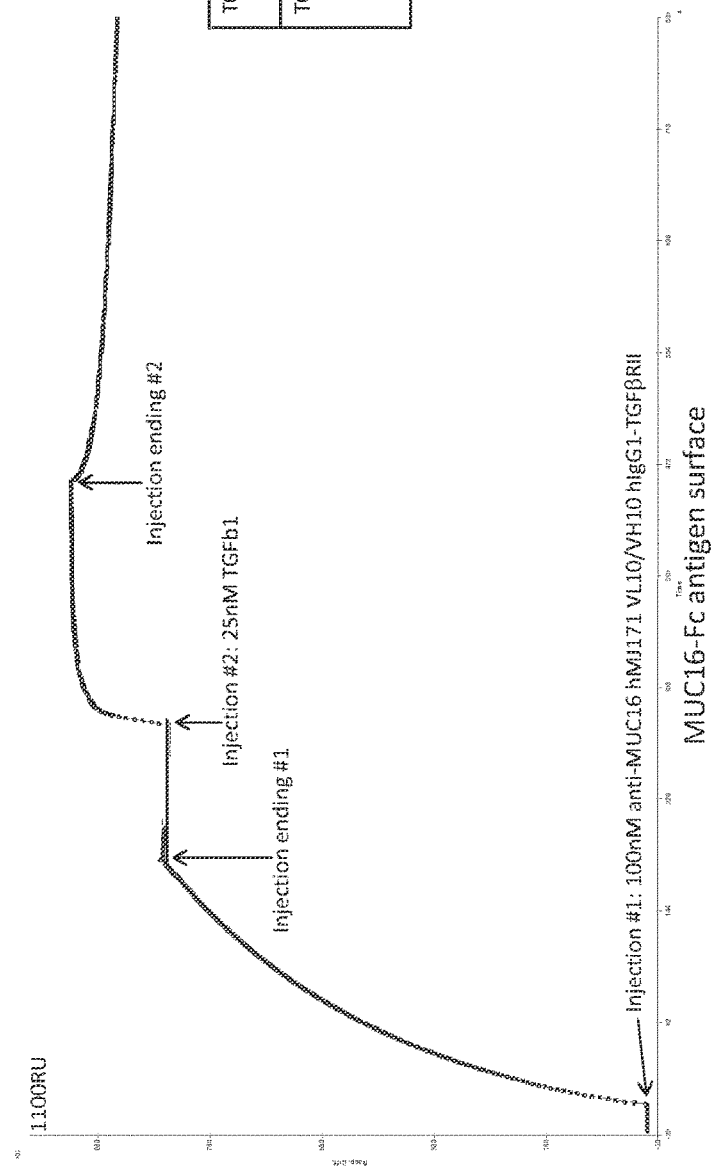
FIG. 39 is a graph depicting simultaneous binding of TGF-β1 and MUC 16 to anti-MUC16 $V_L$10/$V_H$10-TGFβRII fusion protein.

Simultaneous binding of TGFβ1 and MUC16 to anti-MUC16 $V_L10/V_H10$ hIgG1-TGFβRII fusion protein was analyzed using Biocore assay. MUC16-Fc antigen was immobilized on Biacore CM5 chip surface. 100 nM anti-MUC16 $V_L10/V_H10$ hIgG1-TGFβRII was injected over sensor surfaces followed by the injection of 25 nM TGFβ1 over sensor surfaces. As observed in FIG. 39, anti-MUC16 VL10/VH10-TGF~RII bound to both of MUC16-Fc antigen and TGF~1 using Biacore simultaneous binding assay.

Figure 40:
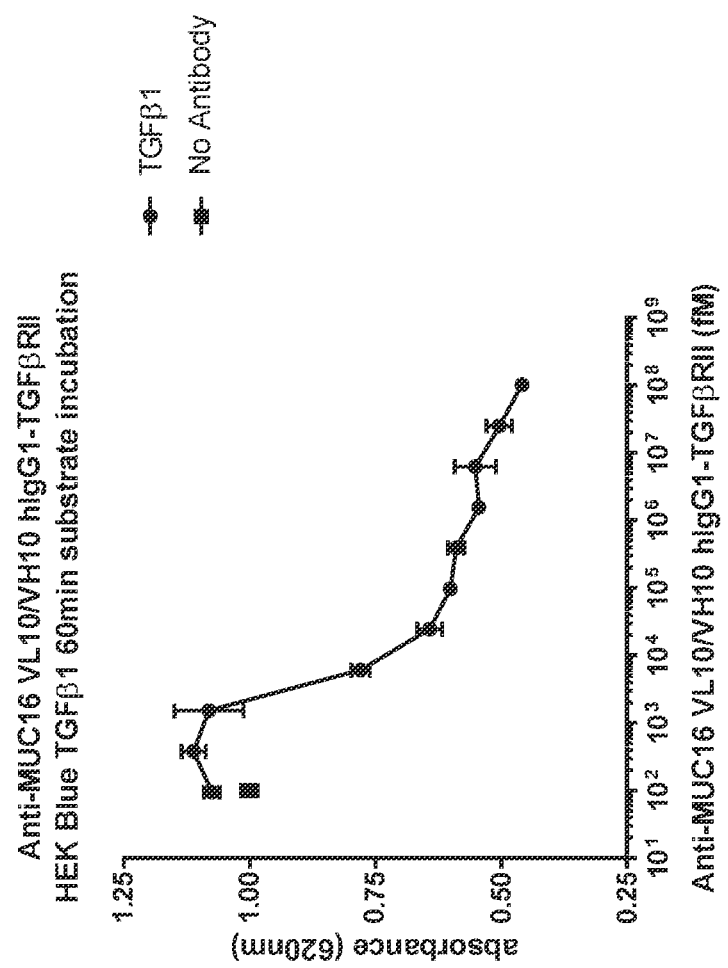
FIG. 40 is a graph showing binding of a TGF-β1 isoform to an anti-MUC16 $V_L$10/$V_H$10-TGFβRII fusion protein.

Example 37: Inhibition of TGFβ1 Induced Reporter Gene Activity by Anti-MUC16 $V_L10/V_H10$ hIgG1-TGFβRII TGFβ1 was diluted and added to a flat-bottom 96-well plate. Anti-MUC16 $V_L10/V_H10$ hIgG1-TGFβRII was diluted to 100 nM and serially diluted four-fold. Trap proteins was added to TGF-β and allowed to incubate. HEK Blue TGF-β1 cells were diluted to 0.7e6 cells/mL and added to the plate following incubation. Following the second incubation, supernatant was removed and added to the Quanti-Blue substrate and the plate will be read on the SpectraMax instrument (620 to 655 nm). As shown in FIG. 40, anti-MUC16 $V_L10/V_H10$ hIgG1-TGFβRII showed binding to TGFβ1 with IC50=3.8 pM using HEK Blue TGF-β assay.

Sequences

Provided herein are tables providing a representative list of certain sequences included in the embodiments described herein.

TABLE 13

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| Anti-PD-1 VH1 | 1 | QVQLVESGGGVVQPGRSLRLSCAASGFTFRSYGMHWVRQAPGKGLEWVAIIFYDGSNKYYADSVKGRFTISRDNSKNTLYLQMNSLRAEDTAVYYCARDDDYWGQGALVTVSS | | |
| Anti-PD-1 VH2 | 2 | EVQLVQSGGGVVQPGRSLRLSCAASGFTFSSYGMHWVRQAPGKGLEWVAVIWYDGSNKYYADSVKGRFTISRDNSKNTLYLQMNSLRAEDTAVYYCAGEGFDYWGQGTLVTVSS | | |
| Anti-PD-1 VH3 | 3 | QVQLVQSGAEVKKPGASVKVSCKASGYTFTGYYMHWVRQAPGQGLEWMGAINPNSGGTNYAQKFQGRVTM | | |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | TRDTSISTAYMELS RLRSDDTAVYYCAR RPDRANWHFDYWGQ GTLVTVSS | | |
| Anti-PD-1 VH4 | 4 | QVQLVQSGAEVKKP GASVKVSCKASGYT FTGYYMHWVRQAPG QGLEWMGAINPNSG GTNYAQKLQGRVTM TTDTSTSTAYMELR SLRSDDTAVYYCAR HGLKGDGYFDYWGQ GTLVTVSS | | |
| Anti-PD-1 VH5 | 5 | QVQLVESGGGVVQP GRSLRLDCKASGIT FSNSGMHWVRQAPG KGLEWVAVIWYDGS KRYYADSVKGRFTI SRDNSKNTLFLQMN SLRAEDTAVYYCAT NNDYWGQGTLVTVS S | | |
| Anti-PD-1 VH6 | 6 | QVQLVESGGGVVQP GRSLRLDCKASGIT FSNSGMHWVRQAPG KGLEWVAVIWYDGS KRYYADSVKGRFTI SRDNSKNTLFLQMN SLRAEDTAVYYCAT NDDYWGQGTLVTVS S | 109 | CAGGTGCAGCTGGTCGAAAGCGGAGGA GGAGTGGTCCAGCCAGGACGATCCCTG AGACTGGATTGTAAGGCCTCTGGAATC ACATTCTCTAACAGTGGAATGCACTGG GTGCGCCAGGCACCAGGAAAAGGACTG GAGTGGGTGGCCGTCATCTGGTACGAC GGGTCAAAGCGATACTATGCAGATAGC GTGAAAGGAAGGTTCACAATTTCACGC GACAACAGCAAGAATACTCTGTTTCTG CAGATGAACTCTCTGAGAGCAGAGGAT ACTGCCGTGTACTATTGTGCTACCAAT GACGATTATTGGGGGCAGGGAACTCTG GTGACCGTCAGTTCA |
| Anti-PD-1 VH7 | 7 | QVQLVQSGVEVKKP GASVKVSCKASGYT FTNYYMWVRQAPG QGLEWMGGINPSNG GTNFNEKFKNRVTL TTDSSTTTAYMELK SLQFDDTAVYYCAR RDYRFDMGFDYWGQ GTTVTVSS | 110 | CAGGTGCAGCTGGTCCAGAGCGGCGTG GAAGTCAAGAAACCCGGGGCCTCAGTG AAGGTCAGCTGTAAAGCTTCCGGCTAC ACCTTCACAAACTACTATATGTATTGG GTGAGACAGGCACCAGGACAGGGACTG GAGTGGATGGGCGGGATTAACCCTAGT AATGGAGGCACTAACTTCAACGAAAAG TTTAAAAACAGGGTGACCCTGACCACA GATTCAAGCACTACCACAGCTTACATG GAGCTGAAGTCCCTGCAGTTTGACGAT ACAGCCGTGTACTATTGTGCTCGGAGA GACTACAGGTTCGATATGGGCTTTGAC TATTGGGGCCAGGGGACTACCGTGACC GTCTCCTCT |
| Anti-PD-1 VL1 | 8 | EIVMTQSPATLSLS PGERATLSCRASQS VSSYLAWYQQKPGQ APRLLIYDASNRAT GIPARFSGSGSGTD FTLTISSLEPEDFA VYYCQQYNNWPRTF GQGTKVEIK | | |
| Anti-PD-1 VL2 | 9 | EIVLTQSPATLSLS PGERATLSCRASQS VSSYLAWYQQKPGQ APRLLIYDASNRAT GIPARFSGSGSGTD FTLTISSLEPEDFA VYYCQQRSNWPKTF GQGTKVEIK | | |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| Anti-PD-1 VL3 | 10 | RNVLTQSPLSLPVTPGEPASISCRSSQSLSSSGYTYLDWYLQKPGQSPQLLIYLASWRDSGVPDRFSGSGSGTDFTLKISRVEAEDVGVYYCMQAEQTPGPGNTFGQGTKLEIK | | |
| Anti-PD-1 VL4 | 11 | DVVMTQSPLSLPVTPGEPASISCRSSQSLLHTNGYNYLHWYLQKPGQSPQLLIYLGSWQDSGVPDRFSGSGSGTDFTLKISRVEAEDVGVYYCMQAEQTPRTFGQGTRLEVK | | |
| Ant-PD-1 VL5 | 12 | EIVLTQSPATLSISPGERATLSCRASQSVSSYLAWYQQKPGQAPRLLIYDASNRATGIPARFSGSGSGTDFTLTISSLEPEDFAVYYCQQSSNWPRTFGQGTKVEIK | 111 | GAGATCGTCCTGACACAGAGTCCAGCAACTCTGAGCCTGTCCCCCGGCGAACGAGCTACTCTGTCCTGCCGGGCATCTCAGAGTGTGTCTAGTTACCTGGCCTGGTATCAGCAGAAGCCCGGCCAGGCTCCTAGGCTGCTGATCTACGACGCCAGCAACAGAGCTACCGGGATTCCTGCCAGGTTCTCAGGCAGCGGGTCCGGAACAGACTTTACCCTGACAATCTCAAGCCTGGAGCCCGAAGATTTCGCTGTGTACTATTGCCAGCAGTCCTCTAATTGGCCTCGCACCTTTGGCCAGGGGACAAAGGTCGAGATCAAG |
| Anti-PD-1 VL6 | 13 | EIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFGGGTKVEIK | 112 | GAGATCGTCCTGACTCAGTCCCCAGCAACCCTGAGTCTGTCACCAGGAGAAAGGGCAACCCTGAGCTGCCGAGCATCCAAGGGGGTGAGCACATCCGGATACTCTTATCTGCACTGGTACCAGCAGAAACCCGGACAGGCTCCTGACTGCTGATCTACCTGGCATCTTATCTGGAGAGTGGCGTGCCTGCTCGGTTCTCTGGGAGTGGATCAGGCACCGATTTTACACTGACTATTTCTAGTCTGGAGCCAGAAGATTTCGCAGTGTACTATTGCCAGCATTCTCGAGACCTGCCCCTGACATTGGCGGGGGAACTAAGGTCGAGATCAAA |
| TGFβRII ECD | 14 | IPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGITFFMCSCSSDECNDNIIFSEEYNTSNPD | | |
| TGFβRII2 ECD | 141 | IPPHVQKSDVEMEAQKDEIICPSCNRTAHPLRHINNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | | |
| TGFβRII min ECD | 142 | PQLCKFCDVRFSTCDNQKSCMSNCSITSICEKPQEVCVAVWRKNDENITLETVCHDPKLPYHDFILEDAA | | |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | SPKCIMKEKKKPGE TFFMCSCSSDECND NIIFSEEYNTSNPD | | |
| TGFβRII | 289 | MGRGLLRGLWPLHI VLWTRIASTIPPHV QKSDVEMEAQKDEI ICPSCNRTAHPLRH INNDMIVTDNNGAV KFPQLCKFCDVRKS TCDNQKSCMSNCSI TSICEKPQEVCVAV WRKNDENITLETVC HDPKLPYHDFILED AASPKCIMKEKKKP GETFFMCSCSSDEC NDNIIFSEEYNTSN PDLLLVIFQVTGIS LLPPLGVAISVIII FYCYRVNRQQKLSS TWETGKTRKLMEFS EHCAIILEDDRSDI SSTCANNINHNTEL LPIELDTLVGKGRF AEVYKAKLKQNTSE QFETVAVKIFPYEE YASWKTEKDIFSDI NLKHENILQFLTAE ERKTELGKQYWLIT AFHAKGNLQEYLTR HVISWEDLRKLGSS LARGIAHLHSDHTP CGRPKMPIVHRDLK SSNILVKNDLTCCL CDFGLSLRLDPTLS VDDLANSGQVGTAR YMAPEVLESRMNLE NVESFKQTDVYSMA LVLWEMTSRCNAVG EVKDYEPPFGSKVR EHPCVESMKDNVLR DRGRPEIPSFWLNH QGIQMVCETLTECW DHDPEARLTAQCVA ERFSELEHLDRLSG RSCSEEKIPEDGSL NTTK | | |
| TGFβRII Isoform B | 290 | MGRGLLRGLWPLHI VLWTRIASTIPPHV QKSVNNDMIVTDNN GAVKFPQLCKFCDV RFSTCDNQKSCMSN CSITSICEKPQEVC VAVWRKNDENITLE TVCHDPKLPYHDFI LEDAASPKCIMKEK KKPGETFFMCSCSS DECNDNIIFSEEYN TSNPDLLLVIFQVT GISLLPPLGVAISV IIIFYCYRVNRQQK LSSTWETGKTRKLM EFSEHCAIILEDDR SDISSTCANNINHN TELLPIELDTLVGK GRFAEVYKAKLKQN TSEQFETVAVKIFP YEEYASWKTEKDIF SDINLKHENILQFL TAEERKTELGKQYW LITAFHAKGNLQEY LTRHVISWEDLRKL GSSLARGIAHLHSD HTPCGRPKMPIVHR | | |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | DLKSSNILVKNDLT CCLCDFGLSLRLDP TLSVDDLANSGQVG TARYMAPEVLESRM NLENVESFKQTDVY SMALVLWEMTSRCN AVGEVKDYEPPFGS KVREHPCVESMKDN VLRDRGRPEIPSFW LNHQGIQMVCETLT ECWDHDPEARLTAQ CVAERFSELEHLDR LSGRSCSEEKIPED GSLNTTK | | |
| Anti-PD-1(VL5) IgG4-(light chain) | 15 | EIVLTQSPATLSLS PGERATLSCRASQS VSSYLAWYQQKPGQ APRLLIYDASNRAT GIPARFSGSGSGTD FTLTISSLEPEDFA VYYCQQSSNWPRTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 299 | GAGATCGTCCTGACACAGAGTCCAGCA ACTCTGAGCCTGTCCCCCGGCGAACGA GCTACTCTGTCCTGCCGGGCATCTCAG AGTGTGTCTAGTTACCTGGCCTGGTAT CAGCAGAAGCCCGGCCAGGCTCCTAGG CTGCTGATCTACGACGCCAGCAACAGA GCTACCGGGATTCCTGCCAGGTTCTCA GGCAGCGGGTCCGGAACAGACTTTACC CTGACAATCTCAAGCCTGGAGCCCGAA GATTTCGCTGTGTACTATTGCCAGCAG TCCTCTAATTGGCCTCGCACCTTTGGC CAGGGGACAAAGGTCGAGATCAAGCGT ACGGTGGCTGCACCATCTGTCTTCATC TTCCCGCCATCTGATGAGCAGTTGAAA TCTGGAACTGCCTCTGTTGTGTGCCTG CTGAATAACTTCTATCCCAGAGAGGCC AAAGTACAGTGGAAGGTGGATAACGCC CTCCAATCGGGTAACTCCCAGGAGAGT GTCACAGAGCAGGACAGCAAGGACAGC ACCTACAGCCTCAGCAGCACCCTGACG CTGAGCAAAGCAGACTACGAGAAACAC AAAGTCTACGCCTGCGAAGTCACCCAT CAGGGCCTGAGCTCGCCCGTCACAAAG AGCTTCAACAGGGGAGAGTGT |
| Anti-PD-1(VL6) IgG4-(light chain) | 296 | EIVLTQSPATLSLS PGERATLSCRASKG VSTSGYSYLHWYQQ KPGQAPRLLIYLAS YLESGVPARFSGSG SGTDFTLTISSLEP EDFAVYYCQHSRDL PLTFGGGTKVEIKR TVAAPSVFIFPPSD EQLKSGTASVVCLL NNFYPREAKVQWKV DNALQSGNSQESVT EQLKSGTASVVCLL LTLSKADYEKHKVY ACEVTHQGLSSPVT KSFNRGEC | 300 | GAGATCGTCCTGACTCAGTCCCCAGCA ACCCTGAGTCTGTCACCAGGAGAAAGG GCAACCCTGAGCTGCCGAGCATCCAAG GGGGTGAGCACATCCGGATACTCTTAT CTGCACTGGTACCAGCAGAAACCCGGA CAGGCTCCTCGACTGCTGATCTACCTG GCATCTTATCTGGAGAGTGGCGTGCCT GCTCGGTTCTCTGGGAGTGGATCAGGC ACCGATTTTACACTGACTATTTCTAGT CTGGAGCCAGAAGATTTCGCAGTGTAC TATTGCCAGCATTCTCGAGACCTGCCC CTGACATTTGGCGGGGGAACTAAGGTC GAGATCAAACGTACGGTGGCTGCACCA TCTGTCTTCATCTTCCCGCCATCTGAT GAGCAGTTGAAATCTGGAACTGCCTCT GTTGTGTGCCTGCTGAATAACTTCTAT CCCAGAGAGGCCAAAGTACAGTGGAAG GTGGATAACGCCCTCCAATCGGGTAAC TCCCAGGAGAGTGTCACAGAGCAGGAC AGCAAGGACAGCACCTACAGCCTCAGC AGCACCCTGACGCTGAGCAAAGCAGAC TACGAGAAACACAAAGTCTACGCCTGC GAAGTCACCCATCAGGGCCTGAGCTCG CCCGTCACAAAGAGCTTCAACAGGGGA GAGTGT |
| Anti-PD-1 (VH6) IgG4-linker-TGFβRII | 16 | QVQLVESGGGVVQP GRSLRLDCKASGIT FSNSGMHWVRQAPG KGLEWVAVIWYDGS KRYYADSVKGRFTI SRDNSKNTLFLQMN SLRAEDTAVYYCAT NDDYWGQGTLVTVS SASTKGPSVFPLAP | 113 | CAGGTGCAGCTGGTCGAAAGCGGAGGA GGAGTGGTCCAGCCAGGACGATCCCTG AGACTGGATTGTAAGGCCTCTGGAATC ACATTCTCTAACAGTGGAATGCACTGG GTGCGCCAGGCACCAGGAAAAGGACTG GAGTGGGTGGCCGTCATCTGGTACGAC GGGTCAAAGCGATACTATGCAGATAGC GTGAAAGGAAGGTTCACAATTTCACGC GACAACAGCAAGAATACTCTGTTTCTG |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | CSRSTSESTAALGC LVKDYFPEPVTVSW NSGALTSGVHTFPA VLQSSGLYSLSSVV TVPSSSLGTKTYTC NVDHKPSNTKVDKR VESKYGPPCPSCPA PEFLGGPSVFLFPP KPKDTLMISRTPEV TCVVVDVSQEDPEV QFNWYVDGVEVHNA KTKPREEQFNSTYR VVSVLTVLHQDWLN GKEYKCKVSNKGLP SSIEKTISKAKGQP REPQVYTLPPSQEE MTKNQVSLTCLVKG FYPSDIAVEWESNG QPENNYKTTPPVLD SDGSFFLYSRLTVD KSRWQEGVNFSCSV MHEALHNHYTQKSL SLSPGKGGGGSGGG GSIPPHVQKSVNND MIVTDNNGAVKFPQ LCKFCDVRFSTCDN QKSCMSNCSITSIC EKPQEVCVAVWRKN DENITLETVCHDPK LPYHDFILEDAASP KCIMKEKKKPGETF FMCSCSSDECNDNI IFSEEYNTSNPD | | CAGATGAACTCTCTGAGAGCAGAGGAT ACTGCCGTGTACTATTGTGCTACCAAT GACGATTATTGGGGGCAGGGAACTCTG GTGACCGTCAGTTCAGCTAGCACCAAG GGCCCATCGGTCTTCCCCCTGGCGCCC TGCTCCAGGAGCACCTCCGAGAGCACA GCCGCCCTGGGCTGCCTGGTCAAGGAC TACTTCCCCGAACCGGTGACGGTGTCG TGGAACTCAGGCGCCCTGACCAGCGGC GTGCACACCTTCCCGGCTGTCCTACAG TCCTCAGGACTCTACTCCCTCAGCAGC GTGGTGACCGTGCCCTCCAGCAGCTTG GGCACGAAGACCTACACCTGCAACGTA GATCACAAGCCCAGCAACACCAAGGTG GACAAGAGAGTTGAGTCCAAATATGGT CCCCCATGCCCATCATGCCCAGCACCT GAGTTCCTGGGGGGACCATCAGTCTTC CTGTTCCCCCCAAAACCCAAGGACACT CTCATGATCTCCCGGACCCCTGAGGTC ACGTGCGTGGTGGTGGACGTGAGCCAG GAAGACCCCGAGGTCCAGTTCAACTGG TACGTGGATGGCGTGGAGGTGCATAAT GCCAAGACAAAGCCGCGGGAGGAGCAG TTCAACAGCACGTACCGTGTGGTCAGC GTCCTCACCGTCCTGCACCAGGACTGG CTGAACGGCAAGGAGTACAAGTGCAAG GTCTCCAACAAAGGCCTCCCGTCCTCC ATCGAGAAAACCATCTCCAAAGCCAAA GGGCAGCCCCGAGAGCCACAGGTGTAC ACCCTGCCCCCATCCCAGGAGGAGATG ACCAAGAACCAGGTCAGCCTGACCTGC CTGGTCAAAGGCTTCTACCCCAGCGAC ATCGCCGTGGAGTGGGAGAGCAATGGG CAGCCGGAGAACAACTACAAGACCACG CCTCCCGTGCTGGACTCCGACGGCTCC TTCTTCCTCTACAGCAGGCTCACCGTG GACAAGAGCAGGTGGCAGGAGGGGAAT GTCTTCTCATGCTCCGTGATGCATGAG GCTCTGCACAACCACTACACACAGAAG AGCCTCTCCCTGTCTCCGGGTAAAGGT GGAGGTGGTTCTGGAGGTGGAGGTAGT ATCCCTCCTCACGTACAGAAGTCCGTG AACAATGACATGATTGTCACTGACAAT AACGGAGCCGTCAAGTTTCCTCAGCTA TGTAAGTTCTGCGATGTTCGGTTCTCC ACATGCGATAATCAGAAAAGCTGTATG TCTAATTGCAGTATCACTAGTATATGC GAAAAACCTCAAGAAGTTTGCGTCGCC GTGTGGCGGAAAAATGATGAAAATATC ACGCTTGAGACTGTCTGCCATGATCCA AAGTTACCCTACCACGACTTCATCTTA GAAGACGCCGCATCACCCAAGTGCATT ATGAAAGAGAAAAAGAAGCCAGGAGAA ACATTCTTTATGTGCTCATGCTCCTCT GACGAATGCAACGACAACATTATCTTC TCTGAGGAGTATAACACCTCAAATCCA GAC |
| Anti-PD-1 (VH6) IgG4-(S108P)-linker-TGFβRII | 143 | QVQLVESGGGVVQP GRSLRLDCKASGIT FSNSGMHWVRQAPG KGLEWVAVIWYDGS KRYYADSVKGRFTI SRDNSKNTLFLQMN SLRAEDTAVYYCAT NDDYWGQGTLVTVS SASTKGPSVFPLAP CSRSTSESTAALGC LVKDYFPEPVTVSW NSGALTSGVHTFPA VLQSSGLYSLSSVV TVPSSSLGTKTYTC NVDHKPSNTKVDKR VESKYGPPCPPCPA PEFLGGPSVFLFPP | 114 | CAGGTGCAGCTGGTCGAAAGCGGAGGA GGAGTGGTCCAGCCAGGACGATCCCTG AGACTGGATTGTAAGGCCTCTGGAATC ACATTCTCTAACAGTGGAATGCACTGG GTGCGCCAGGCACCAGGAAAAGGACTG GAGTGGGTGGCCGTCATCTGGTACGAC GGGTCAAAGCGATACTATGCAGATAGC GTGAAAGGAAGGTTCACAATTTCACGC GACAACAGCAAGAATACTCTGTTTCTG CAGATGAACTCTCTGAGAGCAGAGGAT ACTGCCGTGTACTATTGTGCTACCAAT GACGATTATTGGGGGCAGGGAACTCTG GTGACCGTCAGTTCAGCTAGCACCAAG GGCCCATCGGTCTTCCCCCTGGCGCCC TGCTCCAGGAGCACCTCCGAGAGCACA GCCGCCCTGGGCTGCCTGGTCAAGGAC TACTTCCCCGAACCGGTGACGGTGTCG |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | KPKDTLMISRTPEV TCVVVDVSQESPEV QFNWYVDGVEVHNA KTKPREEQFNSTYR VVSVLTVLHQDWLN GKEYKCKVSNKGLP SSIEKTISKAKGQP REPQVYTLPPSQEE MTKNQVSLTCLVKG FYPSDIAVEWESNG QPENNYKTTPPVLD SDGSFFLYSRLTVD KSRWQEGNVFSCSV MHEALHNHYTQKSL SLSPGKGGGGSGGG GSIPPHVQKSVNND MIVTDNNGAVKFPQ LCKFCDVRFSTCDN QKSCMSNCSITSIC EKPQEVCVAVWRKN DENITLETVCHDPK LPYHDFILEDAASP KCIMKEKKKPGETF FMCSCSSDECNDNI IFSEEYNTSNPD | | TGGAACTCAGGCGCCCTGACCAGCGGC GTGCACACCTTCCCGGCTGTCCTACAG TCCTCAGGACTCTACTCCCTCAGCAGC GTGGTGACCGTGCCCTCCAGCAGCTTG GGCACGAAGACCTACACCTGCAACGTA GATCACAAGCCCAGCAACACCAAGGTG GACAAGAGAGTTGAGTCCAAATATGGT CCCCCATGCCCACCATGCCCAGCACCT GAGTTCCTGGGGGGACCATCAGTCTTC CTGTTCCCCCCAAAACCCAAGGACACT CTCATGATCTCCCGGACCCCTGAGGTC ACGTGCGTGGTGGTGGACGTGAGCCAG GAAGACCCCGAGGTCCAGTTCAACTGG TACGTGGATGGCGTGGAGGTGCATAAT GCCAAGACAAAGCCGCGGGAGGAGCAG TTCAACAGCACGTACCGTGTGGTCAGC GTCCTCACCGTCCTGCACCAGGACTGG CTGAACGGCAAGGAGTACAAGTGCAAG GTCTCCAACAAAGGCCTCCCGTCCTCC ATCGAGAAAACCATCTCCAAAGCCAAA GGGCAGCCCCGAGAGCCACAGGTGTAC ACCCTGCCCCCATCCCAGGAGGAGATG ACCAAGAACCAGGTCAGCCTGACCTGC CTGGTCAAAGGCTTCTACCCCAGCGAC ATCGCCGTGGAGTGGGAGAGCAATGGG CAGCCGGAGAACAACTACAAGACCACG CCTCCCGTGCTGGACTCCGACGGCTCC TTCTTCCTCTACAGCAGGCTCACCGTG GACAAGAGCAGGTGGCAGGAGGGGAAT GTCTTCTCATGCTCCGTGATGCATGAG GCTCTGCACAACCACTACACACAGAAG AGCCTCTCCCTGTCTCCGGGTAAAGGT GGAGGTGGTTCTGGAGGTGGAGGTAGT ATCCCTCCTCACGTACAGAAGTCCGTG AACAATGACATGATTGTCACTGACAAT AACGGAGCCGTCAAGTTTCCTCAGCTA TGTAAGTTCTGCGATGTTCGGTTCTCC ACATGCGATAATCAGAAAAGCTGTATG TCTAATTGCAGTATCACTAGTATATGC GAAAAACCTCAAGAAGTTTGCGTCGCC GTGTGGCGGAAAAATGATGAAAATATC ACGCTTGAGACTGTCTGCCATGATCCA AAGTTACCCTACCACGACTTCATCTTA GAAGACGCCGCATCACCCAAGTGCATT ATGAAAGAGAAAAAGAAGCCAGGAGAA ACATTCTTTATGTGCTCATGCTCCTCT GACGAATGCAACGACAACATTATCTTC TCTGAGGAGTATAACACCTCAAATCCA GAC |
| Anti-PD-1 VH7 IgG4 (S108P) linker-TGFbRII | 144 | QVQLVQSGVEVKKP GASVKVSCKASGYT FTNYYMYWVRQAPG QGLEWMGGINPSNG GTNFNEKFKNRVTL TTDSSTTTAYMELK SLQFDDTAVYYCAR RDYRFDMGFDYWGQ GTTVTVSSASTKGP SVFPLAPCSRSTSE STAALGCLVKDYFP EPVTVSWNSGALTS GVHTFPAVLQSSGL YSLSSVVTVPSSSL GTKTYTCNVDHKPS NTKVDKRVESKYGP PCPPCPAPEFLGGP SVFLFPPKPKDTLM ISRTPEVTCVVVDV SQESPEVQFNWYVD GVEVHNAKTKPREE QFNSTYRVVSVLTV LHQDWLNGKEYKCK VSNKGLPSSIEKTI SKAKGQPREPQVYT | 115 | CAGGTGCAGCTGGTCCAGAGCGGCGTC GAAGTCAAGAAACCCGGGGCCTCAGTG AAGGTCAGCTGTAAAGCTTCCGGCTAC ACCTTCACAAACTACTATATGTATTGG GTGAGACAGGCACCAGGACAGGGACTG GAGTGGATGGGCGGGATTAACCCTAGT AATGGAGGCACTAACTTCAACGAAAAG TTTAAAAACAGGGTGACCCTGACCACA GATTCAAGCACTACCACAGCTTACATG GAGCTGAAGTCCCTGCAGTTTGACGAT ACAGCCGTGTACTATTGTGCTCGGAGA GACTACAGGTTCGATATGGGCTTTGAC TATTGGGGCCAGGGGACTACCGTGACC GTCTCCTCTGCTAGCACCAAGGGCCCA TCGGTCTTCCCCCTGGCGCCCTGCTCC AGGAGCACCTCCGAGAGCACAGCGGCC CTGGGCTGCCTGGTCAAGGACTACTTC CCCGAACCGGTGACGGTGTCGTGGAAC TCAGGCGCCCTGACCAGCGGCGTGCAC ACCTTCCCGGCTGTCCTACAGTCCTCA GGACTCTACTCCCTCAGCAGCGTGGTG ACCGTGCCCTCCAGCAGCTTGGGCACG AAGACCTACACCTGCAACGTAGATCAC AAGCCCAGCAACACCAAGGTGGACAAG AGAGTTGAGTCCAAATATGGTCCCCCA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | LPPSQEEMTKNQVS<br>LTCLVKGFYSPDIA<br>VEWESNGQPENNYK<br>TTPPVLDSDGSFFL<br>YSRLTVDKSRWQEG<br>NVFSCSVMHEALHN<br>HYTQKSLSLSPGKG<br>GGGSGGGGSIPPHV<br>QKSVNNDMIVTDNN<br>GAVKFPQLCKFCDV<br>RFSTCDNQKSCMSN<br>CSITSICEKPQEVC<br>VAVWRKNDENITLE<br>TVCHDPKLPYHDFI<br>LEDAASPKCIMKEK<br>KKPGETFFMCSCSS<br>DECNDNIIFSEEYN<br>TSNPD* | | TGCCCACCATGCCCAGCACCTGAGTTC<br>CTGGGGGGACCATCAGTCTTCCTGTTC<br>CCCCCAAAACCCAAGGACACTCTCATG<br>ATCTCCCGGACCCCTGAGGTCACGTGC<br>GTGGTGGTGGACGTGAGCCAGGAAGAC<br>CCCGAGGTCCAGTTCAACTGGTACGTG<br>GATGGCGTGGAGGTGCATAATGCCAAG<br>ACAAAGCCGCGGGAGGAGCAGTTCAAC<br>AGCACGTACCGTGTGGTCAGCGTCCTC<br>ACCGTCCTGCACCAGGACTGGCTGAAC<br>GGCAAGGAGTACAAGTGCAAGGTCTCC<br>AACAAAGGCCTCCCGTCCTCCATCGAG<br>AAAACCATCTCCAAAGCCAAAGGGCAG<br>CCCCGAGAGCCACAGGTGTACACCCTG<br>CCCCCATCCCAGGAGGAGATGACCAAG<br>AACCAGGTCAGCCTGACCTGCCTGGTC<br>AAAGGCTTCTACCCCAGCGACATCGCC<br>GTGGAGTGGGAGAGCAATGGGCAGCCG<br>GAGAACAACTACAAGACCACGCCTCCC<br>GTGCTGGACTCCGACGGCTCCTTCTTC<br>CTCTACAGCAGGCTCACCGTGGACAAG<br>AGCAGGTGGCAGGAGGGGAATGTCTTC<br>TCATGCTCCGTGATGCATGAGGCTCTG<br>CACAACCACTACACACAGAAGAGCCTC<br>TCCCTGTCTCCGGGTAAAGGTGGAGGT<br>GGTTCTGGAGGTGGAGGTAGTATCCCT<br>CCTCACGTACAGAAGTCCGTGAACAAT<br>GACATGATTGTCACTGACAATAACGGA<br>GCCGTCAAGTTTCCTCAGCTATGTAAG<br>TTCTGCGATGTTCGGTTCTCCACATGC<br>GATAATCAGAAAAGCTGTATGTCTAAT<br>TGCAGTATCACTAGTATATGCGAAAAA<br>CCTCAAGAAGTTTGCGTCGCCGTGTGG<br>CGGAAAAATGATGAAAATATCACGCTT<br>GAGACTGTCTGCCATGATCCAAAGTTA<br>CCCTACCACGACTTCATCTTAGAAGAC<br>GCCGCATCACCCAAGTGCATTATGAAA<br>GAGAAAAAGAAGCCAGGAGAAACATTC<br>TTTATGTGCTCATGCTCCTCTGACGAA<br>TGCAACGACAACATTATCTTCTCTGAG<br>GAGTATAACACCTCAAATCCAGAC |
| Anti-<br>PD-1<br>VH7<br>IgG4<br>(linker-<br>TGFbRII | 145 | QVQLVQSGVEVKKP<br>GASVKVSCKASGYT<br>FTNYYMYWVRQAPC<br>QGLEWMGGINPSNG<br>GTNFNEKFKNRVTL<br>TTDSSTTTAYMELK<br>SLQFDDTAVYYCAR<br>RDYRFDMGFDYWGQ<br>GTTVTVSSASTKGP<br>SVFPLAPCSRSTSE<br>STAALGCLVKDYFP<br>EPVTVSWNSGALTS<br>GVHTFPAVLQSSGL<br>YSLSSVVTVPSSSL<br>GTKTYTCNVDHKPS<br>NTKVDKRVESKYGP<br>PCPSCPAPEFLGGP<br>SVFLFPPKPKDTLM<br>ISRTPEVTCVVVDV<br>SQEDPEVQFNWYVD<br>GVEVHNAKTKPREE<br>QFNSTYRVVSVLTV<br>LHQDWLNGKEYKCK<br>VSNKGLPSSIEKTI<br>SKAKGQPREPQVYT<br>LPPSQEEMTKNQVS<br>LTCLVKGFYPSDIA<br>VEWESNGQPENNYK<br>TTPPVLDSDGSFFL<br>YSRLTVDKSRWQEG<br>NVFSCSVMHEALHN<br>HYTQKSLSLSPGKG<br>GGGSGGGGSIPPHV | 116 | CAGGTGCAGCTGGTCCAGAGCGGCGTG<br>GAAGTCAAGAAACCCGGGGCCTCAGTG<br>AAGGTCAGCTGTAAAGCTTCCGGCTAC<br>ACCTTCACAAACTACTATATGTATTGG<br>GTGAGACAGGCACCAGGACAGGGACTG<br>GAGTGGATGGGCGGGATTAACCCTAGT<br>AATGGAGGCACTAACTTCAACGAAAAG<br>TTTAAAAACAGGGTGACCCTGACCACA<br>GATTCAAGCACTACCACAGCTTACATG<br>GAGCTGAAGTCCCTGCAGTTTGACGAT<br>ACAGCCGTGTACTATTGTGCTCGGAGA<br>GACTACAGGTTCGATATGGGCTTTGAC<br>TATTGGGGCCAGGGGACTACCGTGACC<br>GTCTCCTCTGCTAGCACCAAGGGCCCA<br>TCGGTCTTCCCCCTGGCGCCCTGCTCC<br>AGGAGCACCTCCGAGAGCACAGCCGCC<br>CTGGGCTGCCTGGTCAAGGACTACTTC<br>CCCGAACCGGTGACGGTGTCGTGGAAC<br>TCAGGCGCCCTGACCAGCGGCGTGCAC<br>ACCTTCCCGGCTGTCCTACAGTCCTCA<br>GGACTCTACTCCCTCAGCAGCGTGGTG<br>ACCGTGCCCTCCAGCAGCTTGGGCACG<br>AAGACCTACACCTGCAACGTAGATCAC<br>AAGCCCAGCAACACCAAGGTGGACAAG<br>AGAGTTGAGTCCAAATATGGTCCCCCA<br>TGCCCATCATGCCCAGCACCTGAGTTC<br>CTGGGGGGACCATCAGTCTTCCTGTTC<br>CCCCCAAAACCCAAGGACACTCTCATG<br>ATCTCCCGGACCCCTGAGGTCACGTGC<br>GTGGTGGTGGACGTGAGCCAGGAAGAC<br>CCCGAGGTCCAGTTCAACTGGTACGTG<br>GATGGCGTGGAGGTGCATAATGCCAAG<br>ACAAAGCCGCGGGAGGAGCAGTTCAAC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | QKSVNNDMIVTDNN GAVKFPQLCKFCDV RFSTCDNQKSCMSN CSITSICEKPQEVC VAVWRKNDENITLE TVCHDPKLPYHDFI LEDAASPKCIMKEK KKPGETFFMCSCSS DECNDNIIFSEEYN TSNPD | | AGCACGTACCGTGTGGTCAGCGTCCTC ACCGTCCTGCACCAGGACTGGCTGAAC GGCAAGGAGTACAAGTGCAAGGTCTCC AACAAAGGCCTCCCGTCCTCCATCGAG AAAACCATCTCCAAAGCCAAAGGGCAG CCCCGAGAGCCACAGGTGTACACCCTG CCCCCATCCCAGGAGGAGATGACCAAG AACCAGGTCAGCCTGACCTGCCTGGTC AAAGGCTTCTACCCCAGCGACATCGCC GTGGAGTGGGAGAGCAATGGGCAGCCG GAGAACAACTACAAGACCACGCCTCCC GTGCTGGACTCCGACGGCTCCTTCTTC CTCTACAGCAGGCTCACCGTGGACAAG AGCAGGTGGCAGGAGGGGAATGTCTTC TCATGCTCCGTGATGCATGAGGCTCTG CACAACCACTACACACAGAAGAGCCTC TCCCTGTCTCCGGGTAAAGGTGGAGGT GGTTCTGGAGGTGGAGGTAGTATCCCT CCTCACGTACAGAAGTCCGTGAACAAT GACATGATTGTCACTGACAATAACGGA GCCGTCAAGTTTCCTCAGCTATGTAAG TTCTGCGATGTTCGGTTCTCCACATGC GATAATCAGAAAAGCTGTATGTCTAAT TGCAGTATCACTAGTATATGCGAAAAA CCTCAAGAAGTTTGCGTCGCCGTGTGG CGGAAAAATGATGAAAATATCACGCTT GAGACTGTCTGCCATGATCCAAAGTTA CCCTACCACGACTTCATCTTAGAAGAC GCCGCATCACCCAAGTGCATTATGAAA GAGAAAAAGAAGCCAGGAGAAACATTC TTTATGTGCTCATGCTCCTCTGACGAA TGCAACGACAACATTATCTTCTCTGAG GAGTATAACACCTCAAATCCAGAC |
| VH6-IgG4 (mut)-linker-ECD | 294 | QVQLVESGGGVVQP GRSLRLDCKASGIT FSNSGMHWVRQAPG KGLEWVAVIWYDGS KRYYADSVKGRFTI SRDNSKNTLFLQMN SLRAEDTAVYYCAT NDDYWGQGTLVTVS SASTKGPSVFPLAP CSRSTSESTAALGC LVKDYFPEPVTVSW NSGALTSGVHTFPA VLQSSGLYSLSSVV TVPSSSLGTKTYTC NVDHKPSNTKVDKR VESKYGPPCPPCPA PEFLGGPSVFLFPP KPKDTLMISRTPEV TCVVVDVSQESPEV QFNWYVDGVEVHNA KTKPREEQFNSTYR VVSVLTVLHQDWLN GKEYKCKVSNKGLP SSIEKTISKAKGQP REPQVYTLPPSQEE MTKNQVSLTCLVKG FYPSDIAVEWESNG QPENNYKTTPPVLD SDGSFFLYSRLTVD KSRWQEGNVFSCSV MHEALHNHYTQKSL SLSLGKGGGGSGGG GSIPPHVQKSVNND MIVTDNNGAVKFPQ LCKFCDVRFSTCDN QKSCMSNCSITSIC EKPQEVCVAVWRKN DENITLETVCHDPK LPYHDFILEDAASP | 297 | CAGGTGCAGCTGGTCGAAAGCGGAGGA GGAGTGGTCCAGCCAGGACGATCCCTG AGACTGGATTGTAAGGCCTCTGGAATC ACATTCTCTAACAGTGGAATGCACTGG GTGCGCCAGGCACCAGGAAAAGGACTG GAGTGGGTGGCCGTCATCTGGTACGAC GGGTCAAAGCGATACTATGCAGATAGC GTGAAAGGAAGGTTCACAATTTCACGC GACAACAGCAAGAATACTCTGTTTCTG CAGATGAACTCTCTGAGAGCAGAGGAT ACTGCCGTGTACTATTGTGCTACCAAT GACGATTATTGGGGGCAGGGAACTCTG GTGACCGTCAGTTCAGCTAGCACCAAG GGCCCATCGGTCTTCCCCCTGGCGCCC TGCTCCAGGAGCACCTCCGAGAGCACA GCCGCCCTGGGCTGCCTGGTCAAGGAC TACTTCCCCGAACCGGTGACGGTGTCG TGGAACTCAGGCGCCCTGACCAGCGGC GTGCACACCTTCCCGGCTGTCCTACAG TCCTCAGGACTCTACTCCCTCAGCAGC GTGGTGACCGTGCCCTCCAGCAGCTTG GGCACGAAGACCTACACCTGCAACGTA GATCACAAGCCCAGCAACACCAAGGTG GACAAGAGAGTTGAGTCCAAATATGGT CCCCCATGCCCACCATGCCCAGCACCT GAGTTCCTGGGGGGACCATCAGTCTTC CTGTTCCCCCCAAAACCCAAGGACACT CTCATGATCTCCCGGACCCCTGAGGTC ACGTGCGTGGTGGTGGACGTGAGCCAG GAAGACCCCGAGGTCCAGTTCAACTGG TACGTGGATGGCGTGGAGGTGCATAAT GCCAAGACAAAGCCGCGGGAGGAGCAG TTCAACAGCACGTACCGTGTGGTCAGC GTCCTCACCGTCCTGCACCAGGACTGG CTGAACGGCAAGGAGTACAAGTGCAAG GTCTCCAACAAAGGCCTCCCGTCCTCC ATCGAGAAAACCATCTCCAAAGCCAAA GGGCAGCCCCGAGAGCCACAGGTGTAC ACCCTGCCCCCATCCCAGGAGGAGATG |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | KCIMKEKKKPGETF FMCSCSSDECNDNI IFSEEYNTSNPD | | ACCAAGAACCAGGTCAGCCTGACCTGC CTGGTCAAAGGCTTCTACCCCAGCGAC ATCGCCGTGGAGTGGGAGAGCAATGGG CAGCCGGAGAACAACTACAAGACCACG CCTCCCGTGCTGGACTCCGACGGCTCC TTCTTCCTCTACAGCAGGCTCACCGTG GACAAGAGCAGGTGGCAGGAGGGGAAT GTCTTCTCATGCTCCGTGATGCATGAG GCTCTGCACAACCACTACACACAGAAG AGCCTCTCCCTGTCTCTGGGTAAAGGT GGAGGTGGTTCTGGAGGTGGAGGTAGT ATCCCTCCTCACGTACAGAAGTCCGTG AACAATGACATGATTGTCACTGACAAT AACGGAGCCGTCAAGTTTCCTCAGCTA TGTAAGTTCTGCGATGTTCGGTTCTCC ACATGCGATAATCAGAAAAGCTGTATG TCTAATTGCAGTATCACTAGTATATGC GAAAAACCTCAAGAAGTTTGCGTCGCC GTGTGGCGGAAAAATGATGAAAATATC ACGCTTGAGACTGTCTGCCATGATCCA AAGTTACCCTACCACGACTTCATCTTA GAAGACGCCGCATCACCCAAGTGCATT ATGAAAGAGAAAAAGAAGCCAGGAGAA ACATTCTTTATGTGCTCATGCTCCTCT GACGAATGCAACGACAACATTATCTTC TCTGAGGAGTATAACACCTCAAATCCA GAC |
| VH7-IgG4 (mut)-linker-ECD | 295 | QVQLVQSGVEVKKP GASVKVSCKASGYT FTNYYMYWVRQAPG QGLEWMGGINPSNG GTNFNEKFKNRVTL TTDSSTTTAYMELK SLQFDDTAVYYCAR RDYRFDMGFDYWGQ GTTVTVSSASTKGP SVFPLAPCSRSTSE STAALGCLVKDYFP EPVTVSWNSGALTS GVHTFPAVLQSSGL YSLSSVVTVPSSSL GTKTYTCNVDHKPS NTKVDKRVESKYGP PCPPCPAPEFLGGP SVFLFPPKPKDTLM ISRTPEVTCVVVDV SQEDPEVQFNWYVD GVEVHNAKTKPREE QFNSTYRVVSVLTV LHQDWLNGKEYKCK VSNKGLPSSIEKTI SKAKGQPREPQVYT LPPSQEEMTKNQVS LTCLVKGFYPSDIA VEWESNGQPENNYK TTPPVLDSDGSFFL YSRLTVDKSRWQEG NVFSCSVMHEALHN HYTQKSLSLSLGKG GGGSGGGGSIPPHV QKSVNNDMIVTDNN GAVKFPQLCKFCDV RFSTCDNQKSCMSN CSITSICEKPQEVC VAVWRKNDENITLE TVCHDPKLPYHDFI LEDAASPKCIMKEK KKPGETFFMCSCSS DECNDNIIFSEEYN TSNPD* | 298 | CAGGTGCAGCTGGTCCAGAGCGGCGTG GAAGTCAAGAAACCCGGGGCCTCAGTG AAGGTCAGCTGTAAAGCTTCCGGCTAC ACCTTCACAAACTACTATATGTATTGG GTGAGACAGGCACCAGGACAGGGACTG GAGTGGATGGGCGGGATTAACCCTAGT AATGGAGGCACTAACTTCAACGAAAAG TTTAAAAAACAGGGTGACCCTGACCACA GATTCAAGCACTACCACAGCTTACATG GAGCTGAAGTCCCTGCAGTTTGACGAT ACAGCCGTGTACTATTGTGCTCGGAGA GACTACAGGTTCGATATGGGCTTTGAC TATTGGGGCCAGGGGACTACCGTGACC GTCTCCTCTGCTAGCACCAAGGGCCCA TCGGTCTTCCCCCTGGCGCCCTGCTCC AGGAGCACCTCCGAGAGCACAGCCGCC CTGGGCTGCCTGGTCAAGGACTACTTC CCCGAACCGGTGACGGTGTCGTGGAAC TCAGGCGCCCTGACCAGCGGCGTGCAC ACCTTCCCGGCTGTCCTACAGTCCTCA GGACTCTACTCCCTCAGCAGCGTGGTG ACCGTGCCCTCCAGCAGCTTGGGCACG AAGACCTACACCTGCAACGTAGATCAC AAGCCCAGCAACACCAAGGTGGACAAG AGAGTTGAGTCCAAATATGGTCCCCCA TGCCCACCATGCCCAGCACCTGAGTTC CTGGGGGGACCATCAGTCTTCCTGTTC CCCCCAAAACCCAAGGACACTCTCATG ATCTCCCGGACCCCTGAGGTCACGTGC GTGGTGGTGGACGTGAGCCAGGAAGAC CCCGAGGTCCAGTTCAACTGGTACGTG GATGGCGTGGAGGTGCATAATGCCAAG ACAAAGCCGCGGGAGGAGCAGTTCAAC AGCACGTACCGTGTGGTCAGCGTCCTC ACCGTCCTGCACCAGGACTGGCTGAAC GGCAAGGAGTACAAGTGCAAGGTCTCC AACAAAGGCCTCCCGTCCTCCATCGAG AAAACCATCTCCAAAGCCAAAGGGCAG CCCCGAGAGCCACAGGTGTACACCCTG CCCCCATCCCAGGAGGAGATGACCAAG AACCAGGTCAGCCTGACCTGCCTGGTC AAAGGCTTCTACCCCAGCGACATCGCC GTGGAGTGGGAGAGCAATGGGCAGCCG GAGAACAACTACAAGACCACGCCTCCC GTGCTGGACTCCGACGGCTCCTTCTTC CTCTACAGCAGGCTCACCGTGGACAAG AGCAGGTGGCAGGAGGGGAATGTCTTC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | | | TCATGCTCCGTGATGCATGAGGCTCTG CACAACCACTACACACAGAAGAGCCTC TCCCTGTCTCTGGGTAAAGGTGGAGGT GGTTCTGGAGGTGGAGGTAGTATCCCT CCTCACGTACAGAAGTCCGTGAACAAT GACATGATTGTCACTGACAATAACGGA GCCGTCAAGTTTCCTCAGCTATGTAAG TTCTGCGATGTTCGGTTCTCCACATGC GATAATCAGAAAAGCTGTATGTCTAAT TGCAGTATCACTAGTATATGCGAAAAA CCTCAAGAAGTTTGCGTCGCCGTGTGG CGGAAAATGATGAAATATCACGCTT GAGACTGTCTGCCATGATCCAAAGTTA CCCTACCACGACTTCATCTTAGAAGAC GCCGCATCACCCAAGTGCATTATGAAA GAGAAAAAGAAGCCAGGAGAAACATTC TTTATGTGCTCATGCTCCTCTGACGAA TGCAACGACAACATTATCTTCTCTGAG GAGTATAACACCTCAAATCCAGAC |
| Linker | 17 | DPGGGGSGGGGSNPGS | | |
| Linker | 18 | GGGGSGGGGSGSDPGS | | |
| Linker | 19 | DPGSGGGGSGGGGSGS | | |
| Linker | 20 | GGGGSGGGGSGGGGSDPGS | | |
| Linker | 21 | DPGSGGGGSGGGGSGGGGS | | |
| Linker 7 | 22 | DPGSGSVPLGSGSNPGS | | |
| Linker 8 | 23 | DPGSGGSVPLGSGGSNPGS | | |
| Linker | 24 | DPGVLEREDKPTTSKPNPGS | | |
| Linker 10 | 25 | DPGVLEREDVPTTSYPNPGS | | |
| Linker | 26 | DPGVLEREDKVTTSKYNPGS | | |
| Linker 12 | 27 | DPVLEREDKVTTSKNPGS | | |
| Linker | 28 | DIEGRMD | | |
| Linker | 29 | GEGKSSGSGSESKAS | | |
| Linker | 30 | GSTSGSGKPGSGEGSTKG | | |
| Linker | 31 | A(EAAAK)$_4$ALEA(EAAAK)$_4$A | | |
| Linker | 32 | (G4S)n, n = 1-10 | | |
| Linker | 33 | (Gly)n, n = 6-8 | | |
| Linker | 34 | (EAAAK)n, n = 1-6 | | |
| hM195 VL | 35 | DIQMTQSPSSLSASVGDRVTITCRASESVDNYGISFMNWFQQKPGKAPKLLIYAASNQGSGVPSRFSGSGSGTDFTLTISSLQP | 72 | GACATTCAGATGACCCAGTCTCCGAGCTCTCTGTCCGCATCAGTAGGAGACAGGGTCACCATCACATGCAGAGCCAGCGAAAGTGTCGACAATTATGGCATTAGCTTTATGAACTGGTTCCAACAGAAACCCGGGAAGGCTCCTAAGCTTCTGATTTACGCT |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | DDFATYYCQQSKEV PWTFGQGTKVEIK | | GCATCCAACCAAGGCTCCGGGGTACCC TCTCGCTTCTCAGGCAGTGGATCTGGG ACAGACTTCACTCTCACCATTTCATCT CTGCAGCCTGATGACTTCGCAACCTAT TACTGTCAGCAAAGTAAGGAGGTTCCG TGGACGTTCGGTCAAGGGACCAAGGTG GAGATCAAA |
| hM195 VH | 36 | QVQLVQSGAEVKKP GSSVKVSCKASGYT FTDYNMHWVRQAPG QGLEWIGYIYPYNG GTGYNQKFKSKATI TADESTNTAYMELS SLRSEDTAVYYCAR GRPAMDYWGQGTLV TVSS | 73 | CAGGTTCAGCTGGTGCAGTCTGGAGCT GAGGTGAAGAAGCCTGGGAGCTCAGTG AAGGTTTCCTGCAAAGCTTCTGGCTAC ACCTTCACTGACTACAACATGCACTGG GTGAGGCAGGCTCCTGGCCAAGGCCTG GAATGGATTGGATATATTTATCCTTAC AATGGTGGTACCGGCTACAACCAGAAG TTCAAGAGCAAGGCCACAATTACAGCA GACGAGAGTACTAACACAGCCTACATG GAACTCTCCAGCCTGAGGTCTGAGGAC ACTGCAGTCTATTACTGCGCAAGAGGG CGCCCCGCTATGGACTACTGGGGCCAA GGGACTCTGGTCACTGTCTCTTCA |
| M2H12 VH | 37 | QVQLQQSGPELVRP GTFVKISCKASGYT FTNYDINWVNQRPG QGLEWIGWIYPGDG STKYNEKFKAKTAL TADKSSSTAYLQLN NLTSENSAVYFCAS GYEDAMDYWGQGTS VTVSS | | |
| M2H12 VL | 38 | DIKMTQSPSSMYAS LGERVIINCKASQD INSYLSWFQQKPGK SPKTLIYRANRLVD GVPSRFSGSGSGQD YSLTISSLEYEDMG IYYCLQYDEFPLTF GAGTKLELKR | | |
| DRB2 VH | 39 | EVKLQESGPELVKP GASVKMSCKASGYK FTDYVVHWLKQKPG QGLEWIGYINPYND GTKYNEKFKGKATL TSDKSSSTAYMEVS SLTSEDSAVYYCAR DYRYEVYGMDYWGQ GYSVTVSS | | |
| DRB2 VL | 40 | DIVLTQSPTIMSAS PGERVTMTCTASSS VNYIH WYQQKSGDSPLRWI FDTSKVASGVPARF SGSGSGTSYSLTIS TMEAEDAATYYCQQ WRSYPLTFGDGTRL ELKRADAAPTVS | | |
| My9-6 VH | 41 | QVQLQQPGAEVVKP GASVKMSCKASGYT FTSYYIHWIKQTPG QGLEWVGVIYPGND DISYNQKFKGKATL TADKSSTTAYMQLS SLTSEDSAVYYCAR EVRLRYFDVWGAGT TVTVSS | | |
| My9-6 VL | 42 | NIMLTQSPSSLAVS AGEKVTMSCKSSQS VFFSSSQKNYLAWY QQIPGQSPKLLIYW | | |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | ASTRESGVPDRFTG SGSGTDFTLTISSV QSEDLAIYYCHQYL SSRTFGGGTKLEIK R | | |
| MUC16-1 VL | 43 | DIELTQSPSSLAVS AGEKVTMSCKSSQS LLNSRTRKNQLAWY QQKPGQSPELLIYW ASTRQSGVPDRFTG SGSGTDFTLTISSV QAEDLAVYYCQQSY NLLTFGPGTKLEVK R | 74 | GACATCGAGCTGACACAGAGCCCATCT AGCCTGGCTGTGTCTGCCGGCGAGAAA GTGACCATGAGCTGCAAGAGCAGCCAG AGCCTGCTGAACAGCCGGACCAGAAAG AATCAGCTGGCCTGGTATCAGCAGAAG CCCGGCCAATCTCCTGAGCTGCTGATC TACTGGGCCAGCACAAGACAGAGCGGC GTGCCCGATAGATTCACAGGATCTGGC AGCGGCACCGACTTCACCCTGACAATC AGTTCTGTGCAGGCCGAGGACCTGGCC GTGTACTACTGTCAGCAGAGCTACAAC CTGCTGACCTTCGGACCCGGCACCAAG CTGGAAGTGAAGAGA |
| MUC16-1 VH | 44 | VKLQESGGGFVKPG GSLKVSCAASGFTF SSYAMSWVRLSPEM RLEWVATISSAGGY IFYSDSVQGRFTIS RDNAKNTLHLQMGS LRSGDTAMYYCARQ GFGNYGDYYAMDYW GQGTTVTVSS | 75 | GTGAAGCTGCAAGAGTCCGGCGGAGGC TTTGTGAAGCCTGGCGGCTCTCTGAAA GTGTCCTGTGCCGCCAGCGGCTTCACC TTTAGCAGCTACGCCATGAGCTGGGTC CGACTGAGCCCTGAGATGAGACTGGAA TGGGTCGCCACCATCAGTAGCGCAGGC GGCTACATCTTCTACAGCGACTCTGTG CAGGGCAGATTCACCATCAGCCGGGAC AACGCCAAGAACACCCTGCACCTCCAG ATGGGCAGTCTGAGAAGCGGCGATACC GCCATGTACTACTGCGCCAGACAAGGC TTCGGCAACTACGGCGACTACTATGCC ATGGATTACTGGGGCCAGGGCACCACC GTGACAGTCTCTTCT |
| MUC16-2 VL | 45 | DIELTQSPSSLAVS AGEKVTMSCKSSQS LLNSRTRKNQLAWY QQKTGQSPELLIYW ASTRQSGVPDRFTG SGSGTDFTLTISSV QAEDLAVYYCQQSY NLLTFGPGTKLEIK R | 76 | GACATCGAGCTGACACAGAGCCCATCT AGCCTGGCTGTGTCTGCCGGCGAGAAA GTGACCATGAGCTGCAAGAGCAGCCAG AGCCTGCTGAACAGCCGGACCAGAAAG AATCAGCTGGCCTGGTATCAGCAGAAA ACCGGACAGAGCCCCGAGCTGCTGATC TACTGGGCCAGCACAAGACAGAGCGGC GTGCCCGATAGATTCACAGGATCTGGC AGCGGCACCGACTTCACCCTGACAATC AGTTCTGTGCAGGCCGAGGACCTGGCC GTGTACTACTGTCAGCAGAGCTACAAC CTGCTGACCTTCGGACCCGGCACCAAG CTGGAAATCAAGAGA |
| MUC16-2 VH | 46 | VKLEESGGGFVKPG GSLKISCAASGFTF RNYAMSWVRLSPEM RLEWVATISSAGGY IFYSDSVQGRFTIS RDNAKNTHLQMGSL RSGDTAMYYCARQG FGNYGDYYAMDYWG QGTTVTVSS | 77 | GTGAAGCTGGAAGAGTCCGGCGGAGGC TTTGTGAAGCCTGGCGGAAGCCTGAAG ATCAGCTGTGCCGCCAGCGGCTTCACC TTCAGAAACTACGCCATGAGCTGGGTC CGACTGAGCCCCGAGATGAGACTGGAA TGGGTCGCCACAATCAGCAGCGCAGGC GGCTACATCTTCTACAGCGATAGCGTG CAGGGCAGATTCACCATCAGCCGGGAC AACGCCAAGAACACCCTGCACCTCCAG ATGGGCAGTCTGAGATCTGGCGACACC GCCATGTACTACTGCGCCAGACAAGGC TTCGGCAACTACGGCGACTACTATGCC ATGGATTACTGGGGCCAGGGCACCACC GTGACAGTCTCTTCT |
| MUC16-3 VL | 47 | DIKMAQSPSSVNAS LGERVTITCKASRD INNFLSWFHQKPGK SPKTLIYRANRLVD GVPSRFSGSGSGQD YSFTISSLEYEDVG IYYCLQYGDLYTFG GGTKLEIK | 78 | GACATCAAGATGGCTCAGTCCCCTTCT AGCGTGAATGCTTCGCTAGGGGAGCGT GTGACCATCACATGTAAAGCATCACGC GACATAAATAATTTCCTTTCCTGGTTT CATCAGAAACCGGGCAAGTCGCCTAAG ACGCTGATTTACAGAGCAAATCGGTTG GTAGATGGAGTGCCAAGCAGATTCAGC GGGAGCGGAAGTGGACAGGATTATAGC TTCACTATTTCATCCCTGGAATACGAG |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | | | GACGTAGGTATCTATTATTGCCTCCAG TATGGCGATCTTTACACATTTGGTGGG GGGACTAAGCTGGAGATTAAG |
| MUC16-3 VH | 48 | DVQLLESGPGLVRP SQSLSLTCSVTGYS IVSHYYWNWIRQFP GNKLEWMGYISSDG SNEYNPSLKNRISI SLDTSKNQFFLKFD FVTTADTATYFCVR GVDYWGQGTTLTVS S | 79 | GACGTGCAACTTCTGGAGAGCGGGCCA GGGCTAGTCAGGCCCTCCCAGTCGCTT TCACTGACTTGCAGTGTGACCGGTTAC TCTATTGTGAGTCACTACTATTGGAAC TGGATTCGGCAGTTCCCAGGCAACAAA CTGGAATGGATGGGGTACATATCTTCC GATGGCTCGAATGAATATAACCCATCA TTGAAAAATCGTATTTCCATCAGTCTG GATACGAGTAAAAACCAGTTTTTCCTC AAATTCGATTTCGTGACTACAGCAGAT ACTGCCACATACTTCTGTGTACGAGGT GTCGATTATTGGGGACAGGGCACAACG CTGACCGTAAGTTCT |
| MUC16-4 VL | 49 | DIQMTQSSSFLSVS LGGRVTITCKASDL IHNWLAWYQQKPGN APRLLISGATSLET GVPSRFSGSGSGND YTLSIASLQTEDAA TYYCQQYWTTPFTF GSGTKLEIK | 80 | GACATCCAGATGACCCAGAGCAGCAGC TTCCTGAGCGTGTCCCTTGGCGGCAGA GTGACCATCACCTGTAAAGCCAGCGAC CTGATCCACAACTGGCTGGCCTGGTAT CAGCAGAAGCCTGGCAACGCTCCCAGA CTGCTGATTAGCGGCGCCACCTCTCTG GAAACAGGCGTGCCAAGCAGATTTTCC GGCAGCGGCTCCGGCAACGACTACACA CTGTCTATTGCCAGCCTGCAGACCGAG GATGCCGCCACCTATTACTGCCAGCAG TACTGGACCACACCTTTCACCTTTGGC AGCGGCACCAAGCTGGAAATCAAG |
| MUC16-4 VH | 50 | DVQLQESGPGLVNP SQSLSLTCTVTGYS ITNDYAWNWIRQFP GNKLEWMGYINYSG YTTYNPSLKSRISI TRDTSKNQFFLHLN SVTTEDTATYYCAR WDGGLTYWGQGTLV TVSA | 81 | GACGTTCAGCTGCAAGAGTCTGGCCCT GGCCTGGTCAATCCTAGCCAGAGCCTG AGCCTGACATGTACCGTGACCGGCTAC AGCATCACCAACGACTACGCCTGGAAC TGGATCAGACAGTTCCCCGGCAACAAG CTGGAATGGATGGGCTACATCAACTAC AGCGGCTACACCACCTACAATCCCAGC CTGAAGTCCCGGATCTCCATCACCAGA GACACCAGCAAGAACCAGTTCTTCCTG CACCTGAACAGCGTGACCACCGAGGAT ACCGCCACCTACTACTGCGCTAGATGG GATGGCGGCCTGACATATTGGGGCCAG GGAACACTGGTCACCGTGTCTGCT |
| MUC16-5 VL | 51 | DIQMTQSPSSLSAS VGDRVTITCKASDL IHNWLAWYQQKPGK APKLLISGATSLET GVPSRFSGSGSGTD FTLTISSLQPEDFA TYYCQQYWTTPFTF GQGTKVEIKR | 82 | GACATCCAGATGACCCAGAGCCCCAGC AGCCTGAGCGCCAGCGTGGGCGACAGG GTGACCATCACCTGCAAGGCCAGCGAC CTGATCCACAACTGGCTGGCCTGGTAC CAGCAGAAGCCCGGCAAGGCCCCCAAG CTGCTGATCAGCGGCGCCACCAGCCTG GAGACCGGCGTGCCCAGCAGGTTCAGC GGCAGCGGCAGCGGCACCGACTTCACC CTGACCATCAGCAGCCTGCAGCCCGAG GACTTCGCCACCTACTACTGCCAGCAG TACTGGACCACCCCCTTCACCTTCGGC CAGGGGCACCAAGGTGGAGATCAAGAGG |
| MUC16-5 VH-L | 52 | EVQLVESGGGLVQP GGSLRLSCAASGYS ITNDYAWNWVRQAP GKGLEWVGYINYSG YTTYNPSLKSRFTI SRDNSKNTLYLQMN SLRAEDTAVYYCAR WDGGLTYWGQGTLV TVSS | 83 | GAGGTGCAGCTGGTGGAGAGCGGCGGC GGCCTGGTGCAGCCCGGCGGCAGCCTG AGGCTGAGCTGCGCCGCCAGCGGCTAC AGCATCACCAACGACTACGCCTGGAAC TGGGTGAGGCAGGCCCCCGGCAAGGGC CTGGAGTGGGTGGGCTACATCAACTAC AGCGGCTACACCACCTACAACCCCAGC CTGAAGAGCAGGTTCACCATCAGCAGG GACAACAGCAAGAACACCCTGTACCTG CAGATGAACAGCCTGAGGGCCGAGGAC ACCGCCGTGTACTACTGCGCCAGGTGG GACGGCGGCCTGACCTACTGGGGCCAG GGCACCCTGGTGACCGTGAGCAGC |
| MUC16-5 VH-F | 53 | EVQLVESGGGLVQP GGSLRLSCAASGYS ITNDYAWNWVRQAP | 84 | GAGGTGCAGCTGGTGGAGAGCGGCGGC GGCCTGGTGCAGCCCGGCGGCAGCCTG AGGCTGAGCTGCGCCGCCAGCGGCTAC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | GKGLEWVGYINYSG YTTYNPSLKSRFTI SRDNSKNTFYLQMN SLRAEDTAVYYCAR WDGGLTYWGQGTLV TVSS | | AGCATCACCAACGACTACGCCTGGAAC TGGGTGAGGCAGGCCCCCGGCAAGGGC CTGGAGTGGGTGGGCTACATCAACTAC AGCGGCTACACCACCTACAACCCCAGC CTGAAGAGCAGGTTCACCATCAGCAGG GACAACAGCAAGAACACCTTCTACCTG CAGATGAACAGCCTGAGGGCCGAGGAC ACCGCCGTGTACTACTGCGCCAGGTGG GACGGCGGCCTGACCTACTGGGGCCAG GGCACCCTGGTGACCGTGAGCAGC |
| MUC16-6 VL | 54 | DIVLTQSPAIMSAS LGERVTMTCTASSS VSSSYLHWYQQKPG SSPKLWIYSTSNLA SGVPGRFSGSGSGT SYSLTISSMEAEDA ATYYCHQYHRSPYT FGGGTKVEIKR | 85 | GACATCGTGCTGACACAGAGCCCTGCC ATCATGTCTGCCAGCCTCGGCGAGCGA GTGACCATGACATGTACAGCCAGCAGC AGCGTGTCCAGCAGCTACCTGCATTGG TATCAGCAGAAGCCCGGCAGCAGCCCC AAGCTGTGGATCTACAGCACAAGCAAT CTGGCCAGCGGCGTGCCAGGCAGATTT TCTGGTTCTGGCAGCGGCACCAGCTAC AGCCTGACAATCAGCAGCATGGAAGCC GAGGATGCCGCCACCTACTACTGCCAC CAGTACCACAGAAGCCCCTACACCTTT GGCGGAGGCACCAAGGTGGAAATCAAG CGG |
| MUC16-7 VL | 55 | DIQMTQSPSSLSAS VGDRVTITCTASSS VSSSYLHWYQQKPG KAPKLLIYSTSNLA SGVPSRFSGSGSGT DFTLTISSLQPEDF ATYYCHQYHRSPYT FGQGTKVEIKR | 86 | GACATCCAGATGACACAGAGCCCTAGC AGCCTGTCTGCCAGCGTGGGAGACAGA GTGACCATCACCTGTACAGCCAGCAGC AGCGTGTCCAGCAGCTACCTGCATTGG TATCAGCAGAAGCCCGGCAAGGCCCCT AAGCTGCTGATCTACAGCACCAGCAAT CTGGCCAGCGGCGTGCCAAGCAGATTT TCTGGCTCTGGCAGCGGCACCGACTTC ACCCTGACCATATCTAGCCTGCAGCCT GAGGACTTCGCCACCTACTACTGCCAC CAGTACCACAGAAGCCCCTACACCTTT GGCCAGGGCACCAAGGTGGAAATCAAG CGG |
| MUC16-7 VH | 56 | EVQLVESGGGLVQP GGSLRLSCAASGFN IKDTYMHWVRQAPG KGLEWVGRVDPANG NTKYDPKFQGRFTI SADTSKNTAYLQMN SLRAEDTAVYYCVR DYYGHTYGFAFWGQ GTLVTVSS | 87 | GAGGTGCAGCTGGTTGAATCTGGCGGA GGACTGGTTCAGCCTGGCGGATCTCTG AGACTGTCTTGTGCCGCCAGCGGCTTC AACATCAAGGACACCTACATGCACTGG GTCCGACAGGCCCCTGGCAAGGACTT GAGTGGGTTGGAAGAGTGGACCCCGCC AACGGCAACACCAAATACGACCCCAAG TTCCAGGGCAGATTCACCATCAGCGCC GACACCAGCAAGAACACCGCCTACCTG CAGATGAACAGCCTGAGAGCCGAGGAC ACCGCCGTGTACTATTGCGTGCGGGAT TACTACGGCCATACCTACGGCTTCGCC TTTTGGGGCCAGGGCACACTGGTTACC GTTAGCTCT |
| CD8alpha hinge | 57 | KPTTTPAPRPPTPA PTIASQPLSLRPEA CRPAAGGAVHTRGL DFACD | 88 | AAGCCCACCACCACCCCTGCCCCTAGA CCTCCAACCCCAGCCCCTACAATCGCC AGCCAGCCCCTGAGCCTGAGGCCCGAA GCCTGTAGACCTGCCGCTGGCGGAGCC GTGCACACCAGAGGCCTGGATTTCGCC TGCGAC |
| CD8alpha 2x | 58 | KPTTTPAPRPPTPA PTIASQPLSLRPEA SRPAAGGAVHTRGL DFASDKPTTTPAPR PPTPAPTIASQPLS LRPEACRPAAGGAV HTRGLDFACD | 89 | AAACCTACTACAACTCCTGCCCCCGG CCTCCTACACCAGCTCCTACTATCGCC TCCCAGCCACTCAGTCTCAGACCCGAG GCTTCTAGGCCAGCGGCCGGAGGCGCG GTCCACACCCGCGGGCTGGACTTTGCA TCCGATAAGCCCACCACCACCCCTGCC CCTAGACCTCCAACCCCAGCCCCTACA ATCGCCAGCCAGCCCCTGAGCCTGAGG CCCGAAGCCTGTAGACCTGCCGCTGGC GGAGCCGTGCACACCAGAGGCCTGGAT TTCGCCTGCGAC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| CD8alpha 3x | 59 | KPTTTPAPRPPTPA PTIASQPLSLRPEA SRPAAGGAVHTRGL DFASDKPTTTPAPR PPTPAPTIASQPLS LRPEASRPAAGGAV HTRGLDFASDKPTT TPAPRPPTPAPTIA SQPLSLRPEACRPA AGGAVHTRGLDFAC D | 90 | AAGCCTACCACCACCCCCGCACCTCGT CCTCCAACCCCTGCACCTACGATTGCC AGTCAGCCTCTTTCACTGCGGCCTGAG GCCAGCAGACCAGCTGCCGGCGGTGCC GTCCATACAAGAGGACTGGACTTCGCG TCCGATAAACCTACTACCACTCCAGCC CCAAGGCCCCCAACCCCAGCACCGACT ATCGCATCACAGCCTTTGTCACTGCGT CCTGAAGCCAGCCGGCCAGCTGCAGGG GGGGCCGTCCACACAAGGGGACTCGAC TTTGCGAGTGATAAGCCCACCACCACC CCTGCCCCTAGACCTCCAACCCCAGCC CCTACAATCGCCAGCCAGCCCCTGAGC CTGAGGCCCGAAGCCTGTAGACCTGCC GCTGGCGGAGCCGTGCACACCAGAGGC CTGGATTTCGCCTGCGAC |
| CD8alpa 4x | 60 | TTPAPRPPTPAPTI ASQPLSLRPEASRP AAGGAVHTRGLDFA SDKPTTTPAPRPPT PAPTIASQPLSLRP EASRPAAGGAVHTR GLDFASDKPTTTPA PRPPTPAPTIASQP LSLRPEASRPAAGG AVHTRGLDFASDKP TTTPAPRPPTPAPT IASQPLSLRPEACR PAAGGAVHTRGLDF ACD | 91 | AAGCCTACCACCACCCCCGCACCTCGT CCTCCAACCCCTGCACCTACGATTGCC AGTCAGCCTCTTTCACTGCGGCCTGAG GCCAGCAGACCAGCTGCCGGCGGTGCC GTCCATACAAGAGGACTGGACTTCGCG TCCGATAAACCTACTACCACTCCAGCC CCAAGGCCCCCAACCCCAGCACCGACT ATCGCATCACAGCCTTTGTCACTGCGT CCTGAAGCCAGCCGGCCAGCTGCAGGG GGGGCCGTCCACACAAGGGGACTCGAC TTTGCGAGTGATAAACTACTACAACT CCTGCCCCCGGCCTCCTACACCAGCT CCTACTATCGCCTCCCAGCCACTCAGT CTCAGACCCGAGGCTTCTAGGCCAGCG GCCGGAGGCGCGGTCCACACCCGCGGG CTGGACTTTGCATCCGATAAGCCCACC ACCACCCCTGCCCCTAGACCTCCAACC CCAGCCCCTACAATCGCCAGCCAGCCC CTGAGCCTGAGGCCCGAAGCCTGTAGA CCTGCCGCTGGCGGAGCCGTGCACACC AGAGGCCTGGATTTCGCCTGCGAC |
| CD8alpha TM | 61 | IYIWAPLAGTCGVL LLSLVITLYCNHRN | 92 | ATCTACATCTGGGCCCCTCTGGCCGGC ACCTGTGGCGTGCTGCTGCTGAGCCTG GTCATCACCCTGTACTGCAACCACCGG AAT |
| CD28 TM | 62 | FWVLVVVGGVLACY SLLVTVAFIIFWV | 93 | TTTTGGGTGCTGGTGGTGGTTGGTGGA GTCCTGGCTTGCTATAGCTTGCTAGTA ACAGTGGCCTTTATTATTTTCTGGGTG |
| 4-1BB signaling domain | 63 | KRGRKKLLYIFKQP FMRPVQTTQEEDGC SCRFPEEEEGGCEL | 94 | AAGAGAGGCCGGAAGAAACTGCTGTAC ATCTTCAAGCAGCCCTTCATGCGGCCC GTGCAGACCACCCAGGAAGAGGACGGC TGCAGCTGCCGGTTCCCCGAGGAAGAG GAAGGCGGCTGCGAACTG |
| CD28 signaling domain | 64 | RSKRSRGGHSDYMN MTPRRPGPTRKHYQ PYAPPRDFAAYRS | 95 | AGGAGCAAGCGGAGCAGAGGCGGCCAC AGCGACTACATGAACATGACCCCCCGG AGGCCTGGCCCCACCCGGAAGCACTAC CAGCCCTACGCCCCCTCCCAGGGACTTC GCCGCCTACCGGAGC |
| DNAX-activation protein 10 (DAP 10) Signaling Domain | 65 | LCARPRRSPAQEDG KVYINMPGRG | 96 | CTGTGCGCACGCCCACGCCGCAGCCCC GCCCAAGAAGATGGCAAAGTCTACATC AACATGCCAGGCAGGGGC |
| DNAX-activation protein 12 (DAP12) Signaling Domain | 66 | YFLGRLVPRGRGAA EAATRKQRITETES PYQELQGQRSDVYS DLNTQRPYYK | 97 | TACTTCCTGGGCCGGCTGGTCCCTCGG GGGCGAGGGGCTGCGGAGGCAGCGACC CGGAAACAGCGTATCACTGAGACCGAG TCGCCTTATCAGGAGCTCCAGGGTCAG AGGTCGGATGTCTACAGCGACCTCAAC ACACAGAGGCCGTATTACAAA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| CD3ζ signaling domain | 67 | RVKFSRSADAPAYQ QGQNQLYNELNLGR REEYDVLDKRRGRD PEMGGKPRRKNPQE GLYNELQKDKMAEA YSEIGMKGERRRGK GHDGLYQGLSTATK DTYDALHMQALPPR | 98 | CGGGTGAAGTTCAGCCGGAGCGCCGAC GCCCCTGCCTACCAGCAGGGCCAGAAC CAGCTGTACAACGAGCTGAACCTGGGC CGGAGGGAGGAGTACGACGTGCTGGAC AAGCGGAGAGGCCGGGACCCTGAGATG GGCGGCAAGCCCCGGAGAAAGAACCCT CAGGAGGGCCTGTATAACGAACTGCAG AAAGACAAGATGGCCGAGGCCTACAGC GAGATCGGCATGAAGGGCGAGCGGCGG AGGGGCAAGGGCCACGACGGCCTGTAC CAGGGCCTGAGCACCGCCACCAAGGAT ACCTACGACGCCCTGCACATGCAGGCC CTGCCCCCCAGA |
| HER1t | 68 | RKVCNGIGIGEFKD SLSINATNIKHFKN CTSISGDLHILPVA FRGDSFTHTPPLDP QELDILKTVKEITG FLLIQAWPENRTDL HAFENLEIIRGRTK QHGQFSLAVVSLNI TSLGLRSLKEISDG DVIISGNKNLCYAN TINWKKLFGTSGQK TKIISNRGENSCKA TGQVCHALCSPEGC WGPEPRDCVSCRNV SRGRECVDKCNLLE GEPREFVENSECIQ CHPECLPQAMNITC TGRGPDNCIQCAHY IDGPHCVKTCPAGV MGENNTLVWKYADA GHVCHLCHPNCTYG CTGPGLEGCPTNGP KIPSIATGMVGALL LLLVVALGIGLFM | 99 | CGCAAAGTGTGTAACGGAATAGGTATT GGTGAATTTAAAGACTCACTCTCCATA AATGCTACGAATATTAAACACTTCAAA AACTGCACCTCCATCAGTGGCGATCTC CACATCCTGCCGGTGGCATTTAGGGGT GACTCCTTCACACATACTCCTCCTCTG GATCCACAGGAACTGGATATTCTGAAA ACCGTAAAGGAAATCACAGGGTTTTTG CTGATTCAGGCTTGGCCTGAAAACAGG ACGGACCTCCATGCCTTTGAGAACCTA GAAATCATACGCGGCAGGACCAAGCAA CATGGTCAGTTTTCTCTTGCAGTCGTC AGCCTGAACATAACATCCTTGGGATTA CGCTCCCTCAAGGAGATAAGTGATGGA GATGTGATAATTTCAGGAAACAAAAAT TTGTGCTATGCAAATACAATAAACTGG AAAAAACTGTTTGGGACCTCCGGTCAG AAAACCAAAATTATAAGCAACAGAGGT GAAAACAGCTGCAAGGCCACAGGCCAG GTCTGCCATGCCTTGTGCTCCCCCGAG GGCTGCTGGGGCCCGGAGCCCAGGGAC TGCGTCTCTTGCCGGAATGTCAGCCGA GGCAGGGAATGCGTGGACAAGTGCAAC CTTCTGGAGGGTGAGCCAAGGGAGTTT GTGGAGAACTCTGAGTGCATACAGTGC CACCCAGAGTGCCTGCCTCAGGCCATG AACATCACCTGCACAGGACGGGGACCA GACAACTGTATCCAGTGTGCCCACTAC ATTGACGGCCCCCACTGCGTCAAGACC TGCCCGGCAGGAGTCATGGGAGAAAAC AACACCCTGGTCTGGAAGTACGCAGAC GCCGGCCATGTGTGCCACCTGTGCCAT CCAAACTGCACCTACGGATGCACTGGG CCAGGTCTTGAAGGCTGTCCAACGAAT GGGCCTAAGATCCCGTCCATCGCCACT GGGATGGTGGGGGCCCTCCTCTTGCTG CTGGTGGTGGCCCTGGGGATCGGCCTC TTCATG |
| HER1t-1 | 69 | RKVCNGIGIGEFKD SLSINATNIKHFKN CTSISGDLHILPVA FRGDSFTHTPPLDP QELDILKTVKEITG FLLIQAWPENRTDL HAFENLEIIRGRTK QHGQFSLAVVSLNI TSLGLRSLKEISDG DVIISGNKNLCYAN TINWKKLFGTSGQK TKIISNRGENSCKA TGQVCHALCSPEGC WGPEPRDCVSGGGG SGGGSGGGGSGGGG SFWVLVVGGVLAC YSLLVTVAFIIFWV RSKRS | 100 | CGCAAAGTGTGTAACGGAATAGGTATT GGTGAATTTAAAGACTCACTCTCCATA AATGCTACGAATATTAAACACTTCAAA AACTGCACCTCCATCAGTGGCGATCTC CACATCCTGCCGGTGGCATTTAGGGGT GACTCCTTCACACATACTCCTCCTCTG GATCCACAGGAACTGGATATTCTGAAA ACCGTAAAGGAAATCACAGGGTTTTTG CTGATTCAGGCTTGGCCTGAAAACAGG ACGGACCTCCATGCCTTTGAGAACCTA GAAATCATACGCGGCAGGACCAAGCAA CATGGTCAGTTTTCTCTTGCAGTCGTC AGCCTGAACATAACATCCTTGGGATTA CGCTCCCTCAAGGAGATAAGTGATGGA GATGTGATAATTTCAGGAAACAAAAAT TTGTGCTATGCAAATACAATAAACTGG AAAAAACTGTTTGGGACCTCCGGTCAG AAAACCAAAATTATAAGCAACAGAGGT GAAAACAGCTGCAAGGCCACAGGCCAG GTCTGCCATGCCTTGTGCTCCCCCGAG GGCTGCTGGGGCCCGGAGCCCAGGGAC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | | | TGCGTCTCTGGTGGCGGTGGCTCGGGC GGTGGTGGGTCGGGTGGCGGCGGATCT GGTGGCGGTGGCTCGTTTTGGGTGCTG GTGGTGGTTGTGGAGTCCTGGCTTGC TATAGCTTGCTAGTAACAGTGGCCTTT ATTATTTTCTGGGTGAGGAGTAAGAGG AGC |
| FL CD20 | 70 | MTTPRNSVNGTFPA EPMKGPIAMQSGPK PLFRRMSSLVGPTQ SFFMRESKTLGAVQ IMNGLFHIALGGLL MIPAGIYAPICVTV WYPLWGGIMYIISG SLLAATEKNSRKCL VKGKMIMNSLSLFA AISGMILSIMDILN IKISHFLKMESLNF IRAHTPYINIYNCE PANPSEKNSPSTQY CYSIQSLFLGILSV MLIFAFFQELVIAG IVENEWKRTCSRPK SNIVLLSAEEKKEQ TIEIKEEVVGLTET SSQPKNEEDIEIIP IQEEEEEETETNFP EPPQDQESSPIEND SSP | 101 | ATGACAACACCCAGAAATTCAGTAAAT GGGACTTTCCCGGCAGAGCCAATGAAA GGGCCCTATTGCTATGCAATCTGGTCCA AAACCACTCTTCAGGAGGATGTCTTCA CTGGTGGGCCCCACGCAAAGCTTCTTC ATGAGGGAATCTAAGACTTTGGGGGCT GTCCAGATTATGAATGGGCTCTTCCAC ATTGCCCTGGGGGGTCTTCTGATGATC CCAGCAGGGATCTATGCACCCATCTGT GTGACTGTGTGGTACCCTCTCTGGGGA GGCATTATGTATATTATTTCCGGATCA CTCCTGGCAGCAACGGAGAAAAACTCC AGGAAGTGTTTGGTCAAAGGAAAAATG ATAATGAATTCATTGAGCCTCTTTGCT GCCATTTCTGGAATGATTCTTTCAATC ATGGACATACTTAATATTAAAATTTCC CATTTTTTAAAAATGGAGAGTCTGAAT TTTATTAGAGCTCACACACCATATATT AACATATACAACTGTGAACCAGCTAAT CCCTCTGAGAAAAACTCCCCATCTACC CAATACTGTTACAGCATACAATCTCTG TTCTTGGGCATTTTGTCAGTGATGCTG ATCTTTGCCTTCTTCCAGGAACTTGTA ATAGCTGGCATCGTTGAGAATGAATGG AAAAGAACGTGCTCCAGACCCAAATCT AACATAGTTCTCCTGTCAGCAGAAGAA AAAAAAGAACAGACTATTGAAATAAAA GAAGAAGTGGTTGGGCTAACTGAAACA TCTTCCCAACCAAAGAATGAAGAAGAC ATTGAAATTATTCCAATCCAAGAAGAG GAAGAAGAAGAAACAGAGACTAACTTT CCAGAACCTCCCCAAGATCAGGAATCC TCACCAATAGAAAATGACAGCTCTCCT |
| CD20t-1 | 71 | MTTPRNSVNGTFPA EPMKGPIAMQSGPK PLFRRMSSLVGPTQ SFFMRESKTLGAVQ IMNGLFHIALGGLL MIPAGIYAPICVTV WYPLWGGIMYIISG SLLAATEKNSRKCL VKGKMIMNSLSLFA AISGMILSIMDILN IKISHFLKMESLNF IRAHTPYINIYNCE PANPSEKNSPSTQY CYSIQSLFLGILSV MLIFAFFQELVIAG IVENEWKRTCSRPK SNIVLLSAEEKKEQ TIEIKEEVVGLTET SSQPKNEEDIE | 102 | ATGACCACACCACGGAACTCTGTGAAT GGCACCTTCCCAGCAGAGCCAATGAAG GGACCAATCGCAATGCAGAGCGGACCC AAGCCTCTGTTTCGGAGAATGAGCTCC CTGGTGGGCCCAACCCAGTCCTTCTTT ATGAGAGAGTCTAAGACACTGGGCGCC GTGCAGATCATGAACGGACTGTTCCAC ATCGCCCTGGGAGGACTGCTGATGATC CCAGCCGGCATCTACGCCCCTATCTGC GTGACCGTGTGGTACCCTCTGTGGGGC GGCATCATGTATATCATCTCCGGCTCT CTGCTGGCCGCCACAGAAGAACAGC AGGAAGTGTCTGGTGAAGGGCAAGATG ATCATGAATAGCCTGTCCCTGTTTGCC GCCATCTCTGGCATGATCCTGAGCATC ATGGACATCCTGAACATCAAGATCAGC CACTTCCTGAAGATGGAGAGCCTGAAC TTCATCAGAGCCCACACCCCTTACATC AACATCTATAATTGCGAGCCTGCCAAC CCATCCGAGAAGAATTCTCCAAGCACA CAGTACTGTTATTCCATCCAGTCTCTG TTCCTGGGCATCCTGTCTGTGATGCTG ATCTTTGCCTTCTTTCAGGAGCTGGTC ATCGCCGGCATCGTGGAGAACGAGTGG AAGAGGACCTGCAGCCGCCCCAAGTCC AATATCGTGCTGCTGTCCGCCGAGGAG AAGAAGGAGCAGACAATCGAGATCAAG GAGGAGGTGGTGGGCCTGACCGAGACA TCTAGCCAGCCTAAGAATGAGGAGGAT ATCGAG |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| mbIL15 | 103 | MDWTWILFLVAAAT RVHSNWVNVISDLK KIEDLIQSMHIDAT LYTESDVHPSCKVT AMKCFLLELQVISL ESGDASIHDTVENL IILANNSLSSNGNV TESGCKECEELEEK NIKEFLQSFVHIVQ MFINTSSGGGSGGG GSGGGGSGGGGSGG GSLQITCPPPMSVE HADIWVKSYSLYSR ERYICNSGFKRKAG TSSLTECVLNKATN VAHWTTPSLKCIRD PALVHQRPAPPSTV TTAGVTPQPESLSP SGKEPAASSPSSNN TAATTAAIVPGSQL MPSKSPSTGTTEIS SHESSHGTPSQTTA KNWELTASASHQPP GVYPQGHSDTTVAI STSTVLLCGLSAVS LLACYLKSRQTPPL ASVEMEAMEALPVT WGTSSRDEDLENCE HHL | 106 | ATGGATTGGACCTGGATTCTGTTTCTG GTGGCCGCTGCCACAAGAGTGCACAGC AACTGGGTGAATGTGATCAGCGACCTG AAGAAGATCGAGGATCTGATCCAGAGC ATGCACATTGATGCCACCCTGTACACA GAATCTGATGTGCACCCTAGCTGTAAA GTGACCGCCATGAAGTGTTTTCTGCTG GAGCTGCAGGTGATTTCTCTGGAAAGC GGAGATGCCTCTATCCACGACACAGTG GAGAATCTGATCATCCTGGCCAACAAT AGCCTGAGCAGCAATGGCAATGTGACA GAGTCTGGCTGTAAGGAGTGTGAGGAG CTGGAGGAGAAGAACATCAAGGAGTTT CTGCAGAGCTTTGTGCACATCGTGCAG ATGTTCATCAATACAAGCTCTGGCGGA GGATCTGGAGGAGGCGGATCTGGAGGA GGAGGCAGTGGAGGCGGAGGATCTGGC GGAGGATCTCTGCAGATTACATGCCCT CCTCCAATGTCTGTGGAGCACGCCGAT ATTTGGGTGAAGTCCTACAGCCTGTAC AGCAGAGAGAGATACATCTGCAACAGC GGCTTTAAGAGAAAGGCCGGACCTCT TCTCTGACAGAGTGCGTGCTGAATAAG GCCACAAATGTGGCCCACTGGACAACA CCTAGCCTGAAGTGCATTAGAGATCCT GCCCTGGTCCACCAGAGGCCTGCCCCT CCATCTACAGTGACAACAGCCGGAGTG ACACCTCAGCCTGAATCTCTGAGCCCT TCTGGAAAAGAACCTGCCGCCAGCTCT CCTAGCTCTAATAATACCGCCGCCACA ACAGCCGCCATTGTGCCTGGATCTCAG CTGATGCCTAGCAAGTCTCCTAGCACA GGCACAACAGAGATCAGCAGCCACGAA TCTTCTCACGGAACACCTTCTCAGACC ACCGCCAAGAATTGGGAGCTGACAGCC TCTGCCTCTCACCAGCCTCCAGGAGTG TATCCTCAGGGCCACTCTGATACAACA GTGGCCATCAGCACATCTACAGTGCTG CTGTGTGGACTGTCTGCCGTGTCTCTG CTGGCCTGTTACCTGAAGTCTAGACAG ACACCTCCTCTGGCCTCTGTGGAGATG GAGGCCATGGAAGCCCTGCCTGTGACA TGGGGAACAAGCAGCAGAGATGAGGAC CTGGAGAATTGTTCTCACCACCTG |
| IL-15 | 104 | NWVNVISDLKKIED LIQSMHIDATLYTE SDVHPSCKVTAMKC FLLELQVISLESGD ASIHDTVENLIILA NNSLSSNGNVTESG CKECEELEEKNIKE FLQSFVHIVQMFIN TS | 107 | AACTGGGTGAATGTGATCAGCGACCTG AAGAAGATCGAGGATCTGATCCAGAGC ATGCACATTGATGCCACCCTGTACACA GAATCTGATGTGCACCCTAGCTGTAAA GTGACCGCCATGAAGTGTTTTCTGCTG GAGCTGCAGGTGATTTCTCTGGAAAGC GGAGATGCCTCTATCCACGACACAGTG GAGAATCTGATCATCCTGGCCAACAAT AGCCTGAGCAGCAATGGCAATGTGACA GAGTCTGGCTGTAAGGAGTGTGAGGAG CTGGAGGAGAAGAACATCAAGGAGTTT CTGCAGAGCTTTGTGCACATCGTGCAG ATGTTCATCAATACAAGC |
| IL-15Rα | 105 | ITCPPPMSVEHADI WVKSYSLYSRERYI CNSGFKRKAGTSSL TECVLNKATNVAHW TTPSLKCIRDPALV HQRPAPPSTVTTAG VTPQPESLSPSGKE PAASSPSSNNTAAT TAAIVPGSQLMPSK SPSTGTTEISSHES SHGTPSQTTAKNWE LTASASHQPPGVYP QGHSDTTVAISTST VLLCGLSAVSLLAC YLKSRQTPPLASVE MEAMEALPVTWGTS | 108 | ATTACATGCCCTCCTCCAATGTCTGTG GAGCACGCCGATATTTGGGTGAAGTCC TACAGCCTGTACAGCAGAGAGAGATAC ATCTGCAACAGCGGCTTTAAGAGAAAG GCCGGCACCTCTTCTCTGACAGAGTGC GTGCTGAATAAGGCCACAAATGTGGCC CACTGGACAACACCTAGCCTGAAGTGC ATTAGAGATCCTGCCCTGGTCCACCAG AGGCCTGCCCCTCCATCTACAGTGACA ACAGCCGGAGTGACACCTCAGCCTGAA TCTCTGAGCCCTTCTGGAAAAGAACCT GCCGCCAGCTCTCCTAGCTCTAATAAT ACCGCCGCCACAACAGCCGCCATTGTG CCTGGATCTCAGCTGATGCCTAGCAAG TCTCCTAGCACAGGCACAACAGAGATC AGCAGCCACGAATCTTCTCACGGAACA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | SRDEDLENCSHHL | | CCTTCTCAGACCACCGCCAAGAATTGG GAGCTGACAGCCTCTGCCTCTCACCAG CCTCCAGGAGTGTATCCTCAGGGCCAC TCTGATACAACAGTGGCCATCAGCACA TCTACAGTGCTGCTGTGTGGACTGTCT GCCGTGTCTCTGCTGGCCTGTTACCTG AAGTCTAGACAGACACCTCCTCTGGCC TCTGTGGAGATGGAGGCCATGGAAGCC CTGCCTGTGACATGGGGAACAAGCAGC AGAGATGAGGACCTGGAGAATTGTTCT CACCACCTG |
| HUMAN Immuno-globulin heavy constant gamma 4 (IgG4 CH) | 146 | ASTKGPSVFPLAPC SRSTSESTAALGCL VKDYFPEPVTVSWN SGALTSGVHTFPAV LQSSGLYSLSSVVT VPSSSLGTKTYTCN VDHKPSNTKVDKRV ESKYGPPCPSCPAP EFLGGPSVFLFPPK PKDTLMISRTPEVT CVVVDVSQESPEVQ FNWYVDGVEVHNAK TKPREEQFNSTYRV VSVLTVLHQDWLNG KEYKCKVSNKGLPS SIEKTISKAKGQPR EPQVYTLPPSQEEM TK NQVSLTCLVKGFYP SDIAVEWESNGQPE NNYKTTPPVLDSDG SFFLYSRLTVDKSR WQEGNVFSCSVMHE ALHNHYTQKSLSLS LGK | | |
| IgG4 CH (S108P, L325P) | 147 | ASTKGPSVFPLAPC SRSTSESTAALGCL VKDYFPEPVTVSWN SGALTSGVHTFPAV LQSSGLYSLSSVVT VPSSSLGTKTYTCN VDHKPSNTKVDKRV ESKYGPPCPPCPAP EFLGGPSVFLFPPK PKDTLMISRTPEVT CVVVDVSQEDPEVQ FNWYVDGVEVHNAK TKPREEQFNSTYRV VSVLTVLHQDWLNG KEYKCKVSNKGLPS SIEKTISKAKGQPR EPQVYTLPPSQEEM TKNQVSLTCLVKGF YPSDIAVEWESNGQ PENNYKTTPPVLDS DGSFFLYSRLTVDK SRWQEGNVFSCSVM HEALHNHYTQKSLS LSPGK | 117 | GCTAGCACCAAGGGCCCATCGGTCTTC CCCCTGGCGCCCTGCTCCAGGAGCACC TCCGAGAGCACAGCCGCCCTGGGCTGC CTGGTCAAGGACTACTTCCCCGAACCG GTGACGGTGTCGTGGAACTCAGGCGCC CTGACCAGCGGCGTGCACACCTTCCCG GCTGTCCTACAGTCCTCAGGACTCTAC TCCCTCAGCAGCGTGGTGACCGTGCCC TCCAGCAGCTTGGGCACGAAGACCTAC ACCTGCAACGTAGATCACAAGCCCAGC AACACCAAGGTGGACAAGAGAGTTGAG TCCAAATATGGTCCCCCATGCCCACCA TGCCCAGCACCTGAGTTCCTGGGGGGA CCATCAGTCTTCCTGTTCCCCCCAAAA CCCAAGGACACTCTCATGATCTCCCGG ACCCCTGAGGTCACGTGCGTGGTGGTG GACGTGAGCCAGGAAGACCCCGAGGTC CAGTTCAACTGGTACGTGGATGGCGTG GAGGTGCATAATGCCAAGACAAAGCCG CGGGAGGAGCAGTTCAACAGCACGTAC CGTGTGGTCAGCGTCCTCACCGTCCTG CACCAGGACTGGCTGAACGGCAAGGAG TACAAGTGCAAGGTCTCCAACAAAGGC CTCCCGTCCTCCATCGAGAAAACCATC TCCAAAGCCAAAGGGCAGCCCCGAGAG CCACAGGTGTACACCCTGCCCCCATCC CAGGAGGAGATGACCAAGAACCAGGTC AGCCTGACCTGCCTGGTCAAAGGCTTC TACCCCAGCGACATCGCCGTGGAGTGG GAGAGCAATGGGCAGCCGGAGAACAAC TACAAGACCACGCCTCCCGTGCTGGAC TCCGACGGCTCCTTCTTCCTCTACAGC AGGCTCACCGTGGACAAGAGCAGGTGG CAGGAGGGGAATGTCTTCTCATGCTCC GTGATGCATGAGGCTCTGCACAACCAC TACACACAGAAGAGCCTCTCCCTGTCT CCGGGTAAA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| IgG4 CH (S108P) | 291 | ASTKGPSVFPLAPC SRSTSESTAALGCL VKDYFPEPVTVSWN SGALTSGVHTFPAV LQSSGLYSLSSVVT VPSSSLGTKTYTCN VDHKPSNTKVDKRV ESKYGPPCPPCPAP EFLGGPSVFLFPPK PKDTLMISRTPEVT CVVVDVSQEDPEVQ FNWYVDGVEVHNAK TKPREEQFNSTYRV VSVLTVLHQDWLNG KEYKCKVSNKGLPS SIEKTISKAKGQPR EPQVYTLPPSQEEM TKNQVSLTCLVKGF YPSDIAVEWESNGQ PENNYKTTPPVLDS DGSFFLYSRLTVDK SRWQEGNVFSCSVM HEALHNHYTQKSLS LSLGK | | |
| IgG4 CH (L325P) | 292 | ASTKGPSVFPLAPC SRSTSESTAALGCL VKDYFPEPVTVSWN SGALTSGVHTFPAV LQSSGLYSLSSVVT VPSSSLGTKTYTCN VDHKPSNTKVDKRV ESKYGPPCPSCPAP EFLGGPSVFLFPPK PKDTLMISRTPEVT CVVVDVSQEDPEVQ FNWYVDGVEVHNAK TKPREEQFNSTYRV VSVLTVLHQDWLNG KEYKCKVSNKGLPS SIEKTISKAKGQPR EPQVYTLPPSQEEM TKNQVSLTCLVKGF YPSDIAVEWESNGQ PENNYKTTPPVLDS DGSFFLYSRLTVDK SRWQEGNVFSCSVM HEALHNHYTQKSLS LSPGK | | |
| Anti-PD-1 (nVL1) | | | 118 | GAGATAGTTATGACTCAAAGCCCCGCT ACATTATCCCTGTCTCCGGGTGAACGG GCCACCCTGTCATGCCGGGCTTCACAG TCAGTGTCAAGCTATCTGGCATGGTAT CAGCAGAAGCCTGGACAGGCCCCAAGG CTACTGATTTATGACGCCAGCAACCGC GCTACAGGTATTCCTGCTAGGTTCTCA GGGTCAGGCTCTGGAACCGACTTTACT CTGACTATCTCCTCTCTTGAACCCGAG GATTTCGCGGTGTACTACTGTCAGCAG TATAATAACTGGCCACGCACATTCGGC GAGGGCACTAAAGTCGAAATTAAG |
| Anti-PD-1 (nVL2) | | | 119 | GAGATCGTACTGACTCAGTCTCCAGCC ACATTGTCCCTGTCCCCAGGGGAGCGC GCCACCCTGAGCTGTAGAGCTTCACAG TCCGTCAGTTCTTACCTCGCGTGGTAT CAGCAAAAACCTGGACAAGCTCCGAGG TTGCTTATCTATGACGCCTCCAACCGC GCCACTGGCATACCAGCAAGGTTCAGC GGATCTGGGTCCGGCACAGATTTTACC CTCACTATTTCTAGCCTTGAGCCGGAA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | | | GATTTCGCTGTTTACTACTGCCAGCAG CGATCCAACTGGCCCAAGACATTCGGC CAGGGAACTAAAGTGGAAATCAAA |
| Anti-PD-1 (nVL3) | 148 | EIVLTQSPATLSLS PGERATLSCRASQS VSSYLAWYQQKPGQ APRLLIYDASNRAN GIPARFSGSGSGTD FTLTISSLEPEDFA VYYCQQSSNWPRTF GQGTKVEIKR | 120 | GAAATTGTGTTGACACAGTCTCCAGCC ACCCTGTCTTTGTCTCCAGGGGAAAGA GCCACCCTCTCCTGCAGGGCCAGTCAG AGTGTTAGTAGTTACTTAGCCTGGTAC CAACAGAAACCTGGCCAGGCTCCCAGG CTCCTCATCTATGATGCATCCAACAGG GCCAACGGCATCCCAGCCAGGTTCAGT GGCAGTGGGTCTGGGACAGACTTCACT CTCACCATCAGCAGCCTAGAGCCTGAA GATTTCGCAGTTTATTACTGTCAGCAG AGTAGCAACTGGCCTCGGACGTTCGGC CAAGGGACCAAGGTGGAAATCAAAGA |
| Anti-PD-1 (pVL1) | | | 121 | CGGAACGTGCTGACCCAGTCCCCCCTT AGCCTCCCCGTCACGCCCGGAGAGCCC GCAAGTATCAGCTGCCGCAGTTCACAA AGTCTGAGTTCTTCTGGATACACCTAT TTGGACTGGTATTTGCAGAAGCCAGGG CAATCCCCACAGCTCCTGATATACCTC GCAAGCTGGAGAGATAGCGGAGTACCT GATCGCTTTTCTGGTAGCGGATCTGGT ACGGATTTCACTCTGAAGATTTCTAGG GTGGAGGCGGAGGACGTGGGAGTGTAC TACTGTATGCAAGCCGAGCAGACTCCC GGCCCAGGTAACACGTTCGGACAGGGG ACCAAACTGGAGATTAAG |
| Anti-PD-1 (pVL2) | | | 122 | GATGTGGTAATGACCCAGTCACCTCTT TCACTGCCTGTCACTCCCGGAGAGCCA GCTTCAATCTCCTGCCGTAGCTCTCAA TCATTGTTGCACACCAATGGATACAAC TACCTCCACTGGTATCTCCAGAAGCCC GGACAAAGCCCGCAGCTGCTGATCTAC CTGGGCAGCTGGCAGGACTCCGGGGTG CCCGACCGATTTAGCGGCAGTGGGAGC GGCACGGACTTTACACTGAAGATCAGC CGAGTAGAGGCGGAGGACGTGGGCGTT TACTACTGTATGCAGGCAGAGCAGACC CCCAGAACCTTCGGCCAGGGCACCCGG CTGGAGGTGAAA |
| Anti-PD-1 (nVH1) | | | 123 | CAGGTGCAGTTGGTTGAAAGCGGAGGA GGCGTGGTTCAACCCGGTAGAAGCCTA CGGCTGTCATGTGCGGCCTCCGGCTTC ACATTTCGATCTTACGGAATGCACTGG GTCAGGCAGGCACCCGGCAAGGGTCTG GAGTGGGTCGCCATAATTTTCTATGAC GGCAGCAACAAGTATTACGCCGACAGT GTTAAGGGGCGGTTTACCATCAGCAGA GACAACTCTAAAAACACTCTTTATCTG CAAATGAACTCTCTGCGGGCAGAGGAT ACCGCTGTTTACTATTGCGCCAGAGAT GACGACTACTGGGGGCAGGGTGCCTTG GTGACTGTGAGCAGC |
| Anti-PD-1 (nVH2) | | | 124 | GAGGTCCAGTTAGTCCAAAGCGGCGGA GGCGTAGTGCAACCTGGCAGAAGCCTG CGGTTATCGTGCGCCGCAAGCGGCTTC ACCTTTAGCTCTTATGGTATGCACTGG GTCAGACAGGCCCCTGGGAAGGGCCTG GAGTGGGTGGCCGTGATCTGGTATGAC GGGAGCAACAAGTATTACGCGGATTCC GTCAAGGGACGGTTCACCATATCCCGC GATAACAGCAAGAATACTCTTTACTTA CAGATGAACAGCCTGAGGGCCGAGGAC ACCGCAGTATATTATTGCGCTGCCGAA GGCTTTGACTATTGGGGTCAGGGCACT CTGGTGACTGTGAGCAGC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| Anti-PD-1 (nVH3) | 149 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNNDYWGQGTLVTVSS | 125 | CAGGTGCAGCTGGTGGAGTCTGGGGGAGGCGTGGTCCAGCCTGGGAGGTCCCTGAGACTCGACTGTAAAGCGTCTGGAATCACCTTCAGTAACTCTGGCATGCACTGGGTCCGCCAGGCTCCAGGCAAGGGGCTGGAGTGGGTGGCAGTTATTTGGTATGATGGAAGTAAAAGATACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTATTACTGTGCGACAAACAACGACTACTGGGGCCAGGGAACCCTGGTCACCGTCTCCTCA |
| Anti-PD-1 (nVH4) | 150 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCARNDDYWGQGTLVTVSS | 126 | CAGGTGCAGCTGGTGGAGTCTGGGGGAGGCGTGGTCCAGCCTGGGAGGTCCCTGAGACTCGACTGTAAAGCGTCTGGAATCACCTTCAGTAACTCTGGCATGCACTGGGTCCGCCAGGCTCCAGGCAAGGGGCTGGAGTGGGTGGCAGTTATTTGGTATGATGGAAGTAAAAGATACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTATTACTGTGCGAGAAACGACGACTACTGGGGCCAGGGAACCCTGGTCACCGTCTCCTCA |
| Anti-PD-1 (pVH1) | 151 | QVQLVQSGAEVKKPGASVKVSCKASGYTFTGYYMHWVRQAPGQGLEWMGAINPNSGGTNYAQKFQGRVTMTRDTSISTAYMELSRLRSDDTAVYYCARRPDRANWHFDYWGQGTLVTVSS | 127 | CAGGTACAGCTGGTGCAGAGCGGCGCAGAGGTGAAGAAGCCAGGCGCTTCTGTAAAGGTATCCTGCAAGGCATCCGGGTATACTTTCACCGGCTATTACATGCACTGGGTTCGTCAGGCACCCGGCCAGGGACTAGAATGGATGGGGGCCATCAACCCTAATAGTGGCGGTACTAACTACGCACAAAAGTTTCAGGGGCGAGTGACCATGACTCGGGATACCTCCATCTCCACGGCATACATGGAGCTGAGTCGCTTGCGGTCAGATGACACTGCGGTGTACTACTGCGCTCGCAGGCCCGACCGAGCTAATTGGCACTTTGACTACTGGGGACAGGGTACACTGGTGACCGTGTCATCA |
| Anti-PD-1 (pVH2) | 152 | QVQLVQSGAEVKKPGASVKVSCKASGYTFTGYYMHWVRQAPGQGLEWMGAINPNSGGTNYAQKLQGRVTMTTDTSTSTAYMELRSLRSDDTAVYYCARHGLKGDGYFDYWGQGTLVTVSS | 128 | CAGGTGCAGCTGGTCCAGAGCGGCGCGGAAGTGAAAAAGCCCGGCGCTTCCGTGAAGGTTTCTTGCAAAGCCTCTGGATACACATTCACTGGCTATTATATGCACTGGGTCAGACAGGCCCCCGGCCAGGGATTGGAGTGGATGGGTGCAATCAACCCCAATTCTGGTGGGACCAATTACGCACAGAAACTCCAGGGCCGAGTGACAATGACCACCGACACTTCTACCAGCACTGCCTACATGGAGCTGCGGTCTCTGCGATCAGACGACACCGCTGTGTACTATTGTGCAAGACACGGGCTGAAGGGCGACGGCTATTTTGACTACTGGGGACAGGGCACGCTGGTTACCGTGAGTTCC |
| Anti-PD-1 (pVH3) | 153 | QVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCARRDYRFYMGFDYWGQGTTVTVSS | 129 | CAGGTCCAGCTCGTGCAAAGCGGAGTGGAAGTGAAAAAGCCTGGCGCTTCCGTCAAGGTCAGCTGTAAGGCCAGCGGATACACATTCACAAACTATTACATGTACTGGGTGAGGCAGGCTCCCGGACAGGGACTGGAATGGATGGGCGGAATCAATCCCTCCAACGGAGGCACAAACTTTAACGAAAAGTTTAAGAATAGAGTCACCCTCACCACAGACTCCAGCACAACCACAGCCTATATGGAACTGAAAAGCCTCCAGTTTGACGATACCGCTGTGTATTACTGTGCCAGGAGAGATTACAGGTTCTACATGGGATTCGATTACTGGGGCCAAGGCACAACCGTCACCGTCAGCTCC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| Anti-PD-1 (pVH4) | 154 | QVQLVQSGVEVKKP GASVKVSCKASGYT FTNYYMYWVRQAPG QGLEWMGGINPSNG GTNFNEKFKNRVTL TTDSSTTTAYMELK SLQFDDTAVYYCAR RDYRFNMGFDYWGQ GTTVTVSS | 130 | CAGGTCCAGCTCGTGCAAAGCGGAGTG GAAGTGAAAAAGCCTGGCGCTTCCGTC AAGGTCAGCTGTAAGGCCAGCGGATAC ACATTCACAAACTATTACATGTACTGG GTGAGGCAGGCTCCCGGACAGGGACTG GAATGGATGGGCGGAATCAATCCCTCC AACGGAGGCACAAACTTTAACGAAAAG TTTAAGAATAGAGTCACCCTCACCACA GACTCCAGCACAACCACAGCCTATATG GAACTGAAAAGCCTCCAGTTTGACGAT ACCGCTGTGTATTACTGTGCCAGGAGA GATTACAGGTTCAACATGGGATTCGAT TACTGGGGCCAAGGCACAACCGTCACC GTCAGCTCC |
| Anti-PD-1 (pVH5) | 155 | QVQLVQSGVEVKKP GASVKVSCKASGYT FTNYYMYWVRQAPG QGLEWMGGIQPSNG GTNFNEKFKNRVTL TTDSSTTTAYMELK SLQFDDTAVYYCAR RDYRFYMGFDYWGQ GTTVTVSS | 131 | CAGGTCCAGCTCGTGCAAAGCGGAGTG GAAGTGAAAAAGCCTGGCGCTTCCGTC AAGGTCAGCTGTAAGGCCAGCGGATAC ACATTCACAAACTATTACATGTACTGG GTGAGGCAGGCTCCCGGACAGGGACTG GAATGGATGGGCGGAATCCAGCCCTCC AACGGAGGCACAAACTTTAACGAAAAG TTTAAGAATAGAGTCACCCTCACCACA GACTCCAGCACAACCACAGCCTATATG GAACTGAAAAGCCTCCAGTTTGACGAT ACCGCTGTGTATTACTGTGCCAGGAGA GATTACAGGTTCTACATGGGATTCGAT TACTGGGGCCAAGGCACAACCGTCACC GTCAGCTCC |
| Anti-PD-1 (pVH6) | 156 | QVQLVQSGVEVKKP GASVKVSCKASGYT FTNYYMYWVRQAPG QGLEWMGGIDPSNG GTNFNEKFKNRVTL TTDSSTTTAYMELK SLQFDDTAVYYCAR YDYRFDMGFDYWGQ GTTVTVSS | 132 | CAGGTCCAGCTCGTGCAAAGCGGAGTG GAAGTGAAAAGCCTGGCGCTTCCGTC AAGGTCAGCTGTAAGGCCAGCGGATAC ACATTCACAAACTATTACATGTACTGG GTGAGGCAGGCTCCCGGACAGGGACTG GAATGGATGGGCGGAATCGACCCCTCC AACGGAGGCACAAACTTTAACGAAAAG TTTAAGAATAGAGTCACCCTCACCACA GACTCCAGCACAACCACAGCCTATATG GAACTGAAAAGCCTCCAGTTTGACGAT ACCGCTGTGTATTACTGTGCCAGGTAC GATTACAGGTTCGATATGGGATTCGAT TACTGGGGCCAAGGCACAACCGTCACC GTCAGCTCC |
| Anti-PD-1 (nVH7) | 157 | QVQLVESGGGVVQP GRSLRLDCKASGFT FSNSGMHWVRQAPG KGLEWVAVIWYDGS KRYYADSVKGRFTI SRDNSKNTLFLQMN SLRAEDTAVYYCAT NNDYWGQGTLVTVS S | 133 | CAGGTGCAGCTGGTGGAGTCTGGGGGA GGCGTGGTCCAGCCTGGGAGGTCCCTG AGACTCGACTGTAAAGCGTCTGGATTC ACCTTCAGTAACTCTGGCATGCACTGG GTCCGCCAGGCTCCAGGCAAGGGGCTG GAGTGGGTGGCAGTTATTTGGTATGAT GGAAGTAAAAGATACTATGCAGACTCC GTGAAGGGCCGATTCACCATCTCCAGA GACAATTCCAAGAACACGCTGTTTCTG CAAATGAACAGCCTGAGAGCCGAGGAC ACGGCTGTGTATTACTGTGCGACAAAC AACGACTACTGGGGCCAGGGAACCCTG GTCACCGTCTCCTCA |
| Anti-PD-1 (nVH8) | 158 | EVQLVQSGGGVVQP GRSLRLSCAASGFT FSSYGMHWVRQAPG KGLEWVAVIWYDGS NKYYADSVKGRFTI SRDNSKNTLYLQMN SLRAEDTAVYYCAT NNDYWGQGTLVTVS S | 134 | GAGGTCCAGTTAGTCCAAAGCGGCGGA GGCGTAGTGCAACCTGGCAGAAGCCTG CGGTTATCGTGCGCCGCAAGCGGCTTC ACCTTTAGCTCTTATGGTATGCACTGG GTCAGACAGGCCCCTGGGAAGGGCCTG GAGTGGGTGGCCGTGATCTGGTATGAC GGGAGCAACAAGTATTACGCGGATTCC GTCAAGGGACGGTTCACCATATCCCGC GATAACAGCAAGAATACTCTTTACTTA CAGATGAACAGCCTGAGGGCCGAGGAC ACCGCAGTATATTATTGCGCTACCAAT AATGACTATTGGGGTCAGGGCACTCTG GTGACTGTGAGCAGC |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| Anti-PD-1 (nVH9) | 159 | EVQLVQSGGGVVQPGRSLRLSCAASGITFSNSMHWVRQAPGKGLEWVAVIWYDGSKRYYADSVKGRFTISRDNSKNTLYLQMNSLRAEDTAVYYCATNNDYWGQGTLVTVSS | 135 | GAGGTGCAACTGGTTCAGTCCGGCGGGGGCGTCGTCCAGCCGGGGCGCAGTCTGCGCTTGAGCTGTGCTGCCTCTGGGATTACCTTTAGCAACTCCATGCATTGGGTGCGGCAGGCACCCGGGAAGGGACTGGAATGGGTCGCAGTGATCTGGTACGATGGATCAAAGCGGTATTACGCCGACTCCGTCAAAGGCCGGTTCACAATCAGCCGCGACAACAGCAAAAATACTTTATATCTTCAGATGAATTCCCTTAGGGCAGAGGATACTGCTGTGTATTACTGCGCTACTAACAACGATTATTGGGGCAGGGGACACTAGTCACTGTTTCTAGT |
| Anti-PD-1 (nVH10) | 160 | EVQLVQSGGGVVQPGRSLRLSCAASGFTFSNSGMHWVRQAPGKGLEWVAVIWYDGSNKYYADSVKGRFTISRDNSKNTLYLQMNSLRAEDTAVYYCATNNDYWGQGTLVTVSS | 136 | GAGGTCCAGTTAGTCCAAAGCGGCGGAGGCGTAGTGCAACCTGGCAGAAGCCTGCGGTTATCGTGCGCCGCAAGCGGCTTCACCTTTAGCAATTCTGGTATGCACTGGGTCAGACAGGCCCCTGGGAAGGGCCTGGAGTGGGTGGCCGTGATCTGGTATGACGGGAGCAACAAGTATTACGCGGATTCCGTCAAGGGACGGTTCACCATATCCCGCGATAACAGCAAGAATACTCTTTACTTACAGATGAACAGCCTGAGGGCCGAGGACACCGCAGTATATTATTGCGCTACCAATAATGACTATTGGGGTCAGGGCACTCTGGTGACTGTGAGCAGC |
| Anti-PD-1 (nVH11) | 161 | EVQLVQSGGGVVQPGRSLRLSCAASGFTFSSYGMHWVRQAPGKGLEWVAVIWYDGSKYYADSVKGRFTISRDNSKNTLYLQMNSLRAEDTAVYYCATNNDYWGQGTLVTVSS | 137 | GAGGTCCAGTTAGTCCAAAGCGGCGGAGGCGTAGTGCAACCTGGCAGAAGCCTGCGGTTATCGTGCGCCGCAAGCGGCTTCACCTTTAGCTCTTATGGTATGCACTGGGTCAGACAGGCCCCTGGGAAGGGCCTGGAGTGGGTGGCCGTGATCTGGTATGACGGGAGCAAGTATTACGCGGATTCCGTCAAGGGACGGTTCACCATATCCCGCGATAACAGCAAGAATACTCTTTACTTACAGATGAACAGCCTGAGGGCCGAGGACACCGCAGTATATTATTGCGCTACCAATAATGACTATTGGGGTCAGGGCACTCTGGTGACTGTGAGCAGC |
| Anti-PD-1 (nVH12) | 162 | QVQLVESGGGVVQPGRSLRLDCKASGITFSNSGMHWVRQAPGKGLEWVAVIWYDGSNKRYYADSVKGRFTISRDNSKNTLFLQMNSLRAEDTAVYYCATNNDYWGQGTLVTVSS | 138 | CAGGTGCAGCTGGTGGAGTCTGGGGGAGGCGTGGTCCAGCCTGGGAGGTCCCTGAGACTCGACTGTAAAGCGTCTGGAATCACCTTCAGTAACTCTGGCATGCACTGGGTCCGCCAGGCTCCAGGCAAGGGGCTGGAGTGGGTGGCAGTTATTTGGTATGATGGAAGTAACAAAAGATACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTATTACTGTGCGACAAACAACGACTACTGGGGCCAGGGAACCCTGGTCACCGTCTCCTCA |
| Anti-PD-1 (nVH12) | 163 | QVQLVESGGGVVQPGRSLRLDCKASGFTFSNSGMHWVRQAPGKGL | 139 | CAGGTGCAGCTGGTGGAGTCTGGGGGAGGCGTGGTCCAGCCTGGGAGGTCCCTGAGACTCGACTGTAAAGCGTCTGGATTCACCTTCAGTAACTCTGGCATGCACTGGGTCCGCCAGGCTCCAGGCAAGGGGCTGGAGTGGGTGGCAGTTATTTGGTATGATGGAAGTAACAAAAGATACTATGCAGACTCCGTGAAGGGCCGATTCACCATCTCCAGAGACAATTCCAAGAACACGCTGTTTCTGCAAATGAACAGCCTGAGAGCCGAGGACACGGCTGTGTATTACTGTGCGACAAACAACGACTACTGGGGCCAGGGAACCCTGGTCACCGTCTCCTCA |
| Anti-PD-1 (nVH14) | 164 | EVQLVQSGGGVVQPGRSLRLSCAASGITFSNSGMHWVRQAPGKGLEWVAVIWYDGSKYYADSVKGRFTIS | 140 | GAGGTGCAACTTGTGCAAAGCGGCGGCGGAGTCGTGCAGCCCGGTCGATCTCTTCGCCTGAGTTGTGCTGCCAGCGGCATTACCTTTAGCAATTCTGGTATGCACTGGGTACGTCAGGCCCCCGGTAAGGGGCTA |

TABLE 13-continued

Non-limiting exemplary polypeptide and nucleotide sequences

| Name | SEQ ID NO | Amino Acid Sequence | SEQ ID NO | NUCLEOTIDE SEQUENCE |
|---|---|---|---|---|
| | | RDNSKNTLYLQMNS LRAEDTAVYYCATN NDYWGQGTLVTVSS | | GAATGGGTGGCTGTGATTTGGTACGAT GGTTCTAAGTACTACGCCGACAGCGTT AAAGGCCGATTCACCATCAGTAGAGAC AACAGTAAGAACACCCTCTACCTCCAG ATGAACAGTCTGCGAGCTGAAGACACT GCTGTGTACTACTGTGCCACCAACAAC GACTACTGGGGACAGGGAACCCTGGTC ACCGTGAGTAGT |

TABLE 14

Exemplary anti-TGFβ VH and VL sequences

| Name | SEQ ID NO | Amino Acid Sequence | SEQ ID NO | Nucleotide Sequence |
|---|---|---|---|---|
| Anti-TGFb clone 1 VL | 165 | DIMMTQSPSSLAVSAGEKV TMSCKSSQSVLYSSNQKNY LAWYQQKPGQSPKLLIYWA STRESGVPDRFTGSGSGTD FTLTISSVQAEDLAVYYCH QYLSSDTFGGGTKLEIKRT VA | 179 | GATATAATGACACAGAGCCCCAGCT CTCTAGCTGTGAGTGCTGGCGAGAA GGTGACCATGAGCTGTAAGAGCAGT CAAAGCGTGCTGTACAGTTCCAATC AGAAAAATTACCTCGCATGGTATCA GAAGCCAGGTCAAAGCCCTAAGCTC CTTATCTACTGGGCCTCAACCCGTG AAAGTGGAGTGCCTGACAGATTTAC TGGTTCAGGGAGCGGCACCGATTTC ACTCTGACTATTAGCTCTGTGCAGG CAGAAGACCTTGCCGTGTATTACTG TCACCAGTATCTGTCTTCAGACACG TTTGGAGGTGGGACCAAACTAGAAA TCAAACGTACTGTCGCA |
| Anti-TGFb clone 1 VH | 166 | QVXLXQSGAELVRPGT SVKVSCKASGYAFTN YLIEWVKQRPGQGLE WIGVNNPGSGGSNYN EKFKGKATLTADKSS STAYMQLSSLTSDDS AVYFCARSGGFYFDY WGQGTTQSPSPQPKR RAH | 180 | CAGGTGNNNCTGNNNCAGAGCGGCG CCGAGCTGGTGAGGCCCGGCACCAG CGTGAAGGTGAGCTGCAAGGCCAGC GGCTACGCCTTCACCAACTACCTGA TCGAGTGGGTGAAGCAGAGGCCCGG CCAGGGCCTGGAGTGGATCGGCGTG AACAACCCCGGCAGCGGCGGCAGCA ACTACAACGAGAAGTTCAAGGGCAA GGCCACCCTGACCGCCGACAAGAGC AGCAGCACCGCCTACATGCAGCTGA GCAGCCTGACCAGCGACGACAGCGC CGTGTACTTCTGCGCCAGGAGCGGC GGCTTCTACTTCGACTACTGGGGCC AGGGCACCACCCAGAGCCCCAGCCC CCAGCCCAAGAGGAGGGCCCAC |
| Anti-TGFb clone 2 VL | 167 | DIQMTQSPSSLSASV GDRVTITCRASQSVL YSSNQKNYLAWYQ QKPGKAPKILIYWA STRESGVPSRFSGSGS GTDFTLTISSLQPED FATYYCHQYLSSDTF GQGTKVEIRTVA | 181 | GACATCCAGATGACCCAGAGCCCCA GCAGCCTGAGCGCCAGCGTGGGCGA CAGGGTGACCATCACCTGCAGGGCC AGCCAGAGCGTGCTGTACAGCAGCA ACCAGAAGAACTACCTGGCCTGGTA CCAGCAGAAGCCCGGCAAGGCCCCC AAGCTGCTGATCTACTGGGCCAGCA CCAGGGAGAGCGGCGTGCCCAGCAG GTTCAGCGGCAGCGGCAGCGGCACC GACTTCACCCTGACCATCAGCAGCC TGCAGCCCGAGGACTTCGCCACCTA CTACTGCCACCAGTACCTGAGCAGC GACACCTTCGGCCAGGGCACCAAGG TGGAGATCAAGAGGACCGTGGCC |
| Anti-TGFb clone 2 VH | 168 | EVQLVESGGGLVQPGG SLRLSCAASGYAFTN YLIEWVRQAPGKGLE WVGVNNPGSGGSNYN EKFKGRATISADNSK NTLYLQMNSLRAEDT AVYYCARSGGFYFDY WGQGTLVTVSSASTK | 182 | GAGGTGCAGCTGGTGGAGAGCGGCG GCGGCCTGGTGCAGCCCGGCGGCAG CCTGAGGCTGAGCTGCGCCGCCAGC GGCTACGCCTTCACCAACTACCTGA TCGAGTGGGTGAGGCAGGCCCCCGG CAAGGGCCTGGAGTGGGTGGGCGTG AACAACCCCGGCAGCGGCGGCAGCA ACTACAACGAGAAGTTCAAGGGCAG |

TABLE 14-continued

Exemplary anti-TGFβ VH and VL sequences

| Name | SEQ ID NO | Amino Acid Sequence | SEQ ID NO | Nucleotide Sequence |
|---|---|---|---|---|
| | | GPS | | GGCCACCATCAGCGCCGACAACAGC AAGAACACCCTGTACCTGCAGATGA ACAGCCTGAGGGCCGAGGACACCGC CGTGTACTACTGCGCCAGGAGCGGC GGCTTCTACTTCGACTACTGGGGCC AGGGCACCCTGGTGACCGTGAGCAG CGCCAGCACCAAGGGCCCCAGC |
| Anti-TGFb clone 3 VH | 169 | LARPGASVKMSCKTSG YTFTNYWMHWVRQRP GQGLEWIGTIYPGNS DTNYNQKFKDKAKLT AVTSATTAYMELSSL TNEDSAVYFCTREDS RSLYYNGWDYFDYWG QGTTLTVSS | 183 | CTGGCCAGGCCCGGCGCCAGCGTGA AGATGAGCTGCAAGACCAGCGGCTA CACCTTCACCAACTACTGGATGCAC TGGGTGAGGCAGAGGCCCGGCCAGG GCCTGGAGTGGATCGGCACCATCTA CCCCGGCAACAGCGACACCAACTAC AACCAGAAGTTCAAGGACAAGGCCA AGCTGACCGCCGTGACCAGCGCCAC CACCGCCTACATGGAGCTGAGCAGC CTGACCAACGAGGACAGCGCCGTGT ACTTCTGCACCAGGGAGGACAGCAG GAGCCTGTACTACAACGGCTGGGAC TACTTCGACTACTGGGGCCAGGGCA CCACCCTGACCGTGAGCAGC |
| Anti-TGFb clone 3 VL | 170 | LTQSPASLAVSLGQRA TISCRASESVDNYGI SFLNWFQQKPGQPPK LLIYAASNQGSGVPA RFSGSGSGTDFSLNI HPMEEDDTGMYFCQQ SKEVPRTFGGGTKLE II | 184 | CTGACCCAGAGCCCCGCCAGCCTGG CCGTGAGCCTGGGCCAGAGGGCCAC CATCAGCTGCAGGGCCAGCGAGAGC GTGGACAACTACGGCATCAGCTTCC TGAACTGGTTCCAGCAGAAGCCCGG CCAGCCCCCCAAGCTGCTGATCTAC GCCGCCAGCAACCAGGGCAGCGGCG TGCCCGCCAGGTTCAGCGGCAGCGG CAGCGGCACCGACTTCAGCCTGAAC ATCCACCCCATGGAGGAGGACGACA CCGGCATGTACTTCTGCCAGCAGAG CAAGGAGGTGCCCAGGACCTTCGGC GGCGGCACCAAGCTGGAGATCATC |
| Anti-TGFb clone 4 VH | 171 | QVQLVQSGAEVKKPGS SVKVSCKASGGTFSS YAISWVRQAPGQGLE WMGGIIPIFGTANYA STAYMELSSLRSEDT AVYYCARGLWEVRAL QKFQGRVTITADEST PSVYWGQGTLVTVSS | 185 | CAGGTGCAGCTGGTGCAGAGCGGCG CCGAGGTGAAGAAGCCCGGCAGCAG CGTGAAGGTGAGCTGCAAGGCCAGC GGCGGCACCTTCAGCAGCTACGCCA TCAGCTGGGTGAGGCAGGCCCCCGG CCAGGGCCTGGAGTGGATGGGCGGC ATCATCCCCATCTTCGGCACCGCCA ACTACGCCCAGAAGTTCCAGGGCAG GGTGACCATCACCGCCGACGAGAGC ACCAGCACCGCCTACATGGAGCTGA GCAGCCTGAGGAGCGAGGACACCGC CGTGTACTACTGCGCCAGGGGCCTG TGGGAGGTGAGGGCCCTGCCCAGCG TGTACTGGGGCCAGGGCACCCTGGT GACCGTGAGCAGC |
| Anti-TGFb clone 4 VL | 172 | SYELTQPPSVSVAPGQ TARITCGANDIGSKS VHWYQQKAGQAPVLV VSEDIIRPSGIPERI SGSNSGNTATLTISR VEAGDEADYYCQVWD RDSDQYVFGTGTKVT VLG | 186 | AGCTACGAGCTGACCCAGCCCCCCA GCGTGAGCGTGGCCCCCGGCCAGAC CGCCAGGATCACCTGCGGCGCCAAC GACATCGGCAGCAAGAGCGTGCACT GGTACCAGCAGAAGGCCGGCCAGGC CCCCGTGCTGGTGGTGAGCGAGGAC ATCATCAGGCCCAGCGGCATCCCCG AGAGGATCAGCGGCAGCAACAGCGG CAACACCGCCACCCTGACCATCAGC AGGGTGGAGGCCGGCGACGAGGCCG ACTACTACTGCCAGGTGTGGGACAG GGACAGCGACCAGTACGTGTTCGGC ACCGGCACCAAGGTGACCGTGCTGG GC |
| Anti-TGFb clone 5 VH | 173 | QVQLVQSGAEVKKPGS SVKVSCKASGYTFSS NVISWVRQAPGQGLE WMGGVIPIVDIANYA QRFKGRVTITADEST | 187 | CAGGTGCAGCTGGTGCAGAGCGGCG CCGAGGTGAAGAAGCCCGGCAGCAG CGTGAAGGTGAGCTGCAAGGCCAGC GGCTACACCTTCAGCAGCAACGTGA TCAGCTGGGTGAGGCAGGCCCCCGG |

TABLE 14-continued

Exemplary anti-TGFβ VH and VL sequences

| Name | SEQ ID NO | Amino Acid Sequence | SEQ ID NO | Nucleotide Sequence |
|---|---|---|---|---|
| | | STTYMELSSLRSEDT AVYYCASTLGLVLDA MDYWGQGTLVTVSS | | CCAGGGCCTGGAGTGGATGGGCGGC GTGATCCCCATCGTGGACATCGCCA ACTACGCCCAGAGGTTCAAGGGCAG GGTGACCATCACCGCCGACGAGAGC ACCAGCACCACCTACATGGAGCTGA GCAGCCTGAGGAGCGAGGACACCGC CGTGTACTACTGCGCCAGCACCCTG GGCCTGGTGCTGGACGCCATGGACT ACTGGGGCCAGGGCACCCTGGTGAC CGTGAGCAGC |
| Anti-TGFb clone 5 VL | 174 | ETVLTQSPGTLSLPG ERATLSCRASQSLGS SYLAWYQQKPGQAPR LLIYGASSRAPGIPD RFSGSGSGTDFTLTI SRLEPEDFAVYYCQQ YADSPITFGQGTRLE IK | 188 | GAGACCGTGCTGACCCAGAGCCCCG GCACCCTGAGCCTGAGCCCCGGCGA GAGGGCCACCCTGAGCTGCAGGGCC AGCCAGAGCCTGGGCAGCAGCTACC TGGCCTGGTACCAGCAGAAGCCCGG CCAGGCCCCCAGGCTGCTGATCTAC GGCGCCAGCAGCAGGGCCCCCGGCA TCCCCGACAGGTTCAGCGGCAGCGG CAGCGGCACCGACTTCACCCTGACC ATCAGCAGGCTGGAGCCCGAGGACT TCGCCGTGTACTACTGCCAGCAGTA CGCCGACAGCCCCATCACCTTCGGC CAGGGCACCAGGCTGGAGATCAAG |
| Anti-TGFb clone 6 VH | 175 | QVQLVQSGAEVKKPGS SVKVSCKASGYTFSS NVISWVRQAPGQGLE WMGGVIPIVDIANYA QRFKGRVTITADEST STTYMELSSLRSEDT AVYYCALPRAFVLDA MDYWGQGTLVTVSS | 189 | CAGGTGCAGCTGGTGCAGAGCGGCG CCGAGGTGAAGAAGCCCGGCAGCAG CGTGAAGGTGAGCTGCAAGGCCAGC GGCTACACCTTCAGCAGCAACGTGA TCAGCTGGGTGAGGCAGGCCCCCGG CCAGGGCCTGGAGTGGATGGGCGGC GTGATCCCCATCGTGGACATCGCCA ACTACGCCCAGAGGTTCAAGGGCAG GGTGACCATCACCGCCGACGAGAGC ACCAGCACCACCTACATGGAGCTGA GCAGCCTGAGGAGCGAGGACACCGC CGTGTACTACTGCGCCCTGCCCAGG GCCTTCGTGCTGGACGCCATGGACT ACTGGGGCCAGGGCACCCTGGTGAC CGTGAGCAGC |
| Anti-TGFb clone 6 VL | 176 | ETVLTQSPGTLSLPG ERATLSCRASQSLGS SYLAWYQQKPGQAPR LLIYGASSRAPGIPD RFSGSGSGTDFTLTI SRLEPEDFAVYYCQQ YADSPITFGQGTRLE IK | 190 | GAGACCGTGCTGACCCAGAGCCCCG GCACCCTGAGCCTGAGCCCCGGCGA GAGGGCCACCCTGAGCTGCAGGGCC AGCCAGAGCCTGGGCAGCAGCTACC TGGCCTGGTACCAGCAGAAGCCCGG CCAGGCCCCCAGGCTGCTGATCTAC GGCGCCAGCAGCAGGGCCCCCGGCA TCCCCGACAGGTTCAGCGGCAGCGG CAGCGGCACCGACTTCACCCTGACC ATCAGCAGGCTGGAGCCCGAGGACT TCGCCGTGTACTACTGCCAGCAGTA CGCCGACAGCCCCATCACCTTCGGC CAGGGCACCAGGCTGGAGATCAAG |
| Anti-TGFb clone 7 VH | 177 | QVQLVQSGAEVKKPGS SVKVSCKASGGTFST SFINWVRQAPGQGLE WMGGIIPIFDITNYA QKFQSRVTITADKST STAYMELSSLRSEDT AVYYCARGNGNYALD AMDYWGQGTLVTVSS | 191 | CAGGTGCAGCTGGTGCAGAGCGGCG CCGAGGTGAAGAAGCCCGGCAGCAG CGTGAAGGTGAGCTGCAAGGCCAGC GGCGGCACCTTCAGCACCAGCTTCA TCAACTGGGTGAGGCAGGCCCCCGG CCAGGGCCTGGAGTGGATGGGCGGC ATCATCCCCATCTTCGACATCACCA ACTACGCCCAGAAGTTCCAGAGCAG GGTGACCATCACCGCCGACAAGAGC ACCAGCACCGCCTACATGGAGCTGA GCAGCCTGAGGAGCGAGGACACCGC CGTGTACTACTGCGCCAGGGGCAAC GGCAACTACGCCCTGGACGCCATGG ACTACTGGGGCCAGGGCACCCTGGT GACCGTGAGCAGC |

TABLE 14-continued

Exemplary anti-TGFβ VH and VL sequences

| Name | SEQ ID NO | Amino Acid Sequence | SEQ ID NO | Nucleotide Sequence |
|---|---|---|---|---|
| Anti-TGFb clone 7 VL | 178 | EIVLTQSPGTLSLSPG ERATLSCRASQSVSS SYFAWYQQKPGQAPR LLIYGASSRATGIPD RFSGSGSGTDFTLTI SRLEPEDFAVYYCQQ YYDSPITFGQGTRLE IK | 192 | GAGATCGTGCTGACCCAGAGCCCCG GCACCCTGAGCCTGAGCCCCGGCGA GAGGGCCACCCTGAGCTGCAGGGCC AGCCAGAGCGTGAGCAGCAGCTACT TCGCCTGGTACCAGCAGAAGCCCGG CCAGGCCCCCAGGCTGCTGATCTAC GGCGCCAGCAGCAGGGCCACCGGCA TCCCCGACAGGTTCAGCGGCAGCGG CAGCGGCACCGACTTCACCCTGACC ATCAGCAGGCTGGAGCCCGAGGACT TCGCCGTGTACTACTGCCAGCAGTA CTACGACAGCCCCATCACCTTCGGC CAGGGCACCAGGCTGGAGATCAAG |

Table 14 provides exemplary TGFβ receptor sequences for use in anti-PD-1 fusion proteins described herein. In any embodiments exemplifying a fusion protein with, e.g., a TGFβRII ECD, an anti-TGFβ antibody (e.g., scFv, Fab) may be employed instead.

TABLE 15

Exemplary TGFβ1 inhibitory peptide and nucleotide sequences

| Name | SEQ ID NO | Amino acid sequence | SEQ ID NO | Nucleotide sequence |
|---|---|---|---|---|
| TGFb1-I36 | 263 | HANFCLGPCPYIWSLA | 268 | CACGCCAACTTCTGCCTGGGCCCCTGCC CCTACATCTGGAGCCTGGCC |
| TGFb1-I37 | 264 | FCLGPCPYIWSLDTA | 269 | TTCTGCCTGGGCCCCTGCCCCTACATCT GGAGCCTGGACACCGCC |
| TGFb1-I38 | 265 | SNPYSAFQVDIIVDIA | 270 | AGCAACCCCTACAGCGCCTTCCAGGTGG ACATCATCGTGGACATCGCC |
| TGFb1-I39 | 266 | TSLDATMIWTMMA | 271 | ACCAGCCTGGACGCCACCATGATCTGGA CCATGATGGCC |
| TGFb1-I40 | 267 | TSLDASIWAMMQNA | 272 | ACCAGCCTGGACGCCAGCATCTGGGCCA TGATGCAGAACGCC |

Table 15 provides exemplary TGFβ1 inhibitory peptides for use in anti-PD-1 fusion proteins described herein. In any embodiments exemplifying a fusion protein with, e.g., a TGFβRII ECD, TGFβ1 inhibitory peptides may be employed instead.

TABLE 16

Exemplary fhuman ADA2 sequences

| Name | SEQ ID NO | Amino Acid Sequence | SEQ ID NO | NUCLEOTIDE SEQUENCE |
|---|---|---|---|---|
| ADA2 mutant 1 | 273 | IDETRAHLLLKEKMM RLGGRLVLNTKEELA NERLMTLKIAEMKEA MRTLIFPPSMHFFQA KHLIERSQVFNILRM MPKGAALHLHDIGIV TMDWLVRNVTYRPHG IALPGDSLLRNFTLV TQHPEVIYTNQNVVL SKFETIFFTISGLIH YAPVFRDYVFRSMQE FYEDNVLYMEIRASL | | |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | LPVYELSGEHHDEEW SVKTYQEVAQDFVET HPEFIGIKIIYSDHR SKDVAVIAESIRMAM GLRIKFPTVVAGFDL VGHEDTGHSLHDYKE ALMIPAKDGVKLPYF FHAGETDWQGTSIDR NILDALMLNTTRIGH GFALSKHPAVRTYSW KKDIPIEVCPISNQV LKLVSDLRNHPVATL MATGHPMVISSDDPA MFGAKGLSYDFYEVF MGIGGMKADLRTLKQ LAMNSIKYSTLLESE KNTFMEIWKKRWDKF IADVATK | | |
| ADA2 mutant 2 | 274 | IDETRAHLLLKEKMM RLGGRLVLNTKEELA NERLMTLKIAEMKEA MRTLIFPPSMHFFQA KHLIERSQVFNILRM MPKGAALHLHDIGIV TMDWLVRNVTYRPHG IALPGDSLLRNFTLV TQHPEVIYTNQNVVW SKFETIVFTISGLIH YAPVFRDYVFRSMQE FYEDNVLYMEIRARL LPVYELSGEHHDEEW SVKTYQEVAQDFVET HPEFIGIKIIYSDHR SKDVAVIAESIRMAM GLRIKFPTVVAGFDL AGHEDTGHSLHDYKE ALMIPAKDGVKLPYF FHAGETDWQGTSIDR NILDALMLNTTRIGH GFALSKHPAVRTYSW KKDIPIEVCPISNQV LKLVSDLRNHPVATL MATGHPMVISSDDPA MFGAKGLSYDFYEVF MGIGGMKADLRTLKQ LAMNSIKYSTLLESE KNTFMEIWKKRWDKF IADVATK | | |
| ADA2 mutant 3 | 275 | EMKEAMRTLIFPPSM HFFQAKHLIERSQVF NILRMMPKGAALHLH DIGIVTMDWLVRNVT YRPHGIALPGDSLLR NFTLVTQHPEVIYTN QNVVLSKFETIVFTI SGLIHYAPVFRDYVF RSMQEFYEDNVLYME IRARLLPVYELSGEH HDEEWSVKTYQEVAQ DFVETHPEFIGIKII YSDHRSKDVAVIAES IRMAMGLRIKFPTVV AGFDLVGHEDTGHSL HDYKEALMIPAKDGV KLPYFFHAGETDWQG TSIDRNILDALMLNT TRIGHGFALSKHPAV RTYSWKKDIPIEVCP ISNQVLKLVSDLRNH PVATLMATGHPMVIS SDDPAMFGAKGLSYD FYEVFMGIGGMKADL RTLKQLAMNSIKYST | | |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | LLESEKNTFMEIWKK RWDKFIADVATK | | |
| ADA2 mutant 4 | 276 | IDETRAHLLLKEKMM RLGGRLVLNTKEELA NERLMTLKIAEMKEA MRTLIFPPSMHFFQA KHLIERSQVFNILRM MPKGAALHLHDIGIV TMDWLGGGGSGGGGS VTEFDDSLLRNFTLV TQHPEVIYTNQNVVW SKFETIFFTISGLIH YAPVFRDYVFRSMQE FYEDNVLYMEIRARL LPVYELSGEHHDEEW SVKTYQEVAQEFVET HPEFIGIKIIYSDHR SRDVAVIAESIRMAM GLRIKFPTVVAGFDL SGHEDTGHSLHDYKE ALMIPAKDGVKLPYF FHAGETDWQGTSIDR NILDALMLNTTRIGH GFALSKHPAVRTYSW KKDIPIEVCPISNQV LKLVSDLRNHPVATL MATGHPMVISSDDPA MFGAKGLSYDFYEVF MGIGGMKADLRTLKQ LAMNSIKYSTLLESE KNTFMEIWKKRWDKF IADVATK | | |
| ADA2 mutant 5 | 277 | IDETRAHLLLKEKMM RLGGRLVLNTKEELA NERLMTLKIAEMKEA MRTLIFPPSMHFFQA KHLIERSQVFNILRM MPKGAALHLHNIGIV TMDWLGGGGSGGGGS VTEFDDSLLRNFTLV TQHPEVIYTNQNVVW SKFETIFFTISGLIH YAPVFRDYVFRSMQE FYEDNVLYMEIRARL LPVYELSGEHHDEEW SVKTYQEVAQDFVET HPEFIGIKIIYSDHR SYDVAVIAESIRMAM GLRIKFPTVVAGFDL VGHEDTGHSLHDYKE ALMIPAKDGVKLPYF FHAGETDWQGTSIDR NILDALMLNTTRIGH GFALSKHPAVRTYSW KKDIPIEVCPISNQV LKLVSDLRNHPVATL MATGHPMVISSDDPA MFGAKGLSYDFYEVF MGIGGMKADLRTLKQ LAMNSIKYSTLLESE KNTFMEIWKKRWDKF IADVATK | | |
| ADA2 mutant 6 | 278 | IDETRAHLLLKEKMM RLGGRLVLNTKEELA NERLMTLKIAEMKEA MRTLIFPPSMHFFQA KHLIERSQVFNILRM MPKGAALHLHDIGIV TMDWLVRNVTYRPHC HICFTPRGIMQFRFA HPTPRPSEKCSKWIL LEDYRKRVQNVTEFD | | |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | DSLLRNFTLVTQHPE VIYTNQNVVWSKFET IFFTISGLIHYAPVF RDYVFRSMQEFYEDN VLYMEIRARLLPVYE LSGEHHDEEWSVKTY QEVAQKFVETHPEFI GIKIIYSDHRSKDVA VIAESIRMAMGLRIK FPTVVAGFDLVGHED TGHSLHDYKEALMIP AKDGVKLPYFFHAGE TDWQGTSIDRNILDA LMLNTTRIGHGFALS KHPAVRTYSWKKDIP IEVCPISNQVLKLVS DLRNHPVATLMATGH PMVISSDDPAMFGAK GLSYDFYEVFMGIGG MKADLRTLKQLAMNS IKYSTLLESEKNTFM EIWKKRWDKFIADVA TK | | |
| ADA2 mutant 7 | 279 | IDETRAHLLLKEKMM RLGGRLVLNTKEELA NERLMTLKIAEMKEA MRTLIFPPSMHFFQA KHLIERSQVFNILRM MPKGAALHLHDIGIV TMDWLVRNVTYRPHC HICFTPRGIMQFRFA HPTPRPSEKCSKWIL LEDYRKRVQNVTEFD DSLLRNFTLVTQHPE VIYTNQNVVWSKFET IFFTISGLIHYAPVF RDYVFRSMQEFYEDN VLYMEIRAQLLPVYE LSGEHHDEEWSVKTY QEVAQKFVETHPEFI GIKIIYNDHRSKDVA VIAESIRMAMGLRIK FPTVVAGFDLVGHED TGHSLHDYKEALMIP AKDGVKLPYFFHAGE TDWQGTSIDRNILDA LMLNTTRIGHGFALS KHPAVRTYSWDKDIP IEVCPISNQVLKLVS DLRNHPVATLMATGH PMVISSDDPAMFGAK GLSYDFYEVFMGIGG MKADLRTLKQLAMNS IKYSTLLESEKNTFM EIWKKRWDKFIADVA TK | | |
| VH6 ADA2 | 280 | QVQLVESGGGVVQPG RSLRLDCKASGITFS NSGMHWVRQAPGKGL EWVAVIWYDGSKRYY ADSVKGRFTISRDNS KNTLFLQMNSLRAED TAVYYCATNDDYWGQ GTLVTVSSASTKGPS VFPLAPCSRSTSEST AALGCLVKDYFPEPV TVSWNSGALTSGVHT FPAVLQSSGLYSLSS VVTVPSSSLGTKTYT CNVDHKPSNTKVDKR VESKYGPPCPPCPAP EFLGGPSVFLFPPKP KDTLMISRTPEVTCV | 285 | CAGGTGCAGCTGGTCGAAAGCGGAGGAGGA GTGGTCCAGCCAGGACGATCCCTGAGACTG GATTGTAAGGCCTCTGGAATCACATTCTCT AACAGTGGAATGCACTGGGTGCGCCAGGCA CCAGGAAAAGGACTGGAGTGGGTGGCCGTC ATCTGGTACGACGGGTCAAAGCGATACTAT GCAGATAGCGTGAAAGGAAGGTTCACAATT TCACGCGACAACAGCAAGAATACTCTGTTT CTGCAGATGAACTCTCTGAGAGCAGAGGAT ACTGCCGTGTACTATTGTGCTACCAATGAC GATTATTGGGGCAGGGAACTCTGGTGACC GTCAGTTCAGCTAGCACCAAGGGCCCATCG GTCTTCCCCCTGGCGCCCTGCTCCAGGAGC ACCTCCGAGAGCACAGCCGCCCTGGGCTGC CTGGTCAAGGACTACTTCCCCGAACCGGTG ACGGTGTCGTGGAACTCAGGCGCCCTGACC AGCGGCGTGCACACCTTCCCGGCTGTCCTA |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | VVDVSQEDPEVQFNW | | CAGTCCTCAGGACTCTACTCCCTCAGCAGC |
| | | YVDGVEVHNAKTKPR | | GTGGTGACCGTGCCCTCCAGCAGCTTGGGC |
| | | EEQFNSTYRVVSVLT | | ACGAAGACCTACACCTGCAACGTAGATCAC |
| | | VLHQDWLNGKEYKCK | | AAGCCCAGCAACACCAAGGTGGACAAGAGA |
| | | VSNKGLPSSIEKTIS | | GTTGAGTCCAAATATGGTCCCCCATGCCCA |
| | | KAKGQPREPQVYTLP | | CCATGCCCAGCACCTGAGTTCCTGGGGGGA |
| | | PSQEEMTKNQVSLTC | | CCATCAGTCTTCCTGTTCCCCCCAAAACCC |
| | | LVKGFYPSDIAVEWE | | AAGGACACTCTCATGATCTCCCGGACCCCT |
| | | SNGQPENNYKTTPPV | | GAGGTCACGTGCGTGGTGGTGGACGTGAGC |
| | | LDSDGSFFLYSRLTV | | CAGGAAGACCCCGAGGTCCAGTTCAACTGG |
| | | DKSRWQEGNVFSCSV | | TACGTGGATGGCGTGGAGGTGCATAATGCC |
| | | MHEALHNHYTQKSLS | | AAGACAAAGCCGCGGGAGGAGCAGTTCAAC |
| | | LSPGKGGGGSGGGGS | | AGCACGTACCGTGTGGTCAGCGTCCTCACC |
| | | IDETRAHLLLKEKMM | | GTCCTGCACCAGGACTGGCTGAACGGCAAG |
| | | RLGGRLVLNTKEELA | | GAGTACAAGTGCAAGGTCTCCAACAAAGGC |
| | | NERLMTLKIAEMKEA | | CTCCCGTCCTCCATCGAGAAAACCATCTCC |
| | | MRTLIFPPSMHFFQA | | AAAGCCAAAGGGCAGCCCCGAGAGCCACAG |
| | | KHLIERSQVFNILRM | | GTGTACACCCTGCCCCCATCCCAGGAGGAG |
| | | MPKGAALHLHDIGIV | | ATGACCAAGAACCAGGTCAGCCTGACCTGC |
| | | TMDWLVRNVTYRPHC | | CTGGTCAAAGGCTTCTACCCCAGCGACATC |
| | | HICFTPRGIMQFRFA | | GCCGTGGAGTGGGAGAGCAATGGGCAGCCG |
| | | HPTPRPSEKCSKWIL | | GAGAACAACTACAAGACCACGCCTCCCGTG |
| | | LEDYRKRVQNVTEFD | | CTGGACTCCGACGGCTCCTTCTTCCTCTAC |
| | | DSLLRNFTLVTQHPE | | AGCAGGCTCACCGTGGACAAGAGCAGGTGG |
| | | VIYTNQNVVWSKFET | | CAGGAGGGGAATGTCTTCTCATGCTCCGTG |
| | | IFFTISGLIHYAPVF | | ATGCATGAGGCTCTGCACAACCACTACACA |
| | | RDYVFRSMQEFYEDN | | CAGAAGAGCCTCTCCCTGTCTCCGGGTAAA |
| | | VLYMEIRARLLPVYE | | GGTGGAGGTGGTTCTGGAGGTGGAGGTAGT |
| | | LSGEHHDEEWSVKTY | | ATCGACGAAACCAGAGCACACTTACTGCTG |
| | | QEVAQKFVETHPEFI | | AAAGAGAAAATGATGCGCCTGGGCGGGAGA |
| | | GIKIIYSDHRSKDVA | | TTGGTGTTAAATACTAAGGAAGAGCTGGCA |
| | | VIAESIRMAMGLRIK | | AATGAAAGACTCATGACACTGAAGATTGCT |
| | | FPTVVAGFDLVGHED | | GAAATGAAGGAGGCGATGAGGAGCGCTGATC |
| | | TGHSLHDYKEALMIP | | TTTCCGCCTTCCATGCACTTCTTCCAAGCT |
| | | AKDGVKLPYFFHAGE | | AAACACCTGATCGAAAGATCCCAAGTGTTT |
| | | TDWQGTSIDRNILDA | | AACATCCTGAGGATGATGCCTAAGGGGGCC |
| | | LMLNTTRIGHGFALS | | GCTCTGCACCTTCACGATATTGGGATTGTA |
| | | KHPAVRTYSWKKDIP | | ACAATGGACTGGCTGGTAAGGAACGTGACA |
| | | IEVCPISNQVLKLVS | | TACAGACCTCATTGCCATATTTGTTTACT |
| | | DLRNHPVATLMATGH | | CCCCGAGGAATCATGCAATTCAGGTTTGCC |
| | | PMVISSDDPAMFGAK | | CACCCAACTCCTCGGCCAAGCGAGAAGTGT |
| | | GLSYDFYEVFMGIGG | | AGTAAGTGGATTTTGCTGGAAGATTACCGT |
| | | MKADLRTLKQLAMNS | | AAGCGCGTGCAGAATGTGACAGAGTTTGAT |
| | | IKYSTLLESEKNTFM | | GACTCCCTGCTCCGCAATTTTACCCTGGTG |
| | | EIWKKRWDKFIADVA | | ACCCAGCACCCCGAAGTTATATACACTAAC |
| | | TK | | CAAAATGTCGTGTGGTCCAAGTTTGAGACG |
| | | | | ATCTTCTTCACGATTTCAGGCTTGATCCAC |
| | | | | TACGCCCCGGTCTTTCGGGATTATGTGTTT |
| | | | | AGGAGTATGCAGGAGTTTTATGAGGATAAT |
| | | | | GTTCTGTACATGGAGATCCGAGCCCGGCTG |
| | | | | CTTCCAGTCTACGAACTATCCGGCGAACAC |
| | | | | CATGACGAGGAATGGAGCGTCAAGACCTAT |
| | | | | CAAGAGGTGGCCCAGAAGTTCGTAGAAACG |
| | | | | CATCCAGAGTTCATCGGTATTAAGATTATC |
| | | | | TACTCTGATCACCGCTCAAAGGATGTGGCT |
| | | | | GTCATCGCCGAGTCTATACGGATGGCCATG |
| | | | | GGCCTGCGGATTAAGTTCCCTACCGTCGTC |
| | | | | GCCGGATTCGACCTCGTTGGGCATGAGGAT |
| | | | | ACTGGCCATAGTCTCCATGACTATAAAGAA |
| | | | | GCCCTTATGATCCCAGCAAAGGACGGAGTG |
| | | | | AAGCTGCCCTACTTCTTCCACGCAGGGGAG |
| | | | | ACCGACTGGCAGGGAACGAGCATCGACCGG |
| | | | | AACATACTTGATGCACTCATGCTTAATACC |
| | | | | ACACGAATCGGCCACGGCTTCGCTCTCTCC |
| | | | | AAGCACCCAGCCGTGAGAACCTACAGCTGG |
| | | | | AAGAAGGATATCCCCATCGAGGTTTGTCCC |
| | | | | ATCAGCAATCAGGTGCTGAAATTGGTGAGT |
| | | | | GACCTGAGAAACCACCCAGTCGCAACATTA |
| | | | | ATGGCCACTGGCCACCCTATGGTGATTTCA |
| | | | | AGCGATGATCCAGCCATGTTCGGAGCAAAA |
| | | | | GGACTCAGTTACGACTTCTATGAGGTATTC |
| | | | | ATGGGTATTGGTGGTATGAAGGCAGACCTG |
| | | | | CGGACTCTTAAGCAGTTGGCAATGAACTCA |
| | | | | ATTAAGTACTCTACCTTATTGGAGTCTGAA |
| | | | | AAGAACACATTTATGGAGATCTGGAAAAAG |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | | | CGCTGGGACAAATTCATCGCAGATGTTGCC<br>ACAAAA |
| VH6<br>ADA2<br>mut 7 | 281 | QVQLVESGGGVVQPG<br>RSLRLDCKASGITFS<br>NSGMHWVRQAPGKGL<br>EWVAVIWYDGSKRYY<br>ADSVKGRFTISRDNS<br>KNTLFLQMNSLRAED<br>TAVYYCATNDDYWGQ<br>GTLVTVSSASTKGPS<br>VFPLAPCSRSTSEST<br>AALGCLVKDYFPEPV<br>TVSWNSGALTSGVHT<br>FPAVLQSSGLYSLSS<br>VVTVPSSSLGTKTYT<br>CNVDHKPSNTKVDKR<br>VESKYGPPCPPCPAP<br>EFLGGPSVFLFPPKP<br>KDTLMISRTPEVTCV<br>VVDVSQEDPEVQFNW<br>YVDGVEVHNAKTKPR<br>EEQFNSTYRVVSVLT<br>VLHQDWLNGKEYKCK<br>VSNKGLPSSIEKTIS<br>KAKGQPREPQVYTLP<br>PSQEEMTKNQVSLTC<br>LVKGFYPSDIAVEWE<br>SNGQPENNYKTTPPV<br>LDSDGSFFLYSRLTV<br>DKSRWQEGNVFSCSV<br>MHEALHNHYTQKSLS<br>LSPGKGGGSGGGGS<br>IDETRAHLLLKEKMM<br>RLGGRLVLNTKEELA<br>NERLMTLKIAEMKEA<br>MRTLIFPPSMHFFQA<br>KHLIERSQVFNILRM<br>MPKGAALHLHDIGIV<br>TMDWLVRNVTYRPHC<br>HICFTPRGIMQFRFA<br>HPTPRPSEKCSKWIL<br>LEDYRKRVQNVTEFD<br>DSLLRNFTLVTQHPE<br>VIYTNQNVVWSKFET<br>IFFTISGLIHYAPVF<br>RDYVFRSMQEFYEDN<br>VLYMEIRAQLLPVYE<br>LSGEHHDEEWSVKTY<br>QEVAQKFVETHPEFI<br>GIKIIYNDHRSKDVA<br>VIAESIRMAMGLRIK<br>FPTVVAGFDLVGHED<br>TGHSLHDYKEALMIP<br>AKDGVKLPYFFHAGE<br>TDWQGTSIDRNILDA<br>LMLNTTRIGHGFALS<br>KHPAVRTYSWDKDIP<br>IEVCPISNQVLKLVS<br>DLRNHPVATLMATGH<br>PMVISSDDPAMFGAK<br>GLSYDFYEVFMGIGG<br>MKADLRTLKQLAMNS<br>IKYSTLLESEKNTFM<br>EIWKKRWDKFIADVA<br>TK | 286 | CAGGTGCAGCTGGTCGAAAGCGGAGGAGGA<br>GTGGTCCAGCCAGGACGATCCCTGAGACTG<br>GATTGTAAGGCCTCTGGAATCACATTCTCT<br>AACAGTGGAATGCACTGGGTGCGCCAGGCA<br>CCAGGAAAAGGACTGGAGTGGGTGGCCGTC<br>ATCTGGTACGACGGGTCAAAGCGATACTAT<br>GCAGATAGCGTGAAAGGAAGGTTCACAATT<br>TCACGCGACAACAGCAAGAATACTCTGTTT<br>CTGCAGATGAACTCTCTGAGAGCAGAGGAT<br>ACTGCCGTGTACTATTGTGCTACCAATGAC<br>GATTATTGGGGCAGGGAACTCTGGTGACC<br>GTCAGTTCAGCTAGCACCAAGGGCCCATCG<br>GTCTTCCCCCTGGCGCCCTGCTCCAGGAGC<br>ACCTCCGAGAGCACAGCCGCCCTGGGCTGC<br>CTGGTCAAGGACTACTTCCCCGAACCGGTG<br>ACGGTGTCGTGGAACTCAGGCGCCCTGACC<br>AGCGGCGTGCACACCTTCCCGGCTGTCCTA<br>CAGTCCTCAGGACTCTACTCCCTCAGCAGC<br>GTGGTGACCGTGCCCTCCAGCAGCTTGGGC<br>ACGAAGACCTACACCTGCAACGTAGATCAC<br>AAGCCCAGCAACACCAAGGTGGACAAGAGA<br>GTTGAGTCCAAATATGGTCCCCCATGCCCA<br>CCATGCCCAGCACCTGAGTTCCTGGGGGGA<br>CCATCAGTCTTCCTGTTCCCCCCAAAACCC<br>AAGGACACTCTCATGATCTCCCGGACCCCT<br>GAGGTCACGTGCGTGGTGGTGGACGTGAGC<br>CAGGAAGACCCCGAGGTCCAGTTCAACTGG<br>TACGTGGATGGCGTGGAGGTGCATAATGCC<br>AAGACAAAGCCGCGGGAGGAGCAGTTCAAC<br>AGCACGTACCGTGTGGTCAGCGTCCTCACC<br>GTCCTGCACCAGGACTGGCTGAACGGCAAG<br>GAGTACAAGTGCAAGGTCTCCAACAAAGGC<br>CTCCCGTCCTCCATCGAGAAAACCATCTCC<br>AAAGCCAAAGGGCAGCCCCGAGAGCCACAG<br>GTGTACACCCTGCCCCCATCCCAGGAGGAG<br>ATGACCAAGAACCAGGTCAGCCTGACCTGC<br>CTGGTCAAAGGCTTCTACCCCAGCGACATC<br>GCCGTGGAGTGGGAGAGCAATGGGCAGCCG<br>GAGAACAACTACAAGACCACGCCTCCCGTG<br>CTGGACTCCGACGGCTCCTTCTTCCTCTAC<br>AGCAGGCTCACCGTGGACAAGAGCAGGTGG<br>CAGGAGGGGAATGTCTTCTCATGCTCCGTG<br>ATGCATGAGGCTCTGCACAACCACTACACA<br>CAGAAGAGCCTCTCCCTGTCTCGGGTAAA<br>GGTGGAGGTGGTTCTGGAGGTGGAGGTAGT<br>ATCGACGAAACCAGAGCACACTTACTGCTG<br>AAAGAGAAAATGATGCGCCTGGGCGGGAGA<br>TTGGTGTTAAATACTAAGGAAGAGCTGGCA<br>AATGAAAGACTCATGACACTGAAGATTGCT<br>GAAATGAAGGAGGCGATGAGGACGCTGATC<br>TTTCCGCCTTCCATGCACTTCTTCCAAGCT<br>AAACACCTGATCGAAAGATCCCAAGTGTTT<br>AACATCCTGAGGATGATGCCTAAGGGGGCC<br>GCTCTGCACCTTCACGATATTGGGATTGTA<br>ACAATGGACTGGCTGGTAAGGAACGTGACA<br>TACAGACCTCATTGCCATATTTGTTTTACT<br>CCCCGAGGAATCATGCAATTCAGGTTTGCC<br>CACCCAACTCCTCGGCCAAGCGAGAAGTGT<br>AGTAAGTGGATTTTGCTGGAAGATTACCGT<br>AAGCGCGTGCAGAATGTGACAGAGTTTGAT<br>GACTCCCTGCTCCGCAATTTTACCCTGGTG<br>ACCCAGCACCCCGAAGTTATATACACTAAC<br>CAAAATGTCGTGTGGTCCAAGTTTGAGACG<br>ATCTTCTTCACGATTTCAGGCTTGATCCAC<br>TACGCCCCGGTCTTTCGGGATTATGTGTTT<br>AGGAGTATGCAGGAGTTTATGAGGATAAT<br>GTTCTGTACATGGAGATCCGAGCCCAGCTG<br>CTTCCAGTCTACGAACTATCCGGCGAACAC<br>CATGACGAGGAATGGAGCGTCAAGACCTAT<br>CAAGAGGTGGCCCAGAAGTTCGTAGAAACG<br>CATCCAGAGTTCATCGGTATTAAGATTATC<br>TACAATGATCACCGCTCAAAGGATGTGGCT |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | | | GTCATCGCCGAGTCTATACGGATGGCCATG |
| | | | | GGCCTGCGGATTAAGTTCCCTACCGTCGTC |
| | | | | GCCGGATTCGACCTCGTTGGGCATGAGGAT |
| | | | | ACTGGCCATAGTCTCCATGACTATAAAGAA |
| | | | | GCCCTTATGATCCCAGCAAAGGACGGAGTG |
| | | | | AAGCTGCCCTACTTCTTCCACGCAGGGGAG |
| | | | | ACCGACTGGCAGGGAACGAGCATCGACCGG |
| | | | | AACATACTTGATGCACTCATGCTTAATACC |
| | | | | ACACGAATCGGCCACGGCTTCGCTCTCTCC |
| | | | | AAGCACCCAGCCGTGAGAACCTACAGCTGG |
| | | | | GATAAGGATATCCCCATCGAGGTTTGTCCC |
| | | | | ATCAGCAATCAGGTGCTGAAATTGGTGAGT |
| | | | | GACCTGAGAAACCACCCAGTCGCAACATTA |
| | | | | ATGGCCACTGGCCACCCTATGGTGATTTCA |
| | | | | AGCGATGATCCAGCCATGTTCGGAGCAAAA |
| | | | | GGACTCAGTTACGACTTCTATGAGGTATTC |
| | | | | ATGGGTATTGGTGGTATGAAGGCAGACCTG |
| | | | | CGGACTCTTAAGCAGTTGGCAATGAACTCA |
| | | | | ATTAAGTACTCTACCTTATTGGAGTCTGAA |
| | | | | AAGAACACATTTATGGAGATCTGGAAAAAG |
| | | | | CGCTGGGACAAATTCATCGCAGATGTTGCC |
| | | | | ACAAAA |
| VH7 ADA2 | 282 | QVQLVQSGVEVKKPG ASVKVSCKASGYTFT NYYMYWVRQAPGQGL EWMGGINPSNGGTNF NEKFKNRVTLTTDSS TTTAYMELKSLQFDD TAVYYCARRDYRFDM GFDYWGQGTTVTVSS ASTKGPSVFPLAPCS RSTSESTAALGCLVK DYFPEPVTVSWNSGA LTSGVHTFPAVLQSS GLYSLSSVVTVPSSS LGTKTYTCNVDHKPS NTKVDKRVESKYGPP CPPCPAPEFLGGPSV FLFPPKPKDTLMISR TPEVTCVVVDVSQED PEVQFNWYVDGVEVH NAKTKPREEQFNSTY RVVSVLTVLHQDWLN GKEYKCKVSNKGLPS SIEKTISKAKGQPRE PQVYTLPPSQEEMTK NQVSLTCLVKGFYPS DIAVEWESNGQPENN YKTTPPVLDSDGSFF LYSRLTVDKSRWQEG NVFSCSVMHEALHNH YTQKSLSLSPGKGGG GSGGGGSIDETRAHL LLKEKMMRLGGRLVL NTKEELANERLMTLK IAEMKEAMRTLIFPP SMHFFQAKHLIERSQ VFNILRMMPKGAALH LHDIGIVTMDWLVRN VTYRPHCHICFTPRG IMQFRFAHPTPRPSE KCSKWILLEDYRKRV QNVTEFDDSLLRNFT LVTQHPEVIYTNQNV VWSKFETIFFTISGL IHYAPVERDYVERSM QEFYEDNVLYMEIRA RLLPVYELSGEHHDE EWSVKTYQEVAQKFV ETHPEFIGIKIIYSD HRSKDVAVIAESIRM AMGLRIKFPTVVAGF DLVGHEDTGHSLHDY KEALMIPAKDGVKLP | 287 | CAGGTGCAGCTGGTCCAGAGCGGCGTGGAA GTCAAGAAACCCGGGGCCTCAGTGAAGGTC AGCTGTAAAGCTTCCGGCTACACCTTCACA AACTACTATATGTATTGGGTGAGACAGGCA CCAGGACAGGGACTGGAGTGGATGGGCGGG ATTAACCCTAGTAATGGAGGCACTAACTTC AACGAAAAGTTTAAAAACAGGGTGACCCTG ACCACAGATTCAAGCACTACCACAGCTTAC ATGGAGCTGAAGTCCCTGCAGTTTGACGAT ACAGCCGTGTACTATTGTGCTCGGAGAGAC TACAGGTTCGATATGGGCTTTGACTATTGG GGCCAGGGGACTACCGTGACCGTCTCCTCT GCTAGCACCAAGGGCCCATCGGTCTTCCCC CTGGCGCCCTGCTCCAGGAGCACCTCCGAG AGCACAGCCGCCCTGGGCTGCCTGGTCAAG GACTACTTCCCCGAACCGGTGACGGTGTCG TGGAACTCAGGCGCCCTGACCAGCGGCGTG CACACCTTCCCGGCTGTCCTACAGTCCTCA GGACTCTACTCCCTCAGCAGCGTGGTGACC GTGCCCTCCAGCAGCTTGGGCACGAAGACC TACACCTGCAACGTAGATCACAAGCCCAGC AACACCAAGGTGGACAAGAGAGTTGAGTCC AAATATGGTCCCCCATGCCCACCATGCCCA GCACCTGAGTTCCTGGGGGGACCATCAGTC TTCCTGTTCCCCCCAAAACCCAAGGACACT CTCATGATCTCCCGGACCCCTGAGGTCACG TGCGTGGTGGTGGACGTGAGCCAGGAAGAC CCCGAGGTCCAGTTCAACTGGTACGTGGAT GGCGTGGAGGTGCATAATGCCAAGACAAAG CCGCGGGAGGAGCAGTTCAACAGCACGTAC CGTGTGGTCAGCGTCCTCACCGTCCTGCAC CAGGACTGGCTGAACGGCAAGGAGTACAAG TGCAAGGTCTCCAACAAAGGCCTCCCGTCC TCCATCGAGAAAACCATCTCCAAAGCCAAA GGGCAGCCCCGAGAGCCACAGGTGTACACC CTGCCCCCATCCCAGGAGGAGATGACCAAG AACCAGGTCAGCCTGACCTGCCTGGTCAAA GGCTTCTACCCCAGCGACATCGCCGTGGAG TGGGAGAGCAATGGGCAGCCGGAGAACAAC TACAAGACCACGCCTCCCGTGCTGGACTCC GACGGCTCCTTCTTCCTCTACAGCAGGCTC ACCGTGGACAAGAGCAGGTGGCAGGAGGGG AATGTCTTCTCATGCTCCGTGATGCATGAG GCTCTGCACAACCACTACACACAGAAGAGC CTCTCCCTGTCTCCGGGTAAAGGTGGAGGT GGTTCTGGAGGTGGAGGTAGTATCGACGAA ACCAGAGCACACTTACTGCTGAAAGAGAAA ATGATGCGCCTGGGCGGGAGATTGGTGTTA AATACTAAGGAAGAGCTGGCAAATGAAAGA CTCATGACACTGAAGATTGCTGAAATGAAG GAGGCGATGAGGACGCTGATCTTTCCGCCT TCCATGCACTTCTTCCAAGCTAAACACCTG |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | YFFHAGETDWQGTSI DRNILDALMLNTTRI GHGFALSKHPAVRTY SWKKDIPIEVCPISN QVLKLVSDLRNHPVA TLMATGHPMVISSDD PAMFGAKGLSYDFYE VFMGIGGMKADLRTL KQLAMNSIKYSTLLE SEKNTFMEIWKKRWD KFIADVATK | | ATCGAAAGATCCCAAGTGTTTAACATCCTG AGGATGATGCCTAAGGGGCCGCTCTGCAC CTTCACGATATTGGGATTGTAACAATGGAC TGGCTGGTAAGGAACGTGACATACAGACCT CATTGCCATATTTGTTTTACTCCCCGAGGA ATCATGCAATTCAGGTTTGCCCACCCAACT CCTCGGCCAAGCGAGAAGTGTAGTAAGTGG ATTTTGCTGGAAGATTACCGTAAGCGCGTG CAGAATGTGACAGAGTTTGATGACTCCCTG CTCCGCAATTTTACCCTGGTGACCCAGCAC CCCGAAGTTATATACACTAACCAAAATGTC GTGTGGTCCAAGTTTGAGACGATCTTCTTC ACGATTTCAGGCTTGATCCACTACGCCCCG GTCTTTCGGGATTATGTGTTTAGGAGTATG CAGGAGTTTTATGAGGATAATGTTCTGTAC ATGGAGATCCGAGCCCGGCTGCTTCCAGTC TACGAACTATCCGGCGAACACCATGACGAG GAATGGAGCGTCAAGACCTATCAAGAGGTG GCCCAGAAGTTCGTAGAAACGCATCCAGAG TTCATCGGTATTAAGATTATCTACTCTGAT CACCGCTCAAAGGATGTGGCTGTCATCGCC GAGTCTATACGGATGGCCATGGGCCTGCGG ATTAAGTTCCCTACCGTCGTCGCCGGATTC GACCTCGTTGGGCATGAGGATACTGGCCAT AGTCTCCATGACTATAAAGAAGCCCTTATG ATCCCAGCAAAGGACGGAGTGAAGCTGCCC TACTTCTTCCACGCAGGGGAGACCGACTGG CAGGGAACGAGCATCGACCGGAACATACTT GATGCACTCATGCTTAATACCACACGAATC GGCCACGGCTTCGCTCTCTCCAAGCACCCA GCCGTGAGAACCTACAGCTGGAAGAAGGAT ATCCCCATCGAGGTTTGTCCCATCAGCAAT CAGGTGCTGAAATTGGTGAGTGACCTGAGA AACCACCCAGTCGCAACATTAATGGCCACT GGCCACCCTATGGTGATTTCAAGCGATGAT CCAGCCATGTTCGGAGCAAAAGGACTCAGT TACGACTTCTATGAGGTATTCATGGGTATT GGTGGTATGAAGGCAGACCTGCGGACTCTT AAGCAGTTGGCAATGAACTCAATTAAGTAC TCTACCTTATTGGAGTCTGAAAAGAACACA TTTATGGAGATCTGGAAAAAGCGCTGGGAC AAATTCATCGCAGATGTTGCCACAAAA |
| VH7 ADA2 mut7 | 283 | QVQLVQSGVEVKKPG ASVKVSCKASGYTFT NYYMYWVRQAPGQGL EWMGGINPSNGGTNF NEKFKNRVTLTTDSS TTTAYMELKSLQFDD TAVYYCARRDYRFDM GFDYWGQGTTVTVSS ASTKGPSVFPLAPCS RSTSESTAALGCLVK DYFPEPVTVSWNSGA LTSGVHTFPAVLQSS GLYSLSSVVTVPSSS LGTKTYTCNVDHKPS NTKVDKRVESKYGPP CPPCPAPEFLGGPSV FLFPPKPKDTLMISR TPEVTCVVVDVSQED PEVQFNWYVDGVEVH NAKTKPREEQFNSTY RVVSVLTVLHQDWLN GKEYKCKVSNKGLPS SIEKTISKAKGQPRE PQVYTLPPSQEEMTK NQVSLTCLVKGFYPS DIAVEWESNGQPENN YKTTPPVLDSDGSFF LYSRLTVDKSRWQEG NVFSCSVMHEALHNH YTQKSLSLSPGKGGG GSGGGGSIDETRAHL LLEKMMRLGGRLVL | 288 | CAGGTGCAGCTGGTCCAGAGCGGCGTGGAA GTCAAGAAACCCGGGGCCTCAGTGAAGGTC AGCTGTAAAGCTTCCGGCTACACCTTCACA AACTACTATATGTATTGGGTGAGACAGGCA CCAGGACAGGGACTGGAGTGGATGGGCGGG ATTAACCCTAGTAATGAGGCACTAACTTC AACGAAAAGTTTAAAAACAGGGTGACCCTG ACCACAGATTCAAGCACTACCACAGCTTAC ATGGAGCTGAAGTCCCTGCAGTTTGACGAT ACAGCCGTGTACTATTGTGCTCGGAGAGAC TACAGGTTCGATATGGGCTTTGACTATTGG GGCCAGGGGACTACCGTGACCGTCTCCTCT GCTAGCACCAAGGGCCCATCGGTCTTCCCC CTGGCGCCCTGCTCCAGGAGCACCTCCGAG AGCACAGCCGCCCTGGGCTGCCTGGTCAAG GACTACTTCCCCGAACCGGTGACGGTGTCG TGGAACTCAGGCGCCCTGACCAGCGGCGTG CACACCTTCCCGGCTGTCCTACAGTCCTCA GGACTCTACTCCCTCAGCAGCGTGGTGACC GTGCCCTCCAGCAGCTTGGGCACGAAGACC TACACCTGCAACGTAGATCACAAGCCCAGC AACACCAAGGTGGACAAGAGAGTTGAGTCC AAATATGGTCCCCCATGCCCACCATGCCCA GCACCTGAGTTCCTGGGGGGACCATCAGTC TTCCTGTTCCCCCCAAAACCCAAGGACACT CTCATGATCTCCCGGACCCCTGAGGTCACG TGCGTGGTGGTGGACGTGAGCCAGGAAGAC CCCGAGGTCCAGTTCAACTGGTACGTGGAT GGCGTGGAGGTGCATAATGCCAAGACAAAG CCGCGGGAGGAGCAGTTCAACAGCACGTAC CGTGTGGTCAGCGTCCTCACCGTCCTGCAC CAGGACTGGCTGAACGGCAAGGAGTACAAG |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | NTKEELANERLMTLK<br>IAEMKEAMRTLIFPP<br>SMHFFQAKHLIERSQ<br>VFNILRMMPKGAALH<br>LHDIGIVTMDWLVRN<br>VTYRPHCHICFTPRG<br>IMQFRFAHPTPRPSE<br>KCSKWILLEDYRKRV<br>QNVTEFDDSLLRNFT<br>LVTQHPEVIYTNQNV<br>VWSKFETIFFTISGL<br>IHYAPVERDYVERSM<br>QEFYEDNVLYMEIRA<br>QLLPVYELSGEHHDE<br>EWSVKTYQEVAQKFV<br>ETHPEFIGIKIIYND<br>HRSKDVAVIAESIRM<br>AMGLRIKFPTVVAGF<br>DLVGHEDTGHSLHDY<br>KEALMIPAKDGVKLP<br>YFFHAGETDWQGTSI<br>DRNILDALMLNTTRI<br>GHGFALSKHPAVRTY<br>SWDKDIPIEVCPISN<br>QVLKLVSDLRNHPVA<br>TLMATGHPMVISSDD<br>PAMFGAKGLSYDFYE<br>VFMGIGGMKADLRTL<br>KQLAMNSIKYSTLLE<br>SEKNTFMEIWKKRWD<br>KFIADVATK | | TGCAAGGTCTCCAACAAAGGCCTCCCGTCC<br>TCCATCGAGAAAACCATCTCCAAAGCCAAA<br>GGGCAGCCCCGAGAGCCACAGGTGTACACC<br>CTGCCCCCATCCCAGGAGGAGATGACCAAG<br>AACCAGGTCAGCCTGACCTGCCTGGTCAAA<br>GGCTTCTACCCCAGCGACATCGCCGTGGAG<br>TGGGAGAGCAATGGGCAGCCGGAGAACAAC<br>TACAAGACCACGCCTCCCGTGCTGGACTCC<br>GACGGCTCCTTCTTCCTCTACAGCAGGCTC<br>ACCGTGGACAAGAGCAGGTGGCAGGAGGGG<br>AATGTCTTCTCATGCTCCGTGATGCATGAG<br>GCTCTGCACAACCACTACACACAGAAGAGC<br>CTCTCCCTGTCTCCGGGTAAAGGTGGAGGT<br>GGTTCTGGAGGTGGAGGTAGTATCGACGAA<br>ACCAGAGCACACTTACTGCTGAAAGAGAAA<br>ATGATGCGCCTGGGCGGGAGATTGGTGTTA<br>AATACTAAGGAAGAGCTGGCAAATGAAAGA<br>CTCATGACACTGAAGATTGCTGAAATGAAG<br>GAGGCGATGAGGACGCTGATCTTTCCGCCT<br>TCCATGCACTTCTTCCAAGCTAAACACCTG<br>ATCGAAAGATCCCAAGTGTTTAACATCCTG<br>AGGATGATGCCTAAGGGGGCCGCTCTGCAC<br>CTTCACGATATTGGGATTGTAACAATGGAC<br>TGGCTGGTAAGGAACGTGACATACAGACCT<br>CATTGCCATATTTGTTTTACTCCCCGAGGA<br>ATCATGCAATTCAGGTTTGCCCACCCAACT<br>CCTCGGCCAAGCGAGAAGTGTAGTAAGTGG<br>ATTTTGCTGGAAGATTACCGTAAGCGCGTG<br>CAGAATGTGACAGAGTTTGATGACTCCCTG<br>CTCCGCAATTTTACCCTGGTGACCCAGCAC<br>CCCGAAGTTATATACACTAACCAAAATGTC<br>GTGTGGTCCAAGTTTGAGACGATCTTCTTC<br>ACGATTTCAGGCTTGATCCACTACGCCCCG<br>GTCTTTCGGGATTATGTGTTTAGGAGTATG<br>CAGGAGTTTTATGAGGATAATGTTCTGTAC<br>ATGGAGATCCGAGCCCAGCTGCTTCCAGTC<br>TACGAACTATCCGGCGAACACCATGACGAG<br>GAATGGAGCGTCAAGACCTATCAAGAGGTG<br>GCCCAGAAGTTCGTAGAAACGCATCCAGAG<br>TTCATCGGTATTAAGATTATCTACAATGAT<br>CACCGCTCAAAGGATGTGGCTGTCATCGCC<br>GAGTCTATACGGATGGCCATGGGCCTGCGG<br>ATTAAGTTCCCTACCGTCGTCGCCGGATTC<br>GACCTCGTTGGGCATGAGGATACTGGCCAT<br>AGTCTCCATGACTATAAAGAAGCCCTTATG<br>ATCCCAGCAAAGGACGGAGTGAAGCTGCCC<br>TACTTCTTCCACGCAGGGGAGACCGACTGG<br>CAGGGAACGAGCATCGACCGGAACATACTT<br>GATGCACTCATGCTTAATACCACACGAATC<br>GGCCACGGCTTCGCTCTCTCCAAGCACCCA<br>GCCGTGAGAACCTACAGCTGGGATAAGGAT<br>ATCCCCATCGAGGTTTGTCCCATCAGCAAT<br>CAGGTGCTGAAATTGGTGAGTGACCTGAGA<br>AACCACCCAGTCGCAACATTAATGGCCACT<br>GGCCACCCTATGGTGATTTCAAGCGATGAT<br>CCAGCCATGTTCGGAGCAAAAGGACTCAGT<br>TACGACTTCTATGAGGTATTCATGGGTATT<br>GGTGGTATGAAGGCAGACCTGCGGACTCTT<br>AAGCAGTTGGCAATGAACTCAATTAAGTAC<br>TCTACCTTATTGGAGTCTGAAAAGAACACA<br>TTTATGGAGATCTGGAAAAGCGCTGGGAC<br>AAATTCATCGCAGATGTTGCCACAAAA |
| Human ADA2 | 284 | SIDETRAHLLLKEKM<br>MRLGGRLVLNTKEEL<br>ANERLMTLKIAEMKE<br>AMRTLIFPPSMHFFQ<br>AKHLIERSQVFNILR<br>MMPKGAALHLHDIGI<br>VTMDWLVRNVTYRPH<br>CHICFTPRGIMQFRF<br>AHPTPRPSEKCSKWI<br>LLEDYRKRVQNVTEF<br>DDSLLRNFTLVTQHP<br>EVIYTNQNVVWSKFE | | |

TABLE 16-continued

Exemplary fhuman ADA2 sequences

| Name | SEQ ID NO | Amino Acid Sequence | SEQ ID NO | NUCLEOTIDE SEQUENCE |
|---|---|---|---|---|
| | | TIFFTISGLIHYAPV | | |
| | | FRDYVFRSMQEFYED | | |
| | | NVLYMEIRARLLPVY | | |
| | | ELSGEHHDEEWSVKT | | |
| | | YQEVAQKFVETHPEF | | |
| | | IGIKIIYSDHRSKDV | | |
| | | AVIAESIRMAMGLRI | | |
| | | KFPTVVAGFDLVGHE | | |
| | | DTGHSLHDYKEALMI | | |
| | | PAKDGVKLPYFFHAG | | |
| | | ETDWQGTSIDRNILD | | |
| | | ALMLNTTRIGHGFAL | | |
| | | SKHPAVRTYSWKKDI | | |
| | | PIEVCPISNQVLKLV | | |
| | | SDLRNHPVATLMATG | | |
| | | HPMVISSDDPAMFGA | | |
| | | KGLSYDFYEVFMGIG | | |
| | | GMKADLRTLKQLAMN | | |
| | | SIKYSTLLESEKNTF | | |
| | | MEIWKKRWDKFIADV | | |
| | | ATK | | |

Table 16 provides exemplary ADA2 sequences for use in anti-PD-1 fusion proteins described herein. In any embodiments exemplifying a fusion protein with, e.g., a TGFβRII ECD, an ADA2 sequence may be employed instead.

TABLE 17

Exemplary anti-PD-1 VH/VL pairs

| Exemplary anti-PD-1 VL | Exemplary anti-PD-1 VH |
|---|---|
| Anti-PD-1 VL5 (SEQ ID NO: 12) | Anti-PD-1 VH6 (SEQ ID NO: 6) |
| Anti-PD-1 VL6 (SEQ ID NO: 13) | Anti-PD-1 VH7 (SEQ ID NO: 7) |
| Anti-PD-1 VL1 (SEQ ID NO: 8) | Anti-PD-1 VH5 (SEQ ID NO: 5) |
| Anti-PD-1 nVL1 (SEQ ID NO: 8) | Anti-PD-1 nVH3 (SEQ ID NO: 149) |
| Anti-PD-1 nVL1 (SEQ ID NO: 8) | Anti-PD-1 nVH7 (SEQ ID NO: 157) |
| Anti PD-1 nVL1 (SEQ ID NO: 8) | Anti-PD-1 nVH8 (SEQ ID NO: 158) |

Table 17 provides exemplary anti-PD-1 VH-/VL pairs for use in the fusion proteins described herein.

TABLE 18

Exemplary anti-PD-1-TGFbRII ECD fusion protein sequences

| Exemplary VL | Exemplary VH-IgG4-ECD |
|---|---|
| VL5 (SEQ ID NO: 15) | VH6-IgG4(wt)-linker-ECD (SEQ NO: 16) |
| VL5 (SEQ ID NO: 15) | VH6-IgG4(mut)-linker-ECD (SEQ NO: 143) |
| VL5 (SEQ ID NO: 15) | VH6-IgG4(mut)-linker-ECD (SEQ NO: 294) |
| VL6 (SEQ ID NO: 296) | VH7-IgG4(wt)-linker-ECD (SEQ NO: 145) |
| VL6 (SEQ ID NO: 296) | VH7-IgG4(mut)-linker-ECD (SEQ NO: 144) |
| VL6 (SEQ ID NO: 296) | VH7-IgG4(mut)-linker-ECD (SEQ NO: 295) |

Table 18 provides exemplary anti-PD-1-TGFbRII ECD fusion protein sequences. The anti-PD-1 fusion proteins comprise a sequence encoding an anti-PD-1 variable region of light chain and a sequence encoding an anti-PD-1 variable region of heavy chain. ECD stands for extracellular domain. As used herein, the abbreviation "wt" refers to the wild type sequence and the abbreviation "mut" refers to a mutant sequence.

TABLE 19

Exemplary anti-PD-1-ADA2 fusion protein sequences

| Exemplary VL | Exemplary VH-IgG4-ADA2 |
|---|---|
| VL5 (SEQ ID NO: 12) | VH6-IgG4(mut)-linker-ADA2 (wt) (SEQ NO: 280) |
| VL5 (SEQ ID NO: 12) | VH6-IgG4(mut)-linker-ADA2 (mut 7) (SEQ NO: 281) |
| VL6 (SEQ ID NO: 13) | VH7-IgG4(mut)-linker-ADA2 (wt) (SEQ NO: 282) |
| VL6 (SEQ ID NO: 13) | VH7-IgG4(mut)-linker-ADA2 (mut 7) (SEQ NO: 283) |

Table 19 provides exemplary anti-PD-1-ADA2 fusion protein sequences. The anti-PD-1 fusion proteins comprise a sequence encoding an anti-PD-1 variable region of light chain and a sequence encoding an anti-PD-1 variable region of heavy chain.

TABLE 20

Exemplary Anti-PD-1 heavy chain CDR sequences

| Name | SEQ ID NO | Amino acid sequence | SEQ ID NO | Nucleotide Sequence |
|---|---|---|---|---|
| Anti-PD-1 heavy chain CDR | 310 | Ser Thr Thr Tyr Tyr Trp Val | 344 | AGTACTACTTACTACTGGGTC |

TABLE 20-continued

Exemplary Anti-PD-1 heavy chain CDR sequences

| Name | SEQ ID NO | Amino acid sequence | SEQ ID NO | Nucleotide Sequence |
|---|---|---|---|---|
| Anti-PD-1 heavy chain CDR | 311 | Ser Ile Ser Tyr Ser Gly Asn Thr Tyr Tyr Asn Pro Ser Leu Lys Ser | 345 | AGTATCTCTTATAGTGGGAACACCTACTAC AATCCGTCCCTCAAGAGT |
| Anti-PD-1 heavy chain CDR | 312 | His Leu Gly Tyr Asn Gly Arg Tyr Leu Pro Phe Asp Tyr | 346 | CATCTAGGGTATAATGGGAGGTACCTCCCC TTTGACTAC |
| Anti-PD-1 heavy chain CDR | 313 | Ser Ser Thr Tyr Tyr Trp Gly | 347 | AGTAGTACTTACTACTGGGGC |
| Anti-PD-1 heavy chain CDR | 314 | Ser Ile Ser Tyr Ser Gly Ser Thr Tyr Tyr Asn Pro Ser Leu Lys Ser | 348 | AGTATCTCTTATAGTGGGAGCACCTACTAC AATCCGTCCCTCAAGAGT |
| Anti-PD-1 heavy chain CDR | 315 | Ser Thr Thr Tyr Tyr Trp Gly | 349 | AGTACTACTTACTACTGGGGC |
| Anti-PD-1 heavy chain CDR | 316 | Ser Ile Ser Tyr Ser Gly Thr Thr Tyr Tyr Asn Pro Ser Leu Lys Ser | 350 | AGTATCTCTTATAGTGGGACCACCTACTAC AACCCGTCCCTCAAGAGT |
| Anti-PD-1 heavy chain CDR | 317 | His Leu Gly Tyr Asn Ser Asn Trp Tyr Pro Phe Asp Tyr | 351 | CATCTCGGGTATAACAGCAACTGGTACCCT TTTGACTAC |
| Anti-PD-1 heavy chain CDR | 318 | Ser His Ala Met Ser | 352 | AGCCATGCCATGAGC |
| Anti-PD-1 heavy chain CDR | 319 | Thr Ile Thr Gly Gly Gly Gly Ser Ile Tyr Tyr Ala Asp Ser Val Lys | 353 | ACTATTACTGGTGGTGGTGGTAGCATATAC TACGCAGACTCCGTGAAGGGC |
| Anti-PD-1 heavy chain CDR | 320 | Asn Arg Ala Gly Glu Gly Tyr Phe Asp Tyr | 354 | AACCGCGCTGGGGAGGGTTACTTTGACTAC |
| Anti-PD-1 heavy chain CDR | 378 | Ser Tyr Ala Ile Ser | | |
| Anti-PD-1 heavy chain CDR | 379 | Gly Ile Ile Pro Ile Phe Asp Thr Ala Asn Tyr Ala Gln Lys Phe Gln | | |

TABLE 20-continued

Exemplary Anti-PD-1 heavy chain CDR sequences

| Name | SEQ ID NO | Amino acid sequence | SEQ ID NO | Nucleotide Sequence |
|---|---|---|---|---|
| Anti-PD-1 heavy chain CDR | 380 | Pro Gly Leu Ala Ala Ala Tyr Asp Thr Gly Ser Leu Asp Tyr | | |

Table 20 provides exemplary CDR sequences for use in anti-PD-1 heavy chains.

TABLE 21

Exemplary anti-PD-1 light chain CDR sequences

| Name | SEQ ID NO | Amino acid sequence | SEQ ID NO | Nucleotide Sequence |
|---|---|---|---|---|
| Anti-PD-1 light chain CDR | 321 | Thr Gly Thr Ser Ser Asp Val Gly Phe Tyr Asn Tyr Val Ser | 355 | ACTGGAACCAGCAGTGACGTTGGTTTTTA TAACTATGTCTCC |
| Anti-PD-1 light chain CDR | 322 | Asp Val Thr Asn Arg Pro Ser | 356 | GATGTCACTAATCGGCCCTCA |
| Anti-PD-1 light chain CDR | 323 | Ser Ser Tyr Thr Ser Ile Ser Thr Trp Val | 357 | AGCTCATATACAAGCATCAGCACTTGGGT G |
| Anti-PD-1 light chain CDR | 324 | Asp Val Ser Asn Arg Pro Ser | 358 | GATGTCAGTAATCGGCCCTCA |
| Anti-PD-1 light chain CDR | 325 | Ser Ser Tyr Thr Asn Ile Ser Thr Trp Val | 359 | AGCTCATATACAAACATCAGCACTTGGGT G |
| Anti-PD-1 light chain CDR | 326 | Thr Gly Thr Ser Ser Asp Val Gly Ser Tyr Asn Arg Val Ser | 360 | ACTGGAACCAGCAGTGACGTTGGTAGTTA TAACCGTGTCTCC |
| Anti-PD-1 light chain CDR | 327 | Glu Val Ser Asn Arg Pro Ser | 361 | GAGGTCAGTAATCGGCCCTCA |
| Anti-PD-1 light chain CDR | 328 | Ser Ser Tyr Thr Ser Ser Ser Thr Trp Val | 362 | AGCTCATATACAAGCAGCAGCACTTGGGT G |
| Anti-PD-1 light chain CDR | 329 | Gly Gly Asp Asn Ile Gly Asn Lys Asp Val His | 363 | GGGGGAGACAACATTGGAAATAAAGATGT GCAC |

TABLE 21-continued

Exemplary anti-PD-1 light chain CDR sequences

| Name | SEQ ID NO | Amino acid sequence | SEQ ID NO | Nucleotide Sequence |
|---|---|---|---|---|
| Anti-PD-1 light chain CDR | 330 | Arg Asp Ser Asn Arg Pro Ser | 364 | AGGGATAGCAACCGGCCCTCT |
| Anti-PD-1 light chain CDR | 331 | Gln Val Trp Asp Ser Ile Trp Val | 365 | CAGGTGTGGGACAGCATTTGGGTG |
| Anti-PD-1 light chain CDR | 332 | Ser Ser Tyr Thr Ser Ile Ser Thr Trp Val | 366 | AGCTCATATACAAGCATCAGCACTTGGGTG |
| Anti-PD-1 light chain CDR | 381 | Arg Ala Ser Gln Ser Val Arg Ser Tyr Leu Ala | | |
| Anti-PD-1 light chain CDR | 382 | Asp Ala Ser Asn Arg Ala Thr | | |
| Anti-PD-1 light chain CDR | 383 | Gln Gln Arg Asn Tyr Trp Pro Leu Thr | | |

Table 21 provides exemplary CDR sequences for use in anti-PD-1 light chains.

TABLE 22

Exemplary anti-PD-1 heavy chain variable region sequences

| Name | SEQ ID NO | Amino acid sequence | SEQ ID NO | Nucleotide Sequence |
|---|---|---|---|---|
| Anti-PD-1 heavy chain variable region | 333 | Gln Leu Gln Leu Gln Glu Ser Gly Pro Gly Leu Val Lys Pro Ser Glu Thr Leu Thr Leu Thr Cys Thr Val Ser Gly Asp Ser Ile Ser Ser Thr Thr Tyr Tyr Trp Val Trp Ile Arg Gln Pro Pro Gly Lys Gly Leu Glu Trp Ile Gly Ser Ile Ser Tyr Ser Gly Asn Thr Tyr Tyr Asn Pro Ser Leu Lys Ser Arg Val Thr Ile Ser Val Asp Thr Ser Lys Asn His Phe Ser Leu Lys Leu Ser Ser Val Ala Ala Thr Asp Thr Ala Leu Tyr Tyr Cys Ala Arg His Leu Gly Tyr Asn | 367 | CAGCTGCAGCTGCAGGAGTCGGGCCCAGGA CTGGTGAAGCCTTCGGAGACCCTGACCCTC ACCTGCACTGTCTCTGGTGACTCCATCAGC AGTACTACTTACTACTGGGTCTGGATCCGC CAGCCCCCAGGGAAGGGACTGGAGTGGATT GGGAGTATCTCTTATAGTGGGAACACCTAC TACAATCCGTCCCTCAAGAGTCGAGTCACC ATATCCGTAGACACGTCCAAGAACCACTTC TCCCTGAAGCTGAGTTCTGTGGCCGCCACA GACACGGCTCTATATTACTGTGCGAGACAT CTAGGGTATAATGGGAGGTACCTCCCCTTT GACTACTGGGGCCAGGGAACCCTGGTCACC GTCTCCTCC |

TABLE 22-continued

Exemplary anti-PD-1 heavy chain variable region sequences

| Name | SEQ ID NO | Amino acid sequence | SEQ ID NO | Nucleotide Sequence |
|---|---|---|---|---|
| | | Gly Arg Tyr Leu<br>Pro Phe Asp Tyr<br>Trp Gly Gln Gly<br>Thr Leu Val Thr<br>Val Ser Ser | | |
| Anti-PD-1 heavy chain variable region | 334 | Gln Leu Gln Leu<br>Gln Glu Ser Gly<br>Pro Gly Leu Val<br>Lys Pro Ser Glu<br>Thr Leu Ser Leu<br>Thr Cys Thr Val<br>Ser Gly Gly Ser<br>Ile Ser Ser Ser<br>Thr Tyr Tyr Trp<br>Gly Trp Ile Arg<br>Gln Pro Pro Gly<br>Lys Gly Leu Glu<br>Trp Ile Gly Ser<br>Ile Ser Tyr Ser<br>Gly Ser Thr Tyr<br>Tyr Asn Pro Ser<br>Leu Lys Ser Arg<br>Val Thr Ile Ser<br>Val Asp Thr Ser<br>Lys Asn Gln Phe<br>Ser Leu Lys Leu<br>Ser Ser Val Thr<br>Asp Ala Asp Thr<br>Ala Val Tyr Tyr<br>Cys Ala Arg His<br>Leu Gly Tyr Asn<br>Gly Arg Tyr Leu<br>Pro Phe Asp Tyr<br>Trp Gly Gln Gly<br>Thr Leu Val Thr<br>Val Ser Ser | 368 | CAGCTGCAGCTGCAGGAGTCGGGCCCAGGA<br>CTGGTGAAGCCTTCGGAGACCCTGTCCCTC<br>ACCTGCACTGTCTCTGGTGGCTCCATCAGC<br>AGTAGTACTTACTACTGGGGCTGGATCCGC<br>CAGCCCCCAGGGAAGGGACTGGAGTGGATT<br>GGGAGTATCTCTTATAGTGGGAGCACCTAC<br>TACAATCCGTCCCTCAAGAGTCGAGTCACC<br>ATATCCGTAGACACGTCCAAGAACCAGTTC<br>TCCCTGAAGCTGAGCTCTGTGACCGACGCA<br>GACACGGCTGTGTATTACTGTGCGAGACAT<br>CTAGGGTATAATGGGAGGTACCTCCCCTTT<br>GACTACTGGGGCCAGGGAACCCTGGTCACC<br>GTCTCCTCC |
| Anti-PD-1 heavy chain variable region | 335 | Gln Leu Gln Leu<br>Gln Glu Ser Gly<br>Pro Gly Leu Val<br>Lys Pro Ser Glu<br>Thr Leu Thr Leu<br>Thr Cys Thr Val<br>Ser Ala Asp Ser<br>Ile Ser Ser Thr<br>Thr Tyr Tyr Trp<br>Val Trp Ile Arg<br>Gln Pro Pro Gly<br>Lys Gly Leu Glu<br>Trp Ile Gly Ser<br>Ile Ser Tyr Ser<br>Gly Ser Thr Tyr<br>Tyr Asn Pro Ser<br>Leu Lys Ser Arg<br>Val Thr Val Ser<br>Val Asp Thr Ser<br>Lys Asn Gln Phe<br>Ser Leu Lys Leu<br>Asn Ser Val Ala<br>Ala Thr Asp Thr<br>Ala Leu Tyr Tyr<br>Cys Ala Arg His<br>Leu Gly Tyr Asn<br>Gly Arg Tyr Leu<br>Pro Phe Asp Tyr<br>Trp Gly Gln Gly<br>Thr Leu Val Thr<br>Val Ser Ser | 369 | CAGCTGCAGCTGCAGGAGTCGGGCCCAGGA<br>CTGGTGAAGCCTTCGGAGACCCTGACCCTC<br>ACCTGCACTGTCTCTGCTGACTCCATCAGC<br>AGTACTACTTACTACTGGGTCTGGATCCGC<br>CAGCCCCCAGGGAAGGGACTGGAGTGGATT<br>GGGAGTATCTCTTATAGTGGGAGCACCTAC<br>TACAATCCGTCCCTCAAGAGTCGAGTCACC<br>GTATCCGTAGACACGTCCAAGAACCAGTTC<br>TCCCTGAAGCTGAACTCTGTGGCCGCCACA<br>GACACGGCTCTATATTACTGTGCGAGACAT<br>CTAGGGTATAATGGGAGGTACCTCCCCTTT<br>GACTACTGGGGCCAGGGAACCCTGGTCACC<br>GTCTCCTCC |
| Anti-PD-1 heavy chain | 336 | Gln Leu Gln Leu<br>Gln Glu Ser Gly<br>Pro Gly Leu Val<br>Lys Pro Ser Glu | 370 | CAGCTGCAGCTGCAGGAGTCGGGCCCAGGA<br>CTGGTGAAGCCCTCGGAGACCCTGTCCCTC<br>ACCTGCACTGTCTCTGGTGGCTCCATCAGC<br>AGTACTACTTACTACTGGGGCTGGATCCGC |

TABLE 22-continued

Exemplary anti-PD-1 heavy chain variable region sequences

| Name | SEQ ID NO | Amino acid sequence | SEQ ID NO | Nucleotide Sequence |
|---|---|---|---|---|
| variable region | | Thr Leu Ser Leu<br>Thr Cys Thr Val<br>Ser Gly Gly Ser<br>Ile Ser Ser Thr<br>Thr Tyr Tyr Trp<br>Gly Trp Ile Arg<br>Gln Pro Pro Gly<br>Lys Gly Leu Glu<br>Trp Ile Gly Ser<br>Ile Ser Tyr Ser<br>Gly Thr Thr Tyr<br>Tyr Asn Pro Ser<br>Leu Lys Ser Arg<br>Val Thr Ile Pro<br>Val Asp Thr Ser<br>Lys Asn Gln Ile<br>Ser Leu Lys Leu<br>Ser Ser Val Thr<br>Ala Ala Asp Thr<br>Ser Leu Tyr Tyr<br>Cys Ala Arg His<br>Leu Gly Tyr Asn<br>Ser Asn Trp Tyr<br>Pro Phe Asp Tyr<br>Trp Gly Gln Gly<br>Thr Leu Val Thr<br>Val Ser Ser | | CAGCCCCAGGGAAGGGGCTGGAGTGGATT<br>GGGAGTATCTCTTATAGTGGGACCACCTAC<br>TACAACCCGTCCCTCAAGAGTCGAGTCACC<br>ATCCCCGTAGACACGTCCAAGAACCAGATC<br>TCCCTGAAACTGAGCTCTGTGACCGCCGCA<br>GACACGTCTTTGTATTATTGTGCGAGACAT<br>CTCGGGTATAACAGCAACTGGTACCCTTTT<br>GACTACTGGGGCCAGGGAACCCTGGTCACC<br>GTCTCCTCA |
| Anti-PD-1 heavy chain variable region | 337 | Glu Val Gln Leu<br>Leu Glu Ser Gly<br>Gly Gly Leu Val<br>Gln Pro Gly Gly<br>Ser Leu Arg Leu<br>Ser Cys Ala Ala<br>Ser Gly Phe Thr<br>Phe Ser Ser His<br>Ala Met Ser Trp<br>Val Arg Gln Ala<br>Pro Gly Lys Gly<br>Leu Glu Trp Val<br>Ser Thr Ile Thr<br>Gly Gly Gly Gly<br>Ser Ile Tyr Tyr<br>Ala Asp Ser Val<br>Lys Gly Arg Phe<br>Thr Ile Ser Arg<br>Asp Asn Ser Lys<br>Asn Thr Leu Tyr<br>Leu Gln Met Asn<br>Ser Leu Arg Ala<br>Glu Asp Thr Ala<br>Val Tyr Tyr Cys<br>Ala Lys Asn Arg<br>Ala Gly Glu Gly<br>Tyr Phe Asp Tyr<br>Trp Gly Gln Gly<br>Thr Leu Val Thr<br>Val Ser Ser | 371 | GAGGTGCAGCTGTTGGAGTCTGGGGGAGGC<br>TTGGTACAGCCTGGGGGGTCCCTGAGACTG<br>TCCTGCGCAGCCTCTGGATTCACCTTTAGC<br>AGCCATGCCATGAGCTGGGTCCGCCAGGCT<br>CCAGGGAAGGGGCTGGAGTGGGTCTCAACT<br>ATTACTGGTGGTGGTGGTAGCATATACTAC<br>GCAGACTCCGTGAAGGGCCGGTTCACCATC<br>TCCAGAGACAATTCCAAGAACACGCTGTAT<br>CTGCAAATGAACAGCCTGAGAGCCGAGGAC<br>ACGGCCGTATATTATTGTGCGAAAAACCGC<br>GCTGGGGAGGGTTACTTTGACTACTGGGGC<br>CAGGGAACCCTGGTCACCGTCTCCTCA |
| Anti-PD-1 heavy chain variable region | 384 | Gln Val Gln Leu<br>Val Gln Ser Gly<br>Ala Glu Val Lys<br>Lys Pro Gly Ser<br>Ser Val Lys Val<br>Ser Cys Lys Ala<br>Ser Gly Gly Thr<br>Phe Ser Ser Tyr<br>Ala Ile Ser Trp<br>Val Arg Gln Ala<br>Pro Gly Gln Gly<br>Leu Glu Trp Met<br>Gly Gly Ile Ile<br>Pro Ile Phe Asp<br>Thr Ala Asn Tyr<br>Ala Gln Lys Phe | | |

TABLE 22-continued

Exemplary anti-PD-1 heavy chain variable region sequences

| Name | SEQ ID NO | Amino acid sequence | SEQ ID NO | Nucleotide Sequence |
|---|---|---|---|---|
| | | Gln Gly Arg Val Thr Ile Thr Ala Asp Glu Ser Thr Ser Thr Ala Tyr Met Glu Leu Ser Ser Leu Arg Ser Glu Asp Thr Ala Val Tyr Tyr Cys Ala Arg Pro Gly Leu Ala Ala Ala Tyr Asp Thr Gly Ser Leu Asp Tyr Trp Gly Gln Gly Thr Leu Val Thr Val Ser Ser | | |

20

Table 22 provides exemplary sequences for use in anti-PD-1 heavy chain variable regions.

Table 23 provides exemplary sequences for use in anti-PD-1 light chain variable regions.

TABLE 23

Exemplary Anti-PD-1 Light Chain Variable Region Sequences

| Name | SEQ ID NO | Amino acid sequence | SEQ ID NO | Nucleotide sequence |
|---|---|---|---|---|
| Anti-PD-1 light chain variable region | 338 | Gln Ser Ala Leu Thr Gln Pro Ala Ser Val Ser Gly Ser Pro Gly Gln Ser Ile Thr Ile Ser Cys Thr Gly Thr Ser Ser Asp Val Gly Phe Tyr Asn Tyr Val Ser Trp Tyr Gln Gln His Pro Gly Lys Ala Pro Glu Leu Met Ile Tyr Asp Val Thr Asn Arg Pro Ser Gly Val Ser Asp Arg Phe Ser Gly Ser Lys Ser Gly Asn Thr Ala Ser Leu Thr Ile Ser Gly Leu Gln Ala Glu Asp Glu Ala Asp Tyr Tyr Cys Ser Ser Tyr Thr Ser Ile Ser Thr Trp Val Phe Gly Gly Gly Thr Lys Leu Thr Val Leu | 372 | CAGTCTGCCCTGACTCAGCCTGCCTCCGTG TCTGGGTCTCCTGGACAGTCGATCACCATC TCCTGCACTGGAACCAGCAGTGACGTTGGT TTTTATAACTATGTCTCCTGGTACCAACAG CACCCAGGCAAAGCCCCCGAACTCATGATT TATGATGTCACTAATCGGCCCTCAGGGGTT TCTGATCGCTTCTCTGGCTCCAAGTCTGGC AACACGGCCTCCCTGACCATCTCTGGGCTC CAGGCTGAGGACGAGGCTGATTATTACTGC AGCTCATATACAAGCATCAGCACTTGGGTG TTCGGCGGAGGGACCAAGCTGACCGTCCTA |
| Anti-PD-1 light chain variable region | 339 | Gln Ser Ala Leu Thr Gln Pro Ala Ser Val Ser Gly Ser Pro Gly Gln Ser Ile Thr Ile Ser Cys Thr Gly Thr Ser Ser Asp Val Gly Phe Tyr Asn Tyr Val Ser Trp Tyr Gln Gln His Pro Gly Lys Ala Pro Glu Val Met Ile Tyr Asp Val Ser Asn Arg Pro Ser Gly Val | 373 | CAGTCTGCCCTGACTCAGCCTGCCTCCGTG TCTGGGTCTCCTGGACAGTCGATCACCATC TCCTGCACTGGAACCAGCAGTGACGTTGGT TTTTATAACTATGTCTCCTGGTACCAACAG CACCCAGGCAAAGCCCCCGAAGTCATGATT TATGATGTCAGTAATCGGCCCTCAGGGGTT TCTGATCGCTTCTCTGGCTCCAAGTCTGGC AACACGGCCTCCCTGACTATCTCTGGGCTC CAGGCTGAGGACGAGGCTGATTATTACTGC AGCTCATATACAAGCATCAGCACTTGGGTG TTCGGCGGAGGGACCAAGCTGACTGTCCTA |

TABLE 23-continued

Exemplary Anti-PD-1 Light Chain Variable Region Sequences

| Name | SEQ ID NO | Amino acid sequence | SEQ ID NO | Nucleotide sequence |
|---|---|---|---|---|
| | | Ser Asp Arg Phe<br>Ser Gly Ser Lys<br>Ser Gly Asn Thr<br>Ala Ser Leu Thr<br>Ile Ser Gly Leu<br>Gln Ala Glu Asp<br>Glu Ala Asp Tyr<br>Tyr Cys Ser Ser<br>Tyr Thr Ser Ile<br>Ser Thr Trp Val<br>Phe Gly Gly Gly<br>Thr Lys Leu Thr<br>Val Leu | | |
| Anti-PD-1 light chain variable region | 340 | Gln Ser Ala Leu<br>Thr Gln Pro Ala<br>Ser Val Ser Gly<br>Ser Pro Gly Gln<br>Ser Ile Thr Ile<br>Ser Cys Thr Gly<br>Thr Ser Ser Asp<br>Val Gly Phe Tyr<br>Asn Tyr Val Ser<br>Trp Tyr Gln Gln<br>His Pro Gly Lys<br>Ala Pro Glu Leu<br>Met Ile Tyr Asp<br>Val Ser Asn Arg<br>Pro Ser Gly Val<br>Ser Asp Arg Phe<br>Ser Gly Ser Lys<br>Ser Gly Asn Thr<br>Ala Ser Leu Thr<br>Ile Ser Gly Leu<br>Gln Ala Glu Asp<br>Glu Ala Asp Tyr<br>Tyr Cys Ser Ser<br>Tyr Thr Asn Ile<br>Ser Thr Trp Val<br>Phe Gly Gly Gly<br>Thr Lys Leu Thr<br>Val Leu | 374 | CAGTCTGCCCTGACTCAGCCTGCCTCCGTG<br>TCTGGGTCTCCTGGACAGTCGATCACCATC<br>TCCTGCACTGGAACCAGCAGTGACGTTGGT<br>TTTTATAACTATGTCTCCTGGTACCAACAG<br>CACCCAGGCAAAGCCCCGAACTCATGATT<br>TATGATGTCAGTAATCGGCCCTCAGGGGTT<br>TCTGATCGCTTCTCTGGCTCCAAGTCTGGC<br>AACACGGCCTCCCTGACCATCTCTGGGCTC<br>CAGGCTGAGGACGAGGCTGATTATTACTGC<br>AGCTCATATACAAACATCAGCACTTGGGTG<br>TTCGGCGGAGGGACCAAGCTGACCGTCCTA |
| Anti-PD-1 light chain variable region | 341 | Gln Ser Ala Leu<br>Thr Gln Pro Pro<br>Ser Val Ser Gly<br>Ser Pro Gly Gln<br>Ser Val Thr Ile<br>Ser Cys Thr Gly<br>Thr Ser Ser Asp<br>Val Gly Ser Tyr<br>Asn Arg Val Ser<br>Trp Tyr Gln Gln<br>Pro Pro Gly Thr<br>Ala Pro Glu Val<br>Ile Ile Tyr Glu<br>Val Ser Asn Arg<br>Pro Ser Gly Val<br>Pro Asp Arg Phe<br>Ser ly Ser Lys<br>Ser <u>G</u>ly Asn Thr<br>Ala Ser Leu Thr<br>Ile Ser Gly Leu<br>Gln Ala Glu Asp<br>Glu Ala Asp Tyr<br>Tyr Cys Ser Ser<br>Tyr Thr Ser Ser<br>Ser Thr Trp Val<br>Phe Gly Gly Gly<br>Thr Lys Leu Thr<br>Val Leu | 375 | CAGTCGGCCCTGACTCAGCCTCCCTCCGTG<br>TCCGGGTCTCCTGGACAGTCAGTCACCATC<br>TCCTGCACTGGAACCAGCAGTGACGTTGGT<br>AGTTATAACCGTGTCTCCTGGTACCAGCAG<br>CCCCCAGGCACAGCCCCCGAAGTCATTATT<br>TATGAGGTCAGTAATCGGCCCTCAGGGGTC<br>CCTGATCGCTTCTCTGGGTCCAAGTCTGGC<br>AACACGGCCTCCCTGACCATCTCTGGGCTC<br>CAGGCTGAGGACGAGGCTGATTATTACTGC<br>AGCTCATATACAAGCAGCAGCACTTGGGTG<br>TTCGGCGGAGGGACCAAGCTGACCGTCCTA |

TABLE 23-continued

Exemplary Anti-PD-1 Light Chain Variable Region Sequences

| Name | SEQ ID NO | Amino acid sequence | SEQ ID NO | Nucleotide sequence |
|---|---|---|---|---|
| Anti-PD-1 light chain variable region | 342 | Ser Tyr Glu Leu Thr Gln Pro Leu Ser Val Ser Val Ala Leu Gly Gln Thr Ala Arg Ile Thr Cys Gly Gly Asp Asn Ile Gly Asn Lys Asp Val His Trp Tyr Gln Gln Lys Pro Gly Gln Ala Pro Val Leu Val Ile Tyr Arg Asp Ser Asn Arg Pro Ser Gly Ile Pro Glu Gly Phe Ser Gly Ser Asn Ser Gly Asn Thr Ala Thr Leu Thr Ile Ser Arg Ala Gln Ala Gly Asp Glu Ala Asp Tyr Tyr Cys Gln Val Trp Asp Ser Ile Trp Val Phe Gly Gly Gly Thr Lys Leu Thr Val Leu | 376 | TCCTATGAGCTGACTCAGCCACTCTCAGTG TCAGTGGCCCTGGGACAGACGGCCAGGATT ACCTGTGGGGGAGACAACATTGGAAATAAA GATGTGCACTGGTACCAGCAGAAGCCAGGC CAGGCCCCTGTGCTGGTCATCTATAGGGAT AGCAACCGGCCCTCTGGGATCCCTGAGGGA TTCTCTGGCTCCAACTCGGGGAACACGGCC ACCCTGACCATCAGCAGAGCCCAAGCCGGG GATGAGGCTGACTATTACTGTCAGGTGTGG GACAGCATTTGGGTGTTCGGCGGAGGGACC AAGCTGACCGTCCTA |
| Anti-PD-1 light chain variable region | 343 | Gln Ser Ala Leu Thr Gln Pro Ala Ser Val Ser Gly Ser Pro Gly Gln Ser Ile Thr Ile Ser Cys Thr Gly Thr Ser Ser Asp Val Gly Phe Tyr Asn Tyr Val Ser Trp Tyr Gln Gln His Pro Gly Lys Ala Pro Glu Leu Met Ile Tyr Asp Val Ser Asn Arg Pro Ser Gly Val Ser Asp Arg Phe Ser Gly Ser Lys Ser Gly Asn Thr Ala Ser Leu Thr Ile Ser Gly Leu Gln Ala Glu Asp Glu Ala Asp Tyr Tyr Cys Ser Ser Tyr Thr Ser Ile Ser Thr Trp Val Phe Gly Gly Gly Thr Lys Leu Thr Val Leu | 377 | CAGTCTGCCCTGACTCAGCCTGCCTCCGTG TCTGGGTCTCCTGGACAGTCGATCACCATC TCCTGCACTGGAACCAGCAGTGACGTTGGT TTTTATAACTATGTCTCCTGGTACCAACAG CACCCAGGCAAAGCCCCCGAACTCATGATT TATGATGTCAGTAATCGGCCCTCAGGGGTT TCTGATCGCTTCTCTGGCTCCAAGTCTGGC AACACGGCCTCCCTGACCATCTCTGGGCTC CAGGCTGAGGACGAGGCTGATTATTACTGC AGCTCATATACAAGCATCAGCACTTGGGTG TTCGGCGGAGGGACCAAGCTGACCGTCCTA |
| Anti-PD-1 light chain variable region | 385 | Glu Ile Val Leu Thr Gln Ser Pro Ala Thr Leu Ser Leu Ser Pro Gly Glu Arg Ala Thr Leu Ser Cys Arg Ala Ser Gln Ser Val Arg Ser Tyr Leu Ala Trp Tyr Gln Gln Lys Pro Gly Gln Ala Pro Arg Leu Leu Ile Tyr Asp Ala Ser Asn Arg Ala Thr Gly Ile Pro Ala Arg Phe Ser Gly Ser Gly Ser Gly Thr Asp Phe Thr | | |

TABLE 23-continued

Exemplary Anti-PD-1 Light Chain Variable Region Sequences

| Name | SEQ ID NO | Amino acid sequence | SEQ ID NO | Nucleotide sequence |
|---|---|---|---|---|
| | | Leu Thr Ile Ser Ser Leu Glu Pro Glu Asp Phe Ala Val Tyr Tyr Cys Gln Gln Arg Asn Tyr Trp Pro Leu Thr Phe Gly Gln Gly Thr Lys Val Glu Ile Lys | | |

Table 24 provides an exemplary sequence for use in an anti-PD-1 heavy chain.

TABLE 24

Exemplary anti-PD-1 heavy chain sequence

| Name | SEQ ID NO | Amino acid sequence | SEQ ID NO | Nucleotide sequence |
|---|---|---|---|---|
| Anti-PD-1 heavy chain | 386 | Gln Val Gln Leu Val Gln Ser Gly Ala Glu Val Lys Lys Pro Gly Ser Ser Val Lys Val Ser Cys Lys Ala Ser Gly Gly Thr Phe Ser Ser Tyr Ala Ile Ser Trp Val Arg Gln Ala Pro Gly Gln Gly Leu Glu Trp Met Gly Gly Ile Ile Pro Ile Phe Asp Thr Ala Asn Tyr Ala Gln Lys Phe Gln Gly Arg Val Thr Ile Thr Ala Asp Glu Ser Thr Ser Thr Ala Tyr Met Glu Leu Ser Ser Leu Arg Ser Glu Asp Thr Ala Val Tyr Tyr Cys Ala Arg Pro Gly Leu Ala Ala Ala Tyr Asp Thr Gly Ser Leu Asp Tyr Trp Gly Gln Gly Thr Leu Val Thr Val Ser Ser Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Lys Thr Tyr Thr Cys Asn | | |

TABLE 24-continued

Exemplary anti-PD-1 heavy chain sequence

| Name | SEQ ID NO | Amino acid sequence | SEQ ID NO | Nucleotide sequence |
|---|---|---|---|---|
| | | Val Asp His Lys Pro Ser Asn Thr Lys Val Asp Lys Arg Val Glu Ser Lys Tyr Gly Pro Pro Cys Pro Pro Cys Pro Ala Pro Glu Phe Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser | | |

TABLE 24-continued

Exemplary anti-PD-1 heavy chain sequence

| Name | SEQ ID NO | Amino acid sequence | SEQ ID NO | Nucleotide sequence |
|---|---|---|---|---|
| | | Cys Ser Val Met<br>His Glu Ala Leu<br>His Asn His Tyr<br>Thr Gln Lys Ser<br>Leu Ser Leu Ser<br>Leu Gly Lys | | |

TABLE 25

Exemplary anti-PD-1 light chain sequence

| Name | SEQ ID NO | Amino acid sequence | SEQ ID NO | Nucleotide sequence |
|---|---|---|---|---|
| Anti-PD-1 light chain | 387 | Glu Ile Val Leu<br>Thr Gln Ser Pro<br>Ala Thr Leu Ser<br>Leu Ser Pro Gly<br>Glu Arg Ala Thr<br>Leu Ser Cys Arg<br>Ala Ser Gln Ser<br>Val Arg Ser Tyr<br>Leu Ala Trp Tyr<br>Gln Gln Lys Pro<br>Gly Gln Ala Pro<br>Arg Leu Leu Ile<br>Tyr Asp Ala Ser<br>Asn Arg Ala Thr<br>Gly Ile Pro Ala<br>Arg Phe Ser Gly<br>Ser Gly Ser Gly<br>Thr Asp Phe Thr<br>Leu Thr Ile Ser<br>Ser Leu Glu Pro<br>Glu Asp Phe Ala<br>Val Tyr Tyr Cys<br>Gln Gln Arg Asn<br>Tyr Trp Pro Leu<br>Thr Phe Gly Gln<br>Gly Thr Lys Val<br>Glu Ile Lys Arg<br>Thr Val Ala Ala<br>Pro Ser Val Phe<br>Ile Phe Pro Pro<br>Ser Asp Glu Gln<br>Leu Lys Ser Gly<br>Thr Ala Ser Val<br>Val Cys Leu Leu<br>Asn Asn Phe Tyr<br>Pro Arg Glu Ala<br>Lys Val Gln Trp<br>Lys Val Asp Asn<br>Ala Leu Gln Ser<br>Gly Asn Ser Gln<br>Glu Ser Val Thr<br>Glu Gln Asp Ser<br>Lys Asp Ser Thr<br>Tyr Ser Leu Ser<br>Ser Thr Leu Thr<br>Leu Ser Lys Ala<br>Asp Tyr Glu Lys<br>His Lys Val Tyr<br>Ala Cys Glu Val<br>Thr His Gln Gly<br>Leu Ser Ser Pro<br>Val Thr Lys Ser<br>Phe Asn Arg Gly<br>Glu Cys | | |

Table 25 provides an exemplary sequences for use in an anti-PD-1 light chain.

Table 26 provides the amino acid sequence and an exemplary nucleic acid sequence for human PD-1. The transmembrane domain, located at residues 170 to 191 (and underlined for emphasis) comprises the amino acids: Val Val Gly Val Val Gly Gly Leu Leu Gly Ser Leu Val Leu Leu Val Trp Val Leu Ala Val Ile (SEQ ID NO: 564).

TABLE 26

Amino acid and nucleic acid sequences for human PD-1

| Name | SEQ ID NO | Amino acid sequence | SEQ ID NO | Nucleotide sequence |
|---|---|---|---|---|
| Human PD-1 | 388 | Phe Leu Asp<br>Ser Pro Asp Arg<br>Pro Trp Asn Pro<br>Pro Thr Phe Ser<br>Pro Ala Leu Leu<br>Val Val Thr Glu<br>Gly Asp Asn Ala<br>Thr Phe Thr Cys<br>Ser Phe Ser Asn<br>Thr Ser Glu Ser<br>Phe Val Leu Asn<br>Trp Tyr Arg Met<br>Ser Pro Ser Asn<br>Gln Thr Asp Lys<br>Leu Ala Ala Phe<br>Pro Glu Asp Arg<br>Ser Gln Pro Gly<br>Gln Asp Cys Arg<br>Phe Arg Val Thr<br>Gln Leu Pro Asn<br>Gly Arg Asp Phe<br>His Met Ser Val<br>Val Arg Ala Arg<br>Arg Asn Asp Ser<br>Gly Thr Tyr Leu<br>Cys Gly Ala Ile<br>Ser Leu Ala Pro<br>Lys Ala Gln Ile<br>Lys Glu Ser Leu<br>Arg Ala Glu Leu<br>Arg Val Thr Glu<br>Arg Arg Ala Glu<br>Val Pro Thr Ala<br>His Pro Ser Pro<br>Ser Pro Arg Pro<br>Ala Gly Gln Phe<br>Gln Thr Leu <u>Val</u><br><u>Val Gly Val Val</u><br><u>Gly Gly Leu Leu</u><br><u>Gly Ser Leu Val</u><br><u>Leu Leu Val Trp</u><br><u>Val Leu Ala Val</u><br><u>Ile</u> Cys Ser Arg<br>Ala Ala Arg Gly<br>Thr Ile Gly Ala<br>Arg Arg Thr Gly<br>Gln Pro Leu Lys<br>Glu Asp Pro Ser<br>Ala Val Pro Val<br>Phe Ser Val Asp<br>Tyr Gly Glu Leu<br>Asp Phe Gln Trp<br>Arg Glu Lys Thr<br>Pro Glu Pro Pro<br>Val Pro Cys Val<br>Pro Glu Gln Thr<br>Glu Tyr Ala Thr<br>Ile Val Phe Pro<br>Ser Gly Met Gly<br>Thr Ser Ser Pro<br>Ala Arg Arg Gly<br>Ser Ala Asp Gly<br>Pro Arg Ser Ala | 389 | |

TABLE 26-continued

Amino acid and nucleic acid sequences for human PD-1

| Name | SEQ ID NO | Amino acid sequence | SEQ ID NO | Nucleotide sequence |
|------|-----------|---------------------|-----------|---------------------|
|      |           | Gln Pro Leu Arg Pro Glu Asp Gly His Cys Ser Trp Pro Leu |  |  |

Table 27 provides the amino acid sequence and nucleic acid sequences for exemplary anti-MUC16 $V_H$ and $V_L$ sequences. The CDRs are underlined.

TABLE 27

Exemplary anti-MUC16 Variable Heavy (VH) and Variable Light (VL) Sequences

| Name | SEQ ID NO | Amino acid sequence | SEQ ID NO | Nucleotide sequence |
|------|-----------|---------------------|-----------|---------------------|
| Anti-MUC16 VH1 | 390 | QVQLQESGPGLVKPS QTLSLTCTVSGYSIV SHYYWSWIRQHPGKG LEWIGYISSDGSNYY NPSLKSLVTISVDTS KNQFSLKLSSVTAAD TAVYYCVRGVDYWGQ GTMVTVSS | 404 | CAGGTGCAACTGCAGGAATCAGGTCCAGGC TTGGTCAAGCCATCGCAGACTCTTAGTCTG ACATGCACCGTGAGTGGCTATAGCATCGTG TCGCACTATTATTGGTCTTGGATCAGGCAG CATCCAGGAAAGGGACTGGAGTGGATCGGG TACATTAGCAGCGATGGGAGCAACTATTAC AACCCATCTCTGAAGTCCCTGGTAACTATT AGCGTGGATACAAGCAAAAATCAGTTTTCA TTAAAGCTCTCTTCAGTGACCGCAGCTGAT ACCGCCGTCTATTATTGCGTGCGGGGGGTG GACTACTGGGGTCAGGGCACCATGGTTACT GTGTCATCA |
| Anti-MUC16 VH2 | 391 | QVQLQESGPGLVKPS DTLSLTCAVSGYSIV SHYYWGWIRQPPGKG LEWIGYISSDGSNYY NPSLKSRVTMSVDTS KNQFSLKLSSVTAVD TAVYYCVRGVDYWGQ GTMVTVSS | 405 | CAGGTACAGCTGCAGGAGAGTGGCCCTGGT TTAGTAAAGCCATCAGATACACTTTCACTT ACCTGCGCCGTGTCTGGTTATTCTATCGTG AGCCACTATTACTGGGGATGGATCCGCCAG CCCCCTGGCAAAGGTCTTGAGTGGATTGGC TATATAAGTTCGGATGGCAGTAACTATTAC AATCCTTCTCTGAAGAGCCGTGTCACTATG AGCGTGGACACTAGCAAAAACCAGTTCAGC CTGAAGCTGTCCTCCGTCACCGCCGTAGAC ACCGCTGTCTACTATTGTGTTAGGGGGGTG GACTACTGGGGCCAAGGCACCATGGTCACG GTGAGCAGC |
| Anti-MUC16 VH3 | 392 | EVQLVESGGGLVQPG GSLRLSCAASGYSIV SHYYMSWVRQAPGKG LEWVSVISSDGSNYY ADSVKGRFTISRDNS KNTLYLQMNSLRAED TAVYYCVRGVDYWGQ GTLVTVSS |  |  |
| Anti-MUC16 VH4 | 393 | EVQLVESGGGLVQPG RSLRLSCAASGYSIV SHYYMHWVRQAPGKG LEWVSAISSDGSNEY ADSVEGRFTISRDNA KNSLYLQMNSLRAED TAVYYCVRGVDYWGQ GTLVTVSS | 406 | GAGGTGCAGCTCGTCGAGTCCGGAGGCGGT CTGGTGCAACCCGGCCGTTCTTTGCGGCTG AGTTGCGCTGCCAGTGGGTATAGCATCGTG AGTCACTATTACATGCATTGGGTTCGTCAA GCCCCTGGCAAGGGACTAGAGTGGGTGTCC GCCATCTCCTCAGACGGTAGTAATGAGTAC GCGGACAGCGTAGAGGGTAGATTCACCATT TCTCGGGACAATGCCAAAAATAGTTATACC TCCAAATGAATTCCCTTAGGGCCGAAGACA CTGCCGTGTACTACTGTGTTCGGGGCGTGG ACTACTGGGGGCAGGGGACATTGGTGACTG TGAGCTCA |
| Anti-MUC16 VH5 | 394 | QVQLQESGPGLVKPS QTLSLTCTVSGYSIV SHYYWSWIRQHPGKG LEWIGYISSDGSNEY NPSLKSLVTISVDTS KNQFSLKLSSVTAAD | 407 | CAGGTCCAACTGCAGGAATCTGGCCCCGGA CTGGTTAAACCATCTCAGACACTCTCCCTG ACCTGCACCGTGTCTGGATACAGCATCGTT TCTCATTATTACTGGTCATGGATTAGGCAG CATCCCGGAAAAGGGCTTGAATGGATTGGC TACATCTCCTCCGACGGCTCCAATGAGTAC |

TABLE 27-continued

Exemplary anti-MUC16 Variable Heavy (VH) and Variable Light (VL) Sequences

| Name | SEQ ID NO | Amino acid sequence | SEQ ID NO | Nucleotide sequence |
|---|---|---|---|---|
| | | TAVYFCVRGVDYWGQ GTMVTVSS | | AACCCATCACTTAAATCTCTGGTCACGATA AGCGTAGACACATCTAAAAATCAGTTCTCA TTAAAGCTCAGCTCTGTTACAGCTGCCGAC ACCGCTGTGTACTTCTGTGTGCGAGGGGTT GACTACTGGGGGCAGGGCACAATGGTGACA GTGTCTTCC |
| Anti-MUC16 VH6 | 395 | QVQLVQSGAEVKKPG SSVKVSCKASGYSIV SHYYISWVRQAPGQG LEWMGGISSDGSNNY AQKFQGRVTITADES TSTAYMELSSLRSED TAVYYCVRGVDYWGQ GTLVTVSS | 408 | CAGGTTCAACTGGTTCAGTCCGGAGCCGAG GTCAAAAAGCCTGGATCCTCTGTGAAGGTG TCATGTAAGGCTTCTGGCTACAGCATCGTC TCACATTATTACATATCTTGGGTGCGACAA GCCCCCGGCCAGGGGCTCGAGTGGATGGGA GGTATTTCCTCCGACGGGAGTAACAATTAC GCTCAGAAATTTCAGGGCCGGGTGACCATT ACCGCCGACGAAAGTACAAGCACCGCTTAT ATGGAATTAAGCTCTTTAAGATCAGAGGAC ACGGCTGTGTACTACTGTGTAAGGGGCGTG GATTACTGGGGTCAGGGGACGCTCGTCACC GTCTCGAGC |
| Anti-MUC16 VH7 | 396 | QVQLQESGPGLVKPS ETLSLTCTVSGYSIV SHYYWSWIRQPPGKG LEWIGYISSDGSNNY NPSLKSRVTISVDTS KNQFSLKLSSVTAAD TAVYYCVRGVDYWGQ GTTVT VSS | 409 | CAGGTCCAGCTCCAGGAATCCGGCCCAGGG TTGGTGAAGCCTTCGGAGACCCTGTCTCTG ACATGCACAGTCAGCGGCTATAGTATCGTC TCCCACTATTATTGGTCTTGGATTCGGCAA CCTCCAGGCAAGGGGTTAGAATGGATTGGA TACATCTCAAGCGATGGGTCCAATAACTAC AACCCAAGTCTCAAAAGTAGAGTGACTATC TCTGTGGATACCAGTAAAAACCAGTTTTCA CTCAAGTTGAGTTCCGTCACCGCCGCCGAC ACAGCCGTTTACTACTGTGTTCGGGGAGTG GACTACTGGGGCCAAGGTACCACGGTTACC GTGAGCAGC |
| Anti-MUC16 VH8 | 397 | QVQLQESGPGLVKPS DTLSLTCAVSGYSIV SHYYWHWIRQPPGKG LEWMGYISSDGSNDF NPSLKTRITISRDTS KNQFSLKLSSVTAVD TAVYYCVRGVDYWGQ GTLVTVSS | 410 | CAGGTGCAGCTGCAGGAGAGCGGCCCCGGC CTGGTGAAGCCCAGCGACACCCTGAGCCTG ACCTGCGCCGTGAGCGGCTACAGCATCGTG AGCCACTACTACTGGCACTGGATCAGACAG CCCCCCGGCAAGGGCCTGGAGTGGATGGGC TACATCAGCAGCGACGGCAGCAACGACTTC AACCCCAGCCTGAAGACCAGAATCACCATC AGCAGAGACACCAGCAAGAACCAGTTCAGC CTGAAGCTGAGCAGCGTGACCGCCGTGGAC ACCGCCGTGTACTACTGCGTGAGAGGCGTG GACTACTGGGGCCAGGGCACCCTGGTGACC GTGAGCAGC |
| Anti-MUC16 VH9 | 398 | QVQLQESGPGLVKPS QTLSLTCAVYGYSIV SHYYWSWIRQPPGKG LEWIGEISSDGSNNY NPSLKSRVTISVDTS KNQFSLKLSSVTAAD TAVYYCVRGVDYWGQ GTLVTVSS | 411 | CAGGTGCAGCTGCAGGAGAGCGGCCCCGGC CTGGTGAAGCCCAGCCAGACCCTGAGCCTG ACCTGCGCCGTGTACGGCTACAGCATCGTG AGCCACTACTACTGGAGCTGGATCAGACAG CCCCCCGGCAAGGGCCTGGAGTGGATCGGC GAGATCAGCAGCGACGGCAGCAACAACTAC AACCCCAGCCTGAAGAGCAGAGTGACCATC AGCGTGGACACCAGCAAGAACCAGTTCAGC CTGAAGCTGAGCAGCGTGACCGCCGCCGAC ACCGCCGTGTACTACTGCGTGAGAGGCGTG GACTACTGGGGCCAGGGCACCCTGGTGACC GTGAGCAGC |
| Anti-MUC16 VH10 | 399 | QVQLQESGPGLVKPS ETLSLTCAVSGYSIV SHYYWGWIRQPPGKG LEWIGSISSDGSNYY NPSLKSRVTISVDTS KNQFSLKLSSVTAAD TAVYYCVRGVDYWGQ GTLVTVSS | 412 | CAGGTGCAGCTGCAGGAGAGCGGCCCCGGC CTGGTGAAGCCCAGCGAGACCCTGAGCCTG ACCTGCGCCGTGAGCGGCTACAGCATCGTG AGCCACTACTACTGGGGCTGGATCAGACAG CCCCCCGGCAAGGGCCTGGAGTGGATCGGC AGCATCAGCAGCGACGGCAGCAACTACTAC AACCCCAGCCTGAAGAGCAGAGTGACCATC AGCGTGGACACCAGCAAGAACCAGTTCAGC CTGAAGCTGAGCAGCGTGACCGCCGCCGAC ACCGCCGTGTACTACTGCGTGAGAGGCGTG GACTACTGGGGCCAGGGCACCCTGGTGACC GTGAGCAGC |

TABLE 27-continued

Exemplary anti-MUC16 Variable Heavy (VH) and Variable Light (VL) Sequences

| Name | SEQ ID NO | Amino acid sequence | SEQ ID NO | Nucleotide sequence |
|---|---|---|---|---|
| Anti-MUC16 VH11 | 400 | QVQLVESGGGVVQPGRSLRLSCAASGYSIVSHYYWNWVRQAPGKGLEWVAYISSDGSNEYNPSLKNRFTISRDNSKNTLYLQMNSLRAEDTAVYYCVRGVDYWGQGTTVTVSS | 413 | CAGGTGCAGCTGGTGGAGAGCGGCGGCGGCGTGGTGCAGCCCGGCAGAAGCCTGAGACTGAGCTGCGCCGCCAGCGGCTACAGCATCGTGAGCCACTACTACTGGAACTGGGTGAGACAGGCCCCCGGCAAGGGCCTGGAGTGGGTGGCCTACATCAGCAGCGACGGCAGCAACGAGTACAACCCCAGCCTGAAGAACAGATTCACCATCAGCAGAGACAACAGCAAGAACACCCTGTACCTGCAGATGAACAGCCTGAGAGCCGAGGACACCGCCGTGTACTACTGCGTGAGAGGCGTGGACTACTGGGGCCAGGGCACCACCGTGACCGTGAGCAGC |
| Anti-MUC16 VH12 | 401 | QVQLQESGPGLVKPSQTLSLTCTVSGYSIVSHYYWNWIRQHPGKGLEWIGYISSDGSNEYNPSLKNLVTISVDTSKNQFSLKLSSVTAADTAVYYCVRGVDYWGQGTMVTVSS | 414 | CAGGTGCAGCTGCAGGAGAGCGGCCCCGGCCTGGTGAAGCCCAGCCAGACCCTGAGCCTGACCTGCACCGTGAGCGGCTACAGCATCGTGAGCCACTACTACTGGAACTGGATCAGACAGCACCCCGGCAAGGGCCTGGAGTGGATCGGCTACATCAGCAGCGACGGCAGCAACGAGTACAACCCCAGCCTGAAGAACCTGGTGACCATCAGCGTGGACACCAGCAAGAACCAGTTCAGCCTGAAGCTGAGCAGCGTGACCGCCGCCGACACCGCCGTGTACTACTGCGTGAGAGGCGTGGACTACTGGGGCCAGGGCACCATGGTGACCGTGAGCAGC |
| Anti-MUC16 VH13 | 402 | QVQLQESGPGLVKPSDTLSLTCAVSGYSIVSHYYWNWIRQPPGKGLEWIGYISSDGSNEYNPSLKNRVTMSVDTSKNQFSLKLSSVTAVDTAVYYCVRGVDYWGQGTM VTVSS | 415 | CAGGTGCAGCTGCAGGAGAGCGGCCCCGGCCTGGTGAAGCCCAGCGACACCCTGAGCCTGACCTGCGCCGTGAGCGGCTACAGCATCGTGAGCCACTACTACTGGAACTGGATCAGACAGCCCCCCGGCAAGGGCCTGGAGTGGATCGGCTACATCAGCAGCGACGGCAGCAACGAGTACAACCCCAGCCTGAAGAACAGAGTGACCATGAGCGTGGACACCAGCAAGAACCAGTTCAGCCTGAAGCTGAGCAGCGTGACCGCCGTGGACACCGCCGTGTACTACTGCGTGAGAGGCGTGGACTACTGGGGCCAGGGCACCATGGTGACCGTGAGCAGC |
| Anti-MUC16 VH14 | 403 | EVQLLESGGGLVQPGGSLRLSCAASGYSIVSHYYWNWVRQAPGKGLEWVSYISSDGSNEYNPSLKNRFTISRDNSKNTLYLQMNSLRAEDTAVYYCVRGVDYWGQGT LVTVSS | 416 | GAGGTGCAGCTGCTGGAGAGCGGCGGCGGCCTGGTGCAGCCCGGCGGCAGCCTGAGACTGAGCTGCGCCGCCAGCGGCTACAGCATCGTGAGCCACTACTACTGGAACTGGGTGAGACAGGCCCCCGGCAAGGGCCTGGAGTGGGTGAGCTACATCAGCAGCGACGGCAGCAACGAGTACAACCCCAGCCTGAAGAACAGATTCACCATCAGCAGAGACAACAGCAAGAACACCCTGTACCTGCAGATGAACAGCCTGAGAGCCGAGGACACCGCCGTGTACTACTGCGTGAGAGGCGTGGACTACTGGGGCCAGGGCACCCTGGTGACCGTGAGCAGC |
| Anti-MUC16 VL1 | 417 | DIQMTQSPSSLSASVGDRVTITCQASRDINNFLNWYQQKPGKAPKLLIYRANNLETGVPSRFSGSGSGTDFTFTISSLQPEDIATYFCLQYGDLYTFGGGTKVEIK | 429 | GACATACAGATGACTCAGAGCCCCTCCTCACTCTCGGCATCAGTCGGCGACAGGGTCACAATTACCTGTCAGGCTTCTCGCGACATTAATAACTTCCTGAATTGGTATCAGCAAAAGCCCGGGAAGGCCCCTAAGCTGTTGATTTATAGAGCAAATAATCTCGAAACCGGCGTGCCCAGTAGGTTTAGCGGGTCCGGGAGCGGAACAGACTTCACATTCACCATTTCTAGTTTGCAGCCCGAAGACATTGCTACATATTTTTGCCTGCAGTACGGGGATCTCTACACTTTCGGGGGCGGAACAAAGGTTGAGATAAAA |
| Anti-MUC16 VL2 | 418 | DIQMTQSPSSLSASVGDRVTITCQASRDINNFLNWYQQKPGKAPKLLIYRANNLETGVPSRFSGSGSGTDFTFTI | 430 | GATATTCAAATGACGCAGTCACCCTCATCGCTCTCTGCGTCAGTAGGGGATCGTGTCACGATAACCTGTCAAGCATCAAGGGACATCAACAACTTCCTCAACTGGTACCAACAGAAGCCTGGCAAGGCACCTAAACTCCTGATCTACCGG |

TABLE 27-continued

Exemplary anti-MUC16 Variable Heavy (VH) and Variable Light (VL) Sequences

| Name | SEQ ID NO | Amino acid sequence | SEQ ID NO | Nucleotide sequence |
|---|---|---|---|---|
| | | SSLQPEDIATYYCLQ YGDLYTFGGGTKVEI K | | GCTAACAACCTAGAAACCGGGGTTCCGAGC CGATTCAGTGGGTCTGGAAGCGGGACAGAC TTTACGTTCACTATTAGTTCGCTACAGCCC GAAGACATTGCGACATATTACTGTCTTCAG TATGGGGATTTGTATACCTTTGGGGGAGGC ACCAAGGTAGAGATAAAG |
| Anti-MUC16 VL3 | 419 | DIQMTQSPSSLSASV GDRVTITCRASRDIN NFLGWYQQKPGKAPK RLIYRANSLQSGVPS RFSGSGSGTEFTLTI SSLQPEDFATYYCLQ YGDLYTFGQGTKVEI K | 431 | GACATCCAGATGACTCAGAGCCCGTCTTCT CTATCCGCAAGTGTAGGCGATCGTGTCACC ATCACATGCCGGGCTTCCCGGGATATCAAC AACTTCCTTGGGTGGTATCAGCAGAAGCCC GGAAAAGCCCCCAAACGGCTCATCTACAGA GCGAATTCCCTGCAGTCAGGTGTCCCCAGT AGGTTCAGCGGATCAGGCTCGGGGACCGAA TTCACTCTGACCATTAGCTCACTGCAGCCT GAGGATTTCGCTACTTACTATTGCCTGCAA TACGGCGATCTGTACACTTTCGGGCAGGGC ACCAAGGTGGAAATAAAA |
| Anti-MUC16 VL4 | 420 | EIVLTQSPGTLSLSP GERATLSCRASRDIN NFLAWYQQKPGQAPR LLIYRANSRATGIPD RFSGSGSGTDFTLTI SRLEPEDFAVYYCLQ YGDLYTFGQGTKVEI K | 432 | GAAATCGTACTGACCCAGTCTCCCGGAACC CTGAGTCTCTCACCCGGCGAGCGCGCAACA CTGTCGTGTAGGGCCAGTAGGGACATAAAT AACTTCCTAGCCTGGTACCAACAAAAACCG GGTCAGGCTCCAAGACTGTTGATCTATAGA GCTAACTCCAGGGCCACCGGCATCCCAGAC CGATTCTCAGGCTCCGGATCTGGAACCGAC TTCACGCTCACCATTAGCCGACTAGAACCT GAGGACTTTGCTGTATACTATTGCCTGCAG TACGGCGACCTGTATACCTTTGGACAGGGT ACCAAGGTCGAGATCAAG |
| Anti-MUC16 VL5 | 421 | EIVLTQSPATLSLSP GERATLSCRASRDIN NFLAWYQQKPGQAPR LLIYRANNRATGIPA RFSGSGPGTDFTLTI SSLEPEDFAVYYCLQ YGDLYTFGGGTKVEI K | 433 | GAGATCGTACTTACGCAGAGCCCAGCAACT CTGTCTCTGTCCCCCGGAGAACGGGCCACC CTGTCGTGTGCCGGGCCAGCCGTGATATTAAT AATTTCCTGGCCTGGTATCAACAAAAACCG GGGCAGGCTCCTCGACTGTTGATCTACCGG GCCAACAATAGAGCAACTGGTATCCCTGCT CGCTTCTCCGGCAGTGGGCCAGGTACAGAC TTCACCCTGACTATTTCGTCACTCGAACCA GAAGACTTTGCCGTGTATTATTGCTTACAA TACGGGGATCTGTACACTTTCGGAGGAGGA ACTAAGGTCGAAATTAAG |
| Anti-MUC16 VL6 | 422 | EIVLTQSPDFQSVTP KEKVTITCRASRDIN NFLHWYQQKPDQSPK LLIKRANQSFSGVPS RFSGSGSGTDFTLTI NSLEAEDAATYYCLQ YGDLYTFGQGTKVEI K | 434 | GAGATCGTGCTGACCCAGAGCCCCGACTTC CAGAGCGTGACCCCCAAGGAGAAGGTGACC ATCACCTGCAGAGCCAGCAGAGACATCAAC AACTTCCTGCACTGGTACCAGCAGAAGCCC GACCAGAGCCCCAAGCTGCTGATCAAGAGA GCCAACCAGAGCTTCAGCGGCGTGCCCAGC AGATTCAGCGGCAGCGGCAGCGGCACCGAC TTCACCCTGACCATCAACAGCCTGGAGGCC GAGGACGCCGCCACCTACTACTGCCTGCAG TACGGCGACCTGTACACCTTCGGCCAGGGC ACCAAGGTGGAGATCAAG |
| Anti-MUC16 VL7 | 423 | DIQMTQSPSSLSASV GDRVTITCRASRDIN NFLAWFQQKPGKAPK SLIYRANSLQSGVPS RFSGSGSGTDFTLTI SSLQPEDFATYYCLQ YGDLYTFGGGTKVEI K | 435 | GACATCCAGATGACCCAGAGCCCCAGCAGC CTGAGCGCCAGCGTGGGCGACAGAGTGACC ATCACCTGCAGAGCCAGCAGAGACATCAAC AACTTCCTGGCCTGGTTCCAGCAGAAGCCC GGCAAGGCCCCCAAGAGCCTGATCTACAGA GCCAACAGCCTGCAGAGCGGCGTGCCCAGC AGATTCAGCGGCAGCGGCAGCGGCACCGAC TTCACCCTGACCATCAGCAGCCTGCAGCCC GAGGACTTCGCCACCTACTACTGCCTGCAG TACGGCGACCTGTACACCTTCGGCGGCGGC ACCAAGGTGGAGATCAAG |

TABLE 27-continued

Exemplary anti-MUC16 Variable Heavy (VH) and Variable Light (VL) Sequences

| Name | SEQ ID NO | Amino acid sequence | SEQ ID NO | Nucleotide sequence |
|---|---|---|---|---|
| Anti-MUC16 VL8 | 424 | DIQMTQSPSSLSASVGDRVTITCRASRDINNFLAWYQQKPGKAPKLLLYRANRLESGVPSRFSGSGSGTDYTLTISSLQPEDFATYYCLQYGDLYTFGGGTKVEIK | 436 | GACATCCAGATGACCCAGAGCCCCAGCAGCCTGAGCGCCAGCGTGGGCGACAGAGTGACCATCACCTGCAGAGCCAGCAGAGACATCAACAACTTCCTGGCCTGGTACCAGCAGAAGCCCGGCAAGGCCCCCAAGCTGCTGCTGTACAGAGCCAACAGACTGGAGAGCGGCGTGCCCAGCAGATTCAGCGGCAGCGGCAGCGGCACCGACTACACCCTGACCATCAGCAGCCTGCAGCCCGAGGACTTCGCCACCTACTACTGCCTGCAGTACGGCGACCTGTACACCTTCGGCGGCGGCACCAAGGTGGAGATCAAG |
| Anti-MUC16 VL9 | 425 | DIQMTQSPSSLSASVGDRVTITCKASRDINNFLSWYQQKPGKAPKLLIYRANRLVDGVPSRFSGSGSGTDFTFTISSLQPEDIATYYCLQYGDLYTFGGGTKVEIK | 437 | GACATCCAGATGACCCAGAGCCCCAGCAGCCTGAGCGCCAGCGTGGGCGACAGAGTGACCATCACCTGCAAGGCCAGCAGAGACATCAACAACTTCCTGAGCTGGTACCAGCAGAAGCCCGGCAAGGCCCCCAAGCTGCTGATCTACAGAGCCAACAGACTGGTGGACGGCGTGCCCAGCAGATTCAGCGGCAGCGGCAGCGGCACCGACTTCACCTTCACCATCAGCAGCCTGCAGCCCGAGGACATCGCCACCTACTACTGCCTGCAGTACGGCGACCTGTACACCTTCGGCGGCGGCACCAAGGTGGAGATCAAG |
| Anti-MUC16 VL10 | 426 | DIQMTQSPSSLSASVGDRVTITCKASRDINNFLSWYQQKPGKAPKLLIYRANRLVDGVPSRFSGSGSGTDFTLTISSLQPEDFATYYCLQYGDLYTFGQGTKVEIK | 438 | GACATCCAGATGACCCAGAGCCCCAGCAGCCTGAGCGCCAGCGTGGGCGACAGAGTGACCATCACCTGCAAGGCCAGCAGAGACATCAACAACTTCCTGAGCTGGTACCAGCAGAAGCCCGGCAAGGCCCCCAAGCTGCTGATCTACAGAGCCAACAGACTGGTGGACGGCGTGCCCAGCAGATTCAGCGGCAGCGGCAGCGGCACCGACTTCACCCTGACCATCAGCAGCCTGCAGCCCGAGGACTTCGCCACCTACTACTGCCTGCAGTACGGCGACCTGTACACCTTCGGCCAGGGCACCAAGGTGGAGATCAAG |
| Anti-MUC16 VL11 | 427 | EIVLTQSPGTLSLSPGERATLSCKASRDINNFLSWYQQKPGQAPRLLIYRANRLVDGIPDRFSGSGSGTDFTLTISRLEPEDFAVYYCLQYGDLYTFGQGTKVEIK | 439 | GAGATCGTGCTGACCCAGAGCCCCGGCACCCTGAGCCTGAGCCCCGGCGAGAGAGCCACCCTGAGCTGCAAGGCCAGCAGAGACATCAACAACTTCCTGAGCTGGTACCAGCAGAAGCCCGGCCAGGCCCCCAGACTGCTGATCTACAGAGCCAACAGACTGGTGGACGGCATCCCCGACAGATTCAGCGGCAGCGGCAGCGGCACCGACTTCACCCTGACCATCAGCAGACTGGAGCCCGAGGACTTCGCCGTGTACTACTGCCTGCAGTACGGCGACCTGTACACCTTCGGCCAGGGCACCAAGGTGGAGATCAAG |
| Anti-MUC16 VL12 | 428 | EIVLTQSPATLSLSPGERATLSCKASRDINNFLSWYQQKPGQAPRLLIYRANRLVDGIPARFSGSGSGTDFTLTISSLEPEDFAVYYCLQYGDLYTFGQGTKVEIK | 440 | GAGATCGTGCTGACCCAGAGCCCCGCCACCCTGAGCCTGAGCCCCGGCGAGAGAGCCACCCTGAGCTGCAAGGCCAGCAGAGACATCAACAACTTCCTGAGCTGGTACCAGCAGAAGCCCGGCCAGGCCCCCAGACTGCTGATCTACAGAGCCAACAGACTGGTGGACGGCATCCCCGCCAGATTCAGCGGCAGCGGCAGCGGCACCGACTTCACCCTGACCATCAGCAGCCTGGAGCCCGAGGACTTCGCCGTGTACTACTGCCTGCAGTACGGCGACCTGTACACCTTCGGCCAGGGCACCAAGGTGGAGATCAAG |

Table 28 provides exemplary anti-MUC16 HC-linker-TGFβRII ECD sequences. Such heavy chain polypeptides can be paired with an anti-MUC16 light chain, e.g., SEQ ID NO: 443, to make an anti-MUC16 fusion protein. Such heavy chain polypeptides can be paired with an anti-MUC16 variable region, e.g., SEQ ID NOs: 417-428, to make an anti-MUC16 fusion protein.

TABLE 28

Exemplary anti-MUC16 HC-Linker-TGFβRII ECD Sequences

| Name | SEQ ID NO | Amino acid sequence | SEQ ID NO | Nucleotide sequence |
|---|---|---|---|---|
| Anti-MUC16 VH10-IgG1(wt)-linker-TGFβRII ECD | 441 | QVQLQESGPGLVKPSETLSLTCAVSGYSIVSHYYWGWIRQPPGKGLEWIGSISSDGSNYYNPSLKSRVTISVDTSKNQFSLKLSSVTAADTAVYYCVRGVDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKQGGGSGGGGSIPPHVQKSVNNDMIVTDNNGAVKFPQLCKFCDVRFSTCDNQKSCMSNCSITSICEKPQEVCVAVWRKNDENITLETVCHDPKLPYHDFILEDAASPKCIMKEKKKPGETFFMCSCSSDECNDNIIFSEEYNTSNPD | 442 | CAGGTGCAGCTGCAGGAGAGCGGCCCCGGCCTGGTGAAGCCCAGCGAGACCCTGAGCCTGACCTGCGCCGTGAGCGGCTACAGCATCGTGAGCCACTACTACTGGGGCTGGATCAGACAGCCCCCCGGCAAGGGCCTGGAGTGGATCGGCAGCATCAGCAGCGACGGCAGCAACTACTACAACCCCAGCCTGAAGAGCAGAGTGACCATCAGCGTGGACACCAGCAAGAACCAGTTCAGCCTGAAGCTGAGCAGCGTGACCGCCGCCGACACCGCCGTGTACTACTGCGTGAGAGGCGTGGACTACTGGGGCCAGGGCACCCTGGTGACCGTGAGCAGCGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAAGGTGGAGGTGGTTCTGGAGGTGGAGGTAGTATCCCTCCTCACGTACAGAAGTCCGTGAACAATGACATGATTGTCACTGACAATAACGGAGCCGTCAAGTTTCCTCAGCTATGTAAGTTCTGCGATGTTCGGTTCTCCACATGCGATAATCAGAAAAGCTGTATGTCTAATTGCAGTATCACTAGTATATGCGAAAAACCTCAAGAAGTTTGCGTCGCCGTGTGGCGGAAAATGATGAAAATATCACGCTTGAGACTGTCTGCCATGATCCAAAGTTACCCTACCACGACTTCATCTTAGAAGACGCCGCATCACCCAAGTGCATTATGAAAGAGAAAAAGAAGCCAGGAGAAACATTCTTTATGTGCTCATGCTCCTCTGACGAATGCAACGACAACATTATCTTCTCTGAGGAGTATAACACCTCAAATCCAGACTGA |

Table 29 provides exemplary anti-MUC16 LC sequences. Such polypeptides can be paired with an anti-MUC16 heavy chain, e.g., SEQ ID NO: 441, to make a MUC16 fusion protein. Such polypeptides can be paired with an anti-MUC16 variable heavy region, e.g., SEQ ID NOs: 390-403, to make a MUC16 fusion protein.

TABLE 29

Exemplary anti-MUC16 LC Sequence

| Name | SEQ ID NO | Amino acid sequence |
|---|---|---|
| Anti-MUC16 VL10-κCL | 443 | DIQMTQSPSSLSASVGDRVTITCKASRDINNFLSWYQQKPGK APKLLIYRANRLVDGVPSRFSGSGSGTDFTLTISSLQPEDFA TYYCLQYGDLYTFGQGTKVEIKTVAAPSVFIFPPSDEQLKSG TASVVCLLNNFYPREAKVQWKVDNALQSGNSQESVTEQDSKD STYSLSSTLTLSKADYEKHKVYACEVTHQGLSSPVTKSFNRG EC |

Table 30 provides exemplary anti-MUC1 VH and VL sequences. The CDRs are underlined.

TABLE 30

Exemplary anti-MUC1 VH and VL Sequences (CDRs Underlined)

| Name | SEQ ID NO | Amino acid sequence |
|---|---|---|
| Anti-MUC1 VH1 | 444 | QVQLVQSGAEVKKPGSSVKVSCKAS GYAFSNFWMN WVRQAPGQG LEWMG QIYPGDGDTNYNGKFKG RVTITADKSTSTAYMELSSLRS EDTAVYYCARS YYRSAWFAY WGQGTLVTVSS |
| Anti-MUC1 VH2 | 445 | QVQLVQSGAEVKKPGASVKVSCKAS GYAFSNFWMN WVRQAPGQG LEWMG QIYPGDGDTNYNGKFKG RVTMTRDTSTSTVYMELSSLRS EDTAVYYCARS YYRSAWFAY WGQGTLVTVSS |
| Anti-MUC1 VH3 | 446 | QVQLVQSGAEVKKPGASVKVSCKASGYAFSNFWMNWVRQAPGQG LEWMGQIYPGDGDTNYNGKFKGRVTMTRDTSISTAYMELSRLRS DDTAVYYCARSYYRSAWFAYWGQGTLVTVSS |
| Anti-MUC1 VH4 | 447 | QVQLVQSGAEVKKPGATVKISCKVSGYAFSNFWMNWVQQAPGKG LEWMGQIYPGDGDTNYNGKFKGRVTITADTSTDTAYMELSSLRS EDTAVYYCARSYYRSAWFAYWGQGTLVTVSR |
| Anti-MUC1 VH5 | 448 | EVQLVQSGAEVKKPGESLKISCKGSGYAFSNFWMNWVRQMPGKG LEWMGQIYPGDGDTNYNGKFKGQVTISADKSISTAYLQWSSLKA SDTAMYYCARSYYRSAWFAYWGQGTLVTVSL |
| Anti-NW(A VL1 | 449 | EIVLTQSPDFQSVTPKEKVTITCRAS QSIGTSIHW YQQKPDQSP KLLIK YASESIS GVPSRFSGSGSGTDFTLTINSLEAEDAATYYC QQSNNWPLTF GQGTKVEIK |
| Anti-MUC1 VL2 | 450 | EIVMTQSPATLSVSPGERATLSCRASQSIGTSIHWYQQKPGQAP RLLIYYASESISGIPARFSGSGSGTEFTLTISSLQSEDFAVYYC QQSNN WPLTFGGGTKVEIK |
| Anti-MUC1 VL3 | 451 | EIVLTQSPATLSLSPGERATLSCRASQSIGTSIHWYQQKPGQAP RLLIYYASESISGIPARFSGSGSGTDFTLTISSLEPEDFAVYYC QQSNN WPLTFGGGTKVEIK |
| Anti-MUC1 VL4 | 452 | AIQLTQSPSSLSASVGDRVTITCRASQSIGTSIHWYQQKPGKAP KLLIYYASESISGVPSRFSGSGSGTDFTLTISSLQPEDFATYYC QQSNN WPLTFGGGTKVEIK |
| Anti-MUC1 VL5 | 453 | DIVMTQSPSLLSASTGDRVTISCRASQSIGTSIHWYQQKPGKAP ELLIYYASESISGVPSRFSGSGSGTDFTLTISCLQSEDFATYYC QQSNNWPLTFGQGTKVEIK |

Table 31 provides exemplary anti-MUC1 antibody sequences.

TABLE 31

Exemplary Anti-MUC1 Antibody sequences

| Name | SEQ ID NO | Amino acid sequence |
|---|---|---|
| Chimieric antibody_VH-hIgG1CH1 | 454 | QVQLQQSGAELVRPGSSVKISCKTSGYAFSNFWMNWVKQRPGQG LEWIGQIYPGDGDTNYNGKFKGKATLTADKSSSTAYMQLSSLTS EASAVYFCARSYYRSAWFAYWGQGTLVSVSAASTKGPSVFPLAP SSKSTSGGTAALGCLVKDYFPEPVTVSWNSGALTSGVHTFPAVL QSSGLYSLSSVVTVPSSSLGTQTY |
| Chimeric antibody_VL-hIgKCL: | 455 | DILLTQSPAILSVSPGERVSFSCRASQSIGTSIHWYQQRTNGSP RLLIKYASESISGIPSRFSGSGSGTDFTLSINSVESEDIADYYC QQSNNWPLTFGAGTKLELKRTVAAPSVFIFPPSDEQLKSGTASV VCLLNNFYPREAKVQWKVDNALQ |
| VH1-hIgG1CH: | 456 | QVQLVQSGAEVKKPGSSVKVSCKASGYAFSNFWMNWVRQAPGQG LEWMGQIYPGDGDTNYNGKFKGRVTITADKSTSTAYMELSSLRS EDTAVYYCARSYYRSAWFAYWGQGTLVTVSSASTKGPSV |
| VH2-hIgG1CH: | 457 | QVQLVQSGAEVKKPGASVKVSCKASGYAFSNFWMNWVRQAPGQG LEWMGQIYPGDGDTNYNGKFKGRVTMTRDTSTSTVYMELSSLRS EDTAVYYCARSYYRSAWFAYWGQGTLVTVSSASTKGPSV |
| VH3-hIgG1CH: | 458 | QVQLVQSGAEVKKPGASVKVSCKASGYAFSNFWMNWVRQAPGQG LEWMGQIYPGDGDTNYNGKFKGRVTMTRDTSISTAYMELSRLRS DDTAVYYCARSYYRSAWFAYWGQGTLVTVSSASTKGPSV |
| VH4-hIgG1CH: | 459 | QVQLVQSGAEVKKPGATVKISCKVSGYAFSNFWMNWVQQAPGKG LEWMGQIYPGDGDTNYNGKFKGRVTITADTSTDTAYMELSSLRS EDTAVYYCARSYYRSAWFAYWGQGTLVTVSRASTKGPSV |
| VH5-hIgG1CH: | 460 | EVQLVQSGAEVKKPGESLKISCKGSGYAFSNFWMNWVRQMPGKG LEWMGQIYPGDGDTNYNGKFKGQVTISADKSISTAYLQWSSLKA SDTAMYYCARSYYRSAWFAYWGQGTLVTVSLASTKGPSV |
| VL1-hIgKCL | 461 | EIVLTQSPDFQSVTPKEKVTITCRASQSIGTSIHWYQQKPDQSP KLLIKYASESISGVPSRFSGSGSGTDFTLTINSLEAEDAATYYC QQSNWPLTFGQGTKVEIKRTVAAPSVFIFPPSDEQLKS |
| VL2-hIgKCL | 462 | EIVMTQSPATLSVSPGERATLSCRASQSIGTSIHWYQQKPGQAP RLLIYYASESISGIPARFSGSGSGTEFTLTISSLQSEDFAVYYC QQSNN WPLTFGGGTKVEIKRTVAAPSVFIFPPSDEQLKS |
| VL3-hIgKCL | 463 | EIVLTQSPATLSLSPGERATLSCRASQSIGTSIHWYQQKPGQAP RLLIYYASESISGIPARFSGSGSGTDFTLTISSLEPEDFAVYYC QQSNNWPLTFGGGTKVEIKRTVAAPSVFIFPPSDEQLKS |
| VL4-hIgKCL | 464 | AIQLTQSPSSLSASVGDRVTITCRASQSIGTSIHWYQQKPGKAP KLLIYYASESISGVPSRFSGSGSGTDFTLTISSLQPEDFATYYC QQSNNWPLTFGGGTKVEIKRTVAAPSVFIFPPSDEQLKS |
| VL5-hIgKCL | 465 | DIVMTQSPSLLSASTGDRVTISCRASQSIGTSIHWYQQKPGKAP ELLIYYASESISGVPSRFSGSGSGTDFTLTISCLQSEDFATYYC QQSNNWPLTFGQGTKVEIKRTVAAPSVFIFPPSDEQLKS |

Table 32 provides exemplary anti-MUC1-TGFβRII ECD heavy chain sequences. Such heavy chain polypeptides can be paired with an anti-MUC1 light chain, e.g., SEQ ID NO: 467, to make an anti-MUC1 fusion protein. Such heavy chain polypeptides can be paired with an anti-MUC1 variable region, e.g., SEQ ID NOs.: 449-453, to make an anti-MUC1 fusion protein.

TABLE 32

Exemplary anti-MUC1-TGFβRII ECD Heavy Chain Sequences

| Name | SEQ ID NO | Amino acid sequence |
|---|---|---|
| Anti-MUC1 VH1-IgG1(wt) | 466 | QVQLVQSGAEVKKPGSSVKVSCKASGYAFSNFWMNWVRQAPGQG LEWMGQIYPGDGDTNYNGKFKGRVTITADKSTSTAYMELSSLRS EDTAVYYCARSYYRSAWFAYWGQGTLVTVSSASTKGPSVFPLAP SSKSTSGGTAALGCLVKDYFPEPVTVSWNSGALTSGVHTFPAVL |

TABLE 32-continued

Exemplary anti-MUC1-TGFβRII ECD Heavy Chain Sequences

| Name | SEQ ID NO | Amino acid sequence |
|---|---|---|
| -linker-TGFβRII ECD | | QSSGLYSLSSVVTVPSSSLGTQTYICNVNHKPSNTKVDKKVEPK SCDKTHTCPPCPAPELLGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPAPIEKTISKAKGQPREPQVYT LPPSREEMTKNQVSLTCLVKGFYPSDIAVEWESNGQPENNYKTT PPVLDSDGSFFLYSKLTVDKSRWQQGNVESCSVMHEALHNHYTQ KSLSLSPGKGGGGSGGGGSIPPHVQKSVNNDMIVTDNNGAVKFP QLCKFCDVRFSTCDNQKSCMSNCSITSICEKPQEVCVAVWRKND ENITLETVCHDPKLPYHDFILEDAASPKCIMKEKKKPGETFFMC SCSSDECNDNIIFSEEYNTSNPD |

Table 33 provides exemplary anti-MUC1 light chain sequences. Such polypeptides can be paired with an anti-MUC1 heavy chain, e.g., SEQ ID NO: 467, to make an anti-MUC1 fusion protein. Such polypeptides can be paired with an anti-MUC1 variable heavy region, e.g., SEQ ID NOs.: 444-448, to make an anti-MUC1 fusion protein.

TABLE 33

Exemplary anti-MUC1 Light Chain Sequences

| Name | SEQ ID NO | Amino acid sequence |
|---|---|---|
| Anti-MUC1 | 467 | EIVLTQSPDFQSVTPKEKVTITCRASQSIGTSIHWYQQK PDQSPKLLIKYASESISGVPSRFSGSGSGTDFTLTINSL |

TABLE 33-continued

Exemplary anti-MUC1 Light Chain Sequences

| Name | SEQ ID NO | Amino acid sequence |
|---|---|---|
| VL1-κCL | | EAEDAATYYCQQSNNWPLTEGQGTKVEIKTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGEC |

Table 34 provides exemplary TGFβ1 inhibitory peptides for use in MUC1 and MUC16 fusion proteins described herein. In any embodiments exemplifying a fusion protein with, e.g., TGFβRII ECD, a TGFβ1 inhibitory peptide may be used instead.

TABLE 34

Exemplary TGFβ1 Inhibitory Peptide Sequences

| Name | SEQ ID NO | Amino Acid Sequence | SEQ ID NO | Nucleotide Sequence |
|---|---|---|---|---|
| TGFβ1-I1 | 468 | RIWFIPRSSWYERA | 508 | AGGATCTGGTTCATCCCCAGGAGCAGCTGG TACGAGAGGGCC |
| TGFβ1-I2 | 469 | IWFIPRSSWYERA | 509 | ATCTGGTTCATCCCCAGGAGCAGCTGGTAC GAGAGGGCC |
| TGFβ1-I3 | 470 | FIPRSSWYERA | 510 | TTCATCCCCAGGAGCAGCTGGTACGAGAGG GCC |
| TGFβ1-I4 | 471 | FIPRSSWYERA | 511 | TTCATCCCCAGGAGCAGCTGGTACGAGAGG GCC |
| TGFβ1-I5 | 472 | IPRSSWYERA | 512 | ATCCCCAGGAGCAGCTGGTACGAGAGGGCC |
| TGFβ1-I6 | 473 | PRSSWYERA | 513 | CCCAGGAGCAGCTGGTACGAGAGGGCC |
| TGFβ1-I7 | 474 | KRIWFIPRSSWYE R | 514 | AAGAGGATCTGGTTCATCCCCAGGAGCAGC TGGTACGAGAGG |
| TGFβ1-I8 | 475 | KRIWF TPRSSWYE | 515 | AAGAGGATCTGGTTCATCCCCAGGAGCAGC TGGTACGAG |
| TGFβ1-I9 | 476 | KRIWFIPRSSWY | 516 | AAGAGGATCTGGTTCATCCCCAGGAGCAGC TGGTAC |
| TGFβ1-I10 | 477 | KRIWFIPRSSW | 517 | AAGAGGATCTGGTTCATCCCCAGGAGCAGC TGG |

TABLE 34-continued

Exemplary TGFβ1 Inhibitory Peptide Sequences

| Name | SEQ ID NO | Amino Acid Sequence | SEQ ID NO | Nucleotide Sequence |
|---|---|---|---|---|
| TGFβ1-I11 | 478 | KRIWFIPRSS | 518 | AAGAGGATCTGGTTCATCCCCAGGAGCAGC |
| TGFβ1-I12 | 479 | KRIWFIPRS | 519 | AAGAGGATCTGGTTCATCCCCAGGAGC |
| TGFβ1-I13 | 480 | RIWFIPRSSWYER | 520 | AGGATCTGGTTCATCCCCAGGAGCAGCTGGTACGAGAGG |
| TGFβ1-I14 | 481 | IWFIPRSSWYE | 521 | ATCTGGTTCATCCCCAGGAGCAGCTGGTACGAG |
| TGFβ1-I15 | 482 | WFIPRSSWY | 522 | TGGTTCATCCCCAGGAGCAGCTGGTAC |
| TGFβ1-I16 | 483 | DRRTFWWSLRSAPGA | 523 | GACAGGAGGATCTTCTGGTGGAGCCTGAGGAGCGCCCCCGGCGCC |
| TGFβ1-I17 | 484 | HVRLHHYLRHRSLPN | 524 | CACGTGAGGCTGCACCACTACCTGAGGCACAGGAGCCTGCCCAAC |
| TGFβ1-I18 | 485 | RFFTRFPWHYHASRL | 525 | AGGTTCTTCACCAGGTTCCCCTGGCACTACCACGCCAGCAGGCTG |
| TGFβ1-I19 | 486 | RLAHSHRHRSHVALT | 526 | AGGCTGGCCCACAGCCACAGGCACAGGAGCCACGTGGCCCTGACC |
| TGFβ1-I20 | 487 | RRWVRYPVHLHSPTV | 527 | AGGAGGTGGGTGAGGTACCCCGTGCACCTGCACAGCCCCATCGTG |
| TGFβ1-I21 | 488 | PPYHRFWRGHRHAVQ | 528 | CCCCCCTACCACAGGTTCTGGAGGGGCCACAGGCACGCCGTGCAG |
| TGFβ1-I22 | 489 | HRTSHFAHRYLARLH | 529 | CACAGGATCAGCCACTTCGCCCACAGGTACCTGGCCAGGCTGCAC |
| TGFβ1-I23 | 490 | WHWRHRTPLQLAAGR | 530 | TGGCACTGGAGGCACAGGATCCCCCTGCAGCTGGCCGCCGGCAGG |
| TGFβ1-I24 | 491 | GWHSLLHSRYHRTAA | 531 | GGCTGGCACAGCCTGCTGCACAGCAGGTACCACAGGATCGCCGCC |
| TGFβ1-I25 | 492 | FVWVRFHRLPRQTYT | 532 | TTCGTGTGGGTGAGGTTCCACAGGCTGCCCAGGCAGATCTACACC |
| TGFβ1-I26 | 493 | WHKYFLRRPLSVRTR | 533 | TGGCACAAGTACTTCCTGAGGAGGCCCCTGAGCGTGAGGACCAGG |
| TGFβ1-I27 | 494 | VPMALNHGVYVMVSS | 534 | GTGCCCATGGCCCTGAACCACGGCGTGTACGTGATGGTGAGCAGC |
| TGFβ1-I28 | 495 | RKWFLQHRRMPVSVL | 535 | AGGAAGTGGTTCCTGCAGCACAGGAGGATGCCCGTGAGCGTGCTG |
| TGFβ1-I29 | 496 | SGRRHLHRHHTFSLP | 536 | AGCGGCAGGAGGCACCTGCACAGGCACCACATCTTCAGCCTGCCC |
| TGFβ1-I30 | 497 | GWITFHRRHHDRVLS | 537 | GGCTGGATCACCTTCCACAGGAGGCACCACGACAGGGTGCTGAGC |
| TGFβ1-I31 | 498 | RLHGHRSHRFTHVAQ | 538 | AGGCTGCACGGCCACAGGAGCCACAGGTTCACCCACGTGGCCCAG |
| TGFβ1-I32 | 499 | KRIWFIPRSSWYERA | 539 | AAGAGGATCTGGTTCATCCCCAGGAGCAGCTGGTACGAGAGGGCC |
| TGFβ1-I33 | 500 | MPLSRYWWLFSHRPR | 540 | ATGCCCCTGAGCAGGTACTGGTGGCTGTTCAGCCACAGGCCCAGG |
| TGFβ1-I34 | 501 | RHLSHFKWLRSHGLD | 541 | AGGCACCTGAGCCACTTCAAGTGGCTGAGGAGCCACGGCCTGGAC |
| TGFβ1-I35 | 502 | RRFHFHSRMVAVDNS | 542 | AGGAGGTTCCACTTCCACAGCAGGATGGTGGCCGTGGACAACAGC |

TABLE 34-continued

Exemplary TGFβ1 Inhibitory Peptide Sequences

| Name | SEQ ID NO | Amino Acid Sequence | SEQ ID NO | Nucleotide Sequence |
|---|---|---|---|---|
| TGFβ1-I36 | 503 | HANFCLGPCPYTWSLA | 543 | CACGCCAACTTCTGCCTGGGCCCCTGCCCCTACATCTGGAGCCTGGCC |
| TGFβ1-I37 | 504 | FCLGPCPYTWSLDTA | 544 | TTCTGCCTGGGCCCCTGCCCCTACATCTGGAGCCTGGACACCGCC |
| TGF01-I38 | 505 | SNPYSAFQVIDITVDIA | 545 | AGCAACCCCTACAGCGCCTTCCAGGTGGACATCATCGTGGACATCGCC |
| TGF01-I39 | 506 | TSLDATMIWTMMA | 546 | ACCAGCCTGGACGCCACCATGATCTGGACCATGATGGCC |
| TGF01-I40 | 507 | TSLDASIWAMMQNA | 547 | ACCAGCCTGGACGCCAGCATCTGGGCCATGATGCAGAACGCC |

Table 35 provides exemplary aIgG1 sequences for use in fusion proteins describe herein. Variants comprising amino acid substitutions and/or deletions may also be utilized.

TABLE 35

Exemplary IgG1 Sequences

| Name | SEQ ID NO | Amino acid sequence |
|---|---|---|
| CH1 (WT) | 548 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV |
| Hinge (WT) | 549 | EPKSCDKTHTCP |
| CH2 (WT) | 550 | PCPAPELLGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK |

TABLE 35-continued

Exemplary IgG1 Sequences

| Name | SEQ ID NO | Amino acid sequence |
|---|---|---|
| CH3 (WT) | 551 | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CH1 (Variant 1) | 552 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRV |
| CH3 (Variant 1) | 553 | GQPREPQVYTLPPSREELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CH3 (Variant 2) | 554 | GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |

What is claimed is:

1. A fusion protein comprising:
   (a) a first component comprising:
      a $V_L$ region comprising the sequence of any one of SEQ ID NOs: 417-428; and a $V_H$ region comprising the sequence of any one of SEQ ID NOs: 390-403; and
   (b) a second component that is:
      a cytokine trap comprising the sequence of any one of SEQ ID NOs: 14, 141, and 142.

2. The fusion protein of claim 1, wherein the first component comprises: (a) a VL region comprising the sequence of any one of SEQ ID NOs: 417-428; and (b) a $V_H$ region comprising the sequence of any one of SEQ ID NOs: 390-403.

3. The fusion protein of claim 1, wherein the cytokine trap comprises the sequence of SEQ ID NO: 14.

4. The fusion protein of claim 1, wherein the first and second components are connected by a linker comprising:
   (a) $(G4S)_n$, wherein n is 2, 3, 4, 5, or 6 (SEQ ID NO: 555);
   (b) $(Gly)_n$, wherein n is 6, 7, or 8 (SEQ ID NO: 33); (c) $(EAAAK)_n$, wherein n is 1, 2, 3, 4, 5, or 6 (SEQ ID NO: 34);
   (d) $A(EAAAK)_4ALEA(EAAAK)_4A$ (SEQ ID NO: 31); and/or (e) a sequence of any one of SEQ ID NOs: 17-34.

5. A polynucleotide encoding the fusion protein of claim 1.

6. A pharmaceutical composition comprising: (a) the fusion protein of claim 1, or a polynucleotide encoding the same; and (b) a pharmaceutically-acceptable excipient.

7. The fusion protein of claim 1, wherein the first component comprises a V$_L$ region comprising the sequence of any one of SEQ ID NOs: 423, 425, and 426; and (ii) a V$_H$ region comprising the sequence of SEQ ID NO: 399.

8. The fusion protein of claim 1, wherein the first component comprises
a V$_L$ region comprising the sequence of SEQ ID NO: 426; and a V$_H$ region comprising the sequence of SEQ ID NO: 399.

9. The fusion protein of claim 7, wherein the first component comprises a V$_L$ region comprising the sequence of any one of SEQ ID NO: 423.

10. The fusion protein of claim 7, wherein the first component comprises a V$_L$ region comprising the sequence of any one of SEQ ID NO: 425.

11. The fusion protein of claim 7, wherein the first component comprises a V$_L$ region comprising the sequence of any one of SEQ ID NO: 426.

12. The fusion protein of claim 7, wherein the second component is a cytokine trap comprising the sequence of SEQ ID NO: 14.

13. The fusion protein of claim 7, wherein the second component is a cytokine trap comprising the sequence of SEQ ID NO: 141.

14. The fusion protein of claim 7, wherein the second component is a cytokine trap comprising the sequence of SEQ ID NO: 142.

15. The fusion protein of claim 1 wherein:
(a) the first component comprises: (i) a V$_L$ region comprising the sequence of SEQ ID NO: 426; and (ii) a V$_H$ region comprising the sequence of SEQ ID NO: 399; and
(b) the second component is a cytokine trap comprising the sequence of SEQ ID NO: 14.

* * * * *